US011192900B2

(12) United States Patent
Pham et al.

(10) Patent No.: US 11,192,900 B2
(45) Date of Patent: Dec. 7, 2021

(54) SUBSTITUTED 1,6-DIHYDROPYRIDINONES AND 1,2-DIHYDROISOQUINOLINONES AS BET INHIBITORS

(71) Applicant: NUVATION BIO INC., New York, NY (US)

(72) Inventors: Son Minh Pham, San Francisco, CA (US); Sarvajit Chakravarty, Edmond, OK (US); Jayakanth Kankanala, Plymouth, MN (US); Jiyun Chen, Moraga, CA (US); Anjan Kumar Nayak, Uttar Pradesh (IN); Anup Barde, Uttar Pradesh (IN)

(73) Assignee: Nuvation Bio Inc., New York, NY (US)

( * ) Notice: Subject to any disclaimer, the term of this patent is extended or adjusted under 35 U.S.C. 154(b) by 0 days.

(21) Appl. No.: 16/669,421

(22) Filed: Oct. 30, 2019

(65) Prior Publication Data
US 2020/0140459 A1 May 7, 2020

Related U.S. Application Data

(60) Provisional application No. 62/870,022, filed on Jul. 2, 2019, provisional application No. 62/753,022, filed on Oct. 30, 2018.

(51) Int. Cl.
A61K 31/4412 (2006.01)
A61K 31/472 (2006.01)
C07D 211/40 (2006.01)
C07D 217/22 (2006.01)
C07D 513/04 (2006.01)
A61P 35/00 (2006.01)
C07D 213/89 (2006.01)
C07D 471/04 (2006.01)
C07D 239/36 (2006.01)
C07D 237/22 (2006.01)
C07D 239/90 (2006.01)
C07D 417/12 (2006.01)
C07D 401/12 (2006.01)
C07D 409/12 (2006.01)
C07D 411/10 (2006.01)
C07D 491/048 (2006.01)
C07D 495/04 (2006.01)
C07D 498/04 (2006.01)

(52) U.S. Cl.
CPC ............ C07D 513/04 (2013.01); A61P 35/00 (2018.01); C07D 213/89 (2013.01); C07D 237/22 (2013.01); C07D 239/36 (2013.01); C07D 239/90 (2013.01); C07D 401/12 (2013.01); C07D 409/12 (2013.01); C07D 411/10 (2013.01); C07D 417/12 (2013.01); C07D 471/04 (2013.01); C07D 491/048 (2013.01); C07D 495/04 (2013.01); C07D 498/04 (2013.01)

(58) Field of Classification Search
CPC ................ A61K 31/4412; A61K 31/472; C07D 211/40; C07D 217/22
USPC .................. 514/309, 345; 546/141, 290
See application file for complete search history.

(56) References Cited

U.S. PATENT DOCUMENTS

| | | |
|---|---|---|
| 9,050,346 B2 | 6/2015 | Hasvold |
| 9,115,114 B2 | 8/2015 | Bennett |
| 9,663,533 B2 | 5/2017 | Amans et al. |
| 10,034,881 B2 | 7/2018 | Amans |
| 10,035,800 B2 | 7/2018 | Fidanze |
| 10,053,454 B2 | 8/2018 | Poss |
| 10,059,699 B2 | 8/2018 | Atkinson |
| 10,077,259 B2 | 9/2018 | Samajdar |
| 10,253,044 B2 | 4/2019 | Wang |
| 10,292,968 B2 | 5/2019 | Brown |
| 10,307,407 B2 | 6/2019 | Wang |
| 10,328,074 B2 | 6/2019 | Engelhardt |
| 10,336,697 B2 | 7/2019 | Ujjinamatada |
| 10,336,722 B2 | 7/2019 | Bair |
| 10,363,257 B2 | 7/2019 | Quinn |
| 10,370,356 B2 | 8/2019 | Atkinson |
| 10,370,374 B2 | 8/2019 | Ibrahim |
| 10,377,769 B2 | 8/2019 | Bair |
| 10,391,175 B2 | 8/2019 | Wang |
| 10,633,379 B2 | 4/2020 | Hasvold et al. |
| 10,807,982 B2 | 10/2020 | Bennett et al. |
| 10,941,160 B2 | 3/2021 | Boloor |
| 2004/0067955 A1 | 4/2004 | Tabuchi |
| 2009/0093456 A1 | 4/2009 | Arnold |
| 2016/0318916 A1 | 11/2016 | Tanaka |
| 2017/0029418 A1 | 2/2017 | Kawasaki |
| 2017/0158709 A1 | 6/2017 | Boloor |
| 2018/0273547 A1 | 9/2018 | Boloor |

(Continued)

FOREIGN PATENT DOCUMENTS

| | | |
|---|---|---|
| AU | 2019205984 A1 | 8/2019 |
| CN | 110041253 A | 7/2019 |

(Continued)

OTHER PUBLICATIONS

Abedin, S.M. et al. (2016). "BET Inhibitors In The Treatment of Hematologic Malignancies: Current Insights and Future Prospects," OncoTargets and Therapy 9:5943-5953.

(Continued)

Primary Examiner — Douglas M Willis
(74) Attorney, Agent, or Firm — Morrison & Foerster LLP

(57) ABSTRACT

Novel bromodomain and extraterminal domain (BET) inhibitors containing substituted 2-pyridones and therapeutic methods of treating conditions and diseases using these novel BET inhibitors are provided.

25 Claims, 4 Drawing Sheets

(56) References Cited

U.S. PATENT DOCUMENTS

| | | |
|---|---|---|
| 2019/0247509 A1 | 8/2019 | Buckley et al. |
| 2019/0263799 A1 | 8/2019 | Brown |
| 2021/0002293 A1 | 1/2021 | Pham |

FOREIGN PATENT DOCUMENTS

| | | |
|---|---|---|
| EP | 3230277 B1 | 9/2019 |
| WO | 2013097052 A1 | 7/2013 |
| WO | 2013097601 A1 | 7/2013 |
| WO | 2014139324 A1 | 9/2014 |
| WO | 2014206150 A1 | 12/2014 |
| WO | 2014206345 A1 | 12/2014 |
| WO | 2015058160 A1 | 4/2015 |
| WO | 2017083431 A2 | 5/2017 |
| WO | 2017083431 A3 | 8/2017 |
| WO | 2017177955 A1 | 10/2017 |
| WO | 2018086604 A1 | 5/2018 |
| WO | 2019120234 A2 | 6/2019 |
| WO | 2019141131 A1 | 7/2019 |
| WO | 2019120234 A3 | 8/2019 |
| WO | 2020020288 A1 | 1/2020 |
| WO | 2020063976 A1 | 4/2020 |
| WO | 2020160193 A2 | 8/2020 |
| WO | 2020160193 A3 | 9/2020 |
| WO | 2020187123 A1 | 9/2020 |
| WO | 2020253711 A1 | 12/2020 |
| WO | 2021003310 A1 | 1/2021 |

OTHER PUBLICATIONS

Alqahtani, A. et al. (2019, e-pub. Jan. 29, 2019). "Bromodomain and Extra-Terminal Motif Inhibitors: A Review of Preclinical and Clinical Advances In Cancer Therapy," Future Science OA ISO372:1-19.

Andrieu, G. et al. (2016). "Clinical Trials For BET Inhibitors Run Ahead Of The Science," Drug Discovery Today: Technologies 19:45-50.

Asangani, I.A. et al. (Apr. 2016, e-pub. Jan. 20, 2016). "BET Bromodomain Inhibitors Enhance Efficacy and Disrupt Resistance to AR Antagonists in The Treatment of Prostate Cancer," Mo. Cancer Res. 14(4):324-331.

Asangani, I.A. et al. (Jun. 12, 2014). "Therapeutic Targeting of BET Bromodomain Proteins In Castration-Resistant Prostate Cancer," HHS Public Access Author Manuscript 510(7504):278-282, 44 pages.

Attwell, S. et al. (2015). "The Clinical Candidate ZEN-3694, a BET Bromodomain Inhibitor, is Efficacious in the Treatment of a Variety of Solid Tumor and Hematological Malignancies, Alone or in Combination With Several Standard of Care Therapies," Zenith Epigenetics, POSTER, 1 page.

Attwell, S. et al. (Jul. 2016). "Abstract LB-207: Preclinical Characterization of ZEN-3694, A Novel BET Bromodomain Inhibitor Entering Phase I Studies For Metastatic Castration-Resistance Prostate Cancer (mCRPC)," Cancer Research, 4 pages.

Attwell, S. et al. (Jul. 2016). "Abstract LB-207: Preclinical Characterization of ZEN-3694, A Novel BET Bromodomain Inhibitor Entering Phase I Studies For Metastatic Castration-Resistance Prostate Cancer (mCRPC)," Cancer Research, POSTER, 1 page.

Banerjee, C. et al. (2012). "BET Bromodomain Inhibition As a Novel Strategy For Reactivation of HIV-1," J. Leukocyte Biol. 92:1147-1154.

Bates, J. et al. (2016). "Combination of the BET Inhibitors GS-5829 and a BCL2 Inhibitor Resulted in Broader Activity in DLBCL and MCL Cell Lines," Blood 128,5104, 7 pages.

Bernasconi, E. et al. (2017, e-pub. Jun. 27, 2017). "Preclinical Evaluation of the BET Bromodomain Inhibitor BAY 1238097 For The Treatment of Lymphoma," British Journal of Haematology 178:936-948.

Bhattacharya, S. et al. (Jul. 2018). "Bromodomain Inhibitors: What Does the Future Hold?" Clinical Advances in Hematology & Oncolocy 16(7):504-515.

Boi, M. et al. (Apr. 1, 2015, e-pub. Jan. 26, 2015). "The BET Bromodomain Inhibitor OTX015 Affects Pathogenetic Pathways in Preclinical B-Cell Tumor Models and Synergizes With Targeted Drugs," Clinical Cancer Research 21 (7):1628-1638.

Boi, M. et al. (Oct. 25, 2016)."Therapeutic Efficacy of the Bromodomain Inhibitor OTX015/MK-8628 in ALK-Positive Anaplastic Large Cell Lymphoma: An Alternative Modality to Overcome Resistant Phenotypes," Oncotarget 7 (48):79637-79653.

Bui, M.H. et al. (Jun. 1, 2017). "Preclinical Characterization of BET Family Bromodomain Inhibitor ABBV-075 Suggests Combination Therapeutic Strategies," Cancer Research 77(11):2976-2989.

Cai, T. et al. (Jul. 2018). "Abstract LB-261: Targeting BET Family Bromodomain With ABBV-075 and BCL-2 With Venetoclax (ABT-199) Is Synergistic In Primary Acute Myeloid Leukemia Models," Cancer Research, 4 pages.

Carrà, G. et al. (2017). "BET Inhibitors In Chronic Lymphocytic Leukemia: JQ1 Synergizes With Venetoclax In Promoting Apoptosis," Blood 130:2542, 6 pages.

Chen, Y, et al. (Jun. 9, 2016, e-pub. Sep. 28, 2015). "Identification Of An Orally Available Compound With Potent and Broad FLT3 Inhibition Activity," Oncogene 35:2971-2978, 17 pages.

Conery, A.R. et al. (2016, e-pub. Jan. 12, 2016). "Preclinical Anticancer Efficacy of BET Bromodomain Inhibitors Is Determined By The Apoptotic Response," Cancer Research 76(6):1313-1319.

Da Costa, D. et al. (2013). "BET Inhibition as a Signal Or Combined Therapeutic Approach in Primary Pediatric B-Precursor Acute Lymphoblastic Leukemia," Blood Cancer Journal 3:e126, 11 pages.

Dawson, M.A. et al. (Jun. 12, 2013). "Inhibition of BET Recruitment to Chromatin as an Effective Treatment For MLL-Fusion Leukemia," Europe PMC Funders Group 478(7370):529-533.

Delmore, J.E. et al. (Sep. 16, 2011). "BET Bromodomain Inhibition as a Therapeutic Strategy to Target c-Myc," Cell 146:904-917.

Denis, G.V. (Dec. 2010). "Bromodomain Coactivators In Cancer, Obesity, Type 2 Diabetes, and Inflammation," Discovery Medicine 10(55):489-499, 17 pages.

Derenzini, E. et al. (Aug. 21, 2018). "BET Inhibition-Induced GSK3β Feedback Enhances Lymphoma Vulnerability to PI3K Inhibitors," Cell Reports 24:2155-2166, 37 pages.

Doroshow, D.B. et al. (2017, e-pub. Jul. 21, 2017). "BET Inhibitors: A Novel Epigenetic Approach," Annals of Oncology 28:1776-1787.

Du, Z. et al. (2018). "Genome-Wide Transcriptional Analysis of BRD4-Regulated Genes and Pathways in Human Glioma U251 Cells," International Journal of Oncology 52:1415-1426.

Esteve-Arenys, A. et al. (2018, e-pub. Jan. 22, 2018). "The BET Bromodomain Inhibitor CPI203 Overcomes Resistance to ABT-199 (Venetoclax) By Downregulation of BFLL-1/A1 in in vitro and in vivo Models of MYC+/BCL2+ Double Hit Lymphoma," Oncogene 19 pages.

Faivre, E.J. et al. (Jul. 2018). "Abstract 4960: First-ln-Class, Highly BDII-Selective BET Family Inhibitor ABBV-744 Displays Potent Anti-Tumor Activity in Androgen Receptor Positive Prostate Cancer Models and an Improved Tolerability Profile," Cancer Research, 4 pages.

Fidanze, S.D. et al. (2018, e-pub. Apr. 11, 2018). "Discovery and Optimization of Novel Constrained Pyrrolopyridone BET Family Inhibitors," Bioorganic & Medicinal Chemistry Letters 28:1804-1810.

Gaudio, E. et al. (Aug. 1, 2016). "Bromodomain Inhibitor OTX015 (MK-8628) Combined With Targeted Agents Shows Strong in vivo Antitumor Activity in Lymphoma," Oncotarget 7(36):58142-58147.

Gayle, S.S. et al. (2018, e-pub. Nov. 27, 2018). "Targeting BCL-xL Improves the Efficacy of Bromodomain and Extra-Terminal Protein Inhibitors in Triple-Negative Breast Cancer by Eliciting the Death of Senescent Cells," J. Biol Chem. 20 pages.

Gerlach, D. et al. (2018). "The Novel BET Bromodomain Inhibitor BI 894999 Represses Super-Enhancer-Associated Transcription and Synergizes With CDK9 Inhibition in AML," Oncogene 37:2687-2701.

Ghoshal, A. et al. (2016, e-pub. Feb. 29, 2016). "BET Inhibitors in Cancer Therapeutics: A Patent Review," Expert Opinion on Therapeutic Patents, 44 pages.

Gopalakrishnan, R. et al. (Apr. 7, 2016). "Immunomodulatory Drugs Target IKZF1-IRF4-MYC Axis in Primary Effusion Lym-

(56) References Cited

OTHER PUBLICATIONS phoma in a Cereblon-Dependent Manner and Display Synergistic Cytotoxicity With BRD4 Inhibitors," HHS Public Access Author Manuscript 34(14):1797-1810.
Gosmini, R. et al. (2014). "The Discovery of I-BET726 (GSK1324726A), A Potent Tetrahydroquinoline ApoA1 Up-Regulator and Selective BET Bromodomain Inhibitor," J. of Medicinal Chemistry, 21 pages.
Greene, T.W. et al. (1999). Protective Groups in Organic Synthesis, 3rd edition, Wiley.
Guo, Y, et al. (Dec. 6, 2012). "SU11652 Inhibits Tyrosine Kinase Activity of FLT3 and Growth of MV-4-11 Cells," J Hematol Oncol 5:72, 6 pages.
Hogg, S.J. et al. (Feb. 28, 2017). "BET-Bromodomain Inhibitors Engage the Host Immune System and Regulate Expression of the Immune Checkpoint Ligand PD-L1," Cell Reports 18:2162-2174.
Huang, B. et al. (Mar. 2009. e-pub. Dec. 22, 2008). "Brd4 Coactivates Transcriptional Activation of NF-ηB Via Specific Binding To Acetylated RelA," Mol. Cell. Biol. 29(5):1375-1387.
International Search Report and Written Opinion, dated Feb. 10, 2020, for PCT Application No. PCT/US2019/58952, filed Oct. 30, 2019, 12 pages.
Invitation to Pay Additonal Fees, dated Dec. 13, 2019, for PCT Application No. PCT/US2019/58952, filed Oct. 30, 2019, 4 pages.
Jang, M.K. et al. (Aug. 19, 2005). "The Bromodomain Protein Brd4 Is a Positive Regulatory Component of P-TEFb and Stimulates RNA Polymerase II-Dependent Transcription," Mol. Cell 19(4):523-534.
Jauset, T. et al. (2018). "BET Inhibition is an Effective Approach Against KRAS-Driven PDAC and NSCLC," Oncotarget 9(27):18734-18746.
Jin, X. et al. (Aug. 16, 2018). "DUB3 Promotes BET Inhibitor Resistance and Cancer Progression by Deubiquitinating BRD4," Molecular Cell 71:1-14.
Johnson-Farley, N. et al. (2014). "ABT-199, A Bh3 Mimetic That Specifically Targets Bci-2, Enhances the Antitumor Activity of Chemotherapy, Bortezomib, and JQ1 in 'Double Hit' Lymphoma Cells," Leukemia & Lymphoma, 12 pages.
Karakashev, S. et al. (Dec. 19, 2017). "BET Bromodomain Inhibition Synergizes With PARP Inhibitor in Epithelial Ovarian Cancer," Cell Reports 21:3308-3405.
Kati, W. (Apr. 15, 2018). "ABBV-744: A Highly BDII-Selective BET Bromodomain Inhibitor," AACR 2018, 23 pages.
Kharenko, O. et al. "Discovery and Characterization of Covalent BET Bromodomain Inhibitors," POSTER, 1 page, No Date.
Kharenko, O. et al. (2018). "Design and Characterization of Novel Covalent Bromodomain and Extra-Terminal Domain (BET) Inhibitors Targeting a Methionine," J. of Medicinal Chemistry, 44 pages.
Kim, S.R. et al. (2018). "BET Inhibition in Advanced Cutaneous T Cell Lymphoma is Synergistically Potentiated by BCL2 Inhibition or HDAC Inhibition," Oncotarget 9(49):29193-29207.
Lacasce, A.S. (Nov. 3, 2014). "Targeting Bromodomain Proteins in DLBCL," Hematologist 11(6):1-3.
Lam, L.T. et al. (2017, e-pub. May 3, 2017). "Vulnerability of Small-Cell Lung Cancer to Apoptosis Induced by the Combination of BET Bromodomain Proteins and BCL2 Inhibitors," Molecular Cancer Therapeutics 16(8):1-10.
Lasorsa, E. et al. (2015, e-pub. Dec. 10, 2015). "Mitochondrial Protection Impairs BET Bromodomain Inhibitor-Mediated Cell Death and Provides Rationale for Combination Therapeutic Strategies," Cell Death and Disease 6:e2014, 8 pages.
Liu, z. et al. (2018, e-pub. Apr. 3, 2018). "Discovery of Potent and Selective BRD4 Inhibitors Capable of Blocking TLR3-lnduced Acute Airway Inflammation," European Journal of Medicinal Chemistry 151:450-461.
Liu, Z. et al. (Feb. 14, 2017). "Drug Discovery Targeting Bromodomain-Containing Protein 4," J. of Medicinal Chemistry, 26 pages.
Lovén, J. et al. (Apr. 11, 2013). "Selective Inhibition Of Tumor Oncogenes By Disruption Of Super-Enhancers," Cell 153(2):320-334, 27 pages.

Lu, J. et al. (Jun. 18, 2015). "Hijacking the E3 Ubiquitin Ligase Cerebion to Efficiently Target BRD4," Chemistry & Biology 22:755-763.
Matzuk, M.M. et al. (Aug. 17, 2012). "Small-Molecule Inhibition of BRDT For Male Contraception," Cell 150(4):673-684.
McDaniel, K.F. et al. (Sep. 26, 2017). "Discovery of N-(2,4-Difluorophenoxy)-3-(6-methyl-7-oxo-6,y-dihydro-1H-pryrrolo[2,3-c]pyridin-4-yl)phenyl-ethaneesulfonamide (ABBV-075/Miverbresib). A Potent and Orally Available Bromodomain and Extra terminal Domain (BET) Family Bromodomain Inhibitor," J. of Medicinal Chemistry 60:8369-8384.
Mensah, A.A. et al. (2018, e-pub. (Aug. 3, 2018). "Bromodomain and Extra-Terminal Domain Inhibition Modulates the Expression of Pathologically Relevant MictroRNAs in Diffuse Large B-Cell Lymphoma," J. of the European Hematology Association, 21 pages.
Mertz, J.A. et al. (Oct. 4, 2011). "Targeting MYC Dependence in Cancer By Inhibiting BET Bromodomains," PNAS 108(40):16669-16674.
Middleton, S.A. et al. (2018, e-pub. Nov. 22, 2018). "BET Inhibition Improves NASH and Liver Fibrosis," Scientific Reports 8:17257, 13 pages.
Mottok, A. et al. (Jan. 1, 2015, e-puyb. Aug. 27, 2014). "Bromodomain Inhibition in Diffuse Large B-Cell Lymphoma-Giving MYC a Brake," Clinical Cancer Research 21(1):4-6, 4 pages.
Nicodeme, E. et al. (Dec. 23, 2010, e-pub. Nov. 10, 2010). "Suppression Of Inflammation By a Synthetic Histone Mimic," Nature 468(7327):1119-1123, 13 pages.
Nueuvolution (2016). "NUE7770—ABET-BD1 Selective Chemical Probe With Potent Cellular and in vivo Anti-Inflammatory Aclivily," 14th Discovery on Target, 18 pages.
Peirs, S. et al. (2017). "Targeting BET Proteins Improves the Therapeutic Efficacy of BCL-2 Inhibition in T-Cell Acute Lymphoblastic Leukemia," University of Zurich, 36 pages.
PubChem 86591759 (Feb. 2, 2015) "2-Chloro-5-(1-isopropyl-6-oxo-1,6-dihydro-3-pyridazinyl)-6-phenylnicotinonitrile," 9 pages.
PubChem CID: 53245731 (Jul. 17, 2011). "7-(4-Hydroxyphenyl)-Pyridin-4-YI-5h-Thieno[3,2-C]pyridin-4-One," 11 pages.
PubChem CID: 91668542 (Apr. 23, 2015). "7-(3,4-Dimethoxyphenyl_-5-methyl-2-(4-methylsulfonylpiperazine-1-carbonyl)thienol[3,2-c]pyridin-4-one," 11 pages.
Pérez-Salvia, M. et al. (2017). "Bromodomain Inhibitors and Cancer Therapy: From Structures to Applications," Epigenetics 12(5):323-339.
Ramadoss, M. et al. (Jan. 2018). "Targeting the Cancer Epigenome: Synergistic Therapy With Bromodomain Inhibitors," Drug Discovery Today 28(1):76-89.
Ramsey, H. et al. (Dec. 3, 2018). "4074—The BET Inhibitor INCB054329 Primes AML Cells for Venetoclas-Inducted Apoptosis," 616 Acute Myeloid Leukemia: Novel Therapy, Excluding Transplantation: Post III Hematology Disease Topics & Pathways, 2 pages.
Remington's Pharmaceutical Sciences, Mack Publishing Company, Philadelphia, PA, 21th ed. (2000) TOC, 4 Pages.
Rhyssen, G.W. et al. (Jul. 23, 2018). "BRD4 Amplification Facilities an Oncogenic Gene Expression Program in High-Grade Serous Ovarian Cancer and Confers Sensitivity to BET Inhibitors," PLOS One 13(7):e0200826, 23 pages.
Shah, N. et al. (Sep. 11, 2017). "Regulation of the Glucocorticoid Receptor Via a BET-Dependent Enhancer Drives Antiandrogen Resistance in Prostate Cancer," eLife 6:e27861, 19 pages.
Shimamura, T. et al. (2013, e-pub. Sep. 17, 2013). "Efficacy of BET Bromodomain Inhibition in Kras-Mutant Non-Small Cell Lung Cancer," Clinical Cancer Research, 37 pages.
Stubbs, M. et al. (Jul. 2016). "Abstract 3780: Activity of the BET Inhibitor INCB054329 in Models of Lymphoma," Cancer Research, 4 pages.
Sun, B. et al. (Sep. 24, 2015, e-pub. Aug. 7, 2015). "Synergistic Activity of BET Protein Antagonist-Based Combinations in Mantle Cell Lymphoma Cells Sensitive or Resistant to Ibrutinib," Blood 126(13):1565-1574.
Sun, C. et al. (Mar. 12, 2018). BRD4 Inhibition is Synthetic Lethal With PARP Inhibitors Through the Induction of Homologous Recombination Deficiency,: Cancer Cell 33:401-416, 25 pages.

(56) References Cited

OTHER PUBLICATIONS

Takimoto-Shimomura, T. et al. (2018, e-pub. Jun. 21, 2018). "Dual Targeting of Bromodomain-Containing 4 By AZD5153 and BCL2 By AZD4320 Against B-Cell Lymphomas Concomitantly Overexpressing c-MYC and BCL2," Investigational New Drugs, 13 pages.

Tan, Y. et al. (2018). "Inhibition of BRD4 Suppresses Tumor Growth in Prostate Cancer Via the Enhancement of FOXO1 Expression," International Journal of Oncology 53:2503-2517.

Taniguchi, Y. (2016). "The Bromodomain and Extra-Terminal Domain (BET) Family: Functional Anatomy of BET Paralogous Proteins," International J. of Molecular Sciences 17:1849, 24 pages.

Tarantelli, C. et al. (2018). "BET Bromodomain Inhibitor Birabresib in Mantle Cell Lymphoma: in vivo Activity and Identification of Novel Combinations to Overcome Adaptive Resistance," BMJ 3:e000387, 7 pages.

Tontsch-Grunt, U. et al. (2018). "Synergistic Activity of BET Inhibitor BI 894999 With PLK Inhibitor Volasertib in AML in vitro and in vivo," Cancer Letters 421:112-120.

Trabucco, S. E. et al. (2014, e-pub. Jul. 9, 2014). "Inhibition of Bromodomain Proteins For the Treatment of Human Diffuse Large B-Cell Lymphoma," Clinical Cancer Research 21(1):113-122.

Tsujikawa, L. et al. (Apr. 2017). "Abstract LB-038: Preclinical Development and Clinical Validation of a Whole Blood Pharmacodynamic Marker Assay for the BET Bromodomain Inhibitor ZEN-3694 in Metastatic Castration-Resistant Prostate Cancer (mCRPC) Patients," Cancer Research, POSTER, 2 pages.

U.S. Appl. No. 16/918,997, filed Jul. 1, 2020, for Pham et al. (Copy not submitted herewith pursuant to the waiver of 37 C.F.R. § 1 98(a)(2)(iii) issued by the Office on Sep. 21, 2004). (16.00).

Urbanucci, A. et al. (2018, e-pub. Jun. 15, 2017). "Bromodomain-Containing Proteins in Prostate Cancer," Molecular and Cellular Endocrinology 462:31-40.

Urbanucci, A. et al. (Jun. 6, 2017). "Androgen Receptor Deregulation Drives Bromodomain-Mediated Chromatin Alterations in Prostate Cancer," Cell Reports 19:2045-2049.

Villar-Prados, A. (2018). "Identifying Molecular Targets and Validating Novel Therapies For Ovarian Cancer," UT GSBS Dissertations and Theses (Open Access) 840, 127 pages.

Vis, D.J. et al. (May 2016, e-pub. May 16, 2016). "Multilevel Models Improve Precision and Speed Of IC50 Estimates," Pharmacogenomics 17(7):691-700, 14 pages.

Wahlestedt, C. et al. (Sep. 20, 2018). "PLX51107, A Promising Novel Bromodomain and Extra-Terminal Inhibitor in Chronic Lymphoid Leukemia Treatment," Precis. Cancer Med. 8:458-477.

Welti, J. et al. (2018, e-pub. Mar. 19, 2018). "Targeting Bromodomain and Extra-Terminal (BET) Family Proteins in Castration-Resistant Prostate Cancer (CRPC)," Clinical Cancer Research 24(13):3149-3162.

Wyce, A. et al. (2018). "MEK Inhibitors Overcome Resistance to BET Inhibition Across a Number of Solid and Hematologic Cancers," Oncogenesis 7:35, 12 pages.

Yang, L. et al. (Jul. 26, 2017). "Repression of BET Activity Sensitizes Homologous Recombination-Proficient Cancers to PARP Inhibition," Science Translational Medicine 9:eaal1645, 13 pages.

Zenith Epigenetics (Feb. 2019). "Zenith Epigenetic: Advanced Epigenetic Technology," 24 pages.

Zhang, G. et al. (Aug. 17, 2012, e-pub. May 29, 2012). "Down-Regulation Of NF-κB Transcriptional Activity In HIV-Associated Kidney Disease By BRD4 Inhibition," J. Biol. Chem. 287(34):28840-28851.

Zuber, J. et al. (2011). "RNAi Screen Identifies Brd4 as a Therapeutic Target in Acute Myeloid Leukemia," Nature, 8 pages.

International Preliminary Report on Patentability, dated Apr. 27, 2021, for PCT Application No. PCT/US2019/58952, filed Oct. 30, 2019, 7 pages.

SUBSTITUTED 1,6-DIHYDROPYRIDINONES AND 1,2-DIHYDROISOQUINOLINONES AS BET INHIBITORS

CROSS-REFERENCE TO RELATED APPLICATIONS

This application claims priority to U.S. Provisional Application No. 62/753,022, filed Oct. 30, 2018, and U.S. Provisional Application No. 62/870,022, filed Jul. 2, 2019, the contents of which are incorporated herein by reference in their entirety.

FIELD OF THE INVENTION

The present invention relates to novel bromodomain and extraterminal domain (BET) inhibitors and to therapeutic methods of treating conditions and diseases using these novel BET inhibitors.

BACKGROUND OF THE INVENTION

Epigenetic dysregulation has a crucial role in driving aberrant gene expressions leading to various types of cancers. Many components involved in epigenetic regulation have been attractive targets for therapeutic interventions. Among them, the bromodomain and extra-terminal (BET) family of proteins attracted much attention in recent years. The BET family proteins include BRD2, BRD3, BRD4, and the testis-specific BRDT. Via their bromodomains (BRDs), they bind with a high affinity to acetylation motifs, including acetylated histones in chromatin, thereby regulating gene transcription. The genes regulated by BET family proteins include many important oncogenes responsible for cell survival and cell cycle progression.

BET proteins are emerging targets in cancer, directly regulating the expression of oncogenes in hematological and solid tumors. BRD4, in addition to occupying gene promoters, has a strong preference for enhancers and super-enhancers in key driver genes such as c-MYC (Loven et al, Cell 2013; 153(2):320-34). BET family proteins have also been implicated in mediating acute inflammatory responses through the canonical NF-KB pathway (Huang et al., Mol. Cell. Biol. 29: 1375-1387 (2009)) resulting in the upregulation of genes associated with the production of cytokines (Nicodeme et al., Nature 468: 1119-1123, (2010)). In addition, bromodomain function has been implicated in kidney disease (Zhang, et al., J. Biol. Chem. 287: 28840-28851 (2012)). BRD2 function has also been linked to a predisposition for dyslipidemia or improper regulation of adipogenesis, elevated inflammatory profiles and increased susceptibility to autoimmune diseases (Denis, Discovery Medicine 10: 489-499 (2010)). The human immunodeficiency virus utilizes BRD4 to initiate transcription of viral RNA from stably integrated viral DNA (Jang et al., Mol. Cell, 19: 523-534 (2005)). BET bromodomain inhibitors have also been shown to reactivate HIV transcription in models of latent T cell infection and latent monocyte infection (Banerjee, et al., J. Leukocyte Biol. doi:10.1189/jlb.0312165). BRDT has an important role in spermatogenesis (Matzuk, et al., Cell 150: 673-684 (2012)).

Due to this potential as an epigenetic target, a number of small molecule compounds that inhibit the function of BET family proteins have been developed, and many of them have demonstrated promising anti-cancer activities with both solid and hematologic malignancies in preclinical studies. This has led to several early-phase clinical trials. Included among these are RO6870810 (formerly TEN-010), ZEN003694, BMS-986158, CPI-0610, I-BET762, OTX015, FT-1101, INCB054329, PLX51107, GS-5829, and ABBV-075. While these efforts are promising, there is need for better selectivity and improved durability of BET inhibitors that provide enhanced efficacy while reducing toxicity related to off-target effects. The present invention relates to novel BET inhibitors.

SUMMARY OF THE INVENTION

In one aspect, provided is a compound of Formula (I):

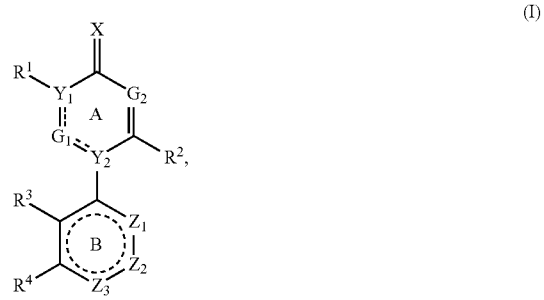

or a tautomer or isomer thereof, or a pharmaceutically acceptable salt of any of the foregoing, wherein X, $Y_1$, $Y_2$, $R^1$, $R^2$, $G_1$, $G_2$, $R^3$, $R^4$, ═══,

$Z_1$, $Z_2$ and $Z_3$ are as detailed herein.

In some embodiments, provided is a compound of Formula (Ia),

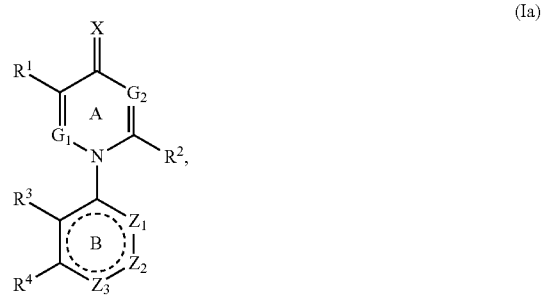

or a tautomer or isomer thereof, or a pharmaceutically acceptable salt of any of the foregoing, wherein X, $R^1$, $R^2$, $G_1$, $G_2$, $R^3$, $R^4$,

$Z_1$, $Z_2$ and $Z_3$ are as detailed herein.

In some embodiments, provided is a compound of Formula (Ib),

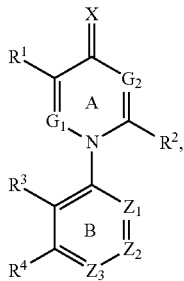

(Ib)

or a tautomer or isomer thereof, or a pharmaceutically acceptable salt of any of the foregoing, wherein X, $R^1$, $R^2$, $G_1$, $G_2$, $Z_1$, $Z_2$ and $Z_3$, $R^3$ and $R^4$ are as detailed herein.

In some embodiments, provided is a compound of Formula (Ic),

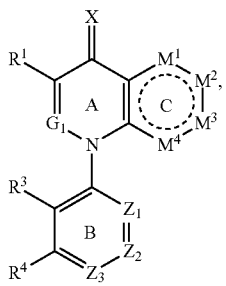

(Ic)

or a tautomer or isomer thereof, or a pharmaceutically acceptable salt of any of the foregoing, wherein X, $R^1$, $M^1$, $M^2$, $M^3$, $M^4$, $G_1$, $R^3$, $R^4$,

$Z_1$, $Z_2$ and $Z_3$ are as detailed herein.

In some embodiments, provided is a compound of Formula (II):

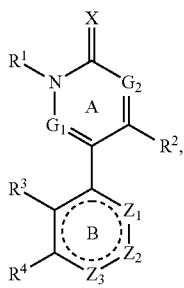

(II)

or a tautomer or isomer thereof, or a pharmaceutically acceptable salt of any of the foregoing, wherein X, $R^1$, $R^2$, $G_1$, $G_2$, $R^3$, $R^4$,

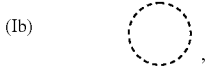

$Z_1$, $Z_2$ and $Z_3$ are as detailed herein.

In some embodiments, provided is a compound of Formula (III),

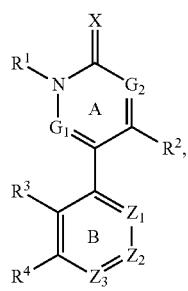

(III)

or a tautomer or isomer thereof, or a pharmaceutically acceptable salt of any of the foregoing, wherein X, $R^1$, $R^2$, $G_1$, $G_2$, $R^3$, $R^4$, $Z_1$, $Z_2$ and $Z_3$ are as detailed herein.

In some embodiments, provided is a compound of Formula (IV):

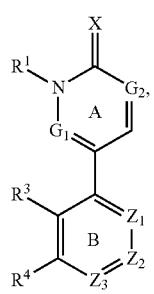

(IV)

or a tautomer or isomer thereof, or a pharmaceutically acceptable salt of any of the foregoing, wherein X, $R^1$, $G_1$, $G_2$, $R^3$, $R^4$, $Z_1$, $Z_2$ and $Z_3$ are as detailed herein.

In some embodiments, provided is a compound of Formula (V):

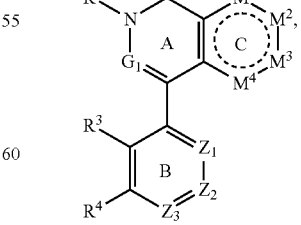

(V)

or a tautomer or isomer thereof, or a pharmaceutically acceptable salt of any of the foregoing, wherein X, $R^1$, $M^1$, $M^2$, $M^3$, $M^4$, $G^1$, $R^3$, $R^4$,

$Z_1$, $Z_2$ and $Z_3$ are as detailed herein.

In some embodiments, the compounds provided herein are BET inhibitors that selectively target and covalently bind the protein of interest. In some embodiments, the BET inhibitors comprise a compound of Formula (I), or any related formulae, such as (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') or (Ve-1 to Ve-5), or a tautomer or isomer thereof, or a pharmaceutically acceptable salt of any of the foregoing.

In some embodiments, the compounds provided herein are BET inhibitors that selectively target and covalently bind the protein of interest. In some embodiments, the BET inhibitors comprise a compound of the Formula (I), or any related formulae, such as (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') or (Ve-1 to Ve-5), or a tautomer or isomer thereof, or a pharmaceutically acceptable salt of any of the foregoing.

In some embodiments, provided herein is a pharmaceutical composition comprising a compound of Formula (I), or any related formulae, such as (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a tautomer or isomer thereof, or a pharmaceutically acceptable salt of any of the foregoing, in combination with at least one pharmaceutically acceptable carrier, diluent, or excipient.

In some embodiments, provided herein is a pharmaceutical composition comprising a compound of Formula (I), or any related formulae, such as (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a tautomer or isomer thereof, or a pharmaceutically acceptable salt of any of the foregoing, in combination with at least one pharmaceutically acceptable carrier, diluent, or excipient.

In some embodiments, use of a compound having the structure of Formula (I), or any related formulae, such as (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a tautomer or isomer thereof, or a pharmaceutically acceptable salt of any of the foregoing, for the manufacture of a medicament is provided.

In some embodiments, use of a compound having the structure of Formula (I), or any related formulae, such as (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a tautomer or isomer thereof, or a pharmaceutically acceptable salt of any of the foregoing, for the manufacture of a medicament is provided.

In some embodiments, provided herein is a method of treating a disease in an individual mediated by the BET family of proteins. In some embodiments, such method comprises administering to the subject an effective amount of a compound having the structure of Formula (I), or any related formulae, such as (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') or (Ve-1 to Ve-5), or a tautomer or isomer thereof, or a pharmaceutically acceptable salt of any of the foregoing, or a pharmaceutical composition comprising the same, at a frequency and for duration sufficient to provide a beneficial effect to the subject.

In some embodiments, provided herein is a method of treating a disease mediated by the BET family of proteins in an individual. In some embodiments, such method comprises administering to the subject an effective amount of a compound having the structure of Formula (I), or any related formulae, such as (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') or (Ve-1 to Ve-5), or a tautomer or isomer thereof, or a pharmaceutically acceptable salt of any of the foregoing, or a pharmaceutical composition comprising the same, at a frequency and for duration sufficient to provide a beneficial effect to the subject.

In some embodiments, provided herein are methods for treating or preventing disorders that are ameliorated by inhibition of BET. In some embodiments, such methods comprise of administering to the subject a therapeutically effective amount of a compound of Formula (I), or any related formulae, such as (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') or (Ve-1 to Ve-5), or a tautomer or isomer thereof, or a pharmaceutically acceptable salt of any of the foregoing, alone, or in combination with a pharmaceutically acceptable carrier.

In some embodiments, provided herein are methods for treating or preventing disorders that are ameliorated by inhibition of BET. In some embodiments, such methods comprise of administering to the subject a therapeutically effective amount of a compound of Formula (I), or any related formulae, such as (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') or (Ve-1 to Ve-5), or a tautomer or isomer thereof, or a pharmaceutically acceptable salt of any of the foregoing, alone, or in combination with a pharmaceutically acceptable carrier.

In another aspect, the methods are directed to methods of treating or preventing an inflammatory disease or cancer or AIDS. In some embodiments, such methods comprise of administering to the subject a therapeutically effective amount of a compound of Formula (I), or any related formulae, such as (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') or (Ve-1 to Ve-5), or a tautomer or isomer thereof, or a pharmaceutically acceptable salt of any of the foregoing, alone, or in combination with a pharmaceutically acceptable carrier.

In another aspect, the methods are directed to methods of treating or preventing an inflammatory disease or cancer or AIDS. In some embodiments, such methods comprise of administering to the subject a therapeutically effective amount of a compound of Formula (I), or any related formulae, such as (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') or (Ve-1 to Ve-5), or a tautomer or isomer thereof, or a pharmaceutically acceptable salt of any of the foregoing, alone, or in combination with a pharmaceutically acceptable carrier.

In another aspect, provided herein is the use of a compound of Formula (I), or any related formulae, such as (Ia), (Ia-1 to Ia-12), (Ib), (Ib-1 to Ib-4), (Ic), (Ic-1 to Ic-19), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') or (Ve-1 to Ve-5), or a tautomer or isomer thereof, or a pharmaceutically acceptable salt of any of the foregoing, alone or in combination with a second active pharmaceutical agent, in the manufacture of a medicament for treating or preventing conditions and disorders disclosed herein, with or without a pharmaceutically acceptable carrier.

In another aspect, provided herein is the use of a compound of Formula (I), or any related formulae, such as (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') or (Ve-1 to Ve-5), or a tautomer or isomer thereof, or a pharmaceutically acceptable salt of any of the foregoing, alone or in combination with a second active pharmaceutical agent, in the manufacture of a medicament for treating or preventing conditions and disorders disclosed herein, with or without a pharmaceutically acceptable carrier.

In another aspect, a method of synthesis is provided for a compound having the structure of Formula (I), or any related formulae, such as (Ia), (Ia-1 to Ia-12), (Ib), (Ib-1 to Ib-4), (Ic), (Ic-1 to Ic-19), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') or (Ve-1 to Ve-5), or a tautomer or isomer thereof, or a pharmaceutically acceptable salt of any of the foregoing, as detailed herein.

In another aspect, a method of synthesis is provided for a compound having the structure of Formula (I), or any related formulae, such as (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') or (Ve-1 to Ve-5), or a tautomer or isomer thereof, or a pharmaceutically acceptable salt of any of the foregoing, as detailed herein.

DETAILED DESCRIPTION OF THE INVENTION

Definitions

Figure 1:
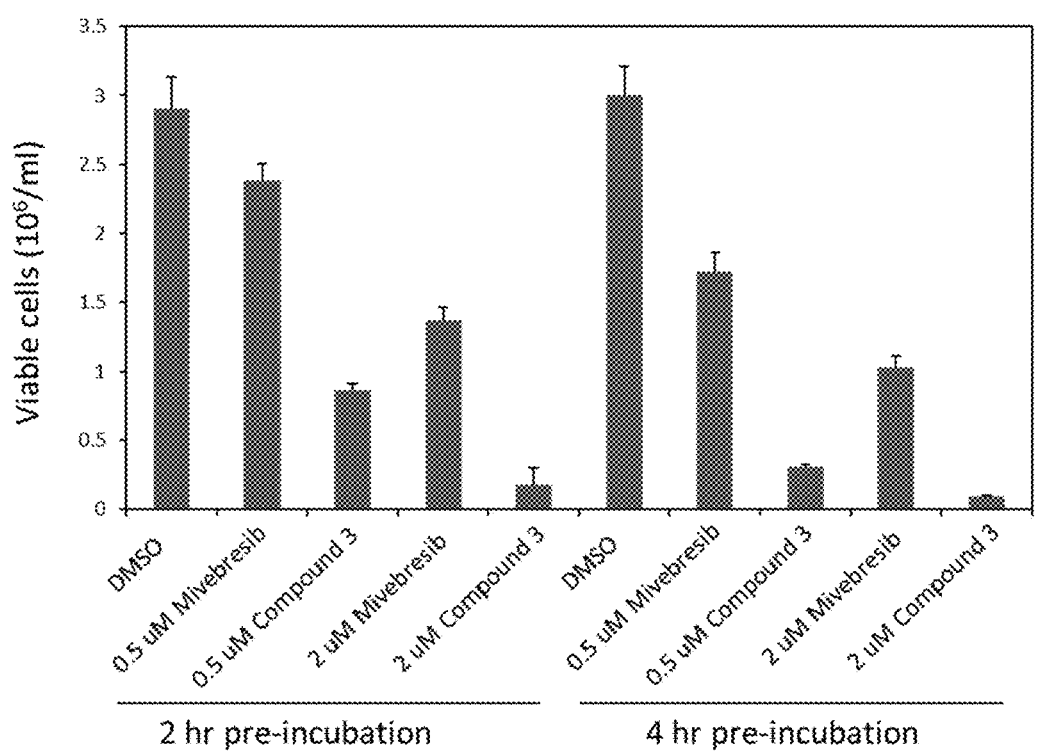
FIG. 1 illustrates the results of cell viability assays in which MV4-11 cells were incubated with compound for 2 or 4 hr followed by wash-off of the compound and re-plating of the cells.

"Alkyl" refers to and includes saturated linear and branched univalent hydrocarbon structures and combination thereof, having the number of carbon atoms designated (i.e., $C_1$-$C_{10}$ means one to ten carbons). Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"). Examples of alkyl include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). The alkenyl group may be in "cis" or "trans" configurations, or alternatively in "E" or "Z" configurations. Particular alkenyl groups are those having 2 to 20 carbon atoms (a "$C_2$-$C_{20}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

"Alkylene" as used herein refers to the same residues as alkyl but having bivalency. Particular alkylene groups are those having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), butylene (—$CH_2CH_2CH_2CH_2$—), and the like.

"Alkynyl" as used herein refers to an unsaturated linear or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "C2-$C_4$ alkynyl"). Examples of alkynyl include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Aryl" refers to and includes polyunsaturated aromatic hydrocarbon groups. Aryl may contain additional fused rings (e.g., from 1 to 3 rings), including additionally fused aryl, heteroaryl, cycloalkyl, and/or heterocyclyl rings. In one variation, the aryl group contains from 6 to 14 annular carbon atoms. Examples of aryl groups include, but are not limited to, phenyl, naphthyl, biphenyl, and the like.

"Carbonyl" refers to the group C=O.

"Cycloalkyl" refers to and includes cyclic univalent hydrocarbon structures, which may be fully saturated, mono- or polyunsaturated, but which are non-aromatic, having the number of carbon atoms designated (e.g., $C_1$-$C_{10}$ means one to ten carbons). Cycloalkyl can consist of one ring, such as cyclohexyl, or multiple rings, such as adamantyl, but excludes aryl groups. A cycloalkyl comprising more than one ring may be fused, spiro or bridged, or combinations thereof. A preferred cycloalkyl is a cyclic hydrocarbon having from 3 to 13 annular carbon atoms. A more preferred cycloalkyl is a cyclic hydrocarbon having from 3 to 8 annular carbon atoms (a "$C_3$-$C_8$ cycloalkyl"). Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like.

"Halo" or "halogen" refers to elements of the Group 17 series having atomic number 9 to 85. Preferred halo groups include fluoro, chloro, bromo and iodo. Where a residue is substituted by more than one halogen, it may be referred to by using a prefix corresponding to the number of halogen moieties attached, e.g., dihaloaryl, dihaloalkyl, trihaloaryl etc. refer to aryl and alkyl substituted by two ("di") or three ("tri") halo groups, which may be but are not necessarily the same halo; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. A heteroaryl group can be attached to the remainder of the molecule at an annular carbon or at an annular heteroatom. Heteroaryl may contain additional fused rings (e.g., from 1 to 3 rings), including additionally fused aryl, heteroaryl, cycloalkyl, and/or heterocyclyl rings. Examples of heteroaryl groups include, but are not limited to, pyridyl, pyrimidyl, pyridazinyl, thiophenyl, furanyl, thiazolyl, pyrrolyl, pyrazolyl, oxazolyl, isooxazolyl, imidazolyl, quinolyl, isoquinolyl, benzimidazolyl, benzpyrazolyl, benzotriazolyl, indole, benzothiazyl, benzoxazolyl, benzisoxazolyl, imidazopyridinyl and the like.

"Heterocycle" or "heterocyclyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl or heteroaryl. Examples of heterocyclyl groups include, but are not limited to, tetrahydropyranyl, dihydropyranyl, piperidinyl, piperazinyl, pyrrolidinyl, thiazolinyl, thiazolidinyl, tetrahydrofuranyl, dihydrooxazolyl, dihydroisoxazolyl, dioxolanyl, morpholinyl, dioxanyl, tetrahydrothiophenyl, and the like.

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same of different. In some embodiments, the substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocycloalkyl, hydroxyl, hydrazino, imino, oxo, nitro, alkylsulfinyl, sulfonic acid, alkylsulfonyl, thiocyanate, thiol, and thione. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 2 to 5, 3 to 5, 2 to 3, 2 to 4, 3 to 4, 1 to 3, 1 to 4 or 1 to 5 substituents.

Term "BET" refers to bromodomain and extraterminal domain family.

As used herein "BRD" refers to one or more bromodomain extraterminal domain family proteins (BRD2, BRD3, BRD4, and BRDT).

"Disease" specifically includes any unhealthy condition of an animal or part thereof. "Optional" or "optionally" means that the subsequently described event or circumstance may or may not occur, and that the description includes instances where the event or circumstance occurs and instances in which it does not.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary-butylacetic acid, lauryl sulfuric acid, gluconic acid, glutamic acid, hydroxynaphthoic acid, salicylic acid, stearic acid, muconic acid, and the like.

In addition, pharmaceutically acceptable salts may be formed when an acidic proton present is capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Therapeutically effective amount" means that amount which, when administered to an animal for treating a disease, is sufficient to affect such treatment for the disease.

"Treating" or "treatment" of a disease includes: (1) preventing the disease from occurring in an animal which may be predisposed to the disease but does not yet experience or display symptoms of the disease; (2) inhibiting the disease, i.e., arresting its development; or (3) relieving the disease, i.e., causing regression of the disease.

Compounds that have identical molecular formulae but differ in the nature or sequence of bonding of their atoms or in the arrangement of their atoms in space are termed "isomers." Isomers that differ in the nature or sequence of bonding of their atoms are termed "constitutional isomers." Isomers that differ only in the arrangement of their atoms in space are termed "stereoisomers." Stereoisomers that are not mirror images of one another are termed "diasteromers" and stereoisomers that are mirror images are termed "enantiomers" or sometimes "optical isomers." Stereoisomers that are superimposable upon their mirror images are termed "achiral" and those not superimposable are termed "chiral." A carbon atom bonded to four different groups is termed a "chiral center" or alternatively an "asymmetric carbon."

When a compound has a chiral center, a pair of enantiomers of opposite chirality is possible. An enantiomer can be characterized by the absolute configuration of its chiral center and described by the R- and S-sequencing rules of Cahn and Prelog (i.e., as (R)- and (S)-isomers) or by the manner in which the molecule rotates the plane of polarized light and designated as dextrorotatory or levorotatory (i.e., as (+)- and (−)-isomers, respectively). A chiral compound can exist as either individual enantiomer or as a mixture thereof. A mixture containing equal proportions of the enantiomers is termed a "racemic mixture" or "racemate" and may be described as the (RS)- or (±)-mixture thereof. Unless indicated otherwise, the description or naming of a particular compound in the specification and claims is intended to include both individual enantiomers and mixtures, racemic or otherwise, thereof. Conventions for stereochemical nomenclature, methods for the determination of stereochemistry and the separation of stereoisomers are well-known in the art (see discussion in Chapter 4 of "Advanced Organic Chemistry", 3rd edition March, Jerry, John Wiley and Sons, New York, 1985).

Compounds

In one aspect, provided is a compound of Formula (I):

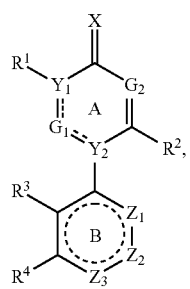

(I)

or a tautomer or isomer thereof, or a pharmaceutically acceptable salt of any of the foregoing, wherein:

X is O or S;

$Y_1$ is N or C;

$Y_2$ is N or C, provided that
  (1) at least one of $Y_1$ and $Y_2$ is N, and
  (2) when both $Y_1$ and $Y_2$ are N, then $G_1$ is $CR^a$ or $CHR^a$;

each ≡≡≡ is independently a single bond or a double bond, provided that
  (i) when $Y_2$ is N and $Y_1$ is C, then the ≡≡≡ between $G_1$ and $Y_1$ is a double bond and the ≡≡≡ between $G_1$ and $Y_2$ is a single bond,
  (ii) when $Y_1$ is N and $Y_2$ is C, then the ≡≡≡ between $G_1$ and $Y_1$ is a single bond and the ≡≡≡ between $G_1$ and $Y_2$ is a double bond, and
  (iii) when both $Y_1$ and $Y_2$ are N, then the ≡≡≡ between $G_1$ and $Y_1$ and the ≡≡≡ between $G_1$ and $Y_2$ are both single bonds;

$R^1$ is hydrogen, cyano, halogen, $C_1$-$C_4$ haloalkyl, $C_1$-$C_4$ alkoxy, $C_1$-$C_4$ alkyl optionally substituted by —OH, $C_3$-$C_6$ cycloalkyl optionally substituted by $C_1$-$C_6$ alkyl, —$(CH_2)_m N(R^f)W_3 R^g$, —$(CH_2)_m N(R^f) C(O)OR^h$, or —$(CH_2)_m W_3 R^g$, provided that when $Y_1$ is N and $G_1$ is N, then $R^1$ is cyano, halogen, $C_1$-$C_4$ haloalkyl, $C_1$-$C_4$ alkoxy, $C_1$-$C_4$ alkyl optionally substituted by —OH, $C_3$-$C_6$ cycloalkyl optionally substituted by $C_1$-$C_6$ alkyl, —$(CH_2)_m N(R^f) W_3 R^g$, —$(CH_2)_m N(R^f) C(O)OR^h$, or —$(CH_2)_m W_3 R^g$;

$G_1$ is $CR^a$, $CHR^a$ or N, wherein:
  $R^a$ is hydrogen, halogen, or $C_1$-$C_4$ alkyl;

$G_2$ is $CR^b$ or N, wherein:
  $R^b$ is hydrogen, halogen, cyano, $C_1$-$C_4$ alkyl, $C_3$-$C_6$ cycloalkyl, 3- to 6-membered heterocyclyl, $C_1$-$C_4$ haloalkyl, $C_1$-$C_4$ alkoxy, $C_1$-$C_4$ haloalkoxy, —$OR^{10}$, —$NR^{10}R^{11}$, —$C(O)NR^{10}R^{11}$, —$NR^{10}C(O)R^{11}$, —$S(O)_2R^{10}$, —$NR^{10}S(O)_2R^{11}$, or —$S(O)_2NR^{10}R^{11}$;

$R^2$ is hydrogen, halogen, cyano, $C_1$-$C_4$ alkyl, $C_3$-$C_6$ cycloalkyl, 3- to 6-membered heterocyclyl, $C_1$-$C_4$ haloalkyl, $C_1$-$C_4$ alkoxy, $C_1$-$C_4$ haloalkoxy, —$NR^{10}R^{11}$, —$C(O)NR^{10}R^{11}$, —$NR^{10}C(O)R^{11}$, —$S(O)_2R^{10}$, —$NR^{10}S(O)_2R^{11}$, or —$S(O)_2NR^{10}R^{11}$, or $R^b$ and $R^2$ are taken together with the atoms to which they are attached to form a 5- or 6-membered C ring, which is optionally substituted by $R^5$, wherein each $R^5$ is independently halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{10}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is optionally substituted by $R^{12}$;

indicates a saturated, partially unsaturated or fully unsaturated ring;

$Z_1$ is CH—$W_1$—$R^c$, C—$W_1$—$R^c$, C=O, $NR^c$, or N, wherein:
  each $W_1$ is independently —O—, —$NR^{w1}$—, or a bond, wherein:
    $R^{w1}$ is hydrogen, $C_3$-$C_6$ cycloalkyl, or $C_1$-$C_4$ alkyl optionally substituted by oxo, —OH, or halogen, and
  each $R^c$ is independently hydrogen, halogen, cyano, $C_1$-$C_4$ alkyl, $C_3$-$C_6$ cycloalkyl, $C_1$-$C_4$ haloalkyl, 3- to 6-membered heterocyclyl, $C_6$-$C_{14}$ aryl, or 5- to 6-membered heteroaryl, wherein $C_3$-$C_6$ cycloalkyl, 3- to 6-membered heterocyclyl, $C_6$-$C_{14}$ aryl, and 5- to 6-membered heteroaryl of $R^c$ are independently optionally substituted by $R^{c1}$, wherein each $R^{c1}$ is independently halogen, $C_1$-$C_4$ alkyl, $C_3$-$C_6$ cycloalkyl, 3- to 6-membered heterocyclyl, cyano, oxo, $C_1$-$C_4$ alkoxy, $C_1$-$C_4$ haloalkoxy, $C_1$-$C_4$ haloalkyl, —$OR^{10}$, —$NR^{10}R^{11}$, —$C(O)NR^{10}R^{11}$, —$NR^{10}C(O)R^{11}$, —$S(O)_2R^{10}$, —$NR^{10}S(O)_2R^{11}$, or —$S(O)_2NR^{10}R^{11}$;

$Z_2$ is CH—$W_2$—$R^d$, C—$W_2$—$R^d$, C=O, $NR^d$, or N, wherein:

each $W_2$ is independently —O—, —$NR^{w2}$—, or a bond, wherein:

$R^{w2}$ is hydrogen, $C_3$-$C_6$ cycloalkyl, or $C_1$-$C_4$ alkyl optionally substituted by oxo, —OH, or halogen, and each $R^d$ is independently hydrogen, 3- to 6-membered heterocyclyl, or $C_1$-$C_4$ alkyl;

or $R^c$ and $R^d$ are taken together with the atoms to which they are attached to form a 5- or 6-membered D ring, which is optionally substituted by $R^6$, wherein each $R^6$ is independently halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)NR^{10}R^{11}$, —$NR^{10}C(O)R^{11}$, —$S(O)_2R^{10}$, —$NR^{10}S(O)_2R^{11}$, or —$S(O)_2NR^{10}R^{11}$, each of which is optionally substituted by $R^{12}$;

$Z_3$ is CH—$R^e$, C—$R^e$, C=O, $NR^e$, or N, wherein:

each $R^e$ is independently hydrogen, halogen, cyano, 3- to 6-membered heterocyclyl, or $C_1$-$C_4$ alkyl, provided that (1) when $Z_2$ is C=O, then $Z_3$ is $NR^e$, (2) when $Z_3$ is C=O, then $Z_2$ is $NR^d$, and (3) no more than two of $Z_1$, $Z_2$, and $Z_3$ are N;

$R^3$ and $R^4$ are each independently hydrogen, halogen, cyano, $C_1$-$C_4$ haloalkyl, $C_1$-$C_4$ alkoxy, $C_1$-$C_4$ haloalkoxy, —$OR^{13}$, —$NR^{13}R^{14}$, —$C(O)NR^{13}R^{14}$, —$NR^{13}C(O)R^{14}$, —$NR^{13}C(O)NR^{13}R^{14}$, —$S(O)_2R^{13}$, —$NR^{13}S(O)_2R^{14}$, —$NR^{13}S(O)_2NR^{13}R^{14}$, —$S(O)_2NR^{13}R^{14}$, —$(CH_2)_mN(R^f)W_3R^g$, —$(CH_2)_mN(R^f)C(O)OR^h$, —$(CH_2)_mW_3R^g$, or $C_1$-$C_4$ alkyl optionally substituted by halogen, oxo, —CN or —OH, provided that (a) when $Y_2$ is C, then at least one of $R^1$, $R^3$ and $R^4$ is —$(CH_2)_mN(R^f)W_3R^g$, —$(CH_2)_mN(R^f)C(O)OR^h$, or —$(CH_2)_mW_3R^g$, and (b) when $Y_2$ is N, then (i) at least one of $R^1$, $R^3$ and $R^4$ is —$(CH_2)_mN(R^f)W_3R^g$, —$(CH_2)_mN(R^f)C(O)OR^h$, or —$(CH_2)_mW_3R^g$, or (ii) $R^4$ is halogen, cyano, $C_1$-$C_4$ haloalkyl, $C_1$-$C_4$ alkoxy, $C_1$-$C_4$ haloalkoxy, —$OR^{13}$, —$NR^{13}R^{14}$, —$C(O)NR^{13}R^{14}$, —$NR^{13}C(O)R^{14}$, —$NR^{13}C(O)NR^{13}R^{14}$, —$S(O)_2R^{13}$, —$NR^{13}S(O)_2R^{14}$, $NR^{13}S(O)_2NR^{13}R^{14}$, —$S(O)_2NR^{13}R^{14}$, —$(CH_2)_mN(R^f)W_3R^g$, —$(CH_2)_mN(R^f)C(O)OR^h$, —$(CH_2)_mW_3R^g$, or $C_1$-$C_4$ alkyl optionally substituted by halogen, oxo, —CN or —OH, and $Z^1$ is CH—$W_1$—$R^c$ or C—$W_1$—$R^c$, wherein $W_1$ is —O— or —$NR^{w1}$— and $R^c$ is $C_3$-$C_6$ cycloalkyl, 3- to 6-membered heterocyclyl, phenyl, or 5- to 6-membered heteroaryl, each of which is optionally substituted by $R^d$;

each m is independently 0, 1, 2, 3, or 4;

$R^f$ is hydrogen, $C_1$-$C_4$ alkyl, or $C_3$-$C_6$ cycloalkyl;

$W_3$ is —C(O)— or —$S(O)_2$—;

$R^g$ is —$CR^{g1}$=$CHR^{g2}$ or —C≡$CR^{g2}$, wherein $R^g$ and $R^{g2}$ are each independently hydrogen, cyano, or $C_1$-$C_4$ alkyl optionally substituted by —OH, —$OCH_3$, —$NH_2$, —$NHCH_3$, or —$N(CH_3)_2$, or for $R^4$, when $R^4$ is —$(CH_2)_mN(R^f)W_3R^g$ and m is 0, the N, $R^f$, $W_3$ and $R^g$ in —$N(R^f)W_3R^g$ may be taken together to form a 5- or 6-membered ring having at least one double bond and optionally substituted by R, wherein each R is independently $C_1$-$C_4$ alkyl, oxo, halogen, or —CN;

$R^h$ is $C_1$-$C_6$ alkyl or $C_3$-$C_6$ cycloalkyl;

$R^{10}$ and $R^{11}$ are each independently hydrogen, $C_1$-$C_4$ alkenyl, $C_3$-$C_6$ cycloalkyl, 3- to 6-membered heterocyclyl, ($C_1$-$C_3$ alkylene)$C_3$-$C_6$ cycloalkyl, ($C_1$-$C_3$ alkylene)$_3$- to 6-membered heterocyclyl, $C(O)R^{12}$, or $C_1$-$C_4$ alkyl optionally substituted by halogen, oxo, —CN, —OH, —$NR^{13}R^{14}$, or —$C(O)NR^{13}R^{14}$ or $R^{10}$ and $R^{11}$ are taken together with the atoms to which they are attached to form a 3- to 6-membered heterocyclyl optionally substituted by halogen, oxo, —CN, —OH, or $C_1$-$C_4$ alkyl optionally substituted by halogen, oxo, —CN, or —OH;

each $R^{12}$ is independently halogen, $C_3$-$C_6$ cycloalkyl, 3- to 6-membered heterocyclyl, or $C_1$-$C_4$ alkyl optionally substituted by halogen, oxo, —CN, —OH, —$NR^{13}R^{14}$ or —$NR^{13}C(O)R^{14}$;

$R^{13}$ and $R^{14}$ are independently hydrogen, $C_3$-$C_6$ cycloalkyl, 3- to 6-membered heterocyclyl, or $C_1$-$C_4$ alkyl optionally substituted by halogen, oxo, —CN, or —OH, or $R^{13}$ and $R^{14}$ are taken together with the atoms to which they are attached to form a 3- to 6-membered heterocyclyl ring optionally substituted by halogen, oxo, —CN, —OH, or $C_1$-$C_4$ alkyl optionally substituted by halogen, oxo, —CN, or —OH.

In some embodiments, provided is a compound of Formula (I):

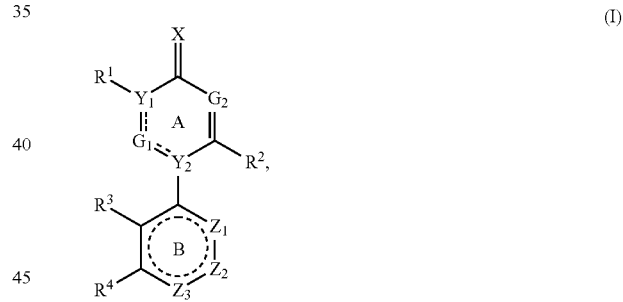

(I)

or a tautomer or isomer thereof, or a pharmaceutically acceptable salt of any of the foregoing, wherein:

X is O or S;

$Y_1$ is N or C;

$Y_2$ is N or C, provided that (1) at least one of $Y_1$ and $Y_2$ is N, and (2) when both $Y_1$ and $Y_2$ are N, then $G_1$ is $CR^a$ or $CHR^a$;

each ═══ is independently a single bond or a double bond, provided that (i) when $Y_2$ is N and $Y_1$ is C, the ═══ between $G_1$ and $Y_1$ is a double bond and the ═══ between $G_1$ and $Y_2$ is a single bond, (ii) when $Y_1$ is N and $Y_2$ is C, the ═══ between $G_1$ and $Y_1$ is a single bond and the ═══ between $G_1$ and $Y_2$ is a double bond, and (iii) when both $Y_1$ and $Y_2$ are N, the ═══ between $G_1$ and $Y_1$ and the ═══ between $G_1$ and $Y_2$ are both single bonds;

$R^1$ is hydrogen, $C_1$-$C_4$ alkyl, $C_3$-$C_6$ cycloalkyl, —$(CH_2)_mN(R^f)W_3R^g$ or —$(CH_2)_mW_3R^g$, provided that when $Y^1$ is N and $G^1$ is N, $R^1$ is $C_1$-$C_4$ alkyl, $C_3$-$C_6$ cycloalkyl, —$(CH_2)_mN(R^f)W_3R^g$ or —$(CH_2)_mW_3R^g$;

$G_1$ is $CR^a$, $CHR^a$ or N, wherein:
  $R^a$ is hydrogen, halogen or $C_1$-$C_4$ alkyl;

$G_2$ is $CR^b$ or N, wherein:
  $R^b$ is hydrogen, halogen, cyano, $C_1$-$C_4$ alkyl, $C_3$-$C_6$ cycloalkyl, 3- to 6-membered heterocyclyl, $C_1$-$C_4$ haloalkyl, $C_1$-$C_4$ alkoxy, $C_1$-$C_4$ haloalkoxy, —$OR^{10}$, —$NR^{10}R^{11}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$;

$R^2$ is hydrogen, halogen, cyano, $C_1$-$C_4$ alkyl, $C_3$-$C_6$ cycloalkyl, 3- to 6-membered heterocyclyl, $C_1$-$C_4$ haloalkyl, $C_1$-$C_4$ alkoxy, $C_1$-$C_4$ haloalkoxy, —$OR^{10}$, —$NR^{10}R^{11}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, or $R^b$ and $R^2$ are taken together with the atoms to which they are attached to form a 5- or 6-membered C ring, which is optionally substituted with $R^5$, wherein each $R^5$ is independently hydrogen, halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{10}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is optionally substituted with $R^{12}$;

indicates a saturated, partially unsaturated or fully unsaturated ring;

$Z_1$ is CH—$W_1$—$R^c$, C—$W_1$—$R^c$, C=O, $NR^c$, or N, wherein:
  each $W_1$ is independently —O—, —$NR^{w1}$—, or a bond, wherein:
    $R^{w1}$ is hydrogen, $C_3$-$C_6$ cycloalkyl or $C_1$-$C_4$ alkyl optionally substituted with oxo, —OH or halogen, and
  each $R^c$ is independently hydrogen, halogen, cyano, $C_1$-$C_4$ alkyl, $C_3$-$C_6$ cycloalkyl, $C_1$-$C_4$ haloalkyl, 3- to 6-membered heterocyclyl, $C_6$-$C_{14}$ aryl, or 5- to 6-membered heteroaryl, wherein $C_3$-$C_6$ cycloalkyl, 3- to 6-membered heterocyclyl, $C_6$-$C_{14}$ aryl, and 5- to 6-membered heteroaryl of $R^c$ are independently optionally substituted with $R^{c}d$, wherein each $R^{c1}$ is independently halogen, $C_1$-$C_4$ alkyl, $C_3$-$C_6$ cycloalkyl, 3- to 6-membered heterocyclyl, cyano, oxo, $C_1$-$C_4$ alkoxy, $C_1$-$C_4$ haloalkoxy, $C_1$-$C_4$ haloalkyl, —$OR^{10}$, —$NR^{10}R^{11}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$;

$Z_2$ is CH—$W_2$—$R^d$, C—$W_2$—$R^d$, C=O, $NR^d$, or N, wherein:
  each $W_2$ is independently —O—, —$NR^{w2}$—, or a bond, wherein:
    $R^{w2}$ is hydrogen, $C_3$-$C_6$ cycloalkyl or $C_1$-$C_4$ alkyl optionally substituted with oxo, OH or halogen, and
  each $R^d$ is independently hydrogen or $C_1$-$C_4$ alkyl;
  or $R^c$ and $R^d$ are taken together with the atoms to which they are attached to form a 5- or 6-membered D ring, which is optionally substituted with $R^6$, wherein each $R^6$ is independently hydrogen, halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is optionally substituted with $R^{12}$;

$Z_3$ is CH—$R^e$, C—$R^e$, C=O, $NR^e$, or N, wherein:
  each $R^e$ is independently hydrogen, halogen, cyano or $C_1$-$C_4$ alkyl,
  provided that
    (1) when $Z_2$ is C=O, $Z_3$ is $NR^e$,
    (2) when $Z_3$ is C=O, $Z_2$ is $NR^d$, and
    (3) no more than two of $Z_1$, $Z_2$ and $Z_3$ are N;

$R_3$ and $R_4$ are each independently hydrogen, halogen, cyano, $C_1$-$C_4$ haloalkyl, $C_1$-$C_4$ alkoxy, $C_1$-$C_4$ haloalkoxy, —$OR^{13}$, —$NR^{13}R^{14}$, —$C(O)NR^{13}R^{14}$, —$NR^{13}C(O)R^{14}$, —$S(O)_2R^{13}$, —$NR^{13}S(O)_2R^{14}$, —$S(O)_2NR^{13}R^{14}$, —$(CH_2)_mN(R^f)W_3R^g$, —$(CH_2)_mW_3R^g$, or $C_1$-$C_4$ alkyl optionally substituted with halogen, oxo, —CN or —OH, provided that
  (a) when $Y_2$ is C, at least one of $R^1$, $R^3$ and $R^4$ is —$(CH_2)_mN(R^f)W_3R^g$ or —$(CH_2)_mW_3R^g$, and
  (b) when $Y_2$ is N,
    (i) at least one of $R^1$, $R^3$ and $R^4$ is —$(CH_2)_mN(R^f)W_3R^g$ or —$(CH_2)_mW_3R^g$, or
    (ii) $R^4$ is halogen, cyano, $C_1$-$C_4$ haloalkyl, $C_1$-$C_4$ alkoxy, $C_1$-$C_4$ haloalkoxy, —$OR^{13}$, —$NR^{13}R^{14}$, —$C(O)NR^{13}R^{14}$, —$NR^{13}C(O)R^{14}$, —$S(O)_2R^{13}$, —$NR^{13}S(O)_2R^{14}$, —$S(O)_2NR^{13}R^{14}$, —$(CH_2)_mN(R^f)W_3R^g$, —$(CH_2)_mW_3R^g$, or $C_1$-$C_4$ alkyl optionally substituted with halogen, oxo, —CN or —OH, and $Z_1$ is CH—$W_1$—$R^c$ or C—$W_1$—$R^c$, wherein $W_1$ is —O— or —$NR^{w1}$— and $R^c$ is $C_3$-$C_6$ cycloalkyl, 3- to 6-membered heterocyclyl, phenyl, or 5- to 6-membered heteroaryl, each of which is optionally substituted with $R^d$;

each m is independently 0, 1, 2, 3, or 4;
$R^f$ is hydrogen, $C_1$-$C_4$ alkyl, or $C_3$-$C_6$ cycloalkyl;
$W_3$ is —C(O)— or —$S(O)_2$—;
$R^g$ is —$CR^{g1}$=CH $R^{g2}$ or —C≡$CR^{g2}$, wherein $R^{9g}$ and $R^{g2}$ are independently hydrogen, cyano or $C_1$-$C_4$ alkyl optionally substituted with —OH, —$OCH_3$, —$NH_2$, —$NHCH_3$ or —$N(CH_3)_2$,
or for $R^4$, when $R^4$ is —$(CH_2)_mN(R^f)W_3R^g$ and m is 0, the N, $R^f$, $W_3$ and $R^g$ in —$N(R^f)W_3R^g$ may be taken together to form a 5- or 6-membered ring having at least one double bond and optionally substituted with R, wherein each R is independently $C_1$-$C_4$ alkyl, oxo, halogen or CN;

$R^{10}$ and $R^{11}$ are independently hydrogen, $C_1$-$C_4$ alkenyl, $C_3$-$C_6$ cycloalkyl, $C_3$-$C_6$ heterocyclyl, ($C_1$-$C_3$ alkylene)$C_3$-$C_6$ cycloalkyl, ($C_1$-$C_3$ alkylene)$C_3$-$C_6$ heterocyclyl, C(O)$R^{12}$, or $C_1$-$C_4$ alkyl optionally substituted with halogen, oxo, —CN, —OH, —$NR^{13}R^{14}$ or —$C(O)NR^{13}R^{14}$,
or $R^{10}$ and $R^{11}$ are taken together with the atoms to which they are attached to form a $C_3$-$C_6$ heterocyclyl ring optionally substituted with halogen, oxo, —CN, —OH, or $C_1$-$C_4$ alkyl optionally substituted with halogen, oxo, —CN, or —OH;

$R^{12}$ is $C_3$-$C_6$ cycloalkyl, $C_3$-$C_6$ heterocyclyl or $C_1$-$C_4$ alkyl optionally substituted with halogen, oxo, —CN, —OH, —$NR^{13}R^{14}$ or —$NR^{13}C(O)R^{14}$;

$R^{13}$ and $R^{14}$ are independently hydrogen, $C_3$-$C_6$ cycloalkyl, $C_3$-$C_6$ heterocyclyl or $C_1$-$C_4$ alkyl optionally substituted with halogen, oxo, CN, or OH,
or $R^{13}$ and $R^{14}$ are taken together with the atoms to which they are attached to form a $C_3$-$C_6$ heterocyclyl ring optionally substituted with halogen, oxo, CN, OH, or $C_1$-$C_4$ alkyl optionally substituted with halogen, oxo, CN, or OH.

In some embodiments, in the compound of Formula (I), when $Y_2$ is C, $R^b$ and $R^2$ are taken together to form 5-membered heteroaryl ring, wherein said 5-membered heteroaryl ring is other than

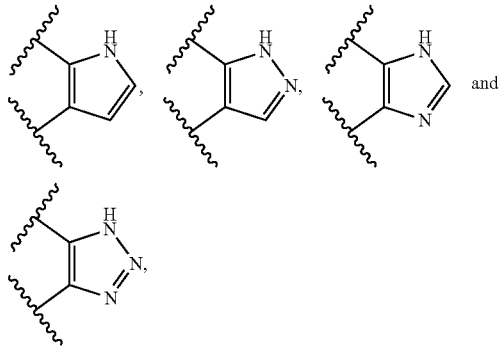

wherein the wavy lines denote attachment points with the another ring.

In some embodiments of a compound of Formula (I), or a tautomer or isomer thereof, or a pharmaceutically acceptable salt of any of the foregoing, the compound is other than the compounds in Table 1X, or a tautomer or isomer thereof, or a pharmaceutically acceptable salt of any of the foregoing. In some embodiments, the compound is other than Compound Nos. 1x-51x in Table 1X, or a tautomer or isomer thereof, or a pharmaceutically acceptable salt of any of the foregoing. In some embodiments, the compound is other than Compound Nos. 1x-54x in Table 1X, or a tautomer or isomer thereof, or a pharmaceutically acceptable salt of any of the foregoing. It is understood that the provisos provided herein are applicable to any related formulae where applicable, such as Formula (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a tautomer or isomer thereof, or a pharmaceutically acceptable salt of any of the foregoing.

TABLE 1X

| | |
|---|---|
| 1x | ethyl (6-methyl-4-oxo-1-phenyl-1,4-dihydropyridazin-3-yl)carbamate |
| 2x | tert-butyl (4-oxo-1-(3-(trifluoromethyl)phenyl)-1,4-dihydrocinnolin-3-yl)carbamate |
| 3x | tert-butyl (6-methyl-4-oxo-1-(4-(trifluoromethyl)phenyl)-1,4-dihydropyridazin-3-yl)carbamate |
| 4x | ethyl (6-methyl-4-oxo-1-(3-(trifluoromethyl)phenyl)-1,4-dihydropyridazin-3-yl)carbamate |
| 5x | tert-butyl (4-hydroxy-2-(3-methyl-4-oxopyridin-1(4H)-yl)cyclohexyl)carbamate |
| 6x | tert-butyl (4-hydroxy-2-(4-oxopyridin-1(4H)-yl)cyclohexyl)carbamate |
| 7x | tert-butyl (5-(7-(3,5-dimethylisoxazol-4-yl)-2-methyl-4-oxoquinolin-1(4H)-yl)-2,4-difluorophenyl)carbamate |
| 8x | tert-butyl (5-(7-chloro-4-oxo-1,8-naphthyridin-1(4H)-yl)-2,4-difluorophenyl)carbamate |
| 9x | tert-butyl (5-(7-(3,5-dimethylisoxazol-4-yl)-2-methyl-4-oxo-1,8-naphthyridin-1(4H)-yl)-2,4-difluorophenyl)carbamate |
| 10x | tert-butyl (5-(7-(3,5-dimethylisoxazol-4-yl)-4-oxoquinolin-1(4H)-yl)-2,4-difluorophenyl)carbamate |
| 11x | tert-butyl (5-(7-(3,5-dimethylisoxazol-4-yl)-2-ethyl-4-oxoquinolin-1(4H)-yl)-2,4-difluorophenyl)carbamate |
| 12x | tert-butyl (5-(7-bromo-2-methyl-4-oxoquinolin-1(4H)-yl)-2,4-difluorophenyl)carbamate |
| 13x | tert-butyl (5-(7-(3,5-dimethylisoxazol-4-yl)-3-fluoro-4-oxoquinolin-1(4H)-yl)-2,4-difluorophenyl)carbamate |
| 14x | tert-butyl (5-(7-chloro-2-methyl-4-oxo-1,8-naphthyridin-1(4H)-yl)-2,4-difluorophenyl)carbamate |
| 15x | tert-butyl (5-(7-chloro-3-methyl-4-oxo-1,8-naphthyridin-1(4H)-yl)-2,4-difluorophenyl)carbamate |
| 16x | tert-butyl (5-(7-bromo-2-ethyl-4-oxoquinolin-1(4H)-yl)-2,4-difluorophenyl)carbamate |
| 17x | tert-butyl (5-(7-(3,5-dimethylisoxazol-4-yl)-3-methyl-4-oxo-1,8-naphthyridin-1(4H)-yl)-2,4-difluorophenyl)carbamate |
| 18x | tert-butyl (5-(7-bromo-4-oxoquinolin-1(4H)-yl)-2,4-difluorophenyl)carbamate |
| 19x | tert-butyl (2-(3-cyano-6-methoxy-1-oxo-4-phenylisoquinolin-2(1H)-yl)ethyl)carbamate |
| 20x | ethyl ((4-mesityl-1-oxophthalazin-2(1H)-yl)methyl)carbamate |
| 21x | tert-butyl methyl(2-(1-oxo-4-phenylphthalazin-2(1H)-yl)ethyl)carbamate |
| 22x | tert-butyl (2-(2-oxo-1,2-dihydropyrimidin-5-yl)phenyl)carbamate |
| 23x | tert-butyl (2-(6-oxo-1,6-dihydropyridin-3-yl)phenyl)carbamate |
| 24x | tert-butyl (3-(2-oxo-1,2-dihydropyrimidin-5-yl)phenyl)carbamate |
| 25x | ethyl (3-(6-oxo-1,6-dihydropyridazin-3-yl)phenyl)carbamate |
| 26x | tert-butyl (3-(6-oxo-1,6-dihydropyridazin-3-yl)benzyl)carbamate |
| 27x | tert-butyl (3-(6-oxo-1,6-dihydropyridin-3-yl)benzyl)carbamate |
| 28x | tert-butyl (3-(6-oxo-1,6-dihydropyridin-3-yl)phenyl)carbamate |
| 29x | tert-butyl methyl(3-(2-methyl-1-oxo-1,2-dihydroisoquinolin-4-yl)phenyl)carbamate |

TABLE 1X-continued 30x tert-butyl (3-(2-oxo-1,2-dihydropyrimidin-5-yl)benzyl)carbamate
31x isobutyl (3-(6-oxo-1,6-dihydropyridazin-3-yl)phenyl)carbamate
32x ethyl (2-methyl-5-(3-methyl-4-oxo-3,4-dihydrophthalazin-1-yl)benzyl)carbamate
33x ethyl (3-(4-oxo-3,4-dihydrophthalazin-1-yl)phenyl)carbamate
34x ethyl (3-(4-methoxy-1-methyl-6-oxo-1,6-dihydropyridazin-3-yl)-4-phenoxyphenyl)carbamate
35x methyl (3-(6-oxo-1,6-dihydropyridazin-3-yl)phenyl)carbamate
36x ethyl (2-cyano-5-(1-isopropyl-6-oxo-1,6-dihydropyridazin-3-yl)-6-phenylpyridin-3-yl)carbamate
37x tert-butyl (5-(1-isopropyl-6-oxo-1,6-dihydropyridazin-3-yl)-2-methyl-6-phenylpyridin-3-yl)carbamate
38x butyl (3-(6-oxo-1,6-dihydropyridazin-3-yl)phenyl)carbamate
39x tert-butyl (5-(1-isopropyl-6-oxo-1,6-dihydropyridazin-3-yl)-6-phenylpyridin-3-yl)carbamate
40x ethyl (1-phenyl-4-thioxo-1,4-dihydroquinazolin-3(2H)-yl)carbamate
41x methyl (1-phenyl-4-thioxo-1,4-dihydroquinazolin-3(2H)-yl)carbamate
42x ethyl (7-chloro-4-oxo-1-(p-tolyl)-1,4-dihydroquinazolin-3(2H)-yl)carbamate
43x (4-oxo-1-(p-tolyl)-1,4-dihydroquinazolin-3(2H)-yl)carbamate
44x ethyl (1-(4-chlorophenyl)-4-oxo-1,4-dihydroquinazolin-3(2H)-yl)carbamate
45x ethyl (7-chloro-4-oxo-1-phenyl-1,4-dihydroquinazolin-3(2H)-yl)carbamate
46x ethyl (4-oxo-1-phenyl-1,4-dihydroquinazolin-3(2H)-yl)carbamate
47x ethyl (1-(4-chlorophenyl)-4-thioxo-1,4-dihydroquinazolin-3(2H)-yl)carbamate
48x ethyl (7-chloro-4-thioxo-1-(p-tolyl)-1,4-dihydroquinazolin-3(2H)-yl)carbamate
49x ethyl (4-thioxo-1-(p-tolyl)-1,4-dihydroquinazolin-3(2H)-yl)carbamate
50x ethyl (7-chloro-1-phenyl-4-thioxo-1,4-dihydroquinazolin-3(2H)-yl)carbamate
51x methyl (7-chloro-1-phenyl-4-thioxo-1,4-dihydroquinazolin-3(2H)-yl)carbamate
52x N-(2-(6-oxo-3-phenylpyridazin-1(6H)-yl)ethyl)but-2-enamide
53x tert-butyl (3-(1-methyl-6-oxo-1,6-dihydropyridin-3-yl)benzyl)carbamate
54x ethyl (4-oxo-1-(p-tolyl)-1,4-dihydroquinazolin-3(2H)-yl)carbamate In some embodiments of a compound of Formula (I) or any related formulae (e.g., Formula (Ia), (Ia-1 to Ia-12), (Ib), (Ib-1 to Ib-4), (Ic), (Ic-1 to Ic-19), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) where applicable), or a tautomer or isomer thereof, or a pharmaceutically acceptable salt of any of the foregoing, (a) when $Y_2$ is C, at least one of $R^3$ and $R^4$ is —$(CH_2)_mN(R^f)W_3R^g$ or —$(CH_2)_mW_3R^g$, and (b) when $Y_2$ is N, (i) at least one of $R^1$, $R^3$ and $R^4$ is —$(CH_2)_mN(R^f)W_3R$ or —$(CH_2)_mW_3R^g$, or (ii) $R^4$ is halogen, cyano, $C_1$-$C_4$ haloalkyl, $C_1$-$C_4$ alkoxy, $C_1$-$C_4$ haloalkoxy, —$OR^{13}$, —$NR^{13}R^{14}$, —$C(O)NR^{13}R^{14}$, —$NR^{13}C(O)R^{14}$, —$S(O)_2R^{13}$, —$NR^{13}S(O)_2R^{14}$, —$S(O)_2NR^{13}R^{14}$, —$(CH_2)_mN(R^f)W_3R^g$, —$(CH_2)_mW_3R^g$, or $C_1$-$C_4$ alkyl optionally substituted with halogen, oxo, —CN or —OH, and $Z_1$ is CH—$W_1$—$R^c$ or C—$W_1$—$R^c$, wherein $W_1$ is —O— or —$NR^{w1}$— and $R^c$ is $C_3$-$C_6$ cycloalkyl, 3- to 6-membered heterocyclyl, phenyl, or 5- to 6-membered heteroaryl, each of which is optionally substituted with $R^{c1}$.

In some embodiments, when $R^1$ is —$(CH_2)_mN(R^f)W_3R^g$ or —$(CH_2)_mN(R^f)C(O)OR^h$, $R^3$ is —$(CH_2)_mN(R^f)C(O)OR^h$, or $R^4$ is —$(CH_2)_mN(R^f)C(O)OR^h$, then $Z_1$ is C—$W_1$—$R^c$, wherein $W_1$ is —O— or —$NR^{w1}$— and $R^c$ is $C_3$-$C_6$ cycloalkyl, 3- to 6-membered heterocyclyl, $C_6$-$C_{14}$ aryl, or 5- to 6-membered heteroaryl, wherein the $C_3$-$C_6$ cycloalkyl, 3- to 6-membered heterocyclyl, $C_6$-$C_{14}$ aryl, or 5- to 6-membered heteroaryl of $R^c$ are each independently substituted by $R^{c1}$. In some embodiments, when $R^1$ is —$(CH_2)_mN(R^f)W_3R^g$ or —$(CH_2)_mN(R^f)C(O)OR^h$, $R^3$ is —$(CH_2)_mN(R^f)C(O)OR^h$, or $R^4$ is —$(CH_2)_mN(R^f)C(O)OR^h$, then $Z_1$ is C—$W_1$—$R^c$, wherein $W_1$ is —O— or —$NR^{w1}$— and $R^c$ is phenyl substituted by $R^{c1}$, wherein each $R^{c1}$ is independently halogen, $C_1$-$C_4$ alkyl, or $C_1$-$C_4$ alkoxy. In some embodiments, $Z_1$ is C—$W_1$—$R^c$, wherein $W_1$ is —O— or —$NR^{w1}$— and $R^c$ is $C_3$-$C_6$ cycloalkyl, 3- to 6-membered heterocyclyl, $C_6$-$C_{14}$ aryl, or 5- to 6-membered heteroaryl, wherein the $C_3$-$C_6$ cycloalkyl, 3- to 6-membered heterocyclyl, $C_6$-$C_{14}$ aryl, or 5- to 6-membered heteroaryl of $R^c$ are each independently substituted by $R^{c1}$. In some embodiments, $Z_1$ is C—$W_1$—$R^c$, wherein $W_1$ is —O— or —$NR^{w1}$— and $R^c$ is phenyl substituted by $R^{c1}$, wherein each $R^{c1}$ is independently halogen, $C_1$-$C_4$ alkyl, or $C_1$-$C_4$ alkoxy. In some embodiments, at least one of $R^3$ and $R^4$ is —$(CH_2)_mN(R^f)W_3R^g$ or —$(CH_2)_mW_3R^g$. In some embodiments, $R^4$ is —$(CH_2)_mN(R^f)W_3R$ or —$(CH_2)_mW_3R^g$.

In some embodiments of a compound of Formula (I) or any related formulae (e.g., Formula (Ia), (Ia-1 to Ia-12), (Ib), (Ib-1 to Ib-4), (Ic), (Ic-1 to Ic-19), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) where applicable), or a tautomer or isomer thereof, or a pharmaceutically acceptable salt of any of the foregoing, one, two, three, four, or five of the following features apply:

(1) when the compound is of Formula (I-X),

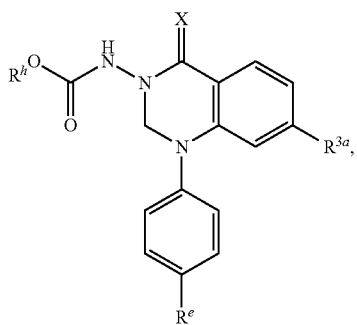

(1-X)

wherein X is O or S, $R^h$ is methyl or ethyl, and $R^e$ is H, methyl, or chloro, then $R^{3a}$ is other than H and chloro;

(2) when the compound is of Formula (2-X):

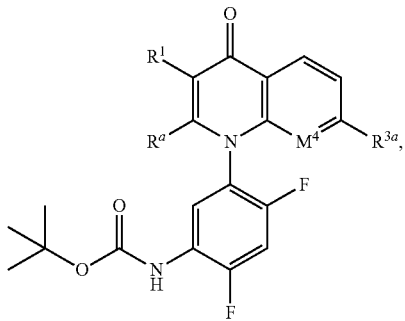

(2-X)

wherein $R^1$ is H, fluoro, or methyl, $R^a$ is H, methyl, or ethyl, and $M^4$ is CH or N, then $R^{3a}$ is other than chloro, bromo, and

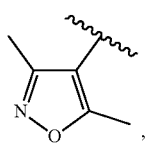

wherein the wavy line indicates the point of attachment to the remainder of the molecule;

(3) when the compound is of Formula (3-X-1), (3-X-2), or (3-X-2):

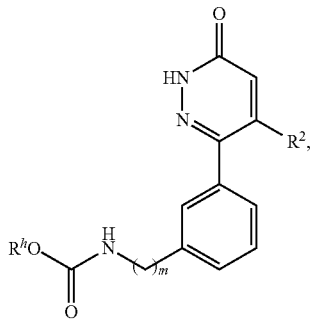

(3-X-1)

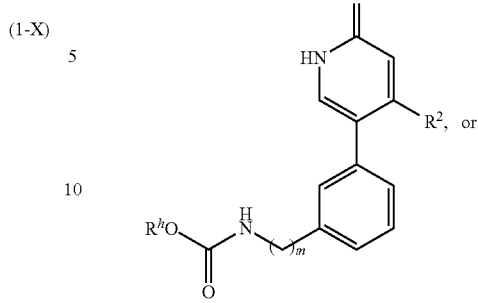

(3-X-2)

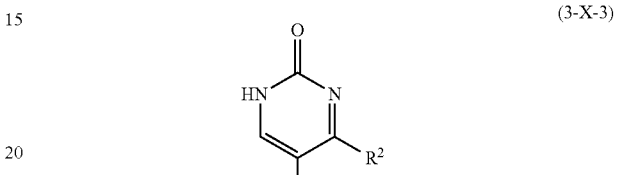

(3-X-3)

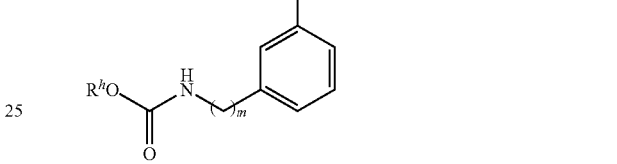

wherein m is 0 or 1 and $R^h$ is $C_1$-$C_4$ alkyl, then $R^2$ is other than H;

(4) when the compound is of Formula (4-X),

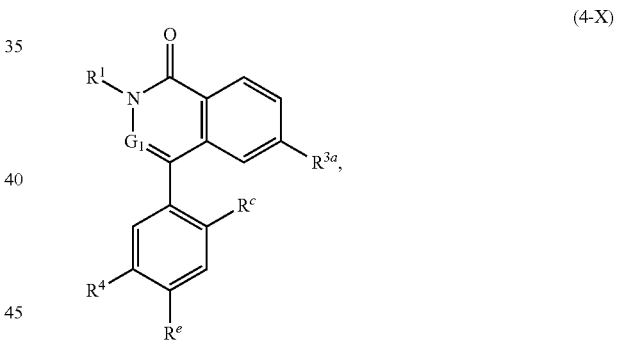

(4-X)

wherein $G_1$ is CH, N, or C—CN, $R^1$ is H methyl,

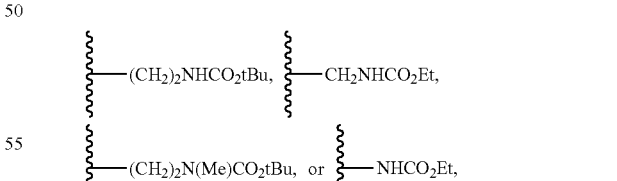

$R^{3a}$ is H or —$OCH_3$, $R^e$ is H or methyl, and $R^4$ is H or

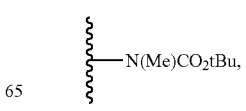

then $R^c$ is other than H; and/or
(5) when the compound is of Formula (5-X),

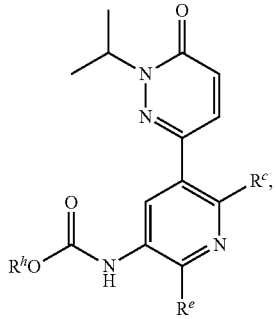
(5-X)

wherein $R^e$ is H, methyl, or —CN, and $R^h$ is ethyl or t-butyl, then $R^c$ is other than phenyl.

In some embodiments, (1) applies. In some embodiments, (2) applies. In some embodiments, (3) applies. In some embodiments, (4) applies. In some embodiments, (5) applies. In some embodiments, (1), (2), (3), (4), and (5) apply.

In some embodiments, the compound of Formula (I), or a tautomer or isomer thereof, or a pharmaceutically acceptable salt of any of the foregoing, is of Formula (Ia), or a tautomer or isomer thereof, or a pharmaceutically acceptable salt of any of the foregoing,

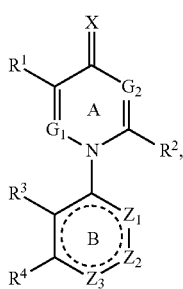
(Ia)

wherein X, $R^1$, $R^2$, $G_1$, $G_2$, $R^3$, $R^4$,

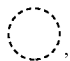

$Z_1$, $Z_2$ and $Z_3$ are as defined herein for Formula (I).

In some embodiments of a compound of Formula (Ia), or a tautomer or isomer thereof, or a pharmaceutically acceptable salt of any of the foregoing, (i) at least one of $R^1$, $R^3$ and $R^4$ is —$(CH_2)_mN(R^f)W_3R^g$ or —$(CH_2)_mW_3R^g$, or (ii) $R^4$ is halogen, cyano, $C_1$-$C_4$ haloalkyl, $C_1$-$C_4$ alkoxy, $C_1$-$C_4$ haloalkoxy, —$OR^{13}$, —$NR^{13}R^{14}$, —$C(O)NR^{13}R^{14}$, —$NR^{13}C(O)R^{14}$, —$S(O)_2R^{13}$, —$NR^{13}S(O)_2R^{14}$, —$S(O)_2NR^{13}R^{14}$, —$(CH_2)_mN(R^f)W_3R^g$, —$(CH_2)_mW_3R^g$, or $C_1$-$C_4$ alkyl optionally substituted with halogen, oxo, —CN or —OH, and $Z_1$ is CH—$W_1$—$R^c$ or C—$W_1$—$R^c$, wherein $W_1$ is —O— or —$NR^{w1}$— and $R^c$ is $C_3$-$C_6$ cycloalkyl, 3- to 6-membered heterocyclyl, phenyl, or 5- to 6-membered heteroaryl, each of which is optionally substituted with $R^{c1}$.
In some embodiments, when $R^1$ is —$(CH_2)_mN(R^f)W_3R^g$ or —$(CH_2)_mN(R^f)C(O)OR^h$, $R^3$ is —$(CH_2)_mN(R^f)C(O)OR^h$, or $R^4$ is —$(CH_2)_mN(R^f)C(O)OR^h$, then $Z_1$ is C—$W_1$—$R^c$, wherein $W_1$ is —O— or —$NR^{w1}$— and $R^c$ is $C_3$-$C_6$ cycloalkyl, 3- to 6-membered heterocyclyl, $C_6$-$C_{14}$ aryl, or 5- to 6-membered heteroaryl, wherein the $C_3$-$C_6$ cycloalkyl, 3- to 6-membered heterocyclyl, $C_6$-$C_{14}$ aryl, or 5- to 6-membered heteroaryl of $R^c$ are each independently substituted by $R^{c1}$. In some embodiments, when $R^1$ is —$(CH_2)_mN(R^f)W_3R^g$ or —$(CH_2)_mN(R^f)C(O)OR^h$, $R^3$ is —$(CH_2)_mN(R^f)C(O)OR^h$, or $R^4$ is —$(CH_2)_mN(R^f)C(O)OR^h$, then $Z_1$ is C—$W_1$—$R^c$, wherein $W_1$ is —O— or —$NR^{w1}$— and $R^c$ is phenyl substituted by $R^cd$, wherein each $R^{c1}$ is independently halogen, $C_1$-$C_4$ alkyl, or $C_1$-$C_4$ alkoxy. In some embodiments, $Z_1$ is C—$W_1$—$R^c$, wherein $W_1$ is —O— or —$NR^{w1}$— and $R^c$ is $C_3$-$C_6$ cycloalkyl, 3- to 6-membered heterocyclyl, $C_6$-$C_{14}$ aryl, or 5- to 6-membered heteroaryl, wherein the $C_3$-$C_6$ cycloalkyl, 3- to 6-membered heterocyclyl, $C_6$-$C_{14}$ aryl, or 5- to 6-membered heteroaryl of $R^c$ are each independently substituted by $R^{c1}$. In some embodiments, $Z_1$ is C—$W_1$—$R^c$, wherein $W_1$ is —O— or —$NR^{w1}$— and $R^c$ is phenyl substituted by $R^{c1}$, wherein each $R^{c1}$ is independently halogen, $C_1$-$C_4$ alkyl, or $C_1$-$C_4$ alkoxy. In some embodiments, at least one of $R^1$, $R^3$ and $R^4$ is —$(CH_2)_mN(R^f)W_3R^g$ or —$(CH_2)_mW_3R^g$. In some embodiments, $R^4$ is —$(CH_2)_mN(R^f)W_3R^g$ or —$(CH_2)_mW_3R^g$.

In some embodiments, the compound of Formula (I), or a tautomer or isomer thereof, or a pharmaceutically acceptable salt of any of the foregoing, is of Formula (Ib), or a tautomer or isomer thereof, or a pharmaceutically acceptable salt of any of the foregoing,

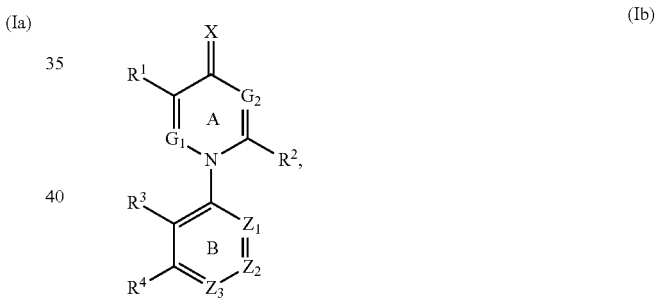
(Ib)

wherein:
$Z_1$ is C—$W_1$—$R^c$ or N;
$Z_2$ is C—$W_2$—$R^d$ or N;
$Z_3$ is C—$R^e$ or N; and
X, $R^1$, $R^2$, $G_1$, $G_2$, $R^3$, $R^4$, $W_1$, $W_2$, $R^c$, $R^d$, and $R^e$ are as defined herein for Formula (I).

In some embodiments of a compound of Formula (Ib), or a tautomer or isomer thereof, or a pharmaceutically acceptable salt of any of the foregoing, (i) at least one of $R^1$, $R^3$ and $R^4$ is —$(CH_2)_mN(R^f)W_3R^g$ or —$(CH_2)_mW_3R^g$, or (ii) $R^4$ is halogen, cyano, $C_1$-$C_4$ haloalkyl, $C_1$-$C_4$ alkoxy, $C_1$-$C_4$ haloalkoxy, —$OR^{13}$, —$NR^{13}R^{14}$, —$C(O)NR^{13}R^{14}$, —$NR^{13}C(O)R^{14}$, —$S(O)_2R^{13}$, —$NR^{13}S(O)_2R^{14}$, —$S(O)_2NR^{13}R^{14}$, —$(CH_2)_mN(R^fW_3R^g$ $(CH_2)_mW_3R^g$, or $C_1$-$C_4$ alkyl optionally substituted with halogen, oxo, —CN or —OH, and $Z_1$ is CH—$W_1$—$R^c$ or C—$W_1$—$R^c$, wherein $W_1$ is —O— or —$NR^{w1}$— and $R^c$ is $C_3$-$C_6$ cycloalkyl, 3- to 6-membered heterocyclyl, phenyl, or 5- to 6-membered heteroaryl, each of which is optionally substituted with $R^{c1}$. In some embodiments, when $R^1$ is —$(CH_2)_mN(R^f)W_3R^g$ or —$(CH_2)_mN(R^f)C(O)OR^h$, $R^3$ is —$(CH_2)_mN(R^f)C(O)OR^h$, or $R^4$ is —$(CH_2)_mN(R^f)C(O)OR^h$, then $Z_1$ is C—$W_1$—$R^c$, wherein $W_1$ is —O— or —$NR^{w1}$— and $R^c$ is $C_3$-$C_6$ cycloalkyl, 3- to 6-membered heterocyclyl, $C_6$-$C_{14}$ aryl, or 5- to 6-membered heteroaryl, wherein the $C_3$-$C_6$ cycloalkyl, 3- to 6-membered heterocyclyl, $C_6$-$C_{14}$ aryl, or 5- to 6-membered heteroaryl of $R^c$ are each independently substituted by $R^{c1}$. In some embodiments, when $R^1$ is —$(CH_2)_m N(R^f) W_3 R^g$ or —$(CH_2)_m N(R^f)C(O)OR^h$, $R^3$ is —$(CH_2)_m N(R^f)C(O)OR^h$, or $R^4$ is —$(CH_2)_m N(R^f)C(O)OR^h$, then $Z_1$ is C—$W_1$—$R^c$, wherein $W_1$ is —O— or —$NR^{w1}$— and $R^c$ is phenyl substituted by $R^{c1}$, wherein each $R^{c1}$ is independently halogen, $C_1$-$C_4$ alkyl, or $C_1$-$C_4$ alkoxy. In some embodiments, $Z_1$ is C—$W_1$—$R^c$, wherein $W_1$ is —O— or —$NR^{w1}$— and $R^c$ is $C_3$-$C_6$ cycloalkyl, 3- to 6-membered heterocyclyl, $C_6$-$C_{14}$ aryl, or 5- to 6-membered heteroaryl, wherein the $C_3$-$C_6$ cycloalkyl, 3- to 6-membered heterocyclyl, $C_6$-$C_{14}$ aryl, or 5- to 6-membered heteroaryl of $R^c$ are each independently substituted by $R^{c1}$. In some embodiments, $Z_1$ is C—$W_1$—$R^c$, wherein $W_1$ is —O— or —$NR^{w1}$— and $R^c$ is phenyl substituted by $R^{c1}$, wherein each $R^{c1}$ is independently halogen, $C_1$-$C_4$ alkyl, or $C_1$-$C_4$ alkoxy. In some embodiments, at least one of $R^1$, $R^3$ and $R^4$ is —$(CH_2)_m N(R^f) W_3 R^g$ or —$(CH_2)_m W_3 R^g$. In some embodiments, $R^4$ is —$(CH_2)_m N(R^f) W_3 R^g$ or —$(CH_2)_m W_3 R^g$.

In some embodiments, provided is a compound of any one of Formula (Ib-1) to (Ib-4):

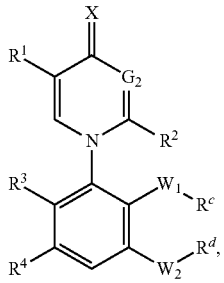

(Ib-1)

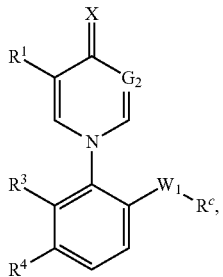

(Ib-2)

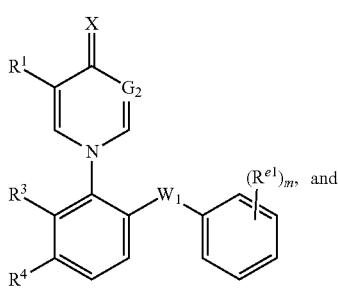

(Ib-3)

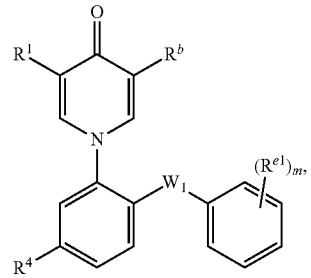

(Ib-4)

or a tautomer or isomer thereof, or a pharmaceutically acceptable salt of any of the foregoing, wherein X, $R^1$, $R^2$, $R^3$, $R^4$, $G_2$, $W_1$, $W_2$, $R^b$, $R^c$, $R^d$, $R^{e1}$ and m are as defined for Formula (Ib).

In some embodiments, the compound of Formula (I), or a tautomer or isomer thereof, or a pharmaceutically acceptable salt of any of the foregoing, is of Formula (Ic), or a tautomer or isomer thereof, or a pharmaceutically acceptable salt of any of the foregoing,

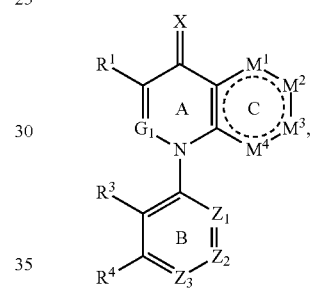

(Ic)

wherein:
$Z_1$ is C—$W_1$—$R^c$ or N;
$Z_2$ is C—$W_2$—$R^d$ or N;
$Z_3$ is C—$R^e$ or N;
$M^1$ is O, S, N, $NR^{1a}$, $CR^{1a}$, or $CR^{1a}R^{1b}$;
$M^2$ is N, $NR^{2a}$, $CR^{2a}$, or $CR^{2a}R^{2b}$;
$M^3$ is N, $NR^{3a}$, $CR^{3a}$, $CR^{3a}R^{3b}$ or absent;
$M^4$ is O, S, N, $NR^4$a, $CR^{4a}$, or $CR^{4a}R^{4b}$,
provided that
(1) no more than three of $M^1$, $M^2$, $M^3$ and $M^4$ are N or N substituted by $R^{1a}$, $R^{2a}$, $R^{3a}$, or $R^{4a}$, and
(2) if $M^3$ is absent, then at least one of $M^1$ and $M^4$ is not O or S;
$R^{1a}$, $R^{1b}$, $R^{2a}$, $R^{2b}$, $R^{3a}$, $R^{3b}$, $R^{4a}$, and $R^{4b}$ are each independently hydrogen, halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, $OR^{10}$, $NR^{10}R^{11}$, C(O)$OR^{10}$, C(O)$NR^{10}R^{11}$, $NR^{10}C(O)R^{11}$, $S(O)_2R^{10}$, $NR^{10}S(O)_2R^{11}$, or $S(O)_2NR^{10}R^{11}$; and X, $R^1$, $G_1$, $R^3$, $R^4$, $W_1$, $W_2$, $R^c$, $R^d$, $R^e$, $R^1$, and $R^{11}$ are as defined for Formula (I).

In some embodiments, the C ring is aryl, in which $M^1$, $M^2$, $M^3$ and $M^4$ are CH. In some embodiments, C ring is heteroaryl, in which any one of $M^1$, $M^2$, $M^3$ and $M^4$ is N, and others are CH. In some embodiments, C ring is heteroaryl, in which any two of $M^1$, $M^2$, $M^3$ and $M^4$ are N, and others are CH. In some embodiments, C ring is heterocyclyl, in which any one of $M^1$, $M^2$, $M^3$ and $M^4$ is NH and other are $CH_2$. In some embodiments, C ring is heterocyclyl, in which $M^1$ and $M^2$ are NH, and $M^3$ and $M^4$ are $CH_2$. In some embodiments, C ring is heterocyclyl, in which $M^1$ is NH, $M^4$ is O, and $M^2$ and $M^3$ are $CH_2$. In some embodiments, C ring is heterocyclyl, in which $M^1$ is O, $M^4$ is NH, and $M^2$ and $M^3$ are $CH_2$. In some embodiments, C ring is heterocyclyl, in which $M^1$ is O, and $M^2$, $M^3$ and $M^4$ are $CH_2$. In some embodiments, C ring is heterocyclyl, in which $M^4$ is O, and $M^1$, $M^2$ and $M^3$ are $CH_2$. In some embodiments, C ring is heterocyclyl, in which $M^1$ and $M^4$ are O, and $M^2$ and $M^3$ are $CH_2$. In some embodiments, C ring is cycloalkyl, in which $M^1$, $M^2$, $M^3$ and $M^4$ are $CH_2$. In some embodiments, C ring is heteroaryl, in which $M^1$ is O, $M^2$ and $M^4$ are CH, and $M^3$ is absent. In some embodiments, C ring is heteroaryl, in which $M^4$ is O, $M^1$ and $M^2$ are CH, and $M^3$ is absent. In some embodiments, C ring is heteroaryl, in which $M^1$ is S, $M^2$ and $M^4$ are CH, and $M^3$ is absent. In some embodiments, C ring is heteroaryl, in which $M^4$ is S, $M^1$ and $M^2$ are CH, and $M^3$ is absent. In some embodiments, C ring is heteroaryl, in which $M^1$ is O, $M^2$ is N, $M^4$ is CH, and $M^3$ is absent. In some embodiments, C ring is heteroaryl, in which $M^1$ is O, $M^4$ is N, $M^2$ is CH, and $M^3$ is absent. In some embodiments, C ring is heteroaryl, in which $M^4$ is O, $M^2$ is N, $M^1$ is CH, and $M^3$ is absent. In some embodiments, C ring is heteroaryl, in which $M^1$ is O, $M^4$ is N, $M^2$ is CH, and $M^3$ is absent. In some embodiments, C ring is heteroaryl, in which $M^4$ is O, $M^1$ is N, $M^2$ is CH, and $M^3$ is absent. In some embodiments, C ring is heteroaryl, in which $M^4$ is S, $M^1$ is N, $M^2$ is CH, and $M^3$ is absent. In some embodiments, C ring is heteroaryl, in which $M^1$ is S, $M^2$ is N, $M^4$ is CH, and $M^3$ is absent. In some embodiments, C ring is heteroaryl, in which $M^1$ is S, $M^4$ is N, $M^2$ is CH, and $M^3$ is absent. In some embodiments, C ring is heteroaryl, in which $M^4$ is S, $M^2$ is N, $M^1$ is CH, and $M^3$ is absent. In some embodiments, C ring is heteroaryl, in which $M^1$ is S, $M^4$ is N, $M^2$ is CH, and $M^3$ is absent. In some embodiments, C ring is heteroaryl, in which $M^1$ and $M^2$ are CH, $M^4$ is NH, and $M^3$ is absent. In some embodiments, C ring is heteroaryl, in which $M^1$ is CH, $M^2$ is N, $M^4$ is CH, and $M^3$ is absent. In some embodiments, C ring is heterocyclyl, in which $M^1$ is NH, $M^2$ and $M^4$ are CH and $M^3$ is absent. In some embodiments, C ring is heterocyclyl, in which $M^4$ is NH, $M^1$ and $M^2$ are CH, and $M^3$ is absent. In some embodiments, C ring is cycloalkyl, in which $M^1$, $M^2$, and $M^4$ are $CH_2$, and $M^3$ is absent.

In some embodiments of a compound of Formula (Ic), or a tautomer or isomer thereof, or a pharmaceutically acceptable salt of any of the foregoing, (i) at least one of $R^1$, $R^3$ and $R^4$ is —$(CH_2)_mN(R^f)W_3R^g$ or —$(CH_2)_mW_3R^g$, or (ii) $R^4$ is halogen, cyano, $C_1$-$C_4$ haloalkyl, $C_1$-$C_4$ alkoxy, $C_1$-$C_4$ haloalkoxy, —$OR^{13}$, —$NR^{13}R^{14}$, —$C(O)NR^{13}R^{14}$, —$NR^{13}C(O)R^{14}$, —$S(O)_2R^{13}$, —$NR^{13}S(O)_2R^{14}$, —$S(O)_2NR^{13}R^{14}$, —$(CH_2)_mN(R^f)W_3R^g$, —$(CH_2)_mW_3R^g$, or $C_1$-$C_4$ alkyl optionally substituted with halogen, oxo, —CN or —OH, and $Z_1$ is CH—$W_1$—$R^c$ or C—$W_1$—$R^c$, wherein $W_1$ is —O— or —$NR^{w1}$— and $R^c$ is $C_3$-$C_6$ cycloalkyl, 3- to 6-membered heterocyclyl, phenyl, or 5- to 6-membered heteroaryl, each of which is optionally substituted with $R^{c1}$. In some embodiments, when $R^1$ is —$(CH_2)_mN(R^f)W_3R^g$ or —$(CH_2)_mN(R^f)C(O)OR^h$, $R^3$ is —$(CH_2)_mN(R^f)C(O)OR^h$, or $R^4$ is —$(CH_2)_mN(R^f)C(O)OR^h$, then $Z_1$ is C—$W_1$—$R^c$, wherein $W_1$ is —O— or —$NR^{w1}$— and $R^c$ is $C_3$-$C_6$ cycloalkyl, 3- to 6-membered heterocyclyl, $C_6$-$C_{14}$ aryl, or 5- to 6-membered heteroaryl, wherein the $C_3$-$C_6$ cycloalkyl, 3- to 6-membered heterocyclyl, $C_6$-$C_{14}$ aryl, or 5- to 6-membered heteroaryl of $R^c$ are each independently substituted by $R^{c1}$. In some embodiments, when $R^1$ is —$(CH_2)_mN(R^f)W_3R^g$ or —$(CH_2)_mN(R^f)C(O)OR^h$, $R^3$ is —$(CH_2)_mN(R^f)C(O)OR^h$, or $R^4$ is —$(CH_2)_mN(R^f)C(O)OR^h$, then $Z_1$ is C—$W_1$—$R^c$, wherein $W_1$ is —O— or —$NR^{w1}$— and $R^c$ is phenyl substituted by $R^{c1}$, wherein each $R^{c1}$ is independently halogen, $C_1$-$C_4$ alkyl, or $C_1$-$C_4$ alkoxy. In some embodiments, Z1 is C—$W_1$—$R^c$, wherein $W_1$ is —O— or —$NR^{w1}$— and $R^c$ is $C_3$-$C_6$ cycloalkyl, 3- to 6-membered heterocyclyl, $C_6$-$C_{14}$ aryl, or 5- to 6-membered heteroaryl, wherein the $C_3$-$C_6$ cycloalkyl, 3- to 6-membered heterocyclyl, $C_6$-$C_{14}$ aryl, or 5- to 6-membered heteroaryl of $R^c$ are each independently substituted by $R^{c1}$. In some embodiments, $Z_1$ is C—$W_1$—$R^c$, wherein $W_1$ is —O— or —$NR^{w1}$— and $R^c$ is phenyl substituted by $R^{11}$, wherein each $R^{c1}$ is independently halogen, $C_1$-$C_4$ alkyl, or $C_1$-$C_4$ alkoxy. In some embodiments, at least one of $R^1$, $R^3$ and $R^4$ is —$(CH_2)_mN(R^f)W_3R^g$ or —$(CH_2)_mW_3R^g$. In some embodiments, $R^4$ is —$(CH_2)_mN(R^f)W_3R^g$ or —$(CH_2)_mW_3R^g$.

In some embodiments, provided is a compound of any one of Formula (Ia-1) to (Ia-12):

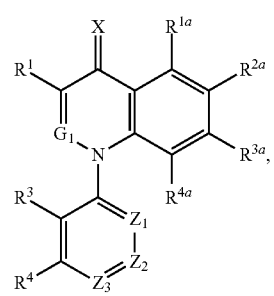
(Ia-1)

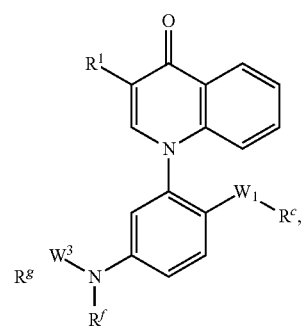
(Ia-2)

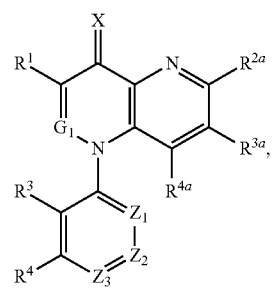
(Ia-3)

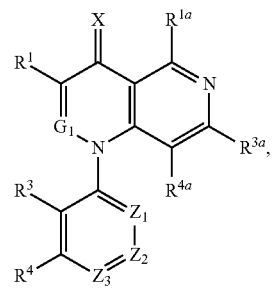
(Ia-4)

(Ia-5)
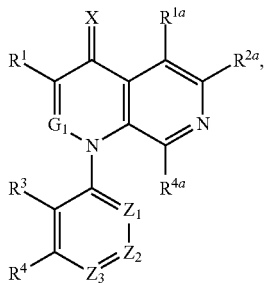
(Ia-6)
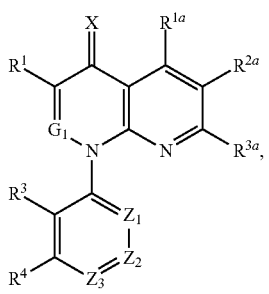
(Ia-7)
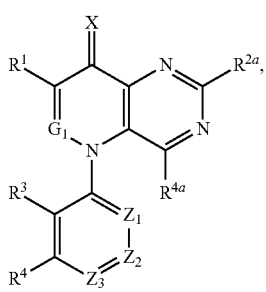
(Ia-8)
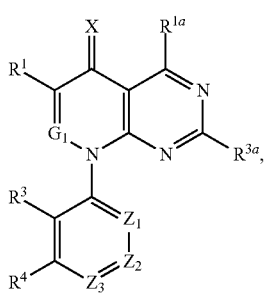
(Ia-9)
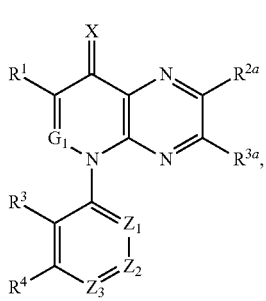
(Ia-10)
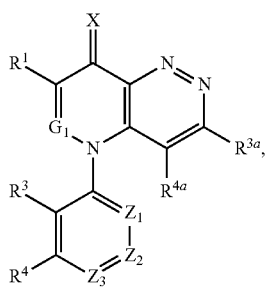
(Ia-11)
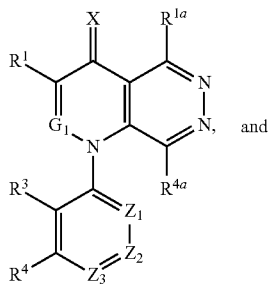
and
(Ia-12)
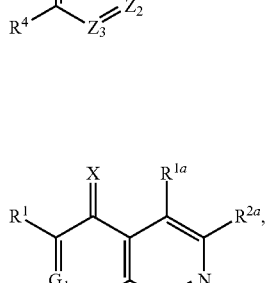
or a tautomer or isomer thereof, or a pharmaceutically acceptable salt of any of the foregoing, wherein X, $R^1$, $R^3$, $R^4$, $R^{1a}$, $R^{2a}$, $R^{3a}$, $R^{4a}$, $W_1$, $W_3$, $R^c$, $R^f$, $R^g$, $G_1$, $Z_1$, $Z_2$, and $Z_3$ are as defined for Formula (Ic).
In some embodiments, provided is a compound of any one of Formula (Ic-1) to (Ic-19):
(Ic-1)
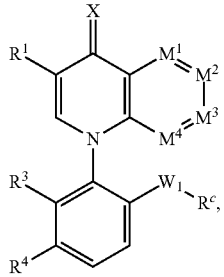

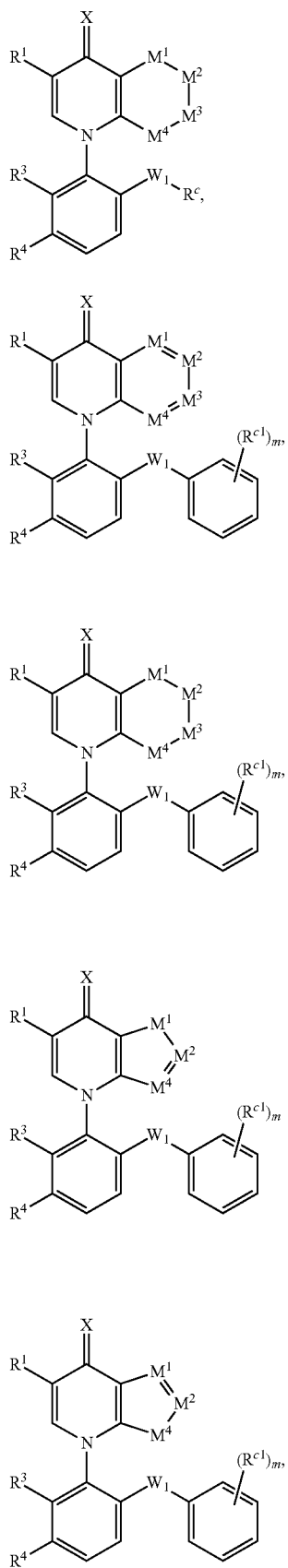
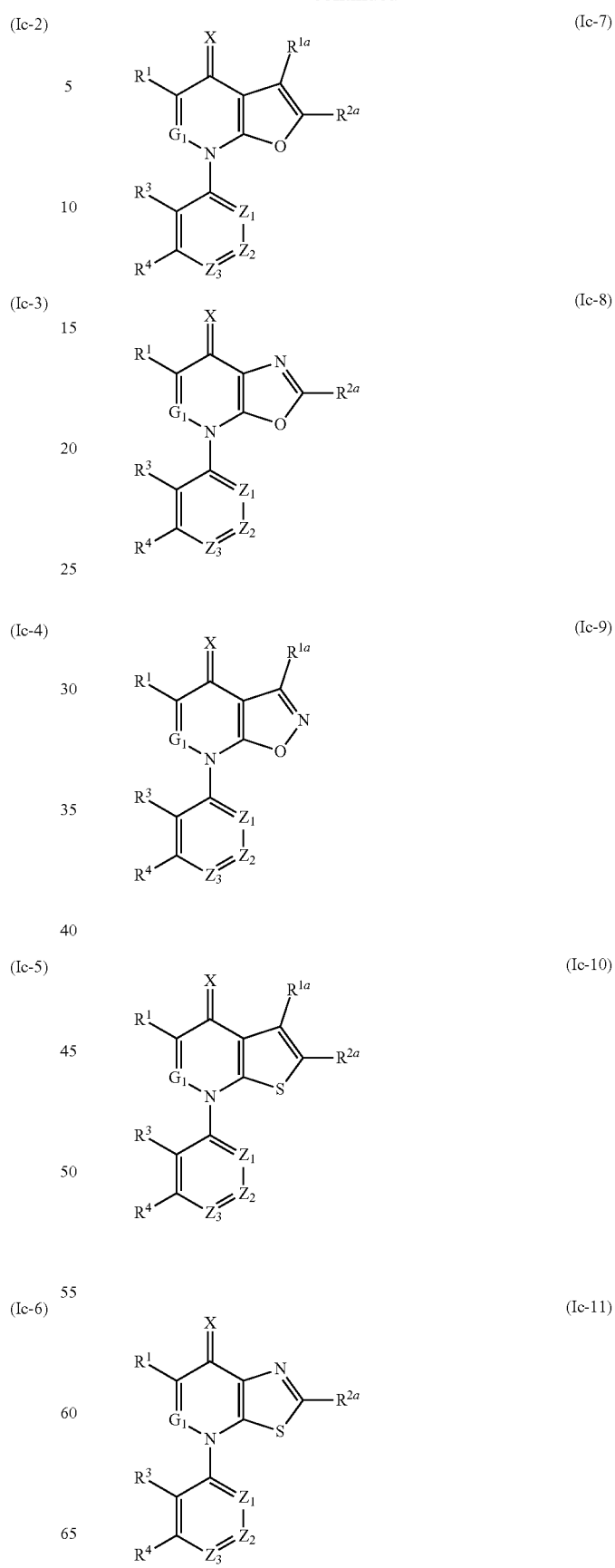

(Ic-12)
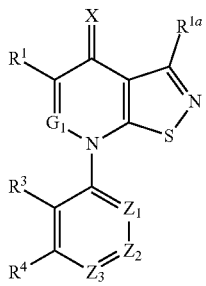

(Ic-13)
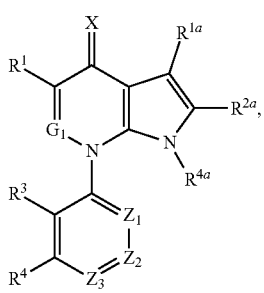

(Ic-14)
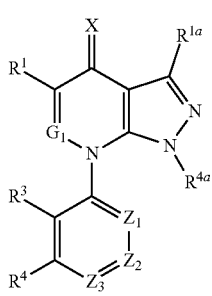

(Ic-15)
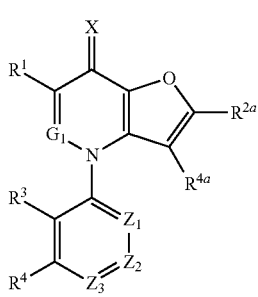

(Ic-16)

(Ic-17)
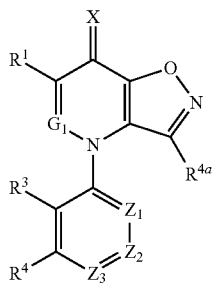

(Ic-18)
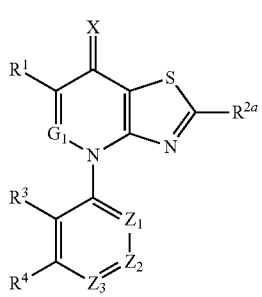

(Ic-19)
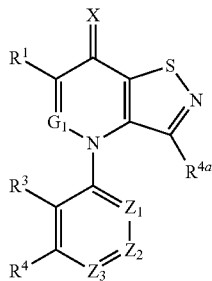

or a tautomer or isomer thereof, or a pharmaceutically acceptable salt of any of the foregoing, wherein $G_1$, $R^{1a}$, $R^{2a}$, $R^{4a}$, $Z_1$, $Z_2$, $Z_3$, X, $R^1$, $R^3$, $R^4$, $M^1$, $M^2$, $M^3$, $M^4$, $W_1$, $R^c$, $R^{c1}$ and m are as defined for Formula (Ic). In some embodiments, provided is a compound of any one of Formula (Ic-i) to (Ic-6), or a tautomer or isomer thereof, or a pharmaceutically acceptable salt of any of the foregoing.

In some embodiments, the compound of Formula (I), or a tautomer or isomer thereof, or a pharmaceutically acceptable salt of any of the foregoing, is of Formula (II), or a tautomer or isomer thereof, or a pharmaceutically acceptable salt of any of the foregoing, (II)
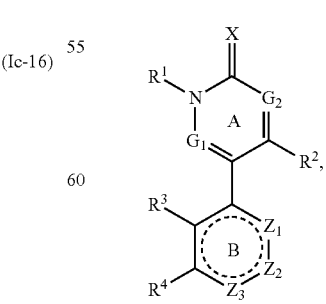

wherein X, $G_1$, $G_2$, $R^1$, $R^2$, $R^3$, $R^4$,

, $Z_1$, $Z_2$ and $Z_3$ are as defined for Formula (I).

In some embodiments of a compound of Formula (II), or a tautomer or isomer thereof, or a pharmaceutically acceptable salt of any of the foregoing, at least one of $R^3$ and $R^4$ is $-(CH_2)_mN(R^f)W_3R^g$ or $-(CH_2)_mW_3R^g$. In some embodiments, when $R^1$ is $-(CH_2)_mN(R^f)W_3R^g$ or $-(CH_2)_mN(R^f)C(O)OR^h$, $R^3$ is $-(CH_2)_mN(R^f)C(O)OR^h$, or $R^4$ is $-(CH_2)_mN(R^f)C(O)OR^h$, then $Z_1$ is $C-W_1-R^c$, wherein $W_1$ is $-O-$ or $-NR^{w1}-$ and $R^c$ is $C_3$-$C_6$ cycloalkyl, 3- to 6-membered heterocyclyl, $C_6$-$C_{14}$ aryl, or 5- to 6-membered heteroaryl, wherein the $C_3$-$C_6$ cycloalkyl, 3- to 6-membered heterocyclyl, $C_6$-$C_{14}$ aryl, or 5- to 6-membered heteroaryl of $R^c$ are each independently substituted by $R^{c1}$. In some embodiments, when $R^1$ is $-(CH_2)_mN(R^f)W_3R^g$ or $-(CH_2)_mN(R^f)C(O)OR^h$, $R^3$ is $-(CH_2)_mN(R^f)C(O)OR^h$, or $R^4$ is $-(CH_2)_mN(R^f)C(O)OR^h$, then $Z_1$ is $C-W_1-R^c$, wherein $W_1$ is $-O-$ or $-NR^{w1}-$ and $R^c$ is phenyl substituted by $R^{c1}$, wherein each $R^{c1}$ is independently halogen, $C_1$-$C_4$ alkyl, or $C_1$-$C_4$ alkoxy. In some embodiments, $Z_1$ is $C-W_1-R^c$, wherein $W_1$ is $-O-$ or $-NR^{w1}-$ and $R^c$ is $C_3$-$C_6$ cycloalkyl, 3- to 6-membered heterocyclyl, $C_6$-$C_{14}$ aryl, or 5- to 6-membered heteroaryl, wherein the $C_3$-$C_6$ cycloalkyl, 3- to 6-membered heterocyclyl, $C_6$-$C_{14}$ aryl, or 5- to 6-membered heteroaryl of $R^c$ are each independently substituted by $R^{c1}$. In some embodiments, $Z_1$ is $C-W_1-R^c$, wherein $W_1$ is $-O-$ or $-NR^{w1}-$ and $R^c$ is phenyl substituted by $R^{c1}$, wherein each $R^{c1}$ is independently halogen, $C_1$-$C_4$ alkyl, or $C_1$-$C_4$ alkoxy. In some embodiments, at least one of $R^1$, $R^3$ and $R^4$ is $-(CH_2)_mN(R^f)W_3R^g$ or $-(CH_2)_mW_3R^g$. In some embodiments, $R^4$ is $-(CH_2)_mN(R^f)W_3R^g$ or $-(CH_2)_mW_3R^g$.

In some embodiments, the compound of Formula (I), or a tautomer or isomer thereof, or a pharmaceutically acceptable salt of any of the foregoing, is of Formula (III), or a tautomer or isomer thereof, or a pharmaceutically acceptable salt of any of the foregoing,

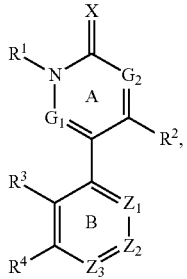

(III)

wherein
$Z_1$ is $C-W_1-R^c$ or N;
$Z_2$ is $C-W_2-R^d$ or N;
$Z_3$ is $C-R^e$ or N; and
X, $R^1$, $R^2$, $G_1$, $G_2$, $R^3$, $R^4$, $W_1$, $W_2$, $R^c$, $R^d$, and $R^e$ are as defined for Formula (I).

In some embodiments of a compound of Formula (III), or a tautomer or isomer thereof, or a pharmaceutically acceptable salt of any of the foregoing, at least one of $R^3$ and $R^4$ is $-(CH_2)_mN(R^f)W_3R^g$ or $-(CH_2)_mW_3R^g$. In some embodiments, when $R^1$ is $-(CH_2)_mN(R^f)W_3R^g$ or $-(CH_2)_mN(R^f)C(O)OR^h$, $R^3$ is $-(CH_2)_mN(R^f)C(O)OR^h$, or $R^4$ is $-(CH_2)_mN(R^f)C(O)OR^h$, then $Z_1$ is $C-W_1-R^c$, wherein $W_1$ is $-O-$ or $-NR^{w1}-$ and $R^c$ is $C_3$-$C_6$ cycloalkyl, 3- to 6-membered heterocyclyl, $C_6$-$C_{14}$ aryl, or 5- to 6-membered heteroaryl, wherein the $C_3$-$C_6$ cycloalkyl, 3- to 6-membered heterocyclyl, $C_6$-$C_{14}$ aryl, or 5- to 6-membered heteroaryl of $R^c$ are each independently substituted by $R^{c1}$. In some embodiments, when $R^1$ is $-(CH_2)_mN(R^f)W_3R^g$ or $-(CH_2)_mN(R^f)C(O)OR^h$, $R^3$ is $-(CH_2)_mN(R^f)C(O)OR^h$, or $R^4$ is $-(CH_2)_mN(R^f)C(O)OR^h$, then $Z_1$ is $C-W_1-R^c$, wherein $W_1$ is $-O-$ or $-NR^{w1}-$ and $R^c$ is phenyl substituted by $R^{c1}$, wherein each $R^{c1}$ is independently halogen, $C_1$-$C_4$ alkyl, or $C_1$-$C_4$ alkoxy. In some embodiments, $Z_1$ is $C-W_1-R^c$, wherein $W_1$ is $-O-$ or $-NR^{w1}-$ and $R^c$ is $C_3$-$C_6$ cycloalkyl, 3- to 6-membered heterocyclyl, $C_6$-$C_{14}$ aryl, or 5- to 6-membered heteroaryl, wherein the $C_3$-$C_6$ cycloalkyl, 3- to 6-membered heterocyclyl, $C_6$-$C_{14}$ aryl, or 5- to 6-membered heteroaryl of $R^c$ are each independently substituted by $R^{c1}$. In some embodiments, $Z_1$ is $C-W_1-R^c$, wherein $W_1$ is $-O-$ or $-NR^{w1}-$ and $R^c$ is phenyl substituted by $R^{c1}$, wherein each $R^{c1}$ is independently halogen, $C_1$-$C_4$ alkyl, or $C_1$-$C_4$ alkoxy. In some embodiments, at least one of $R^1$, $R^3$ and $R^4$ is $-(CH_2)_mN(R^f)W_3R^g$ or $-(CH_2)_mW_3R^g$. In some embodiments, $R^4$ is $-(CH_2)_mN(R^f)W_3R^g$ or $-(CH_2)_mW_3R^g$.

In some embodiments, the compound of Formula (I), or a tautomer or isomer thereof, or a pharmaceutically acceptable salt of any of the foregoing, is of Formula (IV), or a tautomer or isomer thereof, or a pharmaceutically acceptable salt of any of the foregoing,

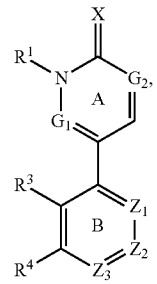

(IV)

wherein
$Z_1$ is $C-W_1-R^c$ or N;
$Z_2$ is $C-W_2-R^d$ or N;
$Z_3$ is $C-R^e$ or N; and
X, $R^1$, $G_1$, $G_2$, $R^3$, $R^4$, $W_1$, $W_2$, $R^c$, $R^d$, and $R^e$ are as defined for Formula (I).

In some embodiments of a compound of Formula (IV), or a tautomer or isomer thereof, or a pharmaceutically acceptable salt of any of the foregoing, at least one of $R^3$ and $R^4$ is $-(CH_2)_mN(R^f)W_3R^g$ or $-(CH_2)_mW_3R^g$. In some embodiments, when $R^1$ is $-(CH_2)_mN(R^f)W_3R$ or $-(CH_2)_mN(R^f)C(O)OR^h$, $R^3$ is $-(CH_2)_mN(R^f)C(O)OR^h$, or $R^4$ is $-(CH_2)_mN(R^f)C(O)OR^h$, then $Z_1$ is $C-W_1-R^c$, wherein $W_1$ is $-O-$ or $-NR^{w1}-$ and $R^c$ is $C_3$-$C_6$ cycloalkyl, 3- to 6-membered heterocyclyl, $C_6$-$C_{14}$ aryl, or 5- to 6-membered heteroaryl, wherein the $C_3$-$C_6$ cycloalkyl, 3- to 6-membered heterocyclyl, $C_6$-$C_{14}$ aryl, or 5- to 6-membered heteroaryl of $R^c$ are each independently substituted by $R^{c1}$. In some embodiments, when $R^1$ is $-(CH_2)_mN(R^f)W_3R^g$ or $-(CH_2)_mN(R^f)C(O)OR^h$, $R^3$ is $-(CH_2)_mN(R^f)C(O)OR^h$, or $R^4$ is $-(CH_2)_mN(R^f)C(O)OR^h$, then $Z_1$ is $C-W_1-R^c$, wherein $W_1$ is $-O-$ or $-NR^{w1}-$ and $R^c$ is phenyl substituted by $R^{c1}$, wherein each $R^{c1}$ is independently halogen, $C_1$-$C_4$ alkyl, or $C_1$-$C_4$ alkoxy. In some embodiments, $Z_1$ is C—$W_1$—$R^c$, wherein $W_1$ is —O— or —$NR^{w1}$— and $R^c$ is $C_3$-$C_6$ cycloalkyl, 3- to 6-membered heterocyclyl, $C_6$-$C_{14}$ aryl, or 5- to 6-membered heteroaryl, wherein the $C_3$-$C_6$ cycloalkyl, 3- to 6-membered heterocyclyl, $C_6$-$C_{14}$ aryl, or 5- to 6-membered heteroaryl of $R^c$ are each independently substituted by $R^{c1}$. In some embodiments, $Z_1$ is C—$W_1$—$R^c$, wherein $W_1$ is —O— or —$NR^{w1}$— and $R^c$ is phenyl substituted by $R^{c1}$, wherein each $R^{c1}$ is independently halogen, $C_1$-$C_4$ alkyl, or $C_1$-$C_4$ alkoxy. In some embodiments, at least one of $R^1$, $R^3$ and $R^4$ is —$(CH_2)_mN(R^f)W_3R^g$ or —$(CH_2)_mW_3R^g$. In some embodiments, $R^4$ is —$(CH_2)_mN(R^f)W_3R$ or —$(CH_2)_mW_3R^g$.

In some embodiments, provided is a compound of any one of Formula (IV-a) to (IV-k):

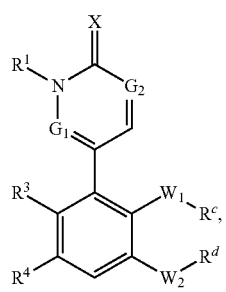
(IV-a)

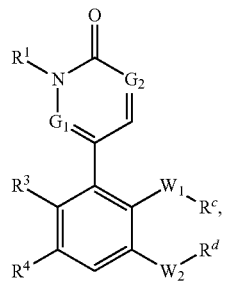
(IV-b)

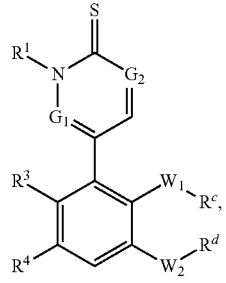
(IV-c)

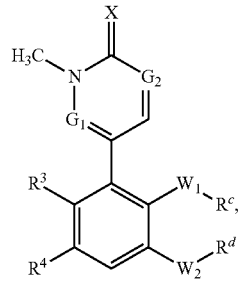
(IV-d)

-continued

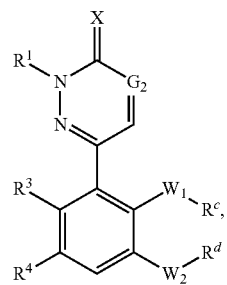
(IV-e)

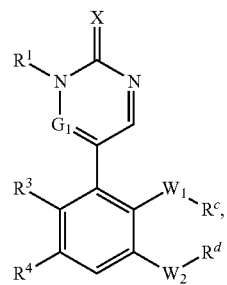
(IV-f)

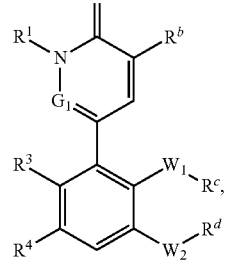
(IV-g)

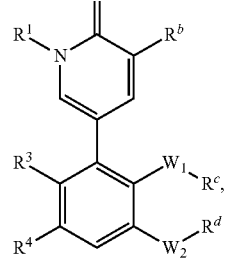
(IV-h)

(IV-i)

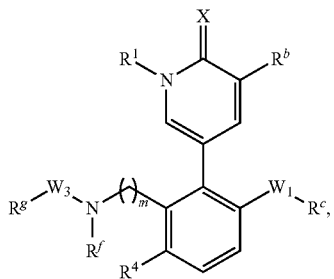
(IV-j)
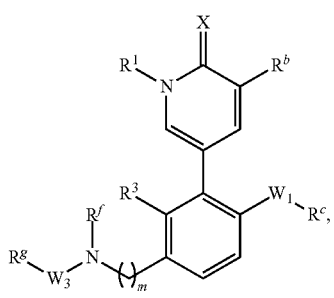
(IV-k)
and
or a tautomer or isomer thereof, or a pharmaceutically acceptable salt of any of the foregoing, wherein X, $R^1$, $R^b$, $G_1$, $G_2$, $W_1$, $W_2$, $W_3$, $R^c$, $R^d$, $R^f$, $R^g$, $R^3$, $R^4$ and m are as defined for formula (IV).
In some embodiments, provided is a compound of any one of Formula (IVg-1) to (IVg-9):
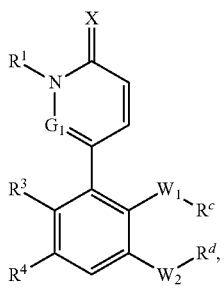
(IV-g-1)
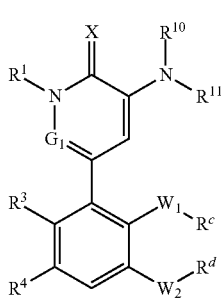
(IV-g-2)
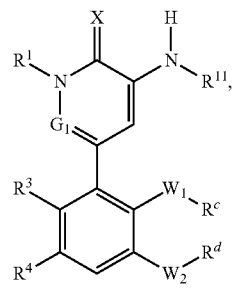
(IV-g-3)
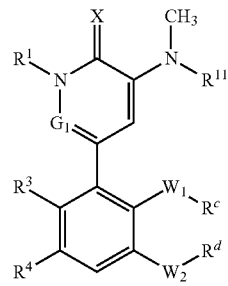
(IV-g-4)
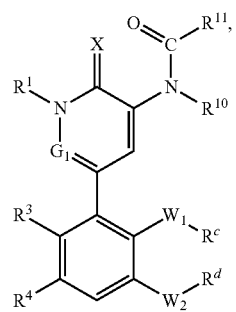
(IV-g-5)
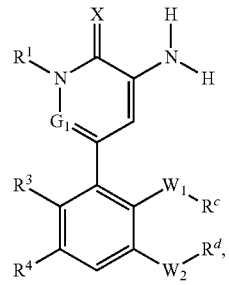
(IV-g-6)
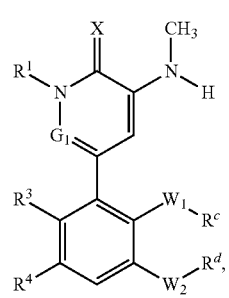
(IV-g-7)

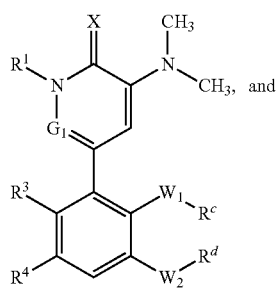
(IV-g-8)
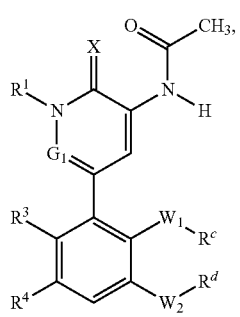
(IV-g-9)
or a tautomer or isomer thereof, or a pharmaceutically acceptable salt of any of the foregoing, wherein X, $R^1$, $G_1$, $R^{10}$, $R^{11}$, $R^{12}$, $W_1$, $W_2$, $R^c$, Rd, $R^3$ and $R^4$ are as defined for formula (IV).
In some embodiments, provided is a compound of any one of Formula (IV-i-1) to (IV-i-11):
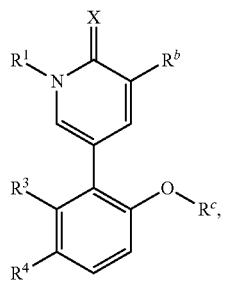
(IV-i-1)
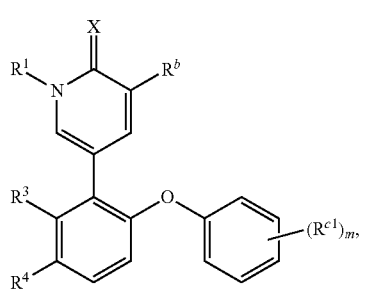
(IV-i-2)
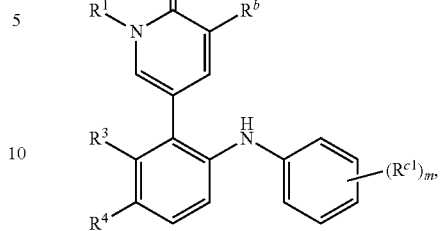
(IV-i-3)
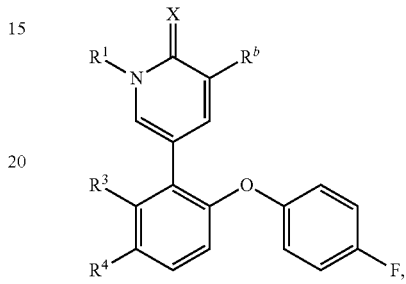
(IV-i-4)
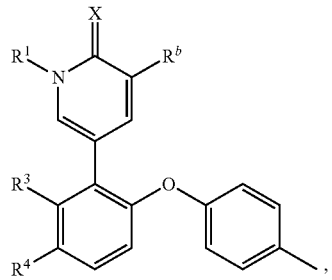
(IV-i-5)
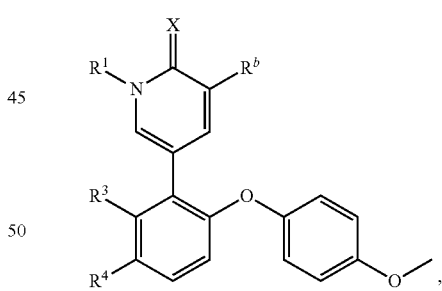
(IV-i-6)
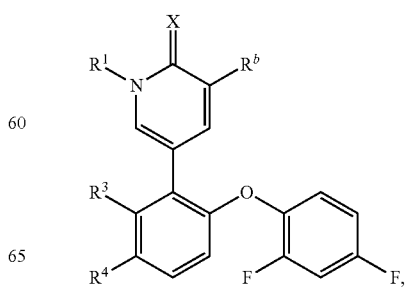
(IV-i-7)

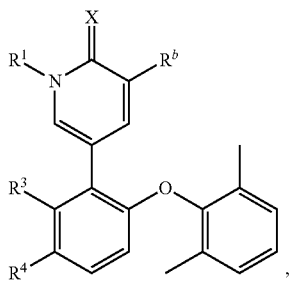 (IV-i-8)
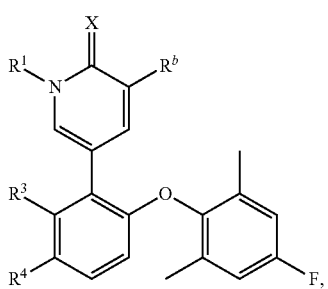 (IV-i-9)
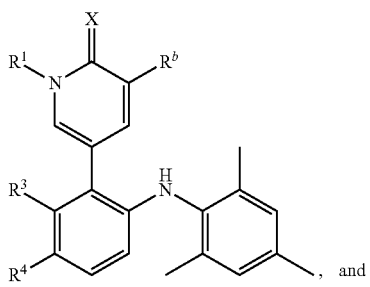 (IV-i-10), and
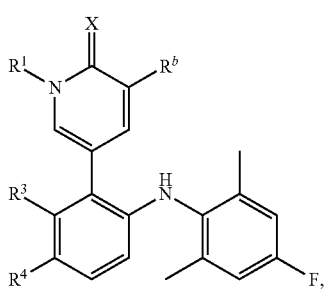 (IV-i-11)
or a tautomer or isomer thereof, or a pharmaceutically acceptable salt of any of the foregoing, wherein X, $R^1$, $R^b$, $G_1$, $G_2$, $W_1$, $R^c$, $R^{c1}$, $R^3$, $R^4$ and m are as defined for Formula (IV).
In some embodiments, provided is a compound of any one of Formula (IV-k-1) to (IV-k-12):
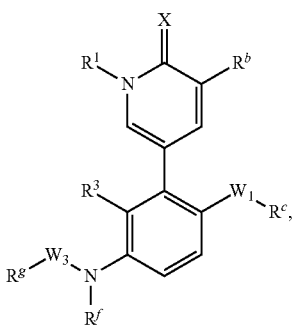 (IV-k-1)
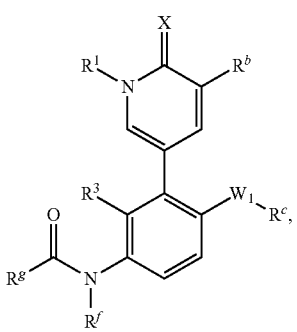 (IV-k-2)
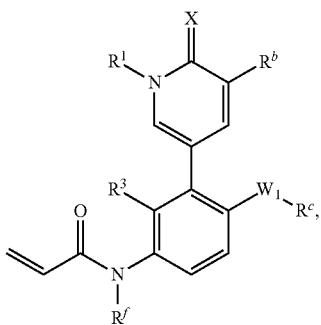 (IV-k-3)
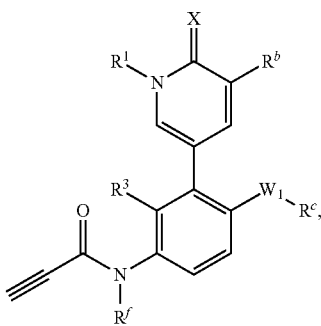 (IV-k-4)
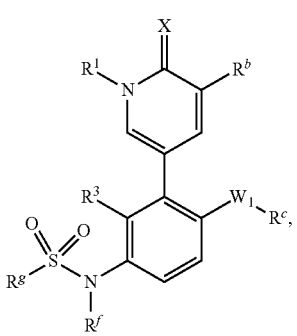 (IV-k-5)

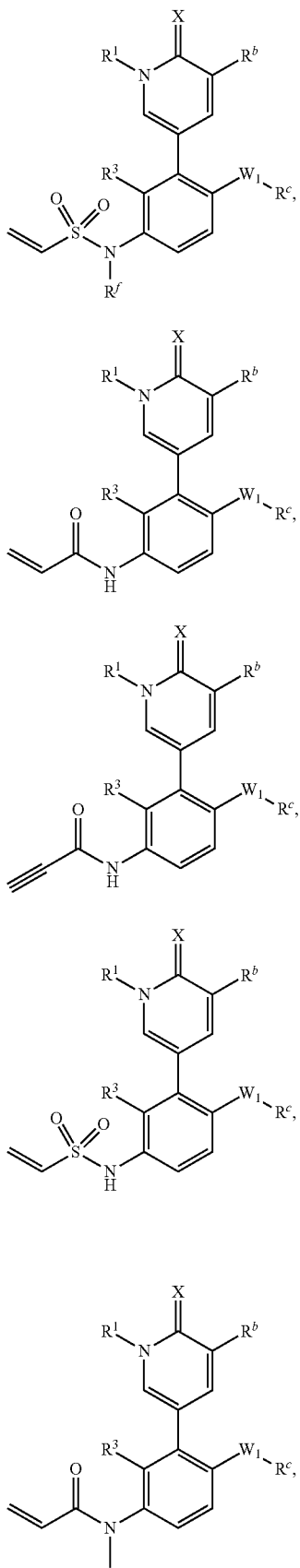
(IV-k-6)
(IV-k-7)
(IV-k-8)
(IV-k-9)
(IV-k-10)

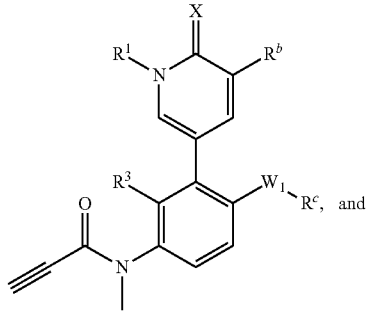
(IV-k-11)

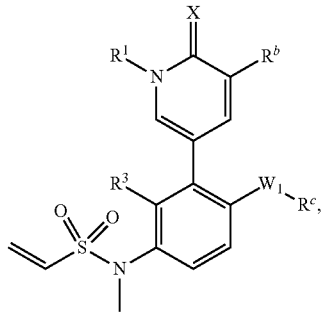
(IV-k-12)

or a tautomer or isomer thereof, or a pharmaceutically acceptable salt of any of the foregoing, wherein X, $R^1$, $R^b$, $W_1$, $W_3$, $R^c$, $R^g$, $R^f$ and $R^3$ are as defined for formula (IV).

In some embodiments, provided is a compound of Formula (V):

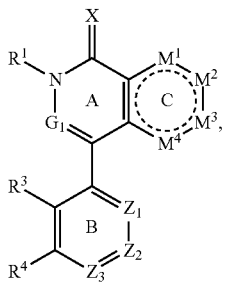
(V)

or a tautomer or isomer thereof, or a pharmaceutically acceptable salt of any of the foregoing,
wherein:
$Z_1$ is C—$W_1$—$R^c$ or N;
$Z_2$ is C—$W_2$—$R^d$ or N;
$Z_3$ is C—$R^e$ or N;
$M^1$ is O, S, N, $NR^{1a}$, $CR^{1a}$, or $CR^{1a}R^{1b}$;
$M^2$ is N, $NR^{2a}$, $CR^{2a}$, or $CR^{2a}R^{2b}$;
$M^3$ is N, $NR^{3a}$, $CR^{3a}$, $CR^{3a}R^{3b}$ or absent;
$M^4$ is O, S, N, $NR^{4a}$, $CR^{4a}$, or $CR^{4a}R^{4b}$, provided that
  (1) no more than three of $M^1$, $M^2$, $M^3$ and $M^4$ are N or N substituted by $R^{1a}$, $R^{2a}$, $R^{3a}$, or $R^{4a}$, and
  (2) if $M^3$ is absent, then at least one of $M^1$ and $M^4$ is not O or S;
$R^{1a}$, $R^{1b}$, $R^{2a}$, $R^{2b}$, $R^{3a}$, $R^{3b}$, $R^{4a}$, and $R^{4b}$ are each independently hydrogen, halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, $OR^{10}$, $NR^{10}R^{11}$, $C(O)OR^0$, C(O)NR$^{10}$R$^{11}$, NR$^{10}$C(O)R$^{11}$, S(O)$_2$R$^{10}$, NR$^{10}$S(O)$_2$R$^{11}$ or S(O)$_2$NR$^{10}$R$^{11}$; and X, R$^1$, G$_1$, R$^3$, R$^4$, W$_1$, W$_2$, R$^c$, R$^d$, R$^e$, R$^{10}$, and R$^{11}$ are as defined herein for Formula (I).

In some embodiments of a compound of Formula (V), or a tautomer or isomer thereof, or a pharmaceutically acceptable salt of any of the foregoing, at least one of R$^3$ and R$^4$ is —(CH$_2$)$_m$N(R$^f$)W$_3$R$^g$ or —(CH$_2$)$_m$W$_3$R$^g$. In some embodiments, when R$^1$ is —(CH$_2$)$_m$N(R$^f$)W$_3$R$^g$ or —(CH$_2$)$_m$N(R$^f$)C(O)OR$^h$, R$^3$ is —(CH$_2$)$_m$N(R$^f$)C(O)OR$^h$, or R$^4$ is —(CH$_2$)$_m$N(R$^f$)C(O)OR$^h$, then Z$_1$ is C—W$_1$—R$^c$, wherein W$_1$ is —O— or —NR$^{w1}$— and R$^c$ is C$_3$-C$_6$ cycloalkyl, 3- to 6-membered heterocyclyl, C$_6$-C$_{14}$ aryl, or 5- to 6-membered heteroaryl, wherein the C$_3$-C$_6$ cycloalkyl, 3- to 6-membered heterocyclyl, C$_6$-C$_{14}$ aryl, or 5- to 6-membered heteroaryl of R$^c$ are each independently substituted by R$^{c1}$. In some embodiments, when R$^1$ is —(CH$_2$)$_m$N(R$^f$)W$_3$R$^g$ or —(CH$_2$)$_m$N(R$^f$)C(O)OR$^h$, R$^3$ is —(CH$_2$)$_m$N(R$^f$)C(O)OR$^h$, or R$^4$ is —(CH$_2$)$_m$N(R$^f$)C(O)OR$^h$, then Z$_1$ is C—W$_1$—R$^c$, wherein W$_1$ is —O— or —NR$^{w1}$— and R$^c$ is phenyl substituted by R$^{c1}$, wherein each R$^{c1}$ is independently halogen, C$_1$-C$_4$ alkyl, or C$_1$-C$_4$ alkoxy. In some embodiments, Z$_1$ is C—W$_1$—R$^c$, wherein W$_1$ is —O— or —NR$^{w1}$— and R$^c$ is C$_3$-C$_6$ cycloalkyl, 3- to 6-membered heterocyclyl, C$_6$-C$_{14}$ aryl, or 5- to 6-membered heteroaryl, wherein the C$_3$-C$_6$ cycloalkyl, 3- to 6-membered heterocyclyl, C$_6$-C$_{14}$ aryl, or 5- to 6-membered heteroaryl of R$^c$ are each independently substituted by R$^{c1}$. In some embodiments, Z$_1$ is C—W$_1$—R$^c$, wherein W$_1$ is —O— or —NR$^{w1}$— and R$^c$ is phenyl substituted by R$^{c1}$, wherein each R$^{c1}$ is independently halogen, C$_1$-C$_4$ alkyl, or C$_1$-C$_4$ alkoxy. In some embodiments, at least one of R$^1$, R$^3$ and R$^4$ is —(CH$_2$)$_m$N(R$^f$)W$_3$R$^g$ or —(CH$_2$)$_m$W$_3$R$^g$. In some embodiments, R$^4$ is —(CH$_2$)$_m$N(R$^f$)W$_3$R$^g$ or —(CH$_2$)$_m$W$_3$R$^g$.

In some embodiments of a compound of Formula (V), the C ring is aryl, in which M$^1$, M$^2$, M$^3$ and M$^4$ are CH. In some embodiments of a compound of Formula (V), C ring is heteroaryl, in which any one of M$^1$, M$^2$, M$^3$ and M$^4$ is N, and others are CH. In some embodiments of a compound of Formula (V), C ring is heteroaryl, in which any two of M$^1$, M$^2$, M$^3$ and M$^4$ are N, and others are CH. In some embodiments of a compound of Formula (V), C ring is heterocyclyl, in which any one of M$^1$, M$^2$, M$^3$ and M$^4$ is NH and other are CH$_2$. In some embodiments of a compound of Formula (V), C ring is heterocyclyl, in which M$^1$ and M$^2$ are NH, and M$^3$ and M$^4$ are CH$_2$. In some embodiments of a compound of Formula (V), C ring is heterocyclyl, in which M$^1$ is NH, M$^4$ is O, and M$^2$ and M$^3$ are CH$_2$. In some embodiments of a compound of Formula (V), C ring is heterocyclyl, in which M$^1$ is O, M$^4$ is NH, and M$^2$ and M$^3$ are CH$_2$. In some embodiments of a compound of Formula (V), C ring is heterocyclyl, in which M$^1$ is O, and M$^2$, M$^3$ and M$^4$ are CH$_2$. In some embodiments of a compound of Formula (V), C ring is heterocyclyl, in which M$^4$ is O, and M$^1$, M$^2$ and M$^3$ are CH$_2$. In some embodiments of a compound of Formula (V), C ring is heterocyclyl, in which M$^1$ and M$^4$ are O, and M$^2$ and M$^3$ are CH$_2$. In some embodiments of a compound of Formula (V), C ring is cycloalkyl, in which M$^1$, M$^2$, M$^3$ and M$^4$ are CH$_2$.

In some embodiments of a compound of Formula (V), C ring is heteroaryl, in which M$^1$ is O, M$^2$ and M$^4$ are CH, and M$^3$ is absent. In some embodiments of a compound of Formula (V), C ring is heteroaryl, in which M$^4$ is O, M$^1$ and M$^2$ are CH, and M$^3$ is absent. In some embodiments of a compound of Formula (V), C ring is heteroaryl, in which M$^1$ is S, M$^2$ and M$^4$ are CH, and M$^3$ is absent. In some embodiments of a compound of Formula (V), C ring is heteroaryl, in which M$^4$ is S, M$^1$ and M$^2$ are CH, and M$^3$ is absent. In some embodiments of a compound of Formula (V), C ring is heteroaryl, in which M$^1$ is O, M$^2$ is N, M$^4$ is CH, and M$^3$ is absent. In some embodiments of a compound of Formula (V), C ring is heteroaryl, in which M$^1$ is O, M$^4$ is N, M$^2$ is CH, and M$^3$ is absent. In some embodiments of a compound of Formula (V), C ring is heteroaryl, in which M$^4$ is O, M$^2$ is N, M$^1$ is CH, and M$^3$ is absent. In some embodiments of a compound of Formula (V), C ring is heteroaryl, in which M$^1$ is O, M$^4$ is N, M$^2$ is CH, and M$^3$ is absent. In some embodiments of a compound of Formula (V), C ring is heteroaryl, in which M$^1$ is S, M$^2$ is N, M$^4$ is CH, and M$^3$ is absent. In some embodiments of a compound of Formula (V), C ring is heteroaryl, in which M$^1$ is S, M$^4$ is N, M$^2$ is CH, and M$^3$ is absent. In some embodiments of a compound of Formula (V), C ring is heteroaryl, in which M$^4$ is S, M$^2$ is N, M$^1$ is CH, and M$^3$ is absent. In some embodiments of a compound of Formula (V), C ring is heteroaryl, in which M$^1$ is S, M$^4$ is N, M$^2$ is CH, and M$^3$ is absent. In some embodiments of a compound of Formula (V), C ring is heteroaryl, in which M$^1$ and M$^2$ are CH, M$^4$ is NH, and M$^3$ is absent. In some embodiments of a compound of Formula (V), C ring is heteroaryl, in which M$^1$ is CH, M$^2$ is N, M$^4$ is CH, and M$^3$ is absent. In some embodiments of a compound of Formula (V), C ring is heterocyclyl, in which M$^1$ is NH, M$^2$ and M$^4$ are CH and M$^3$ is absent. In some embodiments of a compound of Formula (V), C ring is heterocyclyl, in which M$^4$ is NH, M$^1$ and M$^2$ are CH, and M$^3$ is absent. In some embodiments of a compound of Formula (V), C ring is cycloalkyl, in which M$^1$, M$^2$, and M$^4$ are CH$_2$, and M$^3$ is absent.

In some embodiments, provided is a compound of any one of Formula (Va) to (Ve):

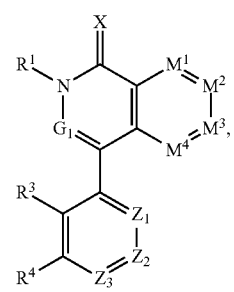

(Va)

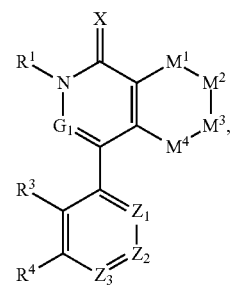

(Vb)

(Vc)
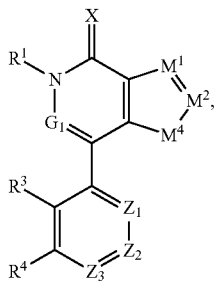
(Vd)
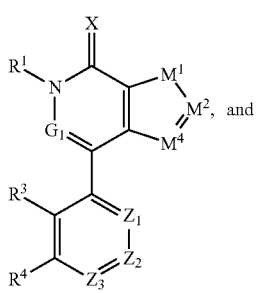
and
(Ve)
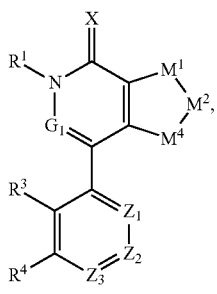
or a tautomer or isomer thereof, or a pharmaceutically acceptable salt of any of the foregoing, wherein X, $R^1$, $R^3$, $R^4$, $M^1$, $M^2$, $M^3$, $M^4$, $G_1$, $Z_1$, $Z_2$, and $Z_3$ are as defined for Formula (V).
In some embodiments, provided is a compound of any one of Formula (Va-1) to (Va-12):
(Va-1)
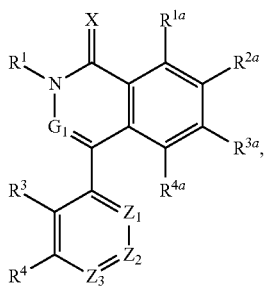
(Va-2)
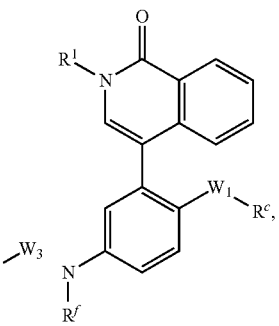
(Va-3)
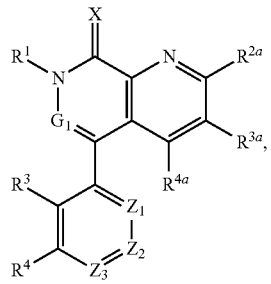
(Va-4)
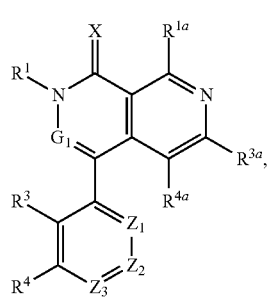
(Va-5)
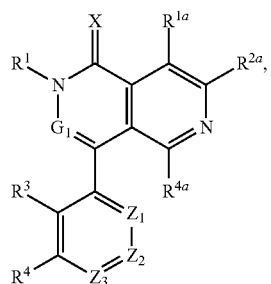
(Va-6)
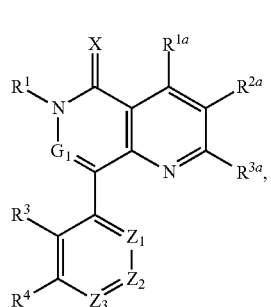

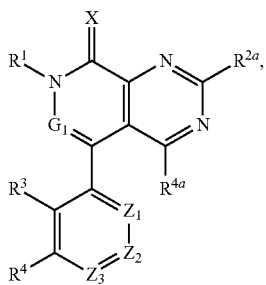 (Va-7)
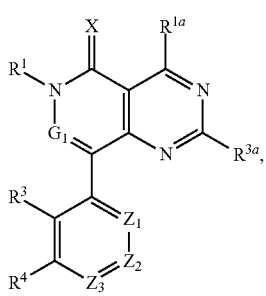 (Va-8)
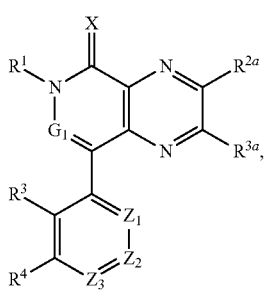 (Va-9)
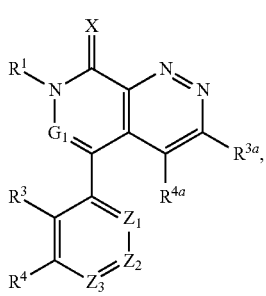 (Va-10)
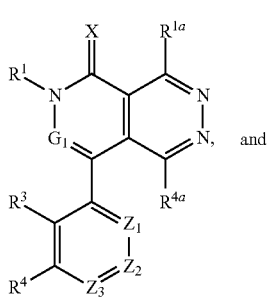 (Va-11)
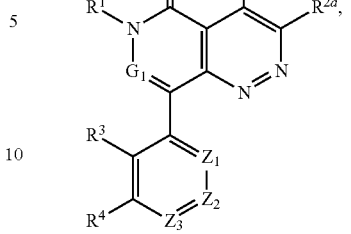 (Va-12)
or a tautomer or isomer thereof, or a pharmaceutically acceptable salt of any of the foregoing, wherein X, $R^1$, $R^3$, $R^4$, $R^{1a}$, $R^{2a}$, $R^{3a}$, $R^{4a}$, $W_1$, $W_3$, $R^c$, $R^f$, $R^g$, $G_1$, $Z_1$, $Z_2$, and $Z_3$ are as defined for Formula (V).
In some embodiments, provided is a compound of any one of Formula (Vb-1) to (Vb-12):
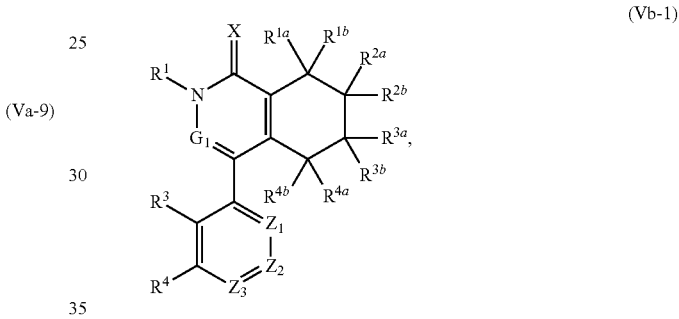 (Vb-1)
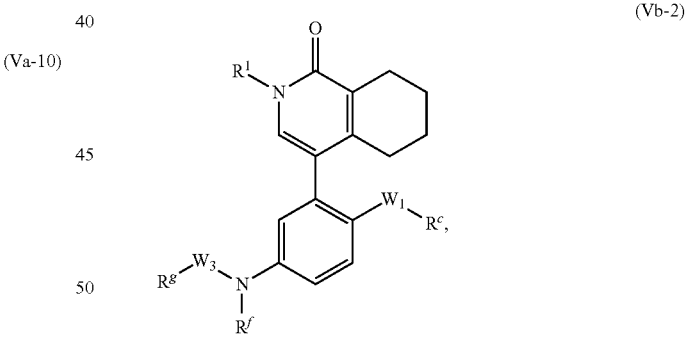 (Vb-2)
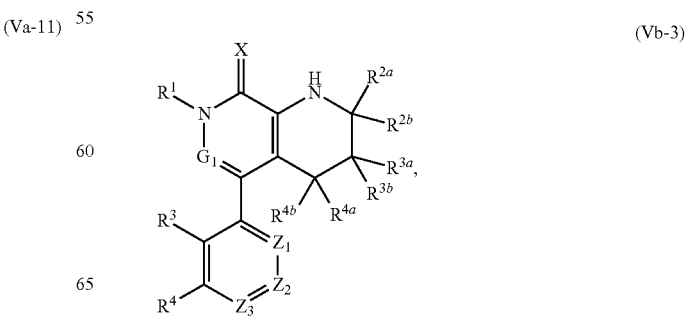 (Vb-3)

-continued
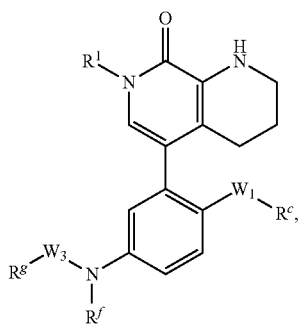
(Vb-4)
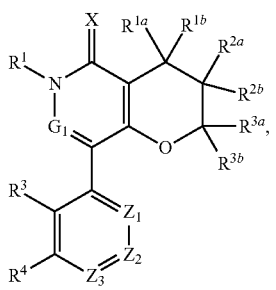
(Vb-5)
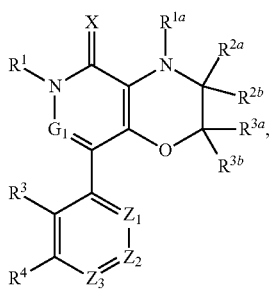
(Vb-6)
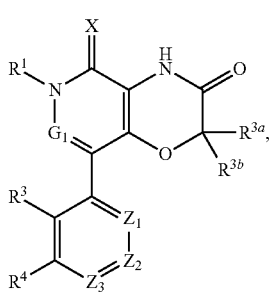
(Vb-7)
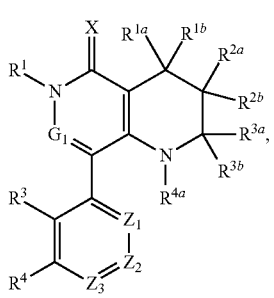
(Vb-8)
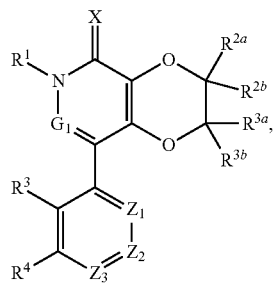
(Vb-9)
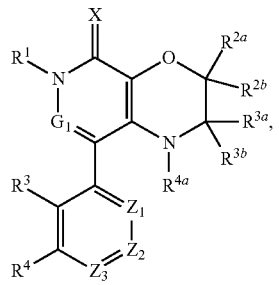
(Vb-10)
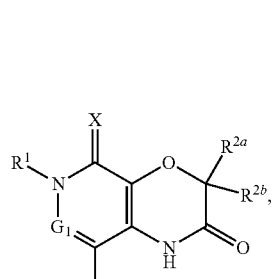
(Vb-11) and
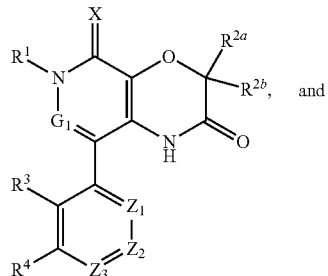
(Vb-12)
or a tautomer or isomer thereof, or a pharmaceutically acceptable salt of any of the foregoing, wherein X, $R^1$, $R^3$, $R^4$, $R^{1a}$, $R^{1b}$, $R^{2a}$, $R^{2b}$, $R^{3a}$, $R^{3b}$, $R^{4a}$, $R^{4b}$, $W_1$, $R^c$, $W_3$, $R^f$, $R^g$, $G_1$, $Z_1$, $Z_2$, and $Z_3$ are as defined for Formula (V).
In some embodiments, provided is a compound of any one of Formula (Vc-1) to (Vc-8):

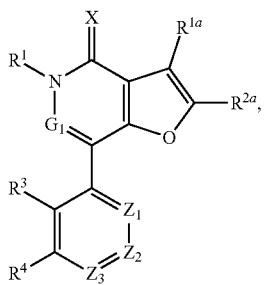
(Vc-1)
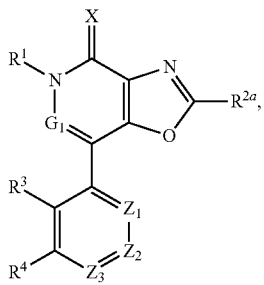
(Vc-2)
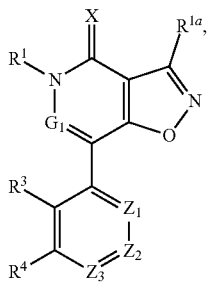
(Vc-3)
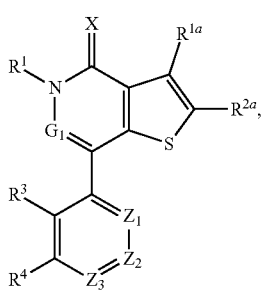
(Vc-4)
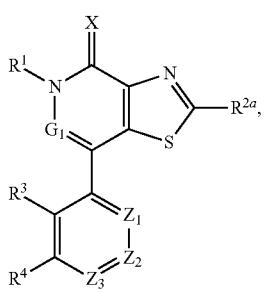
(Vc-5)
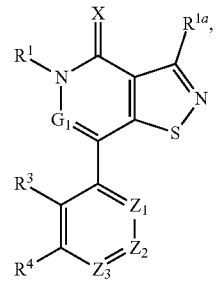
(Vc-6)
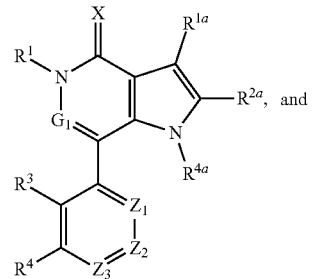
(Vc-7)
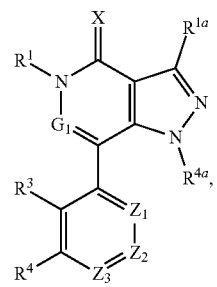
(Vc-8)
or a tautomer or isomer thereof, or a pharmaceutically acceptable salt of any of the foregoing, wherein X, $R^1$, $R^3$, $R^4$, $R^{1a}$, $R^{2a}$, $R^{4a}$, $G_1$, $Z_1$, $Z_2$, and $Z_3$ are as defined for Formula (V).
In some embodiments, provided is a compound of any one of Formula (Vc-1') to (Vc-12'):
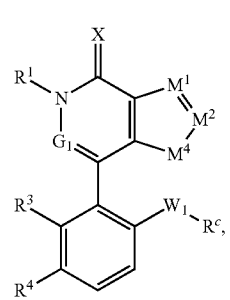
(Vc-1')

-continued
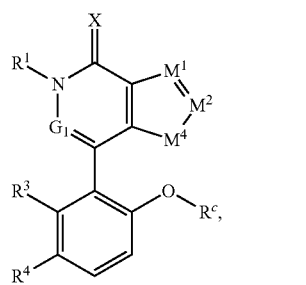
(Vc-2′)
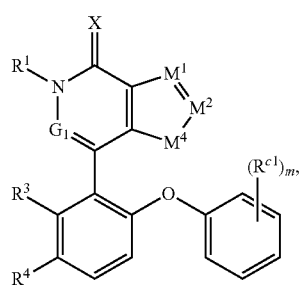
(Vc-3′)
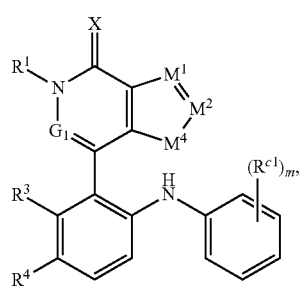
(Vc-4′)
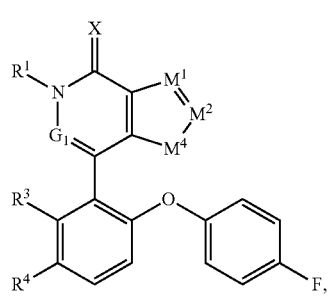
(Vc-5′)
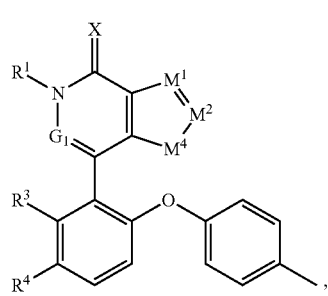
(Vc-6′)
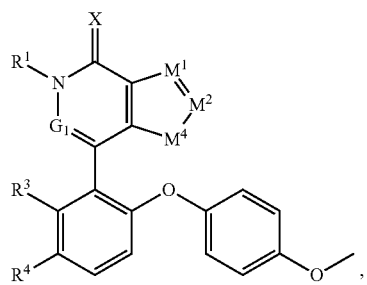
(Vc-7′)
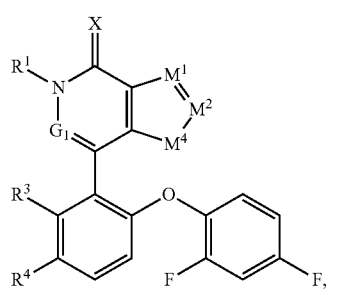
(Vc-8′)
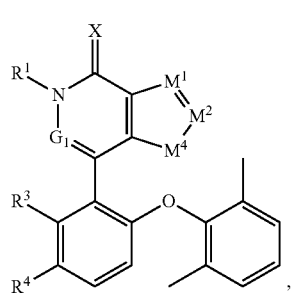
(Vc-9′)
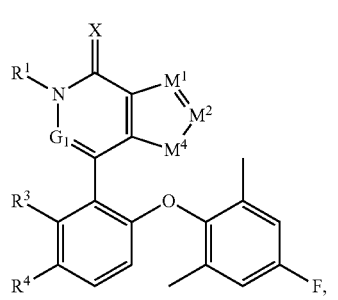
(Vc-10′)
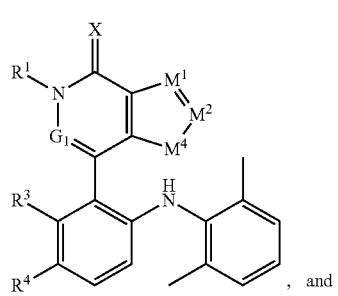
(Vc-11′)
, and

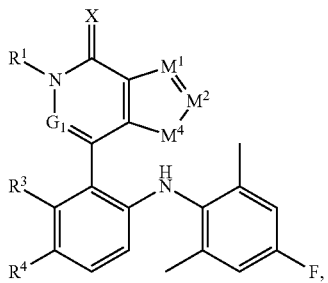
(Vc-12')

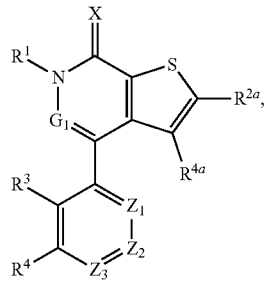
(Vd-4)

or a tautomer or isomer thereof, or a pharmaceutically acceptable salt of any of the foregoing, wherein $M^1$, $M^2$, $M^4$, X, $R^1$, $G_1$, $W_1$, $R^c$, $R^{c1}$, $R^3$, $R^4$ and m are as defined herein for Formula (V).

In some embodiments, provided is a compound of any one of Formula (Vd-1) to (Vd-6):

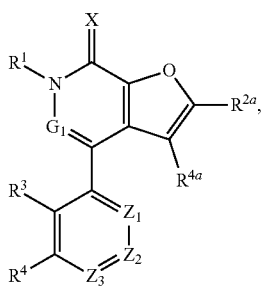
(Vd-1)

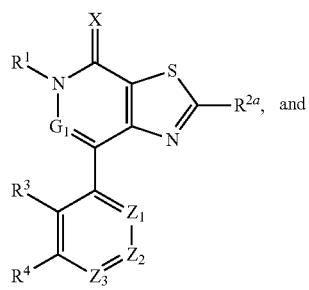
(Vd-5)

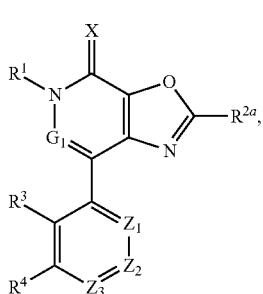
(Vd-2)

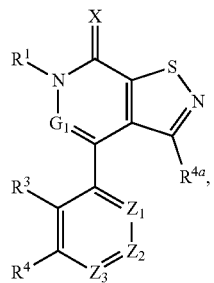
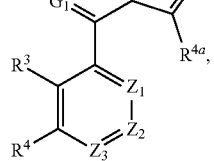
(Vd-6)

or a tautomer or isomer thereof, or a pharmaceutically acceptable salt of any of the foregoing, wherein X, $R^1$, $R^3$, $R^4$, $R^{2a}$, $R^{4a}$, $G_1$, $Z_1$, $Z_2$, and $Z_3$ are as defined for Formula (V).

In some embodiments, provided is a compound of any one of Formula (Vd-1') to (Vd-12'):

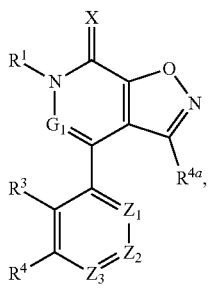
(Vd-3)

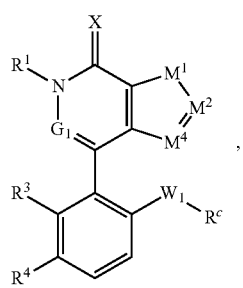
(Vd-1')

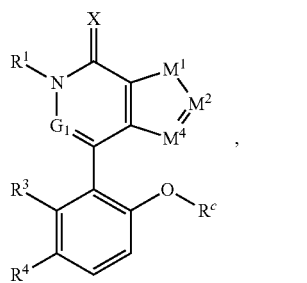
(Vd-2′)
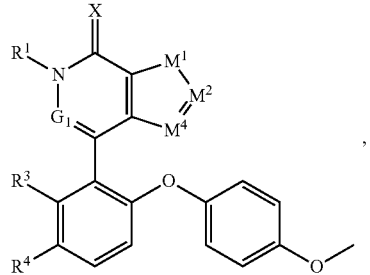
(Vd-7′)
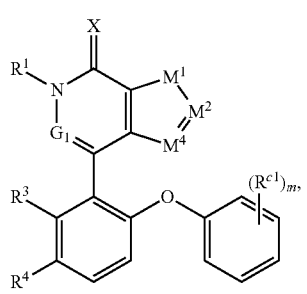
(Vd-3′)
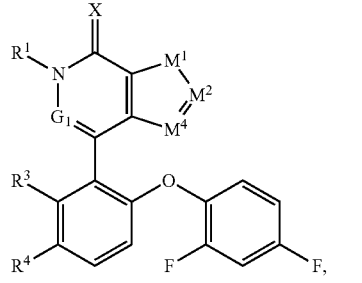
(Vd-8′)
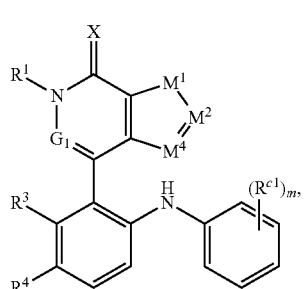
(Vd-4′)
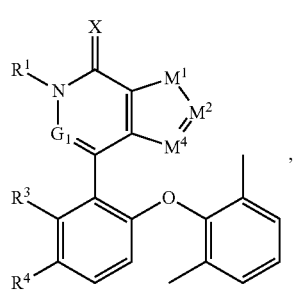
(Vd-9′)
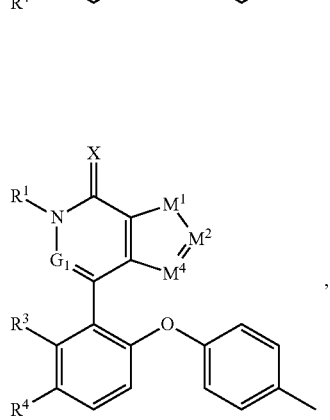
(Vd-5′)
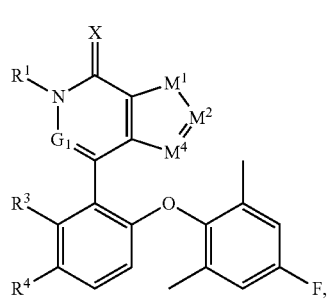
(Vd-10′)
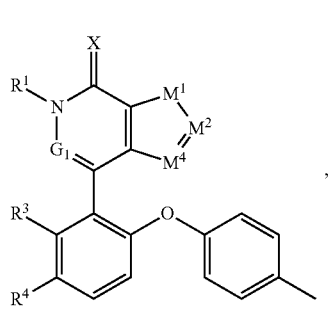
(Vd-6′)
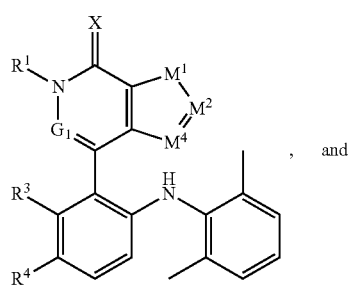
, and
(Vd-11′)

-continued (Vd-12')

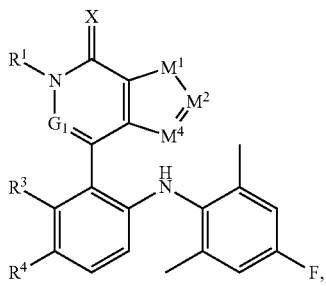

or a tautomer or isomer thereof, or a pharmaceutically acceptable salt of any of the foregoing, wherein $M^1$, $M^2$, $M^4$, X, $R^1$, $G_1$, $W_1$, $R^c$, $R^{c1}$, $R^3$, $R^4$ and m are as defined herein for Formula (V).

In some embodiments, provided is a compound of any one of Formula (Ve-1) to (Ve-5):

(Ve-1)

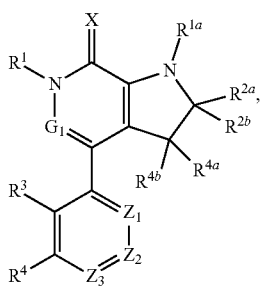

(Ve-2)

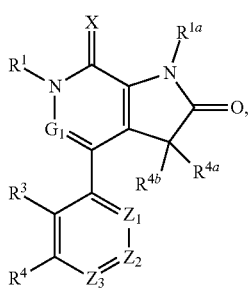

(Ve-3)

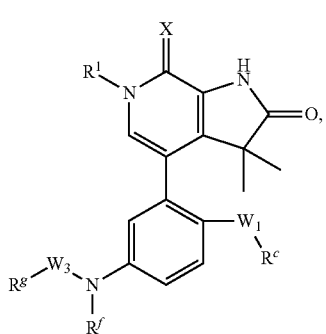

(Ve-4)

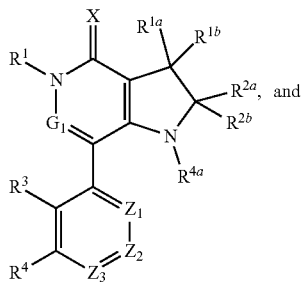

(Ve-5)

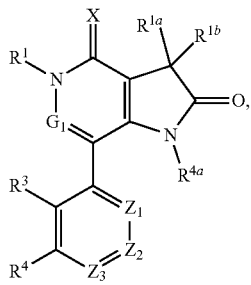

or a tautomer or isomer thereof, or a pharmaceutically acceptable salt of any of the foregoing, wherein X, $R^1$, $R^3$, $R^4$, $R^{1a}$, Rib, $R^{2a}$, $R^{2b}$, $R^{4a}$, $R^{4b}$, $R^f$, $W_3$, $R^g$, $G_1$, $Z_1$, $Z_2$, and $Z_3$ are as defined herein for Formula (V).

Specific values described herein are values for a compound of Formula I or any related formulae where applicable, such as Formula (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a tautomer or isomer thereof, or a pharmaceutically acceptable salt of any of the foregoing. For example, specific values described herein are values for a compound of Formula I or any related formulae, such as Formula (Ia), (Ib), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a pharmaceutically acceptable salt or pharmaceutically acceptable tautomer thereof. It is to be understood that two or more values may combined. Thus, it is to be understood that any variable for a compound of Formula I or any related formulae may be combined with any other variable for a compound of Formula I or any related formulae the same as if each and every combination of variables were specifically and individually listed.

In some embodiments of a compound of Formula (I), $Y_1$ is N and $Y_2$ is C. In some embodiments of a compound of Formula (I), $Y_1$ is C and $Y_2$ is N. In some embodiments of a compound of Formula (I), $Y_1$ and $Y_2$ both are N.

In some embodiments of a compound of Formula (I), X is O. In some embodiments, X is S. In some embodiments, X is O; $Y_1$ is N; and $Y_2$ is C. In some embodiments, X is O; $Y_1$ is C; and $Y_2$ is N. In some embodiments, X is O; $Y_1$ is N; and $Y_2$ is N.

In some embodiments of a compound of Formula (I), $R^1$ is hydrogen, $C_1$-$C_4$ alkyl optionally substituted by —OH, $C_3$-$C_6$ cycloalkyl optionally substituted by $C_1$-$C_6$ alkyl, $C_1$-$C_4$ haloalkyl, $C_1$-$C_4$ alkoxy, —CN, —$(CH_2)_mN(R^f)W_3R^g$, or —$(CH_2)_mW_3R^g$. In some embodiments, $R^1$ is hydrogen, halogen, $C_1$-$C_4$ alkyl optionally substituted by —OH, $C_3$-$C_6$ cycloalkyl optionally substituted by $C_1$-$C_6$ alkyl, $C_1$-$C_4$ haloalkyl, $C_1$-$C_4$ alkoxy, —CN, —$(CH_2)_mN(R^f)W_3R^g$, or —$(CH_2)_mW_3R^g$. In some embodiments, when $Y_1$ is N and $G_1$ is N, then $R^1$ is $C_1$-$C_4$ haloalkyl, $C_1$-$C_4$ alkoxy, $C_1$-$C_4$ alkyl optionally substituted by —OH, $C_3$-$C_6$ cycloalkyl optionally substituted by $C_1$-$C_6$alkyl, —$(CH_2)_mN(R^f)W_3R^g$, —$(CH_2)_mN(R^f)C(O)OR^h$, or —$(CH_2)_mW_3R^g$; In some embodiments, $R^1$ is hydrogen. In some embodiments of a compound of Formula (I), $R^1$ is $C_1$-$C_4$ alkyl optionally substituted by —OH. In some embodiments, $R^1$ is $C_1$-$C_4$ alkyl. In some embodiments, $R^1$ is methyl or isopropyl. In some embodiments, $R^1$ is methyl. In some embodiments of a compound of Formula (I), $R^1$ is $C_3$-$C_6$ cycloalkyl optionally substituted by $C_1$-$C_6$ alkyl. In some embodiments, $R^1$ is

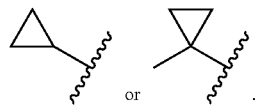

In some embodiments, $R^1$ is

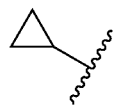

In some embodiments, $R^1$ is $C_1$-$C_4$ haloalkyl such as —$CF_3$. In some embodiments, $R^1$ is $C_1$-$C_4$ alkoxy such as methoxy. In some embodiments, $R^1$ is —CN. In some embodiments, $R^1$ is —$(CH_2)_mN(R^f)W_3R^g$. In some embodiments, $R^1$ is —$(CH_2)_mW_3R^g$. In some embodiments, $R^1$ is —$(CH_2)_mN(R^f)W_3R^g$ and $R^f$ is hydrogen. In some embodiments of a compound of Formula (I), $R^1$ is —$(CH_2)_mN(R^f)W_3R^g$ and $R^f$ is $C_1$-$C_4$ alkyl such as methyl, ethyl, n-propyl or isopropyl. In some embodiments, $R^1$ is —$(CH_2)_mN(R^f)W_3R^g$ and $R^f$ is $C_3$-$C_6$ cycloalkyl such as cyclopropyl. In some embodiments, the $W_3$ in the —$(CH_2)_mW_3R^g$ of $R^1$ is —C(O)—. In some embodiments, the $W_3$ in the —$(CH_2)_mN(R^f)W_3R^g$ of $R^1$ is —C(O)—. In some embodiments, the $W_3$ in the —$(CH_2)_mW_3R^g$ of $R^1$ is —S(O)$_2$—. In some embodiments, the $W_3$ in the —$(CH_2)_mN(R^f)W_3R^g$ of $R^1$ is —S(O)$_2$—. In some embodiments, the $R^g$ in the —$(CH_2)_mN(R^f)W_3R^g$ or —$(CH_2)_mW_3R^g$ of $R^1$ is —$CR^g$=$CHR^{g2}$. In some embodiments, the $R^g$ in the —$(CH_2)_mN(R^f)W_3R^g$ or —$(CH_2)_mW_3R^g$ of $R^1$ is —C—$CR^{g2}$. In some embodiments, the $R^{9g}$ in the —$(CH_2)_mN(R^f)W_3R^g$ or —$(CH_2)_mW_3R^g$ of $R^1$ is hydrogen. In some embodiments, the $R^{9g}$ in the —$(CH_2)_mN(R^f)W_3R^g$ or —$(CH_2)_mW_3R^g$ of $R^1$ is cyano. In some embodiments, the $R^{9g}$ in the —$(CH_2)_mN(R^f)W_3R^g$ or —$(CH_2)_mW_3R^g$ of $R^1$ is $C_1$-$C_4$ alkyl optionally substituted by —OH, —OCH$_3$, —NH$_2$, —NHCH$_3$, or —N(CH$_3$)$_2$. In some embodiments, the $R^{g1}$ in the —$(CH_2)_mN(R^f)W_3R^g$ or —$(CH_2)_mW_3R^g$ of $R^1$ is methyl optionally substituted by OH, OCH$_3$, NH$_2$, NHCH$_3$ or N(CH$_3$)$_2$. In some embodiments, the $R^{g2}$ in the —$(CH_2)_mN(R^f)W_3R^g$ or —$(CH_2)_mW_3R^g$ of $R^1$ is hydrogen. In some embodiments, the $R^{g2}$ in the —$(CH_2)_mN(R^f)W_3R^g$ or —$(CH_2)_mW_3R^g$ of $R^1$ is cyano. In some embodiments, the $R^{g2}$ in the —$(CH_2)_mN(R^f)W_3R^g$ or —$(CH_2)_mW_3R^g$ of $R^1$ is $C_1$-$C_4$ alkyl optionally substituted by —OH, —OCH$_3$, —NH$_2$, —NHCH$_3$, or —N(CH$_3$)$_2$. In some embodiments of a compound of Formula (I), the $R^{g2}$ in the —$(CH_2)_mN(R^f)W_3R^g$ or —$(CH_2)_mW_3R^g$ of $R^1$ is methyl optionally substituted by —OH, —OCH$_3$, —NH$_2$, —NHCH$_3$, or —N(CH$_3$)$_2$. In some embodiments, the m in the —$(CH_2)_mN(R^f)W_3R^g$ or —$(CH_2)_mW_3R^g$ of $R^1$ is 0. In some embodiments, the m in —$(CH_2)_mN(R^f)W_3R^g$ or —$(CH_2)_mW_3R^g$ of $R^1$ is 0 or 1. In some embodiments, the m in —$(CH_2)_mN(R^f)W_3R^g$ or —$(CH_2)_mW_3R^g$ of $R^1$ is 0, 1 or 2. In some embodiments, the m in —$(CH_2)_mN(R^f)W_3R^g$ or —$(CH_2)_mW_3R^g$ of $R^1$ is 0, 1, 2 or 3. In some embodiments, the m in —$(CH_2)_mN(R^f)W_3R^g$ or —$(CH_2)_mW_3R^g$ of $R^1$ is 0, 1, 2, 3 or 4. In some embodiments, $R^1$ is

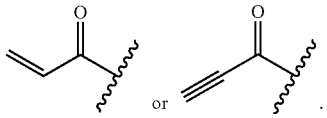

In some embodiments, $R^1$ is

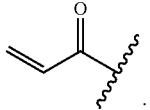

In some embodiments, $R^1$ is

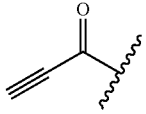

In some embodiments, $R^1$ is hydrogen, methyl, isopropyl, methoxy,

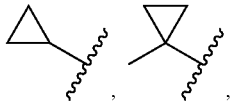

chloro, —$CF_3$, —CN,

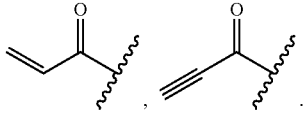

or —$CH_2OH$.

In some embodiments of a compound of Formula (I), $R^1$ is hydrogen, $C_1$-$C_4$ alkyl, $C_3$-$C_6$ cycloalkyl or —$(CH_2)_mN(R^f)W_3R^g$ or —$(CH_2)_mW_3R^g$. In some embodiments of a compound of Formula (I) $R^1$ is hydrogen. In some embodiments of a compound of Formula (I), $R^1$ is $C_1$-$C_4$ alkyl. In some embodiments of a compound of Formula (I), $R^1$ is methyl. In some embodiments of a compound of Formula (I), $R^1$ is $C_3$-$C_6$ cycloalkyl. In some embodiments of a compound of Formula (I), $R^1$ is cyclopropyl. In some embodiments of a compound of Formula (I), $R^1$ is —$(CH_2)_mN(R^f)W_3R^g$. In some embodiments of a compound of Formula (I), $R^1$ is —$(CH_2)_mW_3R^g$. In some embodiments of a compound of Formula (I), $R^f$ is hydrogen. In some embodiments of a compound of Formula (I), $R^f$ is $C_1$-$C_4$ alkyl. In some embodiments of a compound of Formula (I), $R^f$ is methyl, ethyl, propyl or isopropyl. In some embodiments of a compound of Formula (I), $R^f$ is $C_3$-$C_6$ cycloalkyl. In some embodiments of a compound of Formula (I), $R^f$ is cyclopropyl. In some embodiments of a compound of Formula (I), $W_3$ is —C(O)—. In some embodiments of a compound of Formula (I), $W_3$ is —S(O)$_2$—. In some embodiments of a compound of Formula (I), $R^g$ is —$CR^{g1}$=$CHR^{g2}$. In some embodiments of a compound of Formula (I), $R^g$ is —C≡$CR^{g2}$. In some embodiments of a compound of Formula (I), $R^{g1}$ is hydrogen. In some embodiments of a compound of Formula (I), $R^{g1}$ is cyano. In some embodiments of a compound of Formula (I), $R^{g1}$ is $C_1$-$C_4$ alkyl optionally substituted with OH, OCH$_3$, NH$_2$, NHCH$_3$ or N(CH$_3$)$_2$. In some embodiments of a compound of Formula (I), $R^{g1}$ is methyl optionally substituted with OH, OCH$_3$, NH$_2$, NHCH$_3$ or N(CH$_3$). In some embodiments of a compound of Formula (I), $R^{g2}$ is hydrogen. In some embodiments of a compound of Formula (I), $R^{g2}$ is cyano. In some embodiments of a compound of Formula (I), $R^{g2}$ is $C_1$-$C_4$ alkyl optionally substituted with OH, OCH$_3$, NH$_2$, NHCH$_3$, or N(CH$_3$)$_2$. In some embodiments of a compound of Formula (I), $R^{g2}$ is methyl optionally substituted with OH, OCH$_3$, NH$_2$, NHCH$_3$, or N(CH$_3$)$_2$. In some embodiments of a compound of Formula (I) $R^1$ is —CO—CH=CH$_2$. In some embodiments of a compound of Formula (I) $R^1$ is —CO—CCH. In some embodiments of a compound of Formula (I), the m in —(CH$_2$)$_m$N(R$^f$)W$_3$R$^g$ or —(CH$_2$)$_m$W$_3$R$^g$ is 0. In some embodiments of a compound of Formula (I), the m in —(CH$_2$)$_m$N(R$^f$)W$_3$R$^g$ or —(CH$_2$)$_m$W$_3$R$^g$ is 0 or 1. In some embodiments of a compound of Formula (I), the m in —(CH$_2$)$_m$N(R$^f$)W$_3$R$^g$ or —(CH$_2$)$_m$W$_3$R$^g$ m is 0, 1 or 2. In some embodiments of a compound of Formula (I), the m in —(CH$_2$)$_m$N(R$^f$)W$_3$R$^g$ or —(CH$_2$)$_m$W$_3$R$^g$ is 0, 1, 2 or 3. In some embodiments of a compound of Formula (I), the m in —(CH$_2$)$_m$N(R$^f$)W$_3$R$^g$ or —(CH$_2$)$_m$W$_3$R$^g$ is 0, 1, 2, 3 or 4.

In some embodiments of a compound of Formula (I), $R^3$ is hydrogen, —(CH$_2$)$_m$N(R$^f$)W$_3$R$^g$, or —(CH$_2$)$_m$W$_3$R$^g$. In some embodiments, $R^3$ is hydrogen. In some embodiments, $R^3$ is —(CH$_2$)$_m$N(R$^f$)W$_3$R$^g$. In some embodiments, $R^3$ is —(CH$_2$)$_m$W$_3$R$^g$. In some embodiments, $R^3$ is —(CH$_2$)$_m$N(R$^f$)W$_3$R$^g$ and $R^f$ is hydrogen. In some embodiments of a compound of Formula (I), $R^3$ is —(CH$_2$)$_m$N(R$^f$)W$_3$R$^g$ and $R^f$ is $C_1$-$C_4$ alkyl such as methyl, ethyl, n-propyl or isopropyl. In some embodiments, $R^3$ is —(CH$_2$)$_m$N(R$^f$)W$_3$R$^g$ and $R^f$ is $C_3$-$C_6$ cycloalkyl such as cyclopropyl. In some embodiments, the $W_3$ in the —(CH$_2$)$_m$W$_3$R$^g$ of $R^3$ is —C(O)—. In some embodiments, the $W_3$ in the —(CH$_2$)$_m$N(R$^f$)W$_3$R$^g$ of $R^3$ is —C(O)—. In some embodiments, the $W_3$ in the —(CH$_2$)$_m$W$_3$R$^g$ of $R^3$ is —S(O)$_2$—. In some embodiments, the $W_3$ in the —(CH$_2$)$_m$N(R$^f$)W$_3$R$^g$ of $R^3$ is —S(O)$_2$—. In some embodiments, the $R^g$ in the —(CH$_2$)$_m$N(R$^f$)W$_3$R$^g$ or —(CH$_2$)$_m$W$_3$R$^g$ of $R^3$ is —$CR^{g1}$=$CHR^{g2}$. In some embodiments, the $R^g$ in the —(CH$_2$)$_m$N(R$^f$)W$_3$R$^g$ or —(CH$_2$)$_m$W$_3$R$^g$ of $R^3$ is —C≡$CR^{g2}$. In some embodiments, the $R^g$ in the —(CH$_2$)$_m$N(R$^f$)W$_3$R$^g$ or —(CH$_2$)$_m$W$_3$R$^g$ of $R^3$ is hydrogen. In some embodiments, the $R^g$ in the —(CH$_2$)$_m$N(R$^f$)W$_3$R$^g$ or —(CH$_2$)$_m$W$_3$R$^g$ of $R^3$ is cyano. In some embodiments, the $R^g$ in the —(CH$_2$)$_m$N(R$^f$)W$_3$R$^g$ or —(CH$_2$)$_m$W$_3$R$^g$ of $R^3$ is $C_1$-$C_4$ alkyl optionally substituted by —OH, —OCH$_3$, —NH$_2$, —NHCH$_3$, or —N(CH$_3$)$_2$. In some embodiments, the $R^g$ in the —(CH$_2$)$_m$N(R$^f$)W$_3$R$^g$ or —(CH$_2$)$_m$W$_3$R$^g$ of $R^3$ is methyl optionally substituted by OH, OCH$_3$, NH$_2$, NHCH$_3$ or N(CH$_3$)$_2$. In some embodiments, the $R^{g2}$ in the —(CH$_2$)$_m$N(R$^f$)W$_3$R$^g$ or —(CH$_2$)$_m$W$_3$R$^g$ of $R^3$ is hydrogen. In some embodiments, the $R^{g2}$ in the —(CH$_2$)$_m$N(R$^f$)W$_3$R$^g$ or —(CH$_2$)$_m$W$_3$R$^g$ of $R^3$ is cyano. In some embodiments, the $R^{g2}$ in the —(CH$_2$)$_m$N(R$^f$)W$_3$R$^g$ or —(CH$_2$)$_m$W$_3$R$^g$ of $R^3$ is $C_1$-$C_4$ alkyl optionally substituted by —OH, —OCH$_3$, —NH$_2$, —NHCH$_3$, or —N(CH$_3$)$_2$. In some embodiments of a compound of Formula (I), the $R^{g2}$ in the —(CH$_2$)$_m$N(R$^f$)W$_3$R$^g$ or —(CH$_2$)$_m$W$_3$R$^g$ of $R^3$ is methyl optionally substituted by —OH, —OCH$_3$, —NH$_2$, —NHCH$_3$, or —N(CH$_3$)$_2$. In some embodiments, the m in the —(CH$_2$)$_m$N(R$^f$)W$_3$R$^g$ or —(CH$_2$)$_m$W$_3$R$^g$ of $R^3$ is 0. In some embodiments, the m in —(CH$_2$)$_m$N(R$^f$)W$_3$R$^g$ or —(CH$_2$)$_m$W$_3$R$^g$ of $R^3$ is 0 or 1. In some embodiments, the m in —(CH$_2$)$_m$N(R$^f$)W$_3$R$^g$ or —(CH$_2$)$_m$W$_3$R$^g$ of $R^3$ is 0, 1 or 2. In some embodiments, the m in —(CH$_2$)$_m$N(R$^f$)W$_3$R$^g$ or —(CH$_2$)$_m$W$_3$R$^g$ of $R^3$ is 0, 1, 2 or 3. In some embodiments, the m in —(CH$_2$)$_m$N(R$^f$)W$_3$R$^g$ or —(CH$_2$)$_m$W$_3$R$^g$ of $R^3$ is 0, 1, 2, 3 or 4. In some embodiments, $R^3$ is hydrogen,

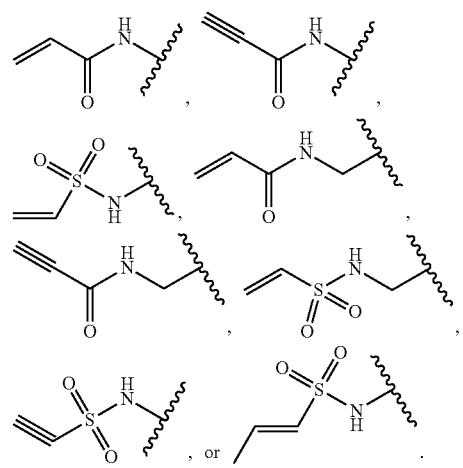

In some embodiments of a compound of Formula (I), $R^4$ is hydrogen, —NR$^{13}$C(O)R$^{14}$, NR$^{13}$S(O)$_2$R$^{14}$, —NR$^{13}$C(O)NR$^{13}$R$^{14}$, —NR$^{13}$S(O)$_2$NR$^{13}$R$^{14}$, —(CH$_2$)N(R$^f$)W$_3$R$^g$ (CH$_2$)W$_3$R$^g$, or $C_1$-$C_4$ alkyl optionally substituted by halogen, oxo, —CN or —OH. In some embodiments, $R^4$ is hydrogen, —NR$^{13}$C(O)R$^{14}$, —NR$^{13}$S(O)$_2$R$^{14}$, —NR$^{13}$C(O)NR$^{13}$R$^{14}$, —NR$^{13}$S(O)$_2$NR$^{13}$R$^{14}$, —(CH$_2$)$_m$N(R$^f$)W$_3$R$^g$, —(CH$_2$)$_m$W$_3$R$^g$, —(CH$_2$)$_m$N(R$^f$)C(O)OR$^h$, or $C_1$-$C_4$ alkyl optionally substituted by halogen, oxo, —CN or —OH. In some embodiments, $R^4$ is hydrogen. In some embodiments, $R^4$ is $C_1$-$C_4$ alkyl optionally substituted by halogen, oxo, —CN or —OH. In some embodiments, $R^4$ is $C_1$-$C_4$ alkyl optionally substituted by —OH, such as

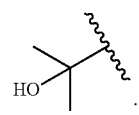

In some embodiments, $R^4$ is —NR$^{13}$C(O)R$^{14}$ such as

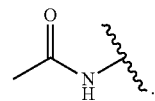

In some embodiments, $R^4$ is $-NR^{13}S(O)_2R^{14}$ such as

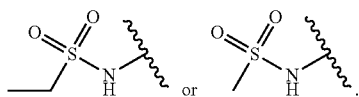

In some embodiments, $R^4$ is $-NR^{13}C(O)NR^{13}R^{14}$ such as

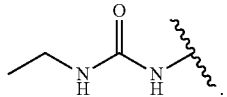

In some embodiments, $R^4$ is $-NR^{13}S(O)_2NR^{13}R^{14}$ such as

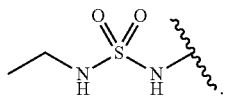

In some embodiments, $R^4$ is $-(CH_2)_mN(R^f)C(O)OR^h$. In some embodiments, $R^4$ is $-(CH_2)_mN(R^f)C(O)OR^h$, wherein m is 0 and $R^f$ is hydrogen. In some embodiments, $R^4$ is $-(CH_2)_nN(R^f)W_3R^g$. In some embodiments, $R^4$ is $-(CH_2)_mW_3R^g$. In some embodiments, $R^4$ is $-(CH_2)_nN(R^f)W_3R^g$ and $R^f$ is hydrogen. In some embodiments of a compound of Formula (I), $R^4$ is $-(CH_2)_nN(R^f)W_3R^g$ and $R^f$ is $C_1$-$C_4$ alkyl such as methyl, ethyl, n-propyl or isopropyl. In some embodiments, $R^4$ is $-(CH_2)_nN(R^f)W_3R^g$ and $R^f$ is $C_3$-$C_6$ cycloalkyl such as cyclopropyl. In some embodiments, the $W_3$ in the $-(CH_2)_mW_3R^g$ of $R^4$ is $-C(O)-$. In some embodiments, the $W_3$ in the $-(CH_2)_mN(R^f)W_3R^g$ of $R^4$ is $-C(O)-$. In some embodiments, the $W_3$ in the $-(CH_2)_mW_3R^g$ of $R^4$ is $-S(O)_2-$. In some embodiments, the $W_3$ in the $-(CH_2)_nN(R^f)W_3R^g$ of $R^4$ is $-S(O)_2-$. In some embodiments, the $R^g$ in the $-(CH_2)_mN(R^f)W_3R$ or $-(CH_2)_mW_3R^g$ of $R^4$ is $-CR^g=CHR^{g2}$. In some embodiments, the $R^g$ in the $-(CH_2)_mN(R^f)W_3R^g$ or $-(CH_2)_mW_3R^g$ of $R^4$ is $-C\equiv CR^{g2}$. In some embodiments, the $R^{9g}$ in the $-(CH_2)_mN(R^f)W_3R^g$ or $-(CH_2)_mW_3R^g$ of $R^4$ is hydrogen. In some embodiments, the $R^{9g}$ in the $-(CH_2)_mN(R^f)W_3R^g$ or $-(CH_2)_mW_3R^g$ of $R^4$ is cyano. In some embodiments, the $R^{9g}$ in the $-(CH_2)_mN(R^f)W_3R^g$ or $-(CH_2)_mW_3R^g$ of $R^4$ is $C_1$-$C_4$ alkyl optionally substituted by $-OH$, $-OCH_3$, $-NH_2$, $-NHCH_3$, or $-N(CH_3)_2$. In some embodiments, the $R^{g1}$ in the $-(CH_2)_mN(R^f)W_3R^g$ or $-(CH_2)_mW_3R^g$ of $R^4$ is methyl optionally substituted by $-OH$, $-OCH_3$, $-NH_2$, $-NHCH_3$ or $-N(CH_3)_2$. In some embodiments, the $R^{g2}$ in the $-(CH_2)_mN(R^f)W_3R^g$ or $-(CH_2)_mW_3R^g$ of $R^4$ is hydrogen. In some embodiments, the $R^{g2}$ in the $-(CH_2)_mN(R^f)W_3R^g$ or $-(CH_2)_mW_3R^g$ of $R^4$ is cyano. In some embodiments, the $R^{g2}$ in the $-(CH_2)_mN(R^f)W_3R^g$ or $-(CH_2)_mW_3R^g$ of $R^4$ is $C_1$-$C_4$ alkyl optionally substituted by $-OH$, $-OCH_3$, $-NH_2$, $-NHCH_3$, or $-N(CH_3)_2$. In some embodiments of a compound of Formula (I), the $R^{g2}$ in the $-(CH_2)_mN(R^f)W_3R^g$ or $-(CH_2)_mW_3R^g$ of $R^4$ is methyl optionally substituted by $-OH$, $-OCH_3$, $-NH_2$, $-NHCH_3$, or $-N(CH_3)_2$. In some embodiments, the m in the $-(CH_2)_mN(R^f)W_3R^g$ or $-(CH_2)_mW_3R^g$ of $R^4$ is 0. In some embodiments, the m in $-(CH_2)_mN(R^f)W_3R^g$ or $-(CH_2)_mW_3R^g$ of $R^4$ is 0 or 1. In some embodiments, the m in $-(CH_2)_mN(R^f)W_3R^g$ or $-(CH_2)_mW_3R^g$ of $R^4$ is 0, 1 or 2. In some embodiments, the m in $-(CH_2)_mN(R^f)W_3R^g$ or $-(CH_2)_mW_3R^g$ of $R^4$ is 0, 1, 2 or 3. In some embodiments, the m in $-(CH_2)_mN(R^f)W_3R^g$ or $-(CH_2)_mW_3R^g$ of $R^4$ is 0, 1, 2, 3 or 4. In some embodiments, $R^4$ is hydrogen,

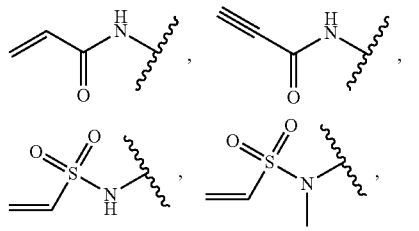

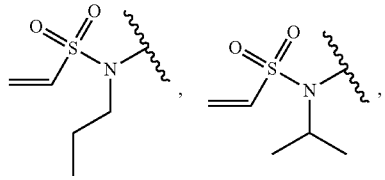

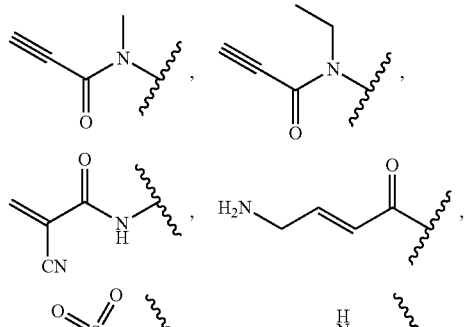

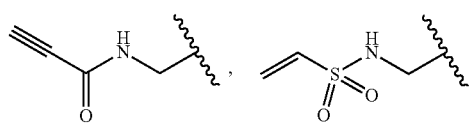

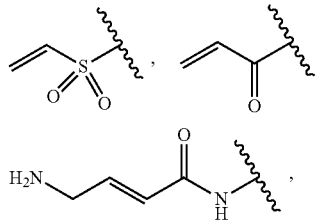

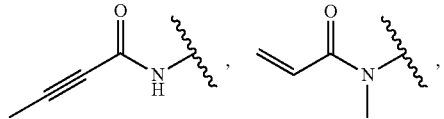

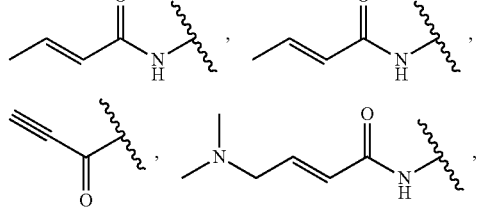

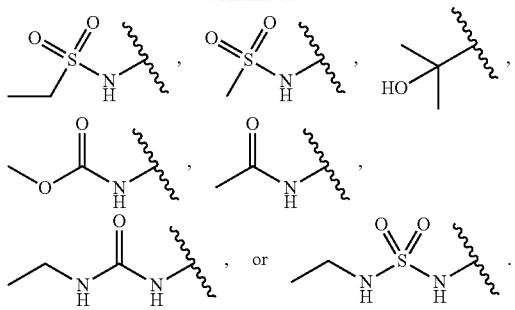

In some embodiments of a compound of Formula (I), when $R^4$ is —$(CH_2)_mN(R^f)W_3R^g$ and m is 0, the N, $R^f$, $W_3$ and $R^g$ in —$N(R^f)W_3R^g$ may be taken together to form a 5- or 6-membered ring having at least one double bond and optionally substituted by R, wherein each R is independently $C_1$-$C_4$ alkyl, oxo, halogen or CN. In some embodiments, $R^4$ is

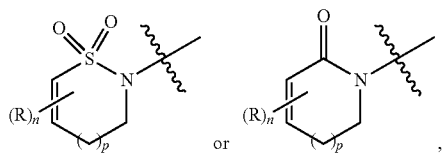

wherein n is 0, 1, 2, 3 or 4 and p is 0 or 1. In some embodiments of a compound of Formula (I), $R^4$ is

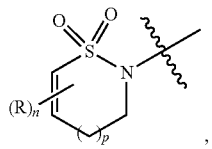

wherein n is 0, 1, 2, 3 or 4 and p is 0 or 1. In some embodiments of a compound of Formula (I), $R^4$ is

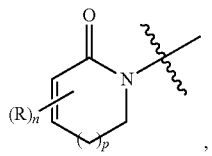

wherein n is 0, 1, 2, 3 or 4 and p is 0 or 1. In some embodiments R is oxo. In some embodiments R is halogen. In some embodiments R is —CN. In some embodiments R is $C_1$-$C_4$ alkyl. In some embodiments R is methyl.

In some embodiments of a compound of Formula (I), $R^4$ is selected from the group of:

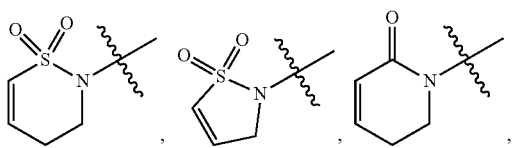

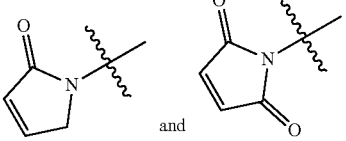

and

In some embodiments of a compound of Formula (I), $R^3$ is hydrogen and $R^4$ is halogen, cyano, $C_1$-$C_4$ haloalkyl, $C_1$-$C_4$ alkoxy, $C_1$-$C_4$ haloalkoxy, —$OR^{13}$, —$NR^{13}R^{14}$, —$C(O)NR^{13}R^{14}$, —$NR^{13}C(O)R^{14}$, —$S(O)_2R^{13}$, —$NR^{13}S(O)_2R^{14}$, —$S(O)_2NR^{13}R^{14}$, —$(CH_2)_mN(R^f)W_3R^g$, —$(CH_2)_mW_3R^g$, or $C_1$-$C_4$ alkyl optionally substituted by halogen, oxo, CN, or —OH. In some embodiments of a compound of Formula (I), $R^4$ is hydrogen and $R^3$ is halogen, cyano, $C_1$-$C_4$ haloalkyl, $C_1$-$C_4$ alkoxy, $C_1$-$C_4$ haloalkoxy, —$OR^{13}$, —$NR^{13}R^{14}$, —$C(O)NR^{13}R^{14}$, —$NR^{13}C(O)R^{14}$, —$S(O)_2R^{13}$, —$NR^{13}S(O)_2R^{14}$, —$S(O)_2NR^{13}R^{14}$, —$(CH_2)_nN(R^f)W_3R^g$, —$(CH_2)_mW_3R$, or $C_1$-$C_4$ alkyl optionally substituted by halogen, oxo, CN, or —OH.

In some embodiments of a compound of Formula (I), $R^3$ is hydrogen and $R^4$ is not hydrogen. In some embodiments of a compound of Formula (I), $R^4$ is hydrogen and $R^3$ is not hydrogen. In some embodiments of a compound of Formula (I), $R^3$ is hydrogen and $R^4$ is —$NR^{13}C(O)R^{14}$. In some embodiments of a compound of Formula (I), $R^3$ is hydrogen and $R^4$ is —$NR^{13}S(O)_2R^{14}$. In some embodiments of a compound of Formula (I), $R^3$ is hydrogen and $R^4$ is —$C(O)NR^{13}R^{14}$. In some embodiments of a compound of Formula (I), $R^3$ is hydrogen and $R^4$ is —$S(O)_2R^{13}$. In some embodiments of a compound of Formula (I), $R^3$ is hydrogen and $R^4$ is $C_1$-$C_4$ alkyl optionally substituted by halogen, oxo, CN, or —OH. In some embodiments of a compound of Formula (I), $R^3$ is hydrogen and $R^4$ is $C_1$-$C_4$ alkyl optionally substituted by —OH. In some embodiments of a compound of Formula (I), $R^3$ is hydrogen and $R^4$ is —$(CH_2)_mN(R^f)W_3R^g$. In some embodiments of a compound of Formula (I), $R^3$ is hydrogen and $R^4$ is —$(CH_2)_mW_3R^g$.

In some embodiments of a compound of Formula (I), $R^4$ is hydrogen and $R^3$ is —$(CH_2)_mN(R^f)W_3R^g$. In some embodiments of a compound of Formula (I), $R^4$ is hydrogen and $R^3$ is —$(CH_2)_mW_3R^g$.

In some embodiments of a compound of Formula (I), $R^1$ is —$(CH_2)_mN(R^f)W_3R^g$ or —$(CH_2)_mW_3R^g$; $R^3$ is hydrogen; and $R^4$ is hydrogen, halogen, cyano, $C_1$-$C_4$ haloalkyl, $C_1$-$C_4$ alkoxy, $C_1$-$C_4$ haloalkoxy, —$OR^{13}$, —$NR^{13}R^{14}$, —$C(O)NR^{13}R^{14}$, —$NR^{13}C(O)R^{14}$, —$S(O)_2R^{13}$, —$NR^{13}S(O)_2R^{14}$ or $S(O)_2NR^{13}R^{14}$, or $C_1$-$C_4$ alkyl optionally substituted by halogen, oxo, CN or OH. In some embodiments of a compound of Formula (I), $R^1$ is —$(CH_2)_mN(R^f)W_3R^g$ or —$(CH_2)_mW_3R^g$; $R^3$ is hydrogen; and $R^4$ is hydrogen. In some embodiments of a compound of Formula (I), $R^1$ is —$(CH_2)_mN(R^f)W_3R^g$ or —$(CH_2)_mW_3R^g$; $R^3$ is hydrogen; and $R^4$ is —$C(O)NR^{13}R^{14}$. In some embodiments of a compound of Formula (I), $R^1$ is —$(CH_2)_mN(R^f)W_3R^g$ or —$(CH_2)_mW_3R^g$; $R^3$ is hydrogen; and $R^4$ is $NR^{13}C(O)R^{14}$. In some embodiments of a compound of Formula (I), $R^1$ is —$(CH_2)_mN(R^f)W_3R^g$ or —$(CH_2)_mW_3R^g$; $R^3$ is hydrogen; and $R^4$ is $S(O)_2R^{13}$. In some embodiments of a compound of Formula (I), $R^1$ is —$(CH_2)_mN(R^f)W_3R^g$ or —$(CH_2)_mW_3R^g$; $R^3$ is hydrogen; and $R^4$ is $NR^{13}S(O)_2R^{14}$. In some embodiments of a compound of Formula (I), $R^1$ is —$(CH_2)_mN(R^f)W_3R^g$ or —$(CH_2)_mW_3R^g$; $R^3$ is hydrogen; and $R^4$ is —$S(O)_2NR^{13}R^{14}$. In some embodiments of a compound of Formula (I), $R^1$ is —$(CH_2)_mN(R^f)W_3R^g$ or —$(CH_2)_mW_3R^g$; $R^3$ is hydrogen; and $R^4$ is $C_1$-$C_4$ alkyl optionally substituted by halogen, oxo, —CN or —OH. In some embodiments of a compound of Formula (I), $R^1$ is —$(CH_2)_mN(R^f)W_3R^g$ or —$(CH_2)_mW_3R^g$; $R^3$ is hydrogen; and $R^4$ is $C_1$-$C_4$ alkyl optionally substituted by —OH.

In some embodiments of a compound of Formula (I), at least one of $R^1$, $R^3$ and $R^4$, such as one of $R^1$, $R^3$ and $R^4$, two of $R^1$, $R^3$ and $R^4$, or all of $R^1$, $R^3$ and $R^4$, are selected from the group consisting of:

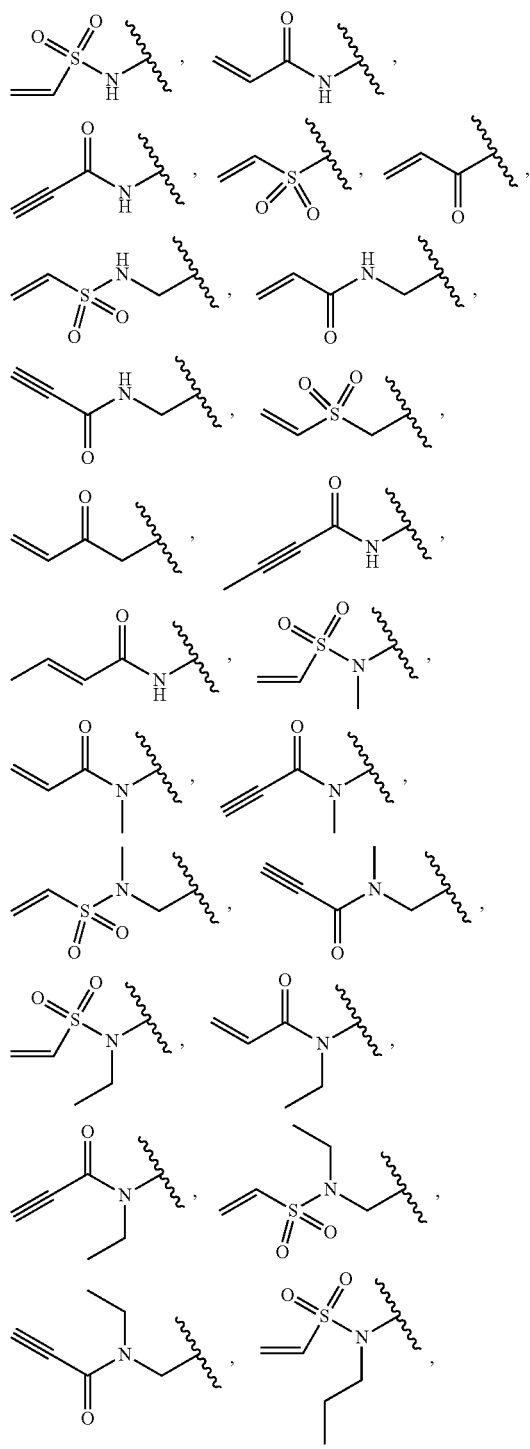

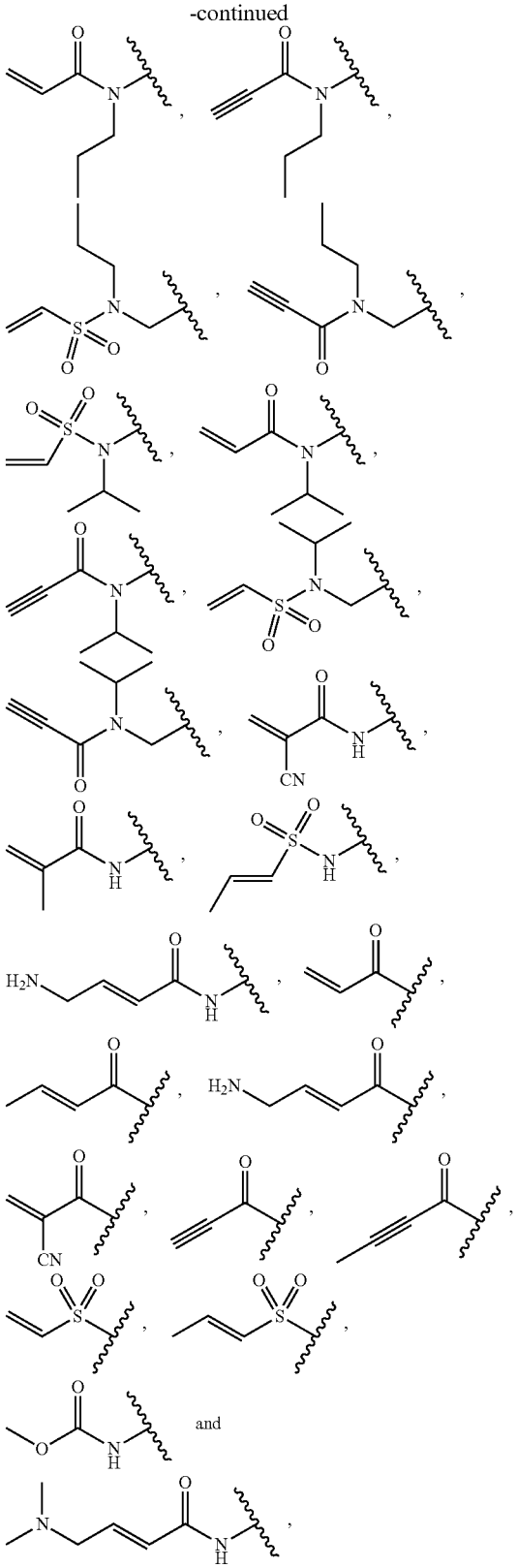

wherein the wavy lines denote attachment points.

In some embodiments of a compound of Formula (I), at least one of $R^1$, $R^3$ and $R^4$, such as one of $R^1$, $R^3$ and $R^4$, two of $R^1$, $R^3$ and $R^4$, or all of $R^1$, $R^3$ and $R^4$ are

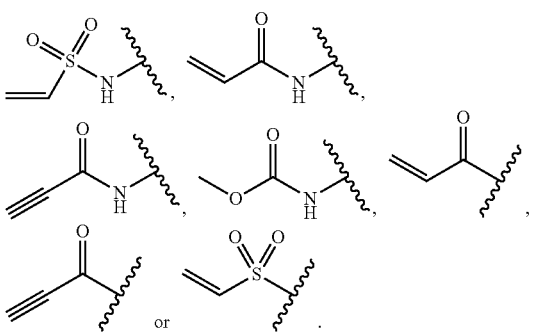

In some embodiments of a compound of Formula (I), $G_1$ is N. In some embodiments of a compound of Formula (I), $G_1$ is $CR^a$. In some embodiments of a compound of Formula (I), $G_1$ is $CHR^a$. In some embodiments of a compound of Formula (I), $G_1$ is $CR^a$, wherein $R^a$ is hydrogen. In some embodiments of a compound of Formula (I), $G_1$ is $CR^a$, wherein $R^a$ is methyl. In some embodiments, X is O; $Y_1$ is N; $Y_2$ is C; and $G_1$ is $CR^a$, wherein $R^a$ is hydrogen. In some embodiments, X is O; $Y_1$ is C; $Y_2$ is N; and $G_1$ is $CR^a$, wherein $R^a$ is hydrogen. In some embodiments, X is O; $Y_1$ is N; $Y_2$ is C; and $G_1$ is N. In some embodiments, X is O; $Y_1$ is C; $Y_2$ is N; and $G_1$ is N.

In some embodiments of a compound of Formula (I), $G_2$ is N. In some embodiments, $G_2$ is $CR^b$. In some embodiments, $R^b$ is hydrogen, halogen, cyano, $C_1$-$C_4$ alkyl, $C_3$-$C_6$ cycloalkyl, 3- to 6-membered heterocyclyl, $C_1$-$C_4$ haloalkyl, $C_1$-$C_4$ alkoxy, $C_1$-$C_4$ haloalkoxy, —$OR^{10}$, —$NR^{10}R^{11}$, —$C(O)NR^{10}R^{11}$, —$NR^{10}C(O)R^{11}$, —$S(O)_2R^{10}$, —$NR^{10}S(O)_2R^{11}$, or —$S(O)_2NR^{10}R^{11}$. In some embodiments, $R^b$ is hydrogen, —$NR^{10}OR^{11}$, —$C(O)NR^{10}R^{11}$, or —$NR^{10}C(O)R^{11}$. In some embodiments of a compound of Formula (I), $R^b$ is —$NR^{10}R^{11}$ such as —$NHCH_3$ or —$N(CH_3)_2$. In some embodiments, $R^b$ is —$NHCH_3$. In some embodiments of a compound of Formula (I), $R^b$ is —$NR^{10}C(O)R^{11}$ such as —$NHCOCH_3$, —$NHCOC_2H_5$, or —$NHCOCH_2CH(CH_3)_2$. In some embodiments, $R^b$ is —$NHCOCH_3$. In some embodiments of a compound of Formula (I), $R^b$ is —$N(CH_3)_2$. In some embodiments of a compound of Formula (I), $R^b$ is —$C(O)NR^{10}R^{11}$ such as —$CONH_2$ or —$CONHC_2H_5$. In some embodiments, $R^b$ is —$CONH_2$. In some embodiments of a compound of Formula (I), $R^b$ is —$CONHC_2H_5$. In some embodiments of a compound of Formula (I), $R^b$ is —$NHCOC_2H_5$. In some embodiments of a compound of Formula (I), $R^b$ is —$NHCOCH_2CH(CH_3)_2$. In some embodiments of a compound of Formula (I), $R^b$ is —$OR^{10}$ such as —$OCH_3$.

In some embodiments of a compound of Formula (I), $R^2$ is hydrogen, halogen, cyano, $C_1$-$C_4$ alkyl, 3- to 6-membered heterocyclyl, $C_1$-$C_4$ haloalkyl, $C_1$-$C_4$ alkoxy, $C_1$-$C_4$ haloalkoxy, —$NR^{10}R^{11}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$. In some embodiments, $R^2$ is hydrogen, halogen, cyano, $C_1$-$C_4$ alkyl, $C_1$-$C_4$ haloalkyl, $C_1$-$C_4$ alkoxy, or $C_1$-$C_4$ haloalkoxy. In some embodiments, $R^2$ is hydrogen. In some embodiments, $R^2$ is $C_1$-$C_4$ alkoxy, such as —O—$C_1$ alkyl, —O—$C_2$ alkyl, —O—$C_3$ alkyl, or —O—$C_4$ alkyl. In some embodiments, $R^2$ is $C_1$-$C_4$ alkoxy such as —$OCH_3$. In some embodiments, $R^2$ is $C_1$-$C_4$ alkoxy such as —$OCH_3$ or —$OCH(CH_3)_2$. In some embodiments of a compound of Formula (I), $R^2$ is cyano. In some embodiments of a compound of Formula (I), $R^2$ is halogen such as F. In some embodiments of a compound of Formula (I), $R^2$ is $C_1$-$C_4$ alkyl such as —$CH_3$ or —$CH_2CH_3$. In some embodiments, $R^2$ is $C_1$-$C_4$ haloalkyl, such as a $C_1$-$C_4$ alkyl substituted with 1, 2, 3, 4, or 5 halogen. In some embodiments, $R^2$ is $C_1$-$C_4$ haloalkoxy, such as a $C_1$-$C_4$ alkoxy substituted with 1, 2, 3, 4, or 5 halogen. In some embodiments of a compound of Formula (I), $R^2$ is $C_1$-$C_4$ haloalkyl such as —$CF_3$. In some embodiments of a compound of Formula (I), $R^2$ is —$CH_2CH_3$. In some embodiments, $R^2$ is —$CH_3$. In some embodiments of a compound of Formula (I), $R^2$ is —$OCF_3$. In some embodiments, $R^2$ is —$OCH_3$.

In some embodiments of a compound of Formula (I), $R^2$ is hydrogen, halogen, cyano, $C_1$-$C_4$ alkyl, $C_3$-$C_6$ cycloalkyl, 3- to 6-membered heterocyclyl, $C_1$-$C_4$ haloalkyl, $C_1$-$C_4$ alkoxy, $C_1$-$C_4$ haloalkoxy, —$OR^{10}$, —$NR^{10}R^{11}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$. In some embodiments of a compound of Formula (I), $R^2$ is hydrogen. In some embodiments of a compound of Formula (I), $R^2$ is —$OR^{10}$ such as —$OCH_3$ or —$OCF_3$. In some embodiments of a compound of Formula (I), $R^2$ is cyano. In some embodiments of a compound of Formula (I), $R^2$ is halogen such as F. In some embodiments of a compound of Formula (I), $R^2$ is $C_1$-$C_4$ alkyl such as —$CH_3$ or —$CH_2CH_3$. In some embodiments of a compound of Formula (I), $R^2$ is $C_1$-$C_4$ haloalkyl such as —$CF_3$. In some embodiments of a compound of Formula (I), $R^2$ is —$CH_2CH_3$. In some embodiments, $R^2$ is —$CH_3$. In some embodiments of a compound of Formula (I), $R^2$ is —$OCF_3$. In some embodiments, $R^2$ is —$OCH_3$.

It is understood that each description of every variation on A ring (X, $Y_1$, $Y_2$, $R^1$, $R^2$, $G_1$, $G_2$) may be combined with each description of every variation on B ring ($R^3$, $R^4$, $Z_1$, $Z_2$, $Z_3$) the same as if each and every combination were specifically and individually listed. It is similarly understood that each description of every variation on A ring (X, $R^1$, $R^2$, $G_1$, $G_2$) may be combined with each description of every variation on C ring ($M_1$, $M_2$, $M_3$, $M_4$) the same as if each and every combination were specifically and individually listed. For example, it is understood that each description of X of A ring may be combined in one aspect with a variation of B ring in which $R^3$ is hydrogen, $R^4$ is

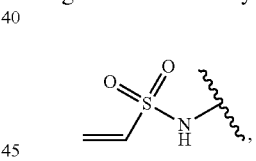

$Z_2$ and $Z_3$ are CH, and $Z_1$ is C—$W_1$—$R^c$, wherein —$W_1$—$R^c$ is

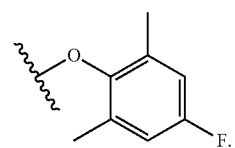 [SMILES: *Oc1c(C)cc(F)cc1C]

In one such variation, A ring is as defined in any variation herein, B ring is with the variables such as $R^3$ is hydrogen, $R^4$ is

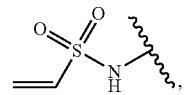

$Z_2$ and $Z_3$ are C—H, and $Z_1$ is C—$W_1$—$R^c$, wherein —$W_1$—$R^c$ is

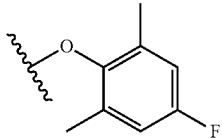 [SMILES: *Oc1c(C)cc(F)cc1C]

and/or C ring is substituted or unsubstituted phenyl. In another variation, A ring is as defined in any variation herein, B ring is with the variables such as $R^3$ is hydrogen, $R^4$ is

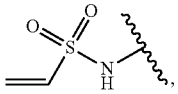

$Z_2$ and $Z_3$ are C—H, and $Z_1$ is C—$W_1$—$R^c$, wherein $W^1$ is —O— and $R^c$ is phenyl optionally substituted with $R^{c1}$.

In some embodiments of a compound of Formula (I), $R^b$ and $R^2$ are taken together with the atoms to which they are attached to form a 5- or 6-membered C ring, which is optionally substituted by $R^5$, wherein each $R^5$ is independently halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{10}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is optionally substituted by $R^{12}$.

In some embodiments of a compound of Formula (I), $R^b$ and $R^2$ of A ring are taken together with the atoms to which they are attached to form a 5- or 6-membered C ring, which is optionally substituted with $R^5$, wherein each $R^5$ is independently hydrogen, halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{10}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is optionally substituted with $R^{12}$.

In some embodiments of a compound of Formula (I), saturated 5- or 6-membered C ring is heterocyclyl or cycloalkyl optionally substituted by $R^5$, wherein each $R^5$ is independently halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{10}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$ each of which is optionally substituted by $R^{12}$. In some embodiments of a compound of Formula (I), the C ring containing $R^2$ and $R^b$ is a saturated 5- or 6-membered heterocyclyl ring containing one and more heteroatom selected from N and O, and optionally substituted by oxo or methyl. In some embodiments of a compound of Formula (I), the C ring containing $R^2$ and $R^b$ is a saturated 5- or 6-membered cycloalkyl ring that is unsubstituted.

In some embodiments of a compound of Formula (I), saturated 5- or 6-membered C ring is heterocyclyl or cycloalkyl optionally substituted with $R^5$, wherein each $R^5$ is independently hydrogen, halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{10}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is optionally substituted with $R^{12}$. In some embodiments of a compound of Formula (I), the C ring containing $R^2$ and $R^b$ is a saturated 5- or 6-membered heterocyclyl ring containing one and more heteroatom selected from N and O, and optionally substituted with oxo or methyl. In some embodiments of a compound of Formula (I), the C ring containing $R^2$ and $R^b$ is a saturated 5- or 6-membered cycloalkyl ring that is unsubstituted.

In some embodiments of a compound of Formula (I), the C ring containing $R^2$ and $R^b$ is aryl or heteroaryl, which is optionally substituted by $R^5$, wherein each $R^5$ is independently halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{10}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is optionally substituted by $R^{12}$. In some embodiments of a compound of Formula (I), the C ring containing $R^2$ and $R^b$ is an unsaturated 5-membered heteroaryl ring containing one and more heteroatom selected from N, O and S, and optionally substituted by $R^5$, wherein each $R^5$ is independently halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{10}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is optionally substituted by $R^{12}$. In some embodiments of a compound of Formula (I), the C ring containing $R^2$ and $R^b$ is a 5-membered heteroaryl ring is furanyl, oxazolyl, isoxazolyl, thiophenyl, thiazolyl, isothiazolyl or pyrrolyl optionally substituted by $R^5$, wherein each $R^5$ is independently halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{10}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is optionally substituted by $R^{12}$. In some embodiments of a compound of Formula (I), the C ring containing $R^2$ and $R^b$ is a 6-membered heteroaryl ring containing one or two N atoms at any position in the ring which is optionally substituted by $R^5$, wherein each $R^5$ is independently hydrogen, halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{10}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$. In some embodiments, each $R^5$ is independently halogen, $C_1$-$C_4$ alkyl, $C_3$-$C_6$ cycloalkyl, cyano, $C_1$-$C_4$ haloalkyl, $C_1$-$C_4$ alkoxy, $C_1$-$C_4$ haloalkoxy, —$OR^{10}$, —$NR^{10}R^{11}$, —$C(O)NR^{10}R^{11}$, —$NR^{10}C(O)R^{11}$, or 5- to 10-membered heteroaryl, each of which is optionally substituted by $R^{12}$. In some embodiments, $R^2$ and $R^b$ are taken together with the atoms to which they attach to form an 6-membered aromatic ring such as phenyl, optionally substituted by cyclopropyl, cyano, —$CF_3$, —$OCF_3$, —$N(CH_3)_2$, —$CONH_2$, or —$CONHC_2H_5$.

In some embodiments of a compound of Formula (I), the C ring containing $R^2$ and $R^b$ is aryl or heteroaryl, which is optionally substituted with $R^5$, wherein each $R^5$ is independently hydrogen, halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{10}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is optionally substituted with $R^{12}$. In some embodiments of a compound of Formula (I), the C ring containing $R^2$ and $R^b$ is an unsaturated 5-membered heteroaryl ring containing one and more heteroatom selected from N, O and S, and optionally substituted with $R^5$, wherein each $R^5$ is independently hydrogen, halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{10}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is optionally substituted with $R^{12}$. In some embodiments of a compound of Formula (I), the C ring containing $R^2$ and $R^b$ is an unsaturated 5-membered heteroaryl ring is furanyl, oxazolyl, isoxazolyl, thiophenyl, thiazolyl, isothiazolyl or pyrrolyl optionally substituted with $R^5$, wherein each $R^5$ is independently hydrogen, halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{10}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is optionally substituted with $R^{12}$. In some embodiments of a compound of Formula (I), the C ring containing $R^2$ and $R^b$ is an unsaturated 6-membered heteroaryl ring containing one or two N atoms at any position in the ring which is optionally substituted with $R^5$, wherein each $R^5$ is independently hydrogen, halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{10}$, —$C(O)NR^{10}R^{11}$, —$NR^{10}C(O)R^{11}$, —$S(O)_2R^{10}$, —$NR^{10}S(O)_2R$ or —$S(O)_2NR^{10}R^{11}$. In some embodiments of a compound of Formula (I), the C ring containing $R^2$ and $R^b$ is an unsaturated 6-membered ring such as phenyl, optionally substituted with cyclopropyl, cyano, $CF_3$, $OCF_3$, $N(CH_3)_2$, $CONH_2$, or $CONHC_2H_5$.

In some embodiments of a compound of Formula (I), the C ring containing $R^2$ and $R^b$ is selected from the group consisting of

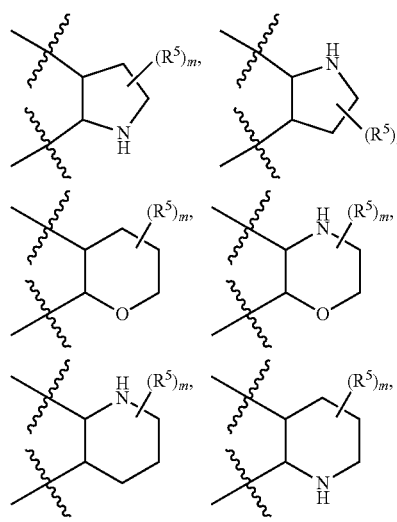

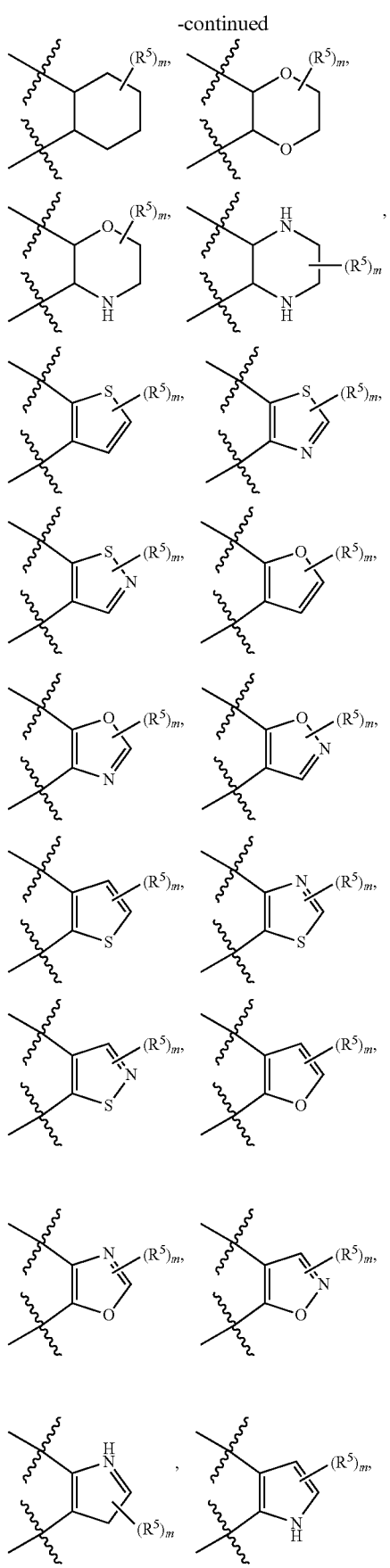

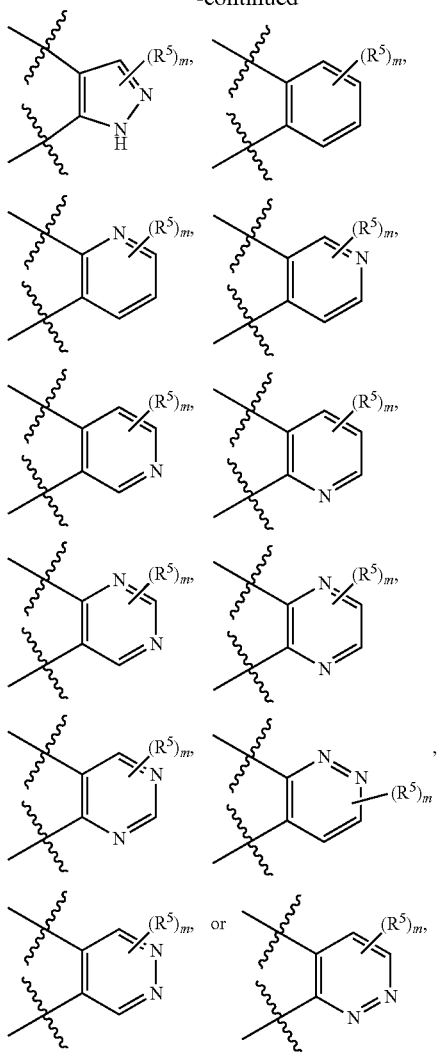

wherein the wavy lines denote attachment points with the A ring. For example, in some embodiments of a compound of Formula I, Ia, Ib, Ic, II, III or V, the C ring containing $R^2$ and $R^b$ is selected from the group consisting of the moieties provided above.

In some embodiments of a compound of Formula I, the C ring containing $R^2$ and $R^b$ is selected from the group consisting of

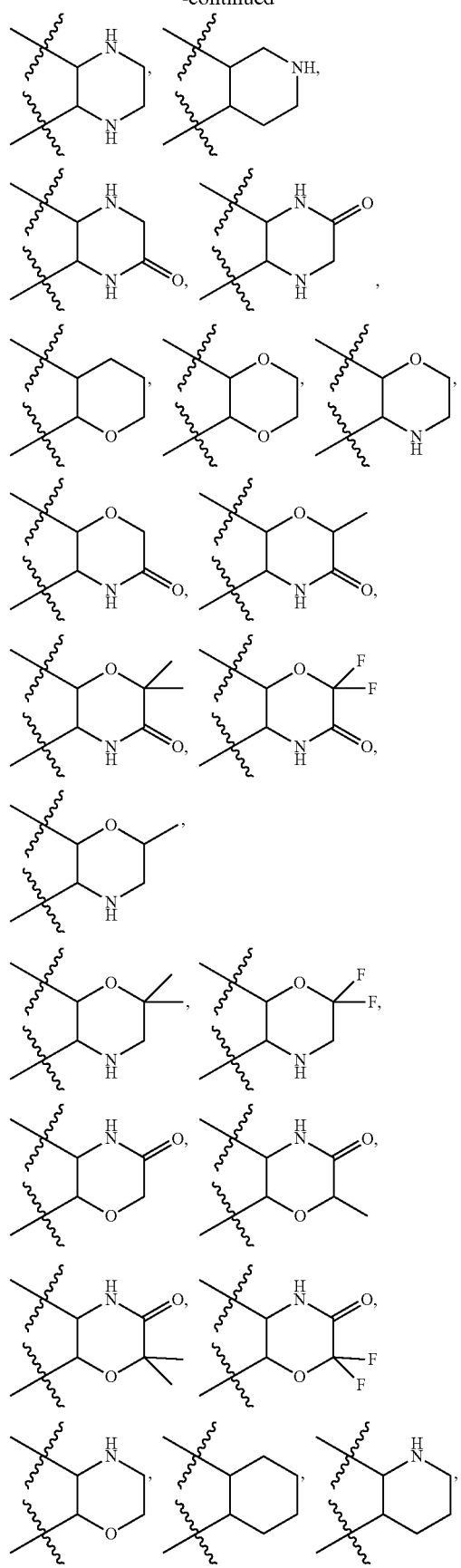

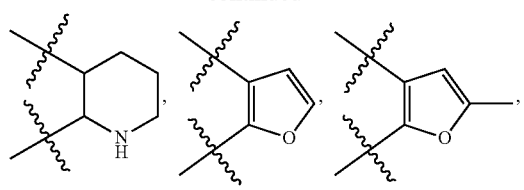
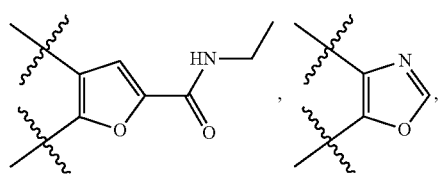
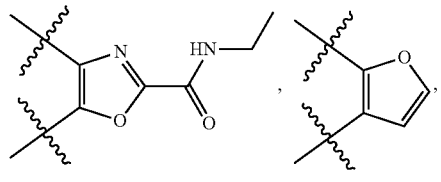
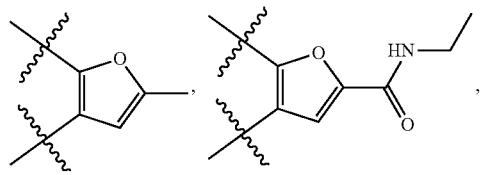
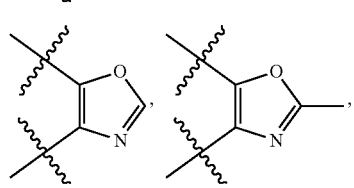
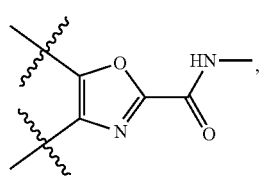
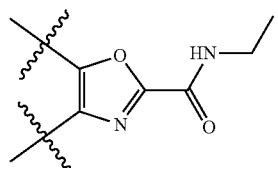
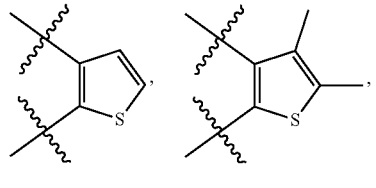
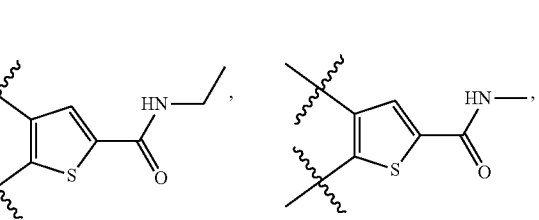
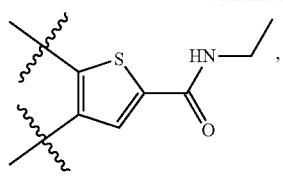
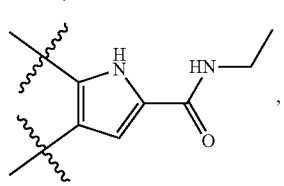
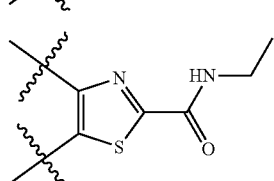
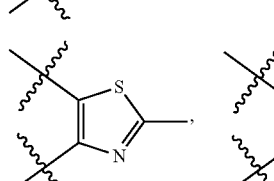
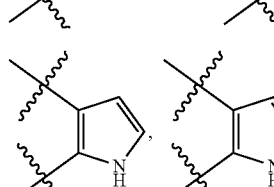
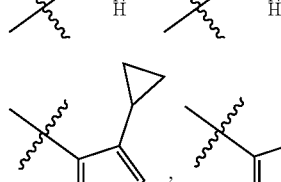
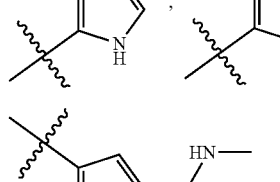
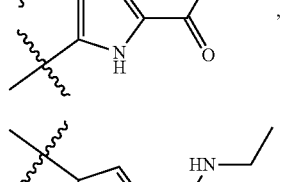
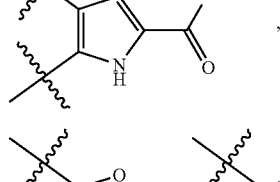
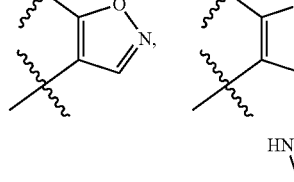

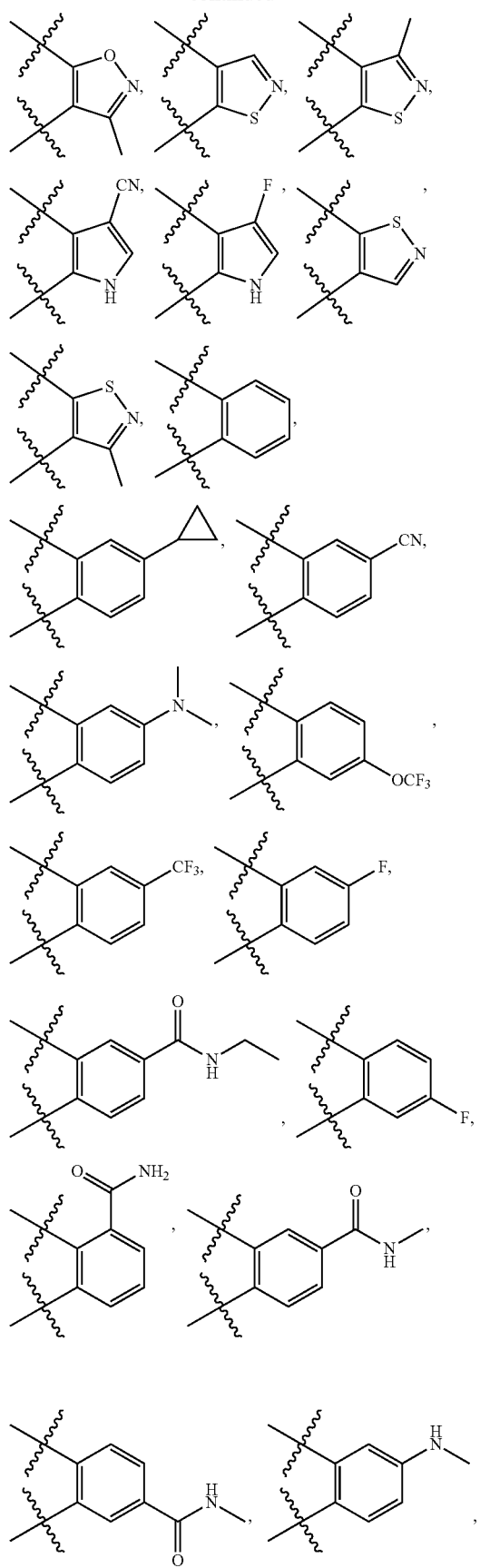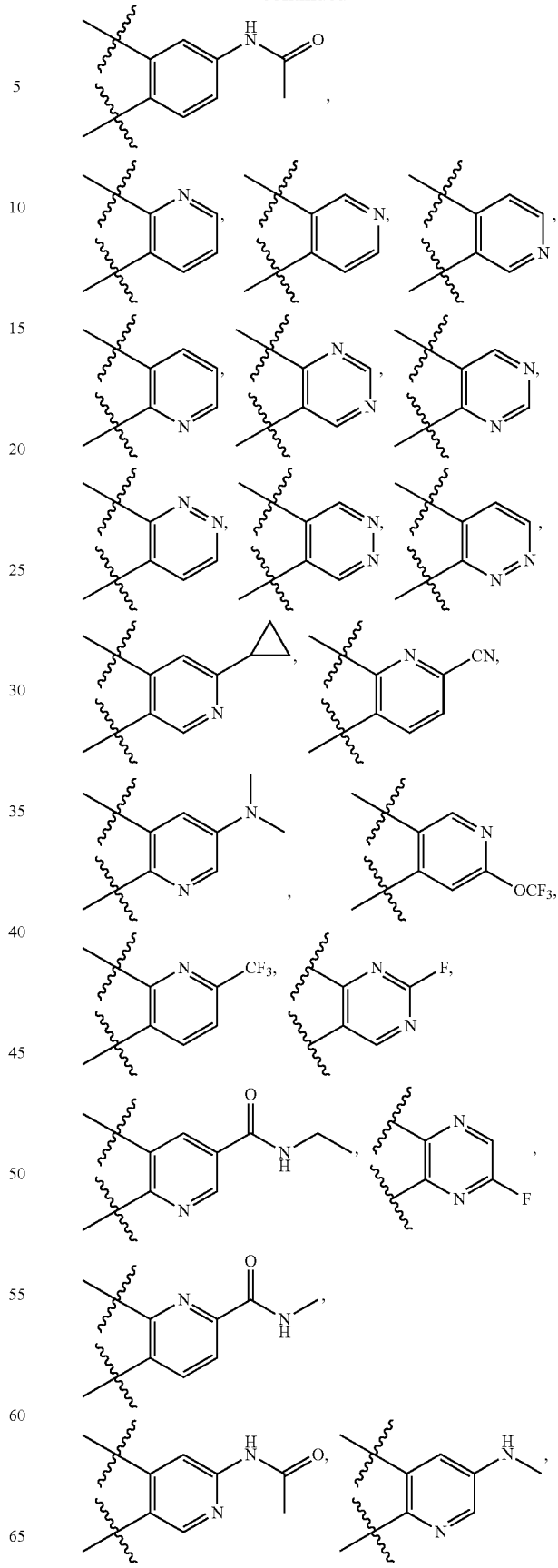

-continued
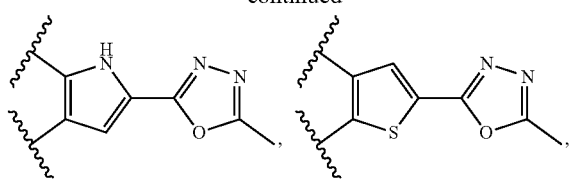
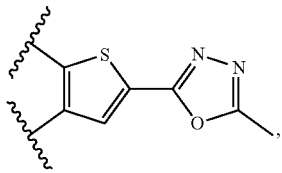
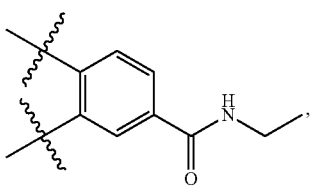
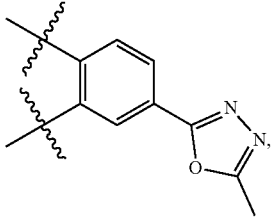
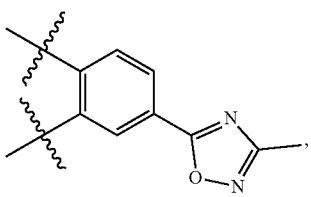
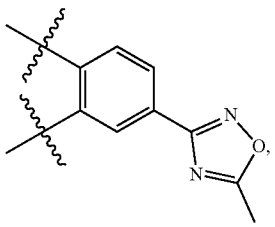
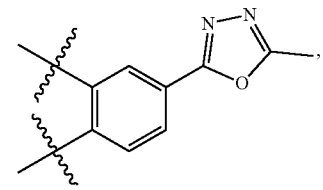
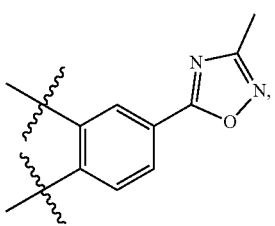
-continued
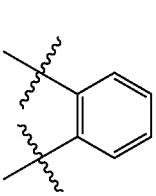
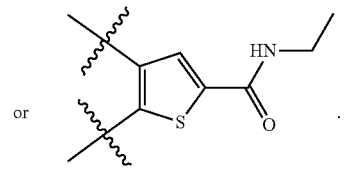 or
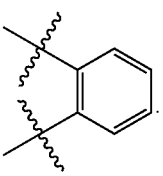 [SMILES: *c1ccccc1*]
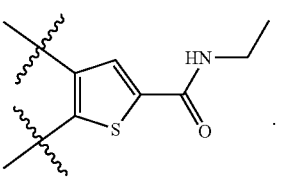 [SMILES: *c1cc(C(=O)NCC)sc1*]
wherein the wavy lines denote attachment points with the A ring.
In some embodiments of a compound of Formula (I), the C ring containing $R^2$ and $R^b$ is
In some embodiments, the C ring containing $R^2$ and $R^b$ is
In some embodiments, the C ring containing $R^2$ and $R^b$ is It is understood that each description of every variation on C ring (M₁, M₂, M₃, M₄) may be combined with each description of every variation on A ring (X, Y₁, Y₂, R¹, G₁) the same as if each and every combination were specifically and individually listed. It is similarly understood that each description of every variation on C ring (M₁, M₂, M₃, M₄) may be combined with each description of every variation on B ring (R³, R⁴, Z₁, Z₂, Z₃) the same as if each and every combination were specifically and individually listed. For example, in one aspect, it is understood that each description of every variation on C ring may be combined in one aspect with a variation of A ring in which X is O, G₁ is hydrogen, Y₁ is N, Y₂ is C and R¹ is methyl. In one such variation, C ring is as defined in any variation herein, A ring is with the variables such as X is O, G₁ is hydrogen, Y₁ is N, Y₂ is C and R¹ is methyl, B ring is with the variables such as R³ is hydrogen, R⁴ is

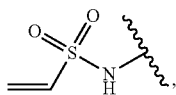

Z₂ and Z₃ are C—H, and Z₁ is C—W₁—R$^c$, wherein —W₁—R$^c$ is

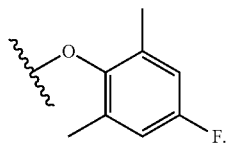 [SMILES: *Oc1c(C)cc(F)cc1C]

In some embodiments of a compound of Formula (I), Z₁ is CH—W₁—R$^c$. In some embodiments of a compound of Formula (I), Z₁ is C—W₁—R$^c$. In some embodiments of a compound of Formula (I), Z₁ is C═O. In some embodiments of a compound of Formula (I), Z₁ is NR$^c$. In some embodiments of a compound of Formula (I), Z₁ is N. In some embodiments of a compound of Formula (I), W₁ is —O—. In some embodiments of a compound of Formula (I), W₁ is NR$^{w1}$. In some embodiments of a compound of Formula (I), W₁ is NH. In some embodiments of a compound of Formula (I), W₁ is a bond. In some embodiments of a compound of Formula (I), W₁ is a bond and R$^c$ is hydrogen. In some embodiments of a compound of Formula (I), when W₁ is O, Z₁ is C—O—R$^c$. In some embodiments of a compound of Formula (I), when W₁ is NR$^{w1}$, Z₁ is C—NR$^{w1}$—R$^c$. In some embodiments of a compound of Formula (I), when W₁ is NH, Z₁ is C—NH—R$^c$. In some embodiments of a compound of Formula (I), when W₁ is a bond, Z₁ is C—R$^c$. In some embodiments of a compound of Formula (I), when W₁ is a bond, Z₁ is C—H. In some embodiments of a compound of Formula (I), R$^{w1}$ is hydrogen, C₃-C₆ cycloalkyl or C₁-C₄ alkyl optionally substituted by oxo, —OH or halogen. In some embodiments of a compound of Formula (I), R$^{w1}$ is hydrogen. In some embodiments of a compound of Formula (I), R$^{w1}$ is C₃-C₆ cycloalkyl. In some embodiments of a compound of Formula (I), R$^{w1}$ is C₁-C₄ alkyl optionally substituted by oxo, —OH or halogen. In some embodiments of a compound of Formula (I), R$^{w1}$ is methyl.

In some embodiments of a compound of Formula (I), R$^c$ is hydrogen, halogen, cyano, C₁-C₄ alkyl, C₃-C₆ cycloalkyl, C₁-C₄ haloalkyl, 3- to 6-membered heterocyclyl, C₆-C₁₄ aryl, or 5- to 6-membered heteroaryl, wherein C₃-C₆ cycloalkyl, 3- to 6-membered heterocyclyl, C₆-C₁₄ aryl, and 5- to 6-membered heteroaryl of R$^c$ are independently optionally substituted by R$^{c1}$, wherein each Rd is independently halogen, C₁-C₄ alkyl, C₃-C₆ cycloalkyl, 3- to 6-membered heterocyclyl, cyano, oxo, C₁-C₄ alkoxy, C₁-C₄ haloalkoxy, C₁-C₄ haloalkyl, —OR¹⁰, —NR¹⁰R¹¹, —C(O)NR¹⁰R¹¹, —NR¹⁰C(O)R¹¹, —S(O)₂R¹⁰, —NR¹⁰S(O)₂R¹¹ or —S(O)₂NR¹⁰R¹. In some embodiments of a compound of Formula (I), R$^c$ is hydrogen. In some embodiments of a compound of Formula (I), R$^c$ is C₁-C₄ alkyl. In some embodiments of a compound of Formula (I), R$^c$ is methyl or isopropyl. In some embodiments of a compound of Formula (I), R$^c$ is C₃-C₆ cycloalkyl optionally substituted by R$^{c1}$. In some embodiments of a compound of Formula (I), R$^c$ is cyclopropyl, cyclopentyl or cyclohexyl, each of which is optionally substituted by R$^{c1}$. In some embodiments of a compound of Formula (I), R$^c$ is C₁-C₄ haloalkyl. In some embodiments of a compound of Formula (I), R$^c$ is —CF₃. In some embodiments of a compound of Formula (I), R$^c$ is 3- to 6-membered heterocyclyl optionally substituted by R$^{c1}$. In some embodiments of a compound of Formula (I), R$^c$ is piperidinyl or pyrrolidinyl, each of which is optionally substituted by R$^{c1}$. In some embodiments of a compound of Formula (I), R$^c$ is C₆-C₁₄ aryl optionally substituted by R$^{c1}$. In some embodiments of a compound of Formula (I), R$^c$ is phenyl optionally substituted by R$^{c1}$. In some embodiments, R$^c$ is phenyl optionally substituted by R$^{c1}$, wherein each Rd is independently halogen, C₁-C₄ alkyl, or C₁-C₄ alkoxy. In some embodiments, R$^c$ is phenyl substituted by F, methyl or —OCH₃. In some embodiments of a compound of Formula (I), R$^c$ is 5- to 6-membered heteroaryl optionally substituted by R$^{c1}$. In some embodiments of a compound of Formula (I), 5-membered heteroaryl of R$^c$ is thiophenyl or thiazolyl, each of which optionally substituted by F or methyl. In some embodiments of a compound of Formula (I), 6-membered heteroaryl of R$^c$ is pyridyl optionally substituted by fluoro or methyl.

In some embodiments of a compound of Formula (I), R$^c$ is selected from the group consisting of: hydrogen, halogen, cyano, C₁-C₄ alkyl, C₁-C₄ haloalkyl,

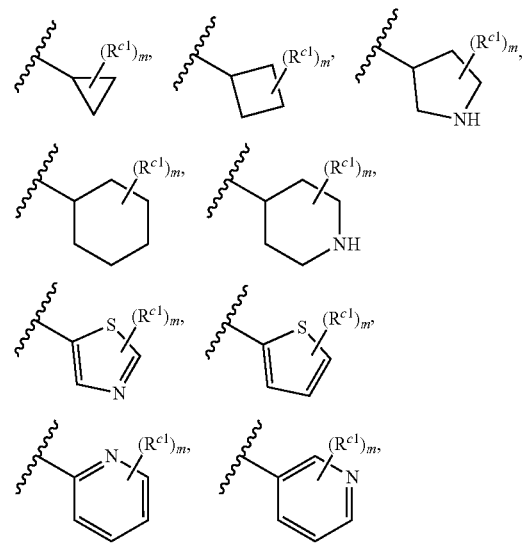

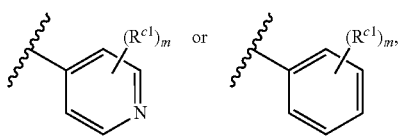

wherein the wavy lines denote attachment points.
In some embodiments, $R^c$ is

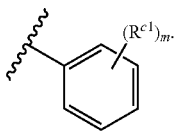

In some embodiments of a compound of Formula (I), $R^c$ is selected from the group consisting of hydrogen, F, Cl, cyano, methyl, ethyl, isopropyl, $CF_3$

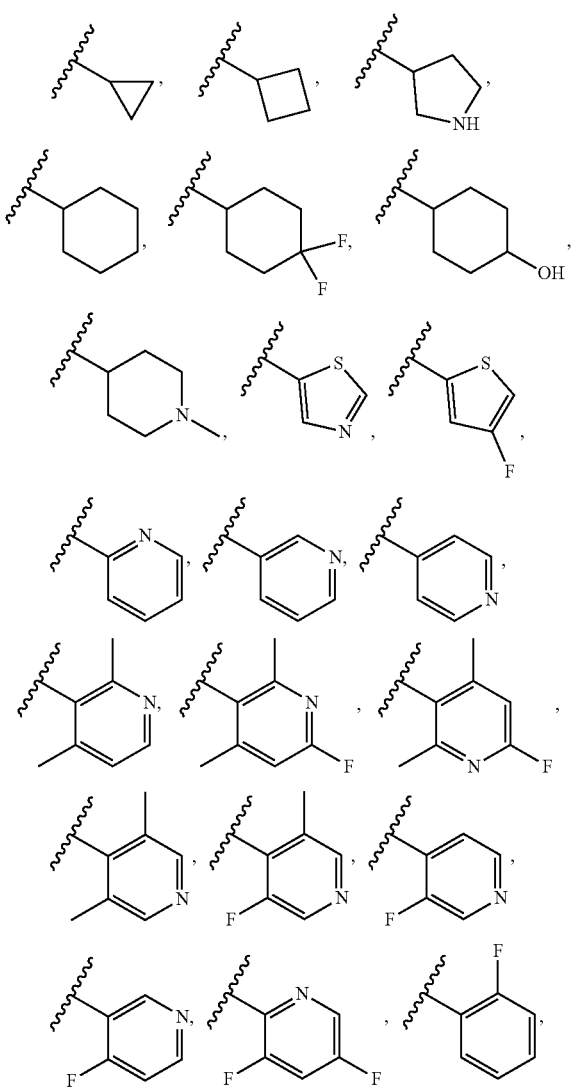

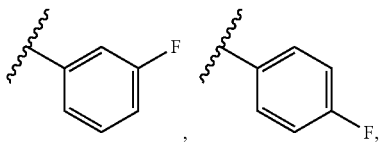

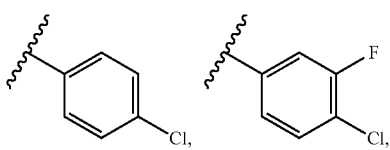

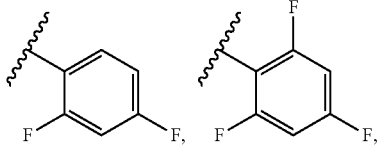

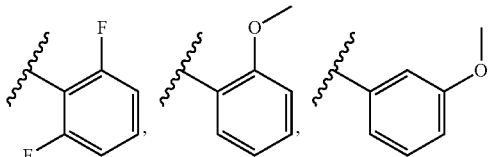

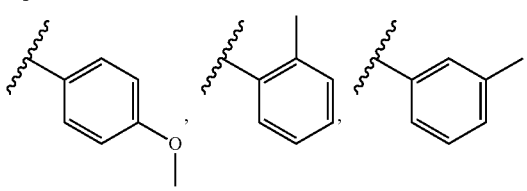

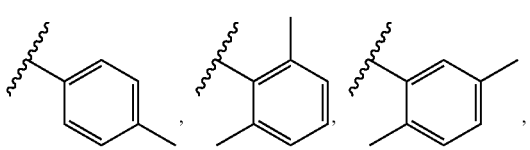

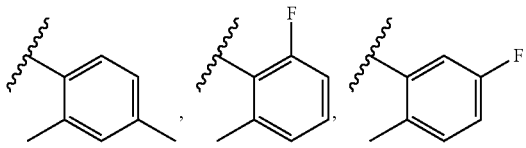

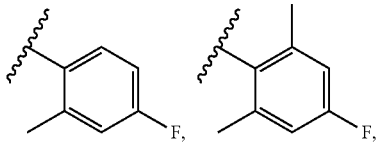

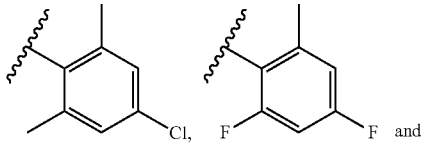 and

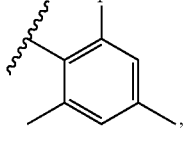

wherein the wavy lines denote attachment points.

In some embodiments of a compound of Formula (I), $R^c$ is selected from the group consisting of methyl, isopropyl, —$CF_3$,

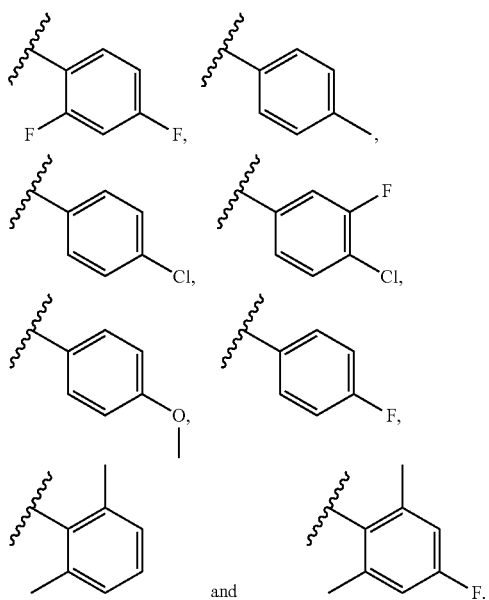

It is understood that each description of $R^c$ may be combined with each description of every variation on B ring ($R^3$, $R^4$, $Z_1$, $Z_2$, $Z_3$) the same as if each and every combination were specifically and individually listed. It is similarly understood that each description $R^c$ may be combined with each description of every variation on A ring (X, $Y_1$, $Y_2$, $R^1$, $R^2$, $G_1$, $G_2$) and/or each description of every variation on C ring ($M_1$, $M_2$, $M_3$, $M_4$) the same as if each and every combination were specifically and individually listed. For example, in one aspect, it is understood that each description of $R^c$ may be combined in one aspect with a variation of B ring in which $R^3$ is hydrogen, $R^4$ is

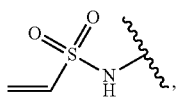

$Z_2$ and $Z_3$ are C—H, and $Z_1$ is C—O—$R^c$. In one such variation, $R^c$ is as defined in any variation herein, B ring is with the variables such as $R^3$ is hydrogen, $R^4$ is

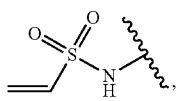

$Z_2$ and $Z_3$ are C—H, and $Z_1$ is C—O—$R^c$, A ring is with the variables such as X is O, $G_1$ is hydrogen, $Y_1$ is N, $Y_2$ is C, $R^1$ is methyl and/or C ring is substituted or unsubstituted phenyl.

In some embodiments of a compound of Formula (I), $Z_2$ is CH—$W_2$—$R^d$. In some embodiments of a compound of Formula (I), $Z_2$ is C—$W_2$—$R^d$. In some embodiments of a compound of Formula (I), $Z_2$ is C=O. In some embodiments of a compound of Formula (I), $Z_2$ is $NR^d$. In some embodiments of a compound of Formula (I), $Z_2$ is N. In some embodiments of a compound of Formula (I), $W_2$ is —O—. In some embodiments of a compound of Formula (I), $W_2$ is $NR^{w2}$. In some embodiments of a compound of Formula (I), $W_2$ is NH. In some embodiments of a compound of Formula (I), $W_2$ is $NCH_3$. In some embodiments of a compound of Formula (I), $W_2$ is a bond. In some embodiments of a compound of Formula (I), when $W_2$ is a bond, $Z_2$ is C—H. In some embodiments of a compound of Formula (I), $R^{w2}$ is hydrogen, $C_3$-$C_6$ cycloalkyl or $C_1$-$C_4$ alkyl optionally substituted by oxo, OH or halogen. In some embodiments of a compound of Formula (I), $R^{w2}$ is hydrogen. In some embodiments of a compound of Formula (I), $R^{w2}$ is $C_3$-$C_6$ cycloalkyl. In some embodiments of a compound of Formula (I), $R^{w2}$ is $C_1$-$C_4$ alkyl optionally substituted by oxo, OH or halogen. In some embodiments of a compound of Formula (I), $R^{w2}$ is methyl.

In some embodiments of a compound of Formula (I), $R^{c1}$ is hydrogen. In some embodiments of a compound of Formula (I), $R^{c1}$ is $C_1$-$C_4$ alkyl. In some embodiments of a compound of Formula (I), $R^{c1}$ is methyl.

In some embodiments of a compound of Formula (I), $R^c$ and $R^{c1}$ are taken together with the atoms to which they are attached to form a 5- or 6-membered D ring, wherein the 5- or 6-membered D ring containing $R^c$ and $R^{c1}$ is optionally substituted by $R^6$, wherein each $R^6$ is independently hydrogen halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, $OR^{10}$, $NR^{10}R^{11}$, $C(O)NR^{10}R^{11}$, $NR^{10}C(O)R^{11}$, $S(O)_2R^{10}$, $NR^{10}S(O)_2R^{11}$ or $S(O)_2NR^{11}R^{11}$. In some embodiments of a compound of Formula (I), the D ring containing $R^c$ and $R^{c1}$ is 5- or 6-membered aryl optionally substituted by $R^6$. In some embodiments of a compound of Formula (I), the D ring containing $R^c$ and $R^{c1}$ is 5- or 6-membered heterocyclyl optionally substituted by $R^6$. In some embodiments of a compound of Formula (I), the D ring containing $R^c$ and $R^{c1}$ is 5- or 6-membered cycloalkyl optionally substituted by $R^6$.

It is understood that each description of every variation on D ring may be combined with each description of every variation on A ring (X, $Y_1$, $Y_2$, $R^1$, $R^2$, $G_1$, $G_2$) the same as if each and every combination were specifically and individually listed. It is similarly understood that each description of every variation on D ring may be combined with each description of every variation on B ring ($R^3$, $R^4$, $Z_3$) the same as if each and every combination were specifically and individually listed. It is similarly understood that each description of every variation on D ring may be combined with each description of every variation on C ring ($M_1$, $M_2$, $M_3$, $M_4$) the same as if each and every combination were specifically and individually listed. For example, in one aspect, it is understood that each description of every variation on D ring may be combined in one aspect with a variation of A ring in which X is O, $Y_1$ is N, $Y_2$ is C, $R_1$ is methyl, $R^2$ is hydrogen, $G_1$ is hydrogen and $G_2$ is C—$NHCH_3$. In one such variation, D ring is as defined in any variation herein, A ring is with the variables such as X is O, $Y_1$ is N, $Y_2$ is C, $R_1$ is methyl, $R^2$ is hydrogen, $G_1$ is hydrogen $G_2$ is C—$NHCH_3$, B ring is with the variables such as $R^3$ is hydrogen, $R^4$ is

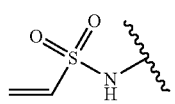 [SMILES: *NS(=O)(=O)C=C]

and $Z_3$ is C—H, and C ring is substituted or unsubstituted phenyl.

In some embodiments of a compound of Formula (I), $Z_3$ is C—$R^e$. In some embodiments of a compound of Formula (I), $Z_3$ is C—H. In some embodiments of a compound of Formula (I), $Z_3$ is C═O. In some embodiments of a compound of Formula (I), $Z_3$ is N. In some embodiments of a compound of Formula (I), $R^e$ is hydrogen. In some embodiments of a compound of Formula (I), $R^e$ is halogen. In some embodiments of a compound of Formula (I), $R^e$ is cyano.

In some embodiments of a compound of Formula (I), $Z_2$ is C═O and $Z_3$ is N. In some embodiments of a compound of Formula (I), $Z_2$ is N and $Z_3$ is C═O. In some embodiments, $Z_2$ and $Z_3$ are C—H, and $Z_1$ is C—$W_1$—$R^c$, wherein $W_1$ is —O— or —$NR^{w1}$— and $R^c$ is phenyl optionally substituted by $R^{c1}$, wherein each $R^{c1}$ is independently halogen, $C_1$-$C_4$ alkyl, or $C_1$-$C_4$ alkoxy. In some embodiments, $Z_2$ and $Z_3$ are C—H, and $Z_1$ is C—$W_1$—$R^c$, wherein $W_1$ is —O— or —$NR^{w1}$— and $R^c$ is phenyl substituted by $R^{c1}$, wherein each $R^{c1}$ is independently halogen, $C_1$-$C_4$ alkyl, or $C_1$-$C_4$ alkoxy.

In some embodiments of a compound of Formula (I), $R_4$ is —$(CH_2)_mN(R^f)W_3R^g$ or —$(CH_2)_mW_3R^g$; $R^3$ is hydrogen; and $R^1$ is hydrogen, $C_1$-$C_4$ alkyl, or $C_3$-$C_6$ cycloalkyl. In some embodiments of a compound of Formula (I), $R^4$ is —$(CH_2)_mN(R^f)W_3R^g$ or —$(CH_2)_mW_3R^g$; $R^3$ is hydrogen; and $R^1$ is hydrogen. In some embodiments of Formula (I), $R^4$ is —$(CH_2)_mN(R^f)W_3R^g$ or —$(CH_2)_mW_3R^g$; $R^3$ is hydrogen; and $R^1$ is $C_1$-$C_4$ alkyl. In some embodiments of a compound of Formula (I), $R^4$ is —$(CH_2)_mN(R^f)W_3R^g$ or —$(CH_2)_mW_3R^g$; $R^3$ is hydrogen; and $R^1$ is methyl. In some embodiments of a compound of Formula (I), $R^4$ is —$(CH_2)_mN(R^f)W_3R^g$ or —$(CH_2)_mW_3R$; $R^3$ is hydrogen; and $R^1$ is $C_3$-$C_6$ cycloalkyl. In some embodiments of a compound of Formula (I), $R^4$ is —$(CH_2)_mN(R^f)W_3R^g$ or —$(CH_2)_mW_3R^g$; $R^3$ is hydrogen; and $R^1$ is cyclopropyl.

In some embodiments of a compound of Formula (I), $R^3$ is —$(CH_2)_mN(R^f)W_3R^g$ or —$(CH_2)_mW_3R^g$; $R^4$ is hydrogen; and $R^1$ is hydrogen, $C_1$-$C_4$ alkyl, or $C_3$-$C_6$ cycloalkyl. In some embodiments of a compound of Formula (I), $R^3$ is —$(CH_2)_mN(R^f)W_3R^g$ or —$(CH_2)_mW_3R^g$; $R^4$ is hydrogen; and $R^1$ is hydrogen. In some embodiments of a compound of Formula (I), $R^3$ is —$(CH_2)_mN(R^f)W_3R^g$ or —$(CH_2)_mW_3R^g$; $R^4$ is hydrogen; and $R^1$ is $C_1$-$C_4$ alkyl. In some embodiments of a compound of Formula (I), $R^3$ is —$(CH_2)_mN(R^f)W_3R^g$ or —$(CH_2)_mW_3R^g$; $R^4$ is hydrogen; and $R^1$ is methyl. In some embodiments of a compound of Formula (I), $R^3$ is —$(CH_2)_mN(R^f)W_3R^g$ or —$(CH_2)_mW_3R^g$; $R^4$ is hydrogen; and $R^1$ is $C_3$-$C_6$ cycloalkyl. In some embodiments of a compound of Formula (I), $R^3$ is —$(CH_2)_mN(R^f)W_3R^g$ or —$(CH_2)_mW_3R^g$; $R^4$ is hydrogen; and $R^1$ is cyclopropyl.

In some embodiments of a compound of Formula (I), $R^f$ is hydrogen. In some embodiments of a compound of Formula (I), $R^f$ is $C_1$-$C_4$ alkyl. In some embodiments of a compound of Formula (I), $R^f$ is methyl, ethyl, propyl or isopropyl. In some embodiments of a compound of Formula (I), $R^f$ is $C_3$-$C_6$ cycloalkyl. In some embodiments of a compound of Formula (I), $R^f$ is cyclopropyl. In some embodiments of a compound of Formula (I), $W_3$ is —C(O)—. In some embodiments of a compound of Formula (I), $W_3$ is —$S(O)_2$—. In some embodiments of a compound of Formula (I), $R^g$ is —$CR^{g1}$═$CHR^{g2}$. In some embodiments of a compound of Formula (I), $R^g$ is —C═$CR^{g2}$. In some embodiments of a compound of Formula (I), $R^{g1}$ is hydrogen. In some embodiments of a compound of Formula (I), $R^{g1}$ is cyano. In some embodiments of a compound of Formula (I), $R^{g1}$ is $C_1$-$C_4$ alkyl optionally substituted with OH, $OCH_3$, $NH_2$, $NHCH_3$ or $N(CH_3)_2$. In some embodiments of a compound of Formula (I), $R^{g1}$ is methyl optionally substituted with —OH, —$OCH_3$, —$NH_2$, —$NHCH_3$ or —$N(CH_3)_2$. In some embodiments of a compound of Formula (I), $R^{g2}$ is hydrogen. In some embodiments of a compound of Formula (I), $R^{g2}$ is cyano. In some embodiments of a compound of Formula (I), $R^{g2}$ is $C_1$-$C_4$ alkyl optionally substituted with —OH, —$OCH_3$, —$NH_2$, —$NHCH_3$, or —$N(CH_3)_2$. In some embodiments of a compound of Formula (I), $R^{g2}$ is methyl optionally substituted with —OH, —$OCH_3$, —$NH_2$, —$NHCH_3$, or —$N(CH_3)_2$. In some embodiments of a compound of Formula (I), the m in —$(CH_2)_mN(R^f)W_3R^g$ or —$(CH_2)_mW_3R^g$ is 0. In some embodiments of a compound of Formula (I), the m in —$(CH_2)_mN(R^f)W_3R^g$ or —$(CH_2)_mW_3R^g$ is 0 or 1. In some embodiments of a compound of Formula (I), the m in —$(CH_2)_mN(R^f)W_3R^g$ or —$(CH_2)_mW_3R^g$ is 0, 1 or 2. In some embodiments of a compound of Formula (I), the m in —$(CH_2)_mN(R^f)W_3R^g$ or —$(CH_2)_mW_3R^g$ is 0, 1, 2 or 3. In some embodiments of a compound of Formula (I), the m in —$(CH_2)_mN(R^f)W_3R^g$ or —$(CH_2)_mW_3R^g$ is 0, 1, 2, 3 or 4. It is understood that, when more than one of $R^1$, $R^3$, and $R^4$ are —$(CH_2)_mN(R^f)W_3R^g$ or —$(CH_2)_mW_3R^g$, the —$(CH_2)_mN(R^f)W_3R^g$ or —$(CH_2)_mW_3R^g$ in $R^1$, $R^3$, and/or $R^4$ can be same or different.

In some embodiments of a compound of Formula (I), at least one of $R^1$, $R^3$ and $R^4$, such as one of $R^1$, $R^3$ and $R^4$, two of $R^1$, $R^3$ and $R^4$, or all of $R^1$, $R^3$ and $R^4$, are selected from the group consisting of

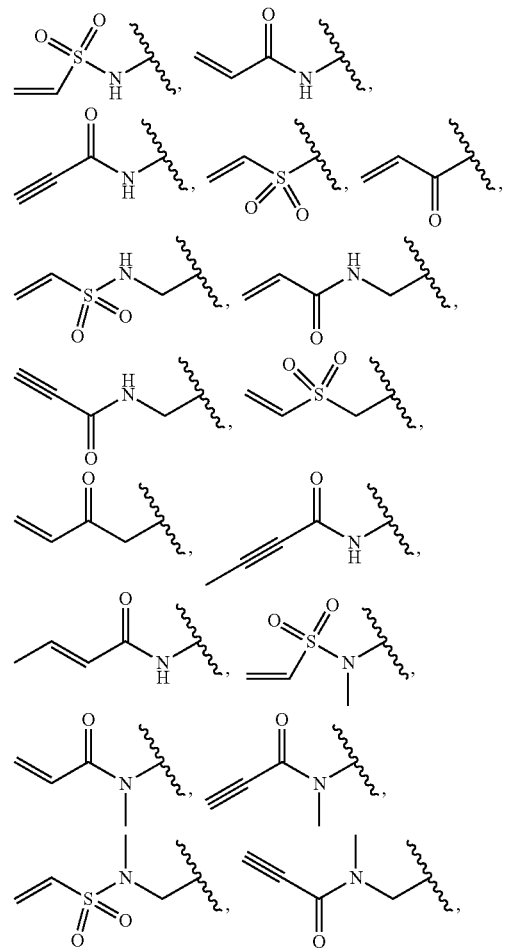

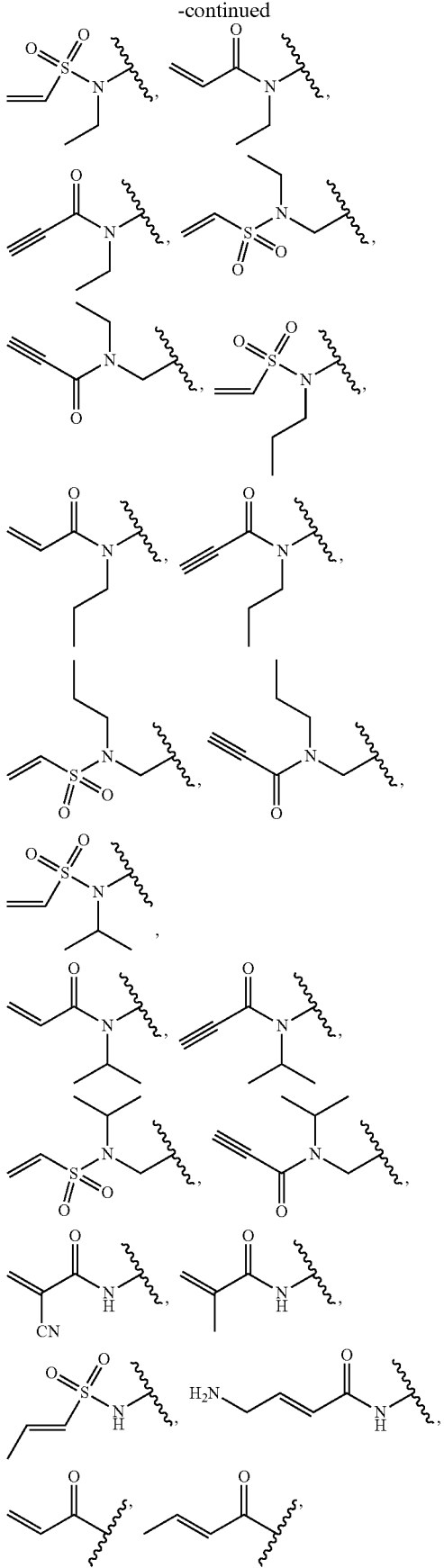

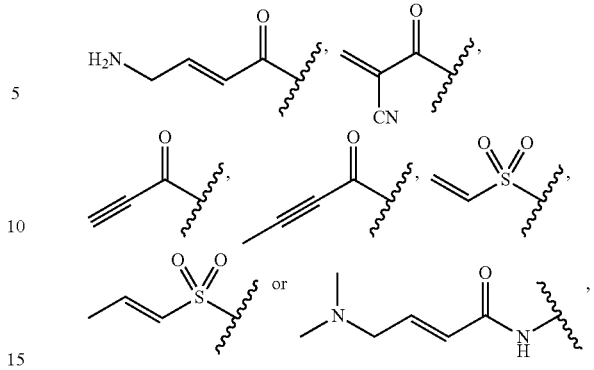

wherein the wavy lines denote attachment points.

In some embodiments of a compound of Formula (I), at least one of $R^1$, $R^3$ and $R^4$, such as one of $R^1$, $R^3$ and $R^4$, two of $R^1$, $R^3$ and $R^4$, or all of $R^1$, $R^3$ and $R^4$ are

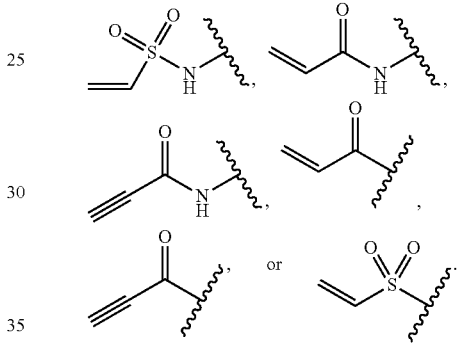

It is understood that each description of $R^3$ and $R^4$ may be independently combined with each description of other variation on B ring ($Z_1$, $Z_2$, $Z_3$) the same as if each and every combination were specifically and individually listed. It is similarly understood that each description of $R^3$ and $R^4$ may be independently combined with each description of every variation on A ring (X, $Y_1$, $Y_2$, $R^1$, $R^2$, $G_1$, $G_2$) and/or each description of every variation on C ring the same as if each and every combination were specifically and individually listed.

It is also understood that each description of every variation on B ring ($R^3$, $R^4$, $Z_1$, $Z_2$, $Z_3$) may be combined with each description of every variation on A ring (X, $Y_1$, $Y_2$, $R^1$, $R^2$, $G_1$, $G_2$) the same as if each and every combination were specifically and individually listed. It is similarly understood that each description of every variation on B ring ($R^3$, $R^4$, $Z_1$, $Z_2$, $Z_3$) may be combined with each description of every variation on C ring ($M_1$, $M_2$, $M_3$, $M_4$) the same as if each and every combination were specifically and individually listed. For example, in one aspect, it is understood that each description of every variation on B ring may be combined in one aspect with a variation of A ring in which X is O, $G_1$ is CH, $Y_1$ is N, $Y_2$ is C, $R^1$ is methyl; and/or $G_2$ is C—NHCH$_3$, $R^2$ is hydrogen (when C ring is absent). In one such variation, B ring is as defined in any variation herein, A ring is with the variables such as X is O, $G_1$ is hydrogen, $Y_1$ is N, $Y_2$ is C, $R^1$ is methyl; and/or $G_2$ is C—NHCH$_3$, $R^2$ is hydrogen (when C ring is absent), and/or C ring is substituted or unsubstituted phenyl.

In some embodiments of a compound of Formula (I), $Y_1$ is C; $Y_2$ is N; $R^1$ is methyl; $R^3$ is hydrogen; and $R^4$ is hydrogen, halogen, cyano, $C_1$-$C_4$ haloalkyl, $C_1$-$C_4$ alkoxy, $C_1$-$C_4$ haloalkoxy, —$OR^{13}$, —$NR^{13}R^{14}$, —$C(O)NR^{13}R^{14}$, —$NR^{13}C(O)R^{14}$, —$S(O)_2R^{13}$, —$NR^{13}S(O)_2R^{14}$, —$S(O)_2NR^{13}R^{14}$, or $C_1$-$C_4$ alkyl optionally substituted by halogen, oxo, CN or OH. In some embodiments of a compound of Formula (I), $Y_1$ is C; $Y_2$ is N; $R^1$ is methyl; $R^3$ is hydrogen; and $R^4$ is $NR^{13}R^{14}$. In some embodiments of a compound of Formula (I), $Y_1$ is C; $Y_2$ is N; $R^1$ is methyl; $R^3$ is hydrogen; and $R^4$ is $C(O)NR^{13}R^{14}$. In some embodiments of a compound of Formula (I), $Y_1$ is C; $Y_2$ is N; $R^1$ is methyl; $R^3$ is hydrogen; and $R^4$ is —$NR^{13}C(O)R^{14}$. In some embodiments of a compound of Formula (I), $Y_1$ is C; $Y_2$ is N; $R^1$ is methyl; $R^3$ is hydrogen; and $R^4$ is —$S(O)_2R^{13}$. In some embodiments of a compound of Formula (I), $Y_1$ is C; $Y_2$ is N; $R^1$ is methyl; $R^3$ is hydrogen; and $R^4$ is $NR^{13}S(O)_2R^{14}$. In some embodiments of a compound of Formula (I), $Y_1$ is C; $Y_2$ is N; $R^1$ is methyl; $R^3$ is hydrogen; and $R^4$ is $S(O)_2NR^{13}R^{14}$. In some embodiments of a compound of Formula (I), $Y_1$ is C; $Y_2$ is N; $R^1$ is methyl; $R^3$ is hydrogen; and $R^4$ is $C_1$-$C_4$ alkyl optionally substituted by halogen, oxo, —CN or —OH. In some embodiments of a compound of Formula (I), $Y_1$ is C; $Y_2$ is N; $R^1$ is methyl; $R^3$ is hydrogen; and $R^4$ is $C_1$-$C_4$ alkyl optionally substituted by —OH.

Also provided are salts of compounds referred to herein, such as pharmaceutically acceptable salts. The invention also includes any or all of the stereochemical forms, including any enantiomeric or diastereomeric forms, and any tautomers or other forms of the compounds described.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, 1% or 0.5% impurity.

Representative compounds are listed in Table 1. It is understood that individual enantiomers and diastereomers are included in the table below by Compound No. and their corresponding structures can be readily determined therefrom.

TABLE 1

| Com. No. | Structure |
|---|---|
| 1 | 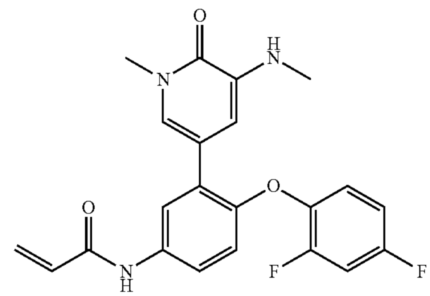 |
| 2 | 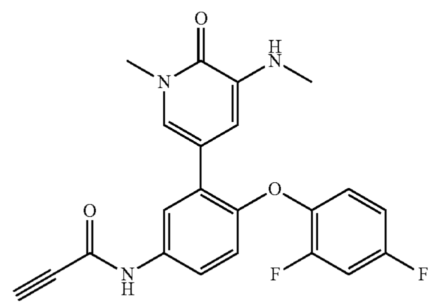 |
| 3 | 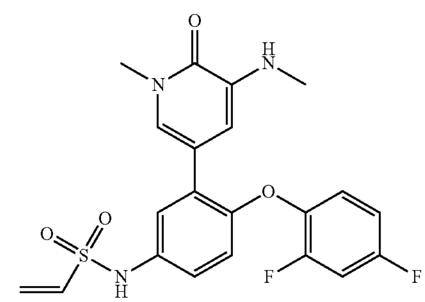 |
| 4 | 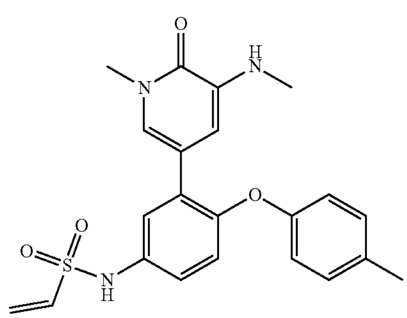 [SMILES: C=CS(=O)(=O)Nc1ccc(Oc2ccc(C)cc2)c(-c2cc(NC)c(=O)n(C)c2)c1] |
| 5 | 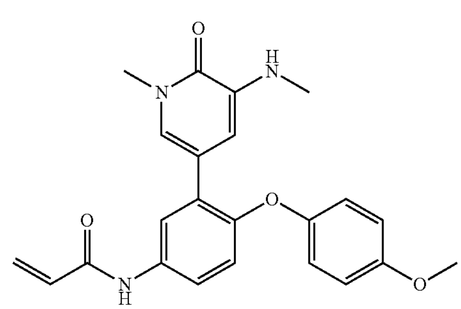 [SMILES: C=CC(=O)Nc1ccc(Oc2ccc(OC)cc2)c(-c2cc(NC)c(=O)n(C)c2)c1] |

TABLE 1-continued

| Com. No. | Structure |
|---|---|
| 6 | 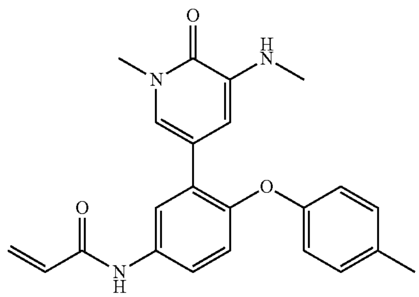 [SMILES: C=CC(=O)Nc1ccc(Oc2ccc(C)cc2)c(-c2cc(NC)c(=O)n(C)c2)c1] |
| 7 | 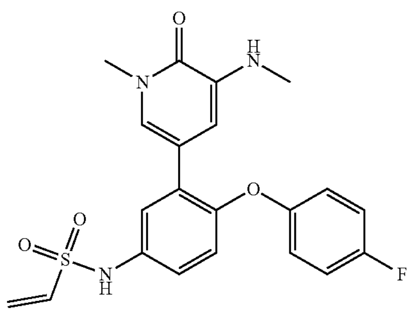 [SMILES: C=CS(=O)(=O)Nc1ccc(Oc2ccc(F)cc2)c(-c2cc(NC)c(=O)n(C)c2)c1] |
| 8 | 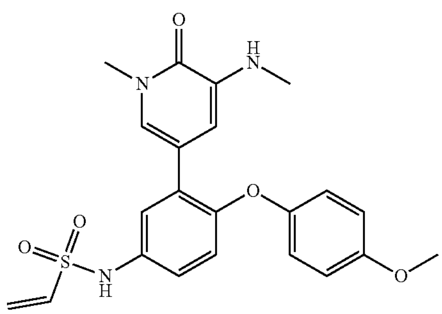 [SMILES: C=CS(=O)(=O)Nc1ccc(Oc2ccc(OC)cc2)c(-c2cc(NC)c(=O)n(C)c2)c1] |
| 9 | 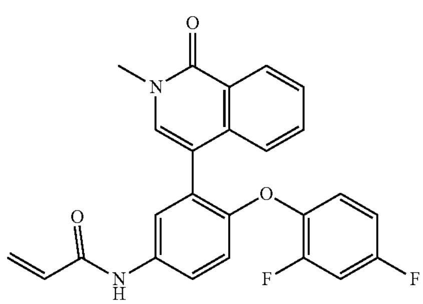 [SMILES: C=CC(=O)Nc1ccc(Oc2ccc(F)cc2F)c(-c2cn(C)c(=O)c3ccccc23)c1] |
| 10 | 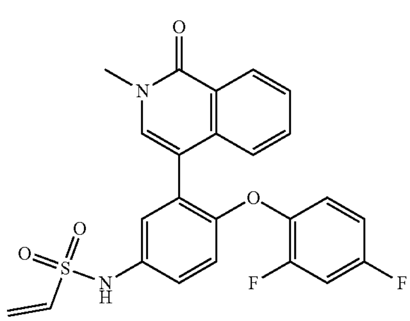 [SMILES: C=CS(=O)(=O)Nc1ccc(Oc2ccc(F)cc2F)c(-c2cn(C)c(=O)c3ccccc23)c1] |
| 11 | 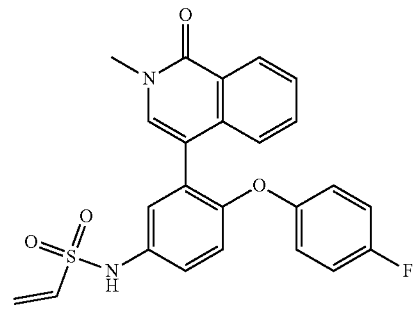 [SMILES: C=CS(=O)(=O)Nc1ccc(Oc2ccc(F)cc2)c(-c2cn(C)c(=O)c3ccccc23)c1] |
| 12 | 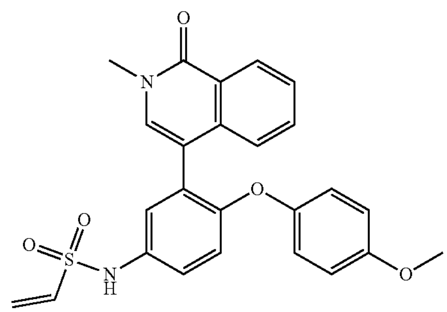 [SMILES: C=CS(=O)(=O)Nc1ccc(Oc2ccc(OC)cc2)c(-c2cn(C)c(=O)c3ccccc23)c1] |
| 13 | 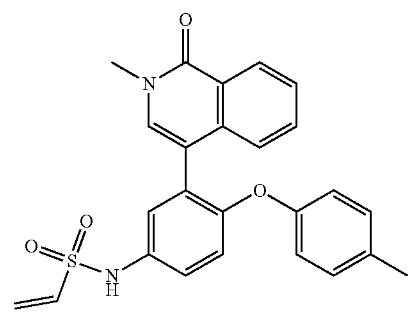 [SMILES: C=CS(=O)(=O)Nc1ccc(Oc2ccc(C)cc2)c(-c2cn(C)c(=O)c3ccccc23)c1] |
| 14 | 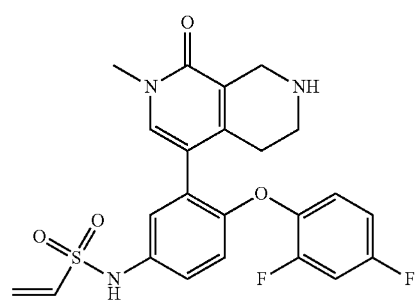 [SMILES: C=CS(=O)(=O)Nc1ccc(Oc2ccc(F)cc2F)c(-c2cn(C)c(=O)c3c2CCNC3)c1] |
| 15 | 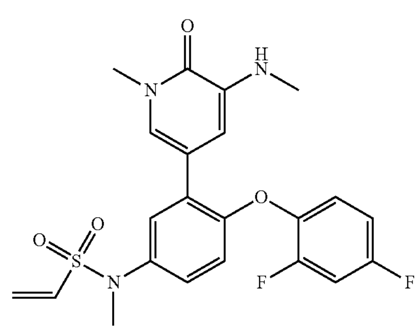 [SMILES: C=CS(=O)(=O)N(C)c1ccc(Oc2ccc(F)cc2F)c(-c2cc(NC)c(=O)n(C)c2)c1] |

TABLE 1-continued

| Com. No. | Structure |
|---|---|
| 16 | 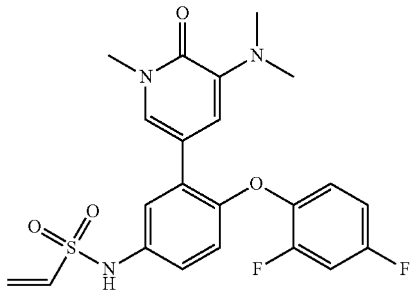 [SMILES: C=CS(=O)(=O)Nc1ccc(Oc2ccc(F)cc2F)c(-c2cc(N(C)C)c(=O)n(C)c2)c1] |
| 17 | 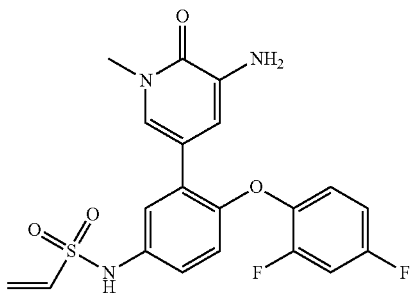 [SMILES: C=CS(=O)(=O)Nc1ccc(Oc2ccc(F)cc2F)c(-c2cc(N)c(=O)n(C)c2)c1] |
| 18 | 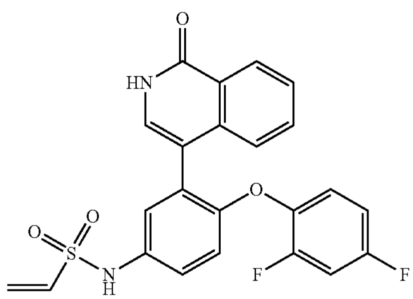 [SMILES: C=CS(=O)(=O)Nc1ccc(Oc2ccc(F)cc2F)c(-c2c[nH]c(=O)c3ccccc23)c1] |
| 19 | 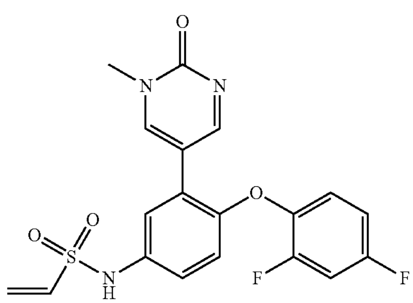 [SMILES: C=CS(=O)(=O)Nc1ccc(Oc2ccc(F)cc2F)c(-c2cnc(=O)n(C)c2)c1] |
| 20 | 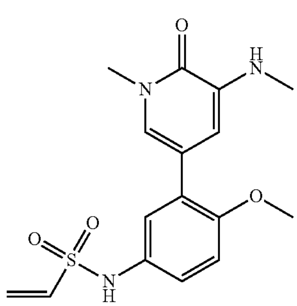 [SMILES: C=CS(=O)(=O)Nc1ccc(OC)c(-c2cc(NC)c(=O)n(C)c2)c1] |
| 21 | |
| 22 | |
| 23 | |
| 24 | |
| 25 | |

TABLE 1-continued

| Com. No. | Structure |
|---|---|
| 26 | (2-methylisoquinolin-1(2H)-one at 3-position of phenyl; 4-(4-fluorophenoxy) on phenyl; acrylamide at 5-position) |
| 27 | (2-methylisoquinolin-1(2H)-one at 3-position of phenyl; 4-(OCF₃) on phenyl; acrylamide at 5-position) |
| 28 | (2-isopropylisoquinolin-1(2H)-one at 3-position of phenyl; 4-(4-fluorophenoxy) on phenyl; acrylamide at 5-position) |
| 29 | (1-methyl-3-(dimethylamino)pyridin-2(1H)-one at 3-position of phenyl; 4-(2,4-difluorophenoxy) on phenyl; acrylamide at 5-position) |
| 30 | (1-methyl-3-(methylamino)pyridin-2(1H)-one at 3-position of phenyl; 4-(4-fluorophenoxy) on phenyl; acrylamide at 5-position) |
| 31 | (2-methylisoquinolin-1(2H)-one at 3-position of phenyl; 4-(4-chlorophenoxy) on phenyl; acrylamide at 5-position) |
| 32 | (2-methylisoquinolin-1(2H)-one at 3-position of phenyl; 4-(3-fluoro-4-chlorophenoxy) on phenyl; acrylamide at 5-position) |
| 33 | (2-methyl-5-(methylamino)pyridazin-3(2H)-one at 3-position of phenyl; 4-(2,4-difluorophenoxy) on phenyl; acrylamide at 5-position) |
| 34 | (1-methyl-3-(methylamino)pyridin-2(1H)-one at 3-position of phenyl; 4-(3-fluorophenoxy) on phenyl; vinylsulfonamide at 5-position) |
| 35 | (1-methyl-3-(methylamino)pyridin-2(1H)-one at 3-position of phenyl; 4-(2-fluorophenoxy) on phenyl; vinylsulfonamide at 5-position) |

TABLE 1-continued

| Com. No. | Structure |
|---|---|
| 36 | 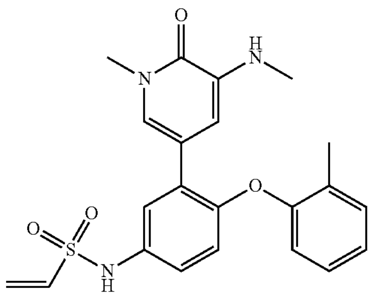 [SMILES: C=CS(=O)(=O)Nc1ccc(Oc2ccccc2C)c(-c2cc(NC)c(=O)n(C)c2)c1] |
| 37 | 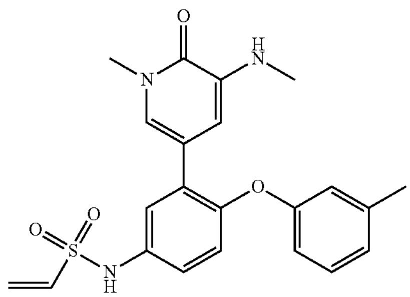 [SMILES: C=CS(=O)(=O)Nc1ccc(Oc2cccc(C)c2)c(-c2cc(NC)c(=O)n(C)c2)c1] |
| 38 | 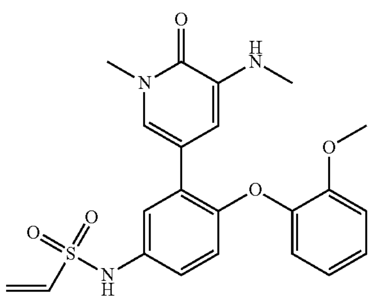 [SMILES: C=CS(=O)(=O)Nc1ccc(Oc2ccccc2OC)c(-c2cc(NC)c(=O)n(C)c2)c1] |
| 39 | 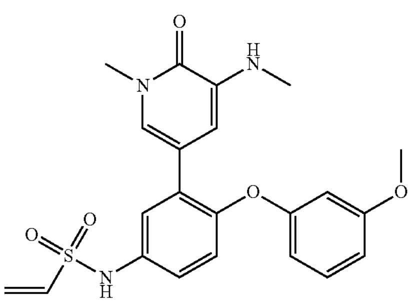 [SMILES: C=CS(=O)(=O)Nc1ccc(Oc2cccc(OC)c2)c(-c2cc(NC)c(=O)n(C)c2)c1] |
| 40 | 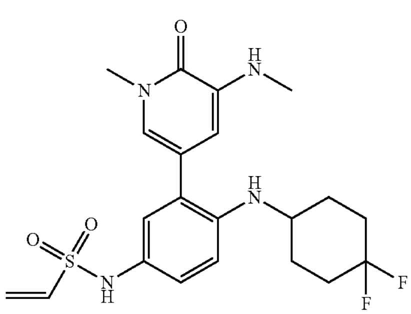 [SMILES: C=CS(=O)(=O)Nc1ccc(NC2CCC(F)(F)CC2)c(-c2cc(NC)c(=O)n(C)c2)c1] |
| 41 | |
| 42 | |
| 43 | |
| 44 | |
| 45 | |

TABLE 1-continued

| Com. No. | Structure |
|---|---|
| 46 | |
| 47 | |
| 48 | |
| 49 | |
| 50 | 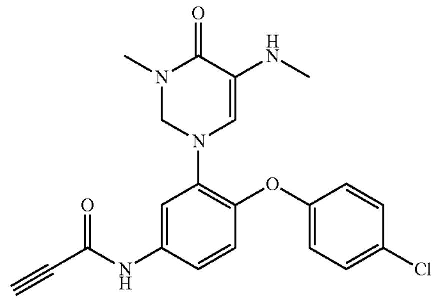 [SMILES: C#CC(=O)Nc1ccc(Oc2ccc(Cl)cc2)c(N2C=C(NC)C(=O)N(C)C2)c1] |
| 51 | 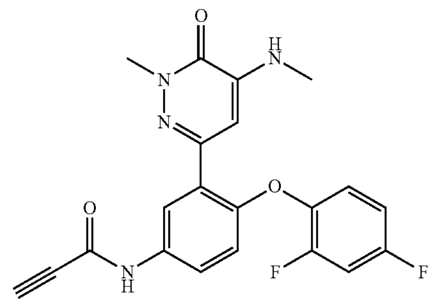 [SMILES: C#CC(=O)Nc1ccc(Oc2ccc(F)cc2F)c(-c2cc(NC)c(=O)n(C)n2)c1] |
| 52 | 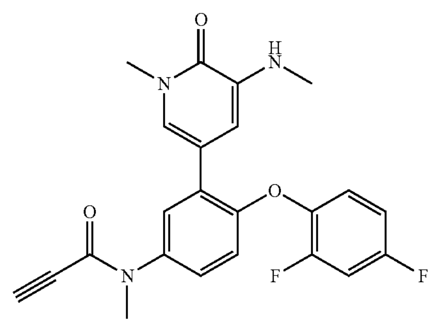 [SMILES: C#CC(=O)N(C)c1ccc(Oc2ccc(F)cc2F)c(-c2cc(NC)c(=O)n(C)c2)c1] |
| 53 | 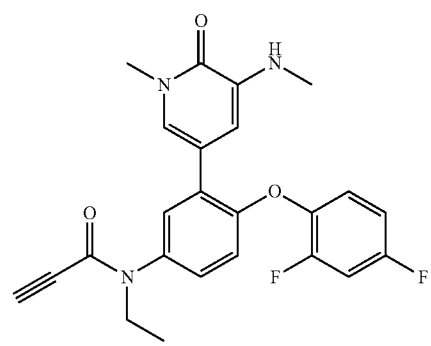 [SMILES: C#CC(=O)N(CC)c1ccc(Oc2ccc(F)cc2F)c(-c2cc(NC)c(=O)n(C)c2)c1] |
| 54 | 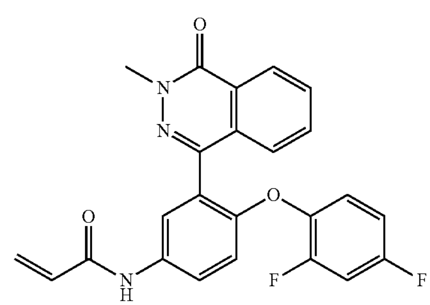 [SMILES: C=CC(=O)Nc1ccc(Oc2ccc(F)cc2F)c(-c2nn(C)c(=O)c3ccccc23)c1] |

TABLE 1-continued

| Com. No. | Structure |
|---|---|
| 55 | (2-methyl-1-oxo-1,2-dihydroisoquinolin-4-yl) with 2-(3-fluorophenoxy)phenyl and ethenesulfonamide |
| 56 | (2-methyl-1-oxo-1,2-dihydroisoquinolin-4-yl) with 2-(2-fluorophenoxy)phenyl and ethenesulfonamide |
| 57 | (2-methyl-1-oxo-1,2-dihydroisoquinolin-4-yl) with 2-(2-methylphenoxy)phenyl and ethenesulfonamide |
| 58 | (2-methyl-7-trifluoromethyl-1-oxo-1,2-dihydroisoquinolin-4-yl) with 2-(3-methylphenoxy)phenyl and ethenesulfonamide |
| 59 | (2-methyl-1-oxo-1,2-dihydroisoquinolin-4-yl) with 2-(2-methoxyphenoxy)phenyl and ethenesulfonamide |

TABLE 1-continued

| Com. No. | Structure |
|---|---|
| 60 | (2-methyl-1-oxo-1,2-dihydroisoquinolin-4-yl) with 2-(3-methoxyphenoxy)phenyl and ethenesulfonamide |
| 61 | (7-cyano-2-methyl-1-oxo-1,2-dihydroisoquinolin-4-yl) with 2-(2,4-difluorophenoxy)phenyl and ethenesulfonamide |
| 62 | (7-cyclopropyl-2-methyl-1-oxo-1,2-dihydroisoquinolin-4-yl) with 2-(2,4-difluorophenoxy)phenyl and ethenesulfonamide |
| 63 | (7-dimethylamino-2-methyl-1-oxo-1,2-dihydroisoquinolin-4-yl) with 2-(2,4-difluorophenoxy)phenyl and ethenesulfonamide |
| 64 | (3-methyl-4-oxo-3,4-dihydrophthalazin-1-yl) with 2-(2,4-difluorophenoxy)phenyl and ethenesulfonamide |

TABLE 1-continued

| Com. No. | Structure |
|---|---|
| 65 | (structure) |
| 66 | (structure) |
| 67 | (structure) |
| 68 | (structure) |
| 69 | (structure) |
| 70 | (structure) |
| 71 | (structure) |
| 72 | (structure) |
| 73 | (structure) |

TABLE 1-continued

| Com. No. | Structure |
|---|---|
| 74 | (structure) |
| 75 | (structure) |
| 76 | (structure) |
| 77 | (structure) |
| 78 | (structure) |
| 79 | (structure) |
| 80 | (structure) |
| 81 | (structure) |
| 82 | (structure) |
| 83 | (structure) |

TABLE 1-continued

| Com. No. | Structure |
|---|---|
| 84 | (structure) |
| 85 | (structure) |
| 86 | (structure) |
| 87 | (structure) |
| 88 | (structure) |
| 89 | (structure) |
| 90 | (structure) |
| 91 | (structure) |
| 92 | (structure) |
| 93 | (structure) |

TABLE 1-continued

| Com. No. | Structure |
|---|---|
| 94 | (structure) |
| 95 | (structure) |
| 96 | (structure) |
| 97 | (structure) |
| 98 | (structure) |
| 99 | (structure) |
| 100 | (structure) |
| 101 | (structure) |
| 102 | (structure) |
| 103 | (structure) |

TABLE 1-continued

| Com. No. | Structure |
|---|---|
| 104 | (structure) |
| 105 | (structure) |
| 106 | (structure) |
| 107 | (structure) |
| 108 | (structure) |
| 109 | (structure) |
| 110 | (structure) |
| 111 | (structure) |
| 112 | (structure) |
| 113 | (structure) |

TABLE 1-continued

| Com. No. | Structure |
|---|---|
| 114 | 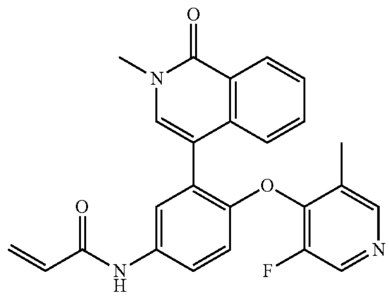 [SMILES: C=CC(=O)Nc1ccc(Oc2c(C)cncc2F)c(-c2cn(C)c(=O)c3ccccc23)c1] |
| 115 | 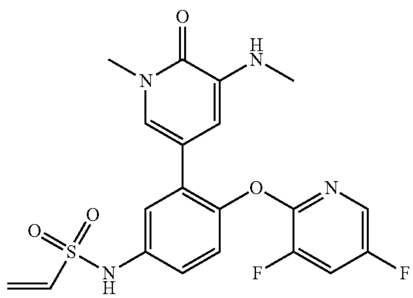 [SMILES: C=CS(=O)(=O)Nc1ccc(Oc2ncc(F)cc2F)c(-c2cc(NC)c(=O)n(C)c2)c1] |
| 116 | 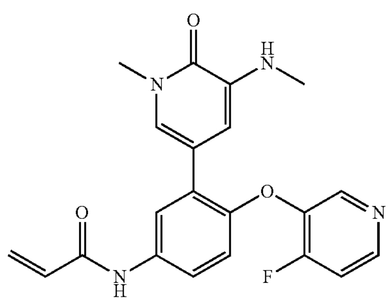 [SMILES: C=CC(=O)Nc1ccc(Oc2cnccc2F)c(-c2cc(NC)c(=O)n(C)c2)c1] |
| 117 | 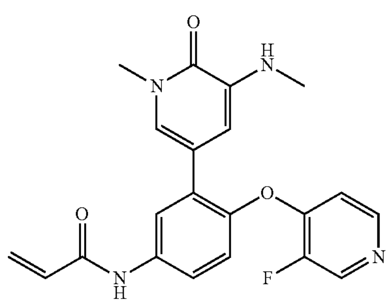 [SMILES: C=CC(=O)Nc1ccc(Oc2ccncc2F)c(-c2cc(NC)c(=O)n(C)c2)c1] |
| 118 | 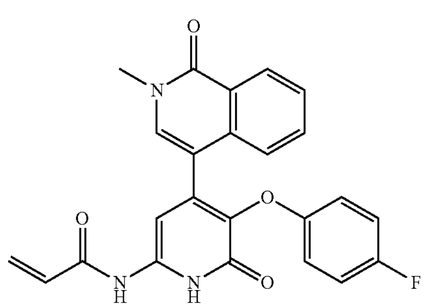 [SMILES: C=CC(=O)Nc1cc(-c2cn(C)c(=O)c3ccccc23)c(Oc2ccc(F)cc2)c(=O)[nH]1] |
| 119 | |
| 120 | |
| 121 | |
| 122 | |
| 123 | |

TABLE 1-continued

| Com. No. | Structure |
|---|---|
| 124 | (structure) |
| 125 | (structure) |
| 126 | (structure) |
| 127 | (structure) |
| 128 | (structure) |
| 129 | (structure) |
| 130 | (structure) |
| 131 | (structure) |
| 132 | (structure) |
| 133 | (structure) |

TABLE 1-continued
| Com. No. | Structure |
|---|---|
| 134 | 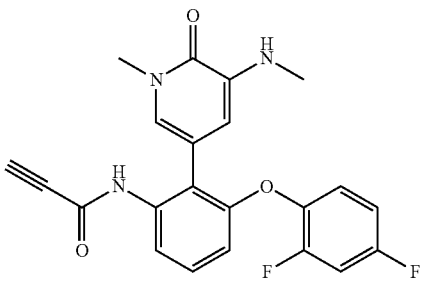 |
| 135 | 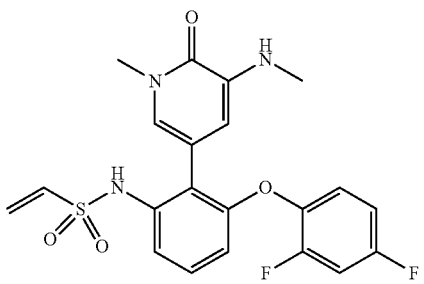 [SMILES: C=CS(=O)(=O)Nc1cccc(Oc2ccc(F)cc2F)c1-c1cc(NC)c(=O)n(C)c1] |
| 136 | 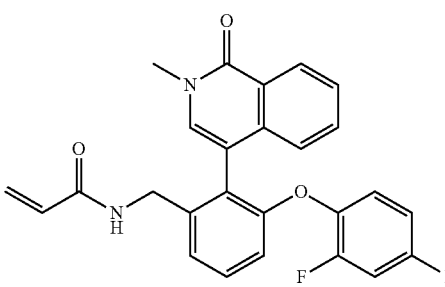 |
| 137 | 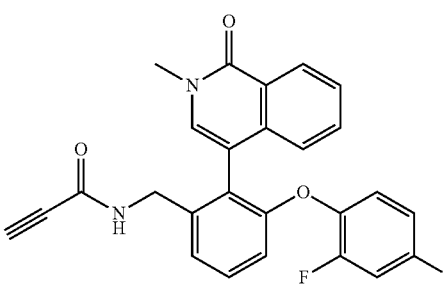 |
| 138 | 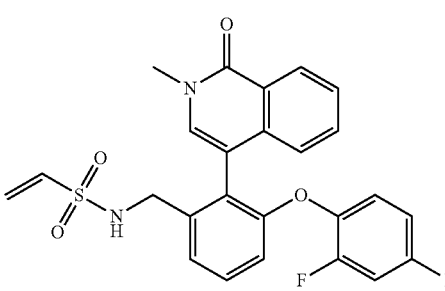 |
| 139 | 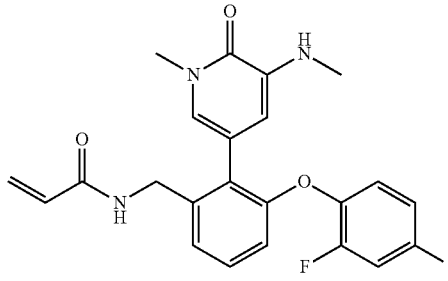 |
| 140 | 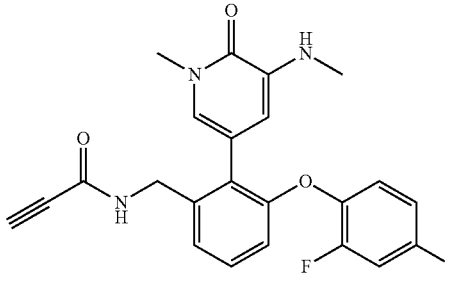 |
| 141 | 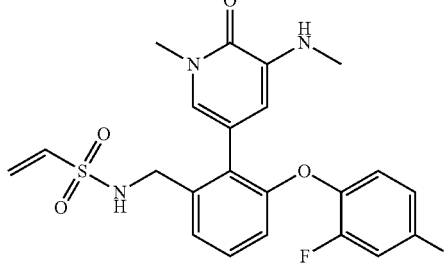 |
| 142 | 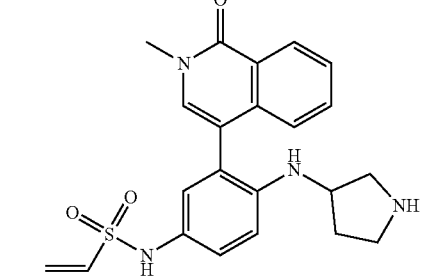 |
| 143 | 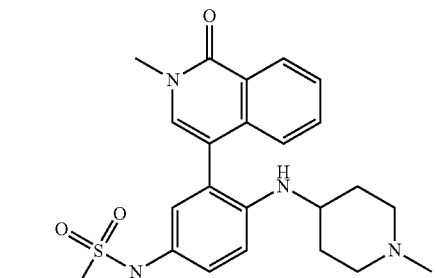 |

TABLE 1-continued

| Com. No. | Structure |
|---|---|
| 144 | (structure) |
| 145 | (structure) |
| 146 | (structure) |
| 147 | (structure) |
| 148 | (structure) |
| 149 | (structure) |
| 150 | (structure) |
| 151 | (structure) |
| 152 | (structure) |

TABLE 1-continued

| Com. No. | Structure |
|---|---|
| 153 | (structure) |
| 154 | (structure) |
| 155 | (structure) |
| 156 | (structure) |
| 157 | (structure) |
| 158 | (structure) |
| 159 | (structure) |
| 160 | (structure) |

TABLE 1-continued

| Com. No. | Structure |
|---|---|
| 161 | (structure) |
| 162 | (structure) |
| 163 | (structure) |
| 164 | (structure) |
| 165 | (structure) |
| 166 | (structure) |
| 167 | (structure) |
| 168 | (structure) |
| 169 | (structure) |
| 170 | (structure) |

US 11,192,900 B2
135
TABLE 1-continued
| Com. No. | Structure |
|---|---|
| 171 | 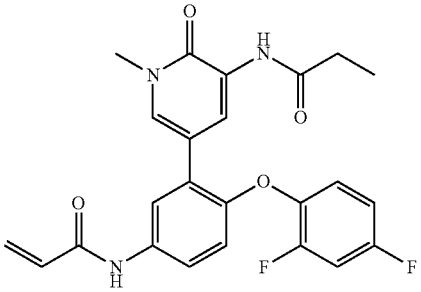 [SMILES: C=CC(=O)Nc1ccc(Oc2ccc(F)cc2F)c(-c2cc(NC(=O)CC)c(=O)n(C)c2)c1] |
| 172 | 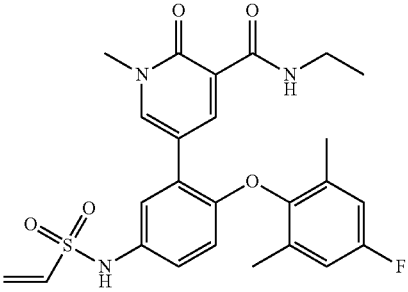 [SMILES: C=CS(=O)(=O)Nc1ccc(Oc2c(C)cc(F)cc2C)c(-c2cc(C(=O)NCC)c(=O)n(C)c2)c1] |
| 173 | 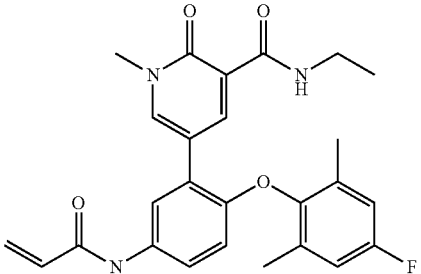 |
| 174 | 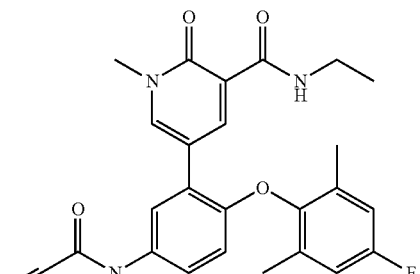 |
| 175 | 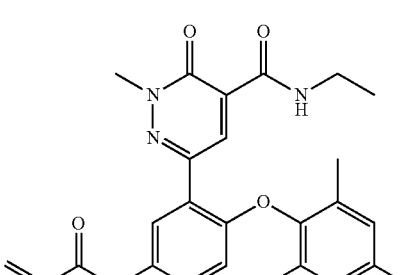 |
136
TABLE 1-continued
| Com. No. | Structure |
|---|---|
| 176 | 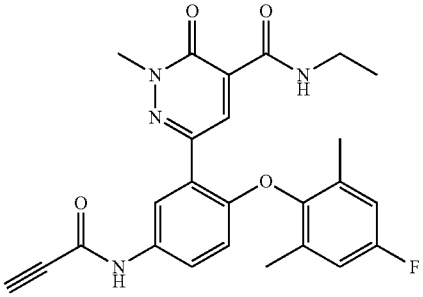 [SMILES: C#CC(=O)Nc1ccc(Oc2c(C)cc(F)cc2C)c(-c2cc(C(=O)NCC)c(=O)n(C)n2)c1] |
| 177 | 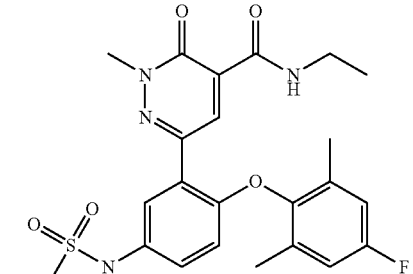 |
| 178 | 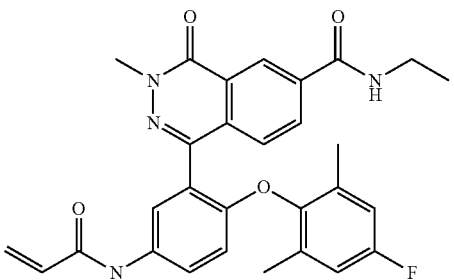 |
| 179 | 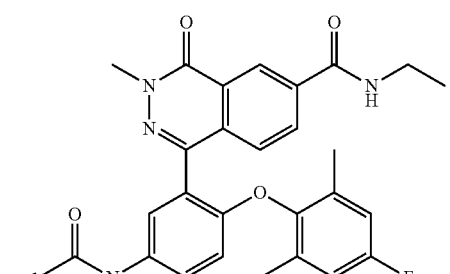 |
| 180 | 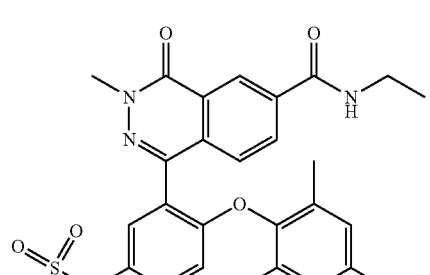 |

TABLE 1-continued

| Com. No. | Structure |
|---|---|
| 181 | (structure) |
| 182 | (structure) |
| 183 | (structure) |
| 184 | (structure) |
| 185 | (structure) |
| 186 | (structure) |
| 187 | (structure) |
| 188 | (structure) |
| 189 | (structure) |
| 190 | (structure) |

TABLE 1-continued

| Com. No. | Structure |
|---|---|
| 191 | (structure) |
| 192 | (structure) |
| 193 | (structure) |
| 194 | (structure) |
| 195 | (structure) |
| 196 | (structure) |
| 197 | (structure) |
| 198 | (structure) |
| 199 | (structure) |
| 200 | (structure) |

TABLE 1-continued

| Com. No. | Structure |
|---|---|
| 201 | (vinylsulfonamide; pyridazinone with N-methyl and methylamino; 2,4-difluorophenoxy) |
| 202 | (propiolamide; pyridazinone with N-methyl and methylamino; 2,4-difluorophenoxy) |
| 203 | (acrylamide; pyridazinone with N-methyl and methylamino; 2,4-difluorophenoxy) |
| 204 | (vinylsulfonamide; pyridinone with N-methyl and methylamino; 4-fluoro-2,6-dimethylphenoxy) |
| 205 | (propiolamide; pyridinone with N-methyl and methylamino; 4-fluoro-2,6-dimethylphenoxy) |
| 206 | (acrylamide; pyridinone with N-methyl and methylamino; 4-fluoro-2,6-dimethylphenoxy) |
| 207 | (vinylsulfonamide; pyridazinone with N-methyl and methylamino; 4-fluoro-2,6-dimethylphenoxy) |
| 208 | (propiolamide; pyridazinone with N-methyl and methylamino; 4-fluoro-2,6-dimethylphenoxy) |
| 209 | (acrylamide; pyridazinone with N-methyl and methylamino; 4-fluoro-2,6-dimethylphenoxy) |
| 210 | (vinylsulfonamide; N-methyl isoquinolinone; 4-fluoro-2,6-dimethylphenoxy) |

TABLE 1-continued
| Com. No. | Structure |
|---|---|
| 211 | 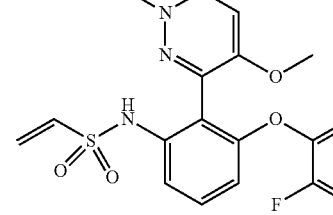 |
| 212 | 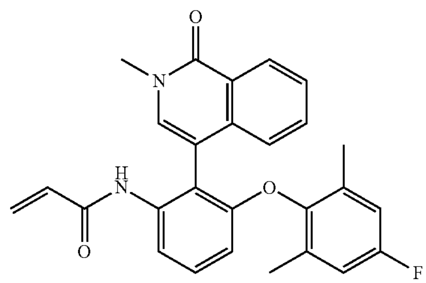 [SMILES: C=CC(=O)Nc1cccc(Oc2c(C)cc(F)cc2C)c1-c1cn(C)c(=O)c2ccccc12] |
| 213 | 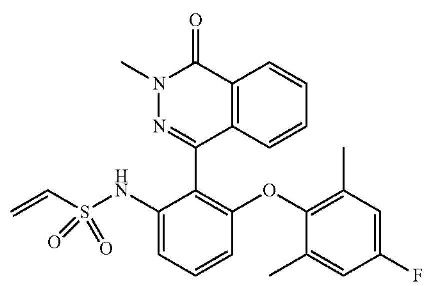 [SMILES: C=CS(=O)(=O)Nc1cccc(Oc2c(C)cc(F)cc2C)c1-c1nn(C)c(=O)c2ccccc12] |
| 214 | 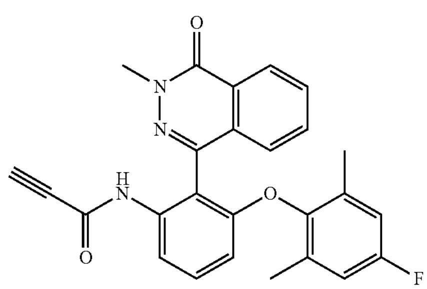 [SMILES: C#CC(=O)Nc1cccc(Oc2c(C)cc(F)cc2C)c1-c1nn(C)c(=O)c2ccccc12] |
| 215 | 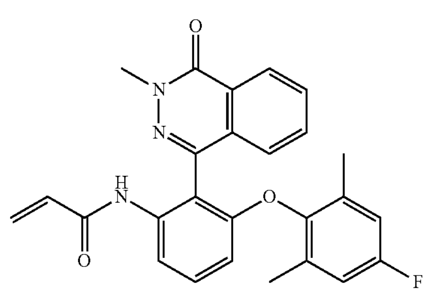 [SMILES: C=CC(=O)Nc1cccc(Oc2c(C)cc(F)cc2C)c1-c1nn(C)c(=O)c2ccccc12] |
TABLE 1-continued
| Com. No. | Structure |
|---|---|
| 216 | 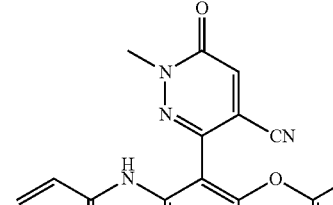 |
| 217 | 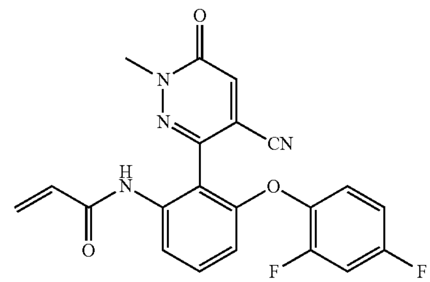 [SMILES: C=CC(=O)Nc1cccc(Oc2ccc(F)cc2F)c1-c1nn(C)c(=O)cc1C#N] |
| 218 | 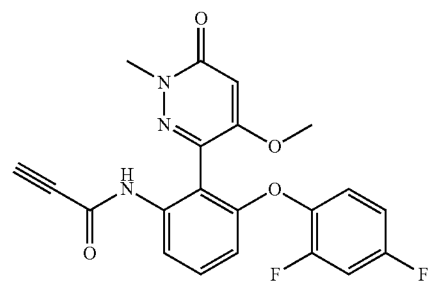 [SMILES: C#CC(=O)Nc1cccc(Oc2ccc(F)cc2F)c1-c1nn(C)c(=O)cc1OC] |
| 219 | 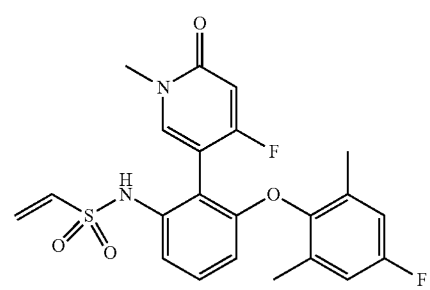 [SMILES: C=CS(=O)(=O)Nc1cccc(Oc2c(C)cc(F)cc2C)c1-c1cn(C)c(=O)cc1F] |
| 220 | 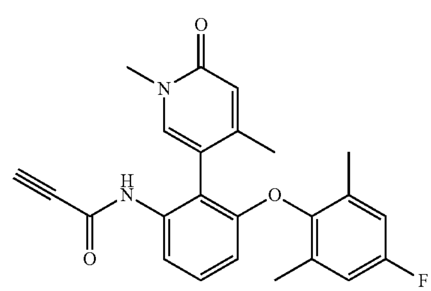 [SMILES: C#CC(=O)Nc1cccc(Oc2c(C)cc(F)cc2C)c1-c1cn(C)c(=O)cc1C] |

TABLE 1-continued

| Com. No. | Structure |
|---|---|
| 221 | (structure) |
| 222 | (structure) |
| 223 | (structure) |
| 224 | (structure) |
| 225 | (structure) |
| 226 | (structure) |
| 227 | (structure) |
| 228 | (structure) |
| 229 | (structure) |
| 230 | (structure) |

TABLE 1-continued

| Com. No. | Structure |
|---|---|
| 231 | (structure) |
| 232 | (structure) |
| 233 | (structure) |
| 234 | (structure) |
| 235 | (structure) |
| 236 | (structure) |
| 237 | (structure) |
| 238 | (structure) |
| 239 | (structure) |
| 240 | (structure) |

TABLE 1-continued

| Com. No. | Structure |
|---|---|
| 241 | 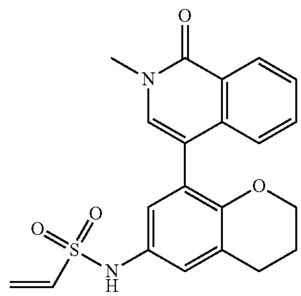 [SMILES: C=CS(=O)(=O)Nc1cc2c(c(-c3cn(C)c(=O)c4ccccc34)c1)OCCC2] |
| 242 | 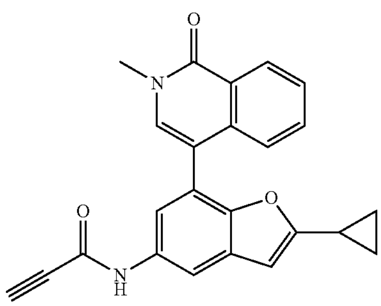 [SMILES: C#CC(=O)Nc1cc(-c2cn(C)c(=O)c3ccccc23)c2oc(C3CC3)cc2c1] |
| 243 | 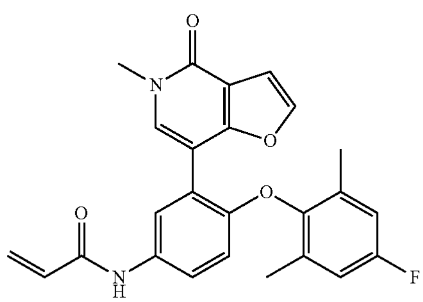 [SMILES: C=CC(=O)Nc1ccc(Oc2c(C)cc(F)cc2C)c(-c2cn(C)c(=O)c3ccoc23)c1] |
| 244 | 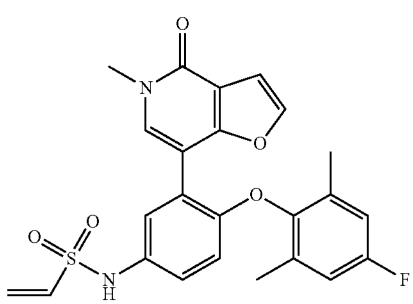 [SMILES: C=CS(=O)(=O)Nc1ccc(Oc2c(C)cc(F)cc2C)c(-c2cn(C)c(=O)c3ccoc23)c1] |
| 245 | 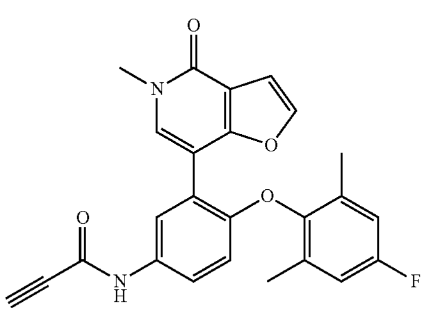 [SMILES: C#CC(=O)Nc1ccc(Oc2c(C)cc(F)cc2C)c(-c2cn(C)c(=O)c3ccoc23)c1] |
| 246 | |
| 247 | |
| 248 | |
| 249 | |
| 250 | |

TABLE 1-continued
| Com. No. | Structure |
|---|---|
| 251 | 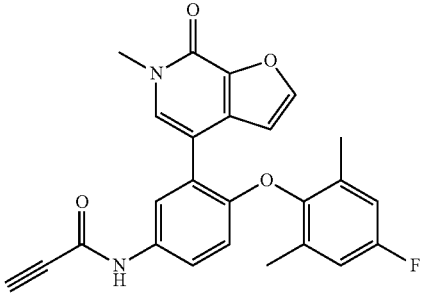 [SMILES: C#CC(=O)Nc1ccc(Oc2c(C)cc(F)cc2C)c(-c2cn(C)c(=O)c3occc23)c1] |
| 252 | 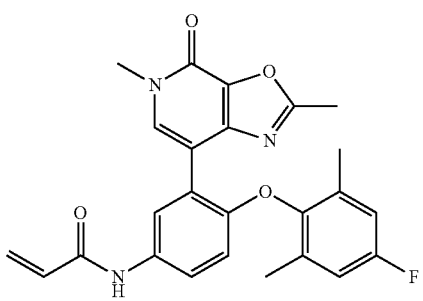 [SMILES: C=CC(=O)Nc1ccc(Oc2c(C)cc(F)cc2C)c(-c2cn(C)c(=O)c3oc(C)nc23)c1] |
| 253 | 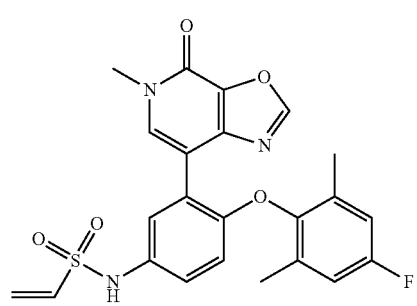 [SMILES: C=CS(=O)(=O)Nc1ccc(Oc2c(C)cc(F)cc2C)c(-c2cn(C)c(=O)c3ocnc23)c1] |
| 254 | 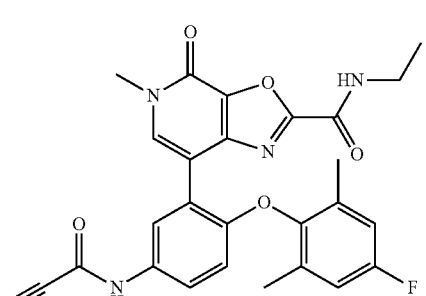 |
| 255 | 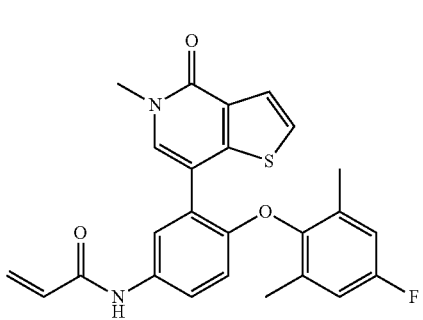 |
TABLE 1-continued
| Com. No. | Structure |
|---|---|
| 256 | 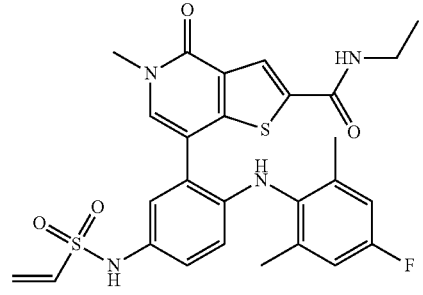 [SMILES: C=CS(=O)(=O)Nc1ccc(Nc2c(C)cc(F)cc2C)c(-c2cn(C)c(=O)c3cc(C(=O)NCC)sc23)c1] |
| 257 | 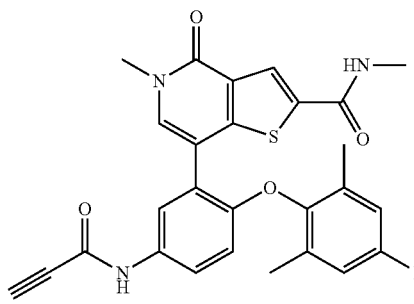 |
| 258 | 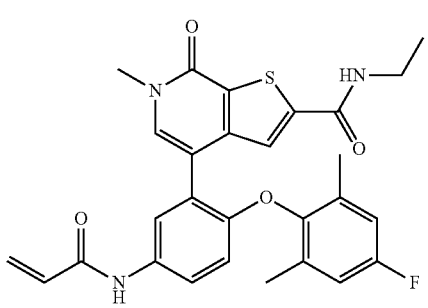 |
| 259 | 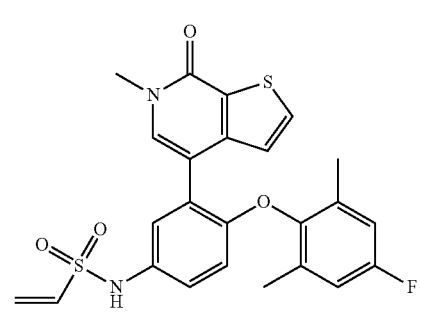 [SMILES: C=CS(=O)(=O)Nc1ccc(Oc2c(C)cc(F)cc2C)c(-c2cn(C)c(=O)c3sccc23)c1] |
| 260 | 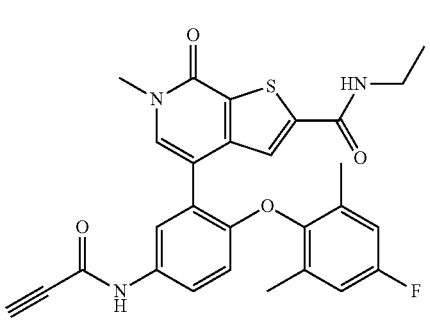 |

TABLE 1-continued
| Com. No. | Structure |
|---|---|
| 261 | 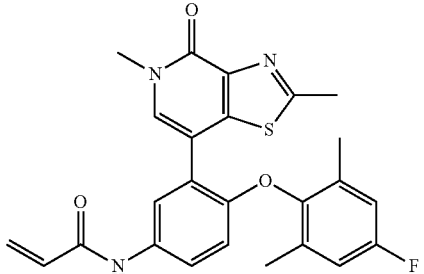 |
| 262 | 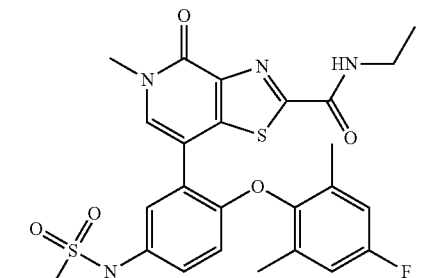 |
| 263 | 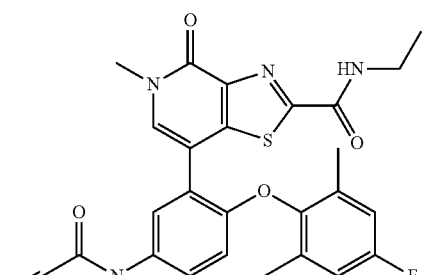 |
| 264 | 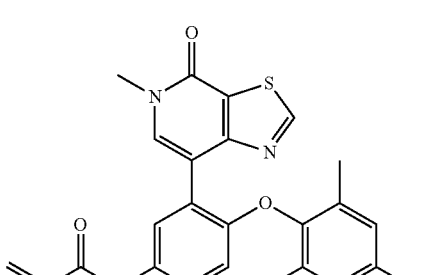 |
| 265 | 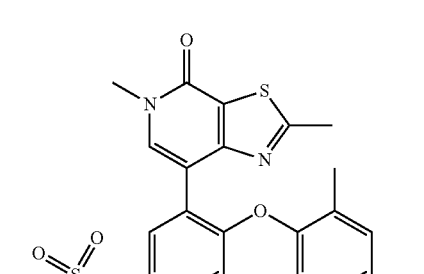 |
TABLE 1-continued
| Com. No. | Structure |
|---|---|
| 266 | 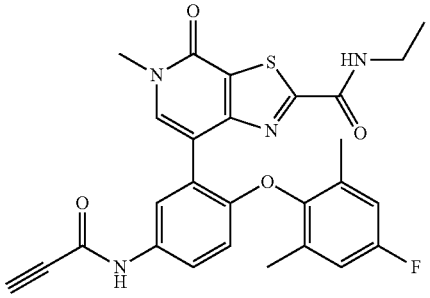 |
| 267 | 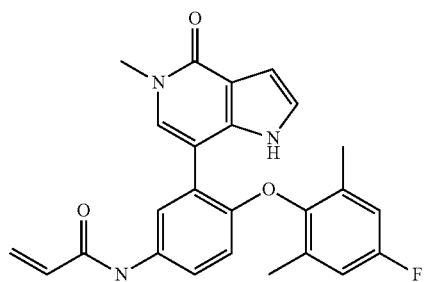 |
| 268 | 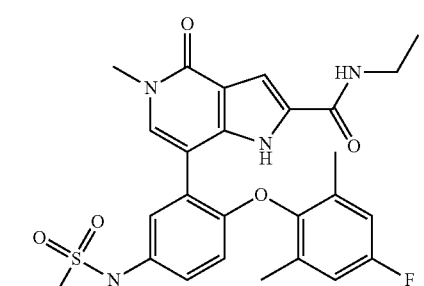 |
| 269 | 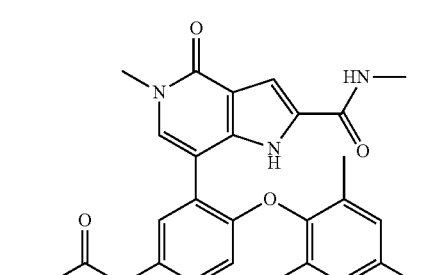 |
| 270 | 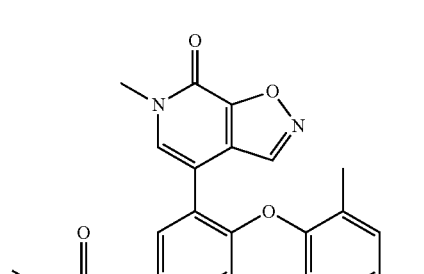 |

TABLE 1-continued

| Com. No. | Structure |
|---|---|
| 271 | (structure) |
| 272 | (structure) |
| 273 | (structure) |
| 274 | (structure) |
| 275 | (structure) |
| 276 | (structure) |
| 277 | (structure) |
| 278 | (structure) |
| 279 | (structure) |
| 280 | (structure) |

TABLE 1-continued

| Com. No. | Structure |
|---|---|
| 281 | (structure) |
| 282 | (structure) |
| 283 | (structure) |
| 284 | (structure) |
| 285 | (structure) |
| 286 | (structure) |
| 287 | (structure) |
| 288 | (structure) |
| 289 | (structure) |
| 290 | (structure) |

TABLE 1-continued

| Com. No. | Structure |
|---|---|
| 291 | 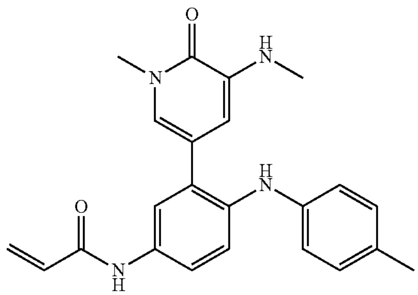 [SMILES: C=CC(=O)Nc1ccc(Nc2ccc(C)cc2)c(-c2cc(NC)c(=O)n(C)c2)c1] |
| 292 | 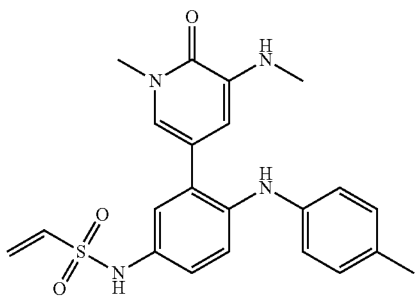 [SMILES: C=CS(=O)(=O)Nc1ccc(Nc2ccc(C)cc2)c(-c2cc(NC)c(=O)n(C)c2)c1] |
| 293 | 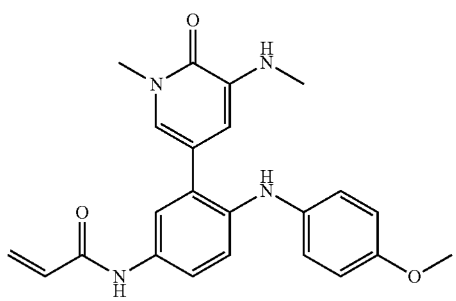 [SMILES: C=CC(=O)Nc1ccc(Nc2ccc(OC)cc2)c(-c2cc(NC)c(=O)n(C)c2)c1] |
| 294 | 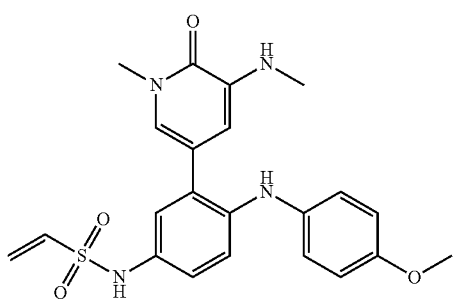 [SMILES: C=CS(=O)(=O)Nc1ccc(Nc2ccc(OC)cc2)c(-c2cc(NC)c(=O)n(C)c2)c1] |
| 295 | 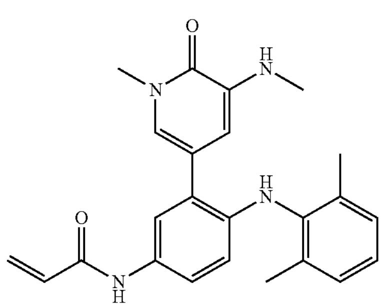 |

TABLE 1-continued

| Com. No. | Structure |
|---|---|
| 296 | |
| 297 | |
| 298 | |
| 299 | |
| 300 | |

TABLE 1-continued

| Com. No. | Structure |
|---|---|
| 301 | (structure) |
| 302 | (structure) |
| 303 | (structure) |
| 304 | (structure) |
| 305 | (structure) |
| 306 | (structure) |
| 307 | (structure) |
| 308 | (structure) |
| 309 | (structure) |
| 310 | (structure) |

TABLE 1-continued

| Com. No. | Structure |
|---|---|
| 311 | (2-methylisoquinolin-1(2H)-one linked to benzene with acrylamide NH and NH-(4-methoxyphenyl)) |
| 312 | (2-methylisoquinolin-1(2H)-one linked to benzene with vinylsulfonamide NH and NH-(4-methoxyphenyl)) |
| 313 | (2-methylisoquinolin-1(2H)-one linked to benzene with acrylamide NH and NH-(2,6-dimethylphenyl)) |
| 314 | (2-methylisoquinolin-1(2H)-one linked to benzene with vinylsulfonamide NH and NH-(2,6-dimethylphenyl)) |
| 315 | (2-methylisoquinolin-1(2H)-one linked to benzene with acrylamide NH and NH-(2,6-dimethyl-4-fluorophenyl)) |
| 316 | (2-methylisoquinolin-1(2H)-one linked to benzene with vinylsulfonamide NH and NH-(2,6-dimethyl-4-fluorophenyl)) |
| 317 | (2-methylisoquinolin-1(2H)-one linked to benzene with acrylamide NH and NH-(4-chlorophenyl)) |
| 318 | (2-methylisoquinolin-1(2H)-one linked to benzene with vinylsulfonamide NH and NH-(4-chlorophenyl)) |
| 319 | (2-methylisoquinolin-1(2H)-one linked to benzene with acrylamide NH and NH-(2,6-difluorophenyl)) |
| 320 | (2-methylisoquinolin-1(2H)-one linked to benzene with vinylsulfonamide NH and NH-(2,6-difluorophenyl)) |

TABLE 1-continued

| Com. No. | Structure |
|---|---|
| 321 | 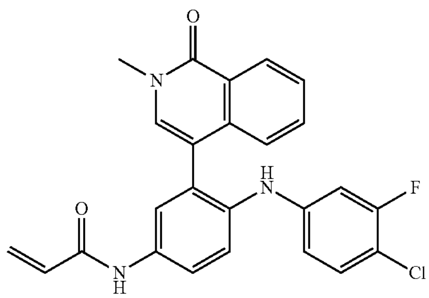 [SMILES: C=CC(=O)Nc1ccc(Nc2ccc(Cl)c(F)c2)c(-c2cn(C)c(=O)c3ccccc23)c1] |
| 322 | 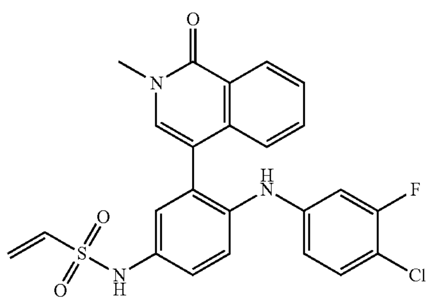 [SMILES: C=CS(=O)(=O)Nc1ccc(Nc2ccc(Cl)c(F)c2)c(-c2cn(C)c(=O)c3ccccc23)c1] |
| 323 | 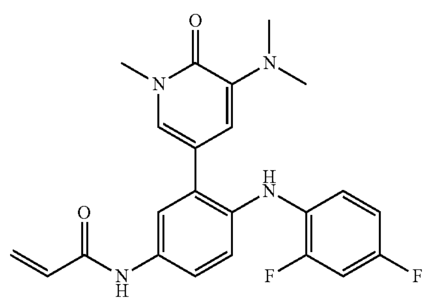 [SMILES: C=CC(=O)Nc1ccc(Nc2ccc(F)cc2F)c(-c2cc(N(C)C)c(=O)n(C)c2)c1] |
| 324 | 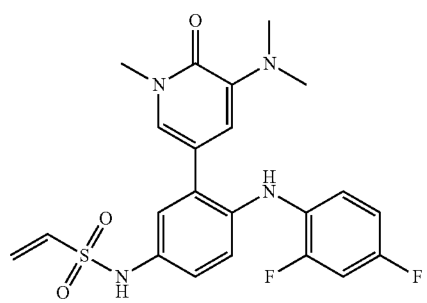 [SMILES: C=CS(=O)(=O)Nc1ccc(Nc2ccc(F)cc2F)c(-c2cc(N(C)C)c(=O)n(C)c2)c1] |
| 325 | 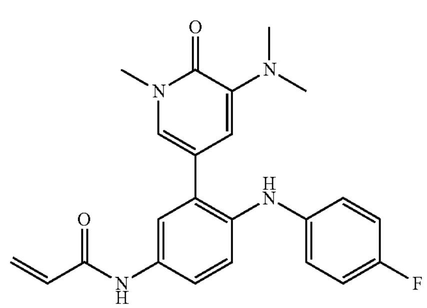 [SMILES: C=CC(=O)Nc1ccc(Nc2ccc(F)cc2)c(-c2cc(N(C)C)c(=O)n(C)c2)c1] |
| 326 | 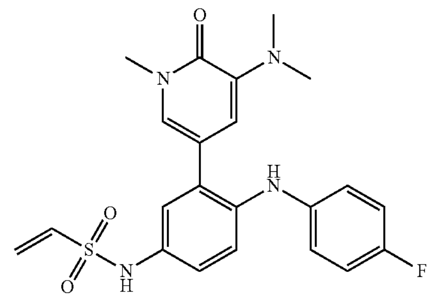 [SMILES: C=CS(=O)(=O)Nc1ccc(Nc2ccc(F)cc2)c(-c2cc(N(C)C)c(=O)n(C)c2)c1] |
| 327 | 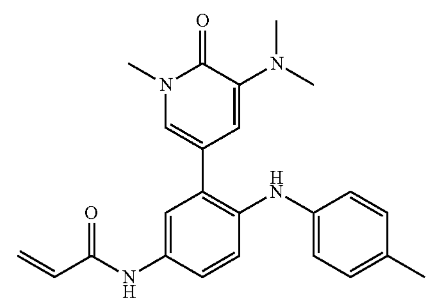 [SMILES: C=CC(=O)Nc1ccc(Nc2ccc(C)cc2)c(-c2cc(N(C)C)c(=O)n(C)c2)c1] |
| 328 | 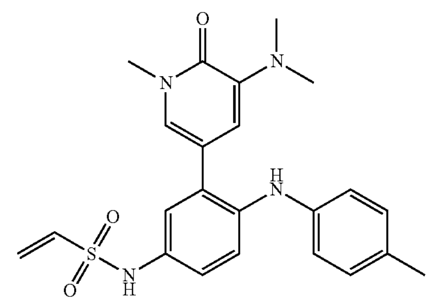 [SMILES: C=CS(=O)(=O)Nc1ccc(Nc2ccc(C)cc2)c(-c2cc(N(C)C)c(=O)n(C)c2)c1] |
| 329 | 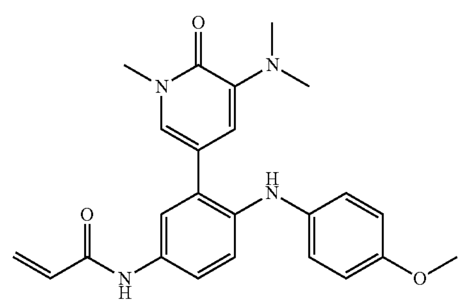 [SMILES: C=CC(=O)Nc1ccc(Nc2ccc(OC)cc2)c(-c2cc(N(C)C)c(=O)n(C)c2)c1] |
| 330 | 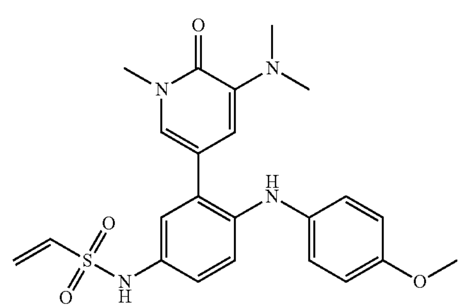 [SMILES: C=CS(=O)(=O)Nc1ccc(Nc2ccc(OC)cc2)c(-c2cc(N(C)C)c(=O)n(C)c2)c1] |

TABLE 1-continued

| Com. No. | Structure |
|---|---|
| 331 | (structure) |
| 332 | (structure) |
| 333 | (structure) |
| 334 | (structure) |
| 335 | (structure) |
| 336 | (structure) |
| 337 | (structure) |
| 338 | (structure) |
| 339 | (structure) |
| 340 | (structure) |

TABLE 1-continued
| Com. No. | Structure |
|---|---|
| 341 | 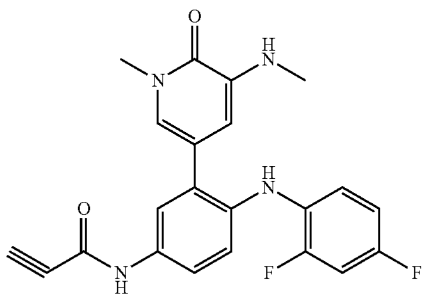 [SMILES: C#CC(=O)Nc1ccc(Nc2ccc(F)cc2F)c(-c2cc(NC)c(=O)n(C)c2)c1] |
| 342 | 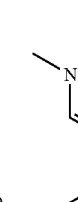 |
| 343 | 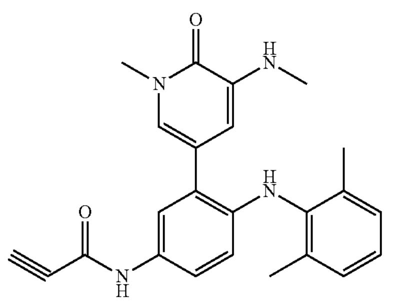 [SMILES: C#CC(=O)Nc1ccc(Nc2c(C)cccc2C)c(-c2cc(NC)c(=O)n(C)c2)c1] |
| 344 | 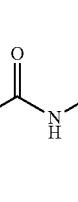 |
| 345 | 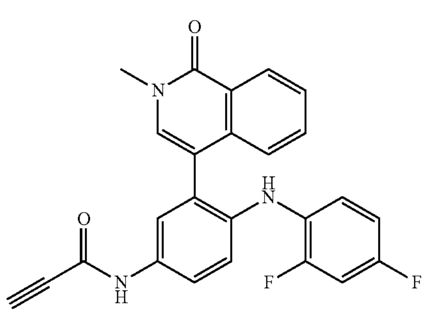 [SMILES: C#CC(=O)Nc1ccc(Nc2ccc(F)cc2F)c(-c2cn(C)c(=O)c3ccccc23)c1] |
| 346 | 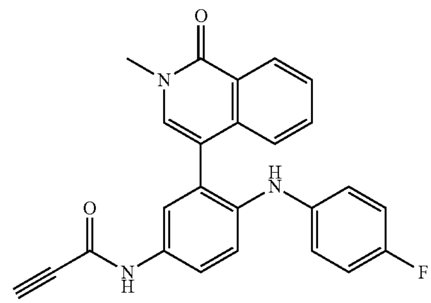 [SMILES: C#CC(=O)Nc1ccc(Nc2ccc(F)cc2)c(-c2cn(C)c(=O)c3ccccc23)c1] |
| 347 | 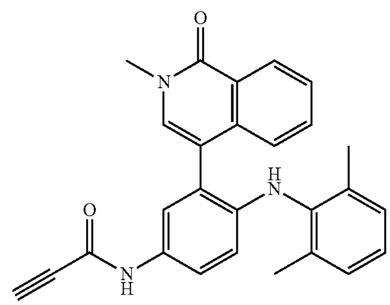 [SMILES: C#CC(=O)Nc1ccc(Nc2c(C)cccc2C)c(-c2cn(C)c(=O)c3ccccc23)c1] |
| 348 | 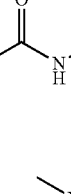 |
| 349 | 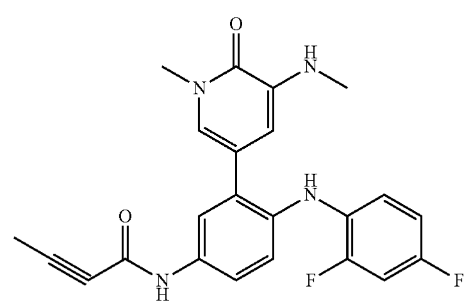 [SMILES: CC#CC(=O)Nc1ccc(Nc2ccc(F)cc2F)c(-c2cc(NC)c(=O)n(C)c2)c1] |
| 350 | 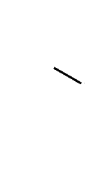 |

TABLE 1-continued
| Com. No. | Structure |
|---|---|
| 351 | 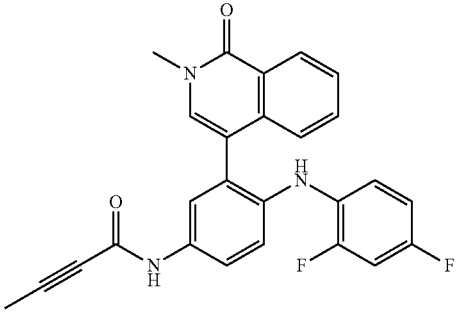 [SMILES: CC#CC(=O)Nc1ccc(Nc2ccc(F)cc2F)c(-c2cn(C)c(=O)c3ccccc23)c1] |
| 352 | 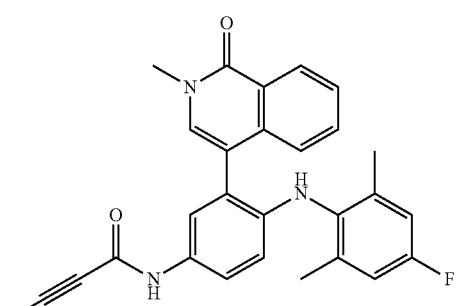 |
| 353 | 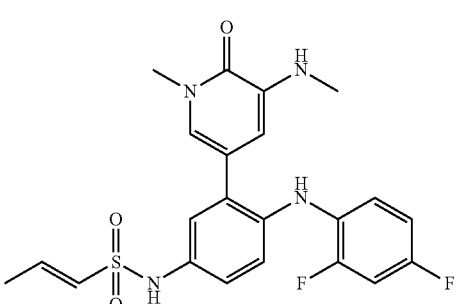 |
| 354 | 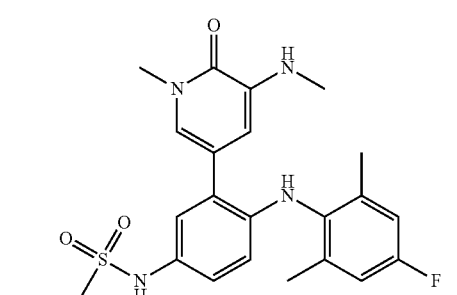 |
| 355 | 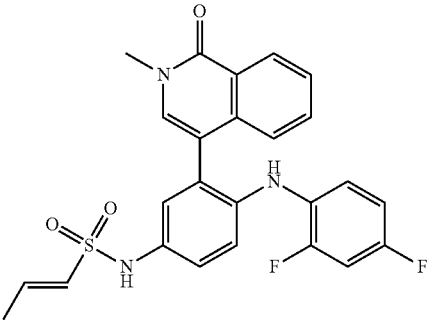 [SMILES: C/C=C/S(=O)(=O)Nc1ccc(Nc2ccc(F)cc2F)c(-c2cn(C)c(=O)c3ccccc23)c1] |
| 356 | 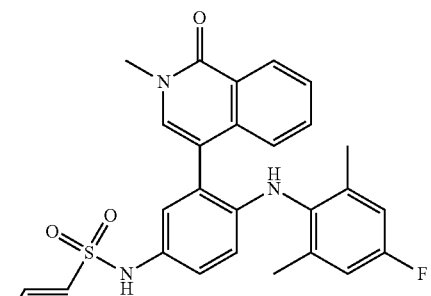 |
| 357 | 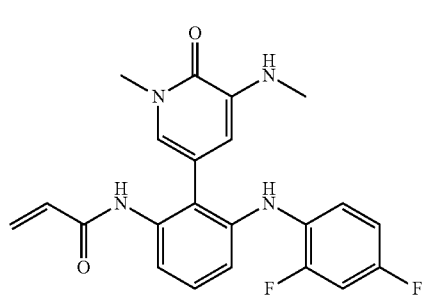 [SMILES: C=CC(=O)Nc1cccc(Nc2ccc(F)cc2F)c1-c1cc(NC)c(=O)n(C)c1] |
| 358 | 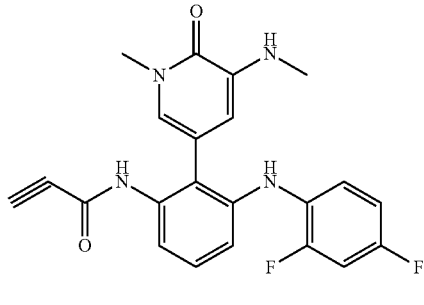 [SMILES: C#CC(=O)Nc1cccc(Nc2ccc(F)cc2F)c1-c1cc(NC)c(=O)n(C)c1] |
| 359 | 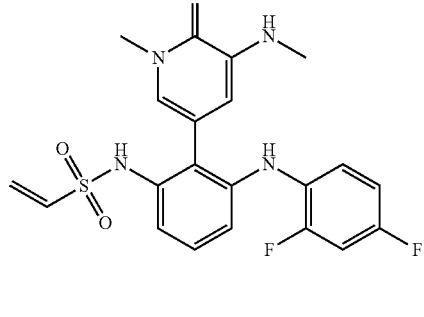 |

TABLE 1-continued

| Com. No. | Structure |
|---|---|
| 360 | (structure) |
| 361 | (structure) |
| 362 | (structure) |
| 363 | (structure) |
| 364 | (structure) |
| 365 | (structure) |
| 366 | (structure) |
| 367 | (structure) |
| 368 | (structure) |
| 369 | (structure) |

TABLE 1-continued

| Com. No. | Structure |
|---|---|
| 370 | 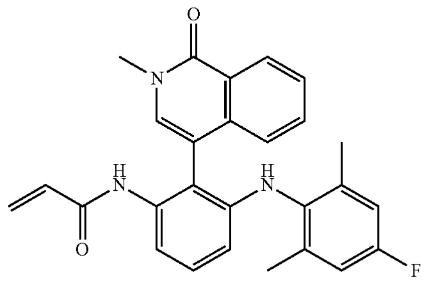 [SMILES: C=CC(=O)Nc1cccc(Nc2c(C)cc(F)cc2C)c1-c1cn(C)c(=O)c2ccccc12] |
| 371 | 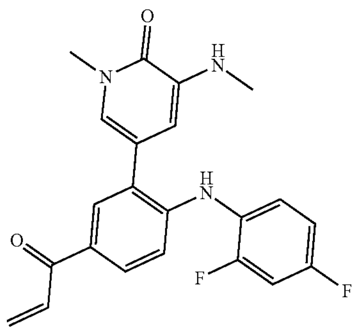 [SMILES: C=CC(=O)c1ccc(Nc2ccc(F)cc2F)c(-c2cc(NC)c(=O)n(C)c2)c1] |
| 372 | 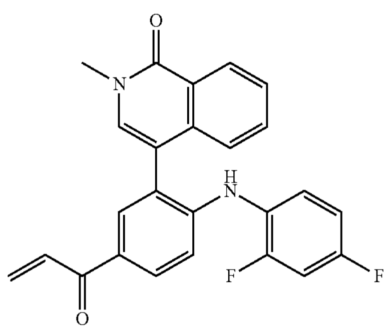 [SMILES: C=CC(=O)c1ccc(Nc2ccc(F)cc2F)c(-c2cn(C)c(=O)c3ccccc23)c1] |
| 373 | 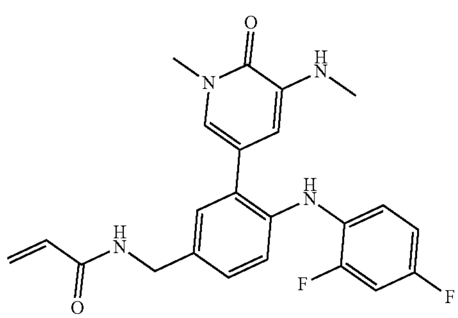 [SMILES: C=CC(=O)NCc1ccc(Nc2ccc(F)cc2F)c(-c2cc(NC)c(=O)n(C)c2)c1] |
| 374 | 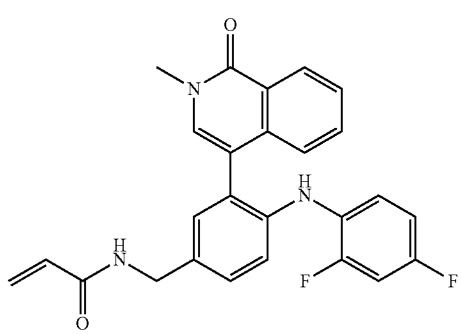 [SMILES: C=CC(=O)NCc1ccc(Nc2ccc(F)cc2F)c(-c2cn(C)c(=O)c3ccccc23)c1] |
| 375 | |
| 376 | |
| 377 | |
| 378 | |
| 379 | |

TABLE 1-continued

| Com. No. | Structure |
|---|---|
| 380 | 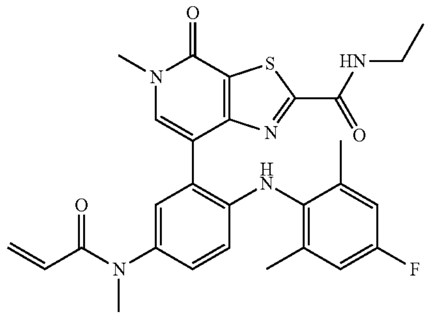 [SMILES: C=CC(=O)N(C)c1ccc(Nc2c(C)cc(F)cc2C)c(-c2cn(C)c(=O)c3sc(C(=O)NCC)nc23)c1] |
| 381 | 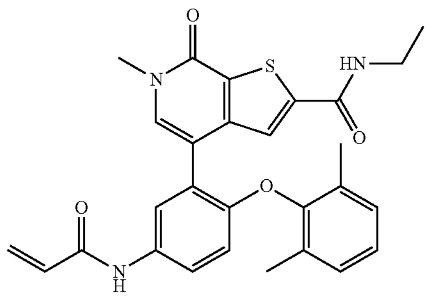 [SMILES: C=CC(=O)Nc1ccc(Oc2c(C)cccc2C)c(-c2cn(C)c(=O)c3sc(C(=O)NCC)cc23)c1] |
| 382 | 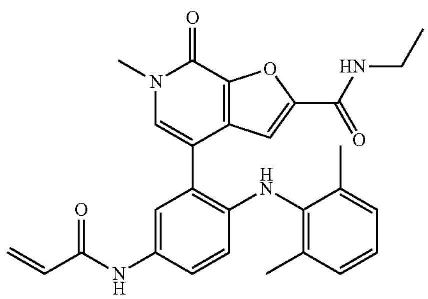 [SMILES: C=CC(=O)Nc1ccc(Nc2c(C)cccc2C)c(-c2cn(C)c(=O)c3oc(C(=O)NCC)cc23)c1] |
| 383 | 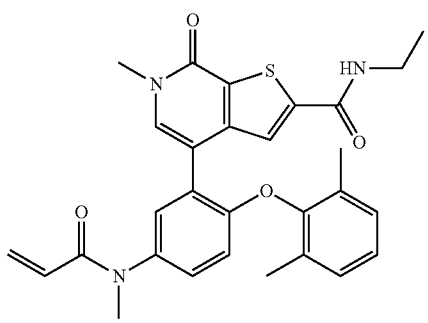 [SMILES: C=CC(=O)N(C)c1ccc(Oc2c(C)cccc2C)c(-c2cn(C)c(=O)c3sc(C(=O)NCC)cc23)c1] |
| 384 | 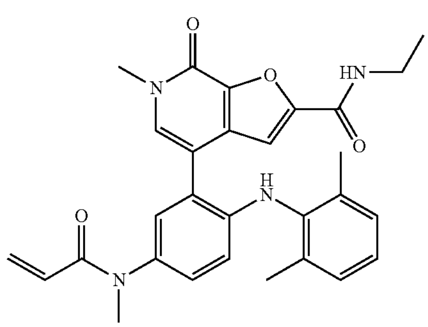 [SMILES: C=CC(=O)N(C)c1ccc(Nc2c(C)cccc2C)c(-c2cn(C)c(=O)c3oc(C(=O)NCC)cc23)c1] |

TABLE 1-continued

| Com. No. | Structure |
|---|---|
| 385 | 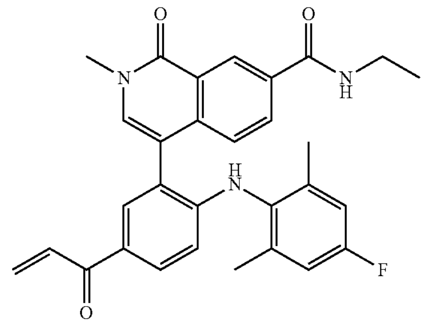 [SMILES: C=CC(=O)c1ccc(Nc2c(C)cc(F)cc2C)c(-c2cn(C)c(=O)c3cc(C(=O)NCC)ccc23)c1] |
| 386 | 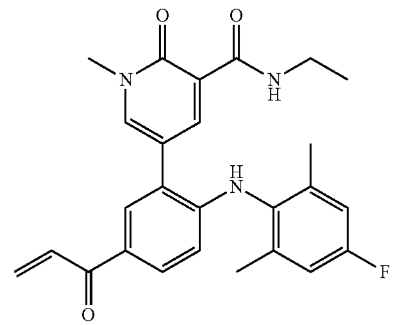 [SMILES: C=CC(=O)c1ccc(Nc2c(C)cc(F)cc2C)c(-c2cc(C(=O)NCC)c(=O)n(C)c2)c1] |
| 387 | 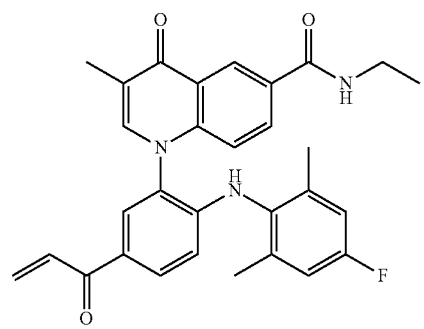 [SMILES: C=CC(=O)c1ccc(Nc2c(C)cc(F)cc2C)c(-n2cc(C)c(=O)c3cc(C(=O)NCC)ccc32)c1] |
| 388 | 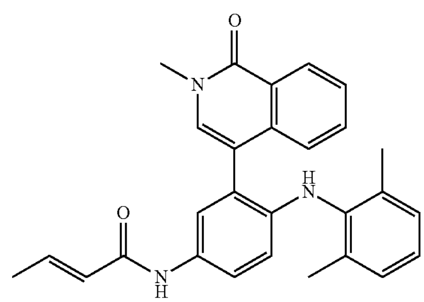 [SMILES: C/C=C/C(=O)Nc1ccc(Nc2c(C)cccc2C)c(-c2cn(C)c(=O)c3ccccc23)c1] |
| 389 | 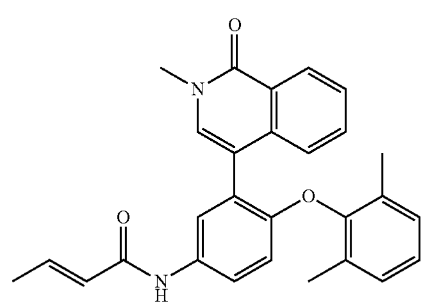 [SMILES: C/C=C/C(=O)Nc1ccc(Oc2c(C)cccc2C)c(-c2cn(C)c(=O)c3ccccc23)c1] |

TABLE 1-continued
| Com. No. | Structure |
|---|---|
| 390 | 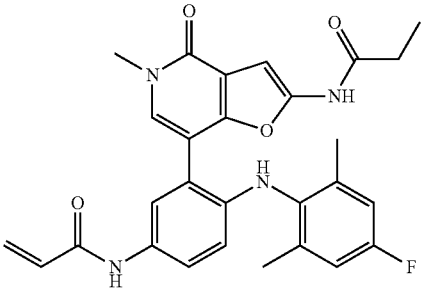 [SMILES: C=CC(=O)Nc1ccc(Nc2c(C)cc(F)cc2C)c(-c2cn(C)c(=O)c3cc(NC(=O)CC)oc23)c1] |
| 391 | 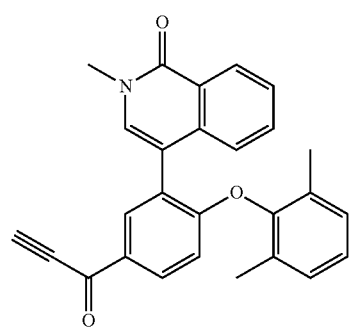 [SMILES: C#CC(=O)c1ccc(Oc2c(C)cccc2C)c(-c2cn(C)c(=O)c3ccccc23)c1] |
| 392 | 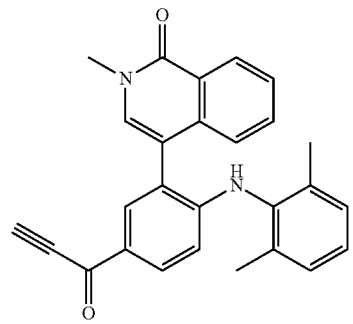 [SMILES: C#CC(=O)c1ccc(Nc2c(C)cccc2C)c(-c2cn(C)c(=O)c3ccccc23)c1] |
| 393 | 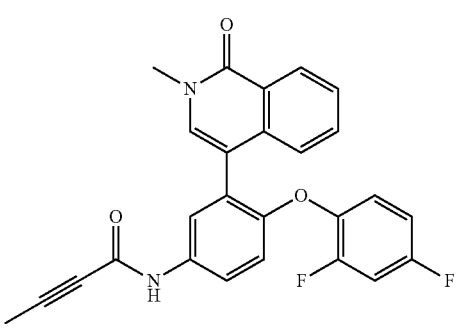 [SMILES: CC#CC(=O)Nc1ccc(Oc2ccc(F)cc2F)c(-c2cn(C)c(=O)c3ccccc23)c1] |
| 394 | 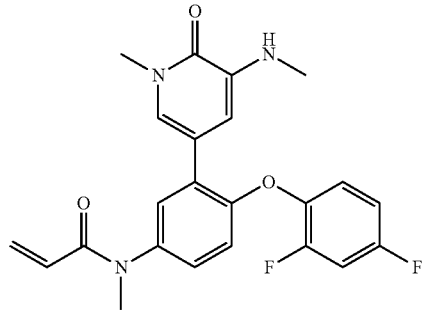 [SMILES: C=CC(=O)N(C)c1ccc(Oc2ccc(F)cc2F)c(-c2cc(NC)c(=O)n(C)c2)c1] |
| 395 | 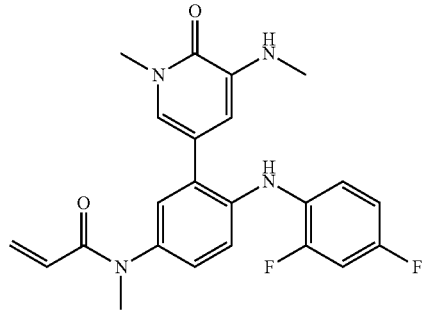 [SMILES: C=CC(=O)N(C)c1ccc(Nc2ccc(F)cc2F)c(-c2cc(NC)c(=O)n(C)c2)c1] |
| 396 | 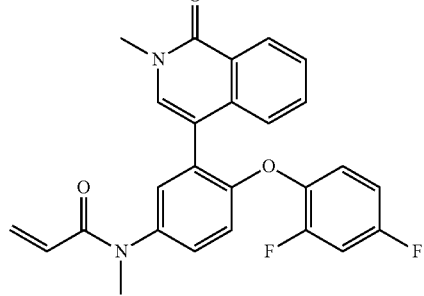 |
| 397 | 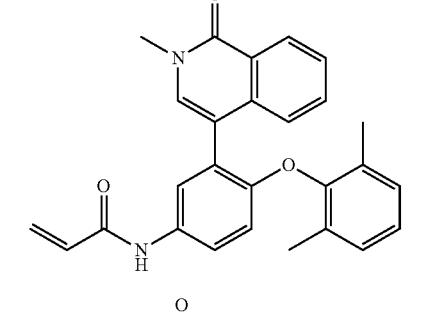 |
| 398 | 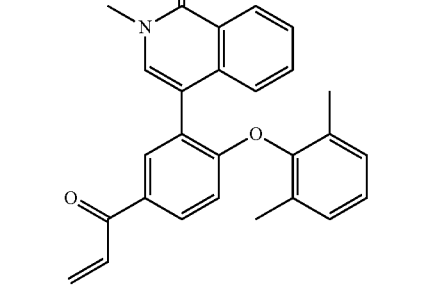 |

TABLE 1-continued

| Com. No. | Structure |
|---|---|
| 399 | 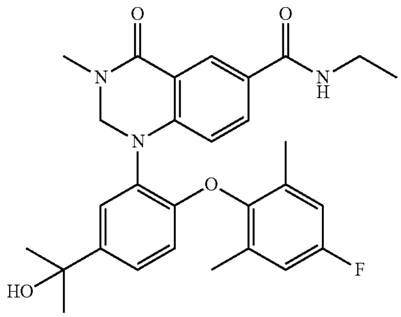 [SMILES: CCNC(=O)c1ccc2c(c1)C(=O)N(C)CN2c1cc(C(C)(C)O)ccc1Oc1c(C)cc(F)cc1C] |
| 400 | 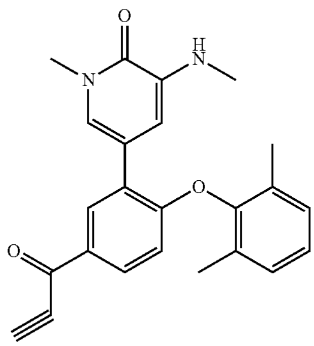 [SMILES: C#CC(=O)c1ccc(Oc2c(C)cccc2C)c(-c2cc(NC)c(=O)n(C)c2)c1] |
| 401 | 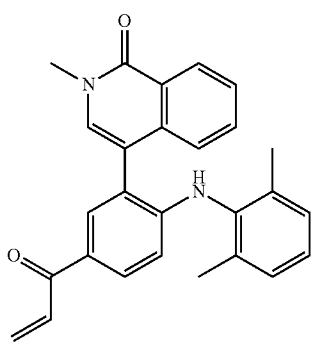 [SMILES: C=CC(=O)c1ccc(Nc2c(C)cccc2C)c(-c2cn(C)c(=O)c3ccccc23)c1] |
| 402 | 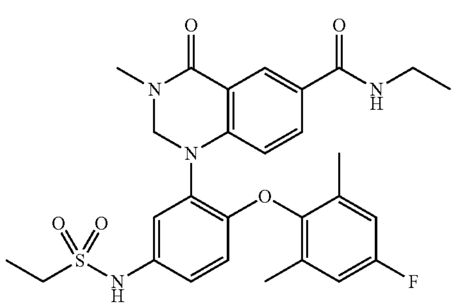 [SMILES: CCNC(=O)c1ccc2c(c1)C(=O)N(C)CN2c1cc(NS(=O)(=O)CC)ccc1Oc1c(C)cc(F)cc1C] |
| 403 | 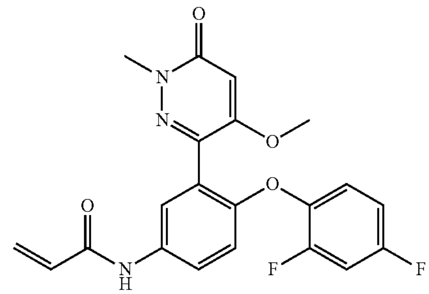 [SMILES: C=CC(=O)Nc1ccc(Oc2ccc(F)cc2F)c(-c2nn(C)c(=O)cc2OC)c1] |
| 404 | 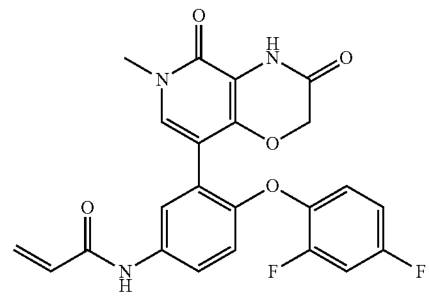 [SMILES: C=CC(=O)Nc1ccc(Oc2ccc(F)cc2F)c(-c2cn(C)c(=O)c3c2OCC(=O)N3)c1] |
| 405 | 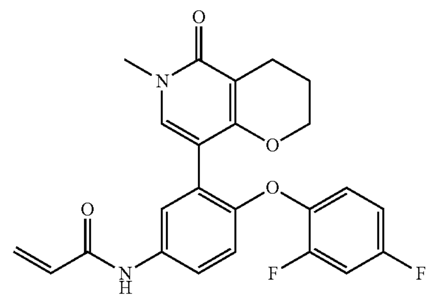 [SMILES: C=CC(=O)Nc1ccc(Oc2ccc(F)cc2F)c(-c2cn(C)c(=O)c3c2OCCC3)c1] |
| 406 | 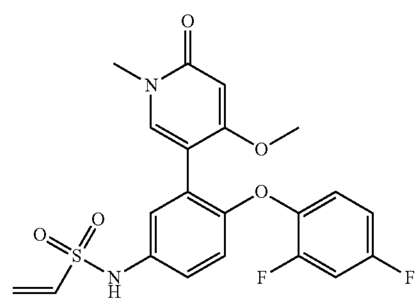 [SMILES: C=CS(=O)(=O)Nc1ccc(Oc2ccc(F)cc2F)c(-c2cn(C)c(=O)cc2OC)c1] |
| 407 | 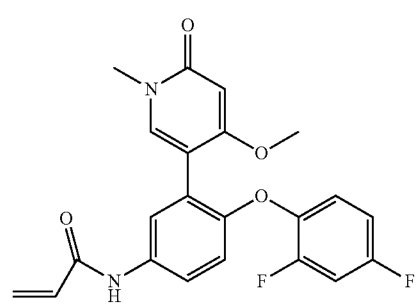 [SMILES: C=CC(=O)Nc1ccc(Oc2ccc(F)cc2F)c(-c2cn(C)c(=O)cc2OC)c1] |

TABLE 1-continued

| Com. No. | Structure |
|---|---|
| 408 | 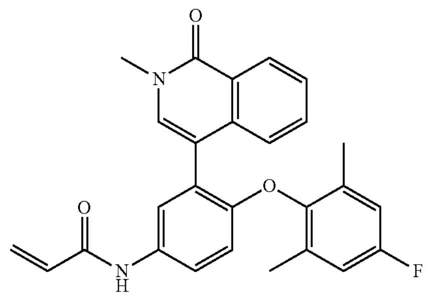 [SMILES: C=CC(=O)Nc1ccc(Oc2c(C)cc(F)cc2C)c(-c2cn(C)c(=O)c3ccccc23)c1] |
| 409 | 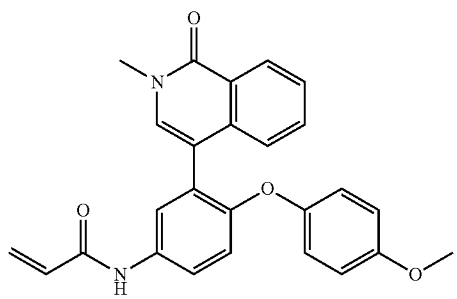 [SMILES: C=CC(=O)Nc1ccc(Oc2ccc(OC)cc2)c(-c2cn(C)c(=O)c3ccccc23)c1] |
| 410 | 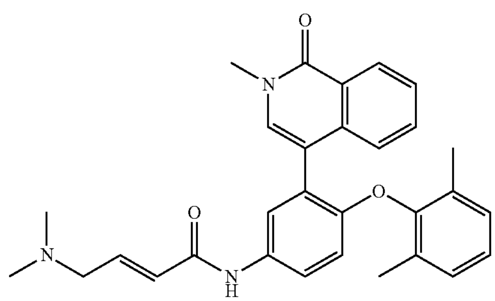 [SMILES: Cc1cccc(C)c1Oc1ccc(NC(=O)/C=C/CN(C)C)cc1-c1cn(C)c(=O)c2ccccc12] |
| 411 | 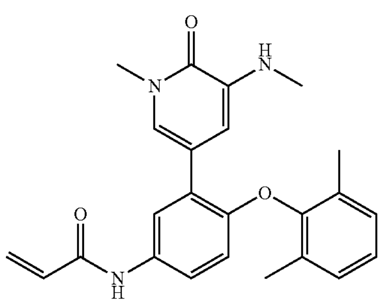 [SMILES: C=CC(=O)Nc1ccc(Oc2c(C)cccc2C)c(-c2cc(NC)c(=O)n(C)c2)c1] |
| 412 | 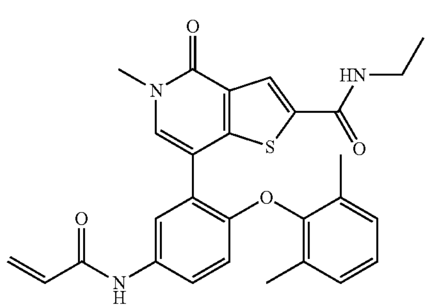 [SMILES: C=CC(=O)Nc1ccc(Oc2c(C)cccc2C)c(-c2cn(C)c(=O)c3cc(C(=O)NCC)sc23)c1] |
| 413 | |
| 414 | |
| 415 | |
| 416 | |
| 417 | |

TABLE 1-continued

| Com. No. | Structure |
|---|---|
| 418 | (structure) |
| 419 | (structure) |
| 420 | (structure) |
| 421 | (structure) |
| 422 | (structure) |
| 423 | (structure) |
| 424 | (structure) |
| 425 | (structure) |
| 426 | (structure) |
| 427 | (structure) |

TABLE 1-continued
| Com. No. | Structure |
|---|---|
| 428 | 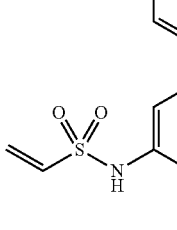 |
| 429 | 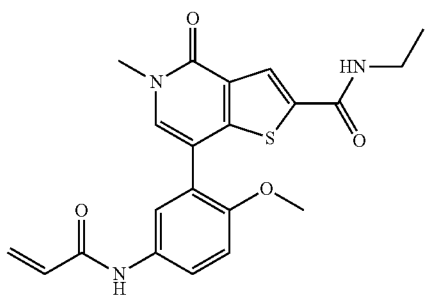 [SMILES: C=CC(=O)Nc1ccc(OC)c(-c2cn(C)c(=O)c3cc(C(=O)NCC)sc23)c1] |
| 430 | 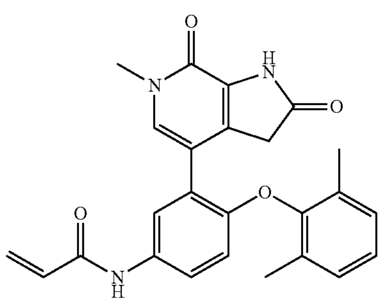 [SMILES: C=CC(=O)Nc1ccc(Oc2c(C)cccc2C)c(-c2cn(C)c(=O)c3c2CC(=O)N3)c1] |
| 431 | 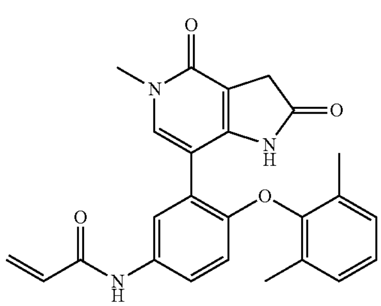 [SMILES: C=CC(=O)Nc1ccc(Oc2c(C)cccc2C)c(-c2cn(C)c(=O)c3c2NC(=O)C3)c1] |
| 432 | 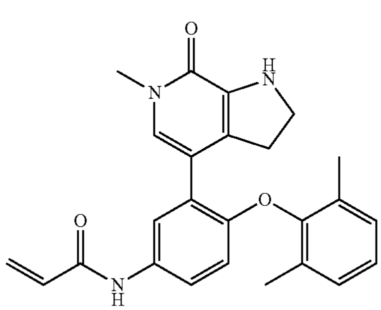 [SMILES: C=CC(=O)Nc1ccc(Oc2c(C)cccc2C)c(-c2cn(C)c(=O)c3c2CCN3)c1] |
| 433 | 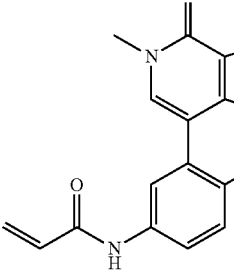 |
| 434 | |
| 435 | |
| 436 | |
| 437 | |

TABLE 1-continued
| Com. No. | Structure |
|---|---|
| 438 | 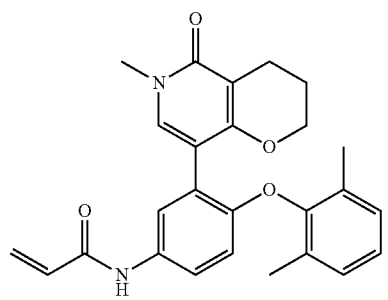 [SMILES: C=CC(=O)Nc1ccc(Oc2c(C)cccc2C)c(-c2cn(C)c(=O)c3c2OCCC3)c1] |
| 439 | 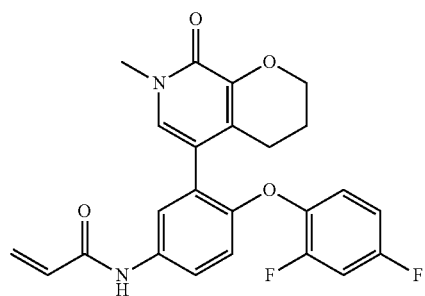 [SMILES: C=CC(=O)Nc1ccc(Oc2ccc(F)cc2F)c(-c2cn(C)c(=O)c3c2CCCO3)c1] |
| 440 | 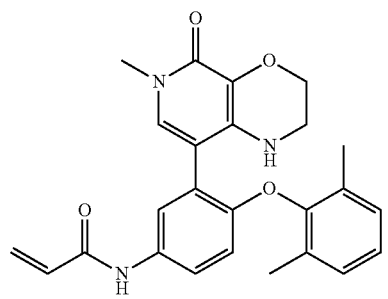 [SMILES: C=CC(=O)Nc1ccc(Oc2c(C)cccc2C)c(-c2cn(C)c(=O)c3c2NCCO3)c1] |
| 441 | 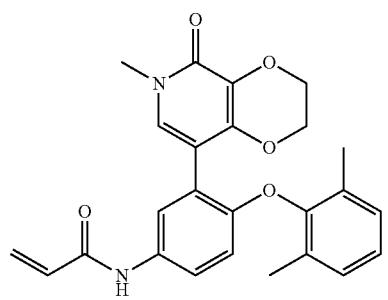 [SMILES: C=CC(=O)Nc1ccc(Oc2c(C)cccc2C)c(-c2cn(C)c(=O)c3c2OCCO3)c1] |
| 442 | 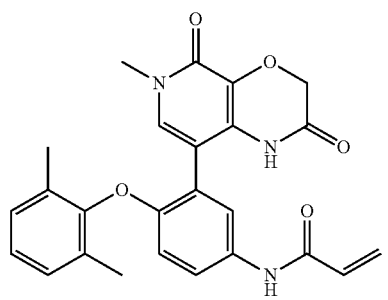 [SMILES: C=CC(=O)Nc1ccc(Oc2c(C)cccc2C)c(-c2cn(C)c(=O)c3c2NC(=O)CO3)c1] |
TABLE 1-continued
| Com. No. | Structure |
|---|---|
| 443 | 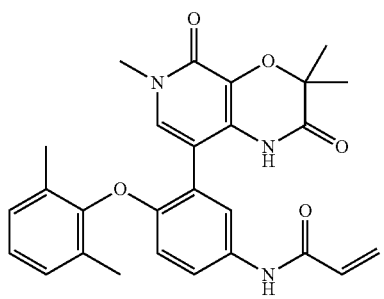 [SMILES: C=CC(=O)Nc1ccc(Oc2c(C)cccc2C)c(-c2cn(C)c(=O)c3c2NC(=O)C(C)(C)O3)c1] |
| 444 | 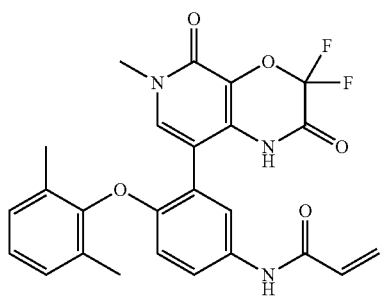 [SMILES: C=CC(=O)Nc1ccc(Oc2c(C)cccc2C)c(-c2cn(C)c(=O)c3c2NC(=O)C(F)(F)O3)c1] |
| 445 | 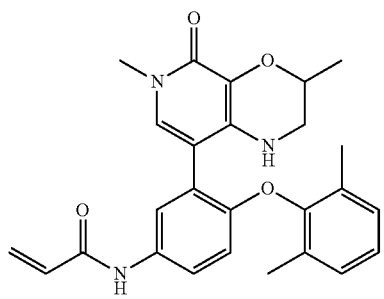 [SMILES: C=CC(=O)Nc1ccc(Oc2c(C)cccc2C)c(-c2cn(C)c(=O)c3c2NCC(C)O3)c1] |
| 446 | 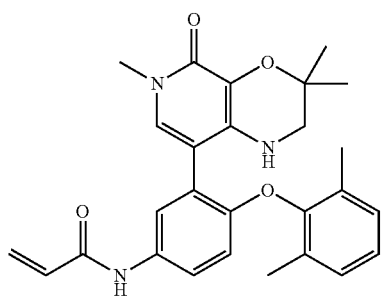 [SMILES: C=CC(=O)Nc1ccc(Oc2c(C)cccc2C)c(-c2cn(C)c(=O)c3c2NCC(C)(C)O3)c1] |
| 447 | 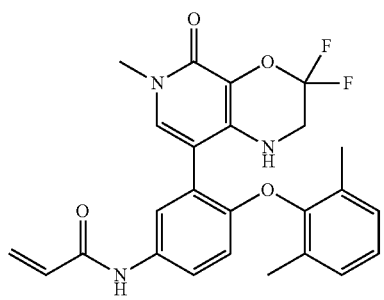 [SMILES: C=CC(=O)Nc1ccc(Oc2c(C)cccc2C)c(-c2cn(C)c(=O)c3c2NCC(F)(F)O3)c1] |

US 11,192,900 B2
191
TABLE 1-continued
| Com. No. | Structure |
|---|---|
| 448 | 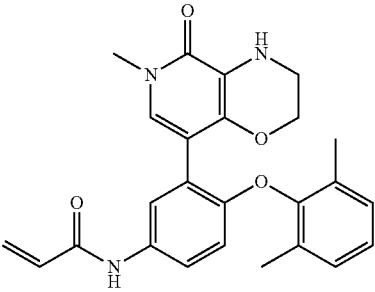 [SMILES: C=CC(=O)Nc1ccc(Oc2c(C)cccc2C)c(-c2cn(C)c(=O)c3c2OCCN3)c1] |
| 449 | 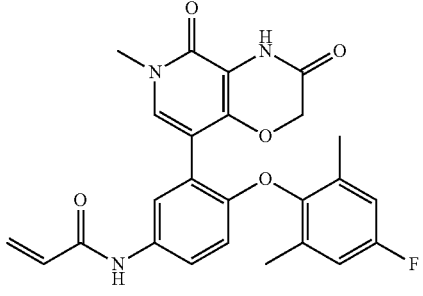 [SMILES: C=CC(=O)Nc1ccc(Oc2c(C)cc(F)cc2C)c(-c2cn(C)c(=O)c3c2OCC(=O)N3)c1] |
| 450 | 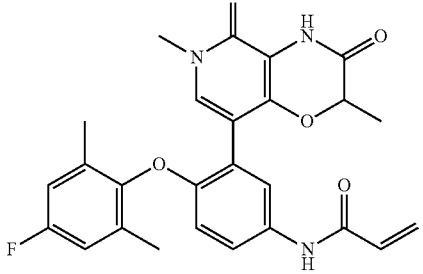 |
| 451 | 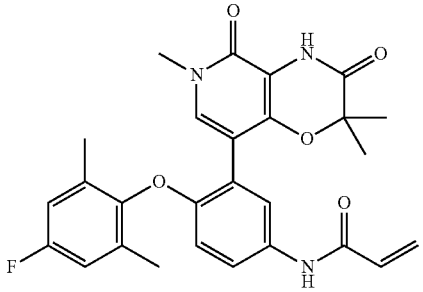 [SMILES: C=CC(=O)Nc1ccc(Oc2c(C)cc(F)cc2C)c(-c2cn(C)c(=O)c3c2OC(C)(C)C(=O)N3)c1] |
| 452 | 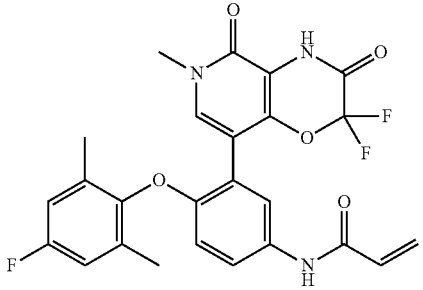 [SMILES: C=CC(=O)Nc1ccc(Oc2c(C)cc(F)cc2C)c(-c2cn(C)c(=O)c3c2OC(F)(F)C(=O)N3)c1] |
192
TABLE 1-continued
| Com. No. | Structure |
|---|---|
| 453 | 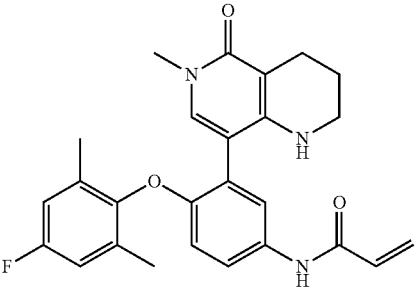 [SMILES: C=CC(=O)Nc1ccc(Oc2c(C)cc(F)cc2C)c(-c2cn(C)c(=O)c3c2NCCC3)c1] |
| 454 | 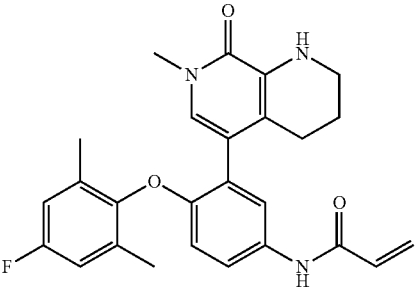 [SMILES: C=CC(=O)Nc1ccc(Oc2c(C)cc(F)cc2C)c(-c2cn(C)c(=O)c3c2CCCN3)c1] |
| 455 | 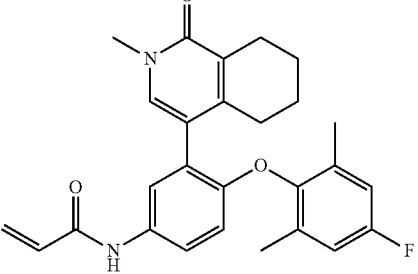 |
| 456 | 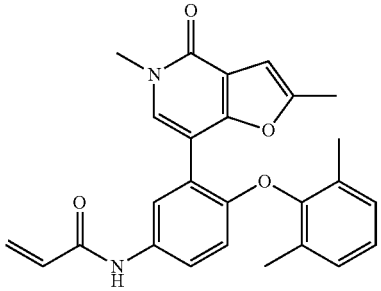 [SMILES: C=CC(=O)Nc1ccc(Oc2c(C)cccc2C)c(-c2cn(C)c(=O)c3cc(C)oc23)c1] |
| 457 | 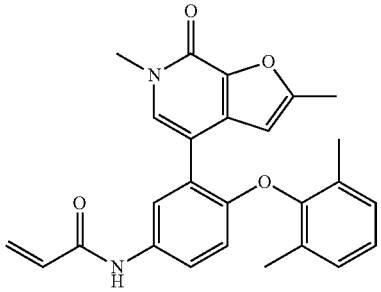 [SMILES: C=CC(=O)Nc1ccc(Oc2c(C)cccc2C)c(-c2cn(C)c(=O)c3oc(C)cc23)c1] |

TABLE 1-continued

| Com. No. | Structure |
|---|---|
| 458 | 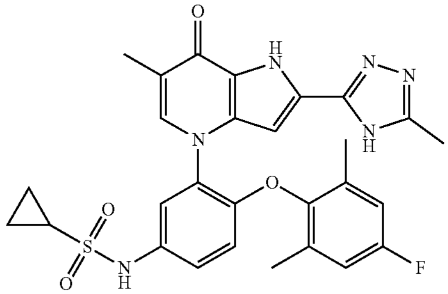 [SMILES: Cc1nnc(-c2cc3c([nH]2)c(=O)c(C)cn3-c2cc(NS(=O)(=O)C3CC3)ccc2Oc2c(C)cc(F)cc2C)[nH]1] |
| 459 | 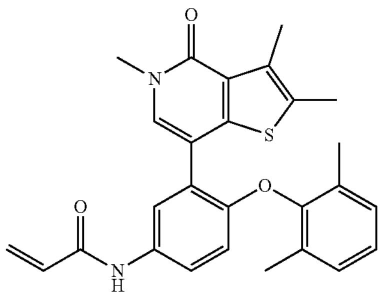 [SMILES: C=CC(=O)Nc1ccc(Oc2c(C)cccc2C)c(-c2cn(C)c(=O)c3c(C)c(C)sc23)c1] |
| 460 | 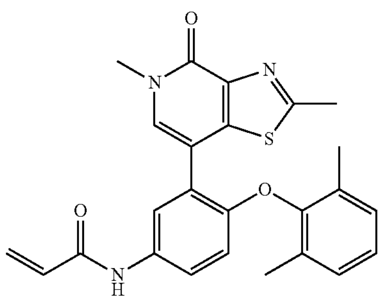 [SMILES: C=CC(=O)Nc1ccc(Oc2c(C)cccc2C)c(-c2cn(C)c(=O)c3nc(C)sc23)c1] |
| 461 | 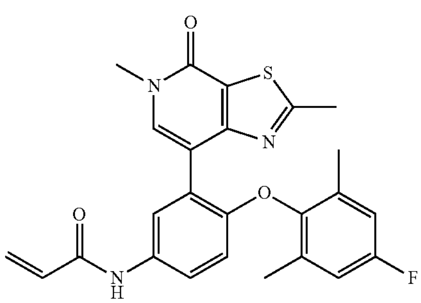 [SMILES: C=CC(=O)Nc1ccc(Oc2c(C)cc(F)cc2C)c(-c2cn(C)c(=O)c3sc(C)nc23)c1] |
| 462 | 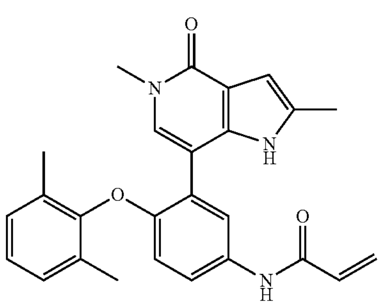 |
| 463 | |
| 464 | |
| 465 | |
| 466 | |

TABLE 1-continued

| Com. No. | Structure |
|---|---|
| 467 | (structure) |
| 468 | (structure) |
| 469 | (structure) |
| 470 | (structure) |
| 471 | (structure) |
| 472 | (structure) |
| 473 | (structure) |
| 474 | (structure) |
| 475 | (structure) |
| 476 | (structure) |

TABLE 1-continued

| Com. No. | Structure |
|---|---|
| 477 | 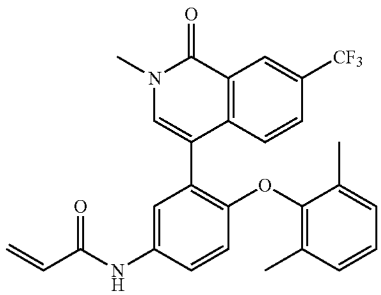 [SMILES: C=CC(=O)Nc1ccc(Oc2c(C)cccc2C)c(-c2cn(C)c(=O)c3cc(C(F)(F)F)ccc23)c1] |
| 478 | 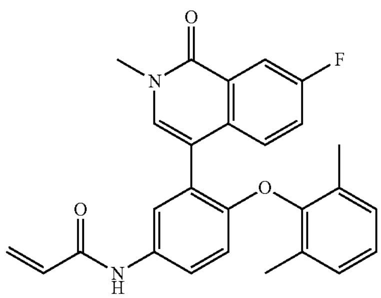 [SMILES: C=CC(=O)Nc1ccc(Oc2c(C)cccc2C)c(-c2cn(C)c(=O)c3cc(F)ccc23)c1] |
| 479 | 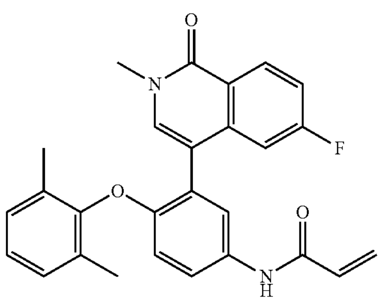 [SMILES: C=CC(=O)Nc1ccc(Oc2c(C)cccc2C)c(-c2cn(C)c(=O)c3ccc(F)cc23)c1] |
| 480 | 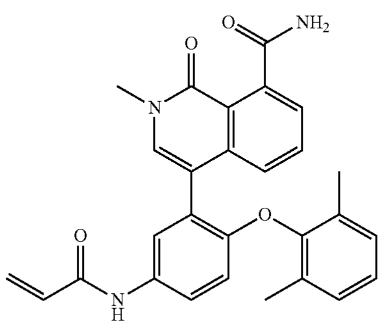 [SMILES: C=CC(=O)Nc1ccc(Oc2c(C)cccc2C)c(-c2cn(C)c(=O)c3c(C(N)=O)cccc23)c1] |
| 481 | 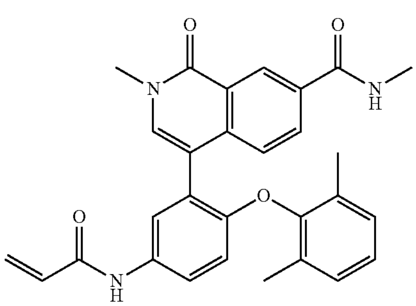 [SMILES: C=CC(=O)Nc1ccc(Oc2c(C)cccc2C)c(-c2cn(C)c(=O)c3cc(C(=O)NC)ccc23)c1] |
| 482 | |
| 483 | |
| 484 | |
| 485 | |
| 486 | |

TABLE 1-continued
| Com. No. | Structure |
|---|---|
| 487 | 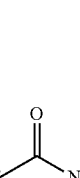 |
| 488 | 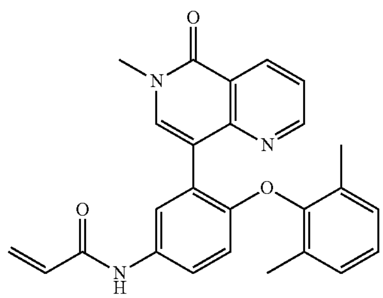 [SMILES: C=CC(=O)Nc1ccc(Oc2c(C)cccc2C)c(-c2cn(C)c(=O)c3cccnc23)c1] |
| 489 | 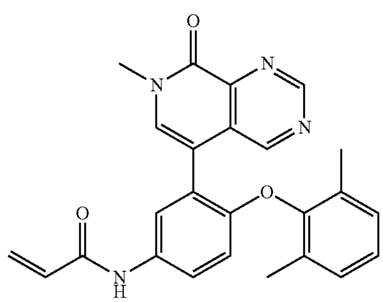 [SMILES: C=CC(=O)Nc1ccc(Oc2c(C)cccc2C)c(-c2cn(C)c(=O)c3ncncc23)c1] |
| 490 | 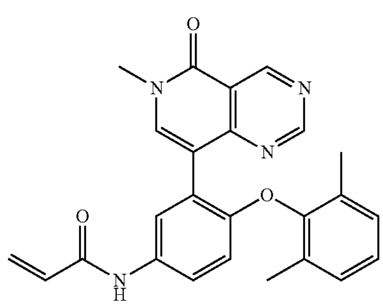 [SMILES: C=CC(=O)Nc1ccc(Oc2c(C)cccc2C)c(-c2cn(C)c(=O)c3cncnc23)c1] |
| 491 | 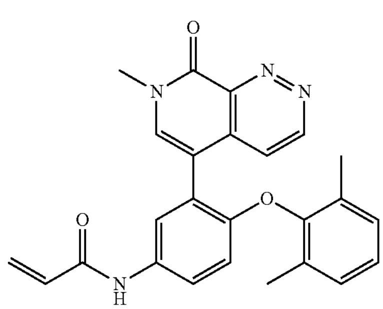 [SMILES: C=CC(=O)Nc1ccc(Oc2c(C)cccc2C)c(-c2cn(C)c(=O)c3nnccc23)c1] |
| 492 |  |
| 493 | |
| 494 | |
| 495 | |
| 496 | |

TABLE 1-continued

| Com. No. | Structure |
|---|---|
| 497 | 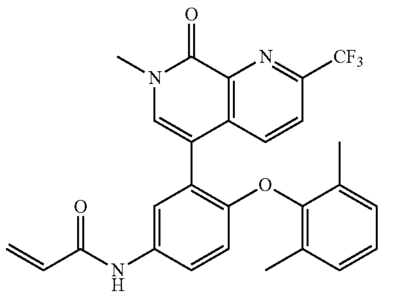 [SMILES: C=CC(=O)Nc1ccc(Oc2c(C)cccc2C)c(-c2cn(C)c(=O)c3nc(C(F)(F)F)ccc23)c1] |
| 498 | 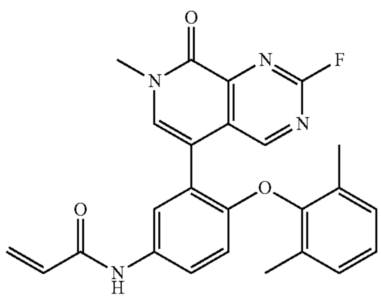 [SMILES: C=CC(=O)Nc1ccc(Oc2c(C)cccc2C)c(-c2cn(C)c(=O)c3nc(F)ncc23)c1] |
| 499 | 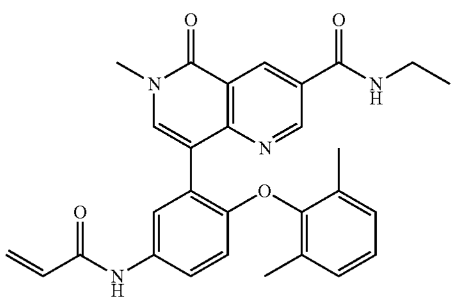 [SMILES: C=CC(=O)Nc1ccc(Oc2c(C)cccc2C)c(-c2cn(C)c(=O)c3cc(C(=O)NCC)cnc23)c1] |
| 500 | 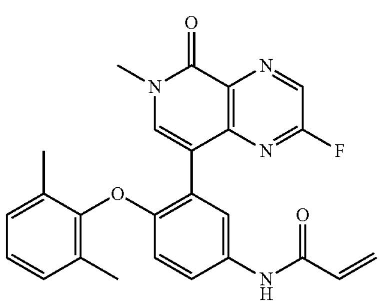 [SMILES: C=CC(=O)Nc1ccc(Oc2c(C)cccc2C)c(-c2cn(C)c(=O)c3ncc(F)nc23)c1] |
| 501 | 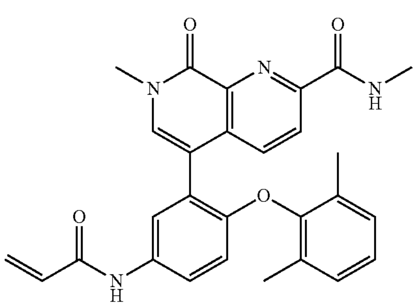 [SMILES: C=CC(=O)Nc1ccc(Oc2c(C)cccc2C)c(-c2cn(C)c(=O)c3nc(C(=O)NC)ccc23)c1] |
| 502 | |
| 503 | |
| 504 | |
| 505 | |
| 506 | |

TABLE 1-continued
| Com. No. | Structure |
|---|---|
| 507 | 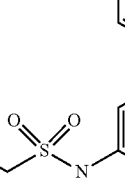 |
| 508 | 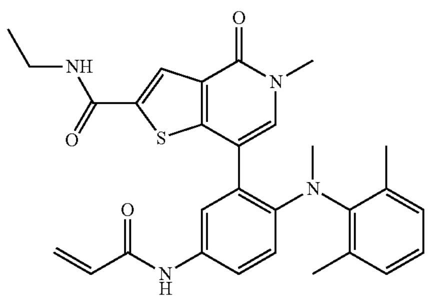 [SMILES: C=CC(=O)Nc1ccc(N(C)c2c(C)cccc2C)c(-c2cn(C)c(=O)c3cc(C(=O)NCC)sc23)c1] |
| 509 | 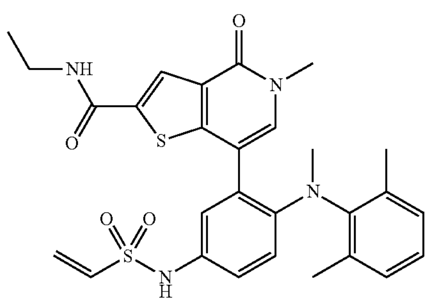 [SMILES: C=CS(=O)(=O)Nc1ccc(N(C)c2c(C)cccc2C)c(-c2cn(C)c(=O)c3cc(C(=O)NCC)sc23)c1] |
| 510 | 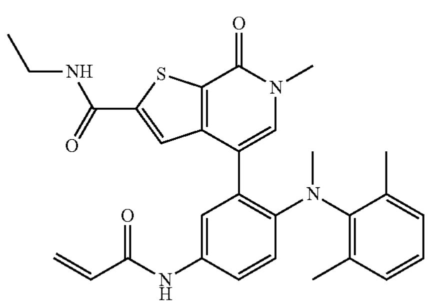 [SMILES: C=CC(=O)Nc1ccc(N(C)c2c(C)cccc2C)c(-c2cn(C)c(=O)c3sc(C(=O)NCC)cc23)c1] |
| 511 | 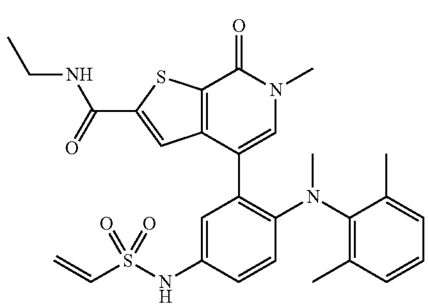 [SMILES: C=CS(=O)(=O)Nc1ccc(N(C)c2c(C)cccc2C)c(-c2cn(C)c(=O)c3sc(C(=O)NCC)cc23)c1] |
TABLE 1-continued
| Com. No. | Structure |
|---|---|
| 512 | 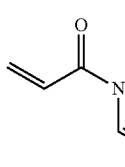 |
| 513 | 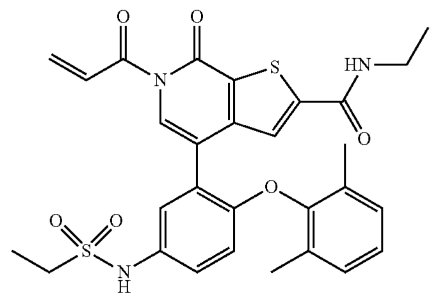 [SMILES: C=CC(=O)n1cc(-c2cc(NS(=O)(=O)CC)ccc2Oc2c(C)cccc2C)c2cc(C(=O)NCC)sc2c1=O] |
| 514 | 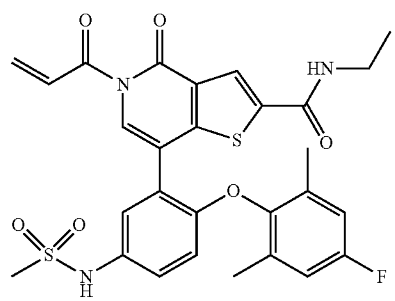 [SMILES: C=CC(=O)n1cc(-c2cc(NS(C)(=O)=O)ccc2Oc2c(C)cc(F)cc2C)c2sc(C(=O)NCC)cc2c1=O] |
| 515 | 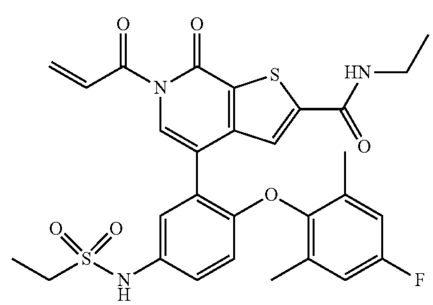 |
| 516 | 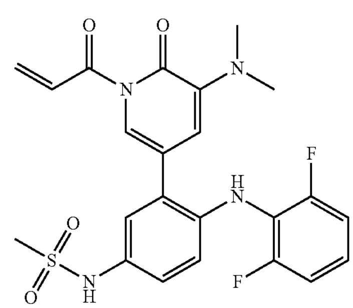 [SMILES: C=CC(=O)n1cc(-c2cc(NS(C)(=O)=O)ccc2Nc2c(F)cccc2F)cc(N(C)C)c1=O] |

TABLE 1-continued

| Com. No. | Structure |
|---|---|
| 517 | (structure) |
| 518 | (structure) |
| 519 | (structure) |
| 520 | (structure) |
| 521 | (structure) |
| 522 | (structure) |
| 523 | (structure) |
| 524 | (structure) |

TABLE 1-continued

| Com. No. | Structure |
|---|---|
| 525 | (structure) |
| 526 | (structure) |
| 527 | (structure) |
| 528 | (structure) |
| 529 | (structure) |
| 530 | (structure) |
| 531 | (structure) |
| 532 | (structure) |
| 533 | (structure) |
| 534 | (structure) |

TABLE 1-continued

| Com. No. | Structure |
|---|---|
| 535 | (structure) |
| 536 | (structure) |
| 537 | (structure) |
| 538 | (structure) |
| 539 | (structure) |
| 540 | (structure) |
| 541 | (structure) |
| 542 | (structure) |
| 543 | (structure) |
| 544 | (structure) |

TABLE 1-continued

| Com. No. | Structure |
|---|---|
| 545 | (structure) |
| 546 | (structure) |
| 547 | (structure) |
| 548 | (structure) |
| 549 | (structure) |
| 550 | (structure) |
| 551 | (structure) |
| 552 | (structure) |
| 553 | (structure) |
| 554 | (structure) |

TABLE 1-continued

| Com. No. | Structure |
|---|---|
| 555 | (structure) |
| 556 | (structure) |
| 557 | (structure) |
| 558 | (structure) |
| 559 | (structure) |
| 560 | (structure) |
| 561 | (structure) |
| 562 | (structure) |
| 563 | (structure) |
| 564 | (structure) |

TABLE 1-continued

| Com. No. | Structure |
|---|---|
| 565 | (structure) |
| 566 | (structure) |
| 567 | (structure) |
| 568 | (structure) |
| 569 | (structure) |
| 570 | (structure) |
| 571 | (structure) |
| 572 | (structure) |
| 573 | (structure) |
| 574 | (structure) |

TABLE 1-continued

| Com. No. | Structure |
|---|---|
| 575 | 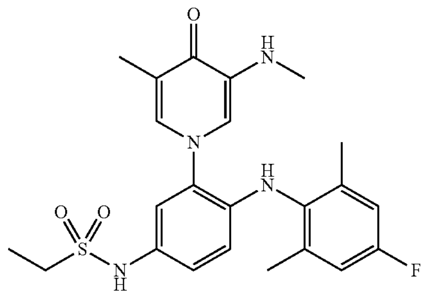 [SMILES: CCS(=O)(=O)Nc1ccc(Nc2c(C)cc(F)cc2C)c(-n2cc(C)c(=O)c(NC)c2)c1] |
| 576 | 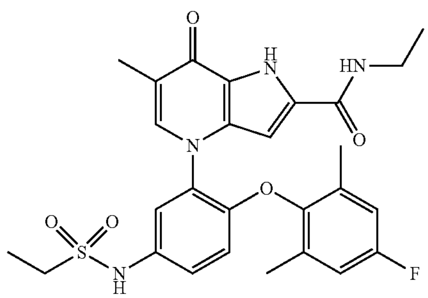 [SMILES: CCNC(=O)c1cc2c([nH]1)c(=O)c(C)cn2-c1cc(NS(=O)(=O)CC)ccc1Oc1c(C)cc(F)cc1C] |
| 577 | 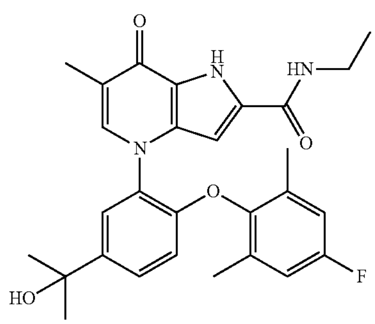 [SMILES: CCNC(=O)c1cc2c([nH]1)c(=O)c(C)cn2-c1cc(C(C)(C)O)ccc1Oc1c(C)cc(F)cc1C] |
| 578 | 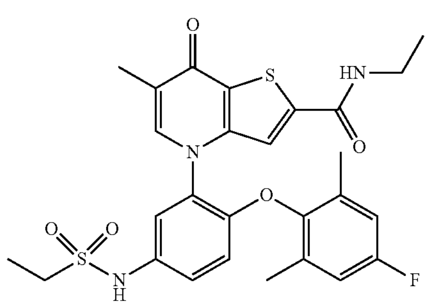 [SMILES: CCNC(=O)c1cc2c(s1)c(=O)c(C)cn2-c1cc(NS(=O)(=O)CC)ccc1Oc1c(C)cc(F)cc1C] |
| 579 | 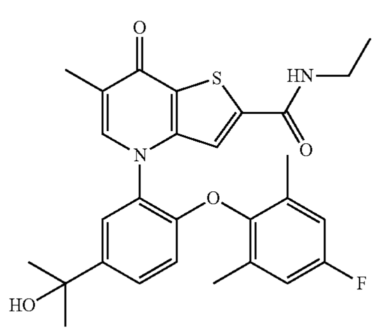 [SMILES: CCNC(=O)c1cc2c(s1)c(=O)c(C)cn2-c1cc(C(C)(C)O)ccc1Oc1c(C)cc(F)cc1C] |
| 580 | |
| 581 | |
| 582 | |
| 583 | |
| 584 | |

TABLE 1-continued

| Com. No. | Structure |
|---|---|
| 585 | 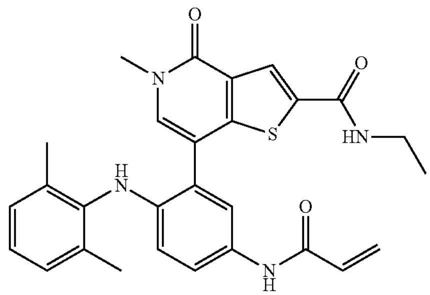 [SMILES: C=CC(=O)Nc1ccc(Nc2c(C)cccc2C)c(-c2cn(C)c(=O)c3cc(C(=O)NCC)sc23)c1] |
| 586 | 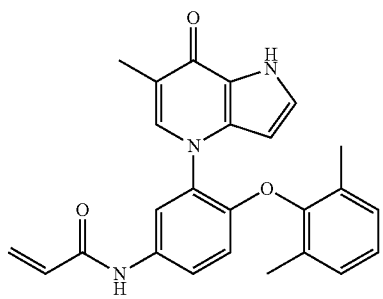 |
| 587 | 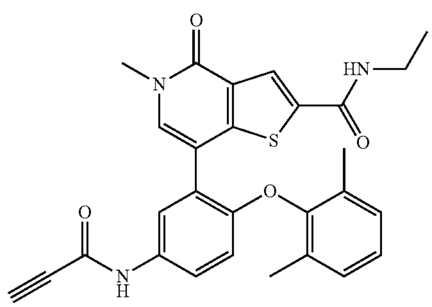 [SMILES: C#CC(=O)Nc1ccc(Oc2c(C)cccc2C)c(-c2cn(C)c(=O)c3cc(C(=O)NCC)sc23)c1] |
| 588 | 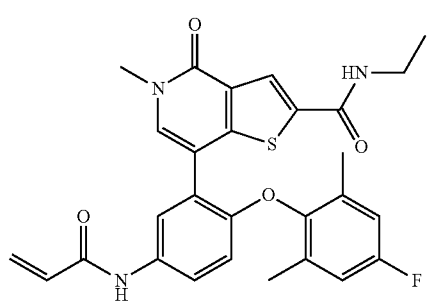 [SMILES: C=CC(=O)Nc1ccc(Oc2c(C)cc(F)cc2C)c(-c2cn(C)c(=O)c3cc(C(=O)NCC)sc23)c1] |
| 589 | 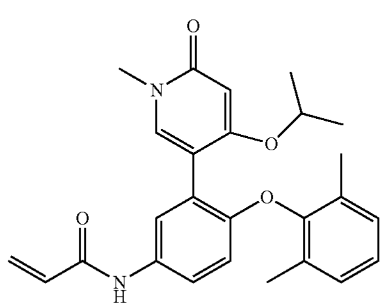 |
| 590 | |
| 591 | |
| 592 | |
| 593 | |
| 594 | |

TABLE 1-continued

| Com. No. | Structure |
|---|---|
| 595 | (structure) |
| 596 | (structure) |
| 597 | (structure) |
| 598 | (structure) |
| 599 | (structure) |
| 600 | (structure) |
| 601 | (structure) |
| 602 | (structure) |
| 603 | (structure) |
| 604 | (structure) |

TABLE 1-continued
| Com. No. | Structure |
|---|---|
| 605 | 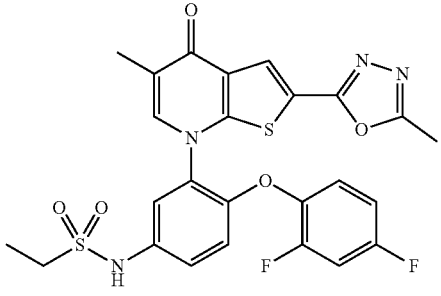 [SMILES: CCS(=O)(=O)Nc1ccc(Oc2ccc(F)cc2F)c(-n2cc(C)c(=O)c3sc(-c4nnc(C)o4)cc32)c1] |
| 606 | 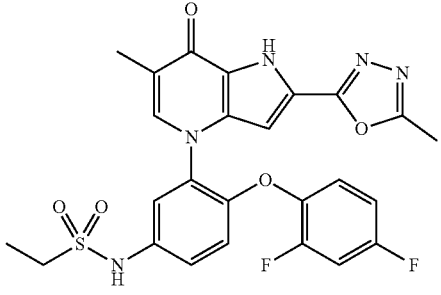 [SMILES: CCS(=O)(=O)Nc1ccc(Oc2ccc(F)cc2F)c(-n2cc(C)c(=O)c3[nH]c(-c4nnc(C)o4)cc32)c1] |
| 607 | 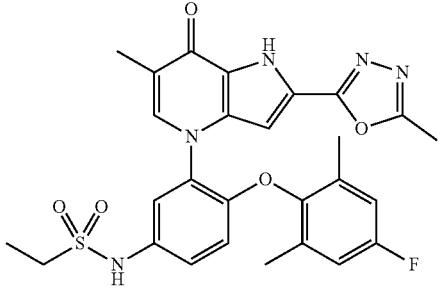 [SMILES: CCS(=O)(=O)Nc1ccc(Oc2c(C)cc(F)cc2C)c(-n2cc(C)c(=O)c3[nH]c(-c4nnc(C)o4)cc32)c1] |
| 608 | 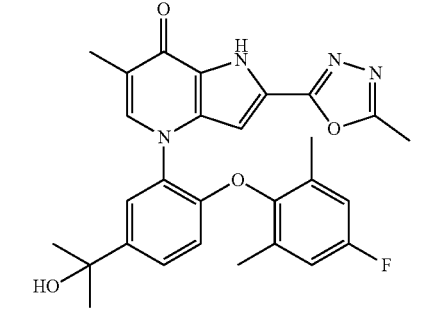 [SMILES: Cc1nnc(-c2cc3c([nH]2)c(=O)c(C)cn3-c2cc(C(C)(C)O)ccc2Oc2c(C)cc(F)cc2C)o1] |
| 609 | 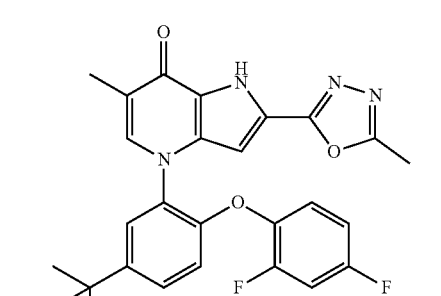 |
| 610 | 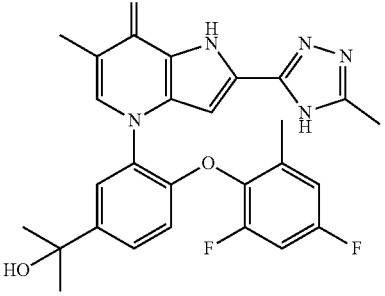 |
| 611 | 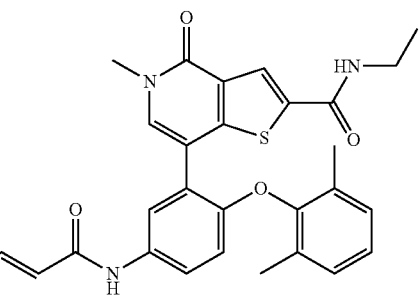 |
| 612 | 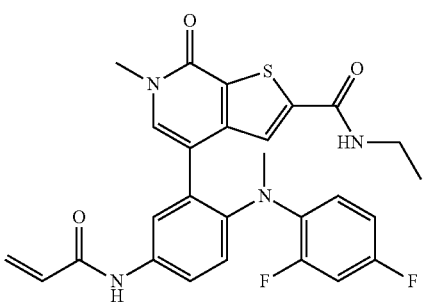 [SMILES: C=CC(=O)Nc1ccc(N(C)c2ccc(F)cc2F)c(-c2cn(C)c(=O)c3sc(C(=O)NCC)cc23)c1] |
| 613 | 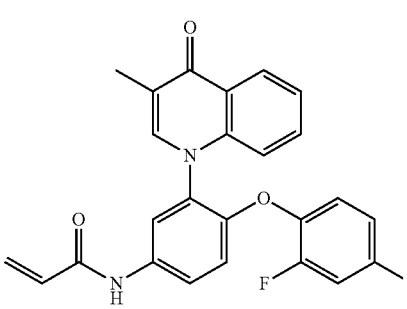 |
| 614 | 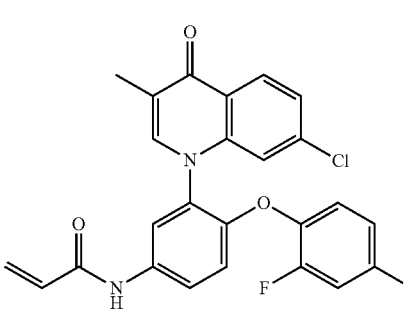 |

TABLE 1-continued

| Com. No. | Structure |
|---|---|
| 615 | (structure) |
| 616 | (structure) |
| 617 | (structure) |
| 618 | (structure) |
| 619 | (structure) |
| 620 | (structure) |
| 621 | (structure) |
| 622 | (structure) |
| 623 | (structure) |
| 624 | (structure) |

TABLE 1-continued

| Com. No. | Structure |
|---|---|
| 625 | 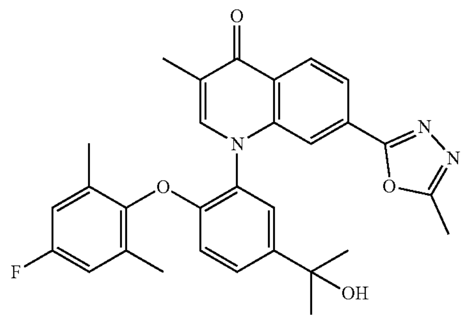 [SMILES: Cc1nnc(-c2ccc3c(=O)c(C)cn(-c4cc(C(C)(C)O)ccc4Oc4c(C)cc(F)cc4C)c3c2)o1] |
| 626 | 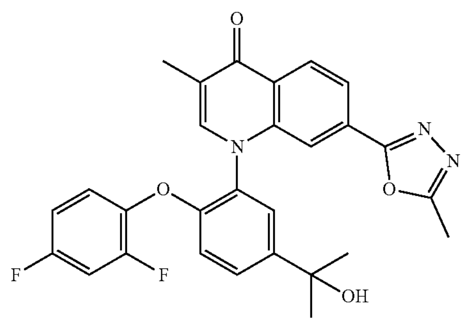 [SMILES: Cc1nnc(-c2ccc3c(=O)c(C)cn(-c4cc(C(C)(C)O)ccc4Oc4ccc(F)cc4F)c3c2)o1] |
| 627 | 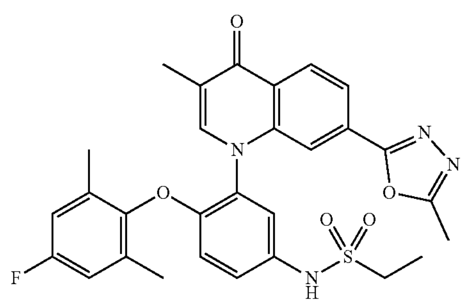 [SMILES: CCS(=O)(=O)Nc1ccc(Oc2c(C)cc(F)cc2C)c(-n2cc(C)c(=O)c3ccc(-c4nnc(C)o4)cc32)c1] |
| 628 | 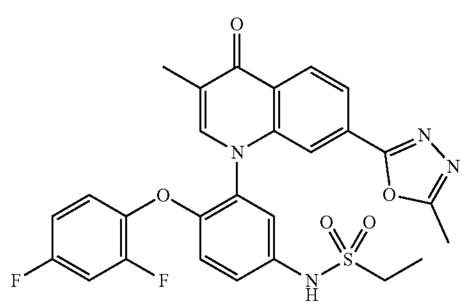 [SMILES: CCS(=O)(=O)Nc1ccc(Oc2ccc(F)cc2F)c(-n2cc(C)c(=O)c3ccc(-c4nnc(C)o4)cc32)c1] |
| 629 | 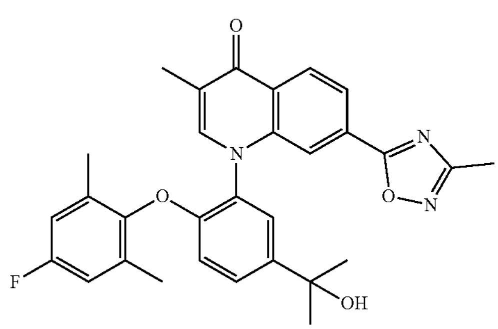 [SMILES: Cc1noc(-c2ccc3c(=O)c(C)cn(-c4cc(C(C)(C)O)ccc4Oc4c(C)cc(F)cc4C)c3c2)n1] |
| 630 | 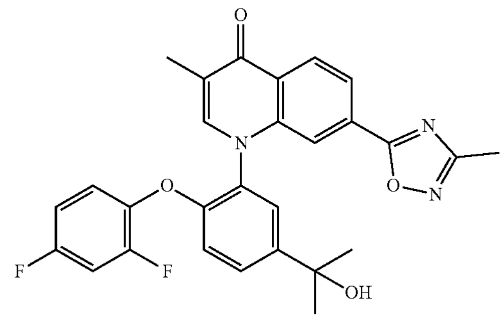 [SMILES: Cc1noc(-c2ccc3c(=O)c(C)cn(-c4cc(C(C)(C)O)ccc4Oc4ccc(F)cc4F)c3c2)n1] |
| 631 | 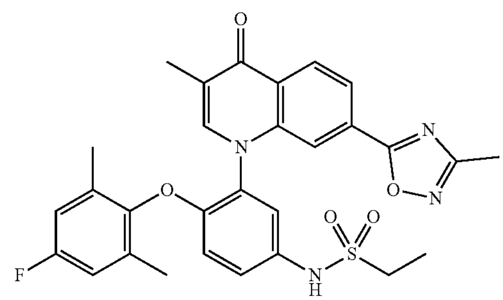 [SMILES: CCS(=O)(=O)Nc1ccc(Oc2c(C)cc(F)cc2C)c(-n2cc(C)c(=O)c3ccc(-c4nc(C)no4)cc32)c1] |
| 632 | 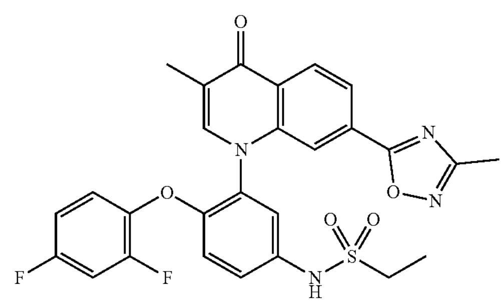 [SMILES: CCS(=O)(=O)Nc1ccc(Oc2ccc(F)cc2F)c(-n2cc(C)c(=O)c3ccc(-c4nc(C)no4)cc32)c1] |
| 633 | 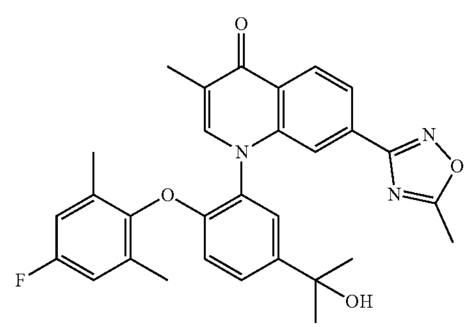 [SMILES: Cc1nc(-c2ccc3c(=O)c(C)cn(-c4cc(C(C)(C)O)ccc4Oc4c(C)cc(F)cc4C)c3c2)no1] |
| 634 | 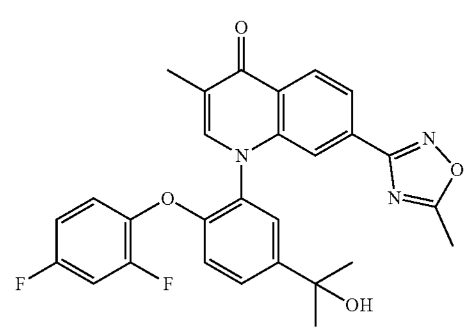 [SMILES: Cc1nc(-c2ccc3c(=O)c(C)cn(-c4cc(C(C)(C)O)ccc4Oc4ccc(F)cc4F)c3c2)no1] |

TABLE 1-continued
| Com. No. | Structure |
|---|---|
| 635 | 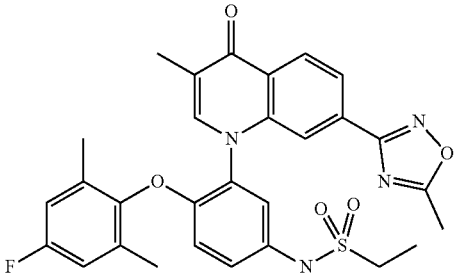 |
| 636 | 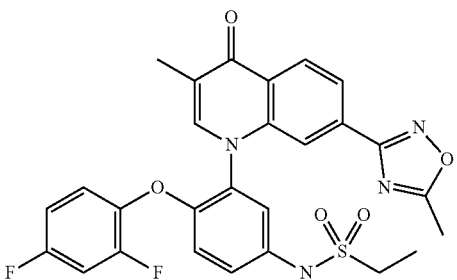 |
| 637 | 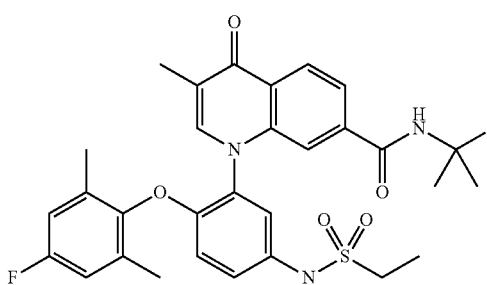 |
| 638 | 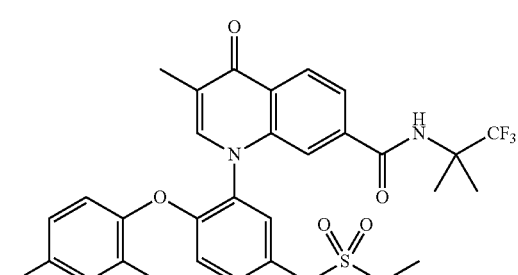 |
| 639 | 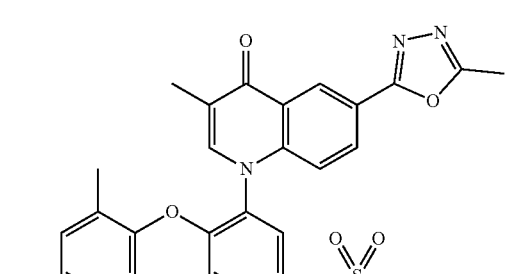 |
| 640 | 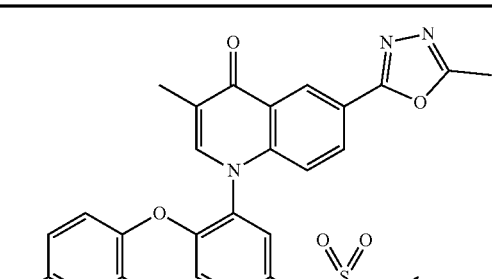 |
| 641 | 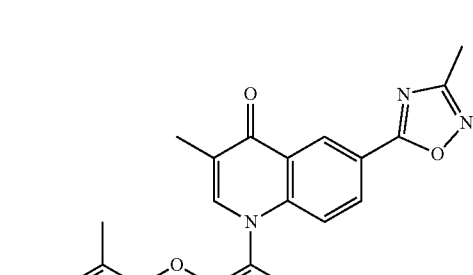 |
| 642 | 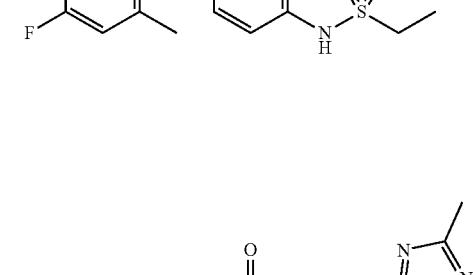 |
| 643 | 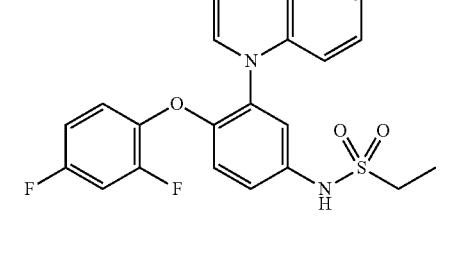 |

TABLE 1-continued

| Com. No. | Structure |
|---|---|
| 644 | (structure) |
| 645 | (structure) |
| 646 | (structure) |
| 647 | (structure) |
| 648 | (structure) |
| 649 | (structure) |
| 650 | (structure) |
| 651 | (structure) |

TABLE 1-continued
| Com. No. | Structure |
|---|---|
| 652 | 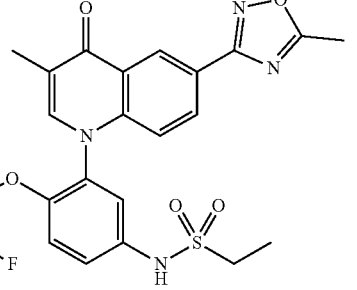 |
| 653 | 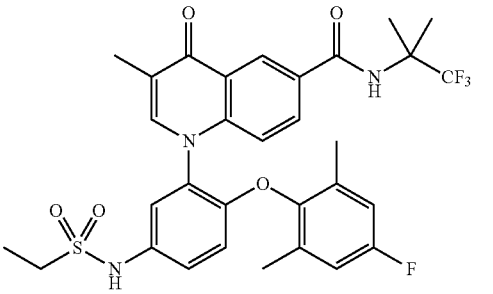 [SMILES: CCS(=O)(=O)Nc1ccc(Oc2c(C)cc(F)cc2C)c(-n2cc(C)c(=O)c3cc(C(=O)NC(C)(C)C(F)(F)F)ccc32)c1] |
| 654 | 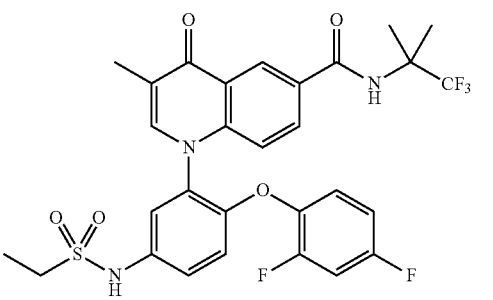 [SMILES: CCS(=O)(=O)Nc1ccc(Oc2ccc(F)cc2F)c(-n2cc(C)c(=O)c3cc(C(=O)NC(C)(C)C(F)(F)F)ccc32)c1] |
| 655 | 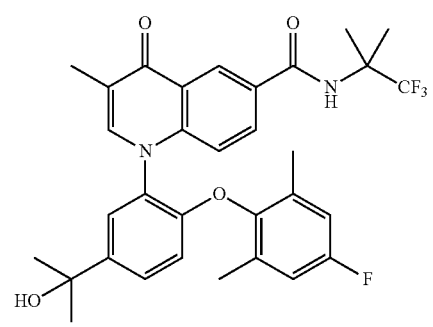 [SMILES: Cc1cc(F)cc(C)c1Oc1ccc(C(C)(C)O)cc1-n1cc(C)c(=O)c2cc(C(=O)NC(C)(C)C(F)(F)F)ccc21] |
| 656 | 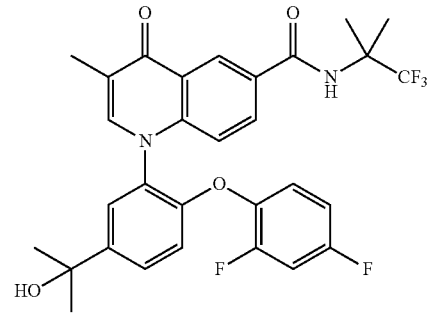 [SMILES: Cc1cn(-c2cc(C(C)(C)O)ccc2Oc2ccc(F)cc2F)c2ccc(C(=O)NC(C)(C)C(F)(F)F)cc2c1=O] |
TABLE 1-continued
| Com. No. | Structure |
|---|---|
| 657 | 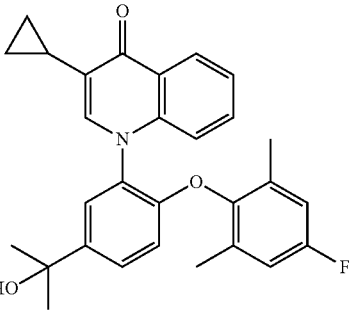 |
| 658 | 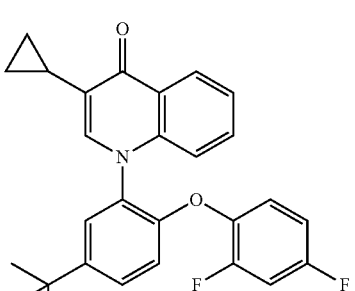 |
| 659 | 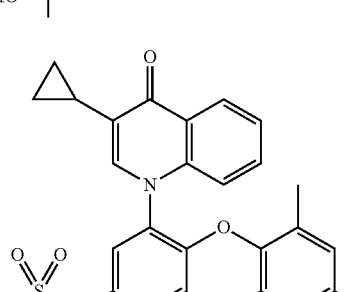 |
| 660 | 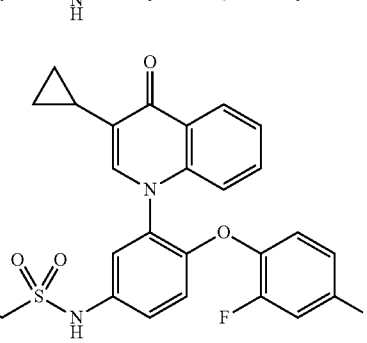 |
| 661 | 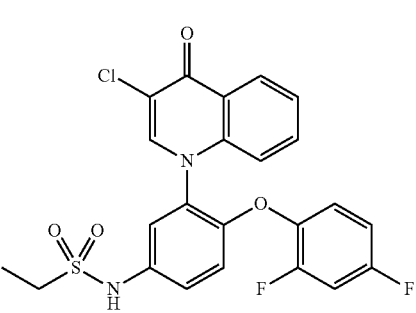 [SMILES: CCS(=O)(=O)Nc1ccc(Oc2ccc(F)cc2F)c(-n2cc(Cl)c(=O)c3ccccc32)c1] |

TABLE 1-continued
| Com. No. | Structure |
|---|---|
| 662 | 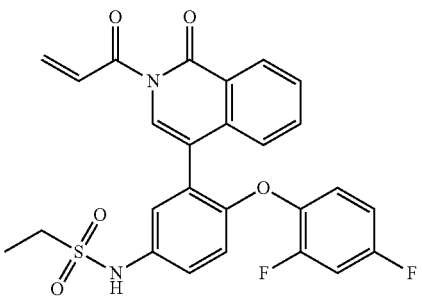 [SMILES: C=CC(=O)n1cc(-c2cc(NS(=O)(=O)CC)ccc2Oc2ccc(F)cc2F)c2ccccc2c1=O] |
| 663 | 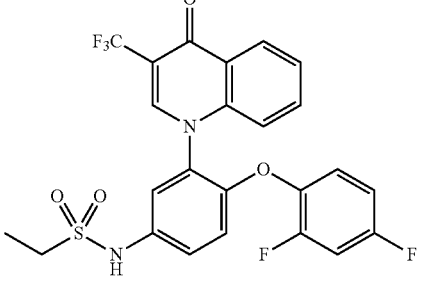 |
| 664 | 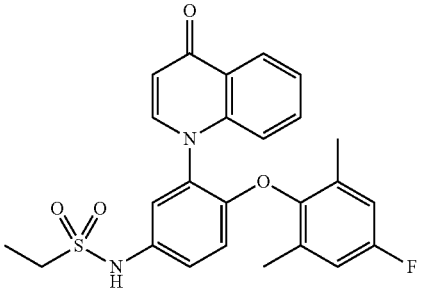 [SMILES: CCS(=O)(=O)Nc1ccc(Oc2c(C)cc(F)cc2C)c(-n2ccc(=O)c3ccccc32)c1] |
| 665 | 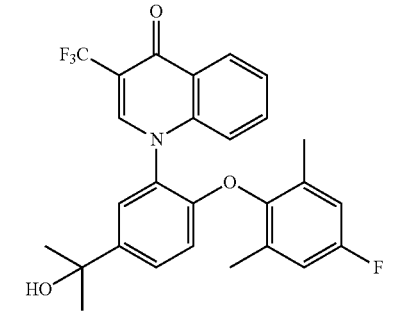 [SMILES: Cc1cc(F)cc(C)c1Oc1ccc(C(C)(C)O)cc1-n1cc(C(F)(F)F)c(=O)c2ccccc21] |
| 666 | 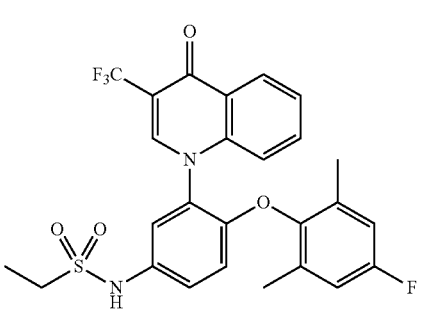 |
| 667 | 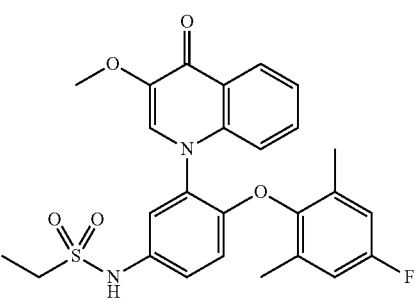 |
| 668 | 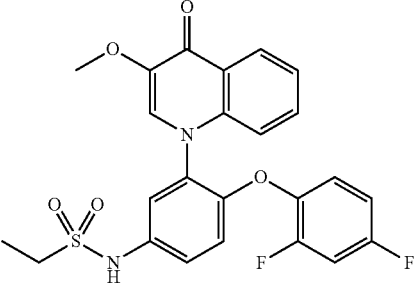 [SMILES: CCS(=O)(=O)Nc1ccc(Oc2ccc(F)cc2F)c(-n2cc(OC)c(=O)c3ccccc32)c1] |
| 669 | 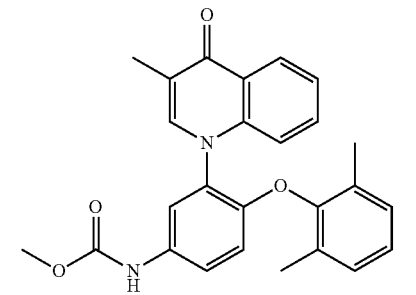 [SMILES: COC(=O)Nc1ccc(Oc2c(C)cccc2C)c(-n2cc(C)c(=O)c3ccccc32)c1] |
| 670 | 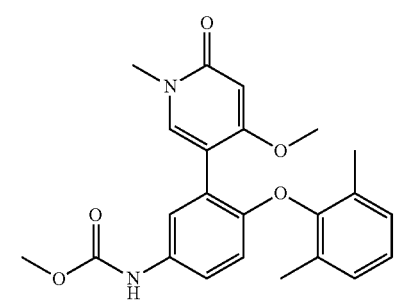 [SMILES: COC(=O)Nc1ccc(Oc2c(C)cccc2C)c(-c2cn(C)c(=O)cc2OC)c1] |
| 671 | 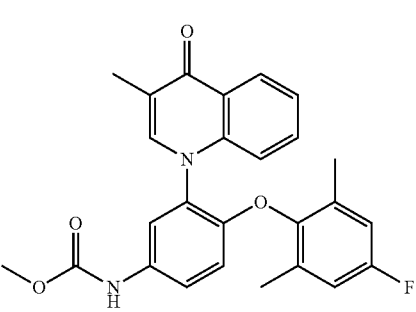 [SMILES: COC(=O)Nc1ccc(Oc2c(C)cc(F)cc2C)c(-n2cc(C)c(=O)c3ccccc32)c1] |

TABLE 1-continued
| Com. No. | Structure |
|---|---|
| 672 | 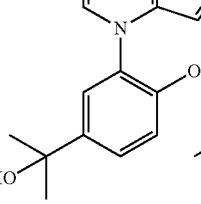 |
| 673 | 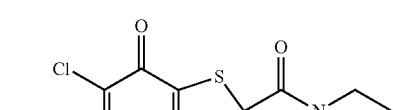 |
| 674 | 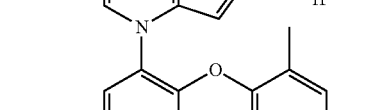 |
| 675 | 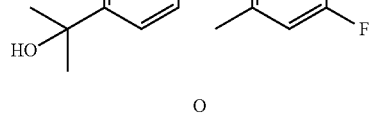 |
| 676 | 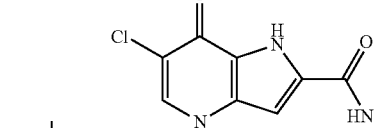 |
| 677 | 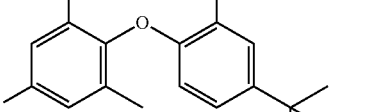 |
| 678 | 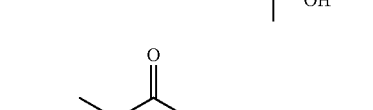 |
| 679 | 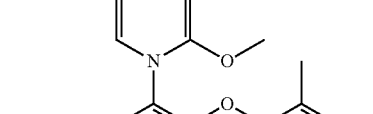 |
| 680 | 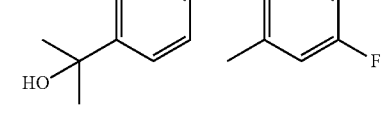 |
| 681 | 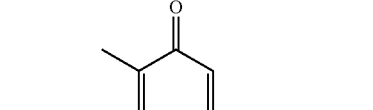 |

TABLE 1-continued

| Com. No. | Structure |
|---|---|
| 682 | 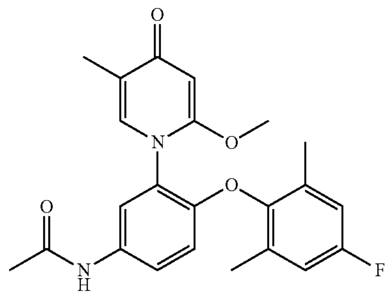 [SMILES: COc1cc(=O)c(C)cn1-c1cc(NC(C)=O)ccc1Oc1c(C)cc(F)cc1C] |
| 683 | 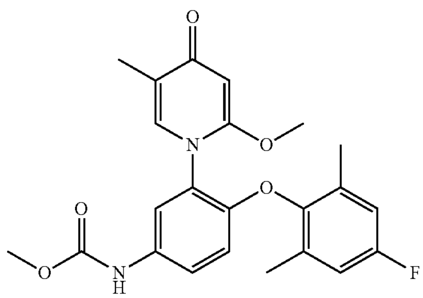 [SMILES: COC(=O)Nc1ccc(Oc2c(C)cc(F)cc2C)c(-n2cc(C)c(=O)cc2OC)c1] |
| 684 | 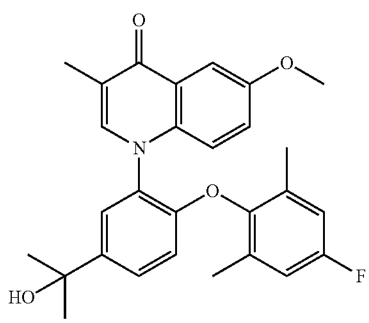 [SMILES: COc1ccc2c(c1)c(=O)c(C)cn2-c1cc(C(C)(C)O)ccc1Oc1c(C)cc(F)cc1C] |
| 685 | 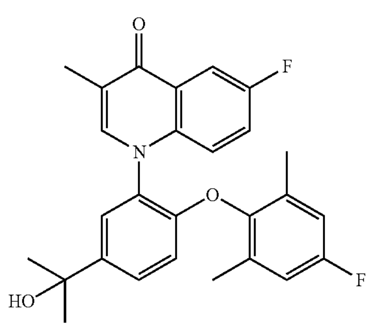 [SMILES: Cc1cc(F)cc(C)c1Oc1ccc(C(C)(C)O)cc1-n1cc(C)c(=O)c2cc(F)ccc21] |
| 686 | 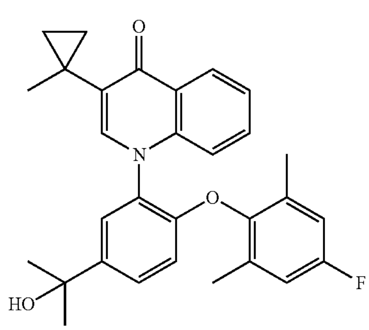 [SMILES: Cc1cc(F)cc(C)c1Oc1ccc(C(C)(C)O)cc1-n1cc(C2(C)CC2)c(=O)c2ccccc21] |
| 687 | |
| 688 | |
| 689 | |
| 690 | |
| 691 | |

TABLE 1-continued
| Com. No. | Structure |
|---|---|
| 692 | 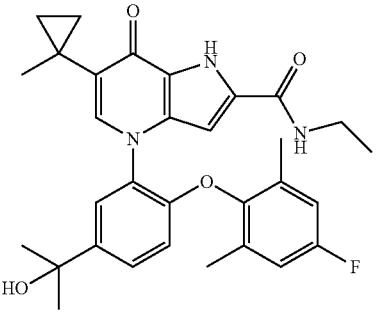 [SMILES: CCNC(=O)c1cc2c([nH]1)c(=O)c(C1(C)CC1)cn2-c1cc(C(C)(C)O)ccc1Oc1c(C)cc(F)cc1C] |
| 693 | 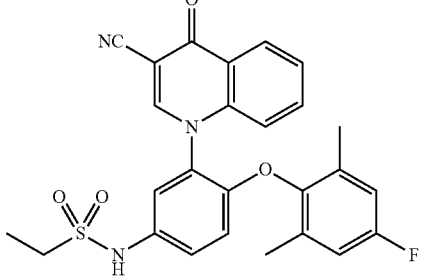 |
| 694 | 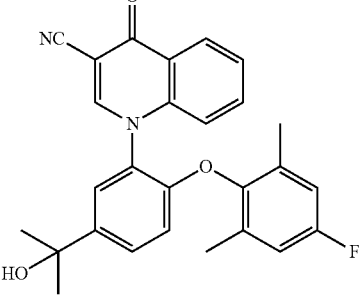 |
| 695 | 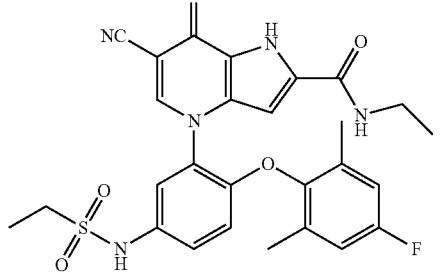 |
| 696 | 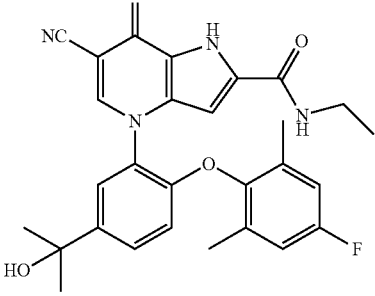 |
TABLE 1-continued
| Com. No. | Structure |
|---|---|
| 697 | 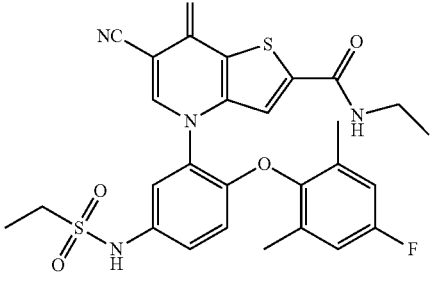 |
| 698 | 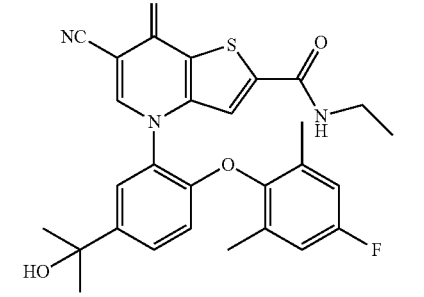 |
| 699 | 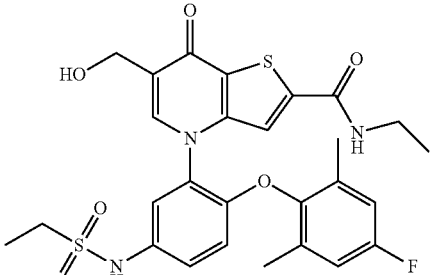 |
| 700 | 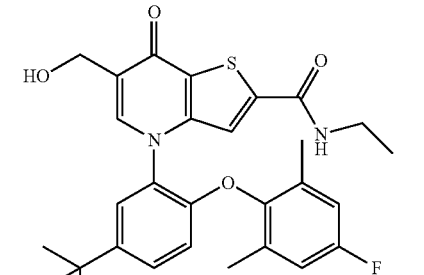 |
| 701 | 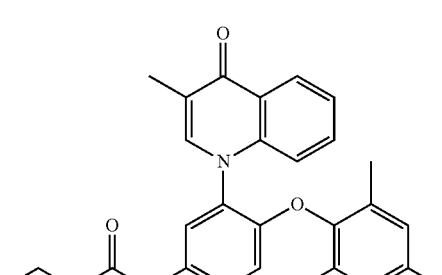 |

TABLE 1-continued

| Com. No. | Structure |
|---|---|
| 702 | (structure) |
| 703 | (structure) |
| 704 | (structure) |
| 705 | (structure) |
| 706 | (structure) |
| 707 | (structure) |
| 708 | (structure) |
| 709 | (structure) |
| 710 | (structure) |
| 711 | (structure) |

TABLE 1-continued
| Com. No. | Structure |
|---|---|
| 712 | 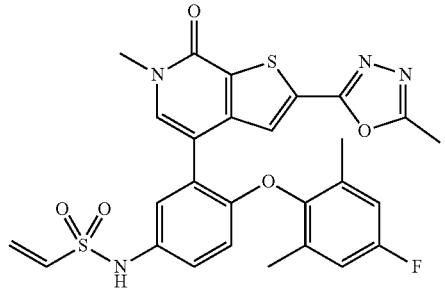 [SMILES: C=CS(=O)(=O)Nc1ccc(Oc2c(C)cc(F)cc2C)c(-c2cn(C)c(=O)c3sc(-c4nnc(C)o4)cc23)c1] |
| 713 | 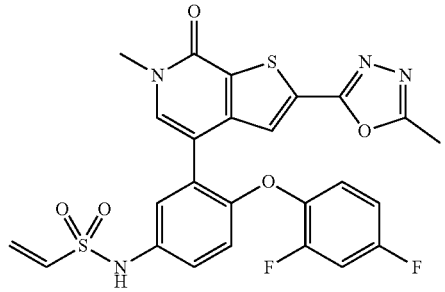 [SMILES: C=CS(=O)(=O)Nc1ccc(Oc2ccc(F)cc2F)c(-c2cn(C)c(=O)c3sc(-c4nnc(C)o4)cc23)c1] |
| 714 | 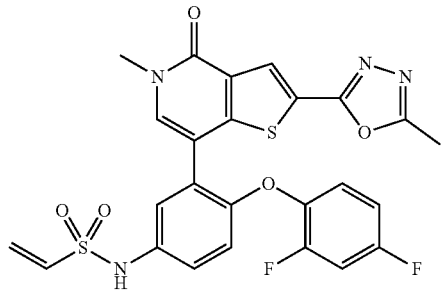 [SMILES: C=CS(=O)(=O)Nc1ccc(Oc2ccc(F)cc2F)c(-c2cn(C)c(=O)c3cc(-c4nnc(C)o4)sc23)c1] |
| 715 | 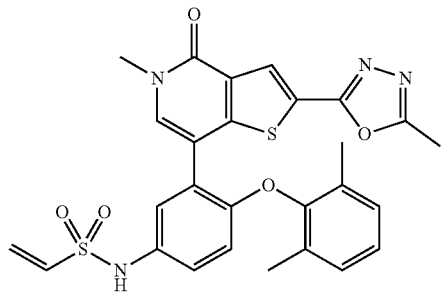 [SMILES: C=CS(=O)(=O)Nc1ccc(Oc2c(C)cccc2C)c(-c2cn(C)c(=O)c3cc(-c4nnc(C)o4)sc23)c1] |
| 716 | 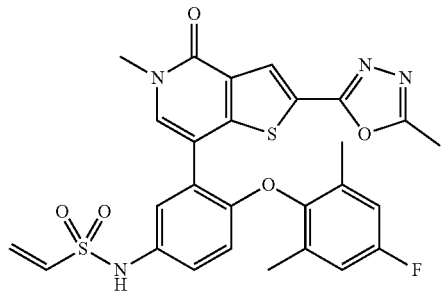 [SMILES: C=CS(=O)(=O)Nc1ccc(Oc2c(C)cc(F)cc2C)c(-c2cn(C)c(=O)c3cc(-c4nnc(C)o4)sc23)c1] |
TABLE 1-continued
| Com. No. | Structure |
|---|---|
| 717 | 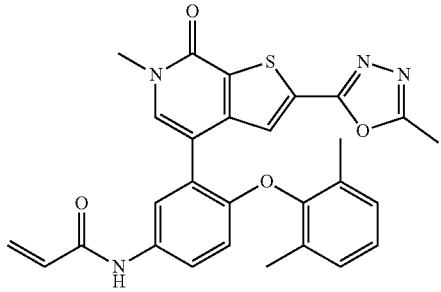 [SMILES: C=CC(=O)Nc1ccc(Oc2c(C)cccc2C)c(-c2cn(C)c(=O)c3sc(-c4nnc(C)o4)cc23)c1] |
| 718 | 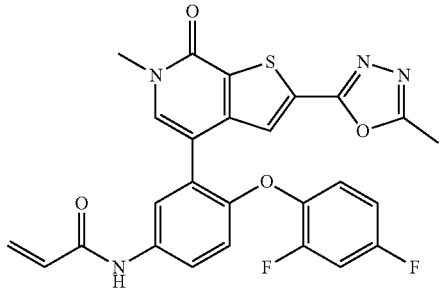 [SMILES: C=CC(=O)Nc1ccc(Oc2ccc(F)cc2F)c(-c2cn(C)c(=O)c3sc(-c4nnc(C)o4)cc23)c1] |
| 719 | 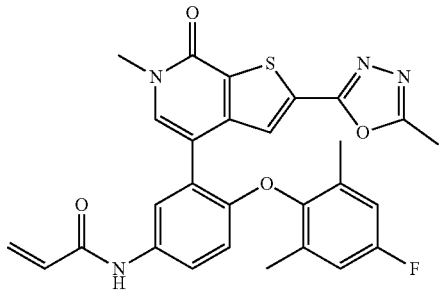 [SMILES: C=CC(=O)Nc1ccc(Oc2c(C)cc(F)cc2C)c(-c2cn(C)c(=O)c3sc(-c4nnc(C)o4)cc23)c1] |
| 720 | 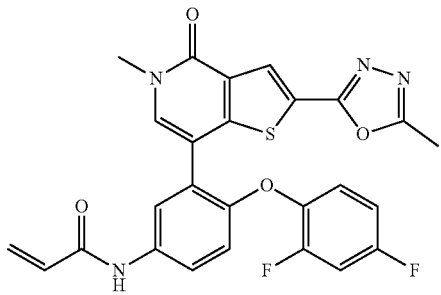 [SMILES: C=CC(=O)Nc1ccc(Oc2ccc(F)cc2F)c(-c2cn(C)c(=O)c3cc(-c4nnc(C)o4)sc23)c1] |
| 721 | 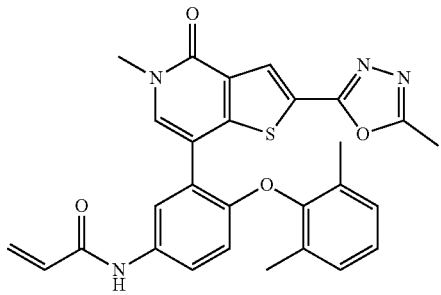 [SMILES: C=CC(=O)Nc1ccc(Oc2c(C)cccc2C)c(-c2cn(C)c(=O)c3cc(-c4nnc(C)o4)sc23)c1] |

TABLE 1-continued

| Com. No. | Structure |
|---|---|
| 722 | 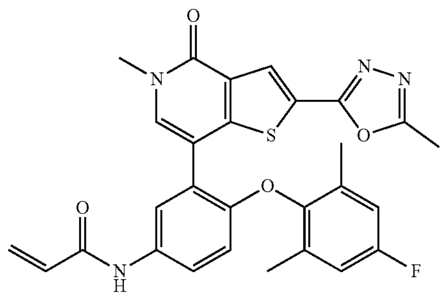 [SMILES: C=CC(=O)Nc1ccc(Oc2c(C)cc(F)cc2C)c(-c2cn(C)c(=O)c3cc(-c4nnc(C)o4)sc23)c1] |
| 723 | 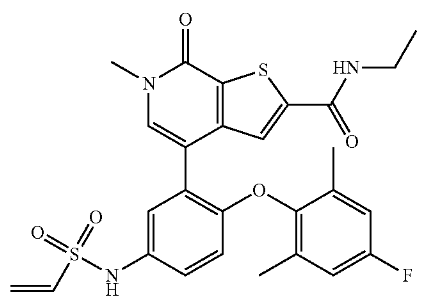 [SMILES: C=CS(=O)(=O)Nc1ccc(Oc2c(C)cc(F)cc2C)c(-c2cn(C)c(=O)c3sc(C(=O)NCC)cc23)c1] |
| 724 | 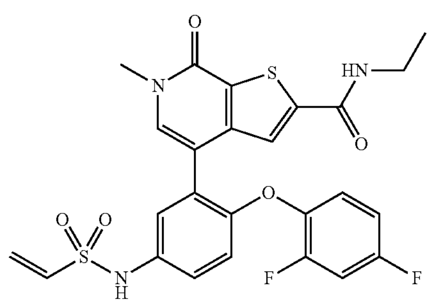 [SMILES: C=CS(=O)(=O)Nc1ccc(Oc2ccc(F)cc2F)c(-c2cn(C)c(=O)c3sc(C(=O)NCC)cc23)c1] |
| 725 | 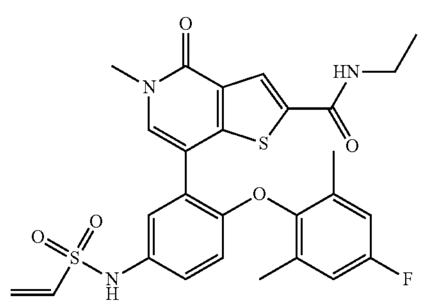 [SMILES: C=CS(=O)(=O)Nc1ccc(Oc2c(C)cc(F)cc2C)c(-c2cn(C)c(=O)c3cc(C(=O)NCC)sc23)c1] |
| 726 | 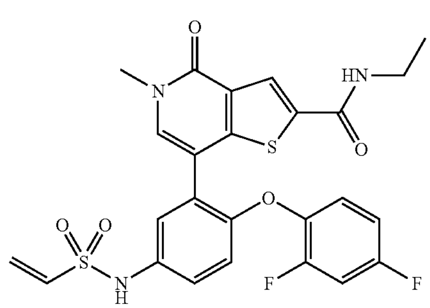 [SMILES: C=CS(=O)(=O)Nc1ccc(Oc2ccc(F)cc2F)c(-c2cn(C)c(=O)c3cc(C(=O)NCC)sc23)c1] |
| 727 | |
| 728 | |
| 729 | |
| 730 | |
| 731 | |

TABLE 1-continued
| Com. No. | Structure |
|---|---|
| 732 | 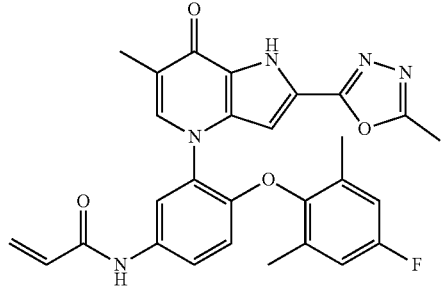 [SMILES: C=CC(=O)Nc1ccc(Oc2c(C)cc(F)cc2C)c(-n2cc(C)c(=O)c3[nH]c(-c4nnc(C)o4)cc32)c1] |
| 733 | 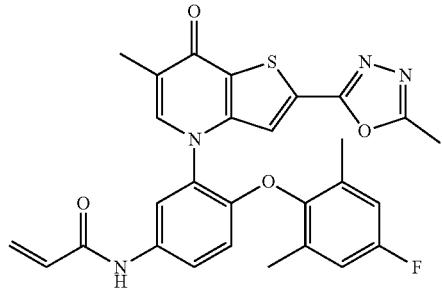 |
| 734 | 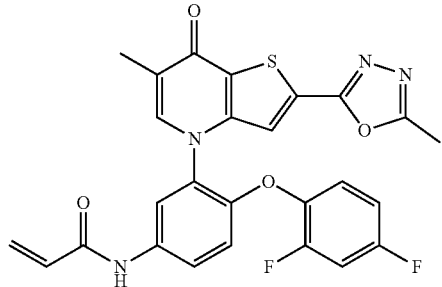 |
| 735 | 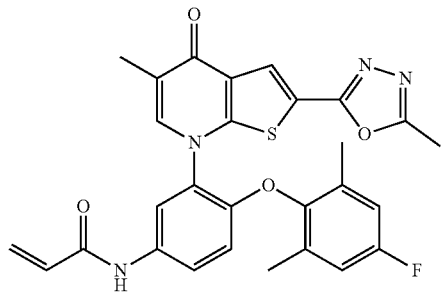 |
| 736 | 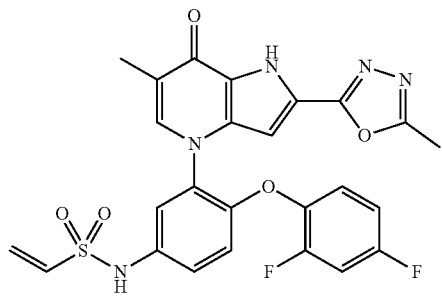 [SMILES: C=CS(=O)(=O)Nc1ccc(Oc2ccc(F)cc2F)c(-n2cc(C)c(=O)c3[nH]c(-c4nnc(C)o4)cc32)c1] |
TABLE 1-continued
| Com. No. | Structure |
|---|---|
| 737 | 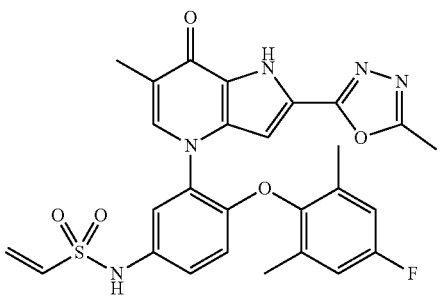 [SMILES: C=CS(=O)(=O)Nc1ccc(Oc2c(C)cc(F)cc2C)c(-n2cc(C)c(=O)c3[nH]c(-c4nnc(C)o4)cc32)c1] |
| 738 | 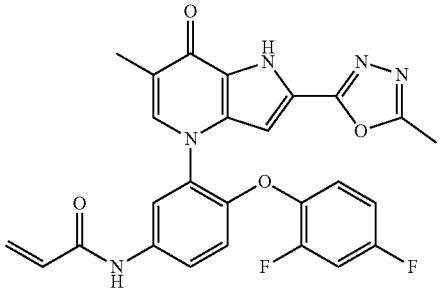 [SMILES: C=CC(=O)Nc1ccc(Oc2ccc(F)cc2F)c(-n2cc(C)c(=O)c3[nH]c(-c4nnc(C)o4)cc32)c1] |
| 739 | 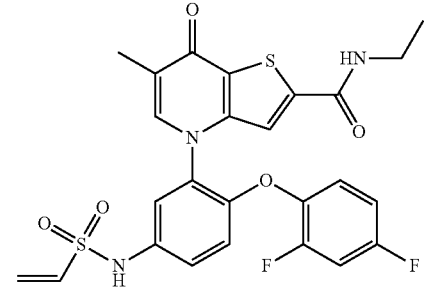 [SMILES: C=CS(=O)(=O)Nc1ccc(Oc2ccc(F)cc2F)c(-n2cc(C)c(=O)c3sc(C(=O)NCC)cc32)c1] |
| 740 | 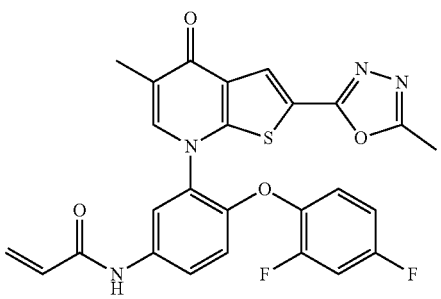 [SMILES: C=CC(=O)Nc1ccc(Oc2ccc(F)cc2F)c(-n2cc(C)c(=O)c3cc(-c4nnc(C)o4)sc32)c1] |
| 741 | 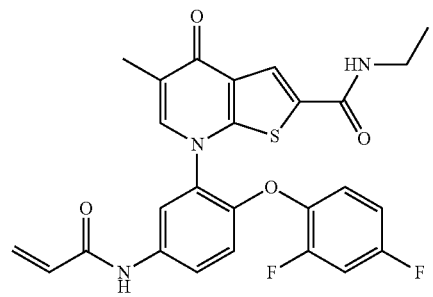 [SMILES: C=CC(=O)Nc1ccc(Oc2ccc(F)cc2F)c(-n2cc(C)c(=O)c3cc(C(=O)NCC)sc32)c1] |

TABLE 1-continued

| Com. No. | Structure |
|---|---|
| 742 | (structure) |
| 743 | (structure) |
| 744 | (structure) |
| 745 | (structure) |
| 746 | (structure) |
| 747 | (structure) |
| 748 | (structure) |
| 749 | (structure) |
| 750 | (structure) |
| 751 | (structure) |

TABLE 1-continued

| Com. No. | Structure |
|---|---|
| 752 | (structure) |
| 753 | (structure) |
| 754 | (structure) |
| 755 | (structure) |
| 756 | (structure) |
| 757 | (structure) |
| 758 | (structure) |

In some embodiments, provided herein are compounds described in Table 1, including or a pharmaceutically acceptable salt, hydrate, solvate, isotope, individual isomer, or mixtures of isomers thereof, and uses thereof.

The embodiments and variations described herein are suitable for compounds of any formulae detailed herein, where applicable.

Representative examples of compounds detailed herein, including intermediates and final compounds according to the present disclosure are depicted herein. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein.

The present disclosure also includes any or all of the stereochemical forms, including any enantiomeric or diastereomeric forms of the compounds described. The structure or name is intended to embrace all possible stereoisomers of a compound depicted, and each unique stereoisomer has a compound number bearing a suffix "a", "b", etc. All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of Formula (I) or variations thereof described herein, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^2H$, $^3H$, $^{11}C$, $^{13}C$, $^{14}C$, $^{13}N$, $^{15}O$, $^{17}O$, $^{35}S$, $^{18}F$, $^{36}Cl$. Certain isotope labeled compounds (e.g. $^3H$ and $^{14}C$) are useful in compound or substrate tissue distribution study. Incorporation of heavier isotopes such as deuterium ($^2H$) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound, such as would be generated in vivo following administration to a human.

Articles of manufacture comprising a compound described herein, or a salt or solvate thereof, in a suitable container are provided. The container may be a vial, jar, ampoule, preloaded syringe, i.v. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., for the treatment of cancer.

General Synthetic Methods

The compounds of the invention may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol.

Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

Abbreviations used in the descriptions of the schemes and the specific examples have the following meanings: EtOH for ethyl alcohol, $B_2Pin_2$ for Bis(pinacolato)diboron, KOAc for potassium acetate, DMSO for dimethyl sulfoxide, Pd(dppf)Cl$_2$ for [1,1'-Bis(diphenylphosphino)ferrocene]dichloropalladium(II); EtOAc for ethyl acetate; Et$_3$N for triethylamine; DCM for dichloromethane, DIPEA for N,N-Diisopropylethylamine, THF for tetrahydrofuran, T$_3$P for Propylphosphonic Anhydride, DMAP for 4-Dimethylaminopyridine and HPLC for high performance liquid chromatography.

The compounds described herein, including compounds of general Formula (I), (Ia), (Ia-1 to Ia-12), (Ib), (Ib-1 to Ib-4), (Ic), (Ic-1 to Ic-19), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), and specific examples, may be prepared, for example, through the reaction routes depicted in the Scheme. The variables $R^1$, $R^2$, $R^4$, $R^{c1}$, $G_1$, $G_2$, $Z_2$, $Z_3$, $W_1$ and m used in the scheme have the meanings as set forth in the summary and detailed description sections unless otherwise noted.

The compounds described herein, including compounds of general Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), and specific examples, may be prepared, for example, through the reaction routes depicted in the Scheme. The variables $R^1$, $R^2$, $R^4$, $R^{c1}$, $G_1$, $G_2$, $Z_2$, $Z_3$, $W_1$ and m used in the scheme have the meanings as set forth in the summary and detailed description sections unless otherwise noted.

Scheme 1
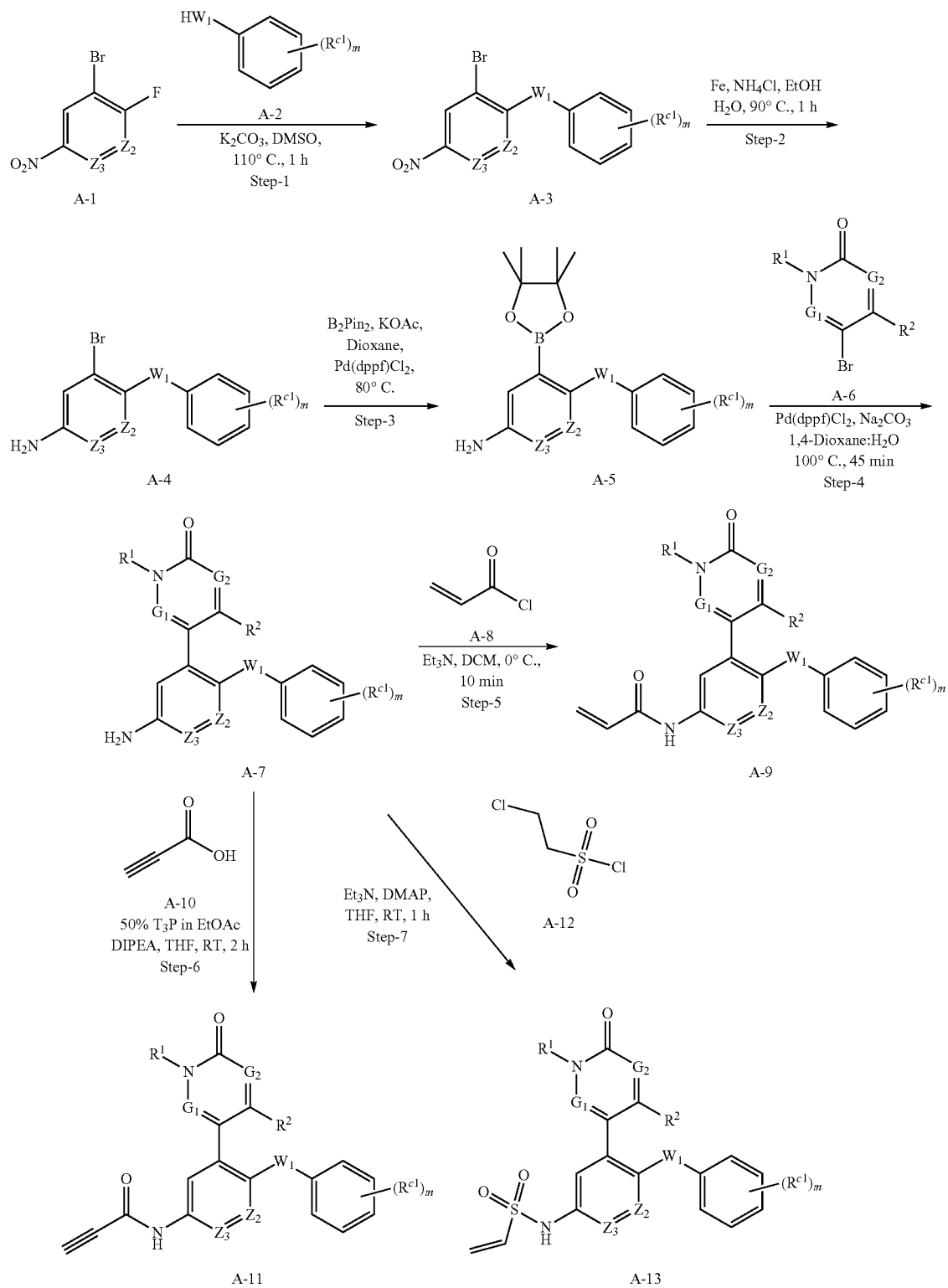
$W_1$ = NH or O

Scheme 2
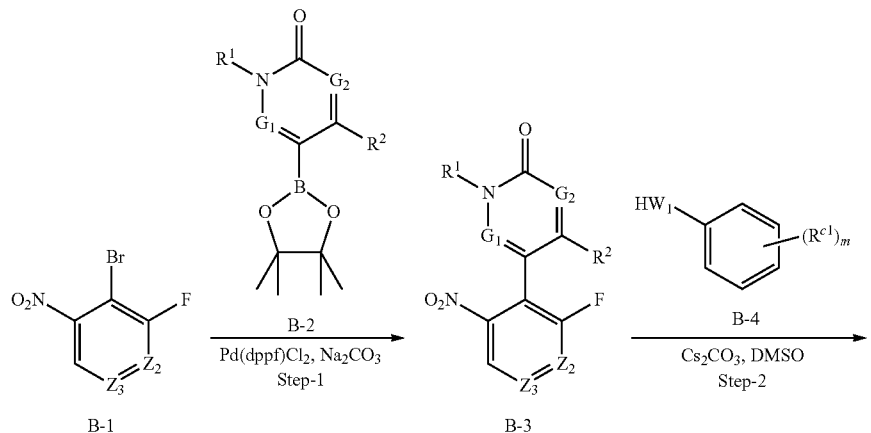
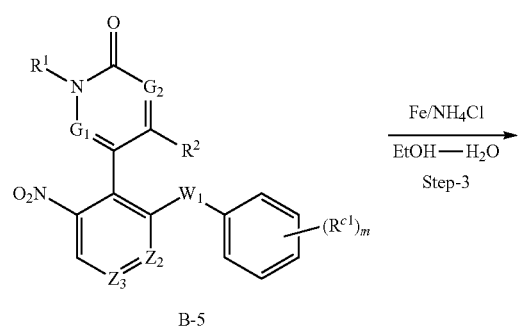
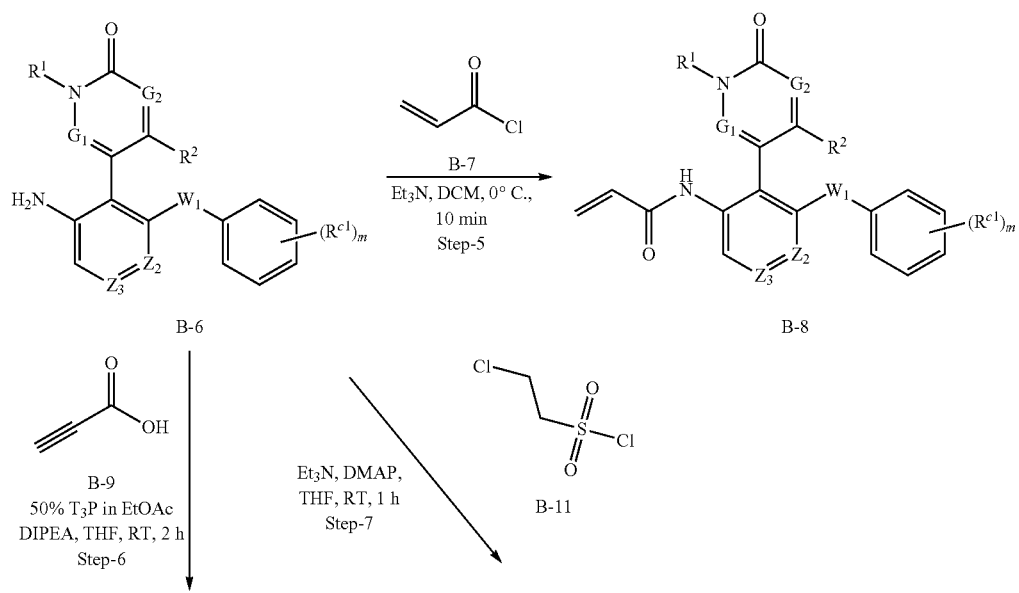

-continued
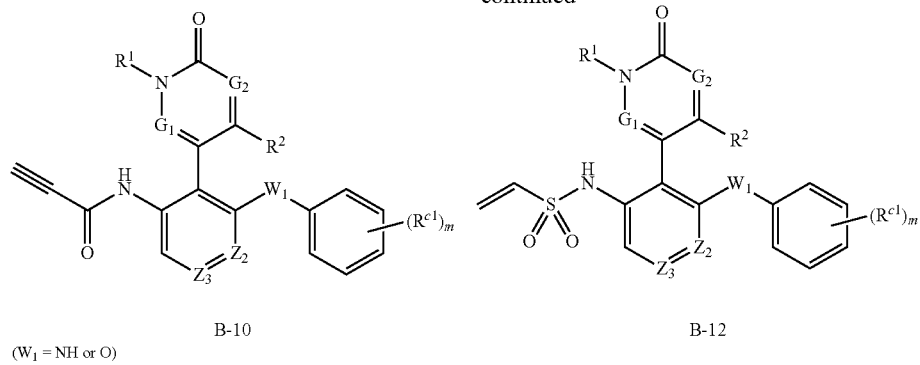
(W₁ = NH or O)
Scheme 3
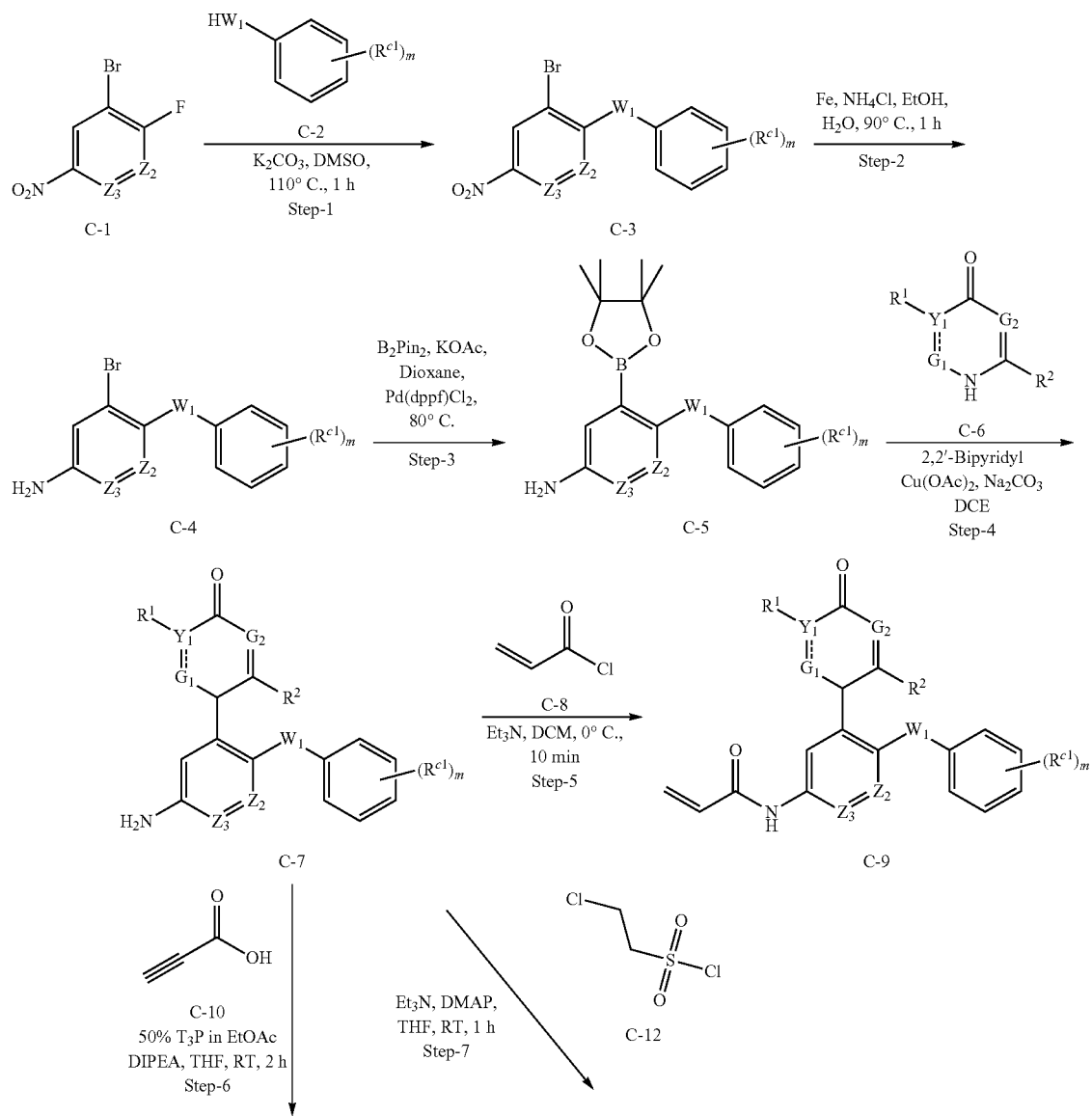

-continued
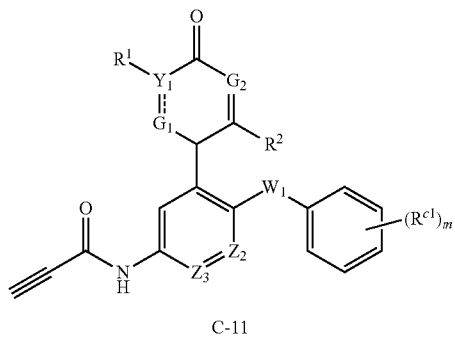
C-11
$W_1$ = NH or O
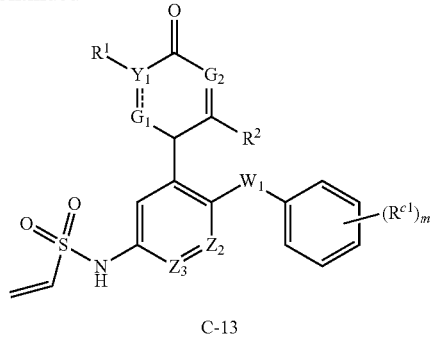
C-13
Scheme 4
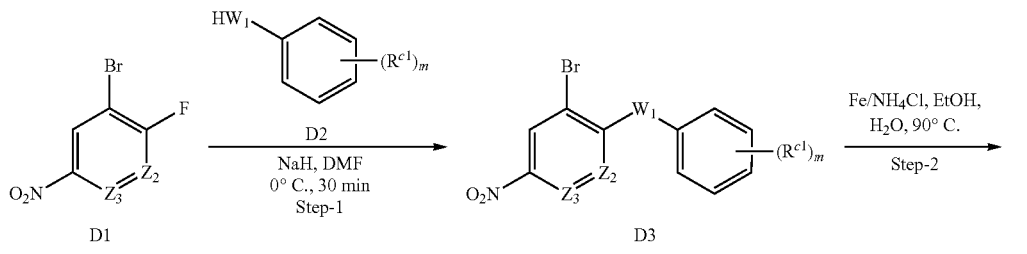
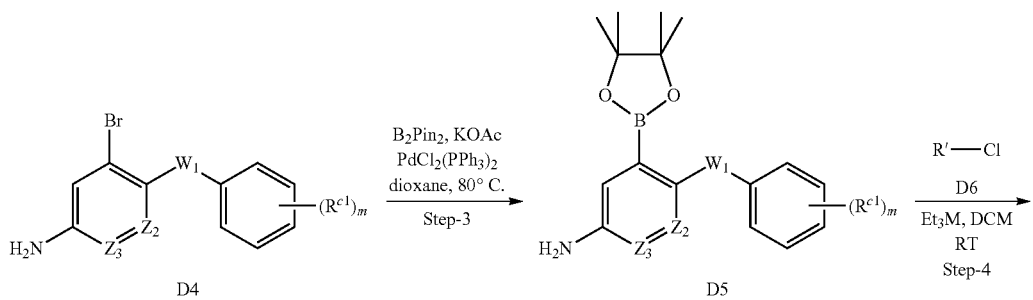
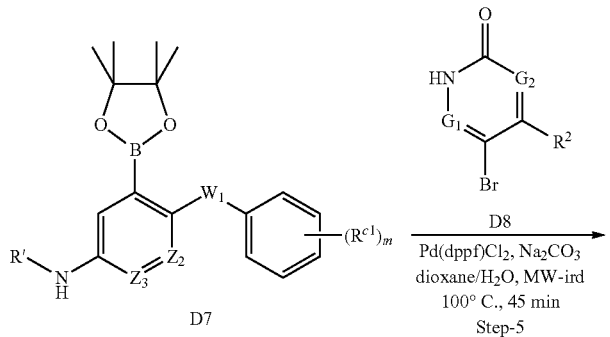

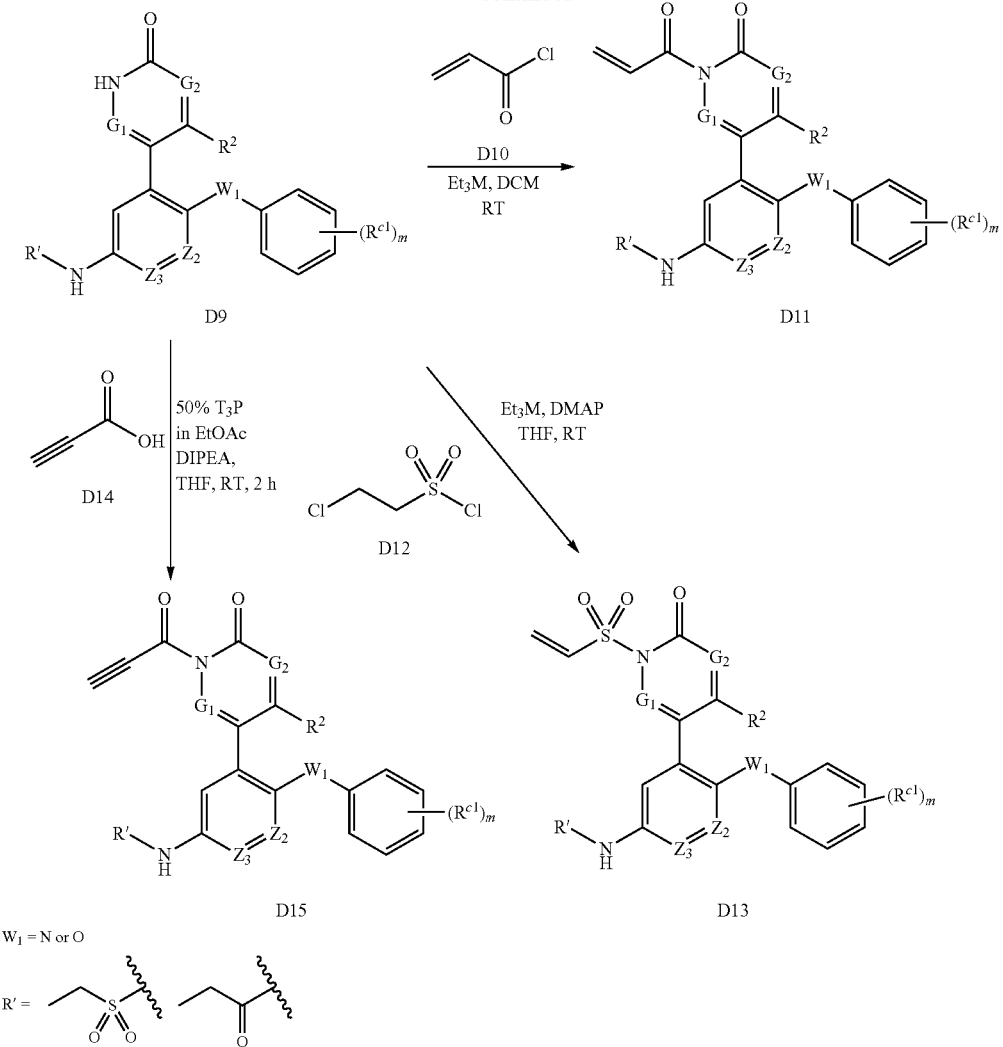

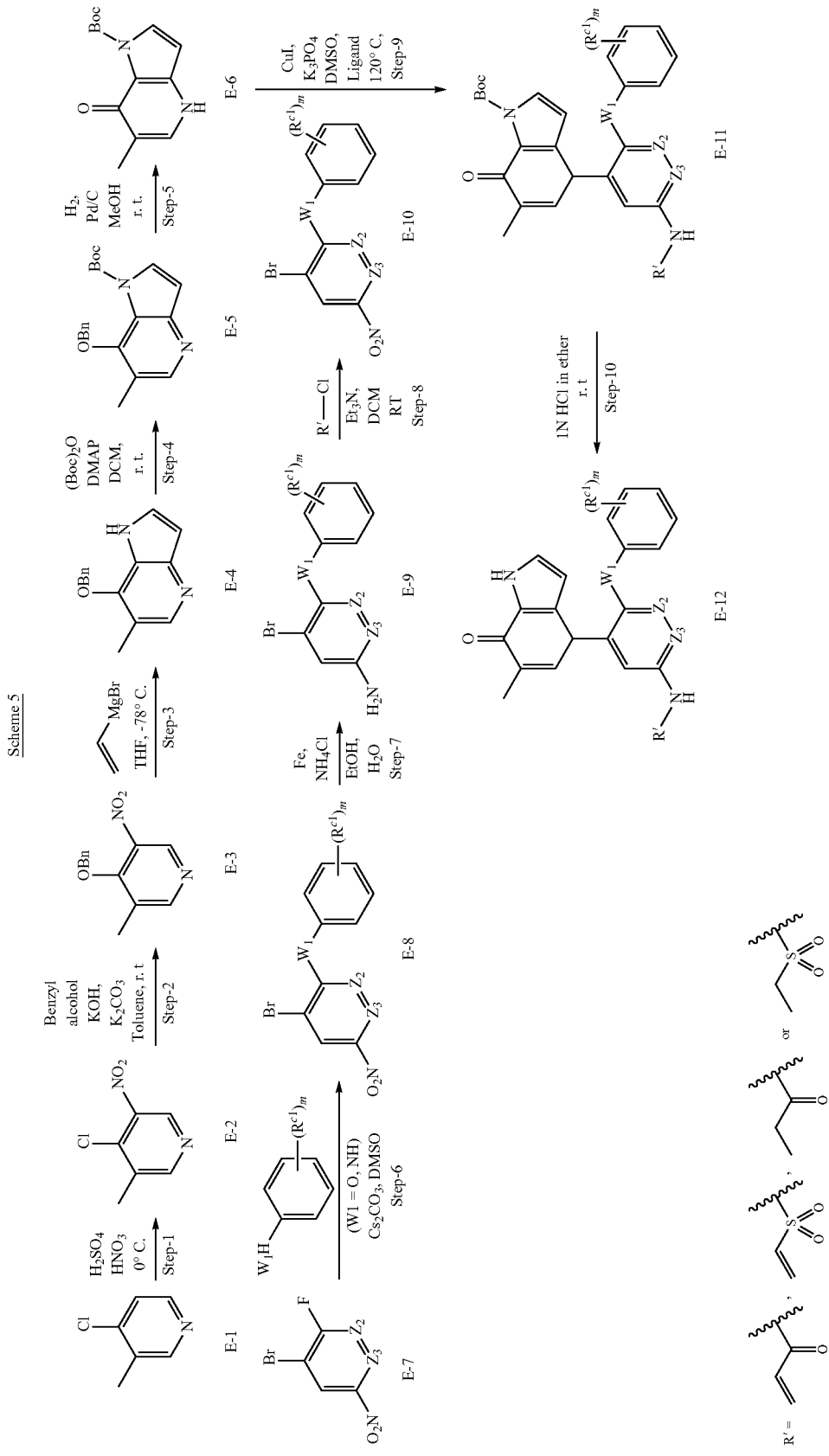

Scheme 6

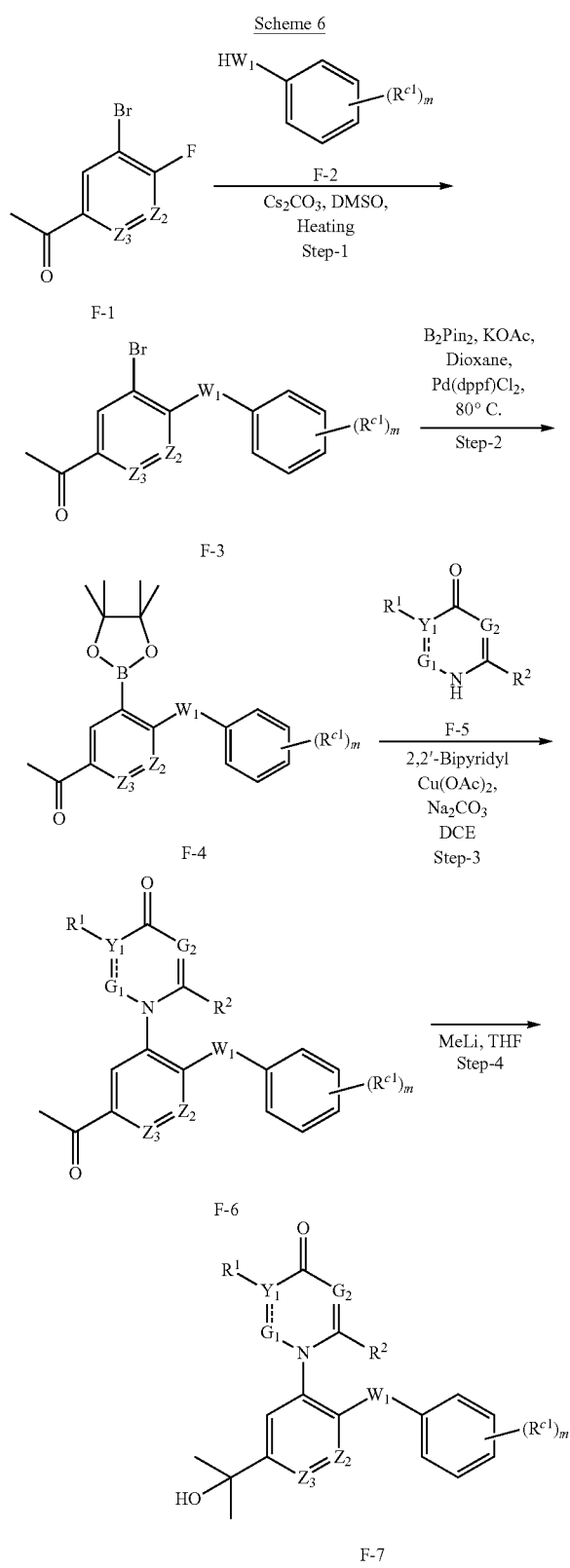

$W_1$ = NH or O

It is understood that General Synthetic Schemes 1 to Schemes 6 and present synthetic routes involving steps clearly familiar to those skilled in the art, wherein the substituents described in compounds of Formula (I), (Ia), (Ia-1 to Ia-12), (Ib), (Ib-1 to Ib-4), (Ic), (Ic-1 to Ic-19), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) herein can be varied with a choice of appropriate starting materials and reagents utilized in the steps presented.

It is understood that General Synthetic Schemes 1 to Schemes 5 and present synthetic routes involving steps clearly familiar to those skilled in the art, wherein the substituents described in compounds of the Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) herein can be varied with a choice of appropriate starting materials and reagents utilized in the steps presented.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Synthetic Examples section. Reactions may be further processed in the conventional manner, e.g. by eliminating the solvent from the residue and further purified according to methodologies generally known in the art such as, but not limited to, crystallization, distillation, extraction, trituration and chromatography.

Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Pharmaceutical Compositions and Formulations

Pharmaceutical compositions of any of the compounds detailed herein are embraced by this disclosure. Thus, the present disclosure includes pharmaceutical compositions comprising a compound as detailed herein or a pharmaceutically acceptable salt thereof and a pharmaceutically acceptable carrier or excipient. In one aspect, the pharmaceutically acceptable salt is an acid addition salt, such as a salt formed with an inorganic or organic acid.

Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oilin-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in Remington's Pharmaceutical Sciences, Mack Publishing Company, Philadelphia, Pa., 20$^{th}$ ed. (2000), which is incorporated herein by reference Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc.

Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 10 mg tablet.

Compositions comprising a compound provided herein are also described. In one variation, the composition comprises a compound or salt thereof and a pharmaceutically acceptable carrier or excipient. In another variation, a composition of substantially pure compound is provided.

Methods of Use

Compounds and compositions detailed herein, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation. In an embodiment, use of a compound having the structure of Formula (I), (Ia), (Ib), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a pharmaceutically acceptable isomer, racemate, hydrate, solvate, isotope, or salt thereof, for the manufacture of a medicament is provided.

Provided herein is a method of treating a disease in an individual comprising administering an effective amount of a compound of Formula (I) or any embodiment, variation or aspect thereof (collectively, a compound of Formula (I) or the present compounds or the compounds detailed or described herein) or a pharmaceutically acceptable salt thereof, to the individual. In some embodiments, a method of treating a disease in an individual is mediated by the BET family of proteins comprising administering an effective amount of a compound of Formula (I), or a pharmaceutically acceptable salt thereof, to the individual. In an embodiment, the present invention provides for methods for treating or preventing disorders that are ameliorated by inhibition of BET. In some embodiments, "treating" or "treatment" of a disease includes: inhibiting the disease, i.e., arresting its development; or relieving the disease, i.e., causing regression of the disease. In some embodiments, "treating" or "treatment" of a disease In some embodiments, "treatment" or "treating" is an approach for obtaining beneficial or desired results including clinical results. For example, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. In reference to a cancer, the number of cancer cells present in a subject may decrease in number and/or size and/or the growth rate of the cancer cells may slow. In some embodiments, treatment may prevent or delay recurrence of the disease. In the case of cancer, the treatment may: (i) reduce the number of cancer cells; (ii) inhibit, retard, slow to some extent and preferably stop cancer cell proliferation; (iii) prevent or delay occurrence and/or recurrence of the cancer; and/or (iv) relieve to some extent one or more of the symptoms associated with the cancer. The methods of the invention contemplate any one or more of these aspects of treatment.

The present compounds or salts thereof are believed to be effective for treating a variety of diseases and disorders. For example, in some embodiments, the present compositions may be used to treat an inflammatory disease, a proliferative disease, such as cancer, or AIDS.

In another aspect, the present invention relates to methods of treating cancer in a subject comprising administering a therapeutically effective amount of a compound of Formula (I), (Ia), (Ia-1 to Ia-12), (Ib), (Ib-1 to Ib-4), (Ic), (Ic-1 to Ic-19), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof, to a subject in need thereof. In certain embodiments, the cancer is selected from the group consisting of: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone sensitive and insensitive prostate cancer, enzalutamide (XTANDI) and abiraterone resistant prostate cancer in the pre- and post-chemo stages, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor. In certain embodiments, the methods further comprise administering a therapeutically effective amount of at least one additional therapeutic agent. In certain embodiments, the additional therapeutic agent is an anti-cancer agent. In particular embodiments, the additional therapeutic agents are selected from the group consisting of cytarabine, bortezomib, and 5-azacitidine.

In another aspect, the present invention relates to methods of treating cancer in a subject comprising administering a therapeutically effective amount of a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof, to a subject in need thereof. In certain embodiments, the cancer is selected from the group consisting of: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone sensitive and insensitive prostate cancer, enzalutamide (XTANDI) and abiraterone resistant prostate cancer in the pre- and post-chemo stages, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor. In certain embodiments, the methods further comprise administering a therapeutically effective amount of at least one additional therapeutic agent. In certain embodiments, the additional therapeutic agent is an anticancer agent. In particular embodiments, the additional therapeutic agents are selected from the group consisting of cytarabine, bortezomib, and 5-azacitidine.

In some embodiments, the cancer is a solid tumor. In some embodiments the cancer is any of adult and pediatric oncology, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer, including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas and osteosarcomas, skin cancers, including melanoma, tumor progression of human skin keratinocytes, squamous cell cancer, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

In some embodiments, the cancer in the individual has one or more mutations or amplification or overexpression of the genes encoding BET proteins. In some embodiments, the cancer in the individual has mutation or amplification or overexpression of BRD4. In some embodiments, the cancer in the individual has mutation or amplification or overexpression of c-MYC. In some embodiments, the cancer in the individual has mutation or amplification or overexpression of MYCN. In some embodiments, the cancer in the individual is characterized by Androgen Receptor (AR) expression.

In some embodiments, a method of treating a cancer in an individual is provided, the method, comprising (a) selecting the individual for treatment based on (i) the mutation or amplification or overexpression of BRD4 or other BET family members, or (ii) presence of mutation or amplification or overexpression of c-MYC in the cancer, and administering an effective amount of the compound of Formula (I), (Ia), (Ia-1 to Ia-12), (Ib), (Ib-1 to Ib-4), (Ic), (Ic-1 to Ic-19), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof, to the individual. In some embodiments, the cancer is sequenced to detect the one or more mutations or amplifications. In some embodiments, the gene is sequenced from the biopsied cancer. In some embodiments, the gene is sequenced by sequencing circulating-tumor DNA (ctDNA) from the individual.

In some embodiments, provided is a method of treating a cancer in an individual, comprising (a) selecting the individual for treatment based on (i) the mutation or amplification or overexpression of BRD4 or other BET family members, or (ii) presence of mutation or amplification or overexpression of c-MYC in the cancer, and administering an effective amount of the compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof, to the individual. In some embodiments, the cancer is sequenced to detect the one or more mutations or amplifications. In some embodiments, the gene is sequenced from the biopsied cancer. In some embodiments, the gene is sequenced by sequencing circulating-tumor DNA (ctDNA) from the individual.

In another aspect, the present invention relates to methods of treating a disease or condition in a subject comprising administering a therapeutically effective amount of a compound of Formula (I), (Ia), (Ia-1 to Ia-12), (Ib), (Ib-1 to Ib-4), (Ic), (Ic-1 to Ic-19), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof, to a subject in need thereof, wherein said disease or condition is selected from the group consisting of: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. In certain embodiments, the methods further comprise administering a therapeutically effective amount of at least one additional therapeutic agent. In certain embodiments, the methods further comprise administering a therapeutically effective amount of at least one additional therapeutic agent.

In another aspect, the present invention relates to methods of treating a chronic kidney disease or condition in a subject comprising administering a therapeutically effective amount of a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, to a subject in need thereof, wherein said disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis. In certain embodiments, the methods further comprise administering a therapeutically effective amount of at least one additional therapeutic agent. In certain embodiments, the methods further comprise administering a therapeutically effective amount of at least one additional therapeutic agent.

In another aspect, the present invention relates to methods of treating a chronic kidney disease or condition in a subject comprising administering a therapeutically effective amount of a compound of Formula (I), (Ia), (Ia-1 to Ia-12), (Ib), (Ib-1 to Ib-4), (Ic), (Ic-1 to Ic-19), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, to a subject in need thereof, wherein said disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis. In certain embodiments, the methods further comprise administering a therapeutically effective amount of at least one additional therapeutic agent. In certain embodiments, the methods further comprise administering a therapeutically effective amount of at least one additional therapeutic agent.

In another aspect, the present invention relates to methods of treating a chronic kidney disease or condition in a subject comprising administering a therapeutically effective amount of a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, to a subject in need thereof, wherein said disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis. In certain embodiments, the methods further comprise administering a therapeutically effective amount of at least one additional therapeutic agent. In certain embodiments, the methods further comprise administering a therapeutically effective amount of at least one additional therapeutic agent.

In another aspect, the present invention relates to methods of treating an acute kidney injury or disease or condition in a subject comprising administering a therapeutically effective amount of a compound of Formula (I), (Ia), (Ia-1 to Ia-12), (Ib), (Ib-1 to Ib-4), (Ic), (Ic-1 to Ic-19), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof, to a subject in need thereof, wherein said acute kidney injury or disease or condition is selected from the group consisting of: ischemia-reperfusion induced, cardiac and major surgery induced, percutaneous coronary intervention induced, radio-contrast agent induced, sepsis induced, pneumonia induced, and drug toxicity induced. In certain embodiments, the methods further comprise administering a therapeutically effective amount of at least one additional therapeutic agent. In certain embodiments, the methods further comprise administering a therapeutically effective amount of at least one additional therapeutic agent.

In another aspect, the present invention relates to methods of treating an acute kidney injury or disease or condition in a subject comprising administering a therapeutically effective amount of a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof, to a subject in need thereof, wherein said acute kidney injury or disease or condition is selected from the group consisting of: ischemia-reperfusion induced, cardiac and major surgery induced, percutaneous coronary intervention induced, radio-contrast agent induced, sepsis induced, pneumonia induced, and drug toxicity induced. In certain embodiments, the methods further comprise administering a therapeutically effective amount of at least one additional therapeutic agent. In certain embodiments, the methods further comprise administering a therapeutically effective amount of at least one additional therapeutic agent.

In another aspect, the present invention relates to methods of treating AIDS in a subject comprising administering a therapeutically effective amount of a compound of Formula (I), (Ia), (Ia-1 to Ia-12), (Ib), (Ib-1 to Ib-4), (Ic), (Ic-1 to Ic-19), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof, to a subject in need thereof. In certain embodiments, the methods further comprise administering a therapeutically effective amount of at least one additional therapeutic agent.

In another aspect, the present invention relates to methods of treating AIDS in a subject comprising administering a therapeutically effective amount of a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof, to a subject in need thereof. In certain embodiments, the methods further comprise administering a therapeutically effective amount of at least one additional therapeutic agent.

In another aspect, the present invention relates to methods of treating obesity, dyslipidemia, hypercholesterolemia, Alzheimer's disease, metabolic syndrome, hepatic steatosis, type II diabetes, insulin resistance, diabetic retinopathy or diabetic neuropathy in a subject comprising administering a therapeutically effective amount of a compound of Formula (I), (Ia), (Ia-1 to Ia-12), (Ib), (Ib-1 to Ib-4), (Ic), (Ic-1 to Ic-19), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof, to a subject in need thereof. In certain embodiments, the methods further comprise administering a therapeutically effective amount of at least one additional therapeutic agent.

In another aspect, the present invention relates to methods of treating obesity, dyslipidemia, hypercholesterolemia, Alzheimer's disease, metabolic syndrome, hepatic steatosis, type II diabetes, insulin resistance, diabetic retinopathy or diabetic neuropathy in a subject comprising administering a therapeutically effective amount of a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof, to a subject in need thereof. In certain embodiments, the methods further comprise administering a therapeutically effective amount of at least one additional therapeutic agent.

In another aspect, the present invention relates to methods of preventing conception by inhibiting spermatogenesis in a subject comprising administering a therapeutically effective amount of a compound of Formula (I), (Ia), (Ia-1 to Ia-12), (Ib), (Ib-1 to Ib-4), (Ic), (Ic-1 to Ic-19), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof, to a subject in need thereof. In certain embodiments, the methods further comprise administering a therapeutically effective amount of at least one additional therapeutic agent.

In another aspect, the present invention relates to methods of preventing conception by inhibiting spermatogenesis in a subject comprising administering a therapeutically effective amount of a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof, to a subject in need thereof. In certain embodiments, the methods further comprise administering a therapeutically effective amount of at least one additional therapeutic agent.

Combination Therapy

As provided herein, the presently disclosed compounds or a salt thereof may be combined with an additional therapeutic agent. In some embodiments, a method of treating a disease in an individual is provided, the method comprising administering an effective amount of a compound of Formula (I), (Ia), (Ia-1 to Ia-12), (Ib), (Ib-1 to Ib-4), (Ic), (Ic-1 to Ic-19), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or any embodiment, variation or aspect thereof (collectively, a compound of formula Formula (I), (Ia), (Ia-1 to Ia-12), (Ib), (Ib-1 to Ib-4), (Ic), (Ic-1 to Ic-19), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)), or the present compounds or the compounds detailed or described herein) or a pharmaceutically acceptable salt thereof, and an additional therapeutic agent to the individual. In some embodiments, the disease is a proliferative disease such as cancer.

As provided herein, the presently disclosed compounds or a salt thereof may be combined with an additional therapeutic agent. In some embodiments, provided herein is a method of treating a disease in an individual comprising administering an effective amount of a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or any embodiment, variation or aspect thereof (collectively, a compound of formula Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)), or the present compounds or the compounds detailed or described herein) or a pharmaceutically acceptable salt thereof, and an additional therapeutic agent to the individual. In some embodiments, the disease is a proliferative disease such as cancer.

In some embodiments, the additional therapeutic agent is a cancer immunotherapy agent. In some embodiments, the additional therapeutic agent is an immunostimulatory agent. In some embodiments, the additional therapeutic agent targets a checkpoint protein (for example an immune checkpoint inhibitor). In some embodiments, the additional therapeutic agent is effective to stimulate, enhance or improve an immune response against a tumor.

In some embodiments, a method of treating a disease in an individual is provided, the method comprising administering an effective amount of Formula (I), (Ia), (Ia-1 to Ia-12), (Ib), (Ib-1 to Ib-4), (Ic), (Ic-1 to Ic-19), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)), or the present compounds or the compounds detailed or described herein) or a pharmaceutically acceptable salt thereof, in combination with radiation therapy.

In some embodiments, provided is a method of treating a disease in an individual comprising administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)), or the present compounds or the compounds detailed or described herein) or a pharmaceutically acceptable salt thereof, in combination with radiation therapy.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a chemotherapeutic agent. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the chemotherapeutic agent. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the chemotherapeutic agent.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a chemotherapeutic agent. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the chemotherapeutic agent. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the chemotherapeutic agent.

Examples of chemotherapeutic agents that can be used in combination with Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof include a DNA alkylating agent (such as cyclophosphamide, mechlorethamine, chlorambucil, melphalan, dacarbazine, or nitrosoureas), a topoisomerase inhibitor (such as a Topoisomerase I inhibitor (e.g., irinotecan or topotecan) or a Topoisomerase II inhibitor (e.g., etoposide or teniposide), an anthracycline (such as daunorubicin, doxorubicin, epirubicin, idarubicin, mitoxantrone, or valrubicin), a histone deacetylase inhibitor (such as vorinostat or romidepsin), another bromodomain inhibitor, other epigenetic inhibitors, a taxane (such as paclitaxel or docetaxel), a kinase inhibitor (such as bortezomib, erlotinib, gefitinib, imatinib, vemurafenib, vismodegib, ibrutinib), a mTOR inhibitor, a DNA Damage Repair (DDR) pathway inhibitor, such as a PARP inhibitor, ATM inhibitor, ATR inhibitor, a Weel inhibitor, a proteasome inhibitor (such as bortezomib), an anti-angiogenic inhibitor, endocrine therapy, antiestrogen therapy, anti-androgen therapy, glucocorticoid receptor inhibitor, a nucleotide analog or precursor analog (such as azacitidine, azathioprine, capecitabine, cytarabine, doxifluridine, 5-fluorouracil, gemcitabine, hydroxyurea, mercaptopurine, methotrexate, or tioguanine), or a platinum-based chemotherapeutic agent (such as cisplatin, carboplatin, or oxaliplatin), pemetrexed, or a combination thereof.

Examples of chemotherapeutic agents that can be used in combination with Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof include a DNA alkylating agent (such as cyclophosphamide, mechlorethamine, chlorambucil, melphalan, dacarbazine, or nitrosoureas), a topoisomerase inhibitor (such as a Topoisomerase I inhibitor (e.g., irinotecan or topotecan) or a Topoisomerase II inhibitor (e.g., etoposide or teniposide), an anthracycline (such as daunorubicin, doxorubicin, epirubicin, idarubicin, mitoxantrone, or valrubicin), a histone deacetylase inhibitor (such as vorinostat or romidepsin), another bromodomain inhibitor, other epigenetic inhibitors, a taxane (such as paclitaxel or docetaxel), a kinase inhibitor (such as bortezomib, erlotinib, gefitinib, imatinib, vemurafenib, vismodegib, ibrutinib), a mTOR inhibitor, a DNA Damage Repair (DDR) pathway inhibitor, such as a PARP inhibitor, ATM inhibitor, ATR inhibitor, a Weel inhibitor, a proteasome inhibitor (such as bortezomib), an anti-angiogenic inhibitor, endocrine therapy, antiestrogen therapy, anti-androgen therapy, glucocorticoid receptor inhibitor, a nucleotide analog or precursor analog (such as azacitidine, azathioprine, capecitabine, cytarabine, doxifluridine, 5-fluorouracil, gemcitabine, hydroxyurea, mercaptopurine, methotrexate, or tioguanine), or a platinum-based chemotherapeutic agent (such as cisplatin, carboplatin, or oxaliplatin), pemetrexed, or a combination thereof.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a DNA damaging agent. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the DNA damaging agent. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the DNA damaging agent.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a DNA damaging agent. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the DNA damaging agent. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the DNA damaging agent.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a DNA alkylating agent (such as cyclophosphamide, mechlorethamine, chlorambucil, melphalan, dacarbazine, or nitrosoureas). In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the DNA alkylating agent. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the DNA alkylating agent.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a DNA alkylating agent (such as cyclophosphamide, mechlorethamine, chlorambucil, melphalan, dacarbazine, or nitrosoureas). In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the DNA alkylating agent. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the DNA alkylating agent.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a topoisomerase inhibitor (such as a Topoisomerase I inhibitor (e.g., irinotecan or topotecan) or a Topoisomerase II inhibitor (e.g., etoposide or teniposide)). In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the topoisomerase inhibitor. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the topoisomerase inhibitor.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a topoisomerase inhibitor (such as a Topoisomerase I inhibitor (e.g., irinotecan or topotecan) or a Topoisomerase II inhibitor (e.g., etoposide or teniposide)). In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the topoisomerase inhibitor. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the topoisomerase inhibitor.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of an anthracycline (such as daunorubicin, doxorubicin, epirubicin, idarubicin, mitoxantrone, or valrubicin). In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the anthracycline. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the anthracycline.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of an anthracycline (such as daunorubicin, doxorubicin, epirubicin, idarubicin, mitoxantrone, or valrubicin). In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the anthracycline. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the anthracycline.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a histone deacetylase inhibitor (such as vorinostat or romidepsin). In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the histone deacetylase inhibitor. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the histone deacetylase inhibitor.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a histone deacetylase inhibitor (such as vorinostat or romidepsin). In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the histone deacetylase inhibitor. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the histone deacetylase inhibitor.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a taxane (such as paclitaxel or docetaxel). In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the taxane. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the taxane.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a taxane (such as paclitaxel or docetaxel). In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the taxane. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the taxane.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a nucleotide analog or precursor analog (such as azacitidine, azathioprine, capecitabine, cytarabine, doxifluridine, 5-fluorouracil, gemcitabine, hydroxyurea, mercaptopurine, methotrexate, or tioguanine). In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the nucleotide analog or precursor analog. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the nucleotide analog or precursor analog.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a nucleotide analog or precursor analog (such as azacitidine, azathioprine, capecitabine, cytarabine, doxifluridine, 5-fluorouracil, gemcitabine, hydroxyurea, mercaptopurine, methotrexate, or tioguanine). In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the nucleotide analog or precursor analog. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the nucleotide analog or precursor analog.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a platinum-based chemotherapeutic agent (such as cisplatin, carboplatin, or oxaliplatin). In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the platinum-based chemotherapeutic agent. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the platinum-based chemotherapeutic agent.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a platinum-based chemotherapeutic agent (such as cisplatin, carboplatin, or oxaliplatin). In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the platinum-based chemotherapeutic agent. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the platinum-based chemotherapeutic agent.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of pemetrexed. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the pemetrexed. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the pemetrexed.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of pemetrexed. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the pemetrexed. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the pemetrexed.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a kinase inhibitor (such as bortezomib, erlotinib, gefitinib, imatinib, vemurafenib, vismodegib, or ibrutinib). In some embodiments, Formula I or a pharmaceutically acceptable salt thereof is administered prior to, after, or simultaneously co-administered with the kinase inhibitor. In some embodiments, Formula I or a pharmaceutically acceptable salt thereof is administered 1 or more hours (such as 2 or more hours, 4 or more hours, 8 or more hours, 12 or more hours, 24 or more hours, or 48 or more hours) prior to or after the kinase inhibitor.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a kinase inhibitor (such as bortezomib, erlotinib, gefitinib, imatinib, vemurafenib, vismodegib, or ibrutinib). In some embodiments, Formula I or a pharmaceutically acceptable salt thereof is administered prior to, after, or simultaneously co-administered with the kinase inhibitor. In some embodiments, Formula I or a pharmaceutically acceptable salt thereof is administered 1 or more hours (such as 2 or more hours, 4 or more hours, 8 or more hours, 12 or more hours, 24 or more hours, or 48 or more hours) prior to or after the kinase inhibitor.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a mTOR inhibitor (such as everolimus). In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the mTOR inhibitor.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a mTOR inhibitor (such as everolimus). In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the mTOR inhibitor.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a PI3K or Akt inhibitor. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the PI3K or Akt inhibitor. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the PI3K or Akt inhibitor.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a PI3K or Akt inhibitor. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the PI3K or Akt inhibitor. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the PI3K or Akt inhibitor.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a Bruton's tyrosine kinase (BTK) inhibitor. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the BTK inhibitor. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the BTK inhibitor.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a Bruton's tyrosine kinase (BTK) inhibitor. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the BTK inhibitor. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the BTK inhibitor.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a Cyclin-dependent kinase (CDK) inhibitor, such as inhibitor of CDK1, CDK2, CDK4, CDK5, CDK6, CDK7, or CDK9, or any combination thereof. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the CDK inhibitor. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the CDK inhibitor.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a Cyclin-dependent kinase (CDK) inhibitor, such as inhibitor of CDK1, CDK2, CDK4, CDK5, CDK6, CDK7, or CDK9, or any combination thereof. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the CDK inhibitor. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the CDK inhibitor.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a DNA damage repair (DDR) pathway inhibitor. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the DDR pathway inhibitor. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the DDR pathway inhibitor. Examples of inhibitors of the DDR pathway include poly(ADP-ribose) polymerase (PARP) inhibitors (such as olaparib, rucaparib, niraparib, or talazoparib), ataxia telangiectasia mutated (ATM) protein inhibitors, ataxia telangiectasia and Rad3-related (ATR) protein inhibitors, checkpoint kinase 1 (Chk1) inhibitors, or combinations thereof.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a DNA damage repair (DDR) pathway inhibitor. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the DDR pathway inhibitor. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the DDR pathway inhibitor. Examples of inhibitors of the DDR pathway include poly(ADP-ribose) polymerase (PARP) inhibitors (such as olaparib, rucaparib, niraparib, or talazoparib), ataxia telangiectasia mutated (ATM) protein inhibitors, ataxia telangiectasia and Rad3-related (ATR) protein inhibitors, checkpoint kinase 1 (Chk1) inhibitors, or combinations thereof.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a PARP inhibitor (such as olaparib, rucaparib, niraparib, or talazoparib). In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the PARP inhibitor. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the PARP inhibitor.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a PARP inhibitor (such as olaparib, rucaparib, niraparib, or talazoparib). In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the PARP inhibitor. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the PARP inhibitor.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of an ATM protein inhibitor. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the ATM protein inhibitor. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the ATM protein inhibitor.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of an ATM protein inhibitor. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the ATM protein inhibitor. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the ATM protein inhibitor.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of an ATR protein inhibitor. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the ATR protein inhibitor. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the ATR protein inhibitor.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of an ATR protein inhibitor. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the ATR protein inhibitor. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the ATR protein inhibitor.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a Chk1 inhibitor. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the Chk1 inhibitor. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the Chk1 inhibitor.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a Chk1 inhibitor. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the Chk1 inhibitor. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the Chk1 inhibitor.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a Wee1 inhibitor. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the Wee1 inhibitor. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the Wee1 inhibitor.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of a Wee1 inhibitor. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the Wee1 inhibitor. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the Wee 1 inhibitor.

In some embodiments, a method of treating a disease in an individual is provided, the method comprising (a) administering an effective amount of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of an endocrine therapy agent. In some embodiments, the endocrine therapy is antiestrogen therapy. In some embodiments, the endocrine therapy is a selective estrogen receptor degrader (SERD, such as fulvestrant). In some embodiments, the endocrine therapy is an aromatase inhibitor (such as letrozole). In some embodiments, the endocrine therapy is an anti-androgen therapy (such as enzalutamide or apalutamide). In some embodiments, the endocrine therapy is a CYP17 inhibitor (such as abiraterone). In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the endocrine therapy agent. In some embodiments, Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the endocrine therapy agent.

In some embodiments, provided is a method of treating a disease in an individual comprising (a) administering an effective amount of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or any embodiment, variation or aspect thereof (collectively, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5)) or a pharmaceutically acceptable salt thereof, and (b) administering an effective amount of an endocrine therapy agent. In some embodiments, the endocrine therapy is antiestrogen therapy. In some embodiments, the endocrine therapy is a selective estrogen receptor degrader (SERD, such as fulvestrant). In some embodiments, the endocrine therapy is an aromatase inhibitor (such as letrozole). In some embodiments, the endocrine therapy is an anti-androgen therapy (such as enzalutamide or apalutamide). In some embodiments, the endocrine therapy is a CYP17 inhibitor (such as abiraterone). In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered prior to, after, or simultaneously co-administered with the endocrine therapy agent. In some embodiments, Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a pharmaceutically acceptable salt thereof is administered 1 or more hours (such as 2 or more hours, 4 or more hours, 8 or more hours, 12 or more hours, 24 or more hours, or 48 or more hours) prior to or after the endocrine therapy agent.

In another aspect, provided herein is a combination therapy in which a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof is coadministered (which may be separately or simultaneously) with one or more additional agents that are effective in stimulating immune responses to thereby further enhance, stimulate or upregulate immune responses in a subject. For example, provided is a method for stimulating an immune response in a subject comprising administering to the subject a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof and one or more immunostimulatory antibodies, such as an anti-PD-1 antibody, an anti-PD-L antibody and/or an anti-CTLA-4 antibody, such that an immune response is stimulated in the subject, for example to inhibit tumor growth. In one embodiment, the subject is administered a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a salt thereof and an anti-PD-1 antibody. In another embodiment, the subject is administered a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof and an anti-PD-L1 antibody. In yet another embodiment, the subject is administered a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a salt thereof and an anti-CTLA-4 antibody. In another embodiment, the immunostimulatory antibody (e.g., anti-PD-1, anti-PD-L1 and/or anti-CTLA-4 antibody) is a human antibody. Alternatively, the immunostimulatory antibody can be, for example, a chimeric or humanized antibody (e.g., prepared from a mouse anti-PD-1, anti-PD-L1 and/or anti-CTLA-4 antibody).

In another aspect, provided herein is a combination therapy in which a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof is coadministered (which may be separately or simultaneously) with one or more additional agents that are effective in stimulating immune responses to thereby further enhance, stimulate or upregulate immune responses in a subject. For example, provided is a method for stimulating an immune response in a subject comprising administering to the subject a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof and one or more immunostimulatory antibodies, such as an anti-PD-1 antibody, an anti-PD-L1 antibody and/or an anti-CTLA-4 antibody, such that an immune response is stimulated in the subject, for example to inhibit tumor growth. In one embodiment, the subject is administered a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a salt thereof and an anti-PD-1 antibody. In another embodiment, the subject is administered a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof and an anti-PD-L1 antibody. In yet another embodiment, the subject is administered a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a salt thereof and an anti-CTLA-4 antibody. In another embodiment, the immunostimulatory antibody (e.g., anti-PD-1, anti-PD-L1 and/or anti-CTLA-4 antibody) is a human antibody. Alternatively, the immunostimulatory antibody can be, for example, a chimeric or humanized antibody (e.g., prepared from a mouse anti-PD-1, anti-PD-L1 and/or anti-CTLA-4 antibody).

In one embodiment, the present disclosure provides a method for treating a proliferative disease (e.g., cancer), comprising administering a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof and an anti-PD-1 antibody or to a subject. In further embodiments, a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a salt thereof is administered at a subtherapeutic dose, the anti-PD-1 antibody is administered at a subtherapeutic dose, or both are administered at a subtherapeutic dose. In another embodiment, the present disclosure provides a method for altering an adverse event associated with treatment of a hyperproliferative disease with an immunostimulatory agent, comprising administering a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof and a subtherapeutic dose of anti-PD-1 antibody to a subject. In certain embodiments, the subject is human. In certain embodiments, the anti-PD-1 antibody is a human sequence monoclonal antibody.

In one embodiment, the present disclosure provides a method for treating a proliferative disease (e.g., cancer), comprising administering a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof and an anti-PD-1 antibody or to a subject. In further embodiments, a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a salt thereof is administered at a subtherapeutic dose, the anti-PD-1 antibody is administered at a subtherapeutic dose, or both are administered at a subtherapeutic dose. In another embodiment, the present disclosure provides a method for altering an adverse event associated with treatment of a hyperproliferative disease with an immunostimulatory agent, comprising administering a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof and a subtherapeutic dose of anti-PD-1 antibody to a subject. In certain embodiments, the subject is human. In certain embodiments, the anti-PD-1 antibody is a human sequence monoclonal antibody.

In one embodiment, the present invention provides a method for treating a hyperproliferative disease (e.g., cancer), comprising administering a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof and an anti-PD-L1 antibody to a subject. In further embodiments, a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a salt thereof is administered at a subtherapeutic dose, the anti-PD-L1 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof and a subtherapeutic dose of anti-PD-L1 antibody to a subject. In certain embodiments, the subject is human. In certain embodiments, the anti-PD-L1 antibody is a human sequence monoclonal antibody.

In one embodiment, the present invention provides a method for treating a hyperproliferative disease (e.g., cancer), comprising administering a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof and an anti-PD-L1 antibody to a subject. In further embodiments, a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a salt thereof is administered at a subtherapeutic dose, the anti-PD-L1 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof and a subtherapeutic dose of anti-PD-L antibody to a subject. In certain embodiments, the subject is human. In certain embodiments, the anti-PD-L1 antibody is a human sequence monoclonal antibody.

In certain embodiments, the combination of therapeutic agents discussed herein can be administered concurrently as a single composition in a pharmaceutically acceptable carrier, or concurrently as separate compositions each in a pharmaceutically acceptable carrier. In another embodiment, the combination of therapeutic agents can be administered sequentially. For example, an anti-CTLA-4 antibody and a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof can be administered sequentially, such as anti-CTLA-4 antibody being administered first and a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof second, or a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof being administered first and anti-CTLA-4 antibody second. Additionally or alternatively, an anti-PD-1 antibody and a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof can be administered sequentially, such as anti-PD-1 antibody being administered first and a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof second, or a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof being administered first and anti-PD-1 antibody second. Additionally or alternatively, an anti-PD-L1 antibody and a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof can be administered sequentially, such as anti-PD-L1 antibody being administered first and a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof second, or a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof being administered first and anti-PD-L1 antibody second.

In certain embodiments, the combination of therapeutic agents discussed herein can be administered concurrently as a single composition in a pharmaceutically acceptable carrier, or concurrently as separate compositions each in a pharmaceutically acceptable carrier. In another embodiment, the combination of therapeutic agents can be administered sequentially. For example, an anti-CTLA-4 antibody and a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof can be administered sequentially, such as anti-CTLA-4 antibody being administered first and a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof second, or a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof being administered first and anti-CTLA-4 antibody second. Additionally or alternatively, an anti-PD-1 antibody and a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof can be administered sequentially, such as anti-PD-1 antibody being administered first and a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof second, or a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof being administered first and anti-PD-1 antibody second. Additionally or alternatively, an anti-PD-L1 antibody and a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof can be administered sequentially, such as anti-PD-L1 antibody being administered first and a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof second, or a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof being administered first and anti-PD-L1 antibody second.

Furthermore, if more than one dose of the combination therapy is administered sequentially, the order of the sequential administration can be reversed or kept in the same order at each time point of administration, sequential administrations can be combined with concurrent administrations, or any combination thereof.

Optionally, the combination of a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof can be further combined with an immunogenic agent, such as cancerous cells, purified tumor antigens (including recombinant proteins, peptides, and carbohydrate molecules), cells, and cells transfected with genes encoding immune stimulating cytokines.

Optionally, the combination of a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof can be further combined with an immunogenic agent, such as cancerous cells, purified tumor antigens (including recombinant proteins, peptides, and carbohydrate molecules), cells, and cells transfected with genes encoding immune stimulating cytokines.

A compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof can also be further combined with standard cancer treatments. For example, a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof can be effectively combined with chemotherapeutic regimens. In these instances, it is possible to reduce the dose of other chemotherapeutic reagent administered with the combination of the instant disclosure. Other combination therapies with a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof include radiation, surgery, or hormone deprivation. Angiogenesis inhibitors can also be combined with a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof. Inhibition of angiogenesis leads to tumor cell death, which can be a source of tumor antigen fed into host antigen presentation pathways.

A compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof can also be further combined with standard cancer treatments. For example, a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof can be effectively combined with chemotherapeutic regimens. In these instances, it is possible to reduce the dose of other chemotherapeutic reagent administered with the combination of the instant disclosure. Other combination therapies with a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof include radiation, surgery, or hormone deprivation. Angiogenesis inhibitors can also be combined with a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof. Inhibition of angiogenesis leads to tumor cell death, which can be a source of tumor antigen fed into host antigen presentation pathways.

In another example, a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof can be used in conjunction with anti-neoplastic antibodies. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4, PD-1, PD-L1 or a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof. In an exemplary embodiment, a treatment of a hyperproliferative disease (e.g., a cancer tumor) can include an anti-cancer antibody in combination with a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a salt thereof and anti-CTLA-4 and/or anti-PD-1 and/or anti-PD-L1 antibodies, concurrently or sequentially or any combination thereof, which can potentiate anti-tumor immune responses by the host. Other antibodies that can be used to activate host immune responsiveness can be further used in combination with a compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a salt thereof.

In another example, a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof can be used in conjunction with anti-neoplastic antibodies. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4, PD-1, PD-L1 or a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof. In an exemplary embodiment, a treatment of a hyperproliferative disease (e.g., a cancer tumor) can include an anti-cancer antibody in combination with a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a salt thereof and anti-CTLA-4 and/or anti-PD-1 and/or anti-PD-L1 antibodies, concurrently or sequentially or any combination thereof, which can potentiate anti-tumor immune responses by the host. Other antibodies that can be used to activate host immune responsiveness can be further used in combination with a compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) or a salt thereof.

In yet further embodiments, the compound of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof is administered in combination with another BET inhibitor.

In yet further embodiments, the compound of Formula (I), (Ia), (Ib), (Ib-1 to Ib-4), (Ic), (Ic-1 to Ic-6), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5), or a salt thereof is administered in combination with another BET inhibitor.

Dosing and Method of Administration

The dose of a compound administered to an individual (such as a human) may vary with the particular compound or salt thereof, the method of administration, and the particular disease, such as type and stage of cancer, being treated. In some embodiments, the amount of the compound or salt thereof is a therapeutically effective amount.

The effective amount of the compound may in one aspect be a dose of between about 0.01 and about 100 mg/kg. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein or a salt thereof and a pharmaceutically acceptable excipient.

A compound or composition of the invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

The compounds provided herein or a salt thereof may be administered to an individual via various routes, including, e.g., intravenous, intramuscular, subcutaneous, oral and transdermal. A compound provided herein can be administered frequently at low doses, known as "metronomic therapy," or as part of a maintenance therapy using compound alone or in combination with one or more additional drugs. Metronomic therapy or maintenance therapy can comprise administration of a compound provided herein in cycles. Metronomic therapy or maintenance therapy can comprise intra-tumoral administration of a compound provided herein.

In one aspect, the invention provides a method of treating cancer in an individual by parenterally administering to the individual (e.g., a human) an effective amount of a compound or salt thereof. In some embodiments, the route of administration is intravenous, intra-arterial, intramuscular, or subcutaneous. In some embodiments, the route of administration is oral. In still other embodiments, the route of administration is transdermal.

The invention also provides compositions (including pharmaceutical compositions) as described herein for the use in treating, preventing, and/or delaying the onset and/or development of cancer and other methods described herein. In certain embodiments, the composition comprises a pharmaceutical formulation which is present in a unit dosage form.

Also provided are articles of manufacture comprising a compound of the disclosure or a salt thereof, composition, and unit dosages described herein in suitable packaging for use in the methods described herein. Suitable packaging is known in the art and includes, for example, vials, vessels, ampules, bottles, jars, flexible packaging and the like. An article of manufacture may further be sterilized and/or sealed kits.

The present disclosure further provides kits for carrying out the methods of the invention, which comprises one or more compounds described herein or a composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for the treatment of cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or subunit doses. For example, kits may be provided that contain sufficient dosages of a compound as disclosed herein and/or a second pharmaceutically active compound useful for a disease detailed herein (e.g., hypertension) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention can be further understood by reference to the following examples, which are provided by way of illustration and are not meant to be limiting Certain representative embodiments are provided below:

Embodiment 1

A compound of Formula (I):

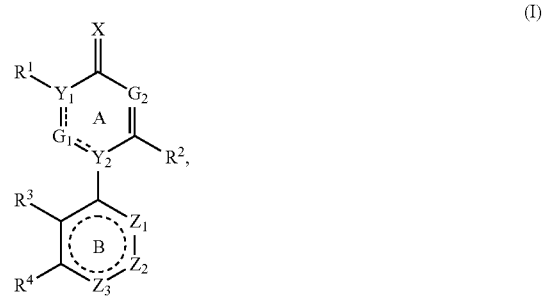

(I)

or a tautomer or isomer thereof, or a pharmaceutically acceptable salt of any of the foregoing,
wherein:
X is O or S;
$Y_1$ is N or C;
$Y_2$ is N or C, provided that
 (1) at least one of $Y_1$ and $Y_2$ is N, and
 (2) when both $Y_1$ and $Y_2$ are N, then $G_1$ is $CR^a$ or $CHR^a$;
each ==== is independently a single bond or a double bond, provided that
 (i) when $Y_2$ is N and $Y_1$ is C, the ==== between $G_1$ and $Y_1$ is a double bond and the ==== between $G_1$ and $Y_2$ is a single bond,
 (ii) when $Y_1$ is N and $Y_2$ is C, the ==== between $G_1$ and $Y_1$ is a single bond and the ==== between $G_1$ and $Y_2$ is a double bond, and
 (iii) when both $Y_1$ and $Y_2$ are N, the ==== between $G_1$ and $Y_1$ and the ==== between $G_1$ and $Y_2$ are both single bonds;
$R^1$ is hydrogen, $C_1$-$C_4$ alkyl, $C_3$-$C_6$ cycloalkyl, —$(CH_2)_mN(R^f)W_3R^g$ or —$(CH_2)_mW_3R^g$, provided that when $Y_1$ is N and $G_1$ is N, $R^1$ is $C_1$-$C_4$ alkyl, $C_3$-$C_6$ cycloalkyl, —$(CH_2)_mN(R^f)W_3R^g$ or —$(CH_2)_mW_3R^g$;
$G_1$ is $CR^a$, $CHR^a$ or N, wherein:
 $R^a$ is hydrogen, halogen or $C_1$-$C_4$ alkyl;
$G_2$ is $CR^b$ or N, wherein:
 $R^b$ is hydrogen, halogen, cyano, $C_1$-$C_4$ alkyl, $C_3$-$C_6$ cycloalkyl, 3- to 6-membered heterocyclyl, $C_1$-$C_4$ haloalkyl, $C_1$-$C_4$ alkoxy, $C_1$-$C_4$ haloalkoxy, —$OR^{10}$, —$NR^{10}R^{11}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$;
$R^2$ is hydrogen, halogen, cyano, $C_1$-$C_4$ alkyl, $C_3$-$C_6$ cycloalkyl, 3- to 6-membered heterocyclyl, $C_1$-$C_4$ haloalkyl, $C_1$-$C_4$ alkoxy, $C_1$-$C_4$ haloalkoxy, —$OR^{10}$, —$NR^{10}R^{11}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$,
or $R^b$ and $R^2$ are taken together with the atoms to which they are attached to form a 5- or 6-membered C ring, which is optionally substituted with $R^5$, wherein each $R^5$ is independently hydrogen, halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^0$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is optionally substituted with $R^{12}$;

indicates a saturated, partially unsaturated or fully unsaturated ring;

$Z_1$ is CH—$W_1$—$R^c$, C—$W_1$—$R^c$, C=O, $NR^c$, or N, wherein:

each $W_1$ is independently —O—, —$NR^{w1}$—, or a bond, wherein:

$R^{w1}$ is hydrogen, $C_3$-$C_6$ cycloalkyl or $C_1$-$C_4$ alkyl optionally substituted with oxo, —OH or halogen, and each $R^c$ is independently hydrogen, halogen, cyano, $C_1$-$C_4$ alkyl, $C_3$-$C_6$ cycloalkyl, $C_1$-$C_4$ haloalkyl, 3- to 6-membered heterocyclyl, $C_6$-$C_{14}$ aryl, or 5- to 6-membered heteroaryl, wherein $C_3$-$C_6$ cycloalkyl, 3- to 6-membered heterocyclyl, $C_6$-$C_{14}$ aryl, and 5- to 6-membered heteroaryl of $R^c$ are independently optionally substituted with $R^{c1}$, wherein each $R^{c1}$ is independently halogen, $C_1$-$C_4$ alkyl, $C_3$-$C_6$ cycloalkyl, 3- to 6-membered heterocyclyl, cyano, oxo, $C_1$-$C_4$ alkoxy, $C_1$-$C_4$ haloalkoxy, $C_1$-$C_4$ haloalkyl, —$OR^{10}$, —$NR^{10}R^{11}$, —C(O)$NR^{10}R^{11}$, —$NR^{10}$C(O)$R^{11}$, —S(O)$_2R^{10}$, —$NR^{10}$S(O)$_2R^{11}$ or —S(O)$_2NR^{10}R^{11}$;

$Z_2$ is CH—$W_2$—$R^d$, C—$W_2$—$R^d$, C=O, $NR^d$, or N, wherein:

each $W_2$ is independently —O—, —$NR^{w2}$—, or a bond, wherein:

$R^{w2}$ is hydrogen, $C_3$-$C_6$ cycloalkyl or $C_1$-$C_4$ alkyl optionally substituted with oxo, OH or halogen, and each $R^{c1}$ is independently hydrogen or $C_1$-$C_4$ alkyl;

or $R^c$ and $R^{c1}$ are taken together with the atoms to which they are attached to form a 5- or 6-membered D ring, which is optionally substituted with $R^6$, wherein each $R^6$ is independently hydrogen halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —C(O)$NR^{10}R^{11}$, —$NR^{10}$C(O)$R^{11}$, —S(O)$_2R^{10}$, —$NR^{10}$S(O)$_2R^{11}$ or —S(O)$_2NR^{10}R^{11}$, each of which is optionally substituted with $R^{12}$;

$Z_3$ is CH—$R^e$, C—$R^e$, C=O, $NR^e$, or N, wherein:

each $R^e$ is independently hydrogen, halogen, cyano or $C_1$-$C_4$ alkyl, provided that (1) when $Z_2$ is C=O, $Z_3$ is $NR^e$, (2) when $Z_3$ is C=O, $Z_2$ is $NR^d$, and (3) no more than two of $Z_1$, $Z_2$ and $Z_3$ are N;

$R^3$ and $R^4$ are each independently hydrogen, halogen, cyano, $C_1$-$C_4$ haloalkyl, $C_1$-$C_4$ alkoxy, $C_1$-$C_4$ haloalkoxy, —$OR^{13}$, —$NR^{13}R^{14}$, —C(O)$NR^{13}R^{14}$, —$NR^{13}$C(O)$R^{14}$, —S(O)$_2R^{13}$, —$NR^{13}$S(O)$_2R^{14}$, —S(O)$_2NR^{13}R^{14}$, —(CH$_2$)$_m$N(R$^f$)W$_3$R$^g$, —(CH$_2$)$_m$W$_3$R$^g$, or $C_1$-$C_4$ alkyl optionally substituted with halogen, oxo, —CN or —OH, provided that (a) when $Y_2$ is C, at least one of $R^1$, $R^3$ and $R^4$ is —(CH$_2$)$_m$N(R$^f$)W$_3$R$^g$ or —(CH$_2$)$_m$W$_3$R$^g$, and (b) when $Y_2$ is N, (i) at least one of $R^1$, $R^3$ and $R^4$ is —(CH$_2$)$_m$N(R$^f$)W$_3$R$^g$ or —(CH$_2$)$_m$W$_3$R$^g$, or (ii) $R^4$ is halogen, cyano, $C_1$-$C_4$ haloalkyl, $C_1$-$C_4$ alkoxy, $C_1$-$C_4$ haloalkoxy, —$OR^{13}$, —$NR^{13}R^{14}$, —C(O)$NR^{13}R^{14}$, —$NR^{13}$C(O)$R^{14}$, —S(O)$_2R^{13}$, —$NR^{13}$S(O)$_2R^{14}$, —S(O)$_2NR^{13}R^{14}$, —(CH$_2$)$_m$N(R$^f$)W$_3$R$^g$, —(CH$_2$)$_m$W$_3$R$^g$, or $C_1$-$C_4$ alkyl optionally substituted with halogen, oxo, —CN or —OH, and $Z^1$ is CH—$W_1$—$R^c$ or C—$W_1$—$R^c$, wherein $W_1$ is —O— or —$NR^{w1}$— and $R^c$ is $C_3$-$C_6$ cycloalkyl, 3- to 6-membered heterocyclyl, phenyl, or 5- to 6-membered heteroaryl, each of which is optionally substituted with $R^d$;

each m is independently 0, 1, 2, 3, or 4;

$R^f$ is hydrogen, $C_1$-$C_4$ alkyl, or $C_3$-$C_6$ cycloalkyl;

$W_3$ is —C(O)— or —S(O)$_2$—;

$R^g$ is —C$R^{g1}$=CH $R^{g2}$ or —C≡C$R^{g2}$, wherein $R^{g1}$ and $R^{g2}$ are independently hydrogen, cyano or $C_1$-$C_4$ alkyl optionally substituted with —OH, —OCH$_3$, —NH$_2$, —NHCH$_3$ or —N(CH$_3$)$_2$, or for $R^4$, when $R^4$ is —(CH$_2$)$_m$N(R$^f$)W$_3$R$^g$ and m is 0, the N, R$^f$, W$_3$ and R$^g$ in —N(R$^f$)W$_3$R$^g$ may be taken together to form a 5- or 6-membered ring having at least one double bond and optionally substituted with R, wherein each R is independently $C_1$-$C_4$ alkyl, oxo, halogen or CN; $R^{10}$ and $R^{11}$ are independently hydrogen, $C_1$-$C_4$ alkenyl, $C_3$-$C_6$ cycloalkyl, $C_3$-$C_6$ heterocyclyl, ($C_1$-$C_3$alkylene)$C_3$-$C_6$ cycloalkyl, ($C_1$-$C_3$ alkylene)$C_3$-$C_6$ heterocyclyl, C(O)$R^{12}$, or $C_1$-$C_4$ alkyl optionally substituted with halogen, oxo, —CN, —OH, —$NR^{13}R^{14}$ or —C(O)$NR^{13}R^{14}$ or $R^{10}$ and $R^{11}$ are taken together with the atoms to which they are attached to form a $C_3$-$C_6$ heterocyclyl ring optionally substituted with halogen, oxo, —CN, —OH, or $C_1$-$C_4$ alkyl optionally substituted with halogen, oxo, —CN, or —OH;

$R^{12}$ is $C_3$-$C_6$ cycloalkyl, $C_3$-$C_6$ heterocyclyl or $C_1$-$C_4$ alkyl optionally substituted with halogen, oxo, —CN, —OH, —$NR^{13}R^{14}$ or —$NR^{13}$C(O)$R^{14}$;

$R^{13}$ and $R^{14}$ are independently hydrogen, $C_3$-$C_6$ cycloalkyl, $C_3$-$C_6$ heterocyclyl or $C_1$-$C_4$ alkyl optionally substituted with halogen, oxo, CN, or OH, or $R^{13}$ and $R^{14}$ are taken together with the atoms to which they are attached to form a $C_3$-$C_6$ heterocyclyl ring optionally substituted with halogen, oxo, CN, OH, or $C_1$-$C_4$ alkyl optionally substituted with halogen, oxo, CN, or OH.

Embodiment 2

The compound of embodiment 1, or a tautomer or isomer thereof, or a pharmaceutically acceptable salt of any of the foregoing, wherein the compound is of Formula (Ia):

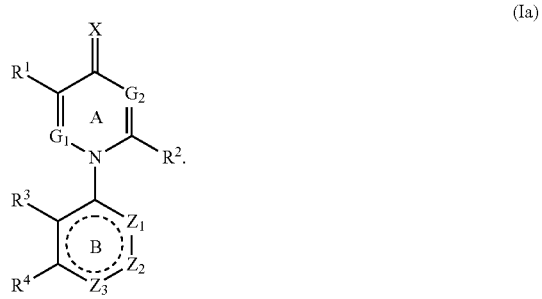

(Ia)

Embodiment 3

The compound of embodiment 1, or a tautomer or isomer thereof, or a pharmaceutically acceptable salt of any of the foregoing, wherein the compound is of Formula (Ib):

317

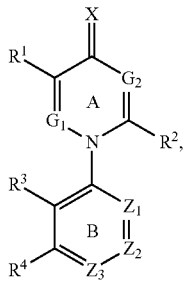

(Ib)

wherein:

$Z_1$ is C—$W_1$—$R^c$ or N;

$Z_2$ is C—$W_2$—$R^d$ or N;

$Z_3$ is C—$R^e$ or N.

Embodiment 4

The compound of embodiment 1, or a tautomer or isomer thereof, or a pharmaceutically acceptable salt of any of the foregoing, wherein the compound is of a structure selected from the group consisting of:

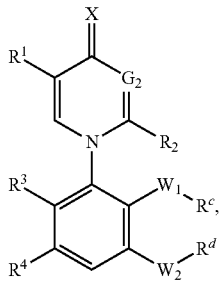

(Ib-1)

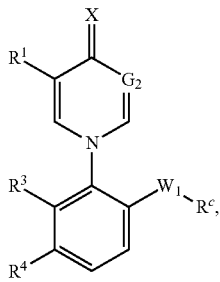

(Ib-2)

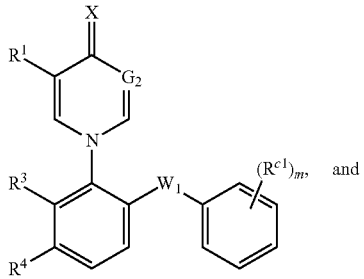 and (Ib-3)

318

-continued

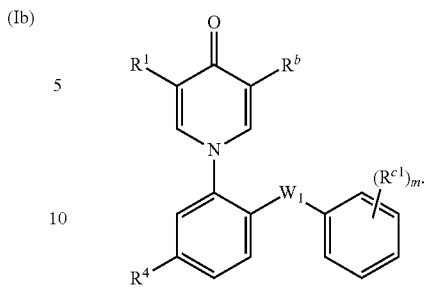

(Ib-4)

Embodiment 5

The compound of embodiment 1, or a tautomer or isomer thereof, or a pharmaceutically acceptable salt of any of the foregoing, wherein the compound is of Formula (Ic):

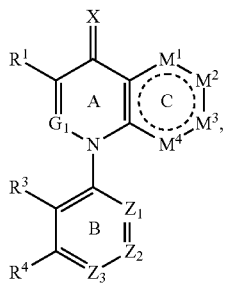

(Ic)

wherein:

$Z_1$ is C—$W_1$—$R^c$ or N;

$Z_2$ is C—$W_2$—$R^d$ or N;

$Z_3$ is C—$R^e$ or N;

$M^1$ is O, S, N, $NR^{1a}$, $CR^{1a}$, or $CR^{1a}R^{1b}$;

$M^2$ is N, $NR^{2a}$, $CR^{2a}$, or $CR^{2a}R^{2b}$;

$M^3$ is N, $NR^{3a}$, $CR^{3a}$, $CR^{3a}R^{3b}$ or absent;

$M^4$ is O, S, N, $NR^4a$, $CR^{4a}$, or $CR^{4a}R^{4b}$, provided that (1) no more than three of $M^1$, $M^2$, $M^3$ and $M^4$ are N or N substituted by $R^{1a}$, $R^{2a}$, $R^{3a}$, or $R^{4a}$, and (2) if $M^3$ is absent, at least one of $M^1$ and $M^4$ is not O or S;

$R^{1a}$, $R^{1b}$, $R^{2a}$, $R^{2b}$, $R^{3a}$, $R^{3b}$, $R^{4a}$, and $R^{4b}$ are each independently hydrogen, halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, $OR^{10}$, $NR^{10}R^{11}$, C(O)$OR^{10}$, C(O)$NR^{10}R^{11}$, $NR^{10}$C(O)$R^{11}$, S(O)$_2R^{10}$, $NR^{10}$S(O)$_2R^{11}$ or S(O)$_2NR^{10}R^{11}$.

Embodiment 6

The compound of embodiment 5, or a tautomer or isomer thereof, or a pharmaceutically acceptable salt of any of the foregoing, wherein the compound is of a structure selected from the group consisting of:

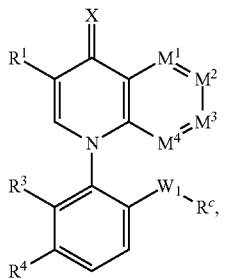 (Ic-1)

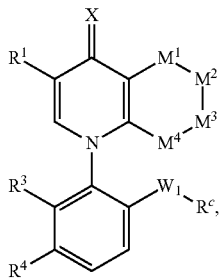 (Ic-2)

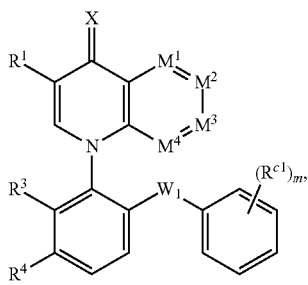 (Ic-3)

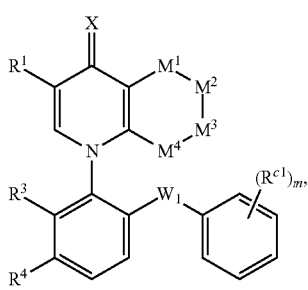 (Ic-4)

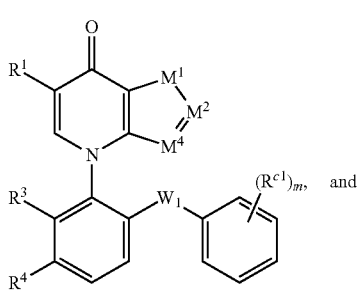 (Ic-5) and

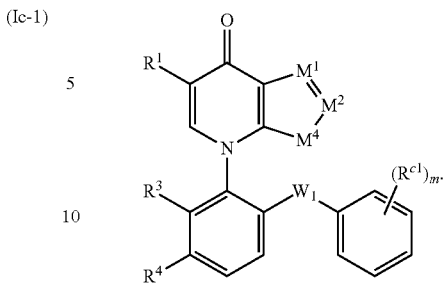 (Ic-6)

Embodiment 7

The compound of embodiment 1, or a tautomer or isomer thereof, or a pharmaceutically acceptable salt of any of the foregoing, wherein the compound is of Formula (II):

 (II)

Embodiment 8

The compound of embodiment 1, or a tautomer or isomer thereof, or a pharmaceutically acceptable salt of any of the foregoing, wherein the compound is of Formula (III):

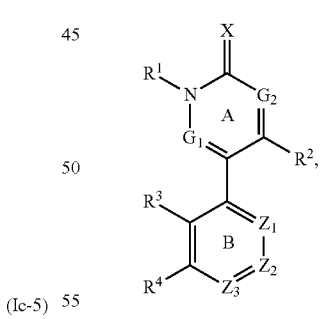 (III)

wherein:
$Z_1$ is C—$W_1$—$R^c$ or N;
$Z_2$ is C—$W_2$—$R^d$ or N;
$Z_3$ is C—$R^e$ or N.

Embodiment 9

The compound of embodiment 1, or a tautomer or isomer thereof, or a pharmaceutically acceptable salt of any of the foregoing, wherein the compound is of Formula (IV):

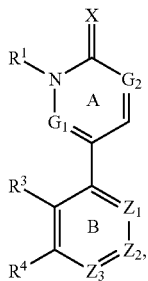
(IV)
wherein:
$Z_1$ is C—$W_1$—$R^c$ or N;
$Z_2$ is C—$W_2$—$R^d$ or N;
$Z_3$ is C—$R^e$ or N.
Embodiment 10
The compound of embodiment 1, or a tautomer or isomer thereof, or a pharmaceutically acceptable salt of any of the foregoing, wherein the compound is of a structure selected from the group consisting of:
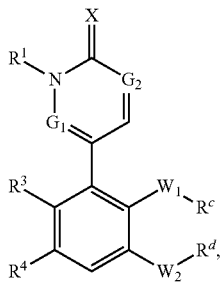
(IV-a)
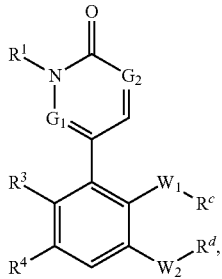
(IV-b)
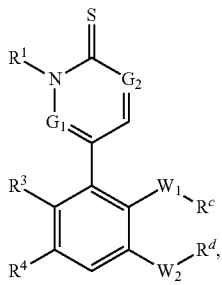
(IV-c)
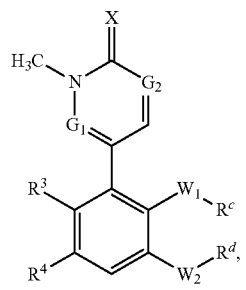
(IV-d)
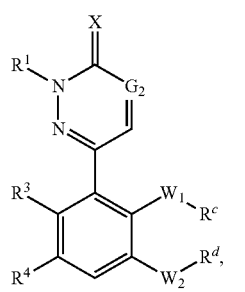
(IV-e)
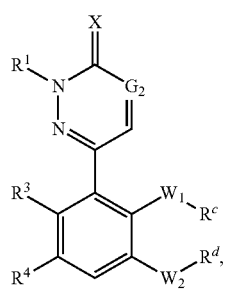
(IV-f)
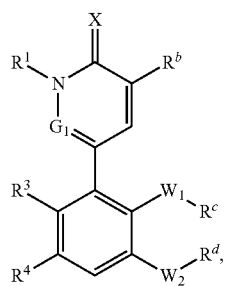
(IV-g)
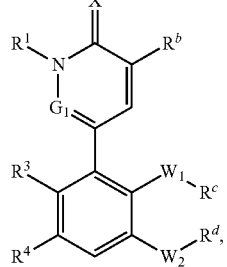
(IV-h)

-continued
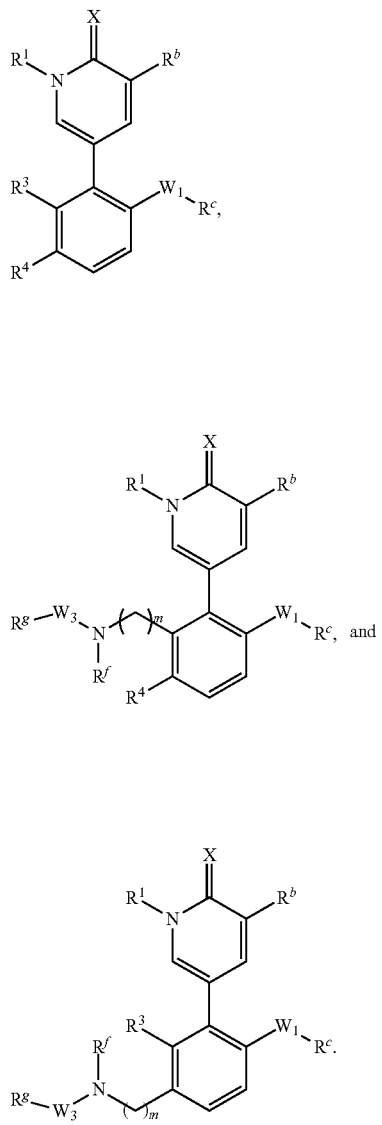
(IV-i)
(IV-j)
(IV-k)
Embodiment 11
The compound of embodiment 1, or a tautomer or isomer thereof, or a pharmaceutically acceptable salt of any of the foregoing, wherein the compound is of a structure selected from the group consisting of:
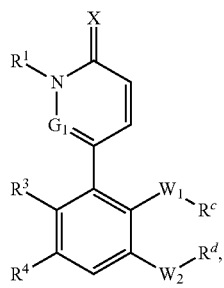
(IVg-1)
-continued
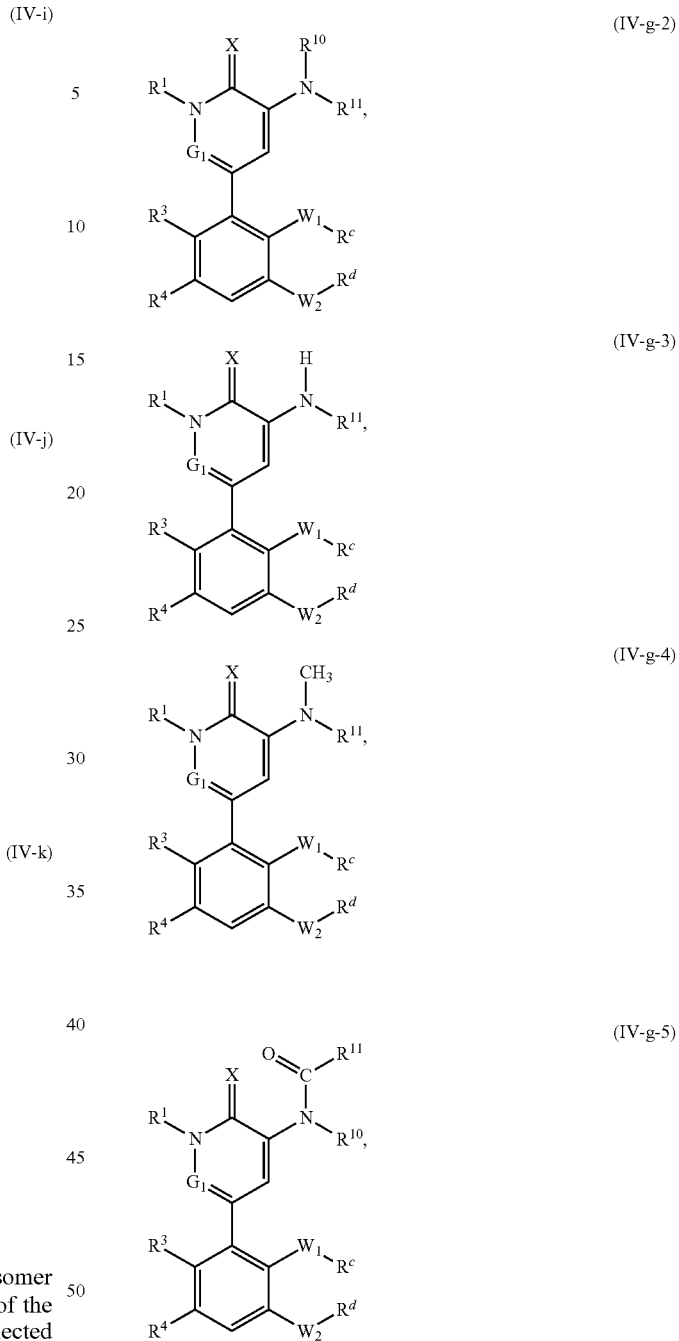
(IV-g-2)
(IV-g-3)
(IV-g-4)
(IV-g-5)
(IV-g-6)

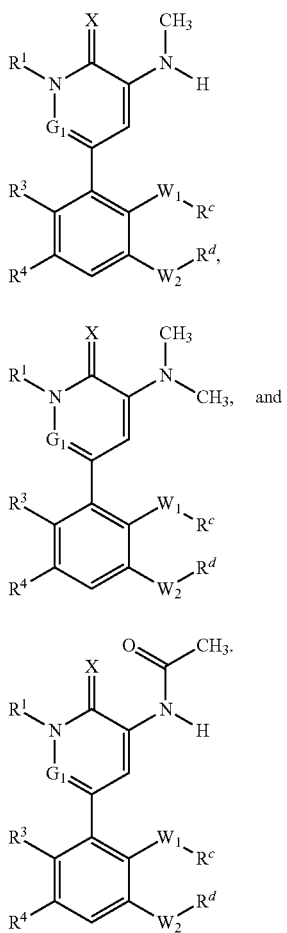
(IV-g-7)
(IV-g-8) and
(IV-g-9)
Embodiment 12
The compound of embodiment 1, or a tautomer or isomer thereof, or a pharmaceutically acceptable salt of any of the foregoing, wherein the compound is of a structure selected from the group consisting of:
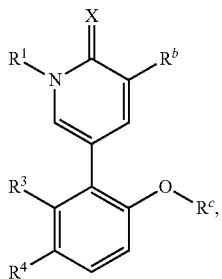
(IV-i-1)
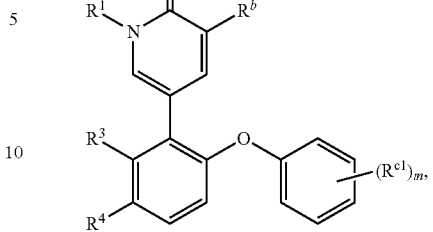
(IV-i-2)
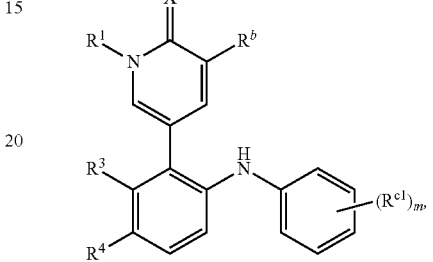
(IV-i-3)
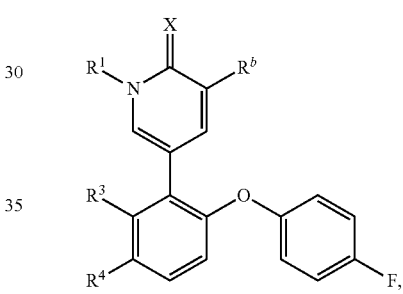
(IV-i-4)
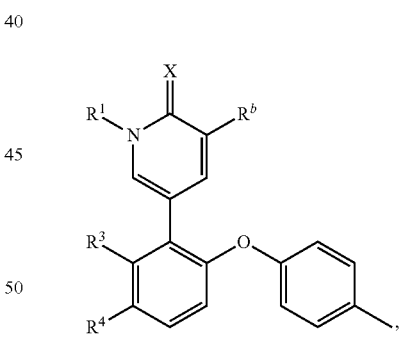
(IV-i-5)
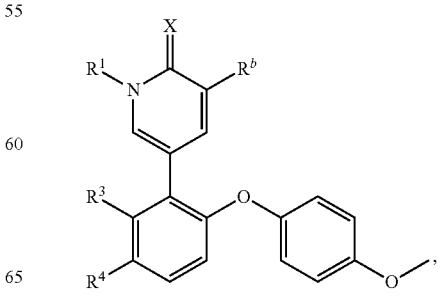
(IV-i-6)

-continued
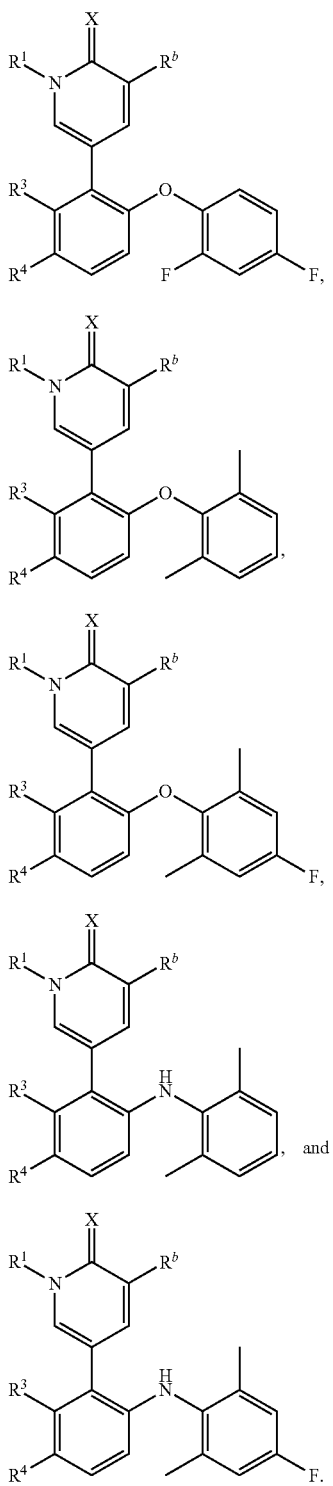
(IV-i-7)
(IV-i-8)
(IV-i-9)
(IV-i-10)
(IV-i-11)
Embodiment 13
The compound of embodiment 1, or a tautomer or isomer thereof, or a pharmaceutically acceptable salt of any of the foregoing, wherein the compound is of a structure selected from the group consisting of:
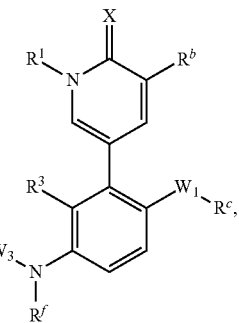
(IV-k-1)
(IV-k-2)
(IV-k-3)
(IV-k-4)
(IV-k-5)

329

-continued

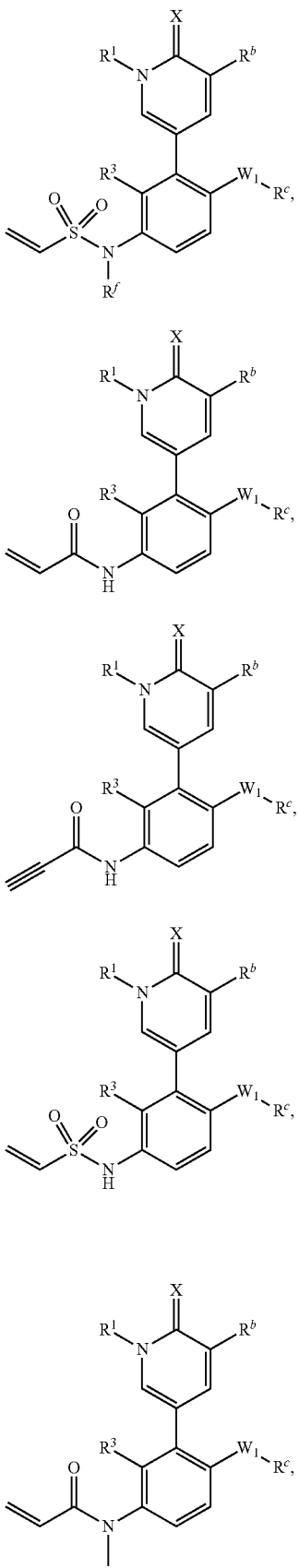

(IV-k-6)
(IV-k-7)
(IV-k-8)
(IV-k-9)
(IV-k-10)

330

-continued

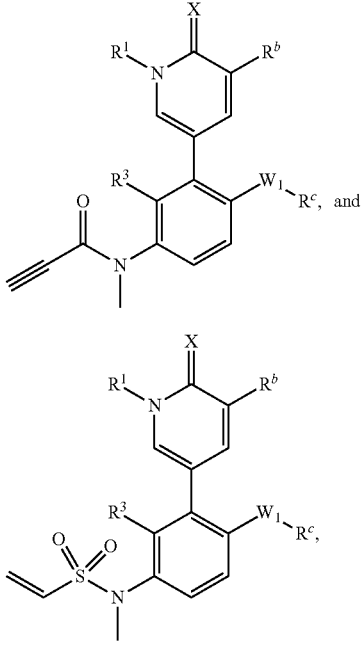

(IV-k-11)
(IV-k-12)

Embodiment 14

The compound of embodiment 1, or a tautomer or isomer thereof, or a pharmaceutically acceptable salt of any of the foregoing, wherein the compound is of Formula (V):

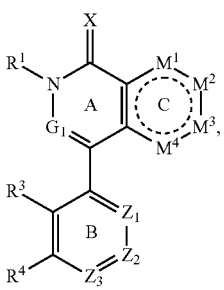

(V)

wherein:
$Z_1$ is C—$W_1$—$R^c$ or N;
$Z_2$ is C—$W_2$—$R^d$ or N;
$Z_3$ is C—$R^e$ or N;
$M^1$ is O, S, N, $NR^{1a}$, $CR^{1a}$, or $CR^{1a}R^{1b}$;
$M^2$ is N, $NR^{2a}$, $CR^{2a}$, or $CR^{2a}R^{2b}$;
$M^3$ is N, $NR^{3a}$, $CR^{3a}$, $CR^{3a}R^{3b}$ or absent;
$M^4$ is O, S, N, $NR^{4a}$, $CR^{4a}$, or $CR^{4a}R^{4b}$, provided that
  (1) no more than three of $M^1$, $M^2$, $M^3$ and $M^4$ are N or N substituted by $R^{1a}$, $R^{2a}$, $R^{3a}$, or $R^{4a}$, and
  (2) if $M^3$ is absent, at least one of $M^1$ and $M^4$ is not O or S;
$R^{1a}$, $R^{1b}$, $R^{2a}$, $R^{2b}$, $R^{3a}$, $R^{3b}$, $R^{4a}$, and $R^{4b}$ are each independently hydrogen, halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, $OR^{10}$, $NR^{10}R^{11}$, $C(O)OR^{10}$, $C(O)NR^{10}R^{11}$, $NR^{10}C(O)R^1$, $S(O)_2R^{10}$, $NR^{10}S(O)_2R^{11}$ or $S(O)_2NR^{10}R^{11}$.

Embodiment 15

The compound of embodiment 14, or a tautomer or isomer thereof, or a pharmaceutically acceptable salt of any of the foregoing, wherein the compound is of a structure selected from the group consisting of:

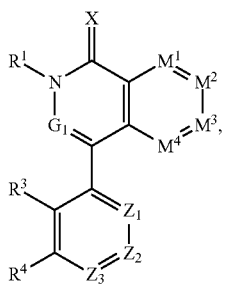
(Va)

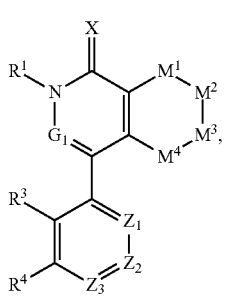
(Vb)

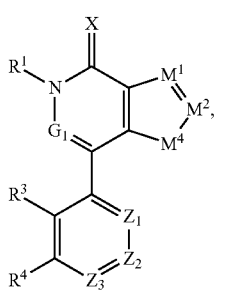
(Vc)

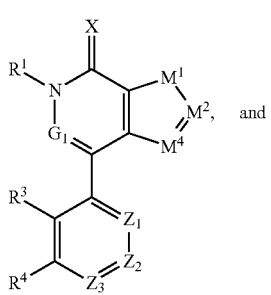
(Vd) and

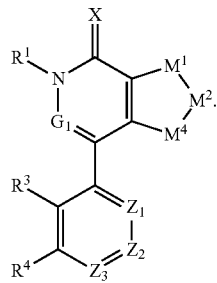
(Ve)

Embodiment 16

The compound of embodiment 14, or a tautomer or isomer thereof, or a pharmaceutically acceptable salt of any of the foregoing, wherein the compound is of a structure selected from the group consisting of:

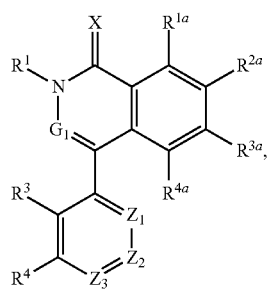
(Va-1)

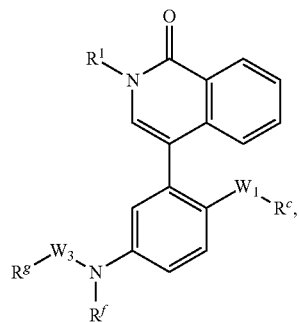
(Va-2)

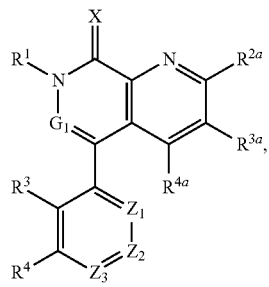
(Va-3)

333
-continued
(Va-4)
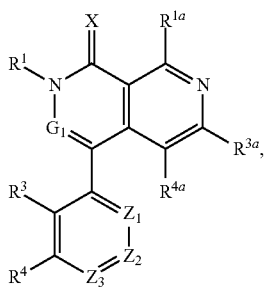
(Va-5)
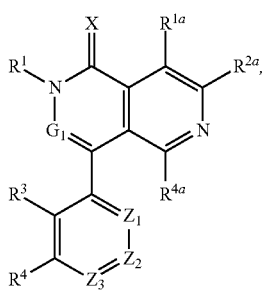
(Va-6)
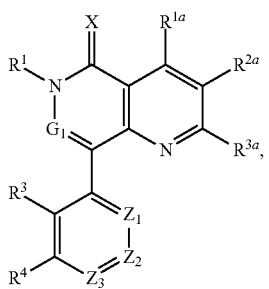
(Va-7)
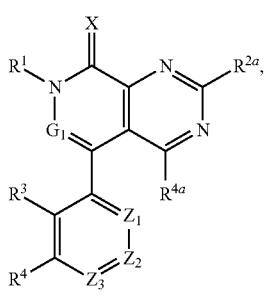
(Va-8)
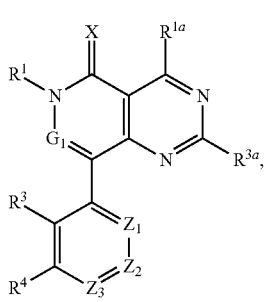
334
-continued
(Va-9)
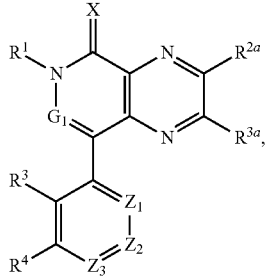
(Va-10)

(Va-11)
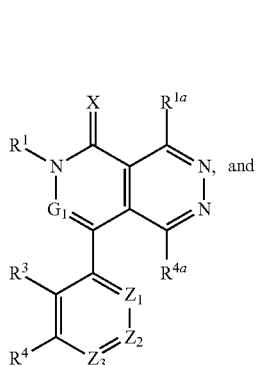
(Va-12)
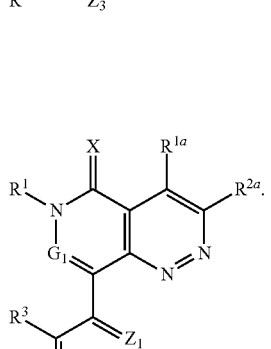
Embodiment 17
The compound of embodiment 14, or a tautomer or isomer thereof, or a pharmaceutically acceptable salt of any of the foregoing, wherein the compound is of a structure selected from the group consisting of:

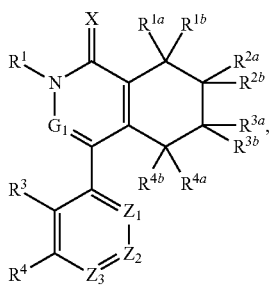 (Vb-1)
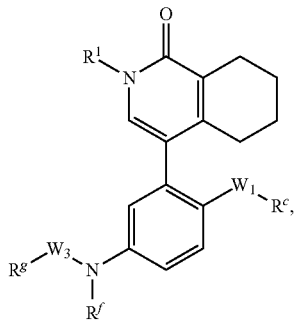 (Vb-2)
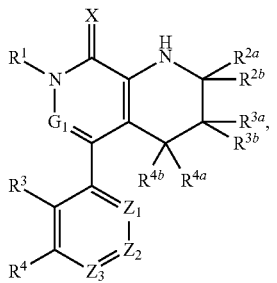 (Vb-3)
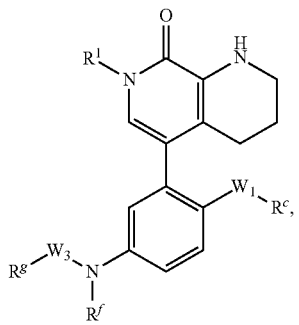 (Vb-4)
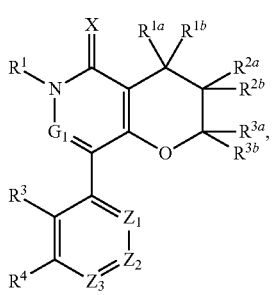 (Vb-5)
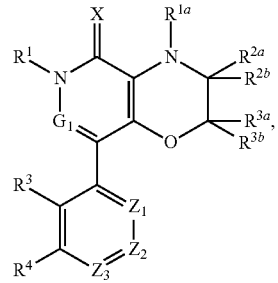 (Vb-6)
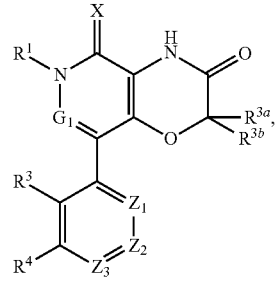 (Vb-7)
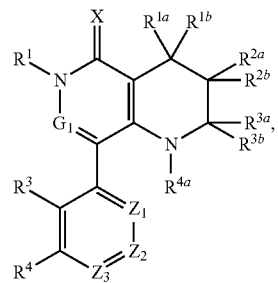 (Vb-8)
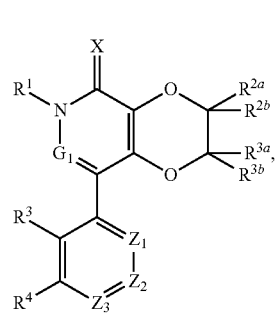 (Vb-9)
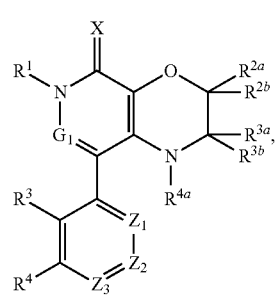 (Vb-10)

337
-continued
(Vb-11)
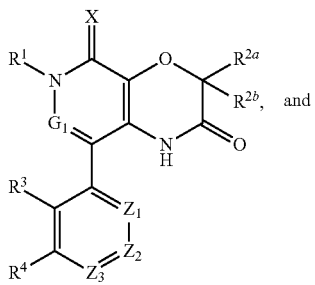
(Vb-12)
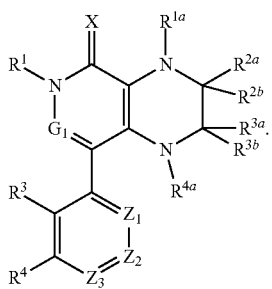
Embodiment 18
The compound of embodiment 14, or a tautomer or isomer thereof, or a pharmaceutically acceptable salt of any of the foregoing, wherein the compound is of a structure selected from the group consisting of:
(Vc-1)
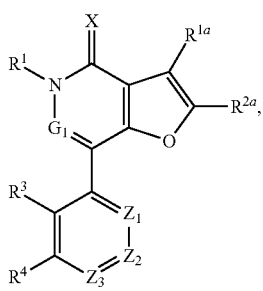
(Vc-2)
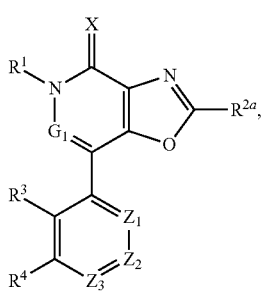
338
-continued
(Vc-3)
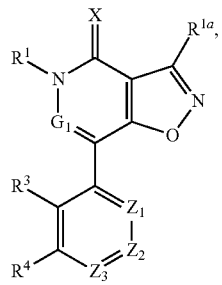
(Vc-4)
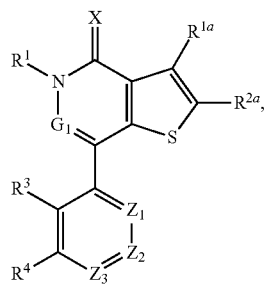
(Vc-5)
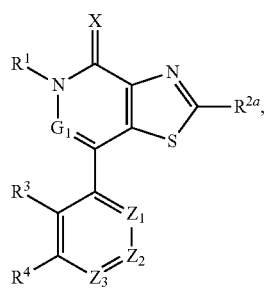
(Vc-6)
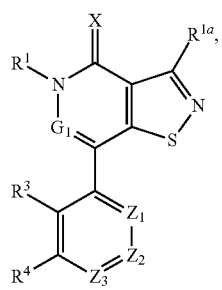
(Vc-7)
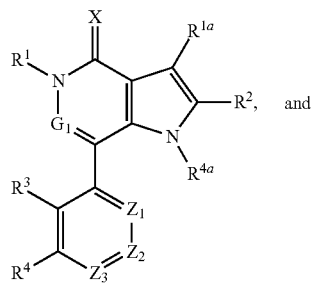

(Vc-8)
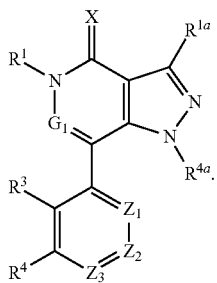
Embodiment 19
The compound of embodiment 14, or a tautomer or isomer thereof, or a pharmaceutically acceptable salt of any of the foregoing, wherein the compound is of a structure selected from the group consisting of:
(Vc-1')
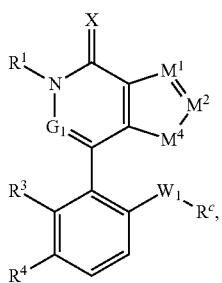
(Vc-2')
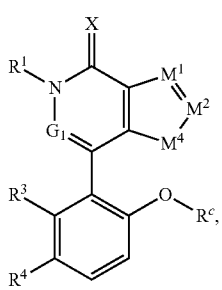
(Vc-3')
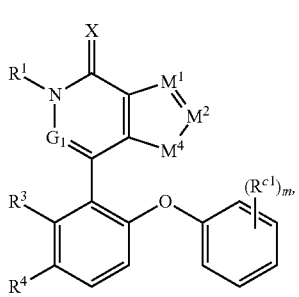
(Vc-4')
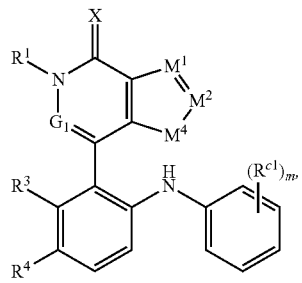
(Vc-5')
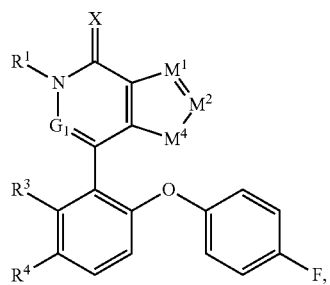
(Vc-6')
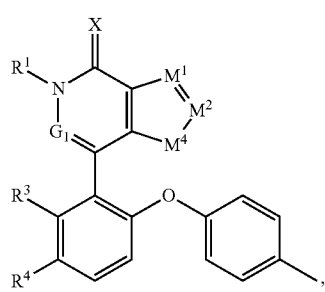
(Vc-7')
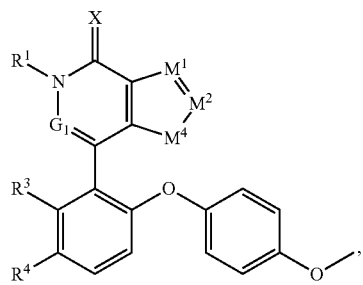
(Vc-8')
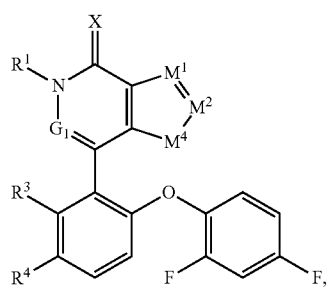

-continued
(Vc-9′)
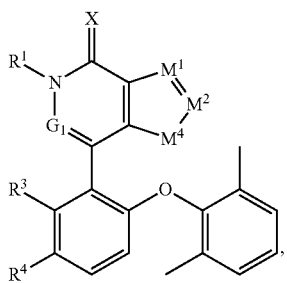
(Vc-10′)
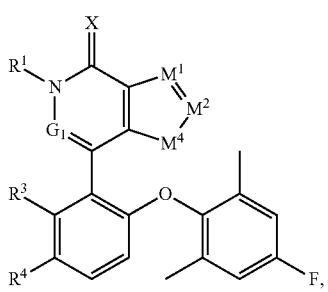
(Vc-11′)
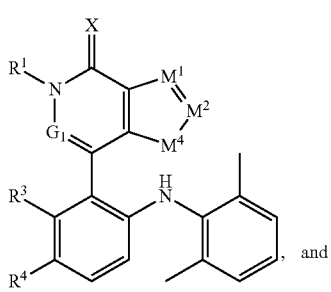, and
(Vc-12′)
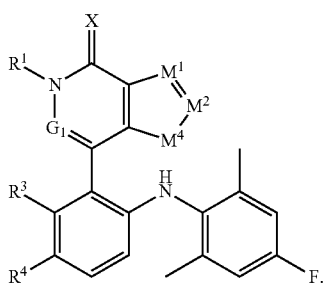.
Embodiment 20
The compound of embodiment 14, or a tautomer or isomer thereof, or a pharmaceutically acceptable salt of any of the foregoing, wherein the compound is of a structure selected from the group consisting of:
(Vd-1)
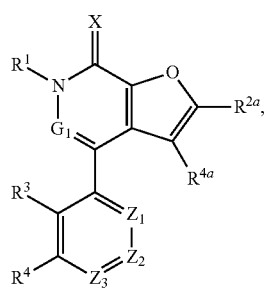
(Vd-2)
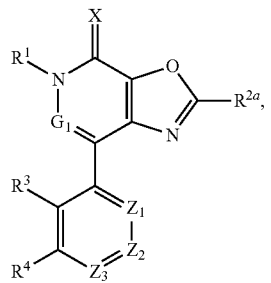
(Vd-3)
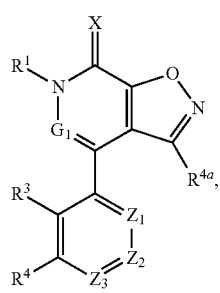,
(Vd-4)
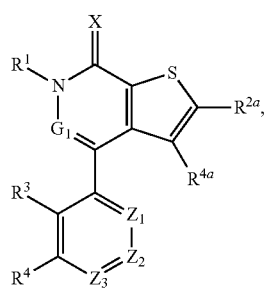
(Vd-5)
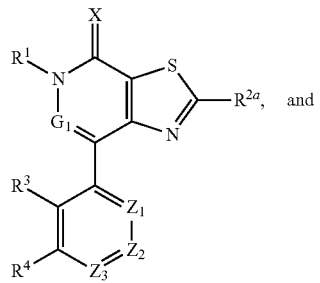, and (Vd-6)
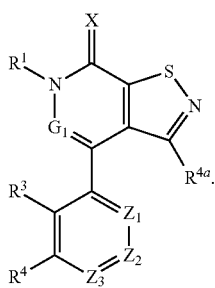
Embodiment 21
The compound of embodiment 14, or a tautomer or isomer thereof, or a pharmaceutically acceptable salt of any of the foregoing, wherein the compound is of a structure selected from the group consisting of:
(Vd-1')
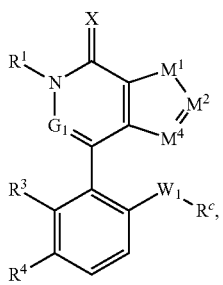
(Vd-2')
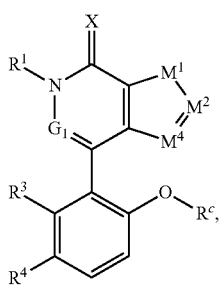
(Vd-3')
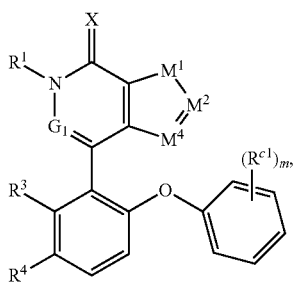
(Vd-4')
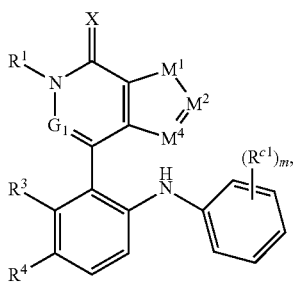
(Vd-5')
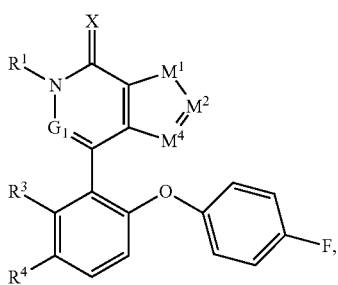
(Vd-6')
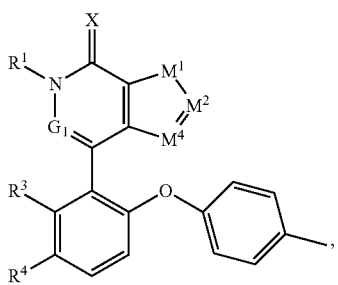
(Vd-7')
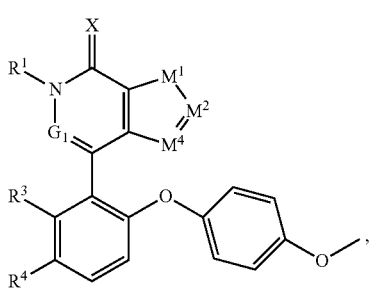
(Vd-8')
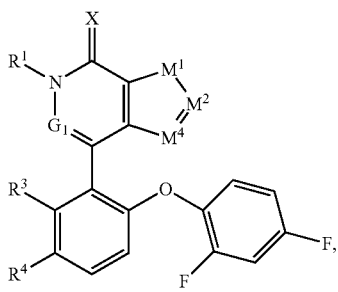

-continued

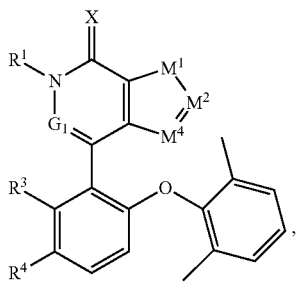
(Vd-9′)

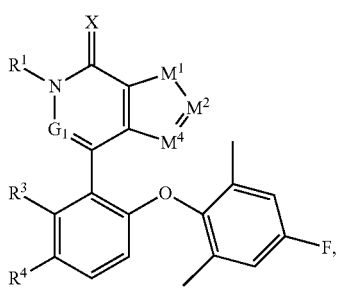
(Vd-10′)

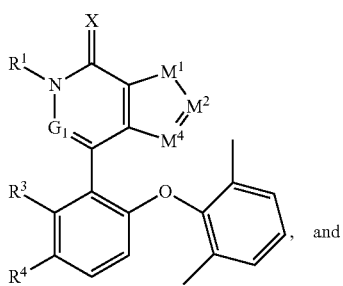
(Vd-11′)

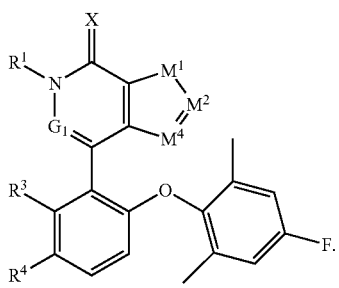
(Vd-12′)

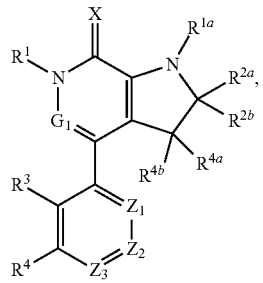
(Ve-1)

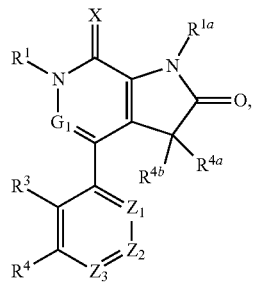
(Ve-2)

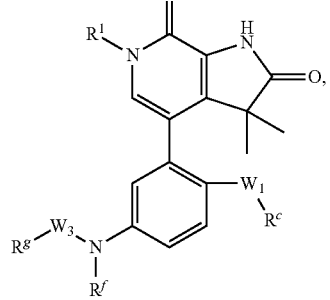
(Ve-3)

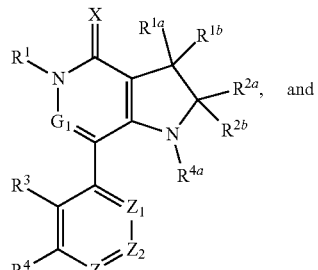
(Ve-4)

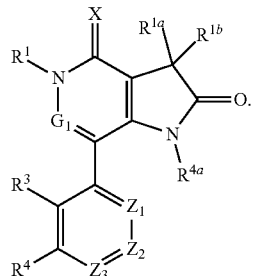
(Ve-5)

Embodiment 22

The compound of embodiment 14, or a tautomer or isomer thereof, or a pharmaceutically acceptable salt of any of the foregoing, wherein the compound is of a structure selected from the group consisting of:

Embodiment 23

The compound of embodiment 1, or a pharmaceutically acceptable salt thereof, wherein the compound is selected from the group consisting of the compounds in Table 1.

Embodiment 24

A pharmaceutical composition comprising the compound of any one of embodiments 1 to 23, or a tautomer or isomer thereof, or a pharmaceutically acceptable salt of any of the foregoing, and a pharmaceutically acceptable carrier.

Embodiment 25

A method of treating disease mediated by bromodomain and extraterminal domain (BET) in an individual in need thereof comprising administering to the individual a therapeutically effective amount of the compound of any one of embodiments 1 to 23, or a tautomer or isomer thereof, or a pharmaceutically acceptable salt of any of the foregoing.

Embodiment 26

A method of treating cancer in an individual in need thereof comprising administering to the individual a therapeutically effective amount of the compound of any one of embodiments 1 to 23, or a tautomer or isomer thereof, or a pharmaceutically acceptable salt of any of the foregoing.

Embodiment 27

A method of inhibiting bromodomain and extraterminal domain (BET) in a cell, comprising administering the compound of any one of embodiments 1 to 23, or a tautomer or isomer thereof, or a pharmaceutically acceptable salt of any of the foregoing, to the cells.

Embodiment 28

Use of the compound of any one of embodiments 1 to 23, or a tautomer or isomer thereof, or a pharmaceutically acceptable salt of any of the foregoing, in the manufacture of a medicament for treatment of a disease mediated by bromodomain and extraterminal domain (BET).

Embodiment 29

A kit comprising the compound of any one of embodiments 1 to 23, or a tautomer or isomer thereof, or a pharmaceutically acceptable salt of any of the foregoing.

General Information

1H NMR spectra was recorded on a Bruker Avance 400 MHz spectrometer. Spectra are referenced to residual chloroform ($\delta$ 7.26, $^1$H), DMSO ($\delta$ 2.54, $^1$H) or methanol ($\delta$ 3.34, $^1$H) unless otherwise noted. Chemical shifts are reported in ppm ($\delta$); multiplicities are indicated by s (singlet), d (doublet), t (triplet), q (quartet), quint (quintet), sext (sextet), m (multiplet) and br (broad). Coupling constants, J, are reported in Hertz. Analytical HPLC was performed on an Agilent 1200 HPLC with an Agilent G1365D diode array detector using an Agilent Eclipse XDB-C18 (4.6×150 mm, 5 µm) column. Analytical LCMS was performed on an Agilent 6410 triple quadrupole LCMS. Commercially available reagents and solvents were used as received unless otherwise indicated.

Synthetic Examples

Example S-1: Synthesis of 4-(4-fluorophenoxy)-3-(4,4,5,5-tetramethyl-1,3,2-dioxaborolan-2-yl)aniline: Intermediate 1 (General Procedure 1)

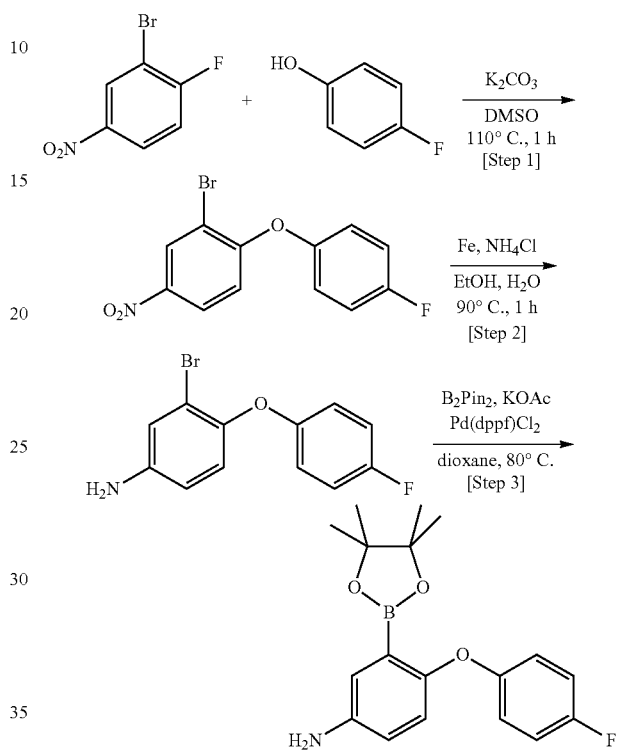

Step 1: Synthesis of 2-bromo-1-(4-fluorophenoxy)-4-nitrobenzene

To a solution of 2-bromo-1-fluoro-4-nitrobenzene (3.0 g, 13.6 mmol) in DMSO (20 mL) was added 4-fluorophenol (1.9 g, 16.4 mmol) and $Cs_2CO_3$ (8.9 g, 27.2 mmol). The resulting mixture was stirred at 110° C. for 1 h. TLC analysis indicated the reaction was complete. The reaction mixture was diluted with water and extracted with EtOAc. The combined organic layers were washed with brine, dried over anhydrous $Na_2SO_4$, filtered and concentrated under reduced pressure to give 2-bromo-1-(4-fluorophenoxy)-4-nitrobenzene (4.5 g, crude) as a brown solid, which was used directly without purification.

Step 2: Synthesis of 3-bromo-4-(4-fluorophenoxy)aniline

To a solution of 2-bromo-1-(4-fluorophenoxy)-4-nitrobenzene (4.5 g, crude) in ethanol (25 mL), a solution of $NH_4Cl$ (7.7 g, 144.0 mmol) in water (25 mL) was added followed by addition of iron powder (6.4 g, 115.0 mmol). The reaction mixture was stirred at 90° C. for 1 h. TLC analysis indicated the reaction was complete. The reaction mixture was filtered through a pad of Celite. The filtrate was diluted with water and extracted with EtOAc. The combined organic layers were washed with brine, dried over anhydrous $Na_2SO_4$, filtered and concentrated under reduced pressure to give 3-bromo-4-(4-fluorophenoxy)aniline (4.5 g, crude) as a brown oil, which was used directly without purification.

Step 3: Synthesis of 4-(4-fluorophenoxy)-3-(4,4,5,5-tetramethyl-1,3,2-dioxaborolan-2-yl)aniline To a solution of 3-bromo-4-(4-fluorophenoxy)aniline (4.5 g, crude) in dioxane (50 mL) was added B$_2$Pin$_2$ (4.9 g, 19.1 mmol), KOAc (4.7 g, 48.0 mmol) and Pd(dppf)Cl$_2$ (1.2 g, 1.6 mmol). The reaction mixture was degassed and purged with N$_2$. Then the mixture was stirred at overnight at 80° C. TLC analysis indicated the reaction was complete. The mixture was concentrated under reduced pressure. The residue was purified by column chromatography on silica gel to give Intermediate 1 (1.5 g, 33% for 3 steps) as a brown oil.

LCMS: 330.2 [M+1]$^+$, RT=2.71 min; HPLC: 98%, RT=5.2 min $^1$H NMR (400 MHz, DMSO-d$_6$): δ 7.09-7.01 (m, 2H), 6.93 (d, J=2.8 Hz, 1H), 6.77-6.65 (m, 4H), 5.04 (br s, 2H), 1.05 (s, 12H).

Example S-2: Synthesis of 3-(4,4,5,5-tetramethyl-1,3,2-dioxaborolan-2-yl)-4-(p-tolyloxy)aniline: Intermediate 2

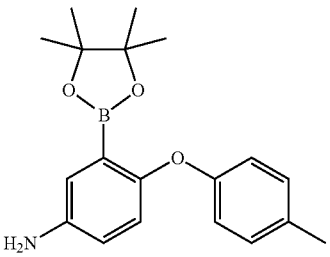 [SMILES: Cc1ccc(Oc2ccc(N)cc2B2OC(C)(C)C(C)(C)O2)cc1]

Intermediate 2 (1 g, 22% for 3 steps) was prepared following General Procedure 1 and using p-cresol (1.8 g, 16.4 mmol).

LCMS: 326.3 [M+1]+, RT=2.70 min; HPLC: 99%, RT=5.2 min $^1$H NMR (400 MHz, DMSO-d$_6$) δ 7.02 (d, J=8.4 Hz, 2H), 6.90 (d, J=1.2 Hz, 1H), 6.71-6.65 (m, 2H), 6.62-6.56 (m, 2H), 4.98 (br s, 2H), 2.20 (s, 3H), 1.05 (s, 12H).

Example S-3: Synthesis of 4-(4-methoxyphenoxy)-3-(4,4,5,5-tetramethyl-1,3,2-dioxaborolan-2-yl)aniline: Intermediate 3

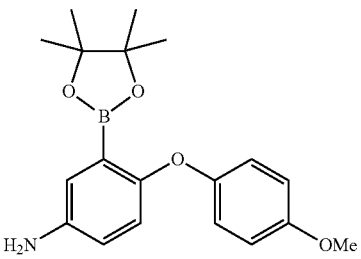 [SMILES: COc1ccc(Oc2ccc(N)cc2B2OC(C)(C)C(C)(C)O2)cc1]

Intermediate 3 (1 g, 21% for 3 steps) was prepared following General Procedure 1 and using 4-methoxyphenol (2.1 g, 16.4 mmol).

LCMS: 342.3 [M+1]+, RT=2.45 min; HPLC: 96%, RT=4.8 min $^1$H NMR (400 MHz, DMSO-d$_6$): δ 6.90 (t, J=1.4 Hz, 1H), 6.84-6.77 (m, 2H), 6.70-6.62 (m, 4H), 4.96 (br s, 2H), 3.67 (s, 3H), 1.08 (s, 12H).

Example S-4: Synthesis of 4-(2, 4-difluorophenoxy)-3-(4, 4, 5, 5-tetramethyl-1, 3, 2-dioxaborolan-2-yl)aniline: Intermediate 4

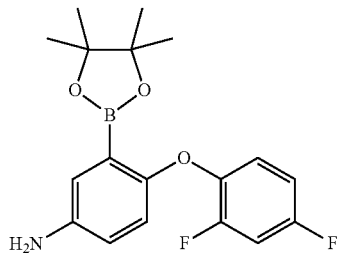 [SMILES: CC1(C)OB(c2cc(N)ccc2Oc2ccc(F)cc2F)OC1(C)C]

Intermediate 4 (36.2 g, 35% for 3 steps) was prepared following General Procedure 1 and using 2,4-difluorophenol (46 g, 350 mmol).

LCMS: 348.1 [M+1]+, RT=4.4 min; HPLC: 99%, RT=5.5 min $^1$H NMR (400 MHz, DMSO-d$_6$): δ 7.31 (m, 1H), 6.94 (d, J=2.8 Hz, 1H), 6.87 (m, 1H), 6.78 (d, J=8.4 Hz, 1H), 6.71 (dd, J=8.4, 2.8 Hz, 1H), 6.50 (m, 1H), 5.09 (br s, 2H), 1.06 (s, 12H).

Example S-5: Synthesis of 2-(2-fluoro-5-nitrophenyl)-4,4,5,5-tetramethyl-1,3,2-dioxaborolane: Intermediate 5

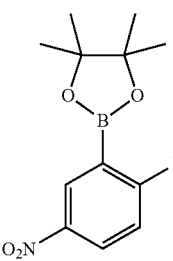

Intermediate 5 (35 g, 57%) was prepared following General Procedure 1, Step 3 and using 2-bromo-1-fluoro-4-nitrobenzene (50 g, 227 mmol).

HPLC: 99%, RT=3.56 min;

$^1$H NMR (400 MHz, CDCl$_3$): δ 8.66-8.64 (m, J=8.4 Hz, 1H), 8.35-8.30 (m, 1H), 7.20-7.16 (m, J=8.4 Hz, 1H), 1.39 (s, 12H).

Example S-6. Synthesis of tert-butyl (5-bromo-1-methyl-2-oxo-1, 2-dihydropyridin-3-yl) (methyl) carbamate: Intermediate 6

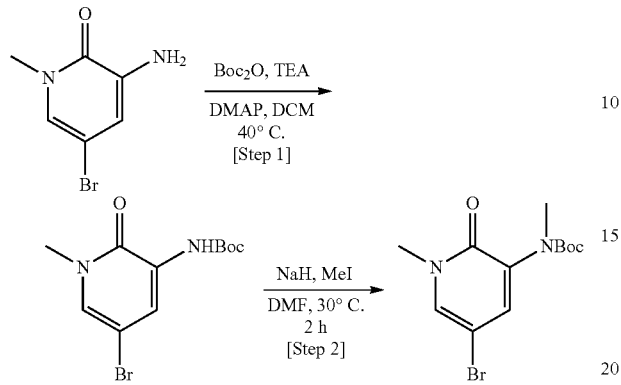

Step 1: Synthesis of tert-butyl (5-bromo-1-methyl-2-oxo-1, 2-dihydropyridin-3-yl) carbamate To a solution of 3-amino-5-bromo-1-methylpyridin-2 (1H)-one (4.7 g, 23.1 mmol) in DCM (300 mL) was added TEA (7.0 g, 69.3 mmol), DMAP (1.4 g, 11.5 mmol) and Boc$_2$O (7.6 g, 34.8 mmol) at 0° C. Then the mixture was stirred at room temperature overnight. TLC analysis indicated the reaction was complete. The mixture was concentrated under reduced pressure. The residue was purified by column chromatography on silica gel to give tert-butyl (5-bromo-1-methyl-2-oxo-1, 2-dihydropyridin-3-yl) carbamate (4.0 g, 57%) as an off-white solid.

Step 2: Synthesis of tert-butyl (5-bromo-1-methyl-2-oxo-1, 2-dihydropyridin-3-yl) (methyl) carbamate To a solution of tert-butyl (5-bromo-1-methyl-2-oxo-1, 2-dihydropyridin-3-yl) carbamate (4.0 g, 13.2 mmol) in DMF (60 mL) was added NaH (1.6 g, 40.0 mmol) in portions at 0° C. The mixture was stirred at 0° C. for 30 min. Then MeI (5.6 g, 40.0 mmol) was added dropwise at 0° C. The reaction mixture was stirred at 30° C. for 2 h. TLC analysis indicated the reaction was complete. The mixture was quenched with saturated aqueous NH$_4$Cl, extracted with EtOAc, washed with brine, dried over anhydrous Na$_2$SO$_4$, filtered and concentrated under reduced pressure to give Intermediate 6 (5.0 g, crude) as an off-white solid, which was used into next step directly.

Example S-7: Synthesis of 5-(5-amino-2-(2, 4-difluorophenoxy) phenyl)-1-methyl-3-(methylamino) pyridin-2(1H)-one: (General Procedure 2) Intermediate 7

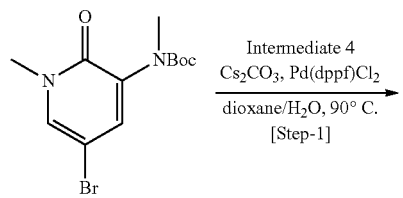

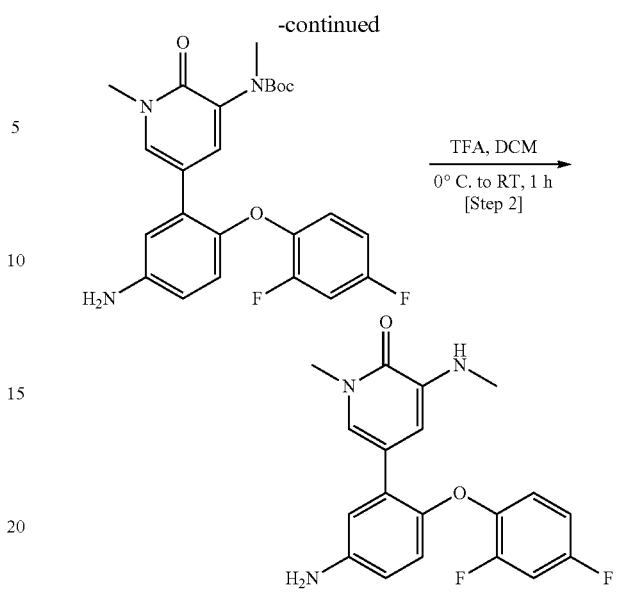

Step 1: Synthesis of tert-butyl (5-(5-amino-2-(2, 4-difluorophenoxy) phenyl)-1-methyl-2-oxo-1, 2-dihydropyridin-3-yl)(methyl)carbamate To a stirred solution of tert-butyl 5-bromo-1-methyl-2-oxo-1,2-dihydropyridin-3-yl(methyl)carbamate (4 g, 12.61 mmol) in 1,4-Dioxane (30 mL)-H$_2$O (6 mL) was added Intermediate 4 (4.81 g, 13.87 mmol, 1.1 eq) and Cs$_2$CO$_3$ (12.3 g, 37.83 mmol, 3 eq) followed by addition of Pd(dppf) Cl$_2$ (0.92 g, 1.26 mmol, 0.1 eq) at RT. The reaction mixture was heated at 100° C. for 16 h and monitored by TLC. The reaction was complete after 16 h and the mixture was diluted with water (500 mL) and extracted with EtOAc (500 mL×2). The combined organic layers were washed with water (250 mL), brine (200 mL) dried over anhydrous Na$_2$SO$_4$, filtered and concentrated under reduced pressure to afford a crude material which was purified by column chromatography—to afford tert-butyl 5-(5-amino-2-(2,4-difluorophenoxy)phenyl)-1-methyl-2-oxo-1,2-dihydropyridin-3-yl(methyl)carbamate (2.6 g, 45%) as a brown solid.

Step 2: Synthesis of 5-(5-amino-2-(2, 4-difluorophenoxy) phenyl)-1-methyl-3-(methylamino) pyridin-2(1H)-one To a solution of tert-butyl 5-(5-amino-2-(2,4-difluorophenoxy)phenyl)-1-methyl-2-oxo-1,2-dihydropyridin-3-yl (methyl)carbamate (2.5 g, 5.4 mmol) in DCM (20 mL) was added TFA (10 mL) at 0° C. Then the reaction mixture was stirred at RT for 1 h. TLC showed the reaction was complete. Then the mixture was concentrated under reduced pressure. The residue was dissolve in DCM, washed with saturated aqueous NaHCO$_3$, brine, dried over anhydrous Na$_2$SO$_4$, filtered and concentrated under reduced pressure to give Intermediate 7 (1.75 g, 90%) as an off-white solid.

LCMS: 358.2 [M+1]+, RT=2.45 min; HPLC: 96%, RT=4.4 min $^1$H NMR (400 MHz, DMSO-d$_6$): δ 7.31 (m, 1H), 6.99 (d, J=2.0 Hz, 1H), 6.94-6.87 (m, 1H), 6.80 (d, J=8.4 Hz, 1H), 6.76-6.70 (m, 1H), 6.69-6.66 (m, 1H), 6.57 (dd, J=8.8, 2.7 Hz, 1H), 6.19 (d, J=2.0 Hz, 1H), 5.52 (br s, 1H), 5.26 (br s, 2H), 3.44 (s, 3H), 2.57 (s, 3H).

Example S-8: Synthesis of N-(4-(2,4-difluorophenoxy)-3-(1-methyl-5-(methylamino)-6-oxo-1,6-dihydropyridin-3-yl)phenyl)acrylamide: (General Procedure 3) Compound 1

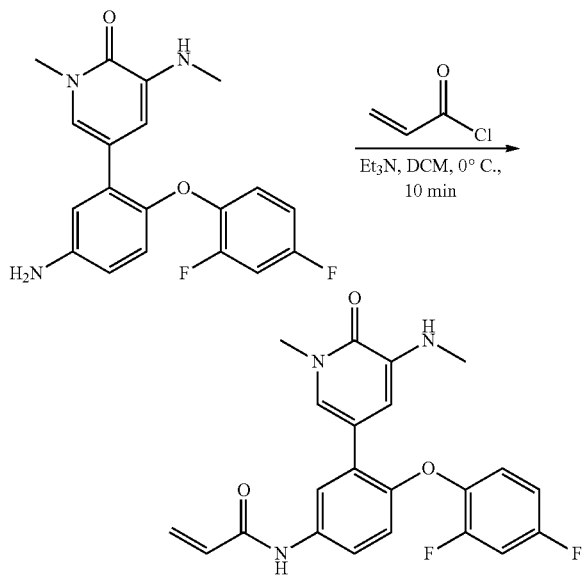

To a stirred solution of Intermediate 7 (0.1 g, 0.28 mmol) in DCM (5 mL) was added triethylamine (28 mg, 0.28 mmol, 1 eq) at 0° C. followed by dropwise addition of acryloyl chloride (26 mg, 0.29 mmol, 1.05 eq) at 0° C. The reaction mixture was stirred at the same temperature and monitored by TLC. The reaction was complete after 10 min and the mixture was diluted with water (100 mL) and extracted with EtOAc (150 mL). The organic layer was washed with water (75 mL), brine (75 mL), dried over anhydrous $Na_2SO_4$, filtered and concentrated under reduced pressure to obtain a crude material which was purified by reversed-phase chromatography to afford Compound 1 (20 mg, 17%) as an off-white solid.

LCMS: 412 [M+1]$^+$ $^1$H NMR (400 MHz, DMSO-d$_6$): δ 7.79 (d, J=2.7 Hz, 1H), 7.56 (dd, J=8.8, 2.7 Hz, 1H), 7.08 (t, J=2.9 Hz, 1H), 7.04 (td, J=8.5, 4.3 Hz, 1H), 6.96 (d, J=8.8 Hz, 1H), 6.86 (pd, J=8.4, 7.9, 5.9 Hz, 2H), 6.51 (d, J=2.3 Hz, 1H), 6.49-6.32 (m, 2H), 5.79 (dd, J=9.3, 2.7 Hz, 1H), 3.59 (s, 3H), 2.78 (s, 3H).

Example S-9: Synthesis of N-(4-(2,4-difluorophenoxy)-3-(1-methyl-5-(methylamino)-6-oxo-1,6-dihydropyridin-3-yl)phenyl)propiolamide: (General Procedure 4) Compound 2

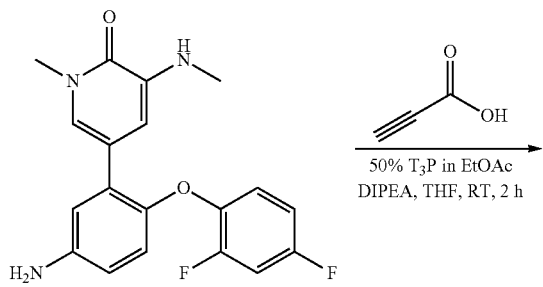

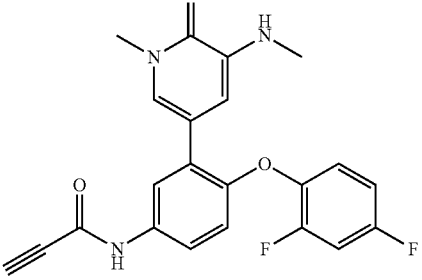

To a stirred solution of propiolic acid (19 mg, 0.28 mmol) in THF (5 mL) was added T$_3$P solution (50% in EtOAc, 266 mg, 0.84 mmol, 3 eq) at 0° C. and the mixture was stirred at 0° C. for 15 min. DIPEA (216 mg, 1.67 mmol, 6 eq) and Intermediate 7 (100 mg, 0.28 mmol) were then successively added to the mixture. The mixture was stirred at RT and monitored by TLC. The reaction was complete after 1 h and the mixture was diluted with water (100 mL) and extracted with EtOAc (150 mL). The organic layer was washed with saturated NaHCO$_3$ solution (100 mL), water (75 mL), brine (75 mL) dried over anhydrous Na$_2$SO$_4$, filtered and concentrated under reduced pressure to obtain a crude material which was purified by reversed-phase chromatography to afford Compound 2 (20 mg, 18%) as an off-white solid.

LCMS: 410 [M+1]$^+$ $^1$H NMR (400 MHz, DMSO-d$_6$): δ 7.69 (d, J=2.6 Hz, 1H), 7.53 (dd, J=8.8, 2.7 Hz, 1H), 7.10-7.00 (m, 2H), 6.94 (d, J=9.0 Hz, 1H), 6.87 (ddd, J=18.0, 9.1, 6.0 Hz, 2H), 6.49 (d, J=2.2 Hz, 1H), 3.76 (s, 1H), 3.59 (s, 3H), 2.78 (s, 3H).

Example S-10: Synthesis of N-(4-(2,4-difluorophenoxy)-3-(1-methyl-5-(methylamino)-6-oxo-1,6-dihydropyridin-3-yl)phenyl)ethenesulfonamide: (General Procedure 5) Compound 3

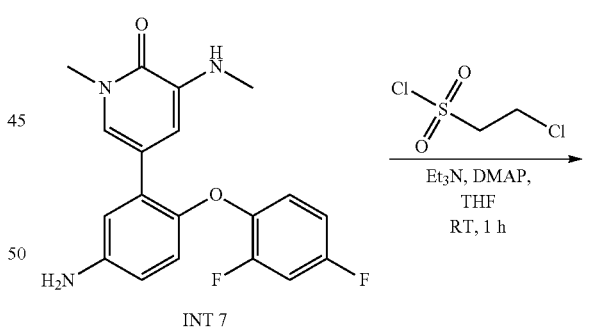

INT 7

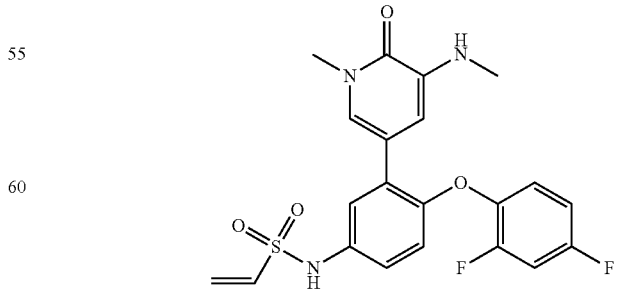

To a stirred solution of Intermediate 7 (0.1 g, 0.28 mmol) in THF (5 mL) was added DMAP (7 mg, 0.056 mmol, 0.2 eq) and triethylamine (84 mg, 0.84 mmol, 3 eq) at 0° C. followed by dropwise addition of 2-chloroethanesulfonyl chloride (50 mg, 0.307 mmol, 1.1 eq) at 0° C. The mixture was stirred at RT and monitored by TLC. The reaction was complete after 1 h and the mixture was diluted with water (100 mL) and extracted with EtOAc (150 mL×2). The combined organic layers were washed with saturated NaHCO$_3$ solution (100 mL), water (75 mL), brine (75 mL) dried over anhydrous Na$_2$SO$_4$, filtered and concentrated under reduced pressure to obtain a crude material which was purified by reversed-phase HPLC to afford Compound 3(15 mg, 12%) as an off-white solid.

LCMS: 448 [M+1]$^+$ $^1$H NMR (400 MHz, DMSO-d$_6$): δ 7.26 (d, J=2.7 Hz, 1H), 7.17 (dd, J=8.7, 2.7 Hz, 1H), 7.05 (dq, J=10.8, 4.0, 3.5 Hz, 2H), 6.91 (d, J=8.8 Hz, 1H), 6.89-6.80 (m, 2H), 6.71 (dd, J=16.5, 9.9 Hz, 1H), 6.46 (d, J=2.1 Hz, 1H), 6.17 (d, J=16.5 Hz, 1H), 6.00 (d, J=10.0 Hz, 1H), 3.58 (s, 3H), 2.77 (s, 3H).

Example S-11: Synthesis of N-(3-(1-methyl-5-(methylamino)-6-oxo-1,6-dihydropyridin-3-yl)-4-(p-tolyloxy)phenyl)ethenesulfonamide: (General Procedure 6) Compound 4

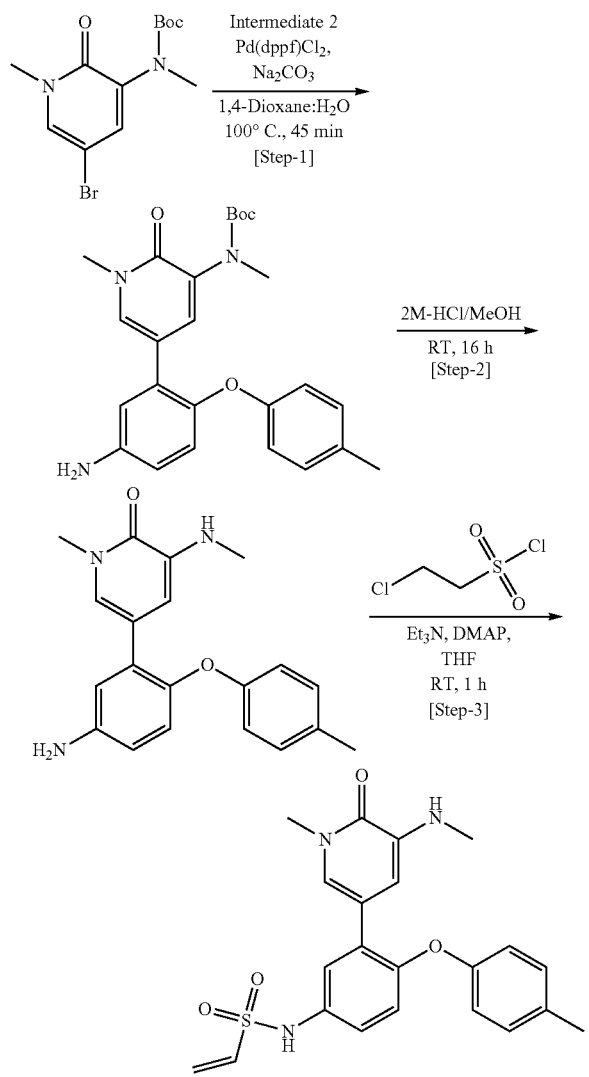

Step 1: Synthesis of tert-butyl 5-(5-amino-2-(p-tolyloxy)phenyl)-1-methyl-2-oxo-1,2-dihydropyridin-3-yl(methyl)carbamate To a stirred solution of Intermediate 6 (300 mg, 0.95 mmol) in 1,4-Dioxane (1 mL) was added Intermediate 2 (390 mg, 1.04 mmol, 1.1 eq) and Na$_2$CO$_3$ (300 mg, 2.83 mmol, 3 eq) dissolved in water (0.3 mL) followed by addition of Pd(dppf)Cl$_2$ (70 mg, 0.095 mmol, 0.1 eq) at RT. The reaction mixture was heated by microwave irradiation at 100° C. and monitored by TLC. The reaction was complete after 45 min and the mixture was diluted with water (200 mL) and extracted with EtOAc (300 mL). The organic layer was washed with water (100 mL), brine (150 mL) dried over anhydrous Na$_2$SO$_4$, filtered and concentrated under reduced pressure to afford a crude material which was purified by CombiFlash chromatography—to afford tert-butyl 5-(5-amino-2-(p-tolyloxy)phenyl)-1-methyl-2-oxo-1,2-dihydropyridin-3-yl(methyl)carbamate (330 mg, 80%) as a brown solid.

LCMS: 436 [M+1]$^+$

Step 2: Synthesis of 5-(5-amino-2-(p-tolyloxy)phenyl)-1-methyl-3-(methylamino)pyridin-2(1H)-one 2M Hydrochloric acid in MeOH (20 mL) was added into tert-butyl 5-(5-amino-2-(p-tolyloxy)phenyl)-1-methyl-2-oxo-1,2-dihydropyridin-3-yl(methyl)carbamate (0.33 g, 0.79 mmol) and the mixture was stirred at RT and monitored by TLC and LC-MS. The reaction was complete after 16 h and the mixture was quenched with saturated NaHCO$_3$ solution and extracted with EtOAc (250 mL×2). The combined organic layers were washed with saturated NaHCO$_3$ solution (100 mL), water (100 mL), brine (150 mL) dried over anhydrous Na$_2$SO$_4$, filtered and concentrated under reduced pressure to afford 5-(5-amino-2-(p-tolyloxy)phenyl)-1-methyl-3-(methylamino)pyridin-2(1H)-one (240 mg, 94%) as an off-white solid.

LCMS: 336 [M+1]$^+$ $^1$H NMR (400 MHz, DMSO-d$_6$): δ 7.08 (d, J=8.33 Hz, 2H), 7.04 (s, 1H), 6.81 (d, J=8.33 Hz, 1H), 6.67-6.75 (m, 3H), 6.60 (d, J=8.77 Hz, 1H), 6.24 (s, 1H), 5.51 (d, J=5.26 Hz, 1H), 5.10 (br s, 2H), 3.47 (s, 3H), 2.24 (s, 3H), 2.01-2.07 (m, 3H).

Step 3: Synthesis of N-(3-(1-methyl-5-(methylamino)-6-oxo-1,6-dihydropyridin-3-yl)-4-(p-tolyloxy)phenyl)ethenesulfonamide Compound 4 (6 mg, 4%) was prepared following General Procedure 5 using 5-(5-amino-2-(p-tolyloxy)phenyl)-1-methyl-3-(methylamino)pyridin-2(1H)-one (0.125 g, 0.373 mmol).

LCMS: 426 [M+1]$^+$ $^1$H NMR (400 MHz, DMSO-d$_6$): δ 10.02-9.91 (m, 1H), 7.22 (d, J=2.7 Hz, 1H), 7.10 (d, J=8.3 Hz, 3H), 7.03 (d, J=2.4 Hz, 1H), 6.93 (d, J=8.7 Hz, 1H), 6.82 (dd, J=16.4, 10.0 Hz, 1H), 6.75 (d, J=8.0 Hz, 2H), 6.19 (d, J=2.2 Hz, 1H), 6.12 (d, J=16.5 Hz, 1H), 6.06 (d, J=9.9 Hz, 1H), 5.60-5.52 (m, 1H), 3.45 (s, 3H), 2.56 (d, J=5.1 Hz, 3H), 2.23 (s, 3H).

Example S-12: Synthesis of N-(4-(4-methoxyphenoxy)-3-(1-methyl-5-(methylamino)-6-oxo-1,6-dihydropyridin-3-yl)phenyl)acrylamide: (General Procedure 7) Compound 5

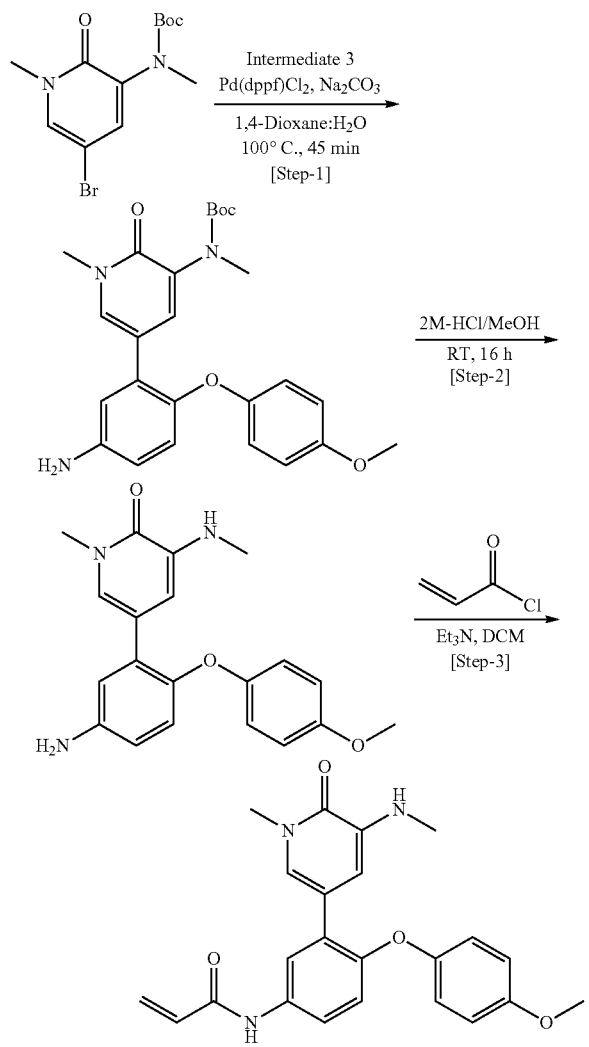

Step 1: Synthesis of tert-butyl 5-(5-amino-2-(4-methoxyphenoxy)phenyl)-1-methyl-2-oxo-1,2-dihydropyridin-3-yl(methyl)carbamate Tert-butyl 5-(5-amino-2-(4-methoxyphenoxy)phenyl)-1-methyl-2-oxo-1,2-dihydropyridin-3-yl(methyl)carbamate (260 mg, 61%, brown solid) was prepared following General Procedure 6, Step 1 using Intermediate 3 (355 mg, 1.04 mmol, 1.1 eq).

LCMS: 452 [M+1]$^+$ $^1$H NMR (400 MHz, DMSO-d$_6$): δ 7.78 (br s, 1H), 7.45 (br s, 1H), 6.81 (d, J=9.21 Hz, 2H), 6.73 (d, J=9.21 Hz, 3H), 6.62 (br s., 1H), 6.56-6.52 (m, 1H), 3.66 (s, 3H), 3.47 (s, 3H), 2.90 (s, 3H), 1.26 (br s, 9H).

Step 2: Synthesis of 5-(5-amino-2-(4-methoxyphenoxy)phenyl)-1-methyl-3-(methylamino)pyridin-2(1H)-one 5-(5-amino-2-(4-methoxyphenoxy)phenyl)-1-methyl-3-(methylamino)-pyridin-2(1H)-one (240 mg, 96%, off-white solid) was prepared following General Procedure 6, Step 2 using tert-butyl 5-(5-amino-2-(4-methoxyphenoxy)phenyl)-1-methyl-2-oxo-1,2-dihydropyridin-3-yl(methyl)carbamate (320 mg, 0.71 mmol).

LCMS: 352 [M+1]$^+$ $^1$H NMR (400 MHz, DMSO-d$_6$): δ 7.04 (s, 1H), 6.86 (d, J=8.77 Hz, 2H), 6.73-6.81 (m, 3H), 6.71 (br s, 1H), 6.59 (d, J=7.89 Hz, 1H), 6.26 (s, 1H), 5.52 (d, J=4.82 Hz, 1H), 5.08 (br s, 2H), 3.70-3.74 (m, 3H), 3.48 (s, 3H), 2.04 (s, 3H)

Step 3: Synthesis of N-(4-(4-methoxyphenoxy)-3-(1-methyl-5-(methylamino)-6-oxo-1,6-dihydropyridin-3-yl)phenyl)acrylamide Compound 5 (18 mg, 13%) was prepared following General Procedure 3 using 5-(5-amino-2-(4-methoxyphenoxy)phenyl)-1-methyl-3-(methylamino)-pyridin-2(1H)-one (120 mg, 0.34 mmol).

LCMS: 406 [M+1]$^+$ $^1$H NMR (400 MHz, Methanol-d$_4$): δ 7.78 (d, J=2.6 Hz, 1H), 7.52 (dd, J=8.8, 2.7 Hz, 1H), 7.08 (d, J=2.1 Hz, 1H), 6.94 (d, J=8.8 Hz, 1H), 6.89-6.78 (m, 4H), 6.54-6.32 (m, 3H), 5.78 (dd, J=9.4, 2.5 Hz, 1H), 3.74 (s, 3H), 3.58 (s, 3H), 2.74 (s, 3H).

Example S-13: Synthesis of N-(3-(1-methyl-5-(methylamino)-6-oxo-1,6-dihydropyridin-3-yl)-4-(p-tolyloxy)phenyl)acrylamide: Compound 6

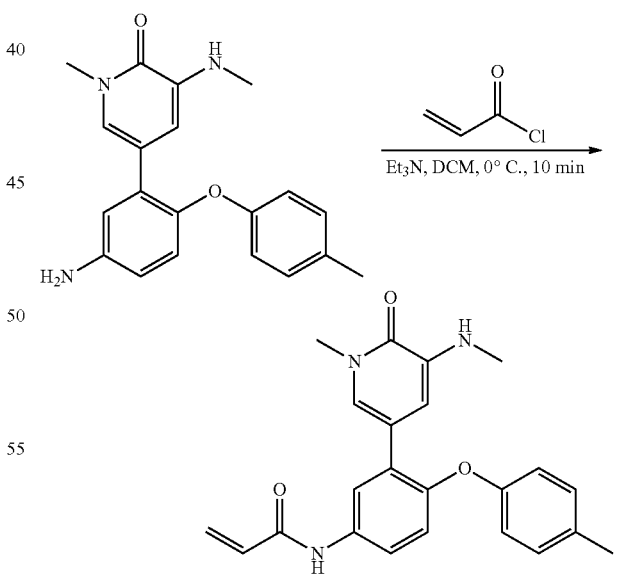

Compound 6 (18 mg, 13%) was prepared following General Procedure 3 using 5-(5-amino-2-(p-tolyloxy)phenyl)-1-methyl-3-(methylamino)-pyridin-2(1H)-one (120 mg, 0.34 mmol) which was prepared following General Procedure 6, Step 1and 2.

LCMS: 390 [M+1]$^+$

¹H NMR (400 MHz, Methanol-d₄): δ 7.80 (d, J=2.7 Hz, 1H), 7.55 (dd, J=8.8, 2.7 Hz, 1H), 7.07 (d, J=8.1 Hz, 2H), 6.99 (d, J=8.8 Hz, 1H), 6.79-6.71 (m, 2H), 6.52-6.33 (m, 4H), 5.79 (dd, J=9.4, 2.4 Hz, 1H), 3.56 (s, 3H), 2.71 (s, 3H), 2.26 (s, 3H).

Example S-14: Synthesis of N-(4-(4-fluorophenoxy)-3-(1-methyl-5-(methylamino)-6-oxo-1,6-dihydropyridin-3-yl)phenyl)ethenesulfonamide: Compound 7

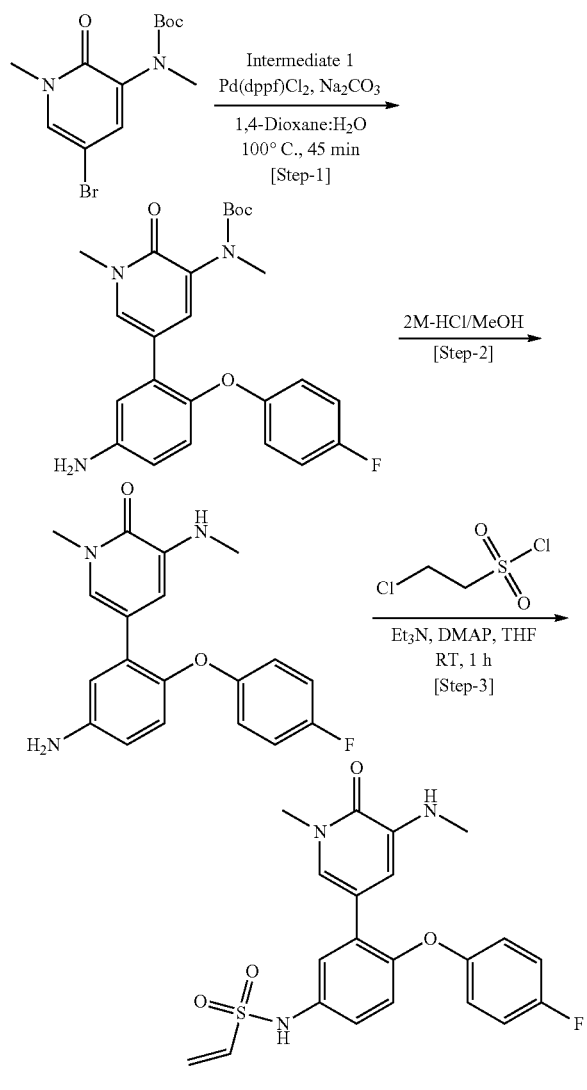

Step 1: Synthesis of tert-butyl 5-(5-amino-2-(4-fluorophenoxy)phenyl)-1-methyl-2-oxo-1,2-dihydropyridin-3-yl(methyl)carbamate Tert-butyl 5-(5-amino-2-(4-fluorophenoxy)phenyl)-1-methyl-2-oxo-1,2-dihydropyridin-3-yl(methyl)carbamate (230 mg, 55%, brown solid) was prepared following General Procedure 6, Step 1 using Intermediate 1 (342 mg, 1.04 mmol, 1.1 eq).
LCMS: 440 [M+1]⁺

Step 2: Synthesis of 5-(5-amino-2-(4-fluorophenoxy)phenyl)-1-methyl-3-(methylamino)pyridin-2(1H)-one 5-(5-amino-2-(4-fluorophenoxy)phenyl)-1-methyl-3-(methylamino)pyridin-2(1H)-one (175 mg, 99%) was prepared following General Procedure 6, Step 2 using tert-butyl 5-(5-amino-2-(4-fluorophenoxy)phenyl)-1-methyl-2-oxo-1,2-dihydropyridin-3-yl(methyl)carbamate (230 mg, 0.52 mmol).
LCMS: 340 [M+1]⁺

Step 3: Synthesis of N-(4-(4-fluorophenoxy)-3-(1-methyl-5-(methylamino)-6-oxo-1,6-dihydropyridin-3-yl)phenyl)ethenesulfonamide Compound 7 (7.5 mg, 7%) was prepared following General Procedure 5 using 5-(5-amino-2-(4-fluorophenoxy)phenyl)-1-methyl-3-(methylamino)pyridin-2(1H)-one (90 mg, 0.26 mmol).
LCMS: 430 [M+1]⁺
¹H NMR (400 MHz, Methanol-d₄): δ 7.28 (d, J=2.8 Hz, 1H), 7.19 (dd, J=8.7, 2.8 Hz, 1H), 6.99 (tt, J=8.7, 4.9 Hz, 4H), 6.84 (dd, J=9.1, 4.3 Hz, 2H), 6.72 (dd, J=16.5, 10.0 Hz, 1H), 6.41 (d, J=2.1 Hz, 1H), 6.18 (d, J=16.5 Hz, 1H), 6.01 (d, J=10.0 Hz, 1H), 3.56 (s, 3H), 2.72 (s, 3H).

Example S-15: Synthesis of N-(4-(4-methoxyphenoxy)-3-(1-methyl-5-(methylamino)-6-oxo-1,6-dihydropyridin-3-yl)phenyl)ethenesulfonamide: Compound 8

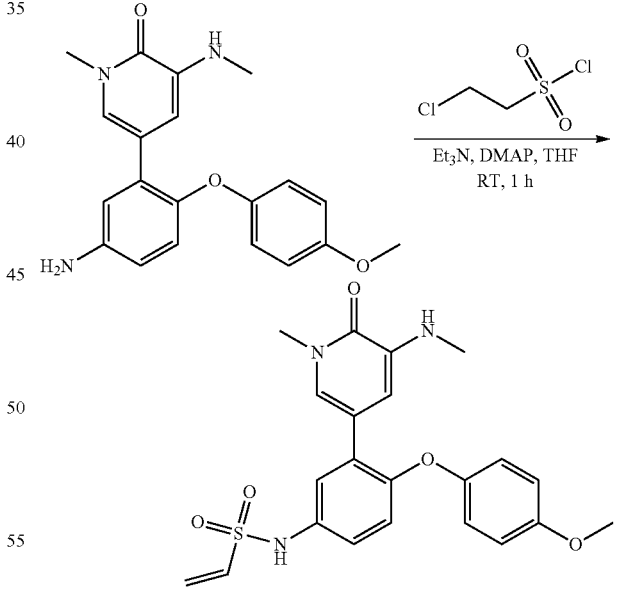

Compound 8 (4.5 mg, 3%) was prepared following General Procedure 5 using 5-(5-amino-2-(4-methoxyphenoxy)phenyl)-1-methyl-3-(methylamino)pyridin-2(1H)-one (120 mg, 0.34 mmol) which was prepared following General Procedure 7, Step 1 and 2.
LCMS: 442 [M+1]⁺
¹H NMR (400 MHz, Methanol-d₄): δ 7.26 (d, J=2.7 Hz, 1H), 7.14 (dd, J=8.7, 2.7 Hz, 1H), 7.03 (d, J=2.2 Hz, 1H), 6.89 (d, J=8.8 Hz, 1H), 6.83 (q, J=9.2 Hz, 4H), 6.70 (dd, J=16.5, 10.0 Hz, 1H), 6.46 (d, J=2.2 Hz, 1H), 6.16 (d, J=16.5 Hz, 1H), 5.99 (d, J=10.0 Hz, 1H), 3.74 (s, 3H), 3.58 (s, 3H), 2.73 (s, 3H).

Example S-16: N-(4-(2,4-difluorophenoxy)-3-(2-methyl-1-oxo-1,2-dihydroisoquinolin-4-yl)phenyl) acrylamide: (General Procedure 8) Compound 9

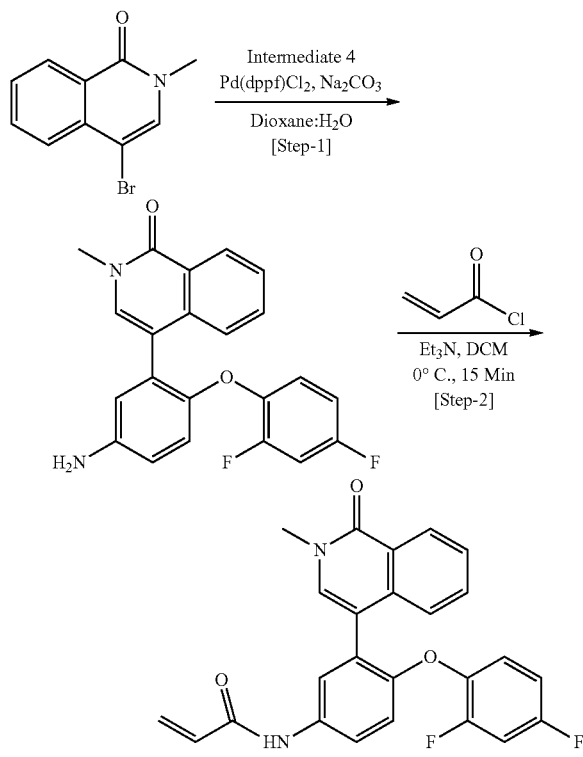

Step 1: Synthesis of 4-(5-amino-2-(2,4-difluorophenoxy)phenyl)-2-methylisoquinolin-1(2H)-one 4-(5-amino-2-(2,4-difluorophenoxy)phenyl)-2-methylisoquinolin-1(2H)-one (330 mg, 83%, brown solid) was prepared following General Procedure 6, Step 1 using Intermediate 4 (401 mg, 0.84 mmol, 1.1 eq).

LCMS: 379 [M+1]$^+$

Step 2: Synthesis of N-(4-(2,4-difluorophenoxy)-3-(2-methyl-1-oxo-1,2-dihydroisoquinolin-4-yl)phenyl)acrylamide Compound 9 (45 mg, 22%) was prepared following General Procedure 3 using 4-(5-amino-2-(2,4-difluorophenoxy)phenyl)-2-methylisoquinolin-1(2H)-one (180 mg, 0.47 mmol).

LCMS: 433 [M+1]$^+$ $^1$H NMR (400 MHz, DMSO-d$_6$): δ 10.30 (s, 1H), 8.26 (d, J=8.0 Hz, 1H), 7.78 (d, J=2.6 Hz, 1H), 7.74-7.61 (m, 2H), 7.52 (d, J=5.9 Hz, 2H), 7.38-7.24 (m, 2H), 7.08 (td, J=9.3, 5.6 Hz, 1H), 6.96 (t, J=8.2 Hz, 2H), 6.43 (dd, J=16.9, 10.1 Hz, 1H), 6.25 (dd, J=16.8, 2.1 Hz, 1H), 5.75 (dd, J=10.0, 2.1 Hz, 1H), 3.53 (s, 3H).

Example S-17: Synthesis of N-(4-(2,4-difluorophenoxy)-3-(2-methyl-1-oxo-1,2-dihydroisoquinolin-4-yl)phenyl)ethenesulfonamide: Compound 10

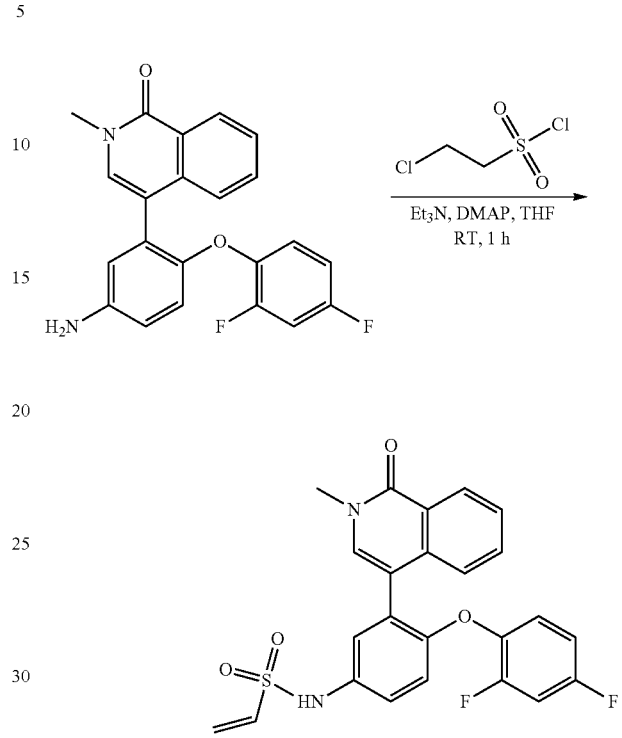

Compound 10 (28 mg, 15%) was prepared following General Procedure 5 using 4-(5-amino-2-(2,4-difluorophenoxy)phenyl)-2-methylisoquinolin-1(2H)-one (150 mg, 0.40 mmol) which was prepared following General Procedure 8, Step 1.

LCMS: 469 [M+1]$^+$ $^1$H NMR (400 MHz, DMSO-d$_6$): δ 8.24 (d, J=8.1 Hz, 1H), 7.64 (t, J=7.7 Hz, 1H), 7.50 (t, J=7.5 Hz, 1H), 7.45 (s, 1H), 7.33-7.20 (m, 2H), 7.12 (d, J=9.0 Hz, 1H), 7.06 (d, J=2.7 Hz, 1H), 7.01 (td, J=9.2, 5.6 Hz, 1H), 6.96-6.89 (m, 1H), 6.87 (d, J=8.8 Hz, 1H), 6.72 (dd, J=16.6, 10.0 Hz, 1H), 5.99 (d, J=16.4 Hz, 1H), 5.89 (d, J=10.0 Hz, 1H), 3.51 (s, 3H)

Example S-18: Synthesis of N-(4-(4-fluorophenoxy)-3-(2-methyl-1-oxo-1,2-dihydroisoquinolin-4-yl)phenyl)ethenesulfonamide: Compound 11

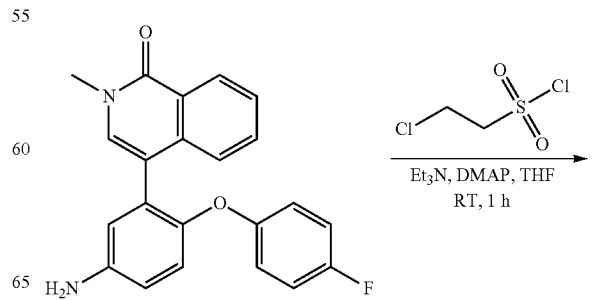

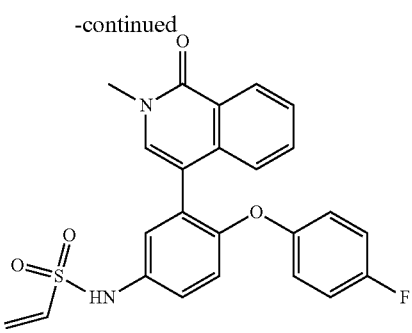

Compound 11 (15 mg, 10%) was prepared following General Procedure 5 using 4-(5-amino-2-(4-fluorophenoxy)phenyl)-2-methylisoquinolin-1(2H)-one (120 mg, 0.33 mmol). 4-(5-amino-2-(4-fluorophenoxy)phenyl)-2-methylisoquinolin-1(2H)-one was prepared following General Procedure 8, Step 1 using Intermediate 1.

LCMS: 451 [M+1]$^+$ $^1$H NMR (400 MHz, Methanol-d$_4$): δ 8.34 (d, J=8.1 Hz, 1H), 7.67 (t, J=7.7 Hz, 1H), 7.53 (t, J=7.6 Hz, 1H), 7.37 (d, J=8.1 Hz, 1H), 7.31 (dd, J=8.7, 2.8 Hz, 1H), 7.27 (s, 1H), 7.24 (d, J=2.8 Hz, 1H), 7.04 (d, J=8.8 Hz, 1H), 6.89 (t, J=8.7 Hz, 2H), 6.79-6.66 (m, 3H), 6.17 (d, J=16.5 Hz, 1H), 6.02 (d, J=10.0 Hz, 1H), 3.58 (s, 3H).

Example S-19: Synthesis of N-(4-(4-methoxyphenoxy)-3-(2-methyl-1-oxo-1,2-dihydroisoquinolin-4-yl)phenyl)ethenesulfonamide: Compound 12

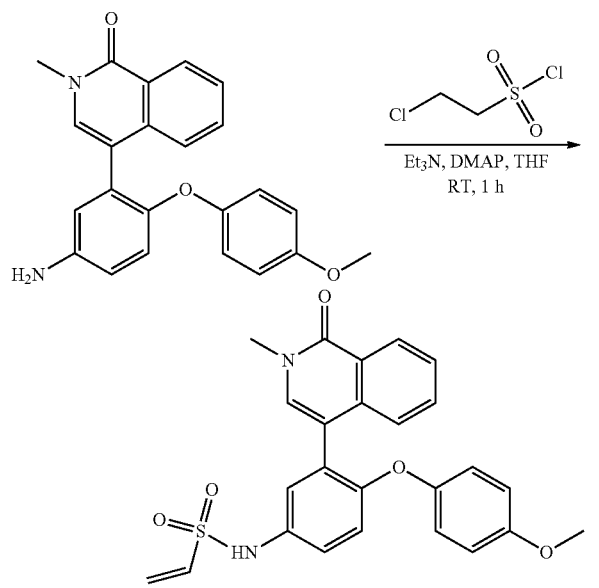

Compound 12 (21 mg, 19%) was prepared following General Procedure 5 using 4-(5-amino-2-(4-methoxyphenoxy)phenyl)-2-methylisoquinolin-1(2H)-one (90 mg, 0.24 mmol). 4-(5-amino-2-(4-methoxyphenoxy)phenyl)-2-methylisoquinolin-1(2H)-one was prepared following General Procedure 8, Step 1 using Intermediate 3.

LCMS: 463 [M+1]$^+$ $^1$H NMR (400 MHz, Methanol-d$_4$) δ 8.35 (d, J=8.1 Hz, 1H), 7.71-7.62 (m, 1H), 7.53 (t, J=7.6 Hz, 1H), 7.37 (d, J=8.2 Hz, 1H), 7.25 (d, J=9.6 Hz, 2H), 7.21 (d, J=2.7 Hz, 1H), 6.93 (d, J=8.7 Hz, 1H), 6.79-6.64 (m, 5H), 6.15 (d, J=16.5 Hz, 1H), 6.00 (d, J=9.9 Hz, 1H), 3.69 (s, 3H), 3.59 (s, 3H).

Example S-20: Synthesis of N-(3-(2-methyl-1-oxo-1,2-dihydroisoquinolin-4-yl)-4-(p-tolyloxy)phenyl)ethenesulfonamide: Compound 13

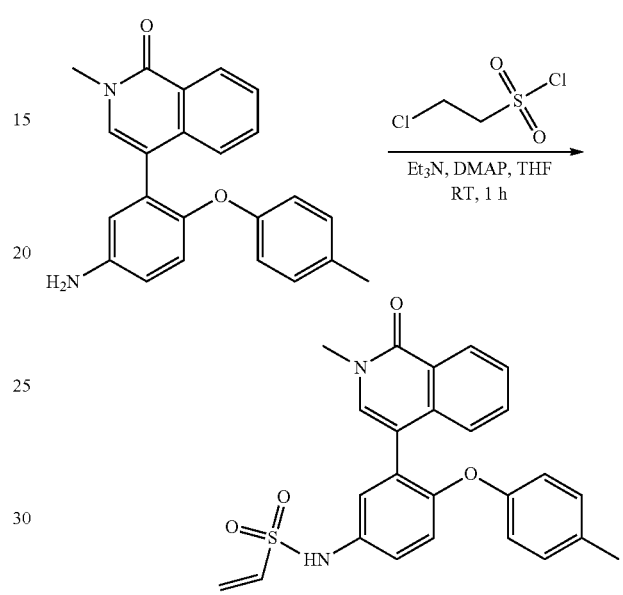

Compound 13 (28 mg, 18%) was prepared following General Procedure 5 using 4-(5-amino-2-(p-tolyloxy)phenyl)-2-methylisoquinolin-1(2H)-one (125 mg, 0.35 mmol). 4-(5-amino-2-(p-tolyloxy)phenyl)-2-methylisoquinolin-1(2H)-one was prepared following General Procedure 8, Step 1 using Intermediate 2.

LCMS: 447 [M+1]$^+$ $^1$H NMR (400 MHz, Methanol-d$_4$): δ 8.34 (d, J=8.1 Hz, 1H), 7.66 (t, J=7.7 Hz, 1H), 7.53 (t, J=7.6 Hz, 1H), 7.37 (d, J=8.1 Hz, 1H), 7.28 (dd, J=8.7, 2.8 Hz, 1H), 7.25-7.19 (m, 2H), 6.99 (t, J=8.7 Hz, 3H), 6.72 (dd, J=16.5, 9.9 Hz, 1H), 6.63-6.56 (m, 2H), 6.17 (d, J=16.5 Hz, 1H), 6.01 (d, J=9.9 Hz, 1H), 3.57 (s, 3H), 2.21 (s, 3H).

Example S-21: Synthesis of N-(4-(2,4-difluorophenoxy)-3-(2-methyl-1-oxo-1,2,5,6,7,8-hexahydro-2,7-naphthyridin-4-yl)phenyl)ethenesulfonamide: (General Procedure 9) Compound 14

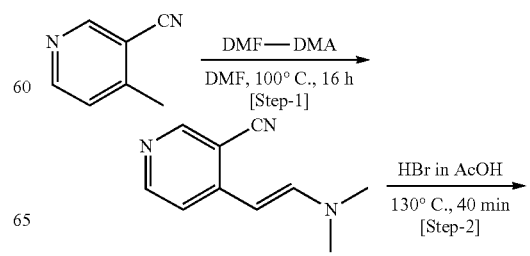

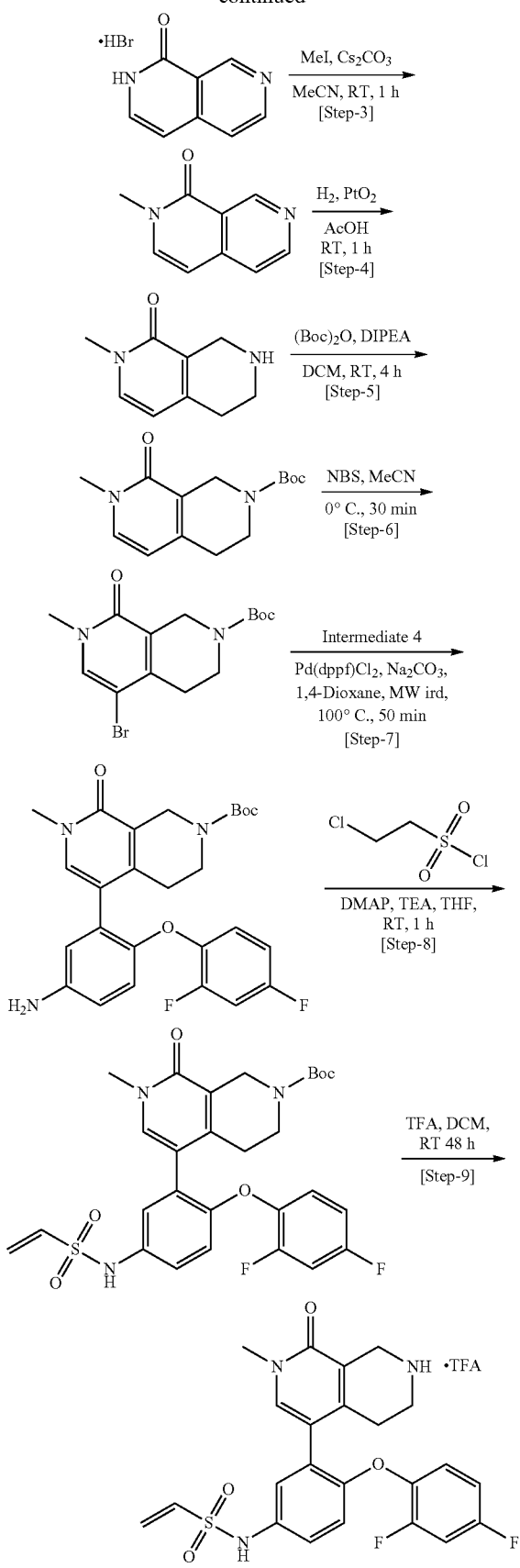

Step 1: Synthesis of (E)-4-(2-(dimethylamino)vinyl)nicotinonitrile

To a stirred solution of 4-methylnicotinonitrile (10 g, 84.65 mmol, I eq) in DMF (30 mL) was added DMF-DMA (25 mL) at RT and the mixture was heated at 100° C. for 16 h and monitored by TLC. The reaction was complete after 16 h and to the mixture was added water (200 mL) to obtain a precipitate which was filtered over Büchner funnel to afford pure of (E)-4-(2-(dimethylamino)vinyl)nicotinonitrile (8 g, 54.79%) as a white solid.

LC-MS: 174 [M+H]$^+$

Step 2: Synthesis of 2,7-naphthyridin-1(2H)-one

To (E)-4-(2-(dimethylamino)vinyl)nicotinonitrile (8 g, 46.242 mmol, 1 eq) was added HBr in AcOH (30-33%; 25 mL) at 0° C. and the mixture was heated at 130° C. and monitored by TLC. The reaction was complete after 40 min and the mixture was concentrated under reduced pressure. To the residue obtained was added DCM (100 mL) and the precipitate was filtered over Büchner funnel, washed with diethyl ether to afford 2,7-naphthyridin-1(2H)-one (4.6 g, 68.18%) as a hydrobromide salt (brown solid).

LC-MS: 147 [M+H]$^+$

Step 3: Synthesis of 2-methyl-2,7-naphthyridin-1(2H)-one

To a stirred solution of 2,7-naphthyridin-1(2H)-one (4.6 g, 20.264 mmol 1 eq) in MeCN (20 mL) was added Cs$_2$CO$_3$ (19.77 g, 60.756 mmol, 3 eq) at RT and the mixture was stirred at RT for 30 min, followed by addition of MeI (1.9 mL, 30.396 mmol, 1.5 eq). The resultant mixture was reaction was stirred at RT and monitored by TLC. The reaction was complete after 1 h and mixture was diluted with water (100 mL) and extracted with 10% MeOH in DCM (300 mL×3). The combined organic layers were washed with water (200 mL), brine (150 mL) dried over Na$_2$SO$_4$, filtered and concentrated under reduced pressure to afford 2-methyl-2,7-naphthyridin-1(2H)-one (1.5 g, 46.29%) as an off-white solid.

LC-MS: 161 [M+H]$^+$

Step 4: Synthesis of 2-methyl-5,6,7,8-tetrahydro-2,7-naphthyridin-1(2H)-one

To a solution of 2-methyl-2,7-naphthyridin-1(2H)-one (1.5 g, 9.375 mmol, 1 eq) in AcOH (20 mL) was added PtO$_2$ (0.15 g) at RT and the mixture was hydrogenated using H$_2$ bladder and monitored by TLC. The reaction was complete after 1 h and mixture was filtered through celite bed, washed with EtOAc (500 mL) and concentrated under reduced pressure to afford 2-methyl-5,6,7,8-tetrahydro-2,7-naphthyridin-1(2H)-one (1.5 g, 98.03%) as a brown solid.

LC-MS: 165 [M+H]$^+$

Step 5: Synthesis of tert-butyl 7-methyl-8-oxo-3,4,7,8-tetrahydro-2,7-naphthyridine-2(1H)-carboxylate To a stirred solution of 2-methyl-5,6,7,8-tetrahydro-2,7-naphthyridin-1(2H)-one (1.5 g, 9.13 mmol, 1 eq) in DCM (20 mL) was added DIPEA (15.91 mL, 91.35 mmol, 10 eq) at RT and the mixture was stirred for 10 min. Di-tert-butyl dicarbonate (2.39 g, 10.96 mmol, 1.2 eq) was then added to the mixture and the mixture was stirred at RT and monitored by TLC. The reaction was complete after 4 h and the mixture was diluted with water (100 mL) and extracted with EtOAc (300 mL). The organic layer was washed with water (150 mL), brine (150 mL) dried over Na₂SO₄, filtered and concentrated under reduced pressure to afford a crude residue which was purified using CombiFlash chromatography to afford tert-butyl 7-methyl-8-oxo-3,4,7,8-tetrahydro-2,7-naphthyridine-2(1H)-carboxylate (1.8 g, 74.68%) as an off white solid.

LC-MS: 265 [M+H]⁺

Step 6: Synthesis of tert-butyl 5-bromo-7-methyl-8-oxo-3,4,7,8-tetrahydro-2,7-naphthyridine-2(1H)-carboxylate To a stirred solution of tert-butyl 7-methyl-8-oxo-3,4,7,8-tetrahydro-2,7-naphthyridine-2(1H)-carboxylate (1.5 g, 5.674 mmol, 1 eq) in MeCN (20 mL) was added NBS (1.11 g, 6.242 mmol, 1.1 eq) at 0° C. slowly and the mixture was stirred at 0° C. and monitored by TLC. The reaction was complete after 30 min and the mixture was diluted with water (100 mL) and extracted with EtOAc (300 mL). The organic layer was washed with water (150 mL), brine (150 mL) dried over Na₂SO₄, filtered and concentrated under reduced pressure to afford a crude which was purified using CombiFlash chromatography to afford tert-butyl 5-bromo-7-methyl-8-oxo-3,4,7,8-tetrahydro-2,7-naphthyridine-2(1H)-carboxylate (0.53 g, 27.31%) as an off white solid.

LC-MS: 343 [M+1]⁺, 345 [M+2]⁺

Step 7: Synthesis of tert-butyl 5-(5-amino-2-(2,4-difluorophenoxy)phenyl)-7-methyl-8-oxo-3,4,7,8-tetrahydro-2,7-naphthyridine-2(1H)-carboxylate tert-butyl 5-(5-amino-2-(2,4-difluorophenoxy)phenyl)-7-methyl-8-oxo-3,4,7,8-tetrahydro-2,7-naphthyridine-2(1H)-carboxylate (0.28 g, 37.53%, off white solid) was prepared following General Procedure 6, Step 1 using Intermediate 4 (0.589 g, 1.698 mmol, 1.1 eq) and tert-butyl 5-bromo-7-methyl-8-oxo-3,4,7,8-tetrahydro-2,7-naphthyridine-2(1H)-carboxylate (0.53 g, 1.544 mmol 1 eq).

LC-MS: 484 [M+H]⁺

Step 8: Synthesis of tert-butyl 5-(2-(2,4-difluorophenoxy)-5-(vinylsulfonamido)phenyl)-7-methyl-8-oxo-3,4,7,8-tetrahydro-2,7-naphthyridine-2(1H)-carboxylate tert-butyl 5-(2-(2,4-difluorophenoxy)-5-(vinylsulfonamido)phenyl)-7-methyl-8-oxo-3,4,7,8-tetrahydro-2,7-naphthyridine-2(1H)-carboxylate (20 mg, 6.06%, off-white solid) was prepared following General Procedure 5 using tert-butyl 5-(5-amino-2-(2,4-difluorophenoxy)phenyl)-7-methyl-8-oxo-3,4,7,8-tetrahydro-2,7-naphthyridine-2(1H)-carboxylate (280 mg, 0.58 mmol, 1 eq).

LC-MS: 574 [M+H]⁺

Step 9: Synthesis of N-(4-(2,4-difluorophenoxy)-3-(2-methyl-1-oxo-1,2,5,6,7,8-hexahydro-2,7-naphthyridin-4-yl)phenyl)ethenesulfonamide To a solution of tert-butyl 5-(2-(2,4-difluorophenoxy)-5-(vinylsulfonamido)phenyl)-7-methyl-8-oxo-3,4,7,8-tetrahydro-2,7-naphthyridine-2(1H)-carboxylate (20 g, 0.034 mmol, 1 eq) in DCM (4 mL) was added TFA (60 mg, 0.51 mmol, 15 eq) at 0° C. slowly and the mixture was stirred at RT and monitored by LC-MS. The reaction was complete after 48 h and the mixture was concentrated under reduced pressure reduced pressure to afford Compound 14 (12 mg, 72.72%) as a trifluoroacetate salt (off white solid).

LC-MS: 474 [M+H]⁺

¹H NMR (400 MHz, Methanol-d₄) δ 7.62 (s, 1H), 7.18 (dd, J=2.19, 4.38 Hz, 2H), 7.05-7.14 (m, 2H), 6.96 (t, J=7.89 Hz, 1H), 6.79-6.85 (m, 1H), 6.70 (dd, J=10.09, 16.66 Hz, 1H), 6.15 (d, J=16.66 Hz, 1H), 5.99 (d, J=9.65 Hz, 1H), 4.10 (s, 2H), 3.59 (s, 3H), 3.40 (t, J=6.14 Hz, 2H), 2.92 (br s, 1H), 2.70 (br s, 1H).

Example S-22: Synthesis of N-(4-(2,4-difluorophenoxy)-3-(1-methyl-5-(methylamino)-6-oxo-1,6-dihydropyridin-3-yl)phenyl)-N-methylethenesulfonamide: (General Procedure 10) Compound 15

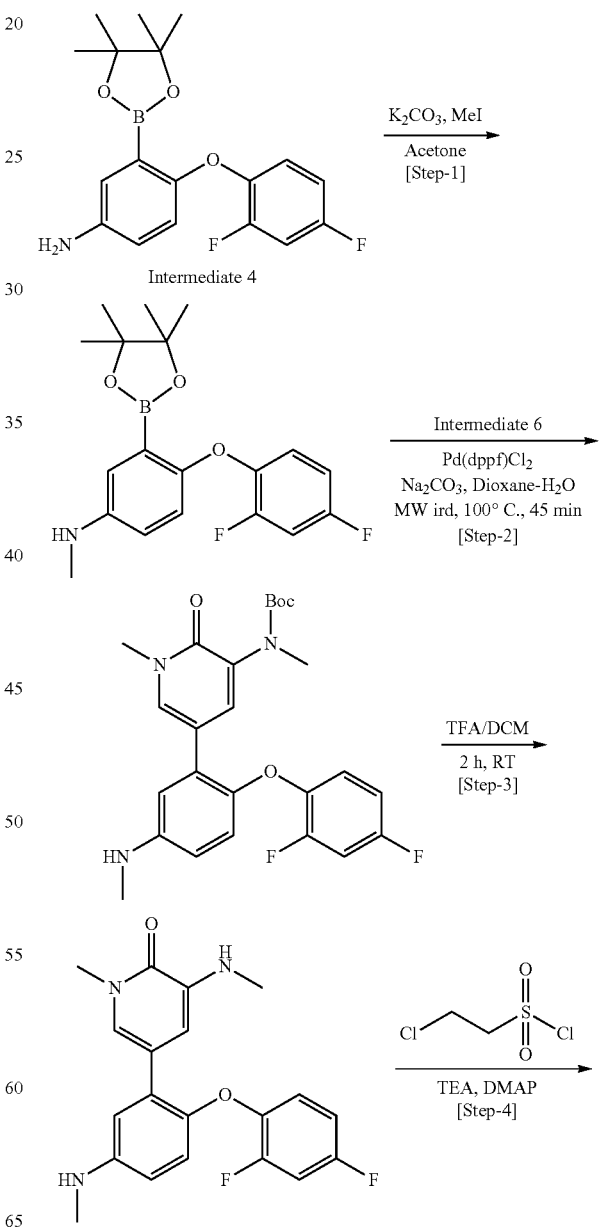

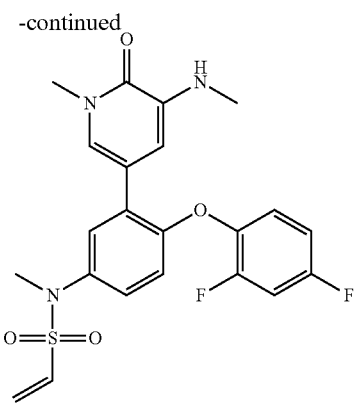

Step 1: Synthesis of 4-(2,4-difluorophenoxy)-N-methyl-3-(4,4,5,5-tetramethyl-1,3,2-dioxaborolan-2-yl)aniline To a stirred solution of Intermediate 4 (500 mg, 1.44 mmol 1 eq) in acetone (50 mL) was added potassium carbonate (238 mg. 1.7290 mmol, 1.2 eq) and the mixture was stirred at room temperature for 15 min. Methyl iodide (245 mg, 1.72 mmol, 1.2 eq) was then added to the mixture at RT and the resultant was stirred at RT for 48 h. After 48 h the mixture was diluted with water (50 mL) and extracted with EtOAc (200 mL). The organic layer was washed with water (100 mL), brine (150 mL) dried over anhydrous $Na_2SO_4$, filtered and concentrated under reduced pressure to afford a crude material which was purified by CombiFlash chromatography—to afford 4-(2,4-difluorophenoxy)-N-methyl-3-(4,4,5,5-tetramethyl-1,3,2-dioxaborolan-2-yl)aniline (180 mg, 34.61%) as a viscous liquid.

$^1$H NMR (400 MHz, DMSO-$d_6$) δ 7.31 (br s, 1H), 6.83-6.91 (m, 3H), 6.68 (dd, J=2.63, 8.77 Hz, 1H), 6.50 (d, J=5.70 Hz, 1H), 5.69 (br s, 1H), 2.62-2.69 (m, 3H), 1.05-1.08 (m, 12H)

Step 2: Synthesis of tert-butyl 5-(2-(2,4-difluorophenoxy)-5-(methylamino)phenyl)-1-methyl-2-oxo-1,2-dihydropyridin-3-yl(methyl)carbamate tert-butyl 5-(2-(2,4-difluorophenoxy)-5-(methylamino) phenyl)-1-methyl-2-oxo-1,2-dihydropyridin-3-yl(methyl) carbamate (85 mg, 41%) light yellow solid) was prepared following General Procedure 6, Step 1 using 4-(2,4-difluorophenoxy)-N-methyl-3-(4,4,5,5-tetramethyl-1,3,2-dioxaborolan-2-yl)aniline (140 mg. 0.4413 mmol, 1.0 eq) and Intermediate 6 (174 mg, 0.4855 mmol, 1.1 eq).

LCMS: 472 [M+1]$^+$

Step 3: Synthesis of 5-(2-(2,4-difluorophenoxy)-5-(methylamino)phenyl)-1-methyl-3-(methylamino) pyridin-2(1H)-one Trifluoroacetic acid (1.2 mL) was added into tert-butyl 5-(2-(2,4-difluorophenoxy)-5-(methylamino)phenyl)-1-methyl-2-oxo-1,2-dihydropyridin-3-yl(methyl)carbamate (85 mg, 0.1804 mmol, 1 eq) at 0° C. and the mixture was stirred at RT for 2 h and monitored by TLC and LC-MS. The reaction was complete after 2 h and the mixture was quenched with saturated $NaHCO_3$ solution and extracted with EtOAc (150 mL×2). The combined organic layers were washed with saturated $NaHCO_3$ solution (100 mL), water (100 mL), brine (150 mL) dried over anhydrous $Na_2SO_4$, filtered and concentrated under reduced pressure to afford 5-(2-(2,4-difluorophenoxy)-5-(methylamino)phenyl)-1-methyl-3-(methylamino)pyridin-2(1H)-one (240 mg, 94%) as an off-white solid.

LCMS: 372 [M+1]$^+$

Step 4: Synthesis of N-(4-(2,4-difluorophenoxy)-3-(1-methyl-5-(methylamino)-6-oxo-1,6-dihydropyridin-3-yl)phenyl)-N-methylethenesulfonamide Compound 15 (7 mg, 0.6%) was prepared following General Procedure 5 using 5-(2-(2,4-difluorophenoxy)-5-(methylamino)phenyl)-1-methyl-3-(methylamino)pyridin-2 (1H)-one (110 mg, 0.2972 mmol, 1 eq). 5-(2-(2,4-difluorophenoxy)-5-(methylamino)phenyl)-1-methyl-3-(methylamino)pyridin-2(1H)-one was prepared following General Procedure 9, Steps 1-3.

LCMS: 462 [M+1]$^+$ $^1$H NMR (400 MHz, Methanol-$d_4$): δ 7.43 (d, J=2.63 Hz, 1H), 7.30 (dd, J=2.63, 8.77 Hz, 1H), 7.05-7.14 (m, 2H), 7.00 (d, J=5.70 Hz, 1H), 6.90 (d, J=8.77 Hz, 2H), 6.69-6.77 (m, 1H), 6.52 (s, 1H), 6.10-6.18 (m, 2H), 3.60 (s, 3H), 3.25 (s, 3H), 2.79 (s, 3H).

Example S-23: Synthesis of N-(4-(2,4-difluorophenoxy)-3-(5-(dimethylamino)-1-methyl-6-oxo-1,6-dihydropyridin-3-yl)phenyl)ethenesulfonamide: (General Procedure 11) Compound 16

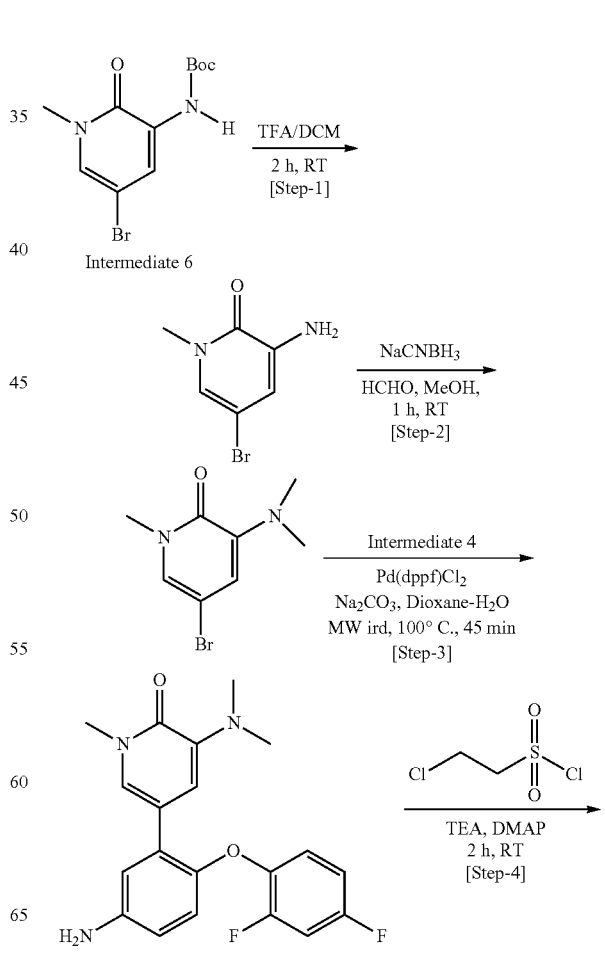

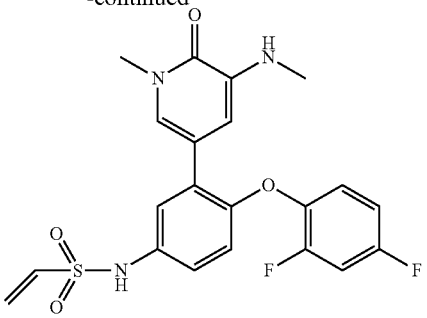

Step 1: Synthesis of 3-amino-5-bromo-1-methylpyridin-2(1H)-one 3-amino-5-bromo-1-methylpyridin-2(1H)-one (280 mg, 83.8%, off-white solid) was prepared following General Procedure 9, Step 2 using Intermediate 6 (500 mg, 1.65 mmol).
LCMS: 203 [M+1]$^+$, 205 [M+2]$^+$

Step 2: Synthesis of 5-bromo-3-(dimethylamino)-1-methylpyridin-2(1H)-one

To a stirred solution of 3-amino-5-bromo-1-methylpyridin-2(1H)-one (250 mg, 1.23 mmol, 1 eq) in methanol (12 mL) was added sodium cyanoborohydride (194 mg, 3.09 mmol, 2.5 eq) portion wise at 0° C. followed by the addition of formaldehyde (0.34 ml) at 0° C. slowly. The mixture was stirred at RT for 2 h; 2N—HCl (20 mL) was then added to the mixture and stirred for 30 min. The reaction was monitored by LC-MS. The reaction was complete after 2.5 h and the mixture was diluted with water (50 mL) and extracted with EtOAc (200 mL). The organic layer was washed with water (50 mL), brine (50 mL) dried over anhydrous Na$_2$SO$_4$, filtered and concentrated under reduced pressure to afford 5-bromo-3-(dimethylamino)-1-methylpyridin-2(1H)-one (200 mg, 70.42%) as an off-white solid.
LCMS: 231 [M+1]$^+$, 233 [M+2]$^+$

Step 3: Synthesis of 5-(5-amino-2-(2,4-difluorophenoxy)phenyl)-3-(dimethylamino)-1-methylpyridin-2(1H)-one 5-(5-amino-2-(2,4-difluorophenoxy)phenyl)-3-(dimethylamino)-1-methylpyridin-2(1H)-one (220 mg, 76%, viscous liquid) was prepared following General Procedure 6, Step 1 using 5-bromo-3-(dimethylamino)-1-methylpyridin-2(1H)-one (180 mg, 0.7826 mmol, 1.0 eq) and Intermediate 4 (298 mg, 0.86 mmol, 1.1 eq).
LCMS: 372 [M+1]$^+$

Step 4: Synthesis of N-(4-(2,4-difluorophenoxy)-3-(5-(dimethylamino)-1-methyl-6-oxo-1,6-dihydropyridin-3-yl)phenyl)ethenesulfonamide Compound 16 (25 mg, 18%) was prepared following General Procedure 5 using 5-(5-amino-2-(2,4-difluorophenoxy)phenyl)-3-(dimethylamino)-1-methylpyridin-2(1H)-one (110 mg, 0.2972 mmol, 1 eq).
LCMS: 462 [M+1]$^+$
$^1$H NMR (400 MHz, Methanol-d$_4$): δ 7.46 (s, 1H), 7.26 (d, J=2.8 Hz, 1H), 7.17 (dd, J=8.8, 2.7 Hz, 1H), 7.12-7.02 (m, 2H), 6.98-6.82 (m, 3H), 6.71 (dd, J=16.5, 10.0 Hz, 1H), 6.17 (d, J=16.5 Hz, 1H), 5.99 (d, J=10.0 Hz, 1H), 3.59 (s, 3H), 2.80 (s, 6H).

Example S-24: Synthesis of N-(3-(5-amino-1-methyl-6-oxo-1,6-dihydropyridin-3-yl)-4-(2,4-difluorophenoxy)phenyl)ethenesulfonamide: Compound 17

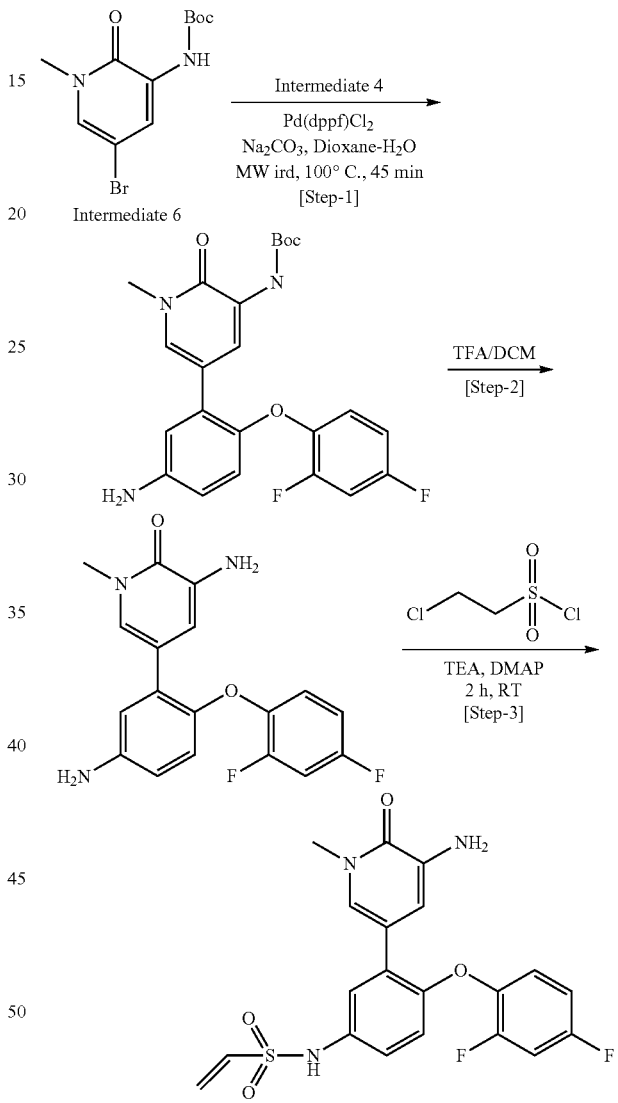

Step 1: Synthesis of tert-butyl 5-(5-amino-2-(2,4-difluorophenoxy)phenyl)-1-methyl-2-oxo-1,2-dihydropyridin-3-ylcarbamate tert-butyl 5-(5-amino-2-(2,4-difluorophenoxy)phenyl)-1-methyl-2-oxo-1,2-dihydropyridin-3-ylcarbamate (210 mg, 96%, viscous solid) was prepared following General Procedure 6, Step 1 using Intermediate 6 (150 mg, 0.50 mmol, 1 eq).
LCMS: 444 [M+1]$^+$

Step 2: Synthesis of 3-amino-5-(5-amino-2-(2,4-difluorophenoxy)phenyl)-1-methylpyridin-2(1H)-one 3-amino-5-(5-amino-2-(2,4-difluorophenoxy)phenyl)-1-methylpyridin-2(1H)-one (130 mg, 73%, viscous solid) was prepared following General Procedure 9, Step 3 using tert-butyl 5-(5-amino-2-(2,4-difluorophenoxy)phenyl)-1-methyl-2-oxo-1,2-dihydropyridin-3-ylcarbamate (230 mg, 0.518 mmol).

LCMS: 344 [M+1]$^+$

Step 3: Synthesis of N-(3-(5-amino-1-methyl-6-oxo-1,6-dihydropyridin-3-yl)-4-(2,4-difluorophenoxy)phenyl)ethenesulfonamide Compound 17 (15 mg, 9%) was prepared following General Procedure 5 using 3-amino-5-(5-amino-2-(2,4-difluorophenoxy)phenyl)-1-methylpyridin-2(1H)-one (130 mg, 0.38 mmol, 1 eq).

LCMS: 434 [M+1]$^+$
$^1$H NMR (400 MHz, Methanol-d$_4$): δ 7.23 (d, J=2.63 Hz, 1H), 7.12-7.16 (m, 2H), 7.07 (br s, 1H), 6.83-6.96 (m, 4H), 6.70 (dd, J=9.87, 16.44 Hz, 1H), 6.16 (d, J=16.66 Hz, 1H), 5.99 (d, J=9.65 Hz, 1H), 3.60 (s, 3H).

Example S-25: Synthesis of N-(4-(2,4-difluorophenoxy)-3-(1-oxo-1,2-dihydroisoquinolin-4-yl)phenyl)ethenesulfonamide: Compound 18

Step 1: Synthesis of 4-(5-amino-2-(2,4-difluorophenoxy)phenyl)isoquinolin-1(2H)-one 4-(5-amino-2-(2,4-difluorophenoxy)phenyl)isoquinolin-1(2H)-one (70 mg, 29%, white sticky solid) was prepared following General Procedure 6, Step 1 using 4-bromoisoquinolin-1(2H)-one (150 mg, 0.70 mmol, 1 eq).

LCMS: 365 [M+1]$^+$, 367 [M+2]$^+$

Step 2: Synthesis of N-(4-(2,4-difluorophenoxy)-3-(1-oxo-1,2-dihydroisoquinolin-4-yl)phenyl)ethenesulfonamide Compound 18 (4 mg, 4.6%) was prepared following General Procedure 5 using 4-(5-amino-2-(2,4-difluorophenoxy)phenyl)isoquinolin-1(2H)-one (70 mg, 0.192 mmol, 1 eq).

LCMS: 455 [M+1]$^+$
$^1$H NMR (400 MHz, Methanol-d$_4$): δ 8.34 (d, J=7.45 Hz, 1H), 7.65-7.72 (m, 1H), 7.54 (t, J=7.24 Hz, 1H), 7.39 (d, J=8.33 Hz, 1H), 7.28 (dd, J=2.63, 8.77 Hz, 1H), 7.22 (d, J=2.63 Hz, 1H), 7.11 (s, 1H), 6.89-6.97 (m, 3H), 6.68-6.81 (m, 2H), 6.16 (d, J=16.66 Hz, 1H), 6.01 (d, J=9.65 Hz, 1H).

Example S-26: Synthesis of N-(4-(2,4-difluorophenoxy)-3-(1-methyl-2-oxo-1,2-dihydropyrimidin-5-yl)phenyl)ethenesulfonamide: Compound 19

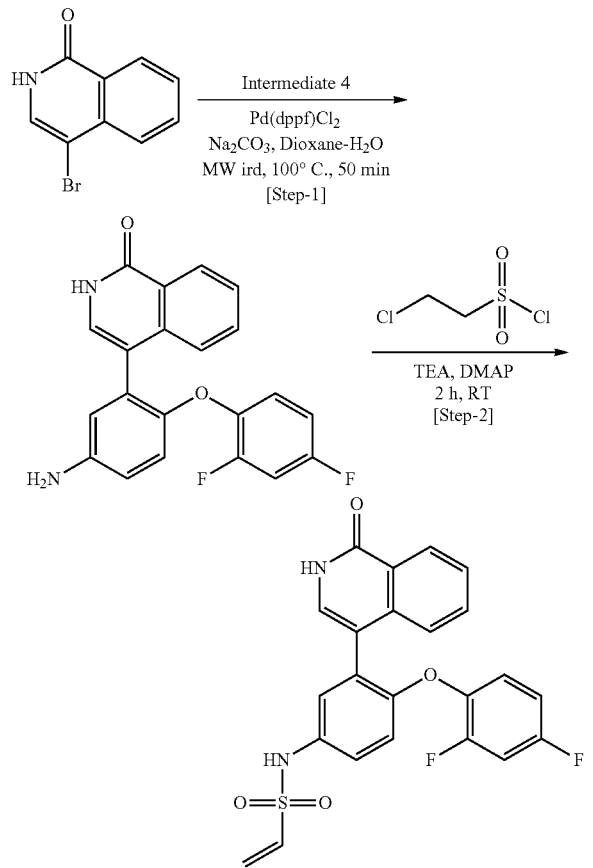

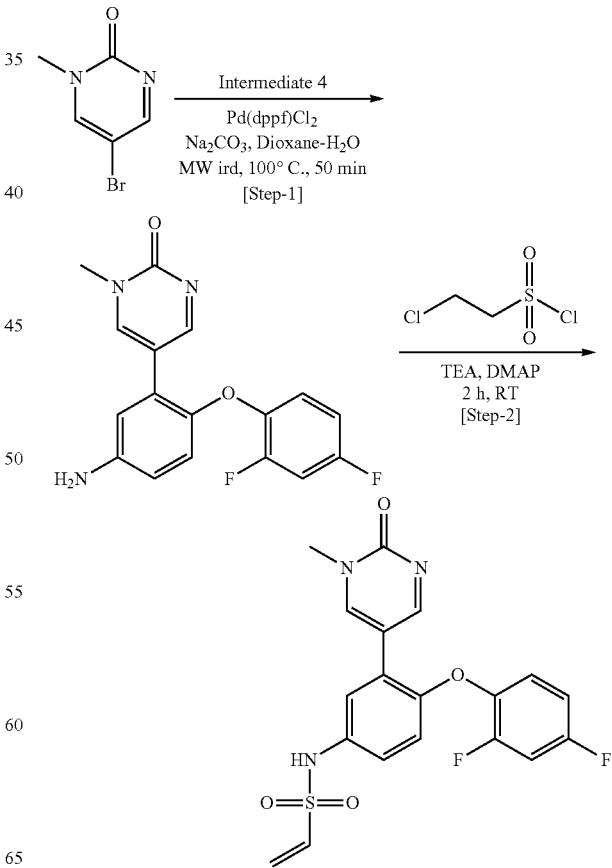

Step 1: Synthesis of 5-(5-amino-2-(2,4-difluorophenoxy)phenyl)-1-methylpyrimidin-2(1H)-one 4-(5-amino-2-(2,4-difluorophenoxy)phenyl)isoquinolin-1(2H)-one (130 mg, 75%, white solid) was prepared following General Procedure 6, Step 1 using 5-bromo-1-methylpyrimidin-2(1H)-one (100 mg, 0.53 mmol, 1 eq).
LCMS: 330 [M+1]+

Step 2: Synthesis of N-(4-(2,4-difluorophenoxy)-3-(1-methyl-2-oxo-1,2-dihydropyrimidin-5-yl)phenyl)ethenesulfonamide Compound 19 (40 mg, 45%) was prepared following General Procedure 5 using 5-(5-amino-2-(2,4-difluorophenoxy)phenyl)-1-methylpyrimidin-2(1H)-one (70 mg, 0.212 mmol, 1 eq).
LCMS: 420 [M+1]+
$^1$H NMR (400 MHz, Methanol-$d_4$) δ 8.87 (br s, 1H), 8.61 (br s, 1H), 7.33 (br s, 1H), 7.06-7.24 (m, 2H), 6.97 (br s, 1H), 6.83 (d, J=8.77 Hz, 1H), 6.71 (dd, J=10.09, 16.66 Hz, 1H), 6.16 (d, J=16.66 Hz, 1H), 5.98 (d, J=10.09 Hz, 1H), 3.68 (s, 3H).

Example S-27: Synthesis of N-(4-methoxy-3-(1-methyl-5-(methylamino)-6-oxo-1,6-dihydropyridin-3-yl)phenyl)ethenesulfonamide: (General Procedure 12) Compound 20

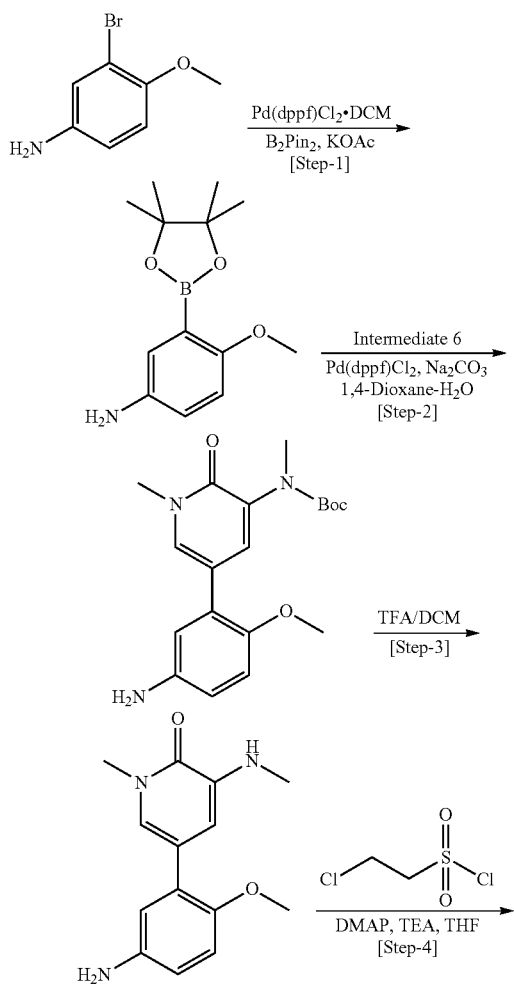

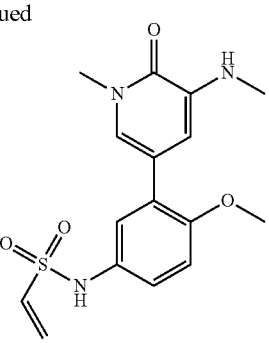

Step 1: Synthesis of 4-methoxy-3-(4,4,5,5-tetramethyl-1,3,2-dioxaborolan-2-yl)aniline 4-methoxy-3-(4,4,5,5-tetramethyl-1,3,2-dioxaborolan-2-yl)aniline (150 mg, 10%, yellowish liquid) was prepared following General Procedure 1, Step 3 using 3-bromo-4-methoxyaniline (1 g, 4.94 mmol, 1 eq).
$^1$H NMR (400 MHz, CDCl$_3$): δ 6.93 (d, J=2.63 Hz, 1H), 6.74 (d, J=8.33 Hz, 1H), 6.60 (dd, J=2.63, 8.77 Hz, 1H), 3.71-3.95 (m, 3H), 1.39-1.63 (m, 12H)

Step 2: Synthesis of tert-butyl 5-(5-amino-2-methoxyphenyl)-1-methyl-2-oxo-1,2-dihydropyridin-3-yl(methyl)carbamate tert-butyl 5-(5-amino-2-methoxyphenyl)-1-methyl-2-oxo-1,2-dihydropyridin-3-yl(methyl)carbamate (150 mg, 82%, brown solid) was prepared following General Procedure 6, Step 1 using Intermediate 6 (0.150 g, 0.605 mmol, 1.2 eq) and 4-methoxy-3-(4,4,5,5-tetramethyl-1,3,2-dioxaborolan-2-yl)aniline (0.160 g, 0.504 mmol, 1 eq).
LCMS: 360 [M+1]+

Step 3: Synthesis of 5-(5-amino-2-methoxyphenyl)-1-methyl-3-(methylamino)pyridine 2(1H)-one 5-(5-amino-2-methoxyphenyl)-1-methyl-3-(methylamino)pyridin-2(1H)-one (110 mg, 99%, brown solid) was prepared following General Procedure 9, Step 3 using tert-butyl 5-(5-amino-2-methoxyphenyl)-1-methyl-2-oxo-1,2-dihydropyridin-3-yl(methyl)carbamate (150 mg, 0.417 mmol).
LCMS: 260 [M+1]+

Step 4: Synthesis N-(4-methoxy-3-(1-methyl-5-(methylamino)-6-oxo-1,6-dihydropyridin-3-yl)phenyl)ethenesulfonamide Compound 20 (2 mg, 1.35%, off-white solid) was prepared following General Procedure 5 using 5-(5-amino-2-methoxyphenyl)-1-methyl-3-(methylamino)pyridin-2(1H)-one (110 mg, 0.424 mmol).
LCMS: 350 [M+1]+
$^1$H NMR (400 MHz, CDCl$_3$): δ 7.12-7.20 (m, 2H), 6.98-7.05 (m, 2H), 6.66 (dd, J=9.87, 16.44 Hz, 1H), 6.45 (s, 1H), 6.09 (d, J=16.66 Hz, 1H), 5.95 (d, J=10.09 Hz, 1H), 3.80 (s, 3H), 3.62 (s, 3H), 2.83 (s, 3H).

Example S-28: Synthesis of N-(4-(2,4-difluorophenylamino)-3-(1-methyl-5-(methylamino)-6-oxo-1,6-dihydropyridin-3-yl)phenyl)ethenesulfonamide: General Procedure 13) Compound 21

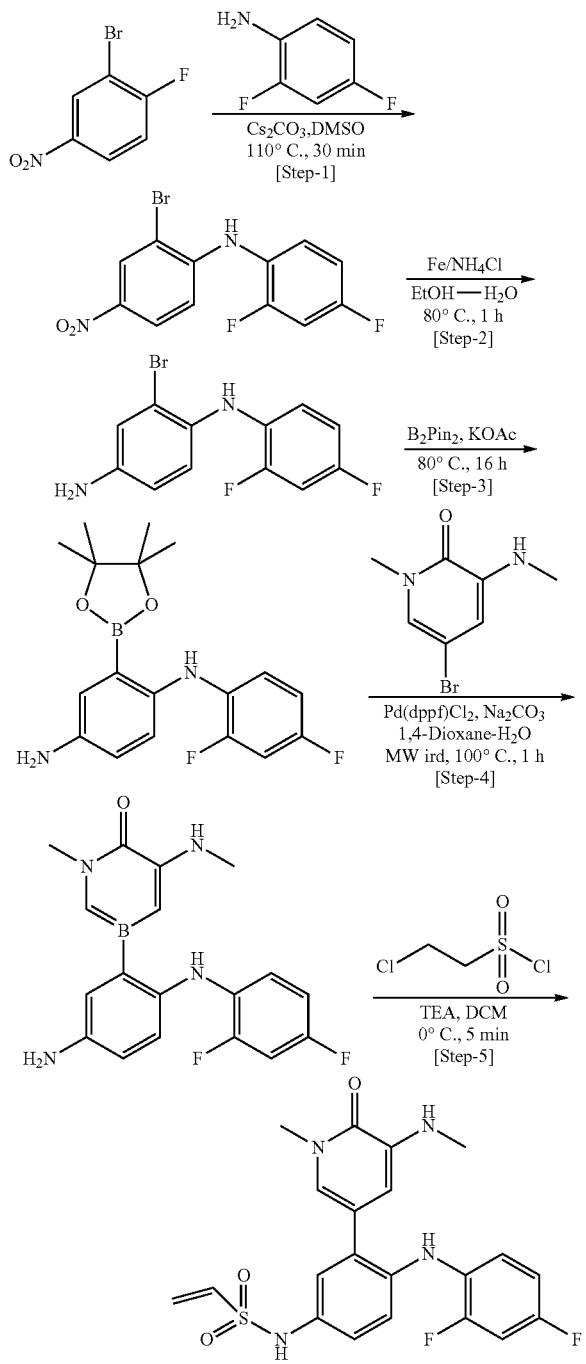

Step 1: Synthesis 2-bromo-N-(2,4-difluorophenyl)-4-nitroaniline

To a solution of 2,4-difluoroaniline (1.0 g, 4.56 mmol, 1.0 eq) in DMSO (15 mL) was added Cs$_2$CO$_3$ (3 g, 13.00 mmol, 3.0 eq) followed by an addition of 2-bromo-1-fluoro-4-nitrobenzene (0.766 g, 5.93 mmol, 1.3 eq). The mixture was heated at 110° C. for 0.5 h and monitored by TLC and LC-MS. The reaction was complete after 2 h and to the mixture was added ice-cold water (50 mL) to obtain a precipitate which was filtered over Büchner funnel; dried under vacuum to afford 2-bromo-N-(2,4-difluorophenyl)-4-nitroaniline (0.500 g, 33.33%) as a yellow solid.

$^1$H NMR (400 MHz, DMSO-d$_6$) δ 8.37 (d, J=7.02 Hz, 1H), 8.03 (d, J=8.33 Hz, 1H), 7.37-7.56 (m, 2H), 7.14-7.25 (m, 1H), 6.52 (d, J=10.52 Hz, 1H)

Step 2: Synthesis of 2-bromo-N$^1$-(2,4-difluorophenyl)benzene-1,4-diamine 2-bromo-N$^1$-(2,4-difluorophenyl)benzene-1,4-diamine (230 mg, 56%, black viscous liquid) was prepared following General Procedure 1, Step 2 using 2-bromo-N-(2,4-difluorophenyl)-4-nitroaniline (0.500 g, 1.52 mmol, 1.0 eq).

LCMS: 299 [M+1]$^+$, 301 [M+2]$^+$

Step 3: Synthesis of N$^1$-(2,4-difluorophenyl)-2-(4,4,5,5-tetramethyl-1,3,2-dioxaborolan-2-yl)benzene-1,4-diamine N$^1$-(2,4-difluorophenyl)-2-(4,4,5,5-tetramethyl-1,3,2-dioxaborolan-2-yl)benzene-1,4-diamine (230 mg, 56%, black viscous liquid) was prepared following General Procedure 1, Step 3 using 2-bromo-N$^1$-(2,4-difluorophenyl)benzene-1,4-diamine (230 mg, 0.7744 mmol, 1.0 eq).

$^1$H NMR: (400 MHz, Methanol-d$_4$) δ 7.17-7.23 (m, 1H), 7.12 (d, J=3.07 Hz, 1H), 7.02 (d, J=8.77 Hz, 1H), 6.84 (d, J=2.63 Hz, 1H), 6.76 (dd, J=2.85, 8.55 Hz, 1H), 6.70-6.66 (m, 1H), 1.30-1.50 (m, 12H)

Step 4: Synthesis of 5-(5-amino-2-(2,4-difluorophenylamino)phenyl)-1-methyl-3-(methylamino)pyridin-2(1H)-one 5-(5-amino-2-(2,4-difluorophenylamino)phenyl)-1-methyl-3-(methylamino)pyridin-2(1H)-one (150 mg, 63.5%, brown solid) was prepared following General Procedure 6, Step 1 using N$^1$-(2,4-difluorophenyl)-2-(4,4,5,5-tetramethyl-1,3,2-dioxaborolan-2-yl)benzene-1,4-diamine (355 mg, 1.02 mmol, 1.3 eq) and 5-bromo-1-methyl-3-(methylamino)pyridin-2(1H)-one (200 mg, 0.79 mmol, 1 eq).

LCMS: 357 [M+1]$^+$

Step 5 Synthesis of N-(4-(2,4-difluorophenylamino)-3-(1-methyl-5-(methylamino)-6-oxo-1,6-dihydropyridin-3-yl)phenyl)ethenesulfonamide Compound 21 (30 mg, 16%, off-white solid) was prepared following General Procedure 5 using 5-(5-amino-2-(2,4-difluorophenylamino)phenyl)-1-methyl-3-(methylamino)pyridin-2(1H)-one (150 mg, 0.420 mmol, 1 eq).

LCMS: 447 [M+1]$^+$ $^1$H NMR (400 MHz, Methanol-d$_4$) δ 7.11 (dd, J=6.0, 2.7 Hz, 2H), 6.99 (d, J=9.3 Hz, 1H), 6.95-6.81 (m, 3H), 6.78-6.63 (m, 2H), 6.33 (d, J=2.1 Hz, 1H), 6.14 (d, J=16.5 Hz, 1H), 5.98 (d, J=10.0 Hz, 1H), 3.57 (s, 3H), 2.71 (s, 3H)

Example S-29: Synthesis of N-(4-(2,4-difluorophenoxy)-3-(5-(methylamino)-6-oxo-1,6-dihydropyridin-3-yl)phenyl)ethenesulfonamide: Compound 22

Step 1: Synthesis of 5-bromo-3-(methylamino)pyridin-2(1H)-one

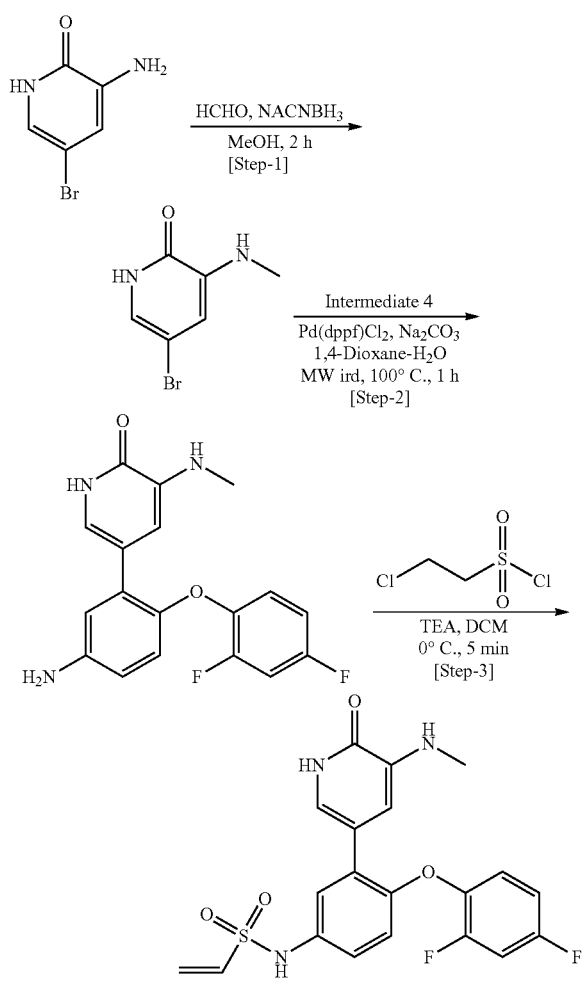

To a stirred solution of 3-amino-5-bromopyridin-2(1H)-one (500 mg, 2.64 mmol, 1 eq) in methanol (10 mL) was added sodium cyanoborohydride (415 mg, 6.61 mmol, 2.5 eq) portion wise at 0° C. followed by the addition of formaldehyde (238 mg, 3.17 mmol, 1.2 eq) at 0° C. slowly. The mixture was stirred at RT for 1 h; 2N—HCl (20 mL) was then added to the mixture and stirred for 5 min at RT. TLC analysis indicated the reaction was complete. The mixture was diluted with water (50 mL) and extracted with EtOAc (200 mL). The organic layer was washed with water (50 mL), brine (50 mL) dried over anhydrous $Na_2SO_4$, filtered and concentrated under reduced pressure to afford a crude residue which was purified by CombiFlash chromatography—to afford 5-bromo-3-(methylamino)pyridin-2 (1H)-one (180 mg, 33.5%) as a viscous liquid.

LCMS: 203 $[M+1]^+$, 205 $[M+2]^+$

Step 2: Synthesis of 5-(5-amino-2-(2,4-difluorophenoxy)phenyl)-3-(methylamino)pyridin-2(1H)-one 5-(5-amino-2-(2,4-difluorophenoxy)phenyl)-3-(methylamino)pyridin-2(1H)-one (100 mg, 33%, brown solid) was prepared following General Procedure 6, Step 1 using Intermediate 4 (371 mg, 1.06 mmol, 1.3 eq) and 5-bromo-3-(methylamino)pyridin-2(1H)-one (180 mg, 0.89 mmol, 1 eq).

LCMS: 344 $[M+1]^+$

Step 3: Synthesis of N-(4-(2,4-difluorophenoxy)-3-(5-(methylamino)-6-oxo-1,6-dihydropyridin-3-yl)phenyl)ethenesulfonamide Compound 22 (7 mg, 0.5%, off-white solid) was prepared following General Procedure 5 using 5-(5-amino-2-(2,4-difluorophenoxy)phenyl)-3-(methylamino)pyridin-2(1H)-one (100 mg, 0.29 mmol, 1 eq).

LCMS: 434 $[M+1]^+$ $^1$H NMR (400 MHz, Methanol-$d_4$): δ 7.27 (d, J=2.63 Hz, 1H), 7.16 (dd, J=2.19, 8.77 Hz, 1H), 7.05 (br s, 1H), 6.90 (d, J=8.77 Hz, 1H), 6.86 (br s, 3H), 6.71 (dd, J=9.87, 16.88 Hz, 1H), 6.52 (s, 1H), 6.17 (d, J=16.66 Hz, 1H), 6.00 (d, J=10.09 Hz, 1H), 2.79 (s, 3H).

Example S-30: Synthesis of N-(3-(4-fluorophenoxy)-2-(1-methyl-5-(methylamino)-6-oxo-1,6-dihydropyridin-3-yl)phenyl)acrylamide: (General Procedure 14) Compound 23

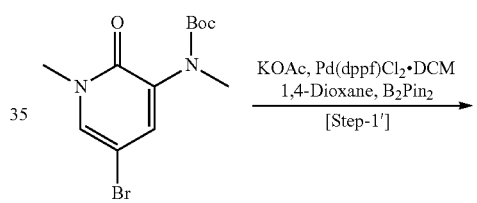

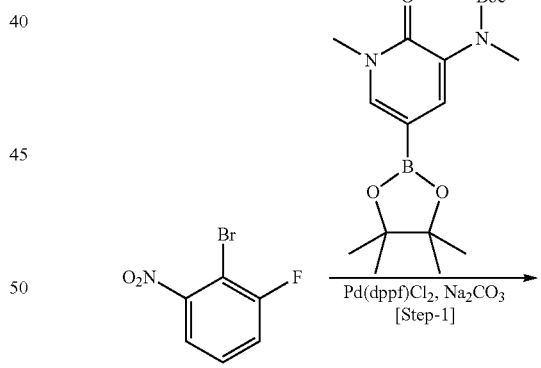

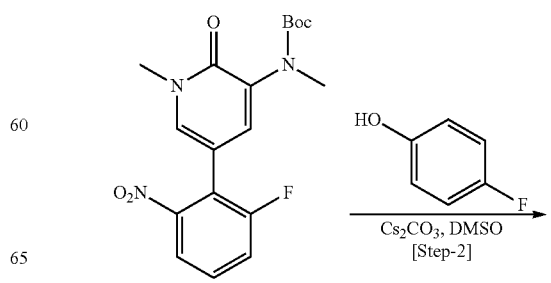

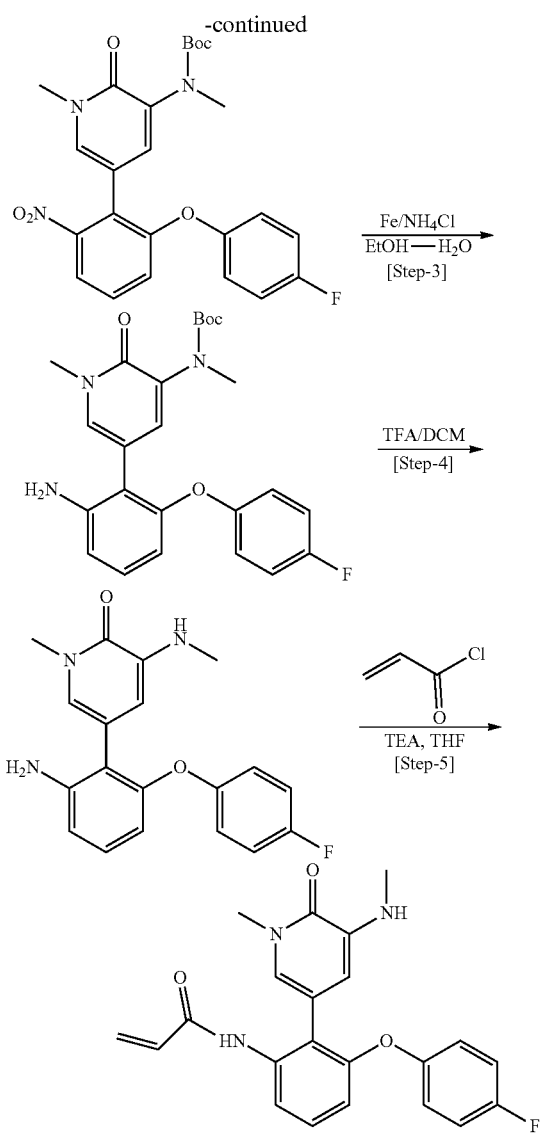

Step 1': Synthesis of tert-butyl methyl(1-methyl-2-oxo-5-(4,4,5,5-tetramethyl-1,3,2-dioxaborolan-2-yl)-1,2-dihydropyridin-3-yl)carbamate tert-butyl methyl(1-methyl-2-oxo-5-(4,4,5,5-tetramethyl-1,3,2-dioxaborolan-2-yl)-1,2-dihydropyridin-3-yl)carbamate (1.2 g, 54%, viscous liquid) was prepared following General Procedure 1, Step 3 using tert-butyl 5-bromo-1-methyl-2-oxo-1,2-dihydropyridin-3-yl(methyl)carbamate (2.0 g, 6.30 mmol, 1.0 eq).

$^1$H NMR: (400 MHz, CDCl$_3$) δ 7.26 (s, 2H), 3.57 (s, 3H), 3.11 (s, 3H), 1.30 (s, 9H), 1.27 (s, 12H)

Step 1: Synthesis of tert-butyl 5-(2-fluoro-6-nitrophenyl)-1-methyl-2-oxo-1,2-dihydropyridin-3-yl(methyl)carbamate tert-butyl 5-(2-fluoro-6-nitrophenyl)-1-methyl-2-oxo-1,2-dihydropyridin-3-yl(methyl)carbamate (800 mg, 59%, brown solid) was prepared following General Procedure 6, Step 1 using 2-bromo-1-fluoro-3-nitrobenzene (0.780 g, 3.54 mmol, 1 eq) and tert-butyl methyl(1-methyl-2-oxo-5-(4,4,5,5-tetramethyl-1,3,2-dioxaborolan-2-yl)-1,2-dihydropyridin-3-yl)carbamate (1.2 g, 3.565 mmol, 1.1 eq).
LCMS: 378 [M+1]$^+$ Step 2: Synthesis of tert-butyl 5-(2-(4-fluorophenoxy)-6-nitrophenyl)-1-methyl-2-oxo-1,2-dihydropyridin-3-yl(methyl)carbamate tert-butyl 5-(2-(4-fluorophenoxy)-6-nitrophenyl)-1-methyl-2-oxo-1,2-dihydropyridin-3-yl(methyl)carbamate (420 mg, 15%, brown solid) was prepared following General Procedure 13, Step 1 using 4-fluorophenol (0.800 g, 7.136 mmol, 1 eq) and tert-butyl 5-(2-fluoro-6-nitrophenyl)-1-methyl-2-oxo-1,2-dihydropyridin-3-yl(methyl)carbamate (0.807 g, 2.140 mmol, 0.3 eq).
LCMS: 470 [M+1]$^+$ Step 3: Synthesis of tert-butyl 5-(2-amino-6-(4-fluorophenoxy)phenyl)-1-methyl-2-oxo-1,2-dihydropyridin-3-yl(methyl)carbamate tert-butyl 5-(2-amino-6-(4-fluorophenoxy)phenyl)-1-methyl-2-oxo-1,2-dihydropyridin-3-yl(methyl)carbamate (280 mg, 71%, brown solid) was prepared following General Procedure 1, Step 2 using tert-butyl 5-(2-(4-fluorophenoxy)-6-nitrophenyl)-1-methyl-2-oxo-1,2-dihydropyridin-3-yl(methyl)carbamate (420 mg, 1.13 mmol, 1 eq).
LCMS: 440 [M+1]$^+$ Step 4: Synthesis of 5-(2-amino-6-(4-fluorophenoxy)phenyl)-1-methyl-3-(methylamino)pyridin-2(1H)-one 5-(2-amino-6-(4-fluorophenoxy)phenyl)-1-methyl-3-(methylamino)pyridin-2(1H)-one (200 mg, 62%, brown solid) was prepared following General Procedure 9, Step 3 using tert-butyl 5-(2-amino-6-(4-fluorophenoxy)phenyl)-1-methyl-2-oxo-1,2-dihydropyridin-3-yl(methyl)carbamate (280 mg, 0.612 mmol).
LCMS: 340 [M+1]$^+$ Step 5: Synthesis of N-(3-(4-fluorophenoxy)-2-(1-methyl-5-(methylamino)-6-oxo-1,6-dihydropyridin-3-yl)phenyl)acrylamide Compound 23 (4 mg, 0.32%, off-white solid) was prepared following General Procedure 3 using 5-(2-amino-6-(4-fluorophenoxy)phenyl)-1-methyl-3-(methylamino)pyridin-2(1H)-one (280 mg, 0.612 mmol).
LCMS: 394 [M+1]$^+$
$^1$H NMR (400 MHz, Methanol-d$_4$) δ 7.51 (br s, 1H), 7.35-7.43 (m, 1H), 7.00 (t, J=8.77 Hz, 2H), 6.92 (d, J=7.45 Hz, 1H), 6.85 (dd, J=4.38, 9.21 Hz, 2H), 6.78 (s, 1H), 6.24-6.39 (m, 2H), 6.12 (s, 1H), 5.73 (dd, J=2.63, 9.21 Hz, 1H), 3.52 (s, 3H), 2.67 (s, 3H).

Example S-31: Synthesis of N-(4-isopropoxy-3-(1-methyl-5-(methylamino)-6-oxo-1,6-dihydropyridin-3-yl)phenyl)acrylamide: (General Procedure 15)
Compound 24

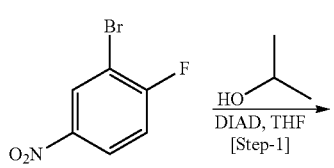

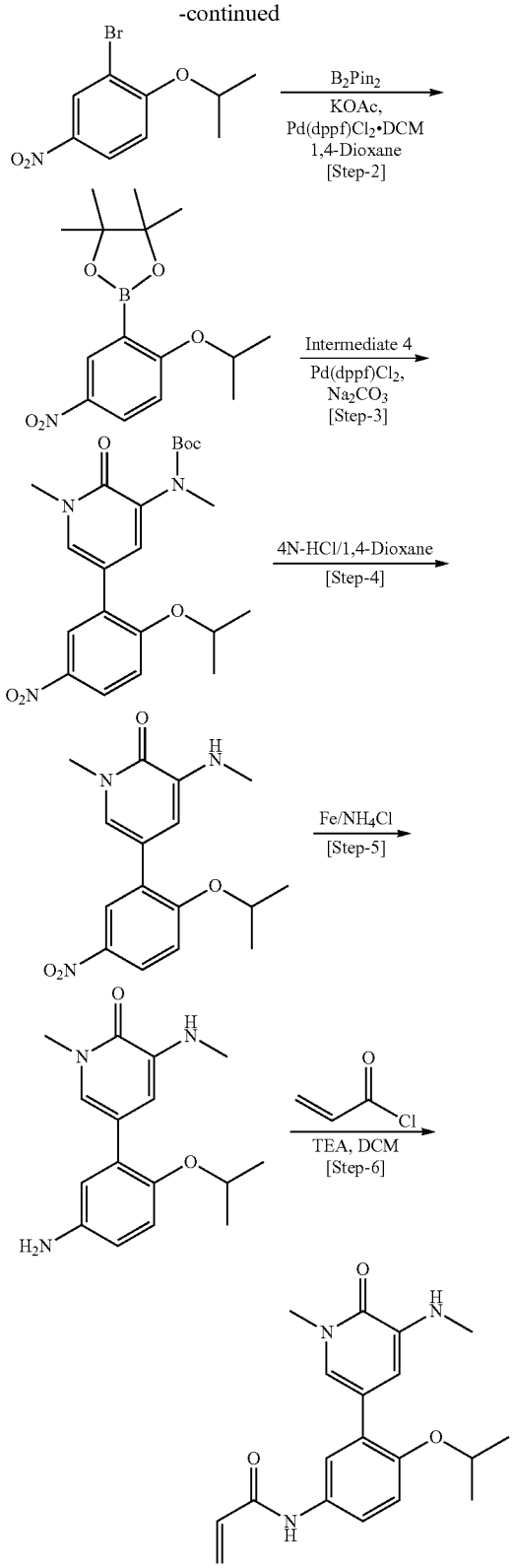

Step 1: Synthesis of
2-bromo-1-isopropoxy-4-nitrobenzene

To a stirred solution 2-bromo-1-fluoro-4-nitrobenzene (1 g, 4.58 mmol, 1 eq) in THF (20 mL) were successively added propan-2-ol (0.7 mL, 9.17 mmoL, 2 eq), triphenylphosphine (4.26 g, 13.7 mmol, 3 eq) and diisopropyl azodicarboxylate (2.7 mL, 13.7 mmol, 3 eq) at RT. The mixture was stirred at RT for 16 h and monitored by TLC. The reaction was complete after 16 h and the mixture was diluted with water (200 mL) and extracted with EtOAc (200 mL×2). The organic layer was washed with water (100 mL), brine (50 mL) dried over anhydrous $Na_2SO_4$, filtered and concentrated under reduced pressure to afford 2-bromo-1-isopropoxy-4-nitrobenzene (600 mg, 51%) as an off-white solid.

LCMS: 260 [M+1]$^+$, 262 [M+2]$^+$

Step 2: Synthesis of 2-(2-isopropoxy-5-nitrophenyl)-4,4,5,5-tetramethyl-1,3,2-dioxaborolane 2-(2-isopropoxy-5-nitrophenyl)-4,4,5,5-tetramethyl-1,3,2-dioxaborolane (300 mg, 42%, black viscous liquid) was prepared following General Procedure 1, Step 3 using 2-bromo-1-isopropoxy-4-nitrobenzene (600 mg, 2.36 mmol, 1.0 eq).

$^1$H NMR (400 MHz, CDCl$_3$) δ 8.46 (d, J=2.63 Hz, 1H), 8.24 (dd, J=2.63, 9.21 Hz, 1H), 6.88 (d, J=9.21 Hz, 1H), 4.58-4.66 (m, 1H), 1.39 (s, 3H), 1.38 (s, 3H), 1.36 (s, 12H).

Step 3: Synthesis of tert-butyl 5-(2-isopropoxy-5-nitrophenyl)-1-methyl-2-oxo-1,2-dihydropyridin-3-yl(methyl)carbamate tert-butyl 5-(2-isopropoxy-5-nitrophenyl)-1-methyl-2-oxo-1,2-dihydropyridin-3-yl(methyl)carbamate (160 mg, 48.6%, brown solid) was prepared following General Procedure 6, Step 1 using Intermediate 4 (250 mg, 0.78 mmol, 1 eq) and 2-(2-isopropoxy-5-nitrophenyl)-4,4,5,5-tetramethyl-1,3,2-dioxaborolane (292 mg, 0.94 mmol, 1.2 eq).

LCMS: 418 [M+1]$^+$

Step 4: Synthesis of 5-(2-isopropoxy-5-nitrophenyl)-1-methyl-3-(methylamino)pyridin-2(1H)-one 4N Hydrochloric acid in 1,4-Dioxane (2 mL) was added into tert-butyl 5-(2-isopropoxy-5-nitrophenyl)-1-methyl-2-oxo-1,2-dihydropyridin-3-yl(methyl)carbamate (160 mg, 0.383 mmol, 1 eq) and the mixture was stirred at RT and monitored by TLC and LC-MS. The reaction was complete after 2 h and the mixture was quenched with saturated NaHCO$_3$ solution and extracted with EtOAc (150 mL×2). The combined organic layers were washed with saturated NaHCO$_3$ solution (50 mL), water (50 mL), brine (50 mL) dried over anhydrous Na$_2$SO$_4$, filtered and concentrated under reduced pressure to afford 5-(2-isopropoxy-5-nitrophenyl)-1-methyl-3-(methylamino)pyridin-2(1H)-one (120 mg, 99%) as a brown solid.

LCMS: 318 [M+1]$^+$

Step 5: Synthesis of 5-(5-amino-2-isopropoxyphenyl)-1-methyl-3-(methylamino)pyridin-2(1H)-one 5-(5-amino-2-isopropoxyphenyl)-1-methyl-3-(methylamino)pyridin-2(1H)-one (95 mg, 88%, brown solid) was prepared following General Procedure 1, Step 2 using 5-(2-isopropoxy-5-nitrophenyl)-1-methyl-3-(methylamino)pyridin-2(1H)-one (120 mg, 0.35 mmol, 1 eq).

LCMS: 288 [M+1]$^+$

Step 6: Synthesis of N-(4-isopropoxy-3-(1-methyl-5-(methylamino)-6-oxo-1,6-dihydropyridin-3-yl)phenyl)acrylamide Compound 24 (18 mg, 16%, off-white solid) was prepared following General Procedure 3 using 5-(5-amino-2-isopropoxyphenyl)-1-methyl-3-(methylamino)pyridin-2(1H)-one (95 mg, 0.33 mmol, 1 eq).

LCMS: 342 [M+1]$^+$ $^1$H NMR (400 MHz, Methanol-$d_4$) δ 7.61 (d, J=2.63 Hz, 1H), 7.50 (dd, J=2.63, 8.77 Hz, 1H), 6.97-7.11 (m, 2H), 6.61 (d, J=1.75 Hz, 1H), 6.29-6.47 (m, 2H), 5.76 (dd, J=2.41, 9.43 Hz, 1H), 4.50-4.58 (m, 1H), 3.63 (s, 3H), 2.85 (s, 3H), 1.28 (s, 3H), 1.27 (s, 3H).

Example S-32: Synthesis of N-(3-(2-methyl-1-oxo-1,2-dihydroisoquinolin-4-yl)-4-(p-tolyloxy)phenyl)acrylamide: Compound 25

Step 2: Synthesis of N-(3-(2-methyl-1-oxo-1,2-dihydroisoquinolin-4-yl)-4-(p-tolyloxy)phenyl)acrylamide Compound 25 (17 mg, 18.5%, off-white solid) was prepared following General Procedure 3 using 4-(5-amino-2-(p-tolyloxy)phenyl)-2-methylisoquinolin-1(2H)-one (80 mg, 0.22 mmol, 1 eq).

LCMS: 411 [M+1]$^+$ $^1$H NMR (400 MHz, Methanol-$d_4$): δ 8.34 (d, J=7.89 Hz, 1H), 7.64-7.75 (m, 3H), 7.53 (s, 1H), 7.44 (d, J=7.89 Hz, 1H), 7.27 (s, 1H), 7.04 (d, J=8.77 Hz, 1H), 6.91-7.01 (m, J=8.33 Hz, 2H), 6.56-6.64 (m, J=8.77 Hz, 2H), 6.31-6.49 (m, 2H), 5.78 (dd, J=2.41, 9.43 Hz, 1H), 3.57 (s, 3H), 2.21 (s, 3H)

Example S-33: Synthesis of N-(4-(4-fluorophenoxy)-3-(2-methyl-1-oxo-1,2-dihydroisoquinolin-4-yl)phenyl)acrylamide: Compound 26

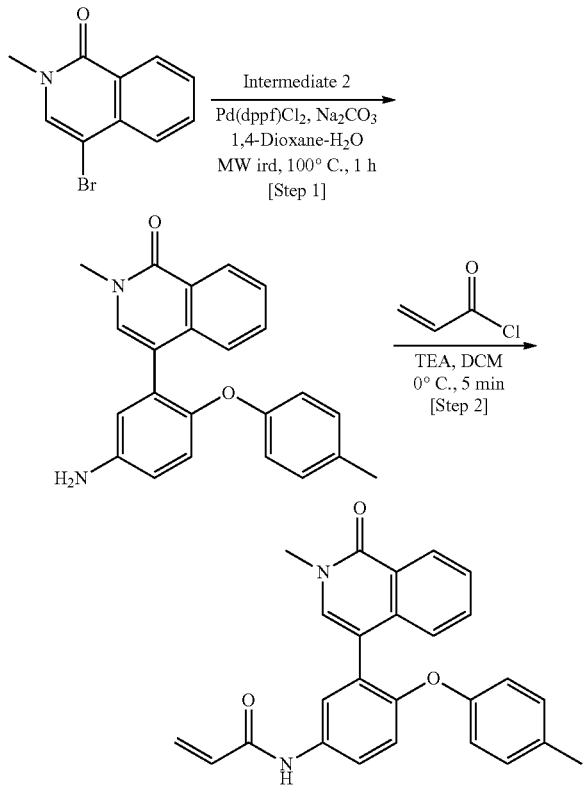

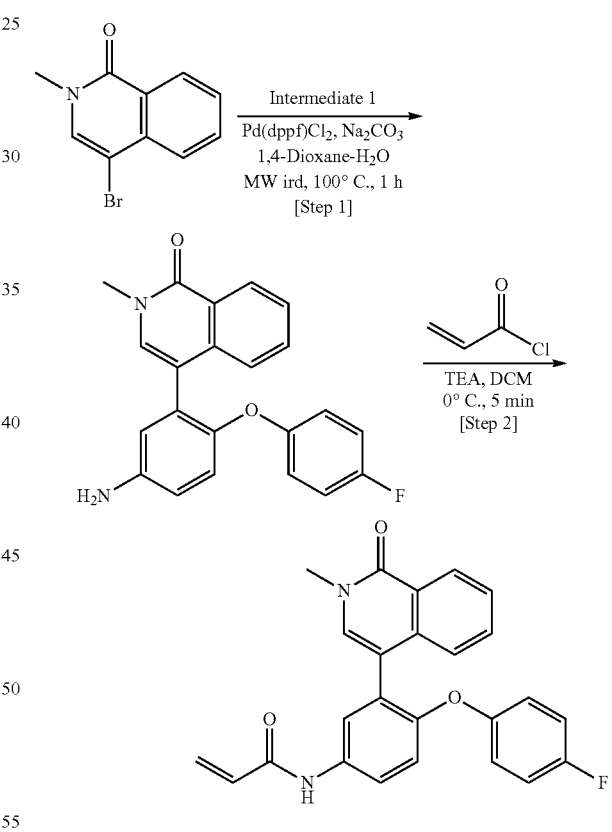

Step 1: Synthesis of 4-(5-amino-2-(p-tolyloxy)phenyl)-2-methylisoquinolin-1(2H)-one 4-(5-amino-2-(p-tolyloxy)phenyl)-2-methylisoquinolin-1(2H)-one (120 mg, 53.5%, brown solid) was prepared following General Procedure 6, Step 1 using Intermediate 2 (225 mg, 0.70 mmol, 1.1 eq) and 4-bromo-2-methylisoquinolin-1(2H)-one (150 mg, 0.63 mmol, 1 eq).

LCMS: 357 [M+1]$^+$

Step 1: Synthesis of 4-(5-amino-2-(4-fluorophenoxy)phenyl)-2-methylisoquinolin-1(2H)-one 4-(5-amino-2-(4-fluorophenoxy)phenyl)-2-methylisoquinolin-1(2H)-one (120 mg, 80%, brown solid) was prepared following General Procedure 6, Step 1 using Intermediate 1 (152 mg, 0.46 mmol, 1.1 eq) and 4-bromo-2-methylisoquinolin-1(2H)-one (100 mg, 0.42 mmol, 1 eq).

LCMS: 361 [M+1]$^+$

Step 2: Synthesis of N-(4-(4-fluorophenoxy)-3-(2-methyl-1-oxo-1,2-dihydroisoquinolin-4-yl)phenyl) acrylamide Compound 26 (32 mg, 23%, off-white solid) was prepared following General Procedure 3 using 4-(5-amino-2-(4-fluorophenoxy)phenyl)-2-methylisoquinolin-1(2H)-one (120 mg, 0.33 mmol, 1 eq).

LCMS: 415 [M+1]+

$^1$H NMR (400 MHz, Methanol-$d_4$): δ 8.35 (d, J=8.33 Hz, 1H), 7.64-7.76 (m, 3H), 7.53 (s, 1H), 7.43 (d, J=8.33 Hz, 1H), 7.30 (s, 1H), 7.08 (d, J=8.77 Hz, 1H), 6.89 (t, J=8.77 Hz, 2H), 6.68-6.73 (m, 2H), 6.33-6.48 (m, 2H), 5.79 (dd, J=2.19, 9.65 Hz, 1H), 3.59 (s, 3H).

Example S-34: Synthesis of N-(3-(2-methyl-1-oxo-1,2-dihydroisoquinolin-4-yl)-4-(trifluoromethoxy)phenyl)acrylamide: Compound 27

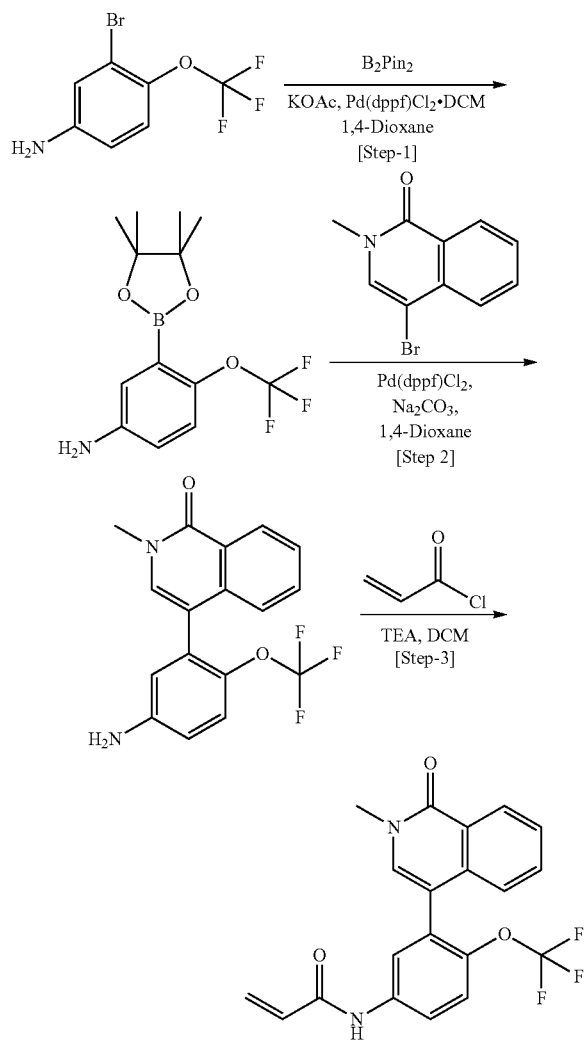

Step 1: Synthesis of 3-(4,4,5,5-tetramethyl-1,3,2-dioxaborolan-2-yl)-4-(trifluoromethoxy)aniline 3-(4,4,5,5-tetramethyl-1,3,2-dioxaborolan-2-yl)-4-(trifluoromethoxy)aniline (400 mg, 34%, black sticky solid) was prepared following General Procedure 1, Step 3 using 3-bromo-4-(trifluoromethoxy)aniline (1 G, 3.90 mmol, 1 eq).

$^1$H NMR (400 MHz, CDCl$_3$): δ 7.26 (s, 2H), 6.99-7.07 (m, 2H), 6.73 (d, J=3.07 Hz, 1H), 1.34 (s, 12H)

Step 2: Synthesis of 4-(5-amino-2-(trifluoromethoxy)phenyl)-2-methylisoquinolin-1(2H)-one 4-(5-amino-2-(trifluoromethoxy)phenyl)-2-methylisoquinolin-1(2H)-one (100 mg, 71.5%, off-white solid) was prepared following General Procedure 6, Step 1 using 3-(4,4,5,5-tetramethyl-1,3,2-dioxaborolan-2-yl)-4-(trifluoromethoxy)aniline (140 mg, 0.46 mmol, 1.1 eq) and 4-bromo-2-methylisoquinolin-1(2H)-one (100 mg, 0.42 mmol, 1 eq).

LCMS: 335 [M+1]+

Step 3: Synthesis of N-(3-(2-methyl-1-oxo-1,2-dihydroisoquinolin-4-yl)-4-(trifluoromethoxy)phenyl) acrylamide Compound 27 (11 mg, 9.5%, off-white solid) was prepared following General Procedure 3 using 4-(5-amino-2-(trifluoromethoxy)phenyl)-2-methylisoquinolin-1(2H)-one (100 mg, 0.3 mmol, 1 eq).

LCMS: 389 [M+1]+

$^1$H NMR (400 MHz, Methanol-$d_4$): δ 8.42 (d, J=7.89 Hz, 1H), 7.77-7.90 (m, 2H), 7.68 (s, 1H), 7.58 (s, 1H), 7.39-7.50 (m, 2H), 7.26 (d, J=7.89 Hz, 1H), 6.38-6.46 (m, 2H), 5.80 (dd, J=2.63, 8.77 Hz, 1H), 3.68 (s, 3H).

Example S-35: Synthesis of N-(4-(4-fluorophenoxy)-3-(2-isopropyl-1-oxo-1,2-dihydroisoquinolin-4-yl)phenyl)acrylamide: (General Procedure 16) Compound 28

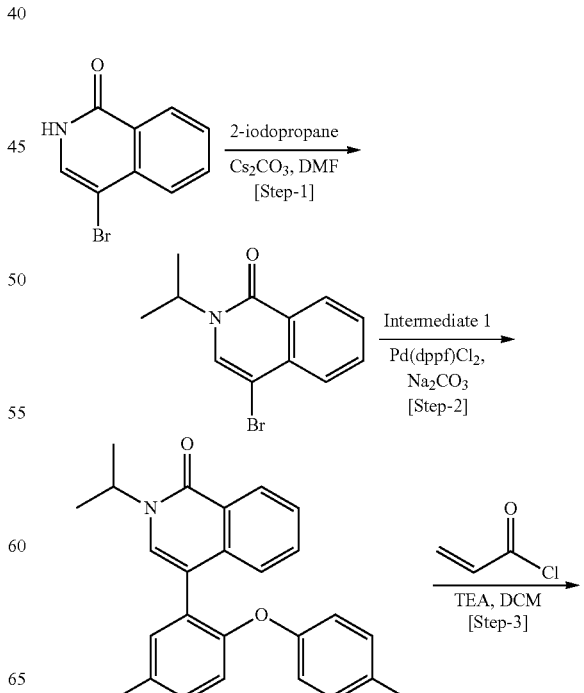

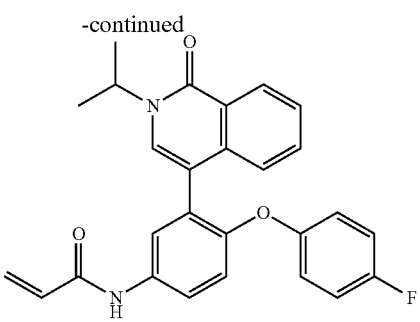

Step 1: Synthesis of 4-bromo-2-isopropylisoquinolin-1(2H)-one

To a stirred solution of 4-bromoisoquinolin-1(2H)-one (200 mg, 0.892 mmol, 1 eq) in DMSO (10 mL) was added $Cs_2CO_3$ (725 mg, 2.23 mmol, 2.5 eq) and the mixture was stirred at RT for 20 min. Then 2-iodopropane (0.303 g, 1.78 mmol 2 eq) was added to the mixture and the mixture was heated at 85° C. and monitored by TLC and LC-MS. The reaction was complete after 2 h and the mixture was diluted with water (100 mL) and extracted with EtOAc (300 mL). The organic layer was washed with brine (100 mL), dried over anhydrous $Na_2SO_4$, filtered and concentrated under reduced pressure to afford crude residue which was purified by Combi Flash chromatography—to afford 4-bromo-2-isopropylisoquinolin-1(2H)-one (140 mg, 59%) as an off-white solid.

LCMS: 266 [M+1]+, 268 [M+2]+

Step 2: Synthesis of 4-(5-amino-2-(4-fluorophenoxy)phenyl)-2-isopropylisoquinolin-1(2H)-one 4-(5-amino-2-(4-fluorophenoxy)phenyl)-2-isopropylisoquinolin-1(2H)-one (90 mg, 44%, off-white solid) was prepared following General Procedure 6, Step 1 using Intermediate 1 (191 mg, 0.58 mmol, 1.1 eq) and 4-bromo-2-isopropylisoquinolin-1(2H)-one (140 mg, 0.53 mmol, 1 eq).

LCMS: 389 [M+1]+

Step 3: Synthesis of N-(4-(4-fluorophenoxy)-3-(2-isopropyl-1-oxo-1,2-dihydroisoquinolin-4-yl)phenyl)acrylamide Compound 28 (31 mg, 30%, off-white solid) was prepared following General Procedure 3 using 4-(5-amino-2-(4-fluorophenoxy)phenyl)-2-isopropylisoquinolin-1(2H)-one (90 mg, 0.23 mmol, 1 eq).

LCMS: 443 [M+1]+

$^1$H NMR (400 MHz, Methanol-$d_4$): δ 8.35 (d, J=7.45 Hz, 1H), 7.73-7.79 (m, 2H), 7.66-7.72 (m, 1H), 7.55 (d, J=7.45 Hz, 1H), 7.43 (d, J=7.89 Hz, 1H), 7.25 (s, 1H), 7.17 (d, J=9.65 Hz, 1H), 6.85 (t, J=8.77 Hz, 2H), 6.57-6.69 (m, 2H), 6.33-6.50 (m, 2H), 5.80 (dd, J=2.19, 9.65 Hz, 1H), 5.20-5.31 (m, 1H), 1.38 (br s, 3H), 1.22 (br s, 3H).

Example S-36: Synthesis of N-(4-(2,4-difluorophenoxy)-3-(5-(dimethylamino)-1-methyl-6-oxo-1,6-dihydropyridin-3-yl)phenyl)acrylamide: Compound 29

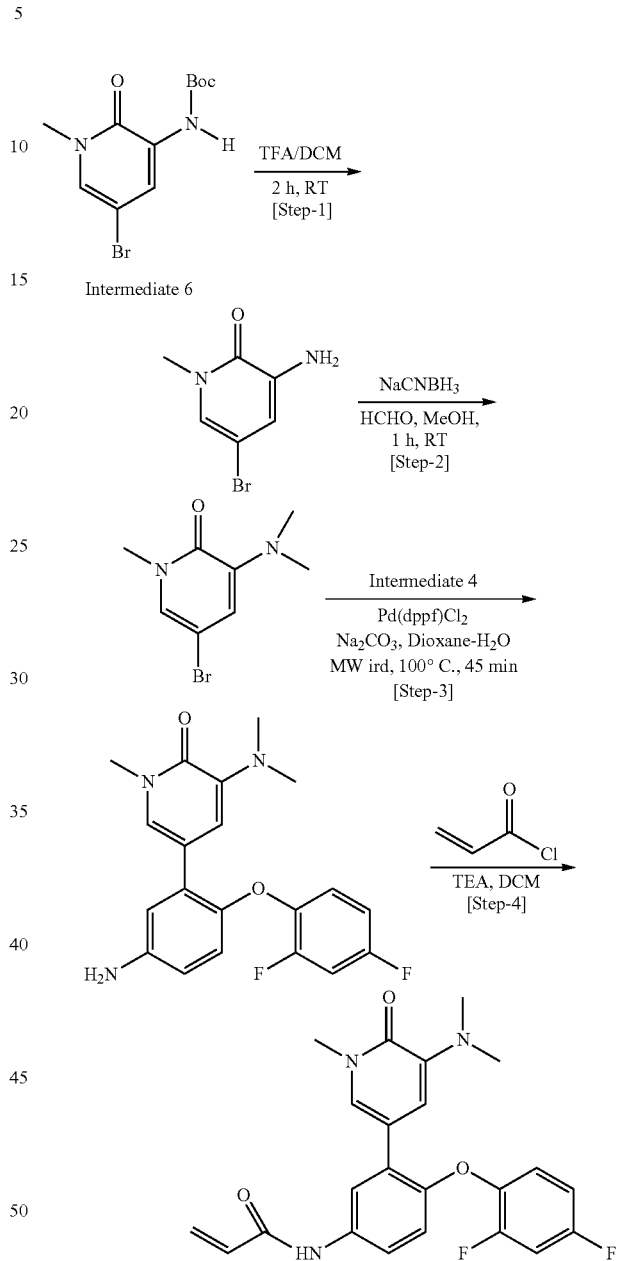

Step 1: Synthesis of 3-amino-5-bromo-1-methylpyridin-2(1H)-one 3-amino-5-bromo-1-methylpyridin-2(1H)-one (280 mg, 83.8%, off-white solid) was prepared following General Procedure 9, Step 2 using Intermediate 6 (500 mg, 1.65 mmol).

LCMS: 203 [M+1]+, 205 [M+2]+

Step 2: Synthesis of 5-bromo-3-(dimethylamino)-1-methylpyridin-2(1H)-one 5-bromo-3-(dimethylamino)-1-methylpyridin-2(1H)-one (200 mg, 70.42%, off-white solid) was prepared following General Procedure 10, Step 2 using 3-amino-5-bromo-1-methylpyridin-2(1H)-one (250 mg, 1.23 mmol, 1 eq).
LCMS: 231 [M+1]⁺, 233 [M+2]⁺

Step 3: Synthesis of 5-(5-amino-2-(2,4-difluorophenoxy)phenyl)-3-(dimethylamino)-1-methylpyridin-2(1H)-one 5-(5-amino-2-(2,4-difluorophenoxy)phenyl)-3-(dimethylamino)-1-methylpyridin-2(1H)-one (220 mg, 76%, viscous liquid) was prepared following General Procedure 6, Step 1 using 5-bromo-3-(dimethylamino)-1-methylpyridin-2(1H)-one (180 mg, 0.7826 mmol, 1.0 eq) and Intermediate 4 (298 mg, 0.86 mmol, 1.1 eq).
LCMS: 372 [M+1]⁺

Step 4: Synthesis of N-(4-(2,4-difluorophenoxy)-3-(5-(dimethylamino)-1-methyl-6-oxo-1,6-dihydropyridin-3-yl)phenyl)acrylamide Compound 29 (22 mg, 19%, off-white solid) was prepared following General Procedure 3 using 5-(5-amino-2-(2,4-difluorophenoxy)phenyl)-3-(dimethylamino)-1-methylpyridin-2(1H)-one (100 mg, 0.27 mmol, 1 eq).
LCMS: 426 [M+1]⁺
¹H NMR (400 MHz, Methanol-d₄): δ 7.88 (d, J=2.63 Hz, 1H), 7.74 (d, J=1.75 Hz, 1H), 7.57 (br s, 1H), 7.50 (dd, J=2.41, 8.55 Hz, 1H), 7.09 (br s, 1H), 6.92-7.01 (m, 2H), 6.89 (br s, 1H), 6.37-6.45 (m, 2H), 5.80 (dd, J=3.07, 9.21 Hz, 1H), 3.64 (s, 3H), 2.98 (s, 6H).

Example S-37: Synthesis of N-(4-(4-fluorophenoxy)-3-(1-methyl-5-(methylamino)-6-oxo-1,6-dihydropyridin-3-yl)phenyl)acrylamide: Compound 30

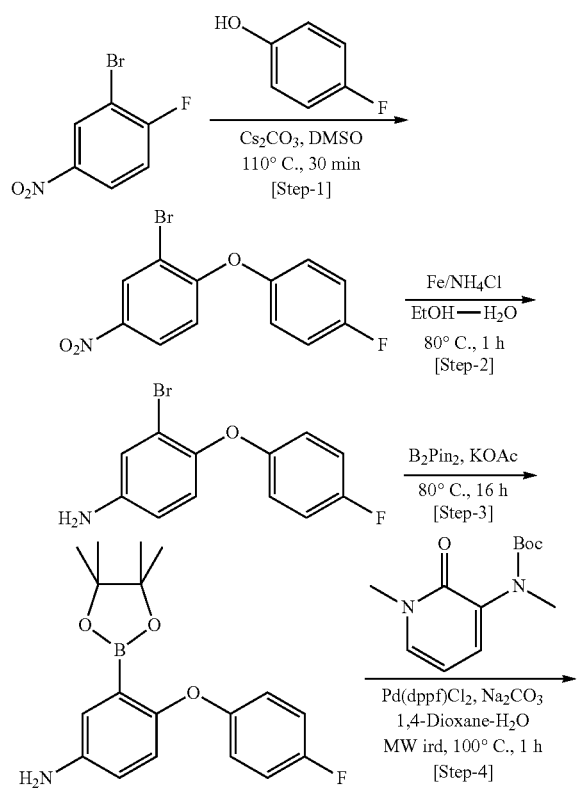

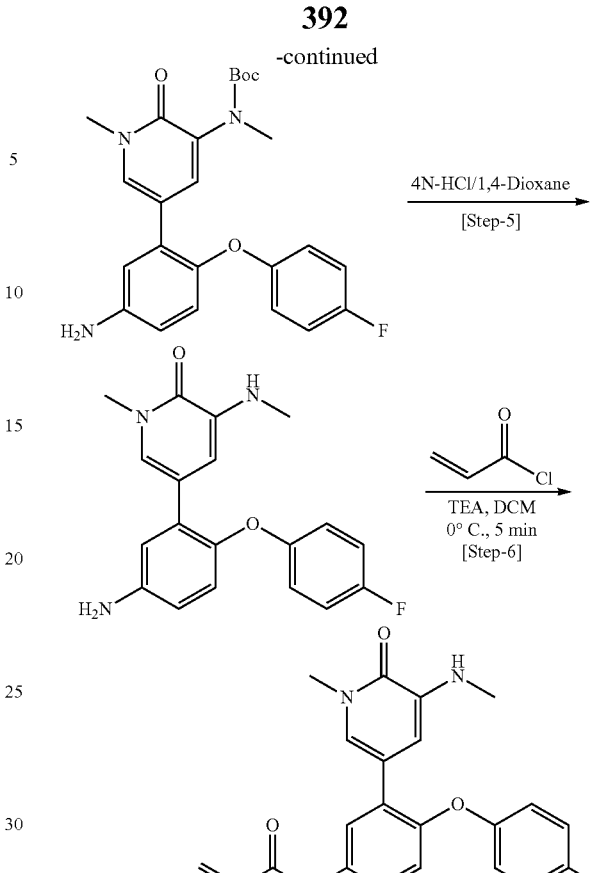

Step 1: Synthesis 2-bromo-1-(4-fluorophenoxy)-4-nitrobenzene 2-bromo-1-(4-fluorophenoxy)-4-nitrobenzene (4.2 g, 99%, black viscous liquid) was prepared following General Procedure 13, Step 1 using 4-fluorophenol (2 g, 3.05 mmol, 1.2 eq).
LCMS: 312 [M+1]⁺, 314 [M+2]⁺
¹H NMR (400 MHz, DMSO-d₆): δ 7.13 (t, J=8.77 Hz, 2H), 6.84-6.90 (m, 2H), 6.77-6.84 (m, 2H), 6.60 (d, J=2.63 Hz, 1H).

Step 2: Synthesis of 3-bromo-4-(4-fluorophenoxy)aniline 3-bromo-4-(4-fluorophenoxy)aniline (3.7 g, 98%, black viscous liquid) was prepared following General Procedure 1, Step 2 using 2-bromo-1-(4-fluorophenoxy)-4-nitrobenzene (4.2 g, 13.46 mmol, 1.0 eq).
LCMS: 282 [M+1]⁺, 284 [M+2]⁺

Step 3: Synthesis of 4-(4-fluorophenoxy)-3-(4,4,5,5-tetramethyl-1,3,2-dioxaborolan-2-yl)aniline 4-(4-fluorophenoxy)-3-(4,4,5,5-tetramethyl-1,3,2-dioxaborolan-2-yl)aniline (3.48 g, 81%, black viscous liquid) was prepared following General Procedure 1, Step 3 using 3-bromo-4-(4-fluorophenoxy)aniline (3.7 g, 13.12 mmol, 1.0 eq).

¹H NMR (400 MHz, CDCl₃): δ 7.08 (d, J=3.07 Hz, 1H), 6.82-6.94 (m, 4H), 6.79 (d, J=3.07 Hz, 1H), 6.73-6.77 (m, 2H), 1.13 (s, 12H).

Step 4: Synthesis of tert-butyl 5-(5-amino-2-(4-fluorophenoxy)phenyl)-1-methyl-2-oxo-1,2-dihydropyridin-3-yl(methyl)carbamate tert-butyl 5-(5-amino-2-(4-fluorophenoxy)phenyl)-1-methyl-2-oxo-1,2-dihydropyridin-3-yl(methyl)carbamate (3.48 g, 58%, light brown solid) was prepared following General Procedure 6, Step 1 using 3-bromo-4-(4-fluorophenoxy)aniline (3.7 g, 13.12 mmol, 1.0 eq).
LCMS: 440 [M+1]⁺

Step 5: Synthesis of 5-(5-amino-2-(4-fluorophenoxy)phenyl)-1-methyl-3-(methylamino)pyridin-2(1H)-one 4N Hydrochloric acid in 1,4-Dioxane (3 mL) was added into tert-butyl 5-(5-amino-2-(4-fluorophenoxy)phenyl)-1-methyl-2-oxo-1,2-dihydropyridin-3-yl(methyl)carbamate (0.240 g, 0.54 mmol) and the mixture was stirred at RT and monitored by TLC and LC-MS. The reaction was complete after 2 h and the mixture was quenched with saturated NaHCO₃ solution and extracted with EtOAc (250 mL×2). The combined organic layers were washed with saturated NaHCO₃ solution (100 mL), water (100 mL), brine (150 mL) dried over anhydrous Na₂SO₄, filtered and concentrated under reduced pressure to afford 5-(5-amino-2-(4-fluorophenoxy) phenyl)-1-methyl-3-(methylamino)pyridin-2(1H)-one (180 mg, 97%) as a thick viscous solid.
LCMS: 340 [M+1]⁺

Step 6: N-(4-(4-fluorophenoxy)-3-(1-methyl-5-(methylamino)-6-oxo-1,6-dihydropyridin-3-yl)phenyl)acrylamide Compound 30 (12 mg, 9%, off-white solid) was prepared following General Procedure 3 using 5-(5-amino-2-(4-fluorophenoxy) phenyl)-1-methyl-3-(methylamino)pyridin-2(1H)-one (120 mg, 0.35 mmol, 1 eq).
LCMS: 394 [M+1]⁺
¹H NMR (400 MHz, Methanol-d₄): δ 7.81 (d, J=2.63 Hz, 1H), 7.57 (s, 1H), 6.96-7.10 (m, 4H), 6.81-6.90 (m, 2H), 6.37-6.49 (m, 3H), 5.79 (dd, J=2.41, 9.43 Hz, 1H), 3.57 (s, 3H), 2.73 (s, 3H).

Example S-38: Synthesis of N-(4-(4-chlorophenoxy)-3-(2-methyl-1-oxo-1,2-dihydroisoquinolin-4-yl)phenyl)acrylamide: Compound 31

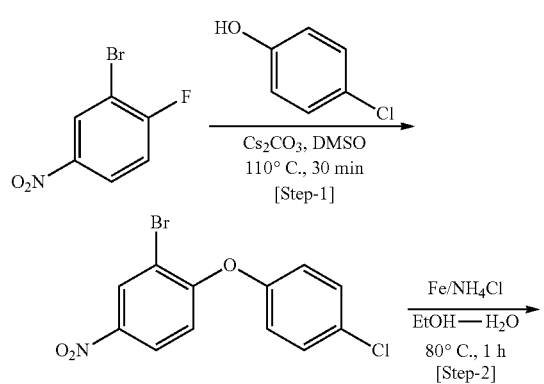

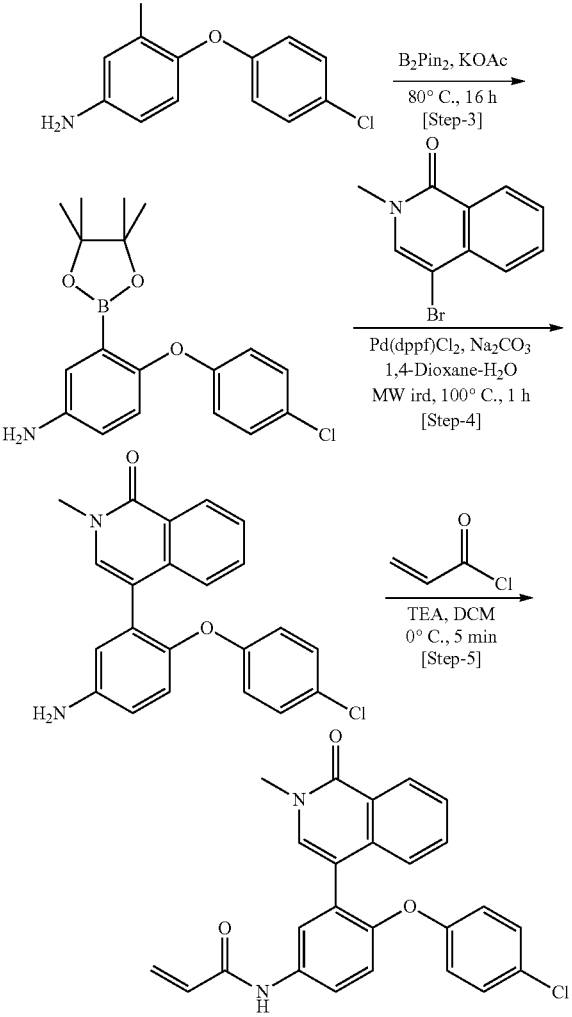

Step 1: Synthesis 2-bromo-1-(4-chlorophenoxy)-4-nitrobenzene 2-bromo-1-(4-chlorophenoxy)-4-nitrobenzene (1.4 g, 94%, brown liquid) was prepared following General Procedure 13, Step 1 using 4-chlorophenol (0.70 g, 5.4 mmol, 1.2 eq).
¹H NMR (400 MHz, CDCl₃) δ 8.55 (d, J=2.63 Hz, 1H), 8.11 (dd, J=2.63, 8.77 Hz, 1H), 7.36-7.48 (m, J=8.33 Hz, 2H), 6.99-7.09 (m, J=8.77 Hz, 2H), 6.86 (d, J=9.21 Hz, 1H).

Step 2: Synthesis of 3-bromo-4-(4-chlorophenoxy)aniline 3-bromo-4-(4-chlorophenoxy)aniline (1.19 g, 94%, black viscous liquid) was prepared following General Procedure 1, Step 2 using 2-bromo-1-(4-chlorophenoxy)-4-nitrobenzene (1.4 g, 4.2 mmol, 1.0 eq).
LCMS: 298 [M+1]⁺, 300 [M+2]⁺

Step 3: Synthesis of 4-(4-chlorophenoxy)-3-(4,4,5,5-tetramethyl-1,3,2-dioxaborolan-2-yl)aniline 4-(4-chlorophenoxy)-3-(4,4,5,5-tetramethyl-1,3,2-dioxaborolan-2-yl)aniline (1 g, 72%, black viscous liquid) was prepared following General Procedure 1, Step 3 using 3-bromo-4-(4-chlorophenoxy)aniline (1.2 g, 4.0 mmol, 1.0 eq).

$^1$H NMR (400 MHz, CDCl$_3$): δ 7.16 (d, J=9.21 Hz, 2H), 7.09 (d, J=2.63 Hz, 1H), 6.83-6.89 (m, 2H), 6.80 (d, J=3.07 Hz, 1H), 6.73-6.77 (m, 1H), 1.12 (s, 12H).

Step 4: Synthesis of 4-(5-amino-2-(4-chlorophenoxy)phenyl)-2-methylisoquinolin-1(2H)-one 4-(5-amino-2-(4-chlorophenoxy)phenyl)-2-methylisoquinolin-1(2H)-one (0.15 g, 95%, light brown solid) was prepared following General Procedure 6, Step 1 using 4-(4-chlorophenoxy)-3-(4,4,5,5-tetramethyl-1,3,2-dioxaborolan-2-yl)aniline (0.17 g, 0.50 mmol, 1.2 eq).

LCMS: 377 [M+1]$^+$

Step 5: N-(4-(4-chlorophenoxy)-3-(2-methyl-1-oxo-1,2-dihydroisoquinolin-4-yl)phenyl)acrylamide Compound 31 (20 mg, 17%, off-white solid) was prepared following General Procedure 3 using 4-(5-amino-2-(4-chlorophenoxy)phenyl)-2-methylisoquinolin-1(2H)-one (100 mg, 0.26 mmol, 1 eq).

LCMS: 431 [M+1]$^+$ $^1$H NMR (400 MHz, Methanol-d$_4$): δ 8.34 (d, J=7.89 Hz, 1H), 7.72-7.79 (m, 2H), 7.66 (s, 1H), 7.53 (s, 1H), 7.42 (d, J=8.33 Hz, 1H), 7.28 (s, 1H), 7.07-7.19 (m, 3H), 6.65 (d, J=8.77 Hz, 2H), 6.33-6.50 (m, 2H), 5.79 (dd, J=2.19, 9.65 Hz, 1H), 3.57 (s, 3H)

Example S-39: Synthesis of N-(4-(4-chloro-3-fluorophenoxy)-3-(2-methyl-1-oxo-1,2-dihydroisoquinolin-4-yl)phenyl)acrylamide: Compound 32

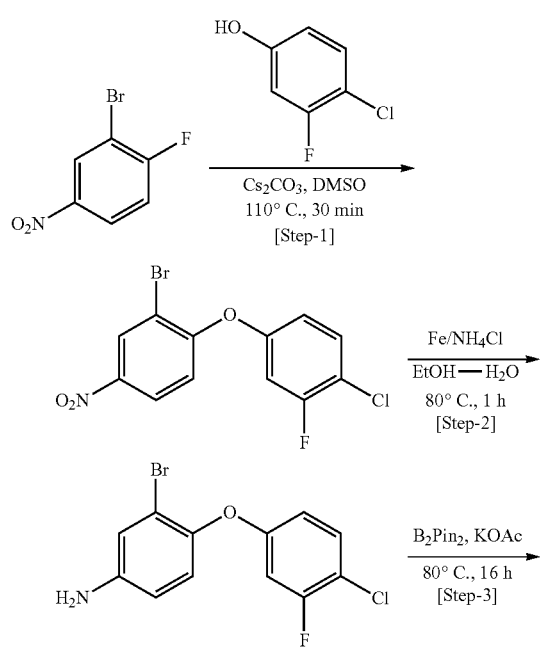

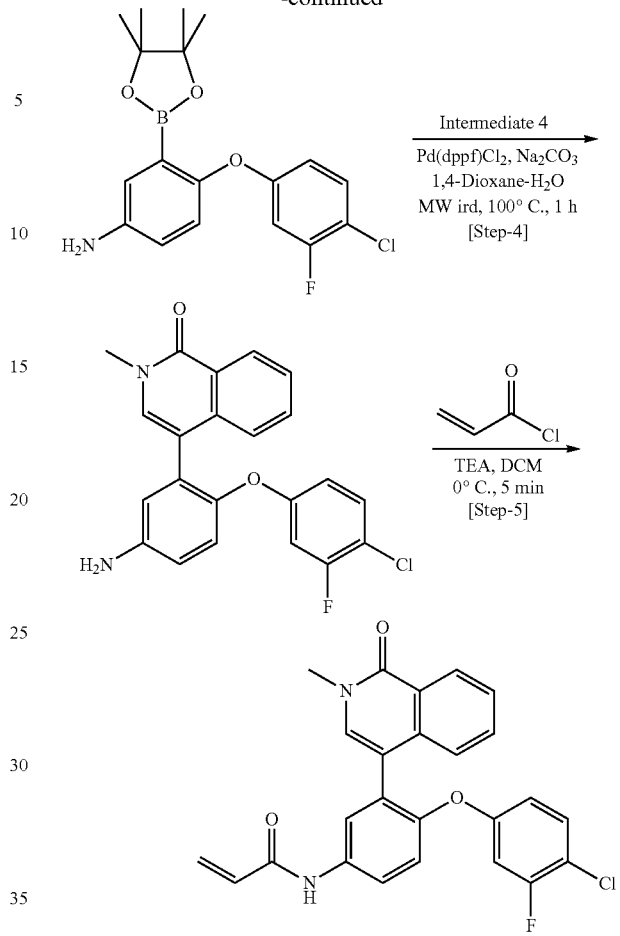

Step 1: Synthesis 2-bromo-1-(4-chloro-3-fluorophenoxy)-4-nitrobenzene 2-bromo-1-(4-chloro-3-fluorophenoxy)-4-nitrobenzene (1 g, 64%, brown liquid) was prepared following General Procedure 13, Step 1 using 4-chloro-3-fluorophenol (0.80 g, 5.4 mmol, 1.2 eq).

$^1$H NMR (400 MHz, CDCl$_3$): δ 8.46-8.62 (m, 1H), 8.16 (dd, J=2.63, 8.77 Hz, 1H), 7.39-7.56 (m, 1H), 6.73-7.02 (m, 3H).

Step 2: Synthesis of 3-bromo-4-(4-chloro-3-fluorophenoxy)aniline 3-bromo-4-(4-chloro-3-fluorophenoxy)aniline (0.97 g, 94%, black viscous liquid) was prepared following General Procedure 1, Step 2 using 2-bromo-1-(4-chloro-3-fluorophenoxy)-4-nitrobenzene (1.4 g, 4.2 mmol, 1.0 eq).

LCMS: 316 [M+1]$^+$, 318 [M+2]$^+$

Step 3: Synthesis of 4-(4-chloro-3-fluorophenoxy)-3-(4,4,5,5-tetramethyl-1,3,2-dioxaborolan-2-yl)aniline 4-(4-chloro-3-fluorophenoxy)-3-(4,4,5,5-tetramethyl-1,3,2-dioxaborolan-2-yl)aniline (0.700 g, 63%, black viscous liquid) was prepared following General Procedure 1, Step 3 using 3-bromo-4-(4-chloro-3-fluorophenoxy)aniline (0.97 g, 3.06 mmol, 1.0 eq).

¹H NMR (400 MHz, CDCl3): δ 7.19 (t, J=8.77 Hz, 1H), 7.10 (d, J=3.07 Hz, 1H), 6.87 (d, J=8.33 Hz, 1H), 6.76-6.82 (m, 1H), 6.69 (d, J=9.21 Hz, 1H), 6.52-6.62 (m, 1H), 1.14 (s, 12H).

Step 4: Synthesis of 4-(5-amino-2-(4-chloro-3-fluorophenoxy)phenyl)-2-methylisoquinolin-1(2H)-one 4-(5-amino-2-(4-chloro-3-fluorophenoxy)phenyl)-2-methylisoquinolin-1(2H)-one (0.100 g, 61%, light brown solid) was prepared following General Procedure 6, Step 1 using 4-(4-chloro-3-fluorophenoxy)-3-(4,4,5,5-tetramethyl-1,3,2-dioxaborolan-2-yl)aniline (0.100 g, 0.42 mmol, 1.0 eq).
LCMS: 395 [M+1]⁺

Step 5: N-(4-(4-chloro-3-fluorophenoxy)-3-(2-methyl-1-oxo-1,2-dihydroisoquinolin-4-yl)phenyl)acrylamide Compound 31 (15 mg, 13%, off-white solid) was prepared following General Procedure 3 using 4-(5-amino-2-(4-chloro-3-fluorophenoxy)phenyl)-2-methylisoquinolin-1(2H)-one (100 mg, 0.25 mmol, 1 eq).
LCMS: 449 [M+1]⁺
¹H NMR (400 MHz, Methanol-d₄): δ 8.34 (d, J=8.33 Hz, 1H), 7.75-7.84 (m, 2H), 7.67 (s, 1H), 7.54 (s, 1H), 7.41 (d, J=8.77 Hz, 1H), 7.31 (s, 1H), 7.16-7.25 (m, 2H), 6.55 (d, J=10.52 Hz, 1H), 6.48 (br s, 1H), 6.35-6.46 (m, 2H), 5.80 (dd, J=2.41, 9.43 Hz, 1H), 3.57 (s, 3H).

Example S-40: Synthesis of N-(4-(2,4-difluorophenoxy)-3-(2-methyl-1-oxo-1,2-dihydroisoquinolin-4-yl)phenyl)propiolamide: Compound 74

Step 1: Synthesis of 4-(5-amino-2-(2,4-difluorophenoxy)phenyl)-2-methylisoquinolin-1(2H)-one 4-(5-amino-2-(2,4-difluorophenoxy)phenyl)-2-methylisoquinolin-1(2H)-one (330 mg, 83%, brown solid) was prepared following General Procedure 6, Step 1 using Intermediate 4 (401 mg, 0.84 mmol, 1.1 eq).
LCMS: 379 [M+1]⁺

Step 2: N-(4-(2,4-difluorophenoxy)-3-(2-methyl-1-oxo-1,2-dihydroisoquinolin-4-yl)phenyl)propiolamide Compound 74 (11 mg, 10%) was prepared following General Procedure 4 using propiolic acid (0.018 g, 0.264 mmol, 1 eq).
LCMS: 431 [M+1]⁺
¹H NMR: (400 MHz, Methanol-d₄) δ 8.35 (d, J=7.89 Hz, 1H), 7.61-7.70 (m, 3H), 7.54 (d, J=7.45 Hz, 1H), 7.33-7.44 (m, 2H), 6.87-7.00 (m, 3H), 6.78 (br s, 2H), 3.64 (s, 3H).

Example S-41: Synthesis of N-(4-(4-methoxyphenoxy)-3-(2-methyl-1-oxo-1,2-dihydroisoquinolin-4-yl)phenyl)acrylamide: Compound 409

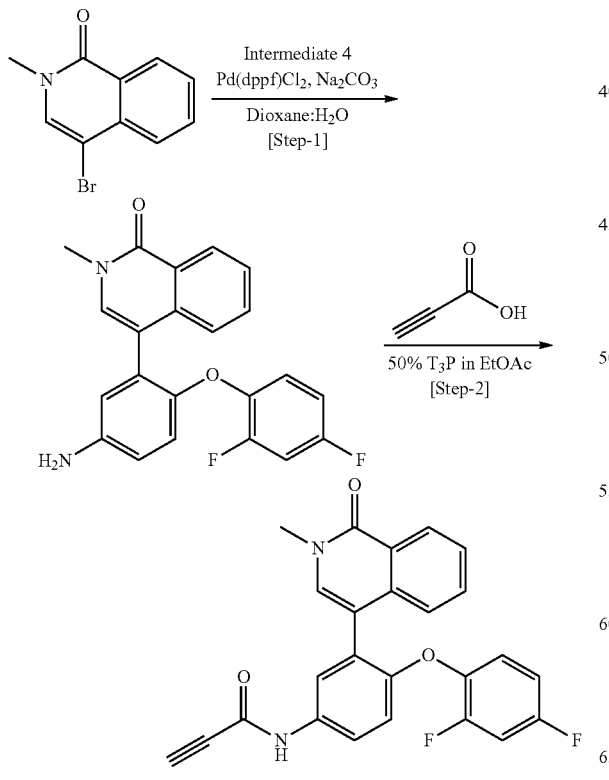

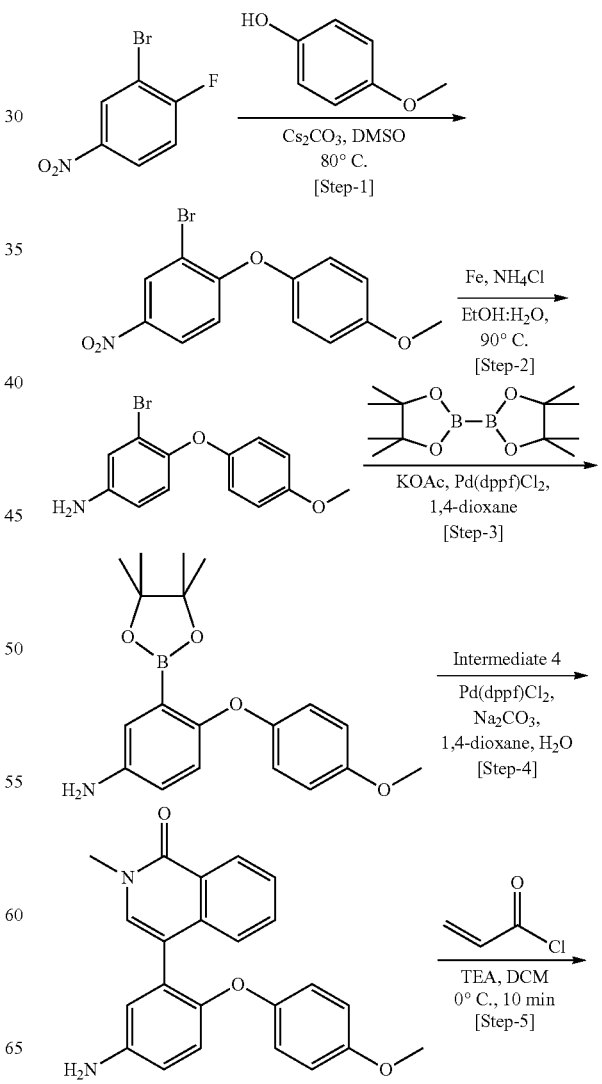

-continued

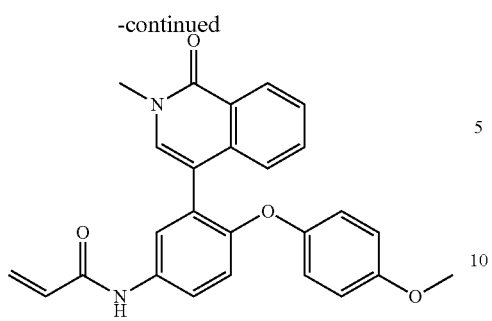

Step 1: Synthesis of 2-bromo-1-(4-methoxyphenoxy)-4-nitrobenzene 2-bromo-1-(4-methoxyphenoxy)-4-nitrobenzene (1.4 g, 95%, brown solid) was prepared following General Procedure 13, Step 1 4-methoxyphenol (0.677 g, 5.44 mmol, 1.2 eq).
LCMS: 324 [M+1]$^+$, 326 [M+2]$^+$

Step 2: Synthesis of 3-bromo-4-(4-methoxyphenoxy)aniline 3-bromo-4-(4-methoxyphenoxy)aniline (1.2 g, 94%, brown solid) was prepared following General Procedure 1, Step 2 using 2-bromo-1-(4-methoxyphenoxy)-4-nitrobenzene (1.4 g, 4.358 mmol, 1 eq).
LCMS: 294 [M+1]$^+$, 296 [M+2]$^+$

Step 3: Synthesis of 4-(4-methoxyphenoxy)-3-(4,4,5,5-tetramethyl-1,3,2-dioxaborolan-2-yl)aniline 4-(4-methoxyphenoxy)-3-(4,4,5,5-tetramethyl-1,3,2-dioxaborolan-2-yl)aniline (0.8 g, 58%, off-white solid) was prepared following General Procedure 1, Step 3 using 3-bromo-4-(4-methoxyphenoxy)aniline (1.2 g, 4.079 mmol, 1 eq).
$^1$H NMR (400 MHz, CDCl$_3$) δ 7.26 (s, 2H), 7.06 (d, J=3.07 Hz, 1H), 6.89 (s, 1H), 6.82 (td, J=2.58, 8.88 Hz, 2H), 6.66 (s, 1H), 3.60 (s, 3H), 1.15 (s, 12H).

Step 4: Synthesis of 4-(5-amino-2-(4-methoxyphenoxy)phenyl)-2-methylisoquinolin-1(2H)-one 4-(5-amino-2-(4-methoxyphenoxy)phenyl)-2-methylisoquinolin-1(2H)-one (0.09 g, 58%, off white solid) was prepared following General Procedure 6, Step 1 using 4-(4-methoxyphenoxy)-3-(4,4,5,5-tetramethyl-1,3,2-dioxaborolan-2-yl)aniline (0.171 g, 0.504 mmol, 1.2 eq).
LCMS: 373 [M+1]$^+$

Step 5: Synthesis of N-(4-(4-methoxyphenoxy)-3-(2-methyl-1-oxo-1,2-dihydroisoquinolin-4-yl)phenyl)acrylamide Compound 409 (9 mg, 9%, off-white solid) was prepared following General Procedure 3 using 4-(5-amino-2-(4-methoxyphenoxy)phenyl)-2-methylisoquinolin-1(2H)-one (0.09 g, 0.241 mmol, 1 eq).
LCMS: 427 [M+1]$^+$
$^1$H NMR (400 MHz, Methanol-d$_4$): δ 8.35 (d, J=7.45 Hz, 1H), 7.61-7.74 (m, 3H), 7.53 (br s, 1H), 7.45 (d, J=8.33 Hz, 1H), 7.30 (s, 1H), 6.99 (d, J=8.33 Hz, 1H), 6.72-6.79 (m, 2H), 6.64-6.72 (m, 2H), 6.31-6.46 (m, 2H), 5.77 (d, J=9.21 Hz, 1H), 3.70 (s, 3H), 3.60 (s, 3H).

Example S-42: Synthesis of N-(4-(2,4-difluorophenoxy)-3-(2-methyl-1-oxo-1,2-dihydroisoquinolin-4-yl)phenyl)but-2-ynamide: Compound 393

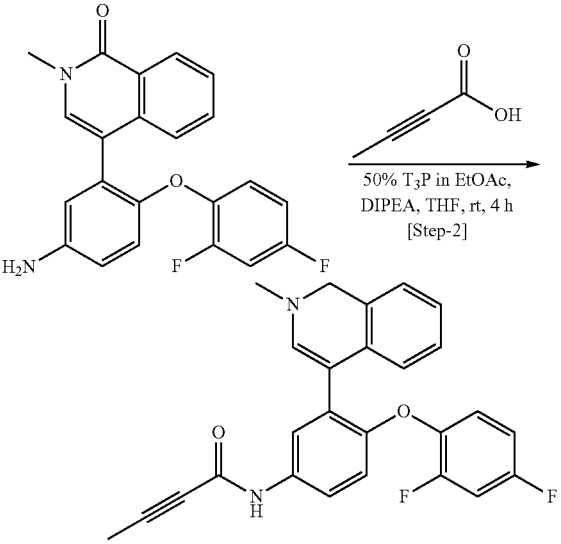

Step 1: Synthesis of 4-(5-amino-2-(2,4-difluorophenoxy)phenyl)-2-methylisoquinolin-1(2H)-one 4-(5-amino-2-(2,4-difluorophenoxy)phenyl)-2-methylisoquinolin-1(2H)-one (0.390 g, 98%, off white solid) was prepared following General Procedure 6, Step 1 using 4-(2,4-difluorophenoxy)-3-(4,4,5,5-tetramethyl-1,3,2-dioxaborolan-2-yl)aniline (0.437 g, 1.26 mmol, 1.2 eq).
LCMS: 379 [M+1]$^+$

Step 2: Synthesis of N-(4-(2,4-difluorophenoxy)-3-(2-methyl-1-oxo-1,2-dihydroisoquinolin-4-yl)phenyl)but-2-ynamide Compound 393 (0.01 g, 9%, off white solid)
LCMS: 445 [M+1]$^+$
$^1$H NMR (400 MHz, Methanol-d$_4$): δ 8.35 (d, J=7.45 Hz, 1H), 7.59-7.72 (m, 3H), 7.54 (d, J=7.02 Hz, 1H), 7.41 (d, J=8.33 Hz, 1H), 7.36 (s, 1H), 6.87-7.00 (m, 3H), 6.77 (br s, 1H), 3.63 (s, 3H), 2.03 (s, 3H).

Example S-43: Synthesis of N-(4-(2,4-difluorophenylamino)-3-(1-methyl-5-(methylamino)-6-oxo-1,6-dihydropyridin-3-yl)phenyl)acrylamide: Compound 288

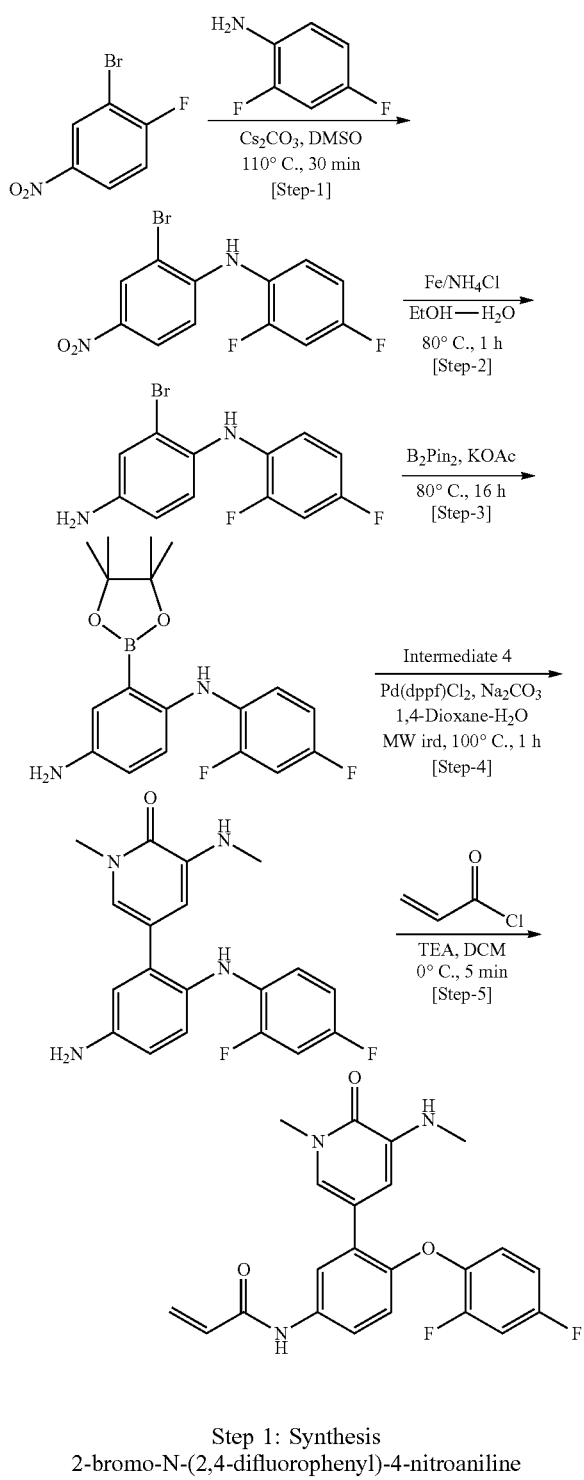

Step 1: Synthesis 2-bromo-N-(2,4-difluorophenyl)-4-nitroaniline 2-bromo-N-(2,4-difluorophenyl)-4-nitroaniline (0.500 g, 33.33%, yellow solid) was prepared following General Procedure 13, Step 1 using 2-bromo-1-fluoro-4-nitrobenzene (0.766 g, 5.93 mmol, 1.3 eq).

$^1$H NMR (400 MHz, DMSO-d$_6$): δ 8.37 (d, J=7.02 Hz, 1H), 8.03 (d, J=8.33 Hz, 1H), 7.37-7.56 (m, 2H), 7.14-7.25 (m, 1H), 6.52 (d, J=10.52 Hz, 1H).

Step 2: Synthesis of 2-bromo-N$^1$-(2,4-difluorophenyl)benzene-1,4-diamine 2-bromo-N$^1$-(2,4-difluorophenyl)benzene-1,4-diamine (230 mg, 56%, black viscous liquid) was prepared following General Procedure 1, Step 2 using 2-bromo-N-(2,4-difluorophenyl)-4-nitroaniline (0.500 g, 1.52 mmol, 1.0 eq).
LCMS: 299 [M+1]$^+$, 300 [M+2]$^+$

Step 3: Synthesis of N$^1$-(2,4-difluorophenyl)-2-(4,4,5,5-tetramethyl-1,3,2-dioxaborolan-2-yl)benzene-1,4-diamine N$^1$-(2,4-difluorophenyl)-2-(4,4,5,5-tetramethyl-1,3,2-dioxaborolan-2-yl)benzene-1,4-diamine (230 mg, 56%, black viscous liquid) was prepared following General Procedure 1, Step 3 using 2-bromo-N$^1$-(2,4-difluorophenyl)benzene-1,4-diamine (230 mg, 0.7744 mmol, 1.0 eq).

$^1$H NMR (400 MHz, Methanol-d$_4$): δ 7.17-7.23 (m, 1H), 7.12 (d, J=3.07 Hz, 1H), 7.02 (d, J=8.77 Hz, 1H), 6.84 (d, J=2.63 Hz, 1H), 6.76 (dd, J=2.85, 8.55 Hz, 1H), 6.7-6.66 (m, 1H), 1.30-1.50 (m, 12H).

Step 4: Synthesis of 5-(5-amino-2-(2,4-difluorophenylamino)phenyl)-1-methyl-3-(methylamino)pyridin-2(1H)-one 5-(5-amino-2-(2,4-difluorophenylamino)phenyl)-1-methyl-3-(methylamino)pyridin-2(1H)-one (90 mg, 46%, brown solid) was prepared following General Procedure 6, Step 1 using N$^1$-(2,4-difluorophenyl)-2-(4,4,5,5-tetramethyl-1,3,2-dioxaborolan-2-yl)benzene-1,4-diamine (287 mg, 0.82 mmol, 1.5 eq) and 5-bromo-1-methyl-3-(methylamino)pyridin-2(1H)-one (120 mg, 0.55 mmol, 1 eq).
LCMS: 357 [M+1]$^+$

Step 5: Synthesis of N-(4-(2,4-difluorophenylamino)-3-(1-methyl-5-(methylamino)-6-oxo-1,6-dihydropyridin-3-yl)phenyl)acrylamide Compound 288 (10 mg, 10%, off-white solid) was prepared following General Procedure 3 using 5-(5-amino-2-(2,4-difluorophenylamino)phenyl)-1-methyl-3-(methylamino)pyridin-2(1H)-one (0.09 g, 0.25 mmol, 1 eq).
LCMS: 411 [M+1]$^+$
$^1$H NMR (400 MHz, Methanol-d$_4$): δ 7.63 (d, J=2.63 Hz, 1H), 7.43-7.53 (m, 1H), 7.06 (d, J=8.33 Hz, 1H), 6.98 (d, J=1.75 Hz, 1H), 6.83-6.93 (m, 2H), 6.73 (br s, 1H), 6.25-6.50 (m, 3H), 5.77 (dd, J=2.19, 9.65 Hz, 2H), 3.58 (s, 3H), 2.72 (s, 3H).

Example S-44: Synthesis of N-(4-(2,4-difluorophenylamino)-3-(2-methyl-1-oxo-1,2-dihydroisoquinolin-4-yl)phenyl)acrylamide: Compound 305

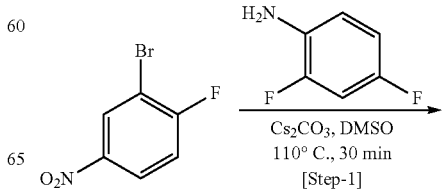

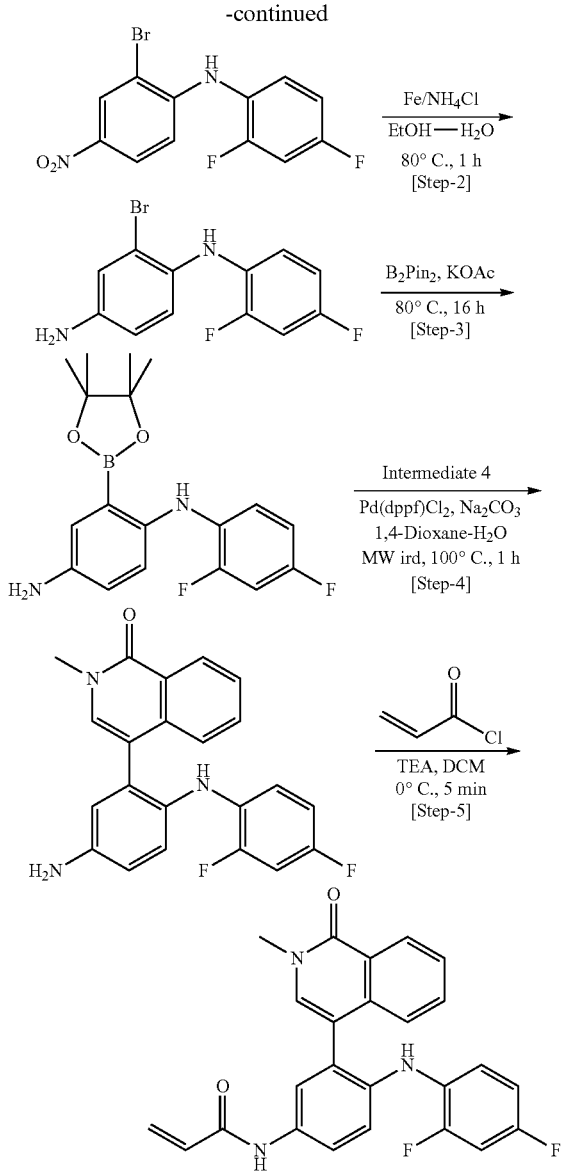

Step 1: Synthesis 2-bromo-N-(2,4-difluorophenyl)-4-nitroaniline 2-bromo-N-(2,4-difluorophenyl)-4-nitroaniline (0.500 g, 33.33%, yellow solid) was prepared following General Procedure 13, Step 1 using 2-bromo-1-fluoro-4-nitrobenzene (0.766 g, 5.93 mmol, 1.3 eq).

$^1$H NMR (400 MHz, DMSO-$d_6$): δ 8.37 (d, J=7.02 Hz, 1H), 8.03 (d, J=8.33 Hz, 1H), 7.37-7.56 (m, 2H), 7.14-7.25 (m, 1H), 6.52 (d, J=10.52 Hz, 1H).

Step 2: Synthesis of 2-bromo-N$^1$-(2,4-difluorophenyl)benzene-1,4-diamine 2-bromo-N$^1$-(2,4-difluorophenyl)benzene-1,4-diamine (230 mg, 56%, black viscous liquid) was prepared following General Procedure 1, Step 2 using 2-bromo-N-(2,4-difluorophenyl)-4-nitroaniline (0.500 g, 1.52 mmol, 1.0 eq).

LCMS: 299 [M+1]$^+$, 301 [M+2]$^+$

Step 3: Synthesis of N$^1$-(2,4-difluorophenyl)-2-(4,4,5,5-tetramethyl-1,3,2-dioxaborolan-2-yl)benzene-1,4-diamine N$^1$-(2,4-difluorophenyl)-2-(4,4,5,5-tetramethyl-1,3,2-dioxaborolan-2-yl)benzene-1,4-diamine (230 mg, 56%, black viscous liquid) was prepared following General Procedure 1, Step 3 using 2-bromo-N$^1$-(2,4-difluorophenyl)benzene-1,4-diamine (230 mg, 0.7744 mmol, 1.0 eq).

$^1$H NMR (400 MHz, Methanol-$d_4$): δ 7.17-7.23 (m, 1H), 7.12 (d, J=3.07 Hz, 1H), 7.02 (d, J=8.77 Hz, 1H), 6.84 (d, J=2.63 Hz, 1H), 6.76 (dd, J=2.85, 8.55 Hz, 1H), 6.7-6.66 (m, 1H), 1.30-1.50 (m, 12H).

Step 4: Synthesis of 4-(5-amino-2-(2,4-difluorophenylamino)phenyl)-2-methylisoquinolin-1(2H)-one 4-(5-amino-2-(2,4-difluorophenylamino)phenyl)-2-methylisoquinolin-1(2H)-one (100 mg, 63%, brown solid) was prepared following General Procedure 6, Step 1 using N$^1$-(2,4-difluorophenyl)-2-(4,4,5,5-tetramethyl-1,3,2-dioxaborolan-2-yl)benzene-1,4-diamine (217 mg, 0.63 mmol, 1.5 eq) and 4-bromo-2-methylisoquinolin-1(2H)-one (100 mg, 0.42 mmol, 1 eq).

LCMS: 378 [M+1]$^+$

Step 5: Synthesis of N-(4-(2,4-difluorophenylamino)-3-(2-methyl-1-oxo-1,2-dihydroisoquinolin-4-yl)phenyl)acrylamide Compound 305 (34 mg, 30%, off-white solid) was prepared following General Procedure 3 using 4-(5-amino-2-(2,4-difluorophenylamino)phenyl)-2-methylisoquinolin-1(2H)-one (0.10 g, 0.26 mmol, 1 eq).

LCMS: 432 [M+1]$^+$ $^1$H NMR (400 MHz, DMSO-$d_6$): δ 10.06 (s, 1H), 8.26 (d, J=7.89 Hz, 1H), 7.52-7.65 (m, 2H), 7.42-7.52 (m, 2H), 7.24 (d, J=7.89 Hz, 1H), 7.12 (br s, 1H), 7.01 (d, J=6.14 Hz, 1H), 6.77-6.89 (m, 2H), 6.38 (d, J=10.09 Hz, 1H), 6.20 (dd, J=1.75, 17.10 Hz, 1H), 5.71 (dd, J=1.75, 10.09 Hz, 1H), 3.54 (s, 3H).

Example S-45: Synthesis of N-(3-(2-methyl-1-oxo-1,2-dihydroisoquinolin-4-yl)-4-(p-tolylamino)phenyl) acrylamide: Compound 309

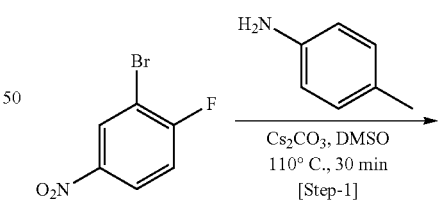

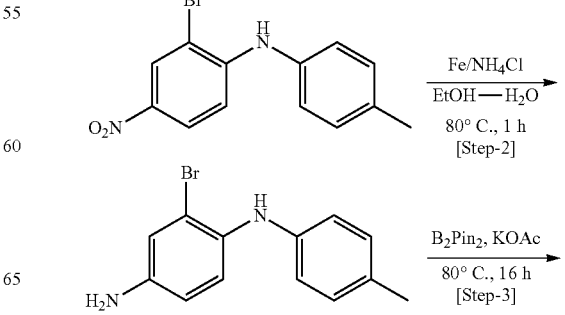

405

-continued

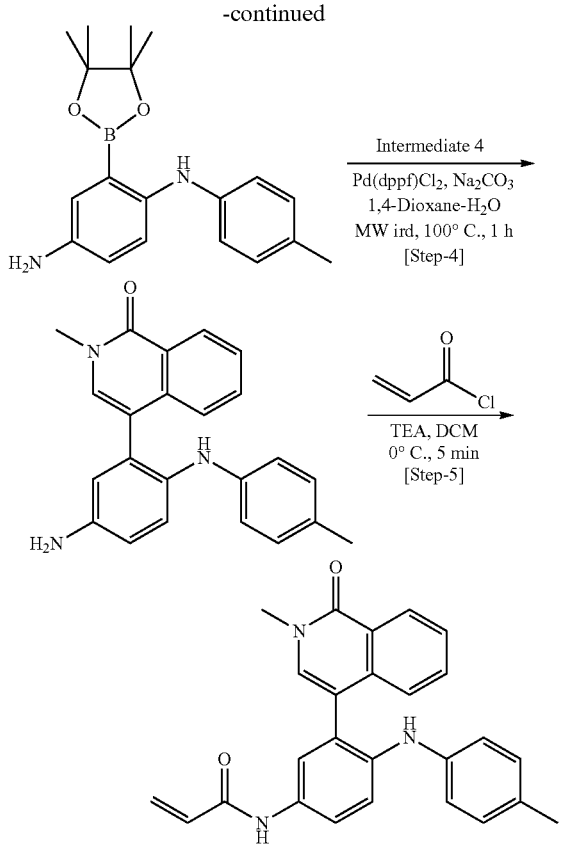

Step 1: Synthesis of 2-bromo-4-nitro-N-p-tolylaniline 2-bromo-4-nitro-N-p-tolylaniline (1 g, 72%, yellowish liquid) was prepared following General Procedure 13, Step 1 using p-toluidine (0.60 g, 5.9 mmol, 1.3 eq).

$^1$H NMR (400 MHz, CDCl$_3$): δ 7.26 (s, 1H), 7.20-7.24 (m, 1H), 7.11-7.16 (m, 1H), 6.94-7.00 (m, J=7.89 Hz, 2H), 6.58-6.63 (m, J=8.33 Hz, 2H).

Step 2: Synthesis of 2-bromo-N1-p-tolylbenzene-1,4-diamine 2-bromo-N1-p-tolylbenzene-1,4-diamine (800 mg, 88%, black viscous liquid) was prepared following General Procedure 1, Step 2 using 2-bromo-4-nitro-N-p-tolylaniline (1 g, 3.2 mmol, 1.0 eq).

LCMS: 277 [M+1]$^+$, 279 [M+2]$^+$

Step 3: Synthesis of 2-(4,4,5,5-tetramethyl-1,3,2-dioxaborolan-2-yl)-N1-p-tolylbenzene-1,4-diamine 2-(4,4,5,5-tetramethyl-1,3,2-dioxaborolan-2-yl)-N1-p-tolylbenzene-1,4-diamine (900 mg, 96%, black viscous liquid) was prepared following General Procedure 1, Step 3 using 2-bromo-N1-p-tolylbenzene-1,4-diamine (800 mg, 2.89 mmol, 1.0 eq).

$^1$H NMR (400 MHz, CDCl$_3$): δ 7.08-7.13 (m, 2H), 7.02-7.08 (m, 2H), 6.97-7.02 (m, 2H), 6.94 (d, J=8.77 Hz, 1H), 2.25-2.32 (m, 3H), 1.24 (s, 12H).

406

Step 4: Synthesis of 4-(5-amino-2-(p-tolylamino)phenyl)-2-methylisoquinolin-1(2H)-one 4-(5-amino-2-(p-tolylamino)phenyl)-2-methylisoquinolin-1(2H)-one (50 mg, 34%, brown solid) was prepared following General Procedure 6, Step 1 using 2-(4,4,5,5-tetramethyl-1,3,2-dioxaborolan-2-yl)-N1-p-tolylbenzene-1,4-diamine (153 mg, 0.50 mmol, 1.2 eq) and 4-bromo-2-methylisoquinolin-1(2H)-one (100 mg, 0.42 mmol, 1 eq).

LCMS: 356 [M+1]$^+$

Step 5: Synthesis of N-(3-(2-methyl-1-oxo-1,2-dihydroisoquinolin-4-yl)-4-(p-tolylamino)phenyl)acrylamide Compound 309 (11 mg, 19%, off-white solid) was prepared following General Procedure 3 using 44-(5-amino-2-(p-tolylamino)phenyl)-2-methylisoquinolin-1(2H)-one (0.50 g, 0.14 mmol, 1 eq).

LCMS: 410 [M+1]$^+$ $^1$H NMR (400 MHz, DMSO-d$_6$): δ 10.06 (s, 1H), 8.27 (d, J=7.89 Hz, 1H), 7.49-7.65 (m, 3H), 7.38-7.48 (m, 2H), 7.22 (t, J=8.77 Hz, 2H), 6.94 (d, J=7.89 Hz, 2H), 6.79-6.89 (m, 2H), 6.39 (d, J=10.09 Hz, 1H), 6.20 (d, J=16.66 Hz, 1H), 5.70 (d, J=10.52 Hz, 1H), 3.54 (s, 3H), 2.17 (s, 3H).

Example S-46: Synthesis of N-(4-(2,6-dimethylphenylamino)-3-(2-methyl-1-oxo-1,2-dihydroisoquinolin-4-yl)phenyl)acrylamide: Compound 313

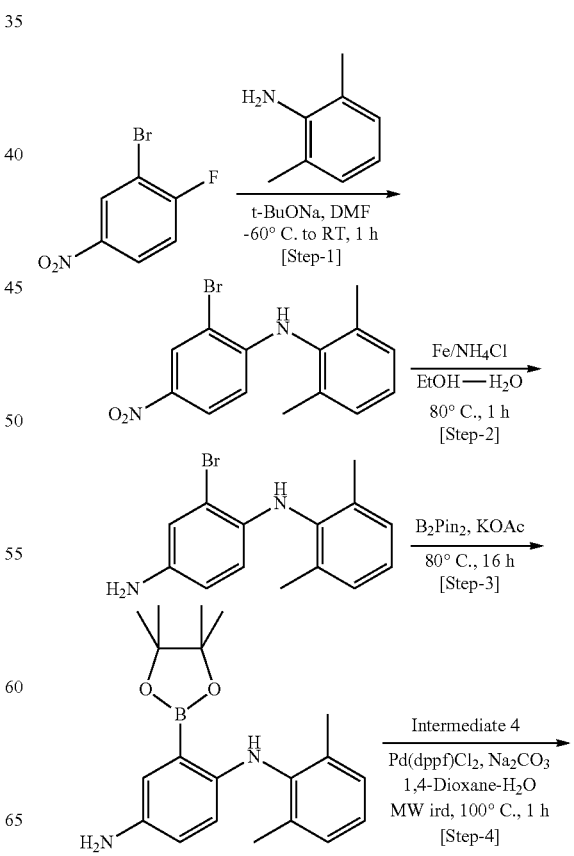

407

-continued

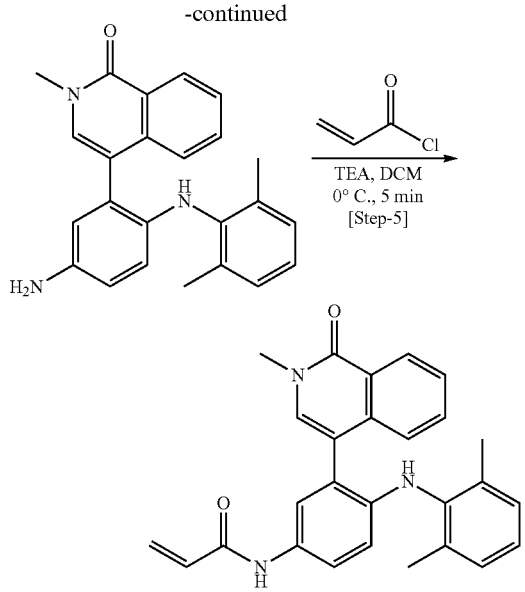

Step 1: Synthesis of 2-bromo-N-(2,6-dimethylphenyl)-4-nitroaniline

To a solution of 2,6-dimethylaniline (2.0 g, 16.58 mmol, 1.0 eq) in DMF (30 mL) was added t-BuONa (11 g, 99 mmol, 60 eq) at −60° C. followed by an addition of 2-bromo-1-fluoro-4-nitrobenzene (4 g, 18.15 mmol, 1.1 eq). The temperature of the mixture was gradually increased to RT over a period of 30 min and monitored by TLC and LC-MS. The reaction was complete after 2 h and to the mixture was added ice-cold water (50 mL) to obtain a precipitate which was filtered over Büchner funnel; dried under vacuum to afford 2-bromo-N-(2,6-dimethylphenyl)-4-nitroaniline (1.1 g, 21%) as a yellow solid.

$^1$H NMR (400 MHz, DMSO-$d_6$): δ 8.37 (d, J=2.63 Hz, 1H), 8.23 (s, 1H), 7.98 (dd, J=2.63, 9.21 Hz, 1H), 7.23 (s, 3H), 2.10 (s, 6H).

Step 2: Synthesis of 2-bromo-N1-(2,6-dimethylphenyl)benzene-1,4-diamine 2-bromo-N1-(2,6-dimethylphenyl)benzene-1,4-diamine (1 g, 100%, black viscous liquid) was prepared following General Procedure 1, Step 2 using 22-bromo-N-(2,6-dimethylphenyl)-4-nitroaniline (1.1 g, 3.43 mmol, 1.0 eq).

LCMS: 291 [M+1]$^+$, 293 [M+2]$^+$

Step 3: Synthesis of N1-(2,6-dimethylphenyl)-2-(4,4,5,5-tetramethyl-1,3,2-dioxaborolan-2-yl)benzene-1,4-diamine N1-(2,6-dimethylphenyl)-2-(4,4,5,5-tetramethyl-1,3,2-dioxaborolan-2-yl)benzene-1,4-diamine (0.6 g, 52%, black viscous liquid) was prepared following General Procedure 1, Step 3 using 2-bromo-N1-(2,6-dimethylphenyl)benzene-1,4-diamine (1 g, 3.43 mmol, 1.0 eq).

$^1$H NMR (400 MHz, CDCl$_3$): δ 7.26 (s, 2H), 7.08 (s, 2H), 6.57 (s, 1H), 6.43 (s, 1H), 2.10-2.25 (s, 6H), 0.02-0.11 (m, 12H).

408

Step 4: Synthesis of 4-(5-amino-2-(2,6-dimethylphenylamino)phenyl)-2-methylisoquinolin-1(2H)-one 4-(5-amino-2-(2,6-dimethylphenylamino)phenyl)-2-methylisoquinolin-1(2H)-one (0.06 g, 39%, brown viscous liquid) was prepared following General Procedure 6, Step 1 using N1-(2,6-dimethylphenyl)-2-(4,4,5,5-tetramethyl-1,3,2-dioxaborolan-2-yl)benzene-1,4-diamine (204 mg, 0.60 mmol, 1.2 eq) and 4-bromo-2-methylisoquinolin-1(2H)-one (120 mg, 0.50 mmol, 1 eq).

LCMS: 370 [M+1]$^+$

Step 5: Synthesis of N-(4-(2,6-dimethylphenylamino)-3-(2-methyl-1-oxo-1,2-dihydroisoquinolin-4-yl)phenyl)acrylamide Compound 313 (3.5 g, 5%, off white solid) was prepared following General Procedure 3 using 4-(5-amino-2-(2,6-dimethylphenylamino)phenyl)-2-methylisoquinolin-1(2H)-one (0.60 g, 0.16 mmol, 1 eq).

LCMS: 424 [M+1]$^+$ $^1$H NMR (400 MHz, Methanol-$d_4$): δ 8.43 (d, J=7.45 Hz, 1H), 7.69 (br s, 1H), 7.57 (s, 1H), 7.42-7.51 (m, 3H), 7.31-7.40 (m, 1H), 7.04 (d, J=5.26 Hz, 2H), 6.24-6.43 (m, 2H), 6.11 (d, J=8.77 Hz, 1H), 5.71 (dd, J=1.97, 9.87 Hz, 2H), 3.70 (s, 3H), 2.09 (s, 6H).

Example S-47: Synthesis of N-(4-(2,4-difluorophenoxy)-3-(1-methyl-5-(methylamino)-6-oxo-1,6-dihydro pyridin-3-yl)phenyl)-N-methylacrylamide: Compound 394

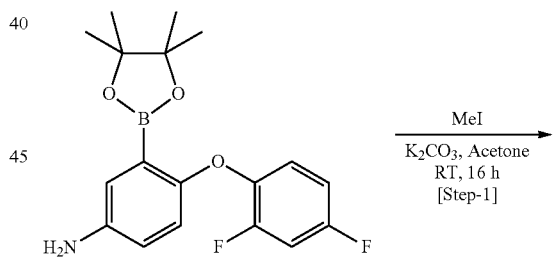

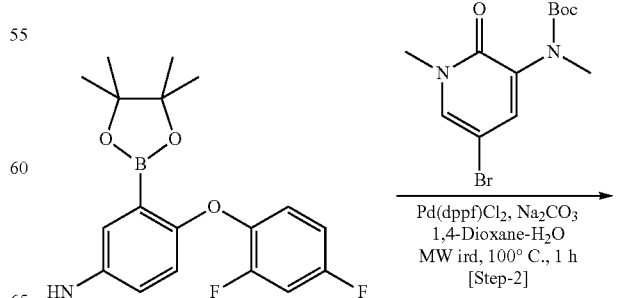

409

-continued

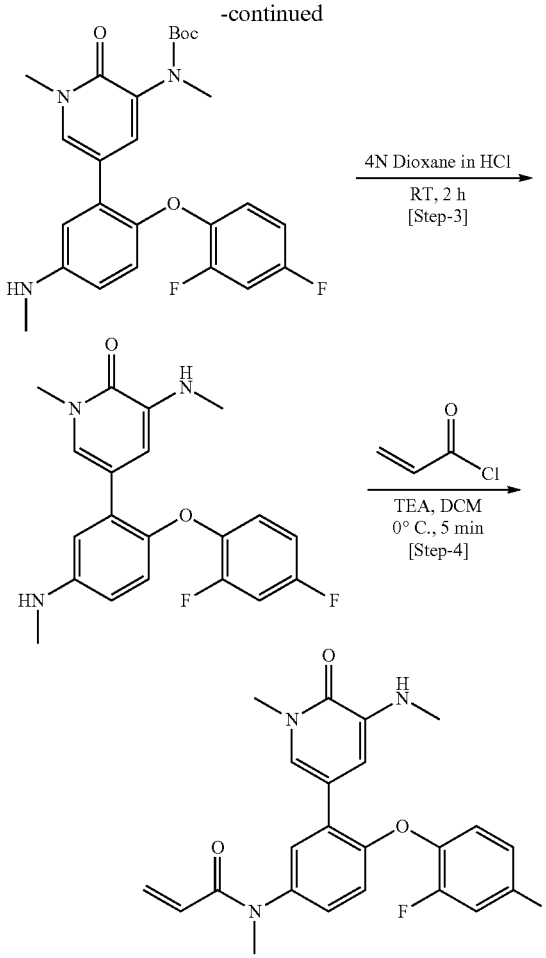

Step 1: Synthesis of 4-(2,4-difluorophenoxy)-N-methyl-3-(4,4,5,5-tetramethyl-1,3,2-dioxaborolan-2-yl)aniline To a stirred solution of 4-(2,4-difluorophenoxy)-3-(4,4,5,5-tetramethyl-1,3,2-dioxaborolan-2-yl)aniline (1.2 g, 3.45 mmol 1 eq) in acetone (15 mL) was added $K_2CO_3$ (0.565 g, 410 mmol 1.2 eq) at RT, followed by addition of methyl iodide (0.589 g, 4.10 mmol, 1.2 eq) and monitored by TLC and LC-MS. The reaction was complete after 16 h and the mixture was diluted with water (100 ml) and extracted with EtOAc (400 mL). The organic layer was washed with water (200 mL), brine (100 mL), dried over anhydrous $Na_2SO_4$, filtered and concentrated under reduced pressure to obtain a crude residue which was purified by CombiFlash chromatography to afford 4-(2,4-difluorophenoxy)-N-methyl-3-(4,4,5,5-tetramethyl-1,3,2-dioxaborolan-2-yl)aniline (180 mg, 33.5%) as a viscous brown solid (450 mg, 36%).

LCMS: 362 [M+1]$^+$

Step 2: Synthesis of tert-butyl 5-(2-(2,4-difluorophenoxy)-5-(methylamino)phenyl)-1-methyl-2-oxo-1,2-dihydropyridin-3-yl(methyl)carbamate tert-butyl 5-(2-(2,4-difluorophenoxy)-5-(methylamino)phenyl)-1-methyl-2-oxo-1,2-dihydropyridin-3-yl(methyl)carbamate (0.150 g, 82%, brown viscous liquid) was prepared following General Procedure 1, Step 3 using 4-(2,4-difluorophenoxy)-N-methyl-3-(4,4,5,5-tetramethyl-1,3,2-dioxaborolan-2-yl)aniline (204 mg, 0.60 mmol, 1.2 eq) and 4-(2,4-difluorophenoxy)-N-methyl-3-(4,4,5,5-tetramethyl-1,3,2-dioxaborolan-2-yl)aniline (140 mg, 0.441 mmol, 1 eq).

LCMS: 472 [M+H]$^+$

Step 3: Synthesis of 5-(2-(2,4-difluorophenoxy)-5-(methylamino)phenyl)-1-methyl-3-(methylamino)pyridin-2(1H)-one 5-(2-(2,4-difluorophenoxy)-5-(methylamino)phenyl)-1-methyl-3-(methylamino)pyridin-2(1H)-one (0.110 g, 93%, brown solid) was prepared following General Procedure 17, Step 5 using tert-butyl 5-(2-(2,4-difluorophenoxy)-5-(methylamino)phenyl)-1-methyl-2-oxo-1,2-dihydropyridin-3-yl(methyl)carbamate ((0.150 g, 0.319 mmol).

LCMS: 372 [M+H]$^+$

Step 4: Synthesis of N-(4-(2,4-difluorophenoxy)-3-(1-methyl-5-(methylamino)-6-oxo-1,6-dihydropyridin-3-yl)phenyl)-N-methylacrylamide N-(4-(2,4-difluorophenoxy)-3-(1-methyl-5-(methylamino)-6-oxo-1,6-dihydropyridin-3-yl)phenyl)-N-methylacrylamide (0.015 g, 12%, off white solid) was prepared following General Procedure 3 using 5-(2-(2,4-difluorophenoxy)-5-(methylamino)phenyl)-1-methyl-3-(methylamino)pyridin-2(1H)-one (0.100 g, 0.297 mmol, 1 eq).

LCMS: 426 [M+H]$^+$ $^1$H NMR (400 MHz, Methanol-$d_4$): δ 7.39 (d, J=2.19 Hz, 1H), 7.20 (dd, J=2.63, 8.33 Hz, 1H), 7.04-7.16 (m, 3H), 6.90-7.00 (m, 2H), 6.54 (d, J=1.75 Hz, 1H), 6.26 (d, J=2.19 Hz, 2H), 5.62 (d, J=9.65 Hz, 1H), 3.60 (s, 3H), 3.33-3.41 (m, 3H), 2.79 (s, 3H).

Example S-48. Synthesis of N-(4-(2,4-difluorophenoxy)-3-(4-methoxy-1-methyl-6-oxo-1,6-dihydropyridin-3-yl)phenyl)acrylamide, Compound 407

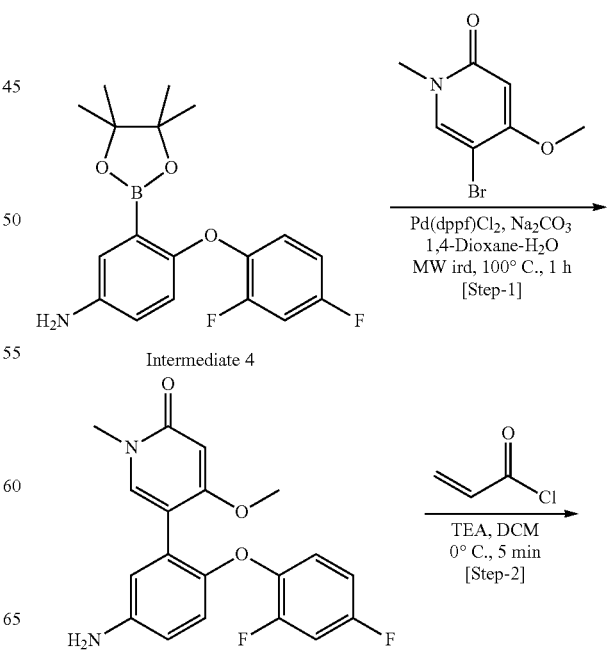

411
-continued

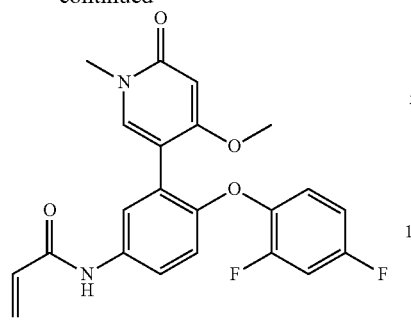

Step 1: Synthesis of 5-(5-amino-2-(2,4-difluorophenoxy)phenyl)-4-methoxy-1-methylpyridin-2(1H)-one 5-(5-amino-2-(2,4-difluorophenoxy)phenyl)-4-methoxy-1-methylpyridin-2(1H)-one (0.160 g, 65%, brown viscous liquid) was prepared following General Procedure 1, Step 3 using Intermediate 4 (204 mg, 0.60 mmol, 1.2 eq) and 5-bromo-4-methoxy-1-methylpyridin-2(1H)-one (150 mg, 0.688 mmol, 1 eq).

LCMS: 359 [M+H]+

Step 2: Synthesis of N-(4-(2,4-difluorophenoxy)-3-(4-methoxy-1-methyl-6-oxo-1,6-dihydropyridin-3-yl)phenyl)acrylamide N-(4-(2,4-difluorophenoxy)-3-(4-methoxy-1-methyl-6-oxo-1,6-dihydropyridin-3-yl)phenyl)acrylamide (0.037 g, 39%, off white solid) was prepared following General Procedure 3 using 5-(5-amino-2-(2,4-difluorophenoxy)phenyl)-4-methoxy-1-methylpyridin-2(1H)-one (0.080 g, 0.223 mmol, 1 eq).

LCMS: 413[M+H]+

$^1$H NMR (400 MHz, Methanol-d$_4$): δ 7.57-7.64 (m, 2H), 7.55 (s, 1H), 7.03 (ddd, J=11.2, 8.6, 2.9 Hz, 1H), 6.91 (d, J=8.77 Hz, 3H), 6.34-6.46 (m, 2H), 5.95 (s, 1H), 5.78 (dd, J=2.63, 9.21 Hz, 1H), 3.71 (s, 3H), 3.51 (s, 3H).

Example S-49. Synthesis of N-(4-(2,4-difluorophenoxy)-3-(4-methoxy-1-methyl-6-oxo-1,6-dihydropyridazin-3-yl)phenyl)acrylamide, Compound 403

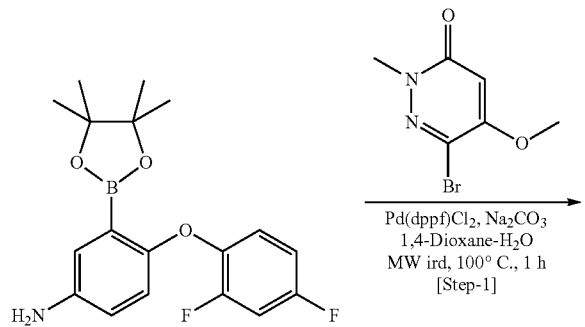

412
-continued

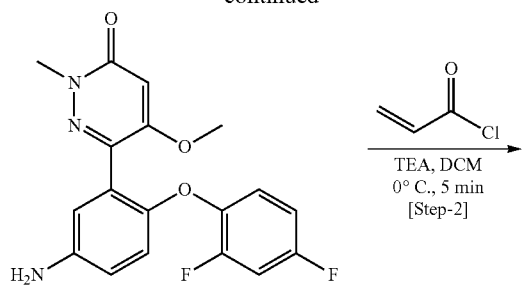

Step 1: Synthesis of 6-(5-amino-2-(2,4-difluorophenoxy)phenyl)-5-methoxy-2-methylpyridazin-3(2H)-one 6-(5-amino-2-(2,4-difluorophenoxy)phenyl)-5-methoxy-2-methylpyridazin-3(2H)-one (0.190 g, 77%, brown viscous liquid) was prepared following General Procedure 1, Step 3 using Intermediate 4 (357.93 mg, 1.034 mmol, 1.2 eq) and 6-bromo-5-methoxy-2-methylpyridazin-3(2H)-one (150 mg, 0.086 mmol, 1 eq).

LCMS: 360[M+H]+

Step 2: Synthesis of N-(4-(2,4-difluorophenoxy)-3-(4-methoxy-1-methyl-6-oxo-1,6-dihydropyridazin-3-yl)phenyl)acrylamide N-(4-(2,4-difluorophenoxy)-3-(4-methoxy-1-methyl-6-oxo-1,6-dihydropyridazin-3-yl)phenyl)acrylamide (0.045 g, 39%, off white solid) was prepared following General Procedure 3 using 6-(5-amino-2-(2,4-difluorophenoxy)phenyl)-5-methoxy-2-methylpyridazin-3(2H)-one (0.100 g, 0.273 mmol, 1 eq).

LCMS: 414[M+H]+

$^1$H NMR (400 MHz, Methanol-d$_4$): δ 7.74 (d, J=2.63 Hz, 1H), 7.68 (dd, J=2.63, 8.77 Hz, 1H), 7.01-7.11 (m, 2H), 6.90 (d, J=8.77 Hz, 2H), 6.35-6.47 (m, 2H), 6.30 (s, 1H), 5.78 (dd, J=2.41, 9.43 Hz, 1H), 3.76 (s, 3H), 3.72 (s, 3H).

Example S-50: Synthesis of N-(4-(2,4-difluorophenoxy)-3-(2-methyl-1-oxo-1,2-dihydroisoquinolin-4-yl)phenyl)-N-methylacrylamide, Compound 396

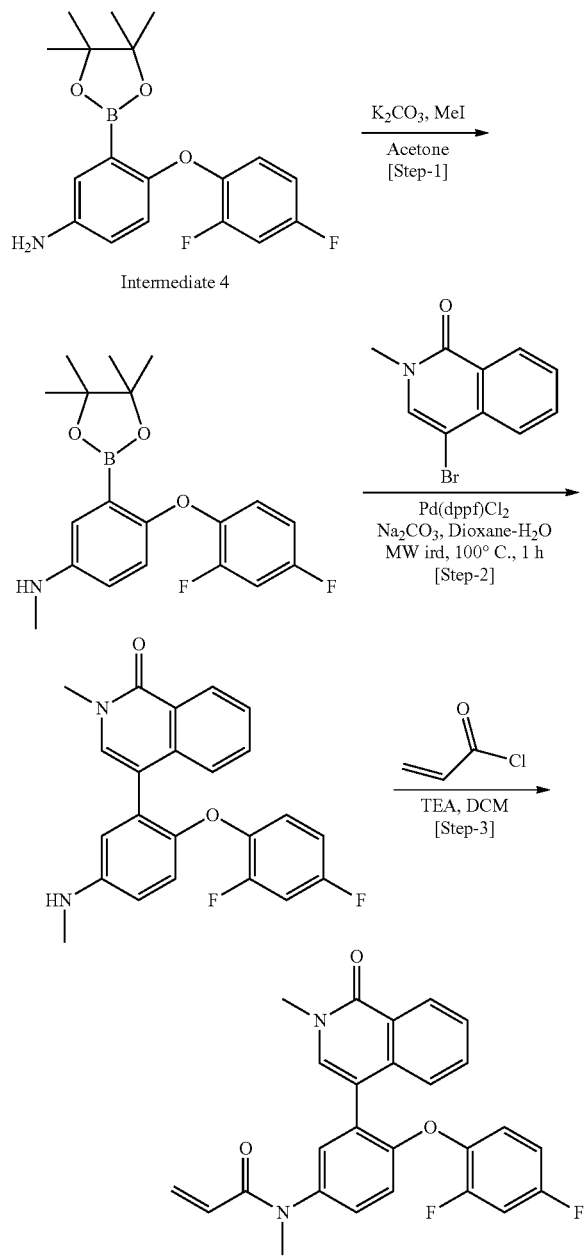

Step 1: Synthesis of 4-(2,4-difluorophenoxy)-N-methyl-3-(4,4,5,5-tetramethyl-1,3,2-dioxaborolan-2-yl)aniline 4-(2,4-difluorophenoxy)-N-methyl-3-(4,4,5,5-tetramethyl-1,3,2-dioxaborolan-2-yl)aniline (450 mg, 36%, brown solid) was prepared following General Procedure 10, Step-1 using Intermediate 4 (1.2 g, 3.45 mmol, 1 eq).
$^1$H NMR: (400 MHz, DMSO-$d_6$) δ 7.31 (br s, 1H), 6.83-6.91 (m, 3H), 6.68 (dd, J=2.63, 8.77 Hz, 1H), 6.50 (d, J=5.70 Hz, 1H), 5.69 (br s, 1H), 2.62-2.69 (m, 3H), 1.09 (m, 12H)

Step 2: Synthesis of 4-(2-(2,4-difluorophenoxy)-5-(methylamino)phenyl)-2-methylisoquinolin-1(2H)-one 4-(2-(2,4-difluorophenoxy)-5-(methylamino)phenyl)-2-methylisoquinolin-1(2H)-one (85 mg, 41%) light yellow solid) was prepared following General Procedure 10, Step 2 using 4-bromo-2-methylisoquinolin-1(2H)-one (100 mg, 0.420 mmol, 1 eq).
LCMS: 393 [M+1]$^+$

Step 3: Synthesis of N-(4-(2,4-difluorophenoxy)-3-(2-methyl-1-oxo-1,2-dihydroisoquinolin-4-yl)phenyl)-N-methylacrylamide N-(4-(2,4-difluorophenoxy)-3-(2-methyl-1-oxo-1,2-dihydroisoquinolin-4-yl)phenyl)-N-methylacrylamide (0.025 g, 31%, off white solid) was prepared following General Procedure 3 using 4-(2-(2,4-difluorophenoxy)-5-(methylamino)phenyl)-2-methylisoquinolin-1(2H)-one (0.070 g, 0.178 mmol, 1 eq).
LCMS: 447[M+H]$^+$
$^1$H NMR (400 MHz, Methanol-$d_4$): δ 8.37 (d, J=7.89 Hz, 1H), 7.68 (d, J=7.02 Hz, 1H), 7.55 (t, J=7.45 Hz, 1H), 7.39-7.47 (m, 2H), 7.30-7.38 (m, 2H), 6.96-7.11 (m, 3H), 6.87 (br s, 1H), 6.28 (d, J=5.70 Hz, 2H), 5.65 (br s, 1H), 3.65 (s, 3H), 3.34-3.44 (m, 3H).

Example S-51. Synthesis of 7-(5-acrylamido-2-(2,6-dimethylphenoxy)phenyl)-N-ethyl-5-methyl-4-oxo-4,5-dihydrothieno[3,2-c]pyridine-2-carboxamide: (General Procedure 18) Compound 412

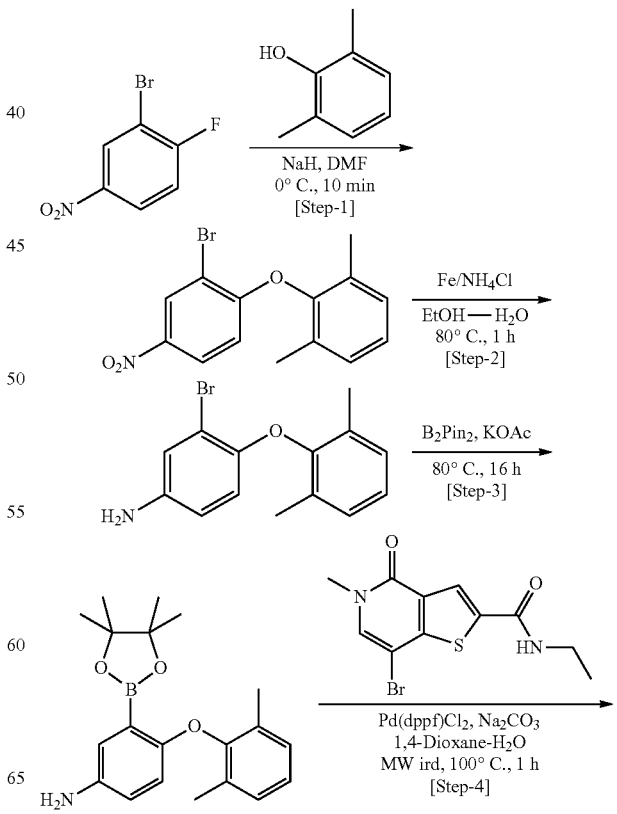

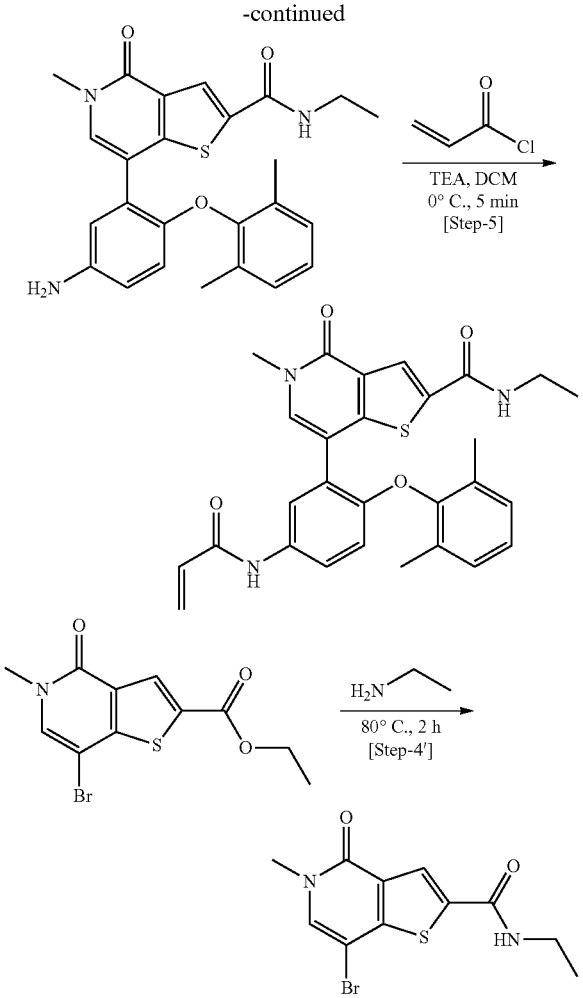

Step 1: Synthesis of 2-(2-bromo-4-nitrophenoxy)-1,3-dimethylbenzene

To a stirred solution of 2,6-dimethylphenol (2.0 g, 16.03 mmol, 1.0 eq) in DMF (10 mL) was added NaH (0.721 g, 18.00 mmol, 1.1 eq) at 0° C. followed by an addition of 2-bromo-1-fluoro-4-nitrobenzene (3.49 g, 18.0 mmol, 1.1 eq) and monitored by TLC and LC-MS. The reaction was complete after 10 min and to the the mixture was added ice-cold water (50 mL) to obtain a precipitate which was filtered over Büchner funnel; dried under vacuum to afford 2-(2-bromo-4-nitrophenoxy)-1,3-dimethylbenzene (4.5 g, 68%) as a yellow solid.
LCMS: 322 [M+1]$^+$, 324 [M+2H]$^+$

Step 2: Synthesis of 3-bromo-4-(2,6-dimethylphenoxy)aniline 3-bromo-4-(2,6-dimethylphenoxy)aniline (3.5 g, 97%, black viscous liquid) was prepared following General Procedure 1, Step 2 using 2-(2-bromo-4-nitrophenoxy)-1,3-dimethylbenzene (4.0 g, 12.46 mmol, 1.0 eq).
LCMS: 292[M+1]$^+$, 294 [M+2]$^+$

Step 3: Synthesis of 4-(2,6-dimethylphenoxy)-3-(4,4,5,5-tetramethyl-1,3,2-dioxaborolan-2-yl)aniline 4-(2,6-dimethylphenoxy)-3-(4,4,5,5-tetramethyl-1,3,2-dioxaborolan-2-yl)aniline (0.700 g, 66%, black viscous liquid) was prepared following General Procedure 1, Step 3 using 3-bromo-4-(2,6-dimethylphenoxy)aniline (1.0 g, 45.6 mmol, 1.0 eq) and Bis(triphenylphosphine) palladium(II) dichloride (0.16 g, 0.228 mmol, 0.05 eq).
$^1$H NMR: (400 MHz, CDCl3) δ 6.97-7.11 (m, 3H), 6.58 (m, 2H), 6.14 (d, J=8.77 Hz, 1H), 2.05-2.18 (m, 6H), 1.23-1.28 (m, 12H).

Step 4': Synthesis of 7-bromo-N-ethyl-5-methyl-4-oxo-4,5-dihydrothieno[3,2-c]pyridine-2-carboxamide To ethyl 7-bromo-5-methyl-4-oxo-4,5-dihydrothieno[3,2-c]pyridine-2-carboxylate (0.100 g, 0.498 mmol 1 eq) was added ethyl amine (2 mL; 70% solution in H$_2$O) and the mixture was heated at 80° C. and monitored by TLC. The reaction was complete after 2 h and to it was added ice-cold water (50 mL) to obtain a precipitate which was filtered over Büchner funnel; dried under vacuum to afford 7-bromo-N-ethyl-5-methyl-4-oxo-4,5-dihydrothieno[3,2-c]pyridine-2-carboxamide (100 mg, 67%) as a brown solid.
LCMS: 315[M+1]$^+$, 317 [M+2]$^+$

Step 4: Synthesis of 7-(5-amino-2-(2,6-dimethylphenoxy)phenyl)-N-ethyl-5-methyl-4-oxo-4,5-dihydrothieno[3,2-c]pyridine-2-carboxamide 7-(5-amino-2-(2,6-dimethylphenoxy) phenyl)-N-ethyl-5-methyl-4-oxo-4,5-dihydrothieno[3,2-c]pyridine-2-carboxamide (0.045 g, 30%, brown viscous liquid) was prepared following General Procedure 1, Step 3 using 4-(2,6-dimethylphenoxy)-3-(4,4,5,5-tetramethyl-1,3,2-dioxaborolan-2-yl) aniline (0.162 g, 0.477 mmol, 1.5 eq) and 7-bromo-N-ethyl-5-methyl-4-oxo-4,5-dihydrothieno[3,2-c]pyridine-2-carboxamide (100 mg, 0.318 mmol, 1 eq).
LCMS: 448[M+H]$^+$

Step 5: Synthesis of 7-(5-acrylamido-2-(2,6-dimethylphenoxy)phenyl)-N-ethyl-5-methyl-4-oxo-4,5-dihydrothieno[3,2-c]pyridine-2-carboxamide 7-(5-acrylamido-2-(2,6-dimethylphenoxy)phenyl)-N-ethyl-5-methyl-4-oxo-4,5-dihydrothieno [3,2-c]pyridine-2-carboxamide was prepared following General Procedure 3 using 7-(5-amino-2-(2,6-dimethylphenoxy)phenyl)-N-ethyl-5-methyl-4-oxo-4,5-dihydrothieno [3,2-c]pyridine-2-carboxamide (0.070 g, 0.178 mmol, 1 eq).
LCMS: 502[M+H]$^+$
$^1$H NMR: (400 MHz, Methanol-d$_4$δ 8.15 (s, 1H), 7.85 (d, J=2.6 Hz, 1H), 7.73 (s, 1H), 7.50 (dd, J=9.0, 2.6 Hz, 1H), 7.13-7.00 (m, 3H), 6.48-6.29 (m, 3H), 5.76 (dd, J=9.6, 2.4 Hz, 1H), 3.73 (s, 3H), 3.40 (q, J=7.3 Hz, 2H), 2.09 (s, 6H), 1.23 (t, J=7.3 Hz, 3H)

Example S-52. Synthesis of N-(4-(2,6-dimethylphenoxy)-3-(2-methyl-1-oxo-1,2-dihydroisoquinolin-4-yl)phenyl)acrylamide, Compound 397

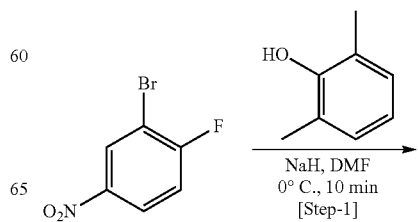

417

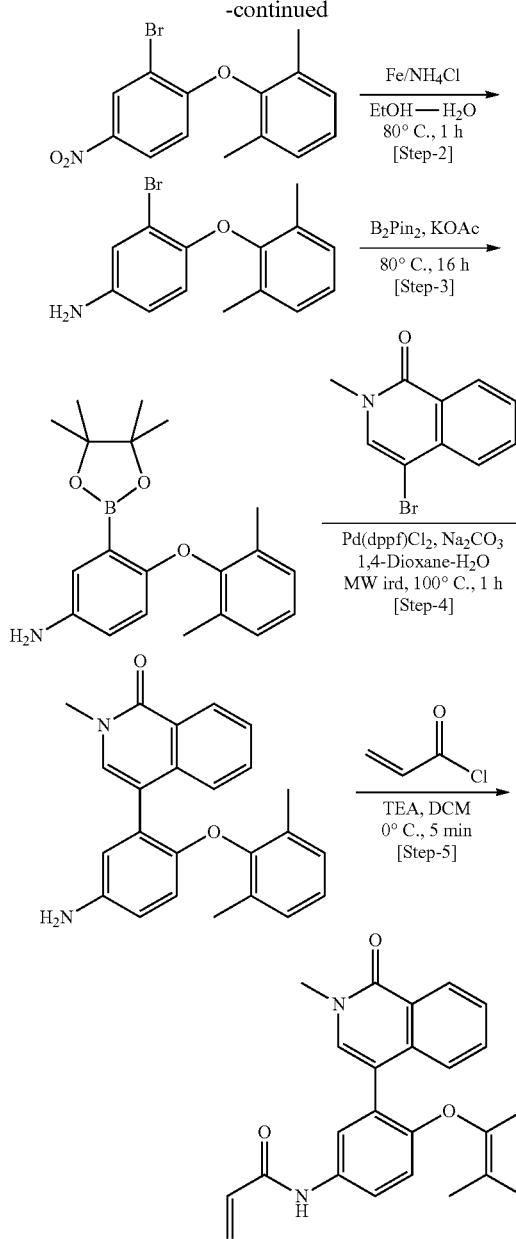

Step 1: Synthesis of 2-(2-bromo-4-nitrophenoxy)-1,3-dimethylbenzene 2-(2-bromo-4-nitrophenoxy)-1,3-dimethylbenzene was prepared following General Procedure 18, Step 1 using 2,6-dimethylphenol (2.0 g, 16.03 mmol, 1.0 eq).
LCMS: 322 [M+H]$^+$, 324 [M+2]$^+$

Step 2: Synthesis of 3-bromo-4-(2,6-dimethylphenoxy)aniline 3-bromo-4-(2,6-dimethylphenoxy)aniline (3.5 g, 97%, black viscous liquid) was prepared following General Procedure 1, Step 2 using 2-(2-bromo-4-nitrophenoxy)-1,3-dimethylbenzene (4.0 g, 12.46 mmol, 1.0 eq).
LCMS: 292[M+H]$^+$, 294 [M+2]$^+$

418

Step 3: Synthesis of 4-(2,6-dimethylphenoxy)-3-(4,4,5,5-tetramethyl-1,3,2-dioxaborolan-2-yl)aniline 4-(2,6-dimethylphenoxy)-3-(4,4,5,5-tetramethyl-1,3,2-dioxaborolan-2-yl)aniline (0.700 g, 66%, black viscous liquid) was prepared following General Procedure 1, Step 3 using 3-bromo-4-(2,6-dimethylphenoxy)aniline (1.0 g, 45.6 mmol, 1.0 eq) and Bis(triphenylphosphine) palladium(II) dichloride (0.16 g, 0.228 mmol, 0.05 eq).
$^1$H NMR: (400 MHz, CDCl$_3$) δ 6.97-7.11 (m, 3H), 6.58 (m, 2H), 6.14 (d, J=8.77 Hz, 1H), 2.05-2.18 (m, 6H), 1.23-1.28 (m, 12H).

Step 4: Synthesis of 4-(5-amino-2-(2,6-dimethylphenoxy)phenyl)-2-methylisoquinolin-1(2H)-one 4-(5-amino-2-(2,6-dimethylphenoxy)phenyl)-2-methylisoquinolin-1(2H)-one (0.100 g, 64%, brown viscous liquid) was prepared following General Procedure 1, Step 3 using 4-(2,6-dimethylphenoxy)-3-(4,4,5,5-tetramethyl-1,3,2-dioxaborolan-2-yl)aniline (0.213 g, 0.630 mmol, 1.5 eq) and 4-bromo-2-methylisoquinolin-1(2H)-one (100 mg, 0.420 mmol, 1 eq).
LCMS: 371[M+H]$^+$

Step 5: Synthesis of N-(4-(2,6-dimethylphenoxy)-3-(2-methyl-1-oxo-1,2-dihydroisoquinolin-4-yl)phenyl)acrylamide N-(4-(2,6-dimethylphenoxy)-3-(2-methyl-1-oxo-1,2-dihydroisoquinolin-4-yl)phenyl)acrylamide (0.029 g, 25%, off white solid) was prepared following General Procedure 3 using 4-(5-amino-2-(2,6-dimethylphenoxy)phenyl)-2-methylisoquinolin-1(2H)-one (0.070 g, 0.178 mmol, 1 eq).
LCMS: 425[M+H]$^+$
$^1$H NMR (400 MHz, Methanol-d$_4$): δ 8.42 (d, J=8.33 Hz, 1H), 7.64-7.75 (m, 2H), 7.57 (s, 1H), 7.42-7.56 (m, 3H), 6.92-7.13 (m, 3H), 6.28-6.47 (m, 3H), 5.76 (dd, J=2.19, 9.65 Hz, 1H), 3.71 (s, 3H), 2.03 (s, 6H).

Example S-53. Synthesis of N-(4-(2,6-dimethylphenoxy)-3-(1-methyl-5-(methylamino)-6-oxo-1,6-dihydropyridin-3-yl)phenyl)acrylamide, Compound 411

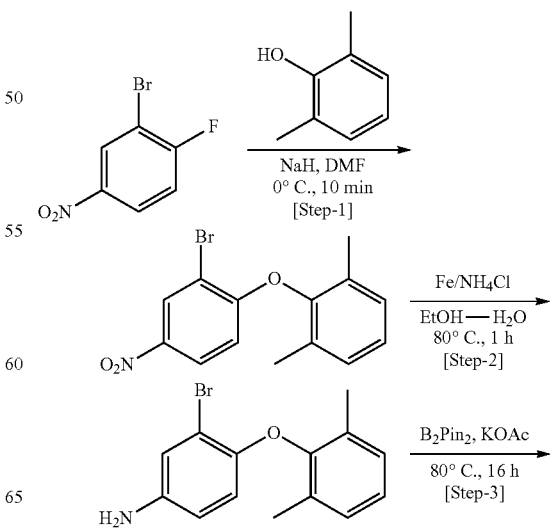

-continued

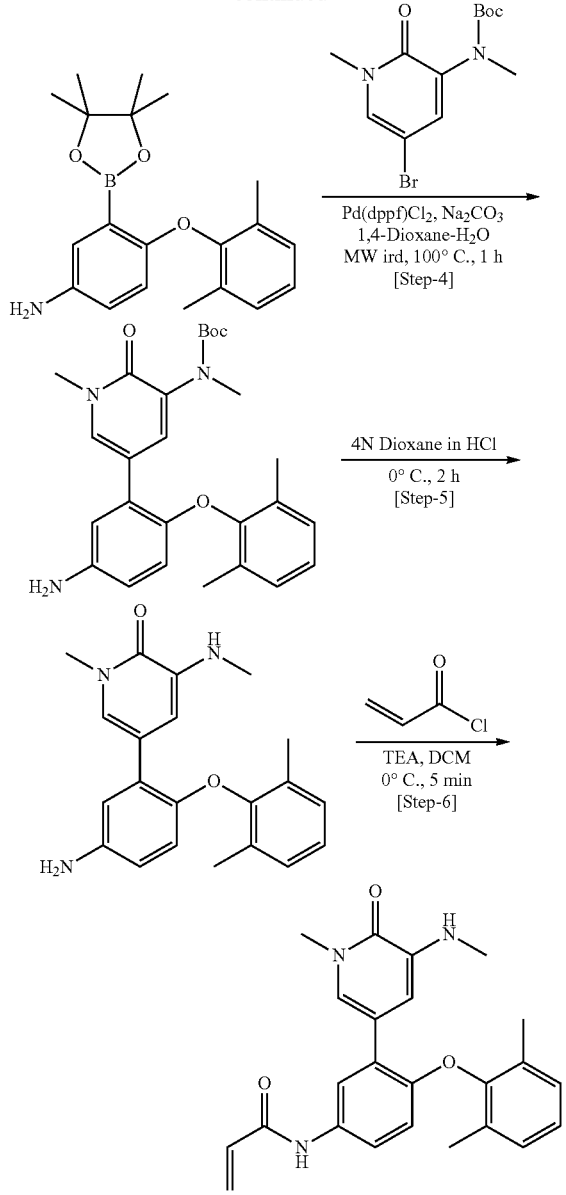

Step 1: Synthesis of
2-(2-bromo-4-nitrophenoxy)-1,3-dimethylbenzene 2-(2-bromo-4-nitrophenoxy)-1,3-dimethylbenzene was prepared following General Procedure 18, Step 1 using 2,6-dimethylphenol (2.0 g, 16.03 mmol, 1.0 eq).

LCMS: 322 [M+H]$^+$, 324 [M+2]N

Step 2: Synthesis of
3-bromo-4-(2,6-dimethylphenoxy)aniline 3-bromo-4-(2,6-dimethylphenoxy)aniline (3.5 g, 97%, black viscous liquid) was prepared following General Procedure, Step 2 using 2-(2-bromo-4-nitrophenoxy)-1,3-dimethylbenzene (4.0 g, 12.46 mmol, 1.0 eq).

LCMS: 292 [M+H]$^+$, 294 [M+2]$^+$

Step 3: Synthesis of 4-(2,6-dimethylphenoxy)-3-(4,4,5,5-tetramethyl-1,3,2-dioxaborolan-2-yl)aniline 4-(2,6-dimethylphenoxy)-3-(4,4,5,5-tetramethyl-1,3,2-dioxaborolan-2-yl)aniline (0.700 g, 66%, black viscous liquid) was prepared following General Procedure 1, Step 3 using 3-bromo-4-(2,6-dimethylphenoxy)aniline (1.0 g, 45.6 mmol, 1.0 eq) and Bis(triphenylphosphine) palladium(II) dichloride (0.16 g, 0.228 mmol, 0.05 eq).

$^1$H NMR (400 MHz, CDCl3): δ 6.97-7.11 (m, 3H), 6.58 (m, 2H), 6.14 (d, J=8.77 Hz, 1H), 2.05-2.18 (m, 6H), 1.23-1.28 (m, 12H).

Step 4: Synthesis of tert-butyl 5-(5-amino-2-(2,6-dimethylphenoxy)phenyl)-1-methyl-2-oxo-1,2-dihydropyridin-3-yl(methyl)carbamate tert-butyl 5-(5-amino-2-(2,6-dimethylphenoxy) phenyl)-1-methyl-2-oxo-1,2-dihydropyridin-3-yl(methyl)carbamate (0.065 g, 30%, brown viscous liquid) was prepared following General Procedure 1, Step 3 using 4-(2,6-dimethylphenoxy)-3-(4,4,5,5-tetramethyl-1,3,2-dioxaborolan-2-yl)aniline (0.252 g, 0.745 mmol, 1.5 eq) and tert-butyl 5-bromo-1-methyl-2-oxo-1,2-dihydropyridin-3-yl(methyl)carbamate (150 mg, 0.496 mmol, 1 eq).

LCMS: 450 [M+H]$^+$

Step 5: Synthesis of 5-(5-amino-2-(2,6-dimethylphenoxy)phenyl)-1-methyl-3-(methylamino)pyridin-2(1H)-one 5-(5-amino-2-(2,6-dimethylphenoxy)phenyl)-1-methyl-3-(methylamino)pyridin-2(1H)-one (50 mg, 99%, thick viscous solid) was prepared following General Procedure 17, Step 5 using tert-butyl 5-(5-amino-2-(2,6-dimethylphenoxy) phenyl)-1-methyl-2-oxo-1,2-dihydropyridin-3-yl(methyl) (0.065 g, 0.144 mmol).

LCMS: 350 [M+H]$^+$

Step 6: Synthesis of N-(4-(2,6-dimethylphenoxy)-3-(1-methyl-5-(methylamino)-6-oxo-1,6-dihydropyridin-3-yl)phenyl)acrylamide N-(4-(2,6-dimethylphenoxy)-3-(1-methyl-5-(methylamino)-6-oxo-1,6-dihydropyridin-3-yl)phenyl)acrylamide (0.009 g, 16%, off white solid) was prepared following General Procedure 3 using 5-(5-amino-2-(2,6-dimethylphenoxy)phenyl)-1-methyl-3-(methylamino)pyridin-2(1H)-one (0.050 g, 0.143 mmol, 1 eq).

LCMS: 404 [M+H]$^+$ $^1$H NMR (400 MHz, Methanol-d$_4$): δ 7.75 (d, J=2.63 Hz, 1H), 7.34 (dd, J=2.63, 8.77 Hz, 1H), 7.22 (d, J=2.19 Hz, 1H), 7.11-7.16 (m, 2H), 7.08 (d, J=6.14 Hz, 1H), 6.72 (d, J=1.75 Hz, 1H), 6.28-6.46 (m, 3H), 5.76 (dd, J=2.41, 9.43 Hz, 1H), 3.66 (s, 3H), 2.86 (s, 3H), 2.11 (s, 6H).

Example S-54. Synthesis of N-(4-(2,4-difluorophenoxy)-3-(6-methyl-3,5-dioxo-3,4,5,6-tetrahydro-2H-pyrido[4,3-b][1,4]oxazin-8-yl)phenyl)acrylamide, Compound 404

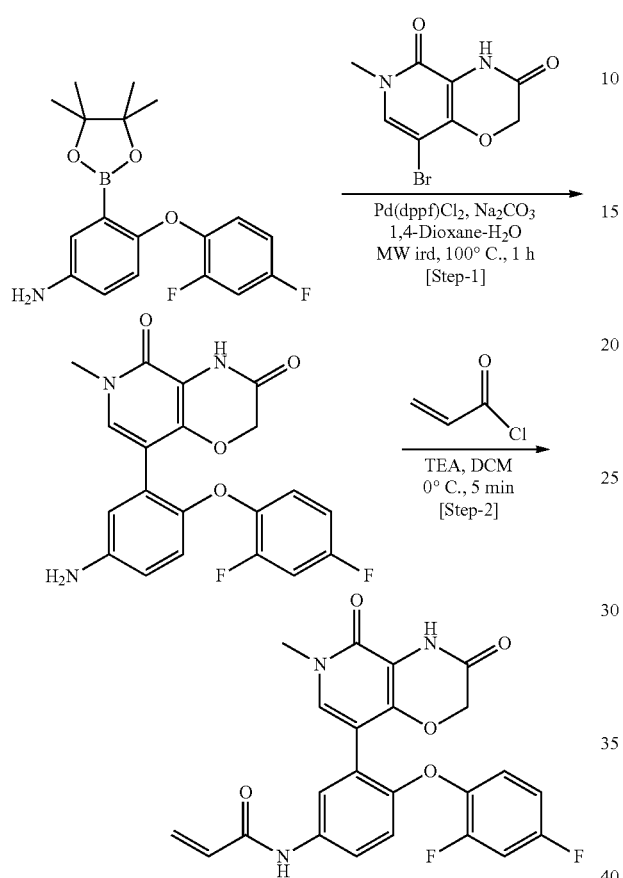

Step 1: Synthesis of 8-(5-amino-2-(2,4-difluorophenoxy)phenyl)-6-methyl-2H-pyrido[4,3-b][1,4]oxazine-3,5(4H,6H)-dione 8-(5-amino-2-(2,4-difluorophenoxy)phenyl)-6-methyl-2H-pyrido[4,3-b][1,4]oxazine-3,5(4H,6H)-dione (0.145 g, 62%, brown viscous liquid) was prepared following General Procedure 1, Step 3 using 4-(2,4-difluorophenoxy)-3-(4,4,5,5-tetramethyl-1,3,2-dioxaborolan-2-yl)aniline (243.09 mg, 0.700 mmol, 1.2 eq) and 8-bromo-6-methyl-2H-pyrido[4,3-b][1,4]oxazine-3,5(4H,6H)-dione (150 mg, 0.580 mmol, 1 eq).
LCMS: 400 [M+H]⁺

Step 2: Synthesis of N-(4-(2,4-difluorophenoxy)-3-(6-methyl-3,5-dioxo-3,4,5,6-tetrahydro-2H-pyrido[4,3-b][1,4]oxazin-8-yl)phenyl)acrylamide N-(4-(2,4-difluorophenoxy)-3-(6-methyl-3,5-dioxo-3,4,5,6-tetrahydro-2H-pyrido[4,3-b][1,4]oxazin-8-yl) phenyl)acrylamide (0.011 g, 6%, off white solid) was prepared following General Procedure 3 using 8-(5-amino-2-(2,4-difluorophenoxy)phenyl)-6-methyl-2H-pyrido[4,3-b][1,4]oxazine-3,5(4H,6H)-dione (0.145 g, 0.363 mmol, 1 eq).
LCMS: 454 [M+1]⁺

$^1$H NMR (400 MHz, DMSO-d$_6$) δ 10.28 (s, 1H), 7.72 (d, J=2.7 Hz, 1H), 7.61 (dd, J=8.9, 2.7 Hz, 1H), 7.51 (s, 1H), 7.45-7.33 (m, 1H), 7.12-6.99 (m, 2H), 6.87 (d, J=8.9 Hz, 1H), 6.43 (dd, J=16.9, 10.1 Hz, 1H), 6.25 (dd, J=16.9, 2.1 Hz, 1H), 5.76 (dd, J=9.9, 2.2 Hz, 1H), 4.43 (s, 2H), 3.48 (s, 3H)

Example S-55. Synthesis of (E)-N-(4-(2,4-difluorophenoxy)-3-(2-methyl-1-oxo-1,2-dihydroisoquinolin-4-yl)phenyl)prop-1-ene-1-sulfonamide, Compound 86

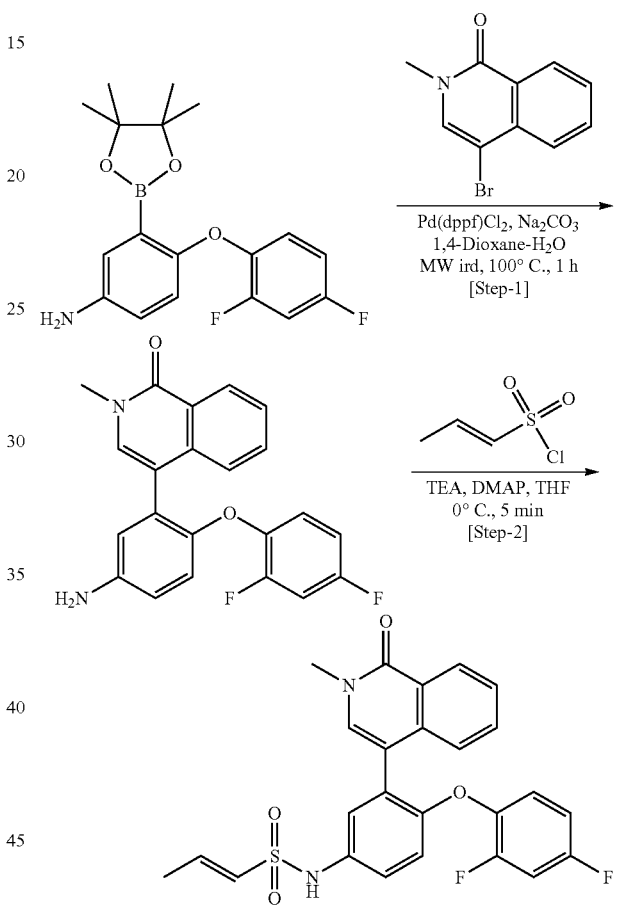

Step 1: Synthesis of 4-(5-amino-2-(2,4-difluorophenoxy)phenyl)-2-methylisoquinolin-1(2H)-one 4-(5-amino-2-(2,4-difluorophenoxy)phenyl)-2-methyl-isoquinolin-1(2H)-one (0.150 g, 94%, brown viscous liquid) was prepared following General Procedure 1, Step 3 using 4-(2,4-difluorophenoxy)-3-(4,4,5,5-tetramethyl-1,3,2-dioxaborolan-2-yl)aniline (174.45 mg, 0.504 mmol, 1.2 eq) and 4-bromo-2-methylisoquinolin-1(2H)-one (100 mg, 0.420 mmol, 1 eq).
LCMS: 379 [M+1]⁺

Step 2: Synthesis of (E)-N-(4-(2,4-difluorophenoxy)-3-(2-methyl-1-oxo-1,2-dihydroisoquinolin-4-yl)phenyl)prop-1-ene-1-sulfonamide To a stirred solution of 4-(5-amino-2-(2,4-difluorophenoxy)phenyl)-2-methylisoquinolin-1(2H)-one (0.100 g, 0.263 mmol) in THF (5 ml) were added triethylamine (0.080 g, 0.791 mmol, 3 eq) and DMAP (0.010 g, 0.052 mmol, 0.2 eq) followed by addition of (E)-prop-1-ene-1-sulfonyl chloride (0.044 g, 0.316 mmol, 1.2 eq) at 0° C. and monitored by TLC & LC-MS. The reaction was complete after 2 h and the mixture was diluted with water (100 ml) extracted with EtOAc (250 mL×2). The combined organic layers were washed with water (100 mL), brine (150 mL) dried over anhydrous Na$_2$SO$_4$, filtered and concentrated under reduced pressure to afford (E)-N-(4-(2,4-difluorophenoxy)-3-(2-methyl-1-oxo-1,2-dihydroisoquinolin-4-yl)phenyl)prop-1-ene-1-sulfonamide (15 mg, 11%) as a thick viscous solid.

LCMS: 483 [M+1]$^+$ $^1$H NMR (400 MHz, Methanol-d$_4$): δ 8.35 (d, J=7.45 Hz, 1H), 7.66 (s, 1H), 7.53 (s, 1H), 7.33-7.40 (m, 2H), 7.27 (dd, J=2.63, 8.77 Hz, 1H), 7.21 (d, J=3.07 Hz, 1H), 6.86-6.99 (m, 3H), 6.76 (d, J=7.02 Hz, 2H), 6.42 (d, J=1.75 Hz, 1H), 3.63 (s, 3H), 1.87 (dd, J=1.53, 6.80 Hz, 3H).

Example S-56. Synthesis of 4-(5-acrylamido-2-(2,6-dimethylphenoxy)phenyl)-N-ethyl-6-methyl-7-oxo-6,7-dihydrothieno[2,3-c]pyridine-2-carboxamide, Compound 381

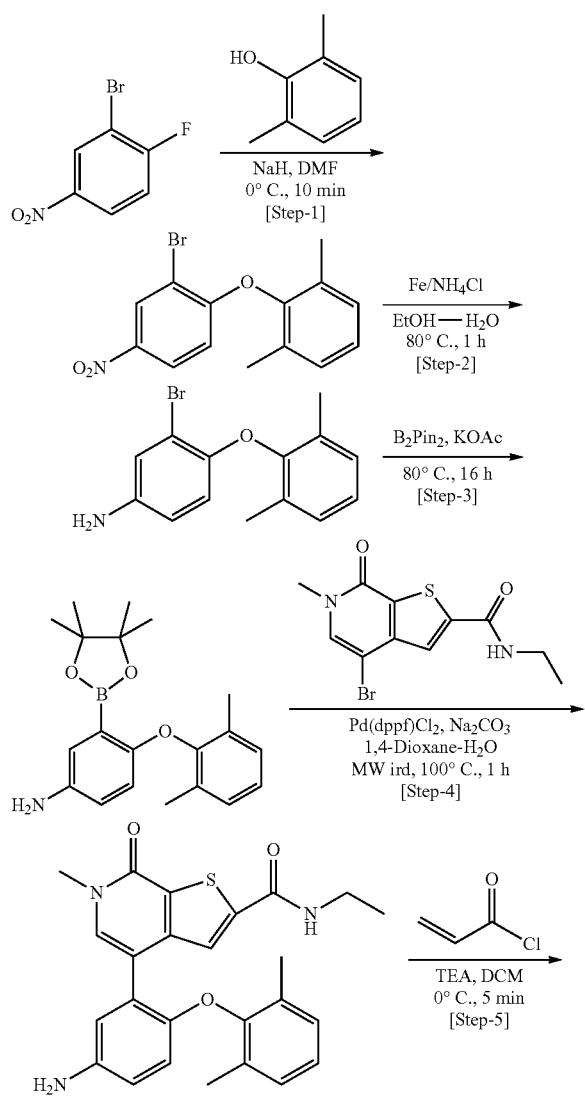

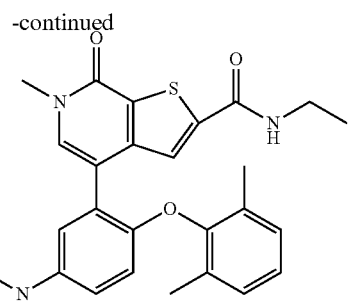

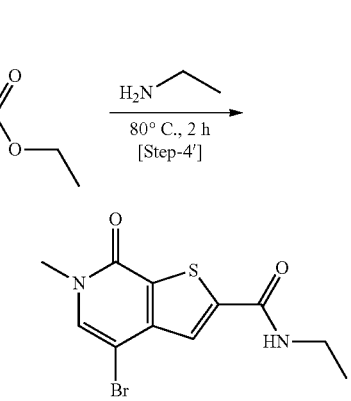

Step 1: Synthesis of 2-(2-bromo-4-nitrophenoxy)-1,3-dimethylbenzene 2-(2-bromo-4-nitrophenoxy)-1,3-dimethylbenzene (4.5 g, 68%, yellow solid) was prepared following General Procedure 17, Step 1 using 2,6-dimethylphenol (2.0 g, 16.03 mmol, 1.0 eq)

LCMS: 322 [M+H]$^+$, 324 [M+2]$^+$

Step 2: Synthesis of 3-bromo-4-(2,6-dimethylphenoxy)aniline 3-bromo-4-(2,6-dimethylphenoxy)aniline (3.5 g, 97%, black viscous liquid) was prepared following General Procedure 1, Step 2 using 2-(2-bromo-4-nitrophenoxy)-1,3-dimethylbenzene (4.0 g, 12.46 mmol, 1.0 eq).

LCMS: 292 [M+H]$^+$, 294 [M+2]$^+$

Step 3: Synthesis of 4-(2,6-dimethylphenoxy)-3-(4,4,5,5-tetramethyl-1,3,2-dioxaborolan-2-yl)aniline 4-(2,6-dimethylphenoxy)-3-(4,4,5,5-tetramethyl-1,3,2-dioxaborolan-2-yl)aniline (0.700 g, 66%, black viscous liquid) was prepared following General Procedure 1, Step 3 using 3-bromo-4-(2,6-dimethylphenoxy)aniline (1.0 g, 45.6 mmol, 1.0 eq) and Bis(triphenylphosphine) palladium(II) dichloride (0.16 g, 0.228 mmol, 0.05 eq).

$^1$H NMR (400 MHz, CDCl$_3$): δ 6.97-7.11 (m, 3H), 6.58 (m, 2H), 6.14 (d, J=8.77 Hz, 1H), 2.05-2.18 (m, 6H), 1.23-1.28 (m, 12H).

Step 4': Synthesis of 4-bromo-N-ethyl-6-methyl-7-oxo-6,7-dihydrothieno[2,3-c]pyridine-2-carboxamide 4-bromo-N-ethyl-6-methyl-7-oxo-6,7-dihydrothieno [2,3-c]pyridine-2-carboxamide (350 mg, 70%, brown solid)

was prepared following General Procedure 18, Step 4a using ethyl 4-bromo-6-methyl-7-oxo-6,7-dihydrothieno[2,3-c] pyridine-2-carboxylate (0.500 g, 0.498 mmol, 1 eq).

LCMS: 315 [M+H]⁺, 317 [M+2]⁺

Step 4: Synthesis of 4-(5-amino-2-(2,6-dimethylphenoxy)phenyl)-N-ethyl-6-methyl-7-oxo-6,7-dihydrothieno[2,3-c]pyridine-2-carboxamide 4-(5-amino-2-(2,6-dimethylphenoxy) phenyl)-N-ethyl-6-methyl-7-oxo-6,7-dihydrothieno[2,3-c]pyridine-2-carboxamide (0.045 g, 30%, brown viscous liquid) was prepared following General Procedure 1, Step 3 using 4-(2,6-dimethylphenoxy)-3-(4,4,5,5-tetramethyl-1,3,2-dioxaborolan-2-yl) aniline (0.162 g, 0.474 mmol, 1.5 eq) and 4-bromo-N-ethyl-6-methyl-7-oxo-6,7-dihydrothieno[2,3-c]pyridine-2-carboxamide (100 mg, 0.318 mmol, 1 eq).

LCMS: 448 [M+H]⁺

Step 5: Synthesis of 4-(5-acrylamido-2-(2,6-dimethylphenoxy)phenyl)-N-ethyl-6-methyl-7-oxo-6,7-dihydrothieno[2,3-c]pyridine-2-carboxamide 4-(5-acrylamido-2-(2,6-dimethylphenoxy)phenyl)-N-ethyl-6-methyl-7-oxo-6,7-dihydrothieno [2,3-c]pyridine-2-carboxamide (0.013 g, 14%, off white solid) was prepared following General Procedure 3 using 4-(5-amino-2-(2,6-dimethylphenoxy)phenyl)-N-ethyl-6-methyl-7-oxo-6,7-dihydrothieno[2,3-c]pyridine-2-carboxamide (0.080 g, 0.178 mmol, 1 eq).

LCMS: 502 [M+H]⁺

¹H NMR (400 MHz, DMSO-d6) δ 10.24 (s, 1H), 8.86 (br s, 1H), 7.89 (s, 1H), 7.75 (s, 2H), 7.60 (d, J=9.21 Hz, 1H), 6.99-7.21 (m, 3H), 6.31-6.50 (m, 2H), 6.23 (d, J=19.29 Hz, 1H), 5.74 (d, J=11.84 Hz, 1H), 3.62 (s, 3H), 3.16-3.28 (m, 2H), 2.00 (s, 6H), 1.09 (t, J=7.24 Hz, 3H).

Example S-57. Synthesis of (E)-4-(dimethylamino)-N-(4-(2,6-dimethylphenoxy)-3-(2-methyl-1-oxo-1,2-dihydroisoquinolin-4-yl)phenyl)but-2-enamide, Compound 410

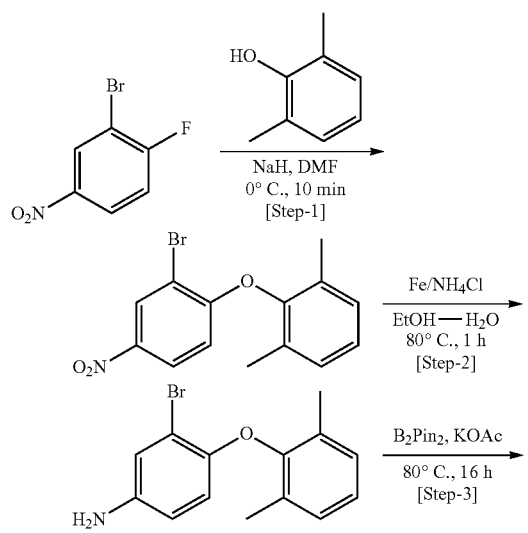

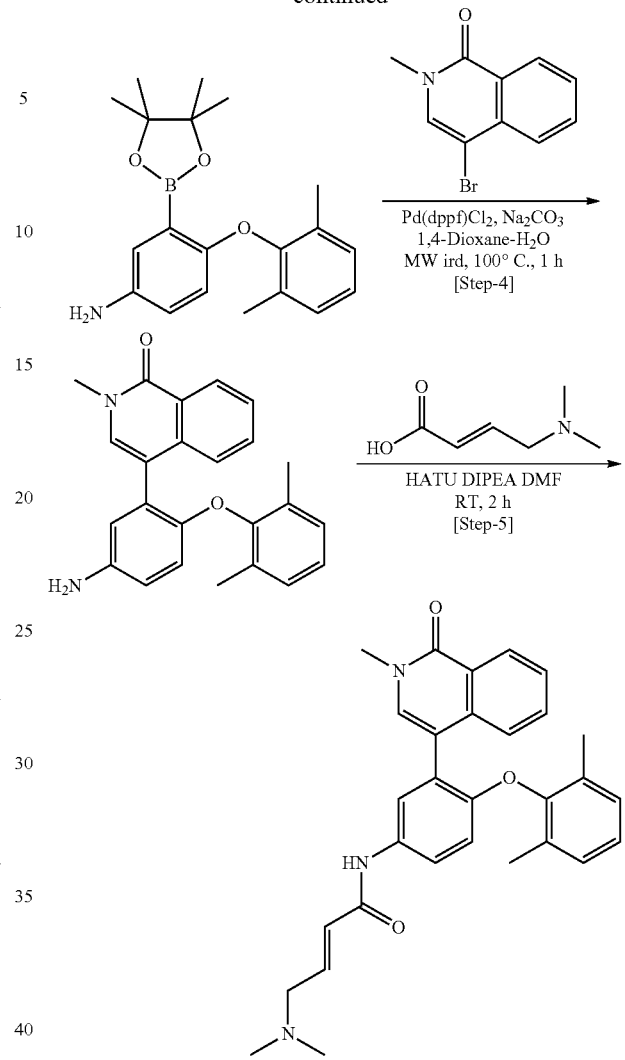

Step 1: Synthesis of 2-(2-bromo-4-nitrophenoxy)-1,3-dimethylbenzene 2-(2-bromo-4-nitrophenoxy)-1,3-dimethylbenzene was prepared following General Procedure 18, Step 1 using 2,6-dimethylphenol (2.0 g, 16.03 mmol, 1.0 eq).

LCMS: 322 [M+H]⁺, 324 [M+2]⁺

Step 2: Synthesis of 3-bromo-4-(2,6-dimethylphenoxy)aniline 3-bromo-4-(2,6-dimethylphenoxy)aniline (3.5 g, 97%, black viscous liquid) was prepared following General Procedure 1, Step 2 using 2-(2-bromo-4-nitrophenoxy)-1,3-dimethylbenzene (4.0 g, 12.46 mmol, 1.0 eq).

LCMS: 292 [M+H]⁺, 294 [M+2]⁺

Step 3: Synthesis of 4-(2,6-dimethylphenoxy)-3-(4,4,5,5-tetramethyl-1,3,2-dioxaborolan-2-yl)aniline 4-(2,6-dimethylphenoxy)-3-(4,4,5,5-tetramethyl-1,3,2-dioxaborolan-2-yl)aniline (0.700 g, 66%, black viscous liquid) was prepared following General Procedure 1, Step 3 using 3-bromo-4-(2,6-dimethylphenoxy)aniline (1.0 g, 45.6 mmol, 1.0 eq) and Bis(triphenylphosphine) palladium(II) dichloride (0.16 g, 0.228 mmol, 0.05 eq).

¹H NMR (400 MHz, CDCl₃): δ 6.97-7.11 (m, 3H), 6.58 (m, 2H), 6.14 (d, J=8.77 Hz, 1H), 2.05-2.18 (m, 6H), 1.23-1.28 (m, 12H).

Step 4: Synthesis of 4-(5-amino-2-(2,6-dimethylphenoxy)phenyl)-2-methylisoquinolin-1(2H)-one 4-(5-amino-2-(2,6-dimethylphenoxy)phenyl)-2-methylisoquinolin-1(2H)-one (0.220 g, 70%, brown viscous liquid) was prepared following General Procedure 1, Step 3 using 4-(2,6-dimethylphenoxy)-3-(4,4,5,5-tetramethyl-1,3,2-dioxaborolan-2-yl)aniline (0.375 g, 1.26 mmol, 1.5 eq)) and 4-bromo-2-methylisoquinolin-1(2H)-one (200 mg, 0.843 mmol, 1 eq).

LCMS: 371 [M+H]⁺

Step 5: (E)-4-(dimethylamino)-N-(4-(2,6-dimethylphenoxy)-3-(2-methyl-1-oxo-1,2-dihydroisoquinolin-4-yl)phenyl)but-2-enamide To a stirred solution of (E)-4-(dimethylamino)but-2-enoic acid (0.040 g, 0.340 mmol, 1 eq) in DMF (4 ml) were added HATU (0.264 g, 0.675 mmol, 2 eq) and DIPEA (0.32 ml, 1.73 mmol, 5 eq) at 0° C. The mixture was stirred at 0° C. for 20 min followed by addition of 4-(5-amino-2-(2,6-dimethylphenoxy)phenyl)-2-methylisoquinolin-1(2H)-one (0.128 g, 0.340 mmol, 1 eq) and monitored by TLC and LC-MS. The reaction was complete after 2 h and to the mixture was added ice-cold water (50 mL) to obtain a precipitate which was filtered over Büchner funnel; dried under vacuum to afford (E)-4-(dimethylamino)-N-(4-(2,6-dimethylphenoxy)-3-(2-methyl-1-oxo-1,2-dihydroisoquinolin-4-yl)phenyl)but-2-enamide (17 mg, 33%).

LCMS: 482 [M+1]⁺

¹H NMR (400 MHz, CDCl₃): δ 10.18 (br s, 1H), 8.32 (d, J=7.45 Hz, 1H), 7.76 (d, J=2.63 Hz, 1H), 7.70 (d, J=7.02 Hz, 1H), 7.50-7.61 (m, 2H), 7.38 (d, J=8.33 Hz, 1H), 7.00-7.15 (m, 3H), 6.70 (d, J=15.35 Hz, 1H), 6.22-6.41 (m, 2H), 3.59 (s, 3H), 2.38 (br s, 6H), 1.98 (br s, 6H), 1.23 (s, 3H).

Example S-58. Synthesis of N-(4-(2, 6-difluorophenylamino)-3-(2-methyl-1-oxo-1,2-dihydroisoquinolin-4-yl)phenyl)acrylamide, Compound 319

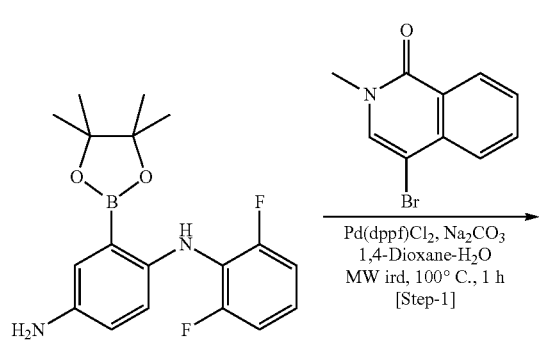

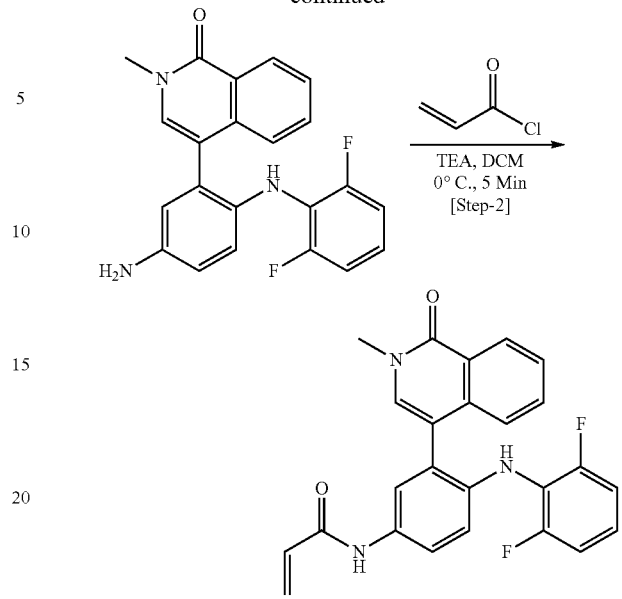

Step 1: Synthesis of 4-(5-amino-2-(2,6-difluorophenylamino)phenyl)-2-methylisoquinolin-1(2H)-one 4-(5-amino-2-(2,6-difluorophenylamino)phenyl)-2-methylisoquinolin-1(2H)-one (0.140 g, 87%, brown viscous liquid) was prepared following General Procedure 6, Step 1 using N1-(2,6-difluorophenyl)-2-(4,4,5,5-tetramethyl-1,3,2-dioxaborolan-2-yl)benzene-1,4-diamine (291.0 mg, 0.630 mmol, 1.5 eq) and 4-bromo-2-methylisoquinolin-1(2H)-one (100 mg, 0.420 mmol, 1 eq).

LCMS: 378 [M+H]⁺

Step 2: Synthesis of N-(4-(2,6-difluorophenylamino)-3-(2-methyl-1-oxo-1,2-dihydroisoquinolin-4-yl)phenyl)acrylamide, Compound 7

N-(4-(2,6-difluorophenylamino)-3-(2-methyl-1-oxo-1,2-dihydroisoquinolin-4-yl)phenyl)acrylamide (0.0065 g, 4%, off white solid) was prepared following General Procedure 3 using 4-(5-amino-2-(2,6-difluorophenylamino)phenyl)-2-methylisoquinolin-1(2H)-one (0.140 g, 0.420 mmol, 1 eq).

LCMS 432 [M+1]⁺

¹H NMR (400 MHz, DMSO-d₆): δ 10.05 (br s, 1H), 8.25 (d, J=7.89 Hz, 1H), 7.56-7.66 (m, 2H), 7.40-7.54 (m, 3H), 7.25 (d, J=8.33 Hz, 1H), 6.91-7.07 (m, 3H), 6.82 (br s, 1H), 6.60 (d, J=8.77 Hz, 1H), 6.38 (d, J=10.09 Hz, 1H), 6.19 (d, J=17.54 Hz, 1H), 5.69 (d, J=10.52 Hz, 1H), 3.54 (s, 3H).

Example S-59. Synthesis of N-(4-(4-fluoro-2,6-dimethylphenoxy)-3-(2-methyl-1-oxo-1,2-dihydroisoquinolin-4-yl)phenyl)acrylamide: (General Procedure 19) Compound 408

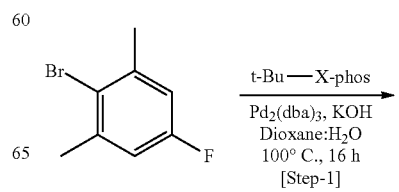

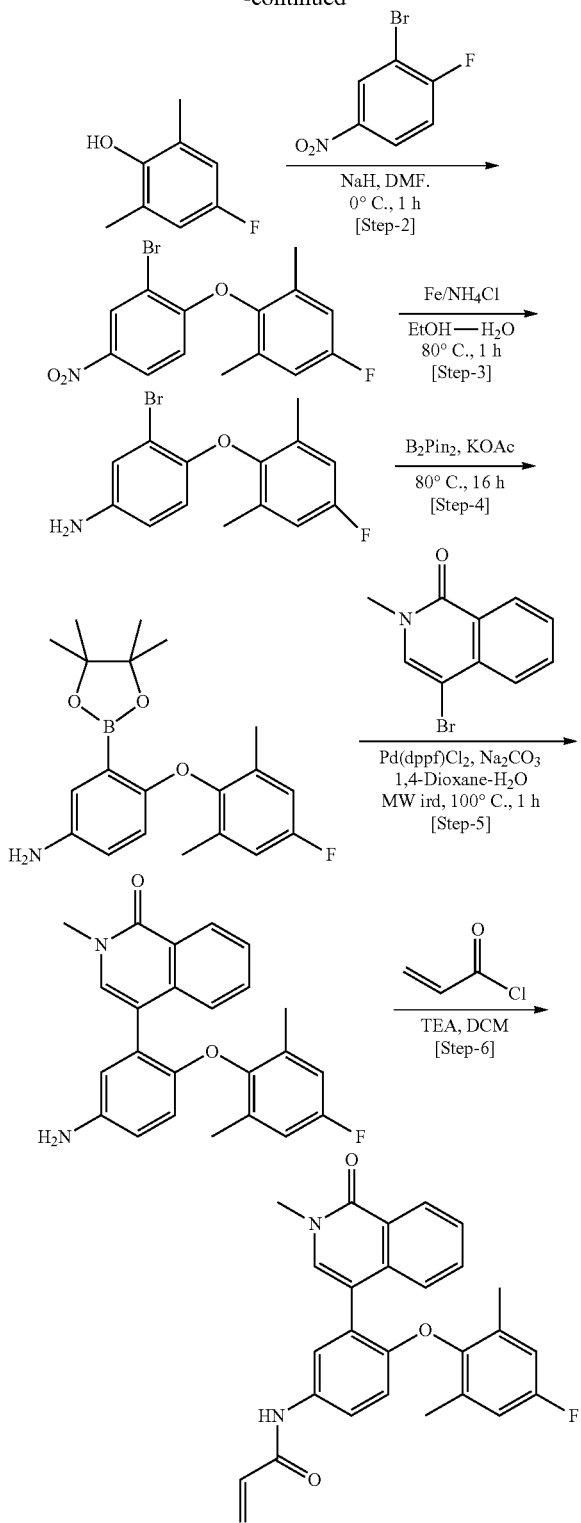

Step 1: Synthesis of 4-fluoro-2,6-dimethylphenol

A solution of 2-bromo-5-fluoro-1,3-dimethylbenzene (5.0 g, 24.7 mmol 1 eq) in 1,4-Dioxane:water (25 mL:25 mL) was added KOH (4.15 g, 74.2 mmol, 3 eq) and the mixture was degassed under nitrogen for 15 min. In an another set-up t-Bu-X-phos (839 mg, 7.98 mmol 0.08 eq) and Pd$_2$(dba)$_3$ (452 mg, 0.49 mmol 0.08 eq) in 1,4-Dioxane:water (10 mL:10 mL) was degassed under nitrogen for 15 min. The contents of the first degassed mixture was transferred into the degassed solution of the second and the mixture was heated at 100° C. and monitored by TLC and LC-MS. The reaction was complete after 16 h and the mixture was acidified with 6N—HCl (pH~2-3) and extracted with EtOAc (700 mL). The organic layer was washed with water (300 mL), brine (200 mL), dried over anhydrous Na$_2$SO$_4$, filtered and concentrated under reduced pressure to obtain a crude residue which was purified by CombiFlash chromatography to afford 4-fluoro-2,6-dimethylphenol (2.2 g, 64%) as a viscous brown solid.

LCMS: 141 [M+1]$^+$

Step 2: Synthesis of 2-(2-bromo-4-nitrophenoxy)-5-fluoro-1,3-dimethylbenzene 2-(2-bromo-4-nitrophenoxy)-5-fluoro-1,3-dimethylbenzene (5.0 g, 94%) was prepared following General Procedure 18, Step 1 using 4-fluoro-2,6-dimethylphenol (2.2 g, 18.7 mmol, 1.0 eq).

LCMS: 340 [M+H]$^+$, 342 [M+2]$^+$

Step 3: Synthesis of 3-bromo-4-(4-fluoro-2,6-dimethylphenoxy)aniline 3-bromo-4-(4-fluoro-2,6-dimethylphenoxy)aniline (2.5 g, 91%, black viscous liquid) was prepared following General Procedure 1, Step 2 using 2-(2-bromo-4-nitrophenoxy)-5-fluoro-1,3-dimethylbenzene (3.0 g, 88.4 mmol, 1.0 eq).

LCMS: 310 [M+H]$^+$, 312 [M+2]$^+$

Step 4: Synthesis of 4-(4-fluoro-2,6-dimethylphenoxy)-3-(4,4,5,5-tetramethyl-1,3,2-dioxaborolan-2-yl)aniline 4-(4-fluoro-2,6-dimethylphenoxy)-3-(4,4,5,5-tetramethyl-1,3,2-dioxaborolan-2-yl)aniline (1.5 g, 87%, black viscous liquid) was prepared following General Procedure 1, Step 3 using 3-bromo-4-(4-fluoro-2,6-dimethylphenoxy)aniline (0.170 g, 0.242 mmol, 0.05 eq).

$^1$H NMR (400 MHz, CDCl$_3$): δ 6.87-7.07 (m, 2H), 6.63 (d, J=17.10 Hz, 1H), 6.47-6.53 (m, 1H), 6.44 (s, 1H), 4.70 (br s, 2H), 1.94-2.16 (m, 6H), 1.09-1.24 (m, 12H).

Step 5: Synthesis of 4-(5-amino-2-(4-fluoro-2,6-dimethylphenoxy)phenyl)-2-methylisoquinolin-1(2H)-one 4-(5-amino-2-(4-fluoro-2,6-dimethylphenoxy)phenyl)-2-methylisoquinolin-1(2H)-one (0.065 g, 39%, brown viscous liquid) was prepared following General Procedure 6, Step 1 using 4-(4-fluoro-2,6-dimethylphenoxy)-3-(4,4,5,5-tetramethyl-1,3,2-dioxaborolan-2-yl)aniline (225.0 mg, 0.632 mmol, 1.5 eq) and 4-bromo-2-methylisoquinolin-1(2H)-one (100 mg, 0.921 mmol, 1 eq).

LCMS: 389 [M+H]$^+$

Step 6: Synthesis of N-(4-(4-fluoro-2,6-dimethylphenoxy)-3-(2-methyl-1-oxo-1,2-dihydroisoquinolin-4-yl)phenyl)acrylamide, Compound 7

N-(4-(4-fluoro-2,6-dimethylphenoxy)-3-(2-methyl-1-oxo-1,2-dihydroisoquinolin-4-yl)phenyl)acrylamide (0.009 g, 12%, off white solid) was prepared following General Procedure 3 using 4-(5-amino-2-(4-fluoro-2,6-dimethylphenoxy)phenyl)-2-methylisoquinolin-1(2H)-one (0.065 g, 0.167 mmol, 1 eq).

LCMS: 443 [M+1]$^+$ $^1$H NMR (400 MHz, DMSO-d$_6$): δ 10.17 (s, 1H), 8.32 (d, J=7.89 Hz, 1H), 7.76 (d, J=2.19 Hz, 1H), 7.70 (s, 1H), 7.44-7.65 (m, 3H), 7.36 (d, J=8.33 Hz, 1H), 6.97 (d, J=8.77 Hz, 2H), 6.33-6.47 (m, 2H), 6.24 (d, J=1.75 Hz, 1H), 5.73 (d, J=11.84 Hz, 1H), 3.59 (s, 3H), 1.98 (br s, 6H).

Example S-60. Synthesis of N-(4-(4-fluoro-2,6-dimethylphenoxy)-3-(1-methyl-5-(methylamino)-6-oxo-1,6-dihydropyridin-3-yl)phenyl)acrylamide, Compound 167

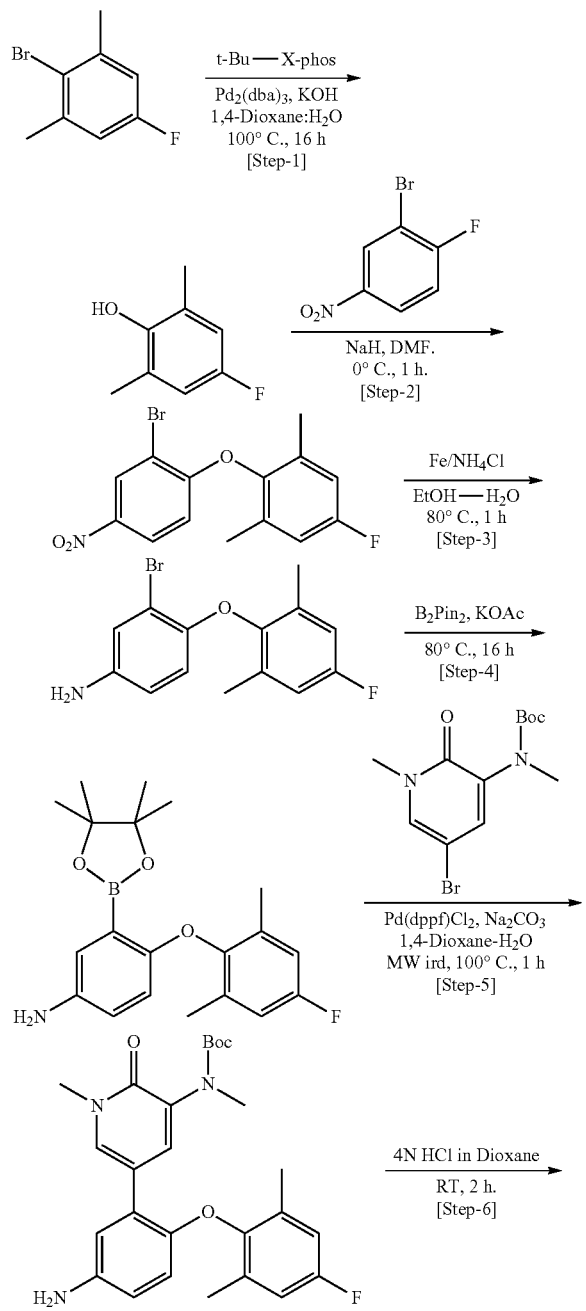

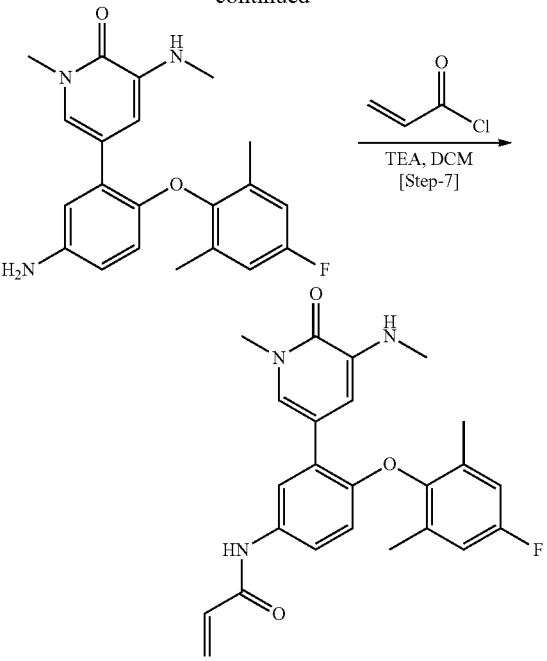

Step 1: Synthesis of 4-fluoro-2,6-dimethylphenol 4-fluoro-2,6-dimethylphenol (2.2 g, 64% viscous brown solid) was prepared following General Procedure 19, Step 1 using 2-bromo-5-fluoro-1,3-dimethylbenzene (5.0 g, 24.7 mmol, 1 eq).

LCMS: 141 [M+1]$^+$

Step 2: Synthesis of 2-(2-bromo-4-nitrophenoxy)-5-fluoro-1,3-dimethylbenzene 2-(2-bromo-4-nitrophenoxy)-5-fluoro-1,3-dimethylbenzene (5.0 g, 94%) was prepared following General Procedure 18, Step 1 using 4-fluoro-2,6-dimethylphenol (2.2 g, 18.7 mmol, 1.0 eq).

LCMS: 340 [M+H]$^+$, 342 [M+2]$^+$

Step 3: Synthesis of 3-bromo-4-(4-fluoro-2,6-dimethylphenoxy)aniline 3-bromo-4-(4-fluoro-2,6-dimethylphenoxy)aniline (2.5 g, 91%, black viscous liquid) was prepared following General Procedure 1, Step 2 using 2-(2-bromo-4-nitrophenoxy)-5-fluoro-1,3-dimethylbenzene (3.0 g, 88.4 mmol, 1.0 eq).

LCMS: 310[M+H]$^+$, 312 [M+2]$^+$

Step 4: Synthesis of 4-(4-fluoro-2,6-dimethylphenoxy)-3-(4,4,5,5-tetramethyl-1,3,2-dioxaborolan-2-yl)aniline 4-(4-fluoro-2,6-dimethylphenoxy)-3-(4,4,5,5-tetramethyl-1,3,2-dioxaborolan-2-yl)aniline (1.5 g, 87%, black viscous liquid) was prepared following General Procedure 1, Step 3 using 3-bromo-4-(4-fluoro-2,6-dimethylphenoxy)aniline (0.170 g, 0.242 mmol, 0.05 eq).

$^1$H NMR (400 MHz, CDCl$_3$): δ 6.87-7.07 (m, 2H), 6.63 (d, J=17.10 Hz, 1H), 6.47-6.53 (m, 1H), 6.44 (s, 1H), 4.70 (br s, 2H), 1.94-2.16 (m, 6H), 1.09-1.24 (m, 12H).

Step 5: Synthesis of tert-butyl 5-(5-amino-2-(4-fluoro-2,6-dimethylphenoxy)phenyl)-1-methyl-2-oxo-1,2-dihydropyridin-3-yl(methyl)carbamate tert-butyl 5-(5-amino-2-(4-fluoro-2,6-dimethylphenoxy)phenyl)-1-methyl-2-oxo-1,2-dihydropyridin-3-yl(methyl)carbamate (0.085 g, 36%, brown viscous liquid) was prepared following General Procedure 6, Step 1 using 4-(4-fluoro-2,6-dimethylphenoxy)-3-(4,4,5,5-tetramethyl-1,3,2-dioxaborolan-2-yl)aniline (271.0 mg, 0.789 mmol, 1.5 eq) and tert-butyl 5-bromo-1-methyl-2-oxo-1,2-dihydropyridin-3-yl(methyl)carbamate (160 mg, 0.506 mmol, 1 eq).

LCMS: 468 [M+H]$^+$

Step 6: Synthesis of 5-(5-amino-2-(4-fluoro-2,6-dimethylphenoxy)phenyl)-1-methyl-3-(methylamino)pyridin-2(1H)-one 5-(5-amino-2-(4-fluoro-2,6-dimethylphenoxy)phenyl)-1-methyl-3-(methylamino)pyridin-2(1H)-one (65 mg, 98%, thick viscous solid) was prepared following General Procedure 17, Step 5 using tert-butyl 5-(5-amino-2-(4-fluoro-2,6-dimethylphenoxy)phenyl)-1-methyl-2-oxo-1,2-dihydropyridin-3-yl(methyl)carbamate (0.085 g, 0.182 mmol).

LCMS: 368 [M+H]$^+$

Step 7: Synthesis of N-(4-(4-fluoro-2,6-dimethylphenoxy)-3-(1-methyl-5-(methylamino)-6-oxo-1,6-dihydropyridin-3-yl)phenyl)acrylamide, Compound 7

N-(4-(4-fluoro-2,6-dimethylphenoxy)-3-(1-methyl-5-(methylamino)-6-oxo-1,6-dihydropyridin-3-yl)phenyl)acrylamide (0.007 g, 7%, off white solid) was prepared following General Procedure 3 using 5-(5-amino-2-(4-fluoro-2,6-dimethylphenoxy)phenyl)-1-methyl-3-(methylamino)pyridin-2(1H)-one (0.065 g, 0.177 mmol, 1 eq).

LCMS: 422 [M+1]$^+$ $^1$H NMR (400 MHz, DMSO-d$_6$): δ 10.11 (br s, 1H), 7.73 (br s, 1H), 7.43 (d, J=10.96 Hz, 1H), 7.16 (s, 1H), 7.04 (d, J=9.21 Hz, 2H), 6.32-6.48 (m, 2H), 6.14-6.31 (m, 2H), 5.72 (d, J=10.52 Hz, 1H), 5.65 (d, J=5.26 Hz, 1H), 3.53 (s, 3H), 2.55-2.82 (m, 3H), 2.05 (s, 6H).

Example S-61. Synthesis of N-(4-(2,6-difluorophenoxy)-3-(2-methyl-1-oxo-1,2-dihydroisoquinolin-4-yl)phenyl)acrylamide, Compound 583

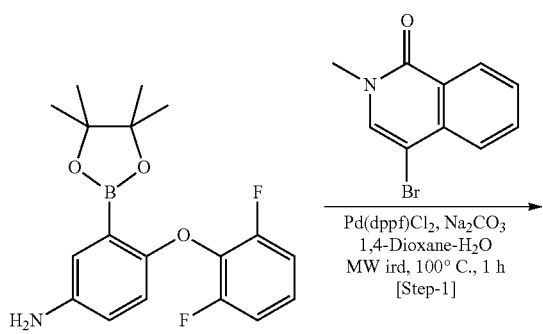

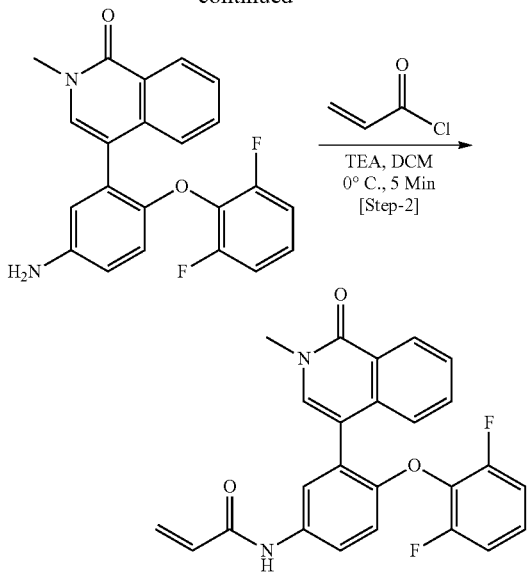

Step 1: Synthesis of 4-(5-amino-2-(2,6-difluorophenoxy)phenyl)-2-methylisoquinolin-1(2H)-one 4-(5-amino-2-(2,6-difluorophenoxy)phenyl)-2-methylisoquinolin-1(2H)-one (0.150 g, 94%, brown viscous liquid) was prepared following General Procedure 6, Step 1 using 4-(2,6-difluorophenoxy)-3-(4,4,5,5-tetramethyl-1,3,2-dioxaborolan-2-yl)aniline (219 mg, 0.630 mmol, 1.5 eq) and 4-bromo-2-methylisoquinolin-1(2H)-one (100 mg, 0.420 mmol, 1 eq).

LCMS: 379[M+H]$^+$

Step 2: Synthesis of N-(4-(2,6-difluorophenoxy)-3-(2-methyl-1-oxo-1,2-dihydroisoquinolin-4-yl)phenyl)acrylamide N-(4-(2,6-difluorophenoxy)-3-(2-methyl-1-oxo-1,2-dihydroisoquinolin-4-yl)phenyl)acrylamide (0.050 g, 29%, off white solid) was prepared following General Procedure 3 using 4-(5-amino-2-(2,6-difluorophenoxy)phenyl)-2-methylisoquinolin-1(2H)-one (0.150 g, 0.40 mmol, 1 eq).

LCMS: 433 [M+1]$^+$ $^1$H NMR: (400 MHz, DMSO-d$_6$) δ 10.24 (s, 1H), 8.26 (d, J=7.34 Hz, 1H), 7.75 (d, J=2.93 Hz, 1H), 7.60-7.70 (m, 2H), 7.46-7.59 (m, 2H), 7.32 (d, J=7.83 Hz, 1H), 7.06-7.26 (m, 3H), 6.82 (d, J=8.80 Hz, 1H), 6.38 (d, J=9.78 Hz, 1H), 6.24 (d, J=1.47 Hz, 1H), 5.73 (d, J=11.74 Hz, 1H), 3.55 (s, 3H).

Example S-62. Synthesis of N-(4-(2,6-dimethylphenoxy)-3-(4-methoxy-1-methyl-6-oxo-1,6-dihydropyridin-3-yl)phenyl)acrylamide, Compound 584

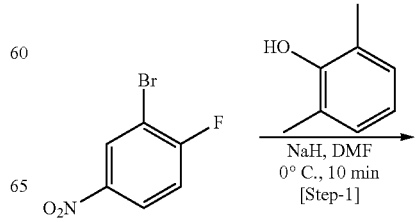

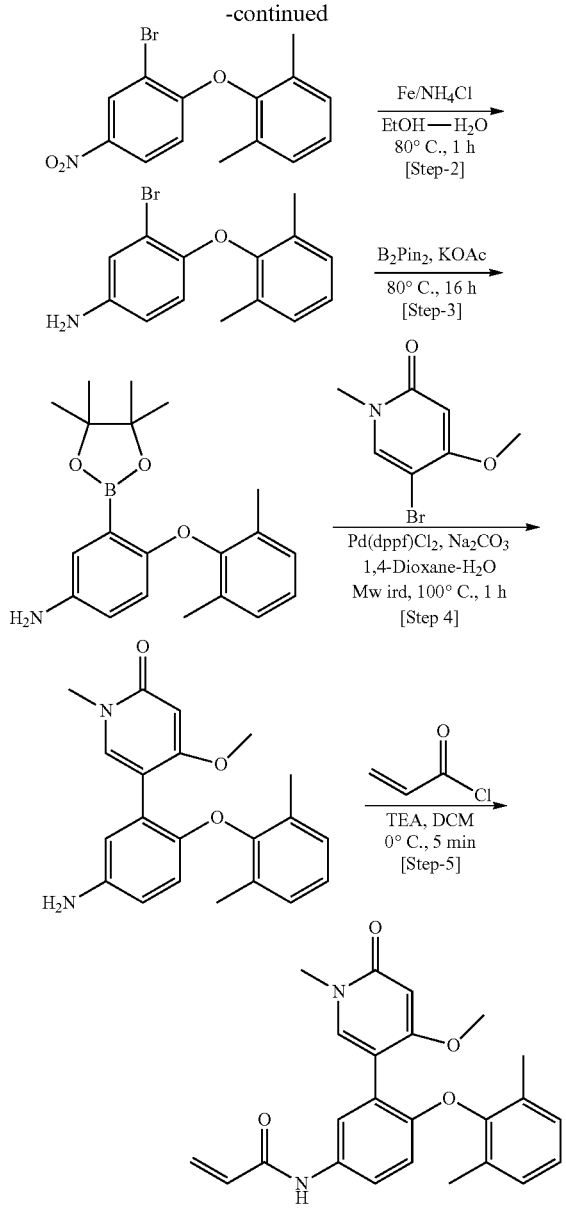

Step 1: Synthesis of 2-(2-bromo-4-nitrophenoxy)-1,3-dimethylbenzene

To a stirred solution of 2,6-dimethylphenol (2.0 g, 16.03 mmol, 1.0 eq) in DMF (10 mL) was added NaH (0.721 g, 18.00 mmol, 1.1 eq) at 0° C. followed by an addition of 2-bromo-1-fluoro-4-nitrobenzene (3.49 g, 18.0 mmol, 1.1 eq) and monitored by TLC and LC-MS. The reaction was complete after 10 min and to the the mixture was added ice-cold water (50 mL) to obtain a precipitate which was filtered over Büchner funnel; dried under vacuum to afford 2-(2-bromo-4-nitrophenoxy)-1,3-dimethylbenzene (4.5 g, 68%) as a yellow solid.

LCMS: 322[M+H]$^+$, 324 [M+2]$^+$

Step 2: Synthesis of 3-bromo-4-(2,6-dimethylphenoxy)aniline 3-bromo-4-(2,6-dimethylphenoxy)aniline (3.5 g, 97%, black viscous liquid) was prepared following General Procedure 1, Step 2 using 2-(2-bromo-4-nitrophenoxy)-1,3-dimethylbenzene (4.0 g, 12.46 mmol, 1.0 eq).

LCMS: 292 [M+1]$^+$, 294 [M+2]$^+$

Step 3: Synthesis of 4-(2,6-dimethylphenoxy)-3-(4,4,5,5-tetramethyl-1,3,2-dioxaborolan-2-yl)aniline 4-(2,6-dimethylphenoxy)-3-(4,4,5,5-tetramethyl-1,3,2-dioxaborolan-2-yl)aniline (0.700 g, 66%, black viscous liquid) was prepared following General Procedure 1, Step 3 using 3-bromo-4-(2,6-dimethylphenoxy)aniline (1.0 g, 45.6 mmol, 1.0 eq) and Bis(triphenylphosphine) palladium(II) dichloride (0.16 g, 0.228 mmol, 0.05 eq).

$^1$H NMR (400 MHz, CDCl$_3$): δ 6.97-7.11 (m, 3H), 6.58 (m, 2H), 6.14 (d, J=8.77 Hz, 1H), 2.05-2.18 (m, 6H), 1.23-1.28 (m, 12H).

Step 4: Synthesis of 5-(5-amino-2-(2,6-dimethylphenoxy)phenyl)-4-methoxy-1-methylpyridin-2(1H)-one 5-(5-amino-2-(2,6-dimethylphenoxy)phenyl)-4-methoxy-1-methyl pyridin-2(1H)-one (0.120 g, 45%, brown viscous liquid) was prepared following General Procedure 1, Step 3 using 4-(2,6-dimethylphenoxy)-3-(4,4,5,5-tetramethyl-1,3,2-dioxaborolan-2-yl)aniline (0.160 g, 0.73 mmol, 1.5 eq) and 5-bromo-4-methoxy-1-methylpyridin-2(1H)-one (166 mg, 0.48 mmol, 1 eq).

LCMS: 351 [M+H]$^+$

Step 5: Synthesis of N-(4-(2,6-dimethylphenoxy)-3-(4-methoxy-1-methyl-6-oxo-1,6-dihydropyridin-3-yl)phenyl)acrylamide N-(4-(2,6-dimethylphenoxy)-3-(4-methoxy-1-methyl-6-oxo-1,6-dihydropyridin-3-yl)phenyl)acrylamide (0.030 g, 21%, off white solid) was prepared following General Procedure 3 using 5-(5-amino-2-(2,6-dimethylphenoxy)phenyl)-4-methoxy-1-methyl pyridin-2(1H)-one (0.120 g, 0.342 mmol, 1 eq).

LCMS: 405 [M+H]$^+$ $^1$H NMR (400 MHz, DMSO-d$_6$) δ 10.07 (s, 1H), 7.67 (s, 1H), 7.61 (d, J=2.45 Hz, 1H), 7.41 (d, J=8.80 Hz, 1H), 7.09-7.20 (m, 2H), 7.08 (d, J=8.31 Hz, 1H), 6.37 (d, J=10.27 Hz, 1H), 6.23 (d, J=1.47 Hz, 1H), 6.18 (d, J=8.80 Hz, 1H), 5.91 (s, 1H), 5.72 (d, J=9.78 Hz, 1H), 3.73 (s, 3H), 3.41 (s, 3H), 2.00 (s, 6H).

Example S-63: Synthesis of 7-(5-acrylamido-2-(2,6-dimethylphenylamino)phenyl)-N-ethyl-5-methyl-4-oxo-4,5-dihydrothieno[3,2-c]pyridine-2-carboxamide, Compound 585

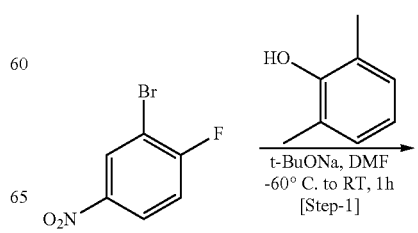

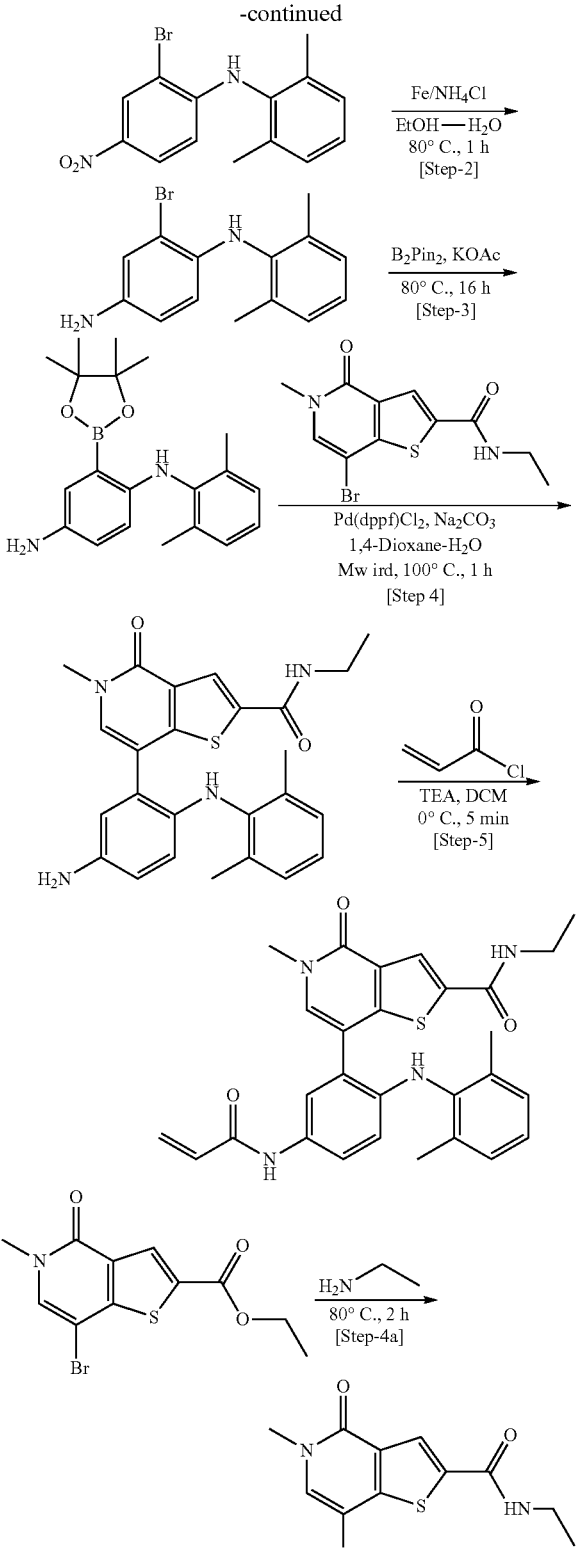

Step 1: Synthesis of 2-bromo-N-(2,6-dimethylphenyl)-4-nitroaniline

To a solution of 2,6-dimethylaniline (2.0 g, 16.58 mmol, 1.0 eq) in DMF (30 mL) was added t-BuONa (11 g, 99 mmol, 60 eq) at −60° C. followed by an addition of 2-bromo-1-fluoro-4-nitrobenzene (4 g, 18.15 mmol, 1.1 eq). The temperature of the mixture was gradually increased to RT over a period of 30 min and monitored by TLC and LC-MS. The reaction was complete after 2 h and to the mixture was added ice-cold water (50 mL) to obtain a precipitate which was filtered over Büchner funnel; dried under vacuum to afford 2-bromo-N-(2,6-dimethylphenyl)-4-nitroaniline (1.1 g, 21%) as a yellow solid.

$^1$H NMR (400 MHz, DMSO-$d_6$): δ 8.37 (d, J=2.63 Hz, 1H), 8.23 (s, 1H), 7.98 (dd, J=2.63, 9.21 Hz, 1H), 7.23 (s, 3H), 2.10 (s, 6H).

Step 2: Synthesis of 2-bromo-N1-(2,6-dimethylphenyl)benzene-1,4-diamine 2-bromo-N1-(2,6-dimethylphenyl)benzene-1,4-diamine (1 g, 100%, black viscous liquid) was prepared following General Procedure 1, Step 2 using 22-bromo-N-(2,6-dimethylphenyl)-4-nitroaniline (1.1 g, 3.43 mmol, 1.0 eq).

LCMS: 291 [M+1]$^+$, 293 [M+2]$^+$

Step 3: Synthesis of N1-(2,6-dimethylphenyl)-2-(4,4,5,5-tetramethyl-1,3,2-dioxaborolan-2-yl)benzene-1,4-diamine N1-(2,6-dimethylphenyl)-2-(4,4,5,5-tetramethyl-1,3,2-dioxaborolan-2-yl)benzene-1,4-diamine (0.6 g, 52%, black viscous liquid) was prepared following General Procedure 1, Step 3 using 2-bromo-N1-(2,6-dimethylphenyl)benzene-1,4-diamine (1 g, 3.43 mmol, 1.0 eq).

$^1$H NMR (400 MHz, CDCl$_3$): δ 7.26 (s, 2H), 7.08 (s, 2H), 6.57 (s, 1H), 6.43 (s, 1H), 2.10-2.25 (s, 6H), 0.02-0.11 (m, 12H).

Step 4a: Synthesis of 4-bromo-N-ethyl-6-methyl-7-oxo-6,7-dihydrothieno[2,3-c]pyridine-2-carboxamide 4-bromo-N-ethyl-6-methyl-7-oxo-6,7-dihydrothieno[2,3-c]pyridine-2-carboxamide (350 mg, 70%, brown solid) was prepared following General Procedure 18, Step 4a using ethyl 4-bromo-6-methyl-7-oxo-6,7-dihydrothieno[2,3-c]pyridine-2-carboxylate (0.500 g, 0.498 mmol 1 eq).

LCMS: 315 [M+1]$^+$, 317 [M+2]$^+$

Step 4: Synthesis of 7-(5-amino-2-(2,6-dimethylphenylamino)phenyl)-N-ethyl-5-methyl-4-oxo-4,5-dihydrothieno[3,2-c]pyridine-2-carboxamide 7-(5-amino-2-(2,6-dimethylphenyl amino)phenyl)-N-ethyl-5-methyl-4-oxo-4,5-dihydrothieno[3,2-c]pyridine-2-carboxamide (0.130 g, 92%, brown viscous liquid) was prepared following General Procedure 6, Step 1 using N1-(2,6-dimethylphenyl)-2-(4,4,5,5-tetramethyl-1,3,2-dioxaborolan-2-yl)benzene-1,4-diamine (214 mg, 0.63 mmol, 1.5 eq) and 7-bromo-N-ethyl-5-methyl-4-oxo-4,5-dihydrothieno[3,2-c]pyridine-2-carboxamide (100 mg, 0.42 mmol, 1 eq).

LCMS: 447 [M+1]$^+$

Step 5: Synthesis of 7-(5-acrylamido-2-(2,6-dimethylphenylamino)phenyl)-N-ethyl-5-methyl-4-oxo-4,5-dihydrothieno[3,2-c]pyridine-2-carboxamide 7-(5-acrylamido-2-(2,6-dimethylphenylamino)phenyl)-N-ethyl-5-methyl-4-oxo-4,5-dihydrothieno [3,2-c]pyridine- 2-carboxamide (0.016 g, 11%, off white solid) was prepared following General Procedure 3 using 7-(5-amino-2-(2,6-dimethylphenylamino)phenyl)-N-ethyl-5-methyl-4-oxo-4,5-dihydro thieno [3,2-c]pyridine-2-carboxamide (0.130 g, 0.29 mmol, 1 eq).

LCMS: 501 [M+1]+

$^1$H NMR (400 MHz, Methanol-d$_4$): δ 9.92 (s, 1H), 8.72 (br s, 1H), 8.29 (s, 1H), 7.70 (s, 1H), 7.64 (d, J=1.96 Hz, 1H), 7.33 (d, J=8.31 Hz, 1H), 6.98-7.13 (m, 2H), 6.59 (s, 1H), 6.35 (d, J=10.27 Hz, 1H), 6.18 (br s, 1H), 6.00 (d, J=8.80 Hz, 1H), 5.67 (d, J=12.23 Hz, 1H), 3.56 (s, 3H), 2.09 (s, 6H), 1.11 (t, J=7.09 Hz, 3H).

Example S-64: 7-(2-(2,6-dimethylphenoxy)-5-propiolamidophenyl)-N-ethyl-5-methyl-4-oxo-4,5-dihydrothieno[3,2-c]pyridine-2-carboxamide, Compound 587

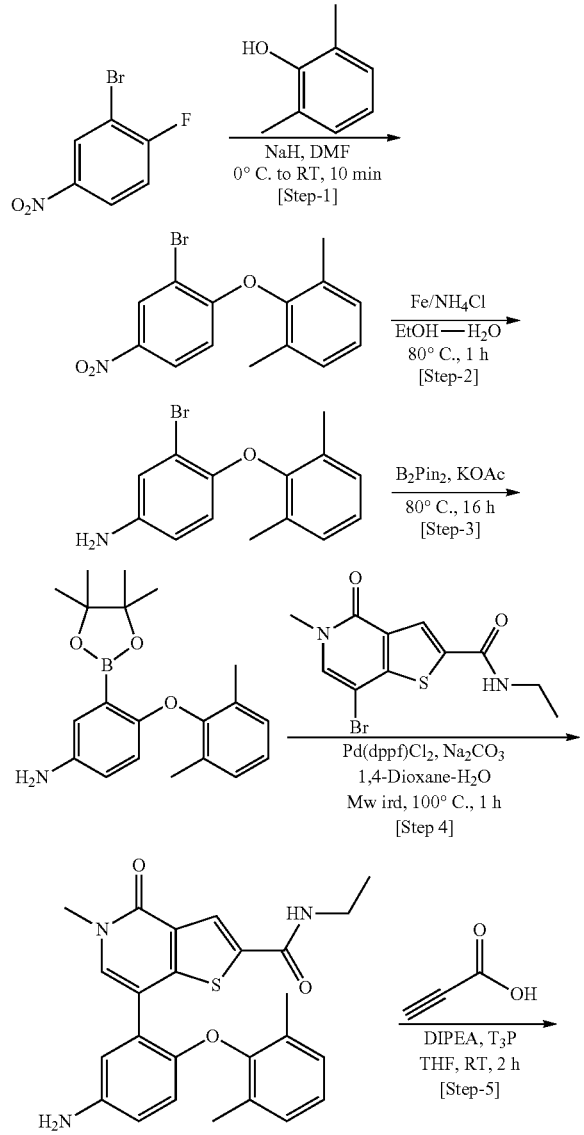

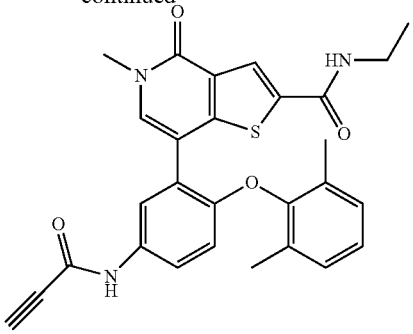

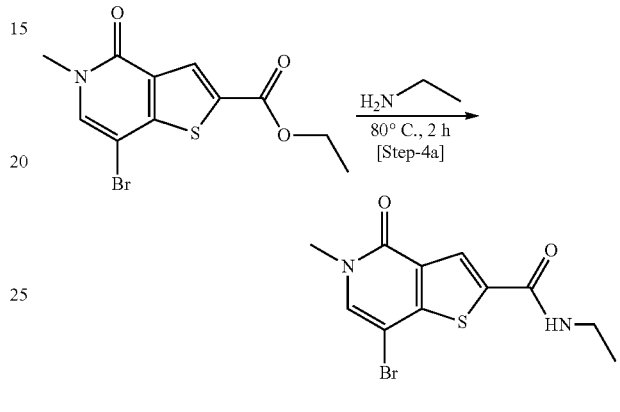

Step 1: Synthesis of 2-(2-bromo-4-nitrophenoxy)-1,3-dimethylbenzene

To a stirred solution of 2,6-dimethylphenol (2.0 g, 16.03 mmol, 1.0 eq) in DMF (10 mL) was added NaH (0.721 g, 18.00 mmol, 1.1 eq) at 0° C. followed by an addition of 2-bromo-1-fluoro-4-nitrobenzene (3.49 g, 18.0 mmol, 1.1 eq) and monitored by TLC and LC-MS. The reaction was complete after 10 min and to the the mixture was added ice-cold water (50 mL) to obtain a precipitate which was filtered over Büchner funnel; dried under vacuum to afford 2-(2-bromo-4-nitrophenoxy)-1,3-dimethylbenzene (4.5 g, 68%) as a yellow solid.

LCMS: 322 [M+1]+, 324 [M+2]+

Step 2: Synthesis of 3-bromo-4-(2,6-dimethylphenoxy)aniline

To a solution of 2-(2-bromo-4-nitrophenoxy)-1,3-dimethylbenzene (4.0 g, 12.42 mmol, 1.0 eq) in ethanol (20 mL), a solution of NH$_4$Cl (6.6 g, 124.16 mmol) in water (22 mL) was added followed by addition of iron powder (5.5 g, 99.3 mmol). The reaction mixture was stirred at 90° C. for 1 h. TLC analysis indicated the reaction was complete. The reaction mixture was filtered through a pad of Celite. The filtrate was diluted with water and extracted with EtOAc. The combined organic layers were washed with brine, dried over anhydrous Na$_2$SO$_4$, filtered and concentrated under reduced pressure to give 3-bromo-4-(2,6-dimethylphenoxy) aniline (3.5 g, 97%) as a black viscous liquid.

LCMS: 292 [M+1]+, 294 [M+2]+

Step 3: Synthesis of 4-(2,6-dimethylphenoxy)-3-(4,4,5,5-tetramethyl-1,3,2-dioxaborolan-2-yl)aniline To a solution of 3-bromo-4-(2,6-dimethylphenoxy)aniline (15 g, 51.5 mmol, 1 eq) in 1,4-Dioxane (200 mL) were added B₂Pin₂ (20.6 g, 77.3 mmol. 1.5 eq), KOAc (16 g, 154.6 mmol, 3 eq) and the mixture was degassed under nitrogen for 20 min. PdCl₂(PPh₃)₂ (3.8 g, 5.1 mmol, 0.1 eq) was then added to the mixture and the mixture was further degassed under nitrogen for 10 min. The mixture was heated at 80° C. for 16 h. TLC analysis indicated the reaction was complete. The mixture was filtered through the celite bed washing with EtOAc (500 mL). The organic layer was washed with water (250 ml×2), brine (300 mL) dried over anhydrous Na₂SO₄, filtered and concentrated under reduced pressure to obtain a crude which was purified by column chromatography to afford 4-(2,6-dimethylphenoxy)-3-(4,4,5,5-tetramethyl-1,3,2-dioxaborolan-2-yl)aniline (7.0 g, Yield: 40%) as a brown solid.

¹H NMR: (400 MHz, CDCl₃): δ 6.97-7.11 (m, 3H), 6.58 (m, 2H), 6.14 (d, J=8.77 Hz, 1H), 2.05-2.18 (m, 6H), 1.23-1.28 (m, 12H)

Step 4a: Synthesis of 7-bromo-N-ethyl-5-methyl-4-oxo-4,5-dihydrothieno[3,2-c]pyridine-2-carboxamide 7-bromo-N-ethyl-5-methyl-4-oxo-4,5-dihydrothieno[3,2-c]pyridine-2-carboxamide (350 mg, 70%, brown solid) was prepared following General Procedure 18, Step 4a using ethyl 7-bromo-5-methyl-4-oxo-4,5-dihydrothieno[3,2-c]pyridine-2-carboxylate (0.500 g, 0.498 mmol, 1 eq).

LCMS: 315 [M+1]⁺, 317 [M+2]⁺

Step 4: Synthesis of 7-(5-amino-2-(2,6-dimethylphenoxy)phenyl)-N-ethyl-5-methyl-4-oxo-4,5-dihydrothieno[3,2-c]pyridine-2-carboxamide 7-(5-amino-2-(2,6-dimethylphenoxy) phenyl)-N-ethyl-5-methyl-4-oxo-4,5-dihydrothieno[3,2-c]pyridine-2-carboxamide (0.130 g, 92%, brown viscous liquid) was prepared following General Procedure 6, Step 1 using 4-(2,6-dimethylphenoxy)-3-(4,4,5,5-tetramethyl-1,3,2-dioxaborolan-2-yl)aniline (214 mg, 0.63 mmol, 1.5 eq) and 7-bromo-N-ethyl-5-methyl-4-oxo-4,5-dihydrothieno[3,2-c]pyridine-2-carboxamide (100 mg, 0.42 mmol, 1 eq).

LCMS: 448 [M+1]⁺

Step 5: Synthesis of 7-(2-(2,6-dimethylphenoxy)-5-propiolamidophenyl)-N-ethyl-5-methyl-4-oxo-4,5-dihydrothieno[3,2-c]pyridine-2-carboxamide 7-(2-(2,6-dimethylphenoxy)-5-propiolamidophenyl)-N-ethyl-5-methyl-4-oxo-4,5-dihydrothieno [3,2-c]pyridine-2-carboxamide (0.014 g, 11%, off white solid) was prepared following General Procedure 4 using 7-(5-amino-2-(2,6-dimethylphenoxy)phenyl)-N-ethyl-5-methyl-4-oxo-4,5-dihydrothieno [3,2-c]pyridine-2-carboxamide (0.116 g, 0.26 mmol, 1 eq).

LCMS: 500 [M+1]⁺

¹H NMR (400 MHz, Methanol-d₄): δ 8.15 (s, 1H), 7.77 (d, J=2.7 Hz, 1H), 7.71 (s, 1H), 7.47 (dd, J=9.0, 2.7 Hz, 1H), 7.13-7.00 (m, 3H), 6.42 (d, J=9.0 Hz, 1H), 3.72 (s, 3H), 3.40 (q, J=7.2 Hz, 2H), 2.08 (s, 6H), 1.34-1.19 (m, 3H).

Example S-65: 7-(5-acrylamido-2-(4-fluoro-2, 6-dimethylphenoxy)phenyl)-N-ethyl-5-methyl-4-oxo-4,5-dihydrothieno[3,2-c]pyridine-2-carboxamide, Compound 588

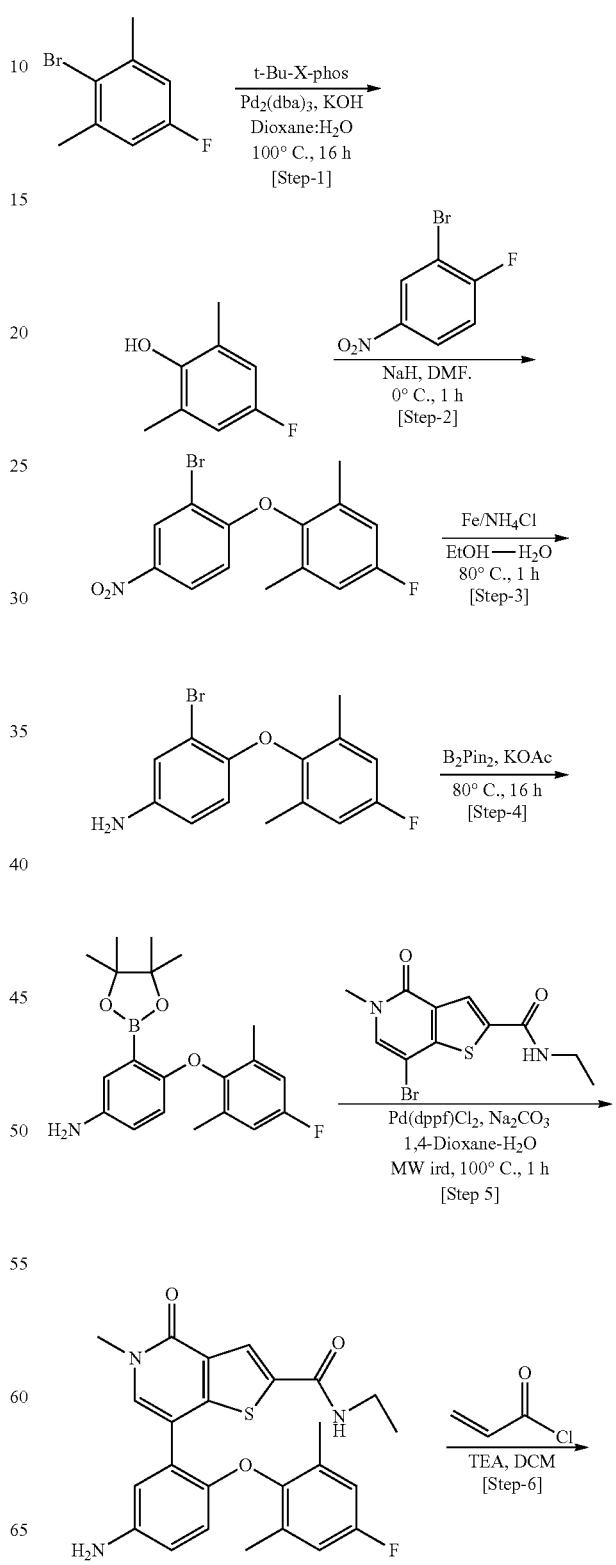

443

-continued

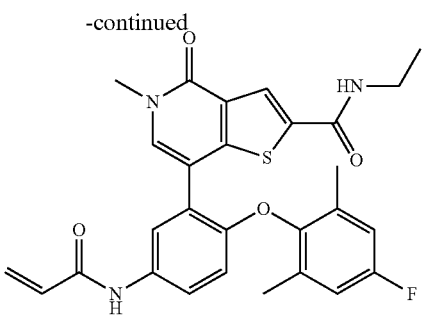

Step 1. Synthesis of 4-fluoro-2,6-dimethylphenol

A solution of 2-bromo-5-fluoro-1,3-dimethylbenzene (5.0 g, 24.7 mmol 1 eq) in 1,4-Dioxane:water (25 mL:25 mL) was added KOH (4.15 g, 74.2 mmol 3 eq) and the mixture was degassed under nitrogen for 15 min. In an another set-up t-Bu-X-phos (839 mg, 7.98 mmol 0.08 eq) and $Pd_2(dba)_3$ (452 mg, 0.49 mmol 0.08 eq) in 1,4-Dioxane:water (10 mL:10 mL) was degassed under nitrogen for 15 min. The contents of the first degassed mixture was transferred into the degassed solution of the second and the mixture was heated at 100° C. and monitored by TLC and LC-MS. The reaction was complete after 16 h and the mixture was acidified with 6N—HCl (pH~2-3) and extracted with EtOAc (700 mL). The organic layer was washed with water (300 mL), brine (200 mL), dried over anhydrous $Na_2SO_4$, filtered and concentrated under reduced pressure to obtain a crude residue which was purified by CombiFlash chromatography to afford 4-fluoro-2,6-dimethylphenol (2.2 g, 64%) as a viscous brown solid.

LCMS: 141 [M+1]$^+$

Step 2. Synthesis of 2-(2-bromo-4-nitrophenoxy)-5-fluoro-1,3-dimethylbenzene 2-(2-bromo-4-nitrophenoxy)-5-fluoro-1,3-dimethylbenzene (5.0 g, 94%) was prepared following General Procedure 18, Step 1 using 4-fluoro-2,6-dimethylphenol (2.2 g, 18.7 mmol, 1.0 eq).

LCMS: 340 [M+H]$^+$, 342 [M+2]$^+$

Step 3. Synthesis of 3-bromo-4-(4-fluoro-2,6-dimethylphenoxy)aniline 3-bromo-4-(4-fluoro-2,6-dimethylphenoxy)aniline (2.5 g, 91%, black viscous liquid) was prepared following General Procedure 1, Step 2 using 2-(2-bromo-4-nitrophenoxy)-5-fluoro-1,3-dimethylbenzene (3.0 g, 88.4 mmol, 1.0 eq).

LCMS: 310 [M+H]$^+$, 312 [M+2]$^+$

Step 4. Synthesis of 4-(4-fluoro-2,6-dimethylphenoxy)-3-(4,4,5,5-tetramethyl-1,3,2-dioxaborolan-2-yl)aniline 4-(4-fluoro-2,6-dimethylphenoxy)-3-(4,4,5,5-tetramethyl-1,3,2-dioxaborolan-2-yl)aniline (1.5 g, 87%, black viscous liquid) was prepared following General Procedure 1, Step 3 using 3-bromo-4-(4-fluoro-2,6-dimethylphenoxy)aniline (0.170 g, 0.242 mmol, 0.05 eq).

$^1$H NMR (400 MHz, CDCl$_3$): δ 6.87-7.07 (m, 2H), 6.63 (d, J=17.10 Hz, 1H), 6.47-6.53 (m, 1H), 6.44 (s, 1H), 4.70 (br s, 2H), 1.94-2.16 (m, 6H), 1.09-1.24 (m, 12H).

444

Step 5. Synthesis of 7-(5-amino-2-(4-fluoro-2,6-dimethylphenoxy)phenyl)-N-ethyl-5-methyl-4-oxo-4,5-dihydrothieno[3,2-c]pyridine-2-carboxamide 7-(5-amino-2-(4-fluoro-2,6-dimethyl phenoxy)phenyl)-N-ethyl-5-methyl-4-oxo-4,5-dihydrothieno[3,2-c]pyridine-2-carboxamide (0.100 g, 68%, brown viscous liquid) was prepared following General Procedure 6, Step 1 using 4-(4-fluoro-2,6-dimethylphenoxy)-3-(4,4,5,5-tetramethyl-1,3,2-dioxaborolan-2-yl)aniline (0.131 g, 0.477 mmol, 1.5 eq) and 7-bromo-N-ethyl-5-methyl-4-oxo-4,5-dihydrothieno[3,2-c]pyridine-2-carboxamide (0.100 g, 0.318 mmol, 1 eq)

LCMS: 466 [M+H]$^+$

Step 6. Synthesis of 7-(5-acrylamido-2-(4-fluoro-2,6-dimethylphenoxy)phenyl)-N-ethyl-5-methyl-4-oxo-4,5-dihydrothieno[3,2-c]pyridine-2-carboxamide 7-(5-acrylamido-2-(4-fluoro-2,6-dimethylphenoxy)phenyl)-N-ethyl-5-methyl-4-oxo-4,5-dihydrothieno [3,2-c]pyridine-2-carboxamide (0.007 g, 6.3%, off white solid) was prepared following General Procedure 3 using 7-(5-amino-2-(4-fluoro-2,6-dimethylphenoxy)phenyl)-N-ethyl-5-methyl-4-oxo-4,5-dihydrothieno[3,2-c]pyridine-2-carboxamide (0.100 g, 0.215 mmol, 1 eq).

LCMS: 520 [M+1]$^+$ $^1$H NMR (400 MHz, DMSO-d$_6$): δ 10.21 (s, 1H), 8.76 (br s, 1H), 8.30 (s, 1H), 7.91 (d, J=2.45 Hz, 1H), 7.81 (s, 1H), 7.53 (d, J=8.80 Hz, 1H), 7.00 (d, J=8.80 Hz, 2H), 6.32-6.50 (m, 2H), 6.25 (br s, 1H), 5.74 (d, J=11.74 Hz, 1H), 3.60 (s, 3H), 3.18-3.28 (m, 2H), 2.03 (s, 6H), 1.12 (t, J=7.09 Hz, 3H).

Example S-66: N-(4-(2,6-dimethylphenoxy)-3-(4-isopropoxy-1-methyl-6-oxo-1,6-dihydropyridin-3-yl)phenyl)acrylamide, Compound 589

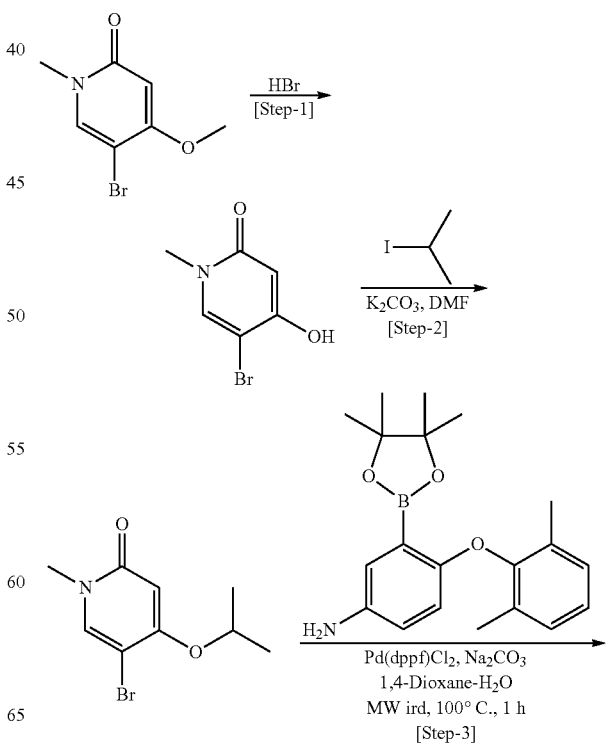

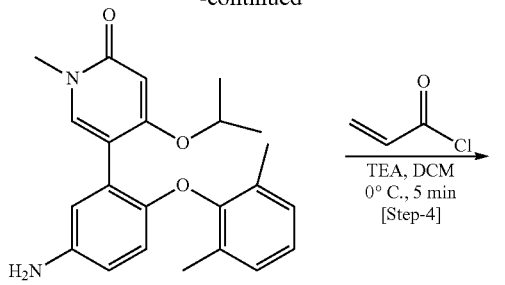

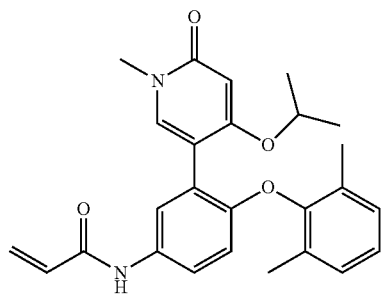

Step 1: Synthesis of
5-bromo-4-hydroxy-1-methylpyridin-2(1H)-one

To 5-bromo-4-methoxy-1-methylpyridin-2(1H)-one (0.300 g, 1.37 mmol, 1.0 eq) was added HBr (48% in $H_2O$, 15 mL) and the mixture was heated at 120° C. and monitored by TLC and LC-MS. The reaction was complete after 16 h and the mixture was neutralized using saturated solution of $NaHCO_3$ under ice-cold condition. The mixture was the extracted with 10% MeOH/DCM (300 mL×2). The combined organic layers were washed with H2O (100 mL), brine (100 mL) dried over anhydrous $Na_2SO_4$, filtered and concentrated under reduced pressure to afford 5-bromo-4-hydroxy-1-methylpyridin-2(1H)-one (0.27 g, 97%) as a thick viscous solid.

LCMS: 204 [M+1]$^+$, 206 [M+2]$^+$

Step 2: Synthesis of
5-bromo-4-isopropoxy-1-methylpyridin-2(1H)-one

To a stirred solution of 5-bromo-4-hydroxy-1-methylpyridin-2(1H)-one (0.300 g, 1.47 mmol, 1.0 eq) in DMF (5 mL) was added K2CO3 (0.405 g, 2.94 mmol, 2.0 eq) at RT and the mixture was stirred for 30 min. 2-iodopropane (0.50 g, 2.94 mmol, 2.0 eq) was then added to the mixture and the mixture was heated at 100° C. and monitored by TLC and LC-MS. The reaction was complete after 16 h and the mixture was diluted with water (100 mL) and extracted with EtOAc (200 mL×2). The combined organic layers were washed with H2O (50 mL), brine (50 mL) dried over anhydrous $Na_2SO_4$, filtered and concentrated under reduced pressure to afford 5-bromo-4-isopropoxy-1-methylpyridin-2(1H)-one (0.15 g, 46%) as a thick viscous solid.

LCMS: 246 [M+1]$^+$, 248 [M+2]$^+$

Step 3: Synthesis of 5-(5-amino-2-(2,4-difluorophenoxy)phenyl)-4-isopropoxy-1-methylpyridin-2(1H)-one 5-(5-amino-2-(2,4-difluorophenoxy)phenyl)-4-isopropoxy-1-methylpyridin-2(1H)-one (0.060 g, 26%, brown viscous liquid) was prepared following General Procedure 6, Step 1 using 4-(2,6-dimethylphenoxy)-3-(4,4,5,5-tetramethyl-1,3,2-dioxaborolan-2-yl)aniline (310 mg, 0.91 mmol, 1.5 eq) and 5-bromo-4-isopropoxy-1-methylpyridin-2(1H)-one (0.15 g, 0.61 mmol, 1 eq).

LCMS: 379 [M+1]$^+$

Step 4: Synthesis of N-(4-(2,6-dimethylphenoxy)-3-(4-isopropoxy-1-methyl-6-oxo-1,6-dihydropyridin-3-yl)phenyl)acrylamide N-(4-(2,6-dimethylphenoxy)-3-(4-isopropoxy-1-methyl-6-oxo-1,6-dihydropyridin-3-yl)phenyl)acrylamide (0.009 g, 16%, off white solid) was prepared following General Procedure 3 using 5-(5-amino-2-(2,4-difluorophenoxy)phenyl)-4-isopropoxy-1-methylpyridin-2(1H)-one (0.05 g, 0.13 mmol, 1 eq).

LCMS: 433 [M+1]$^+$ $^1$H NMR (400 MHz, Methanol-d$_4$): δ 10.06 (s, 1H), 7.62 (s, 1H), 7.60 (d, J=2.7 Hz, 1H), 7.41 (dd, J=8.9, 2.7 Hz, 1H), 7.12 (d, J=7.3 Hz, 2H), 7.06 (dd, J=8.6, 6.2 Hz, 1H), 6.39 (dd, J=17.0, 10.1 Hz, 1H), 6.26-6.21 (m, 1H), 6.19 (d, J=5.3 Hz, 2H), 5.90 (s, 1H), 5.71 (dd, J=10.0, 2.2 Hz, 1H), 4.63 (p, J=6.0 Hz, 1H), 3.39 (s, 3H), 2.02 (s, 6H), 1.19 (d, J=6.0 Hz, 6H)

Example S-67: (E)-7-(5-but-2-enamido-2-(2,6-dimethylphenoxy)phenyl)-N-ethyl-5-methyl-4-oxo-4,5-dihydrothieno[3,2-c]pyridine-2-carboxamide Compound 611

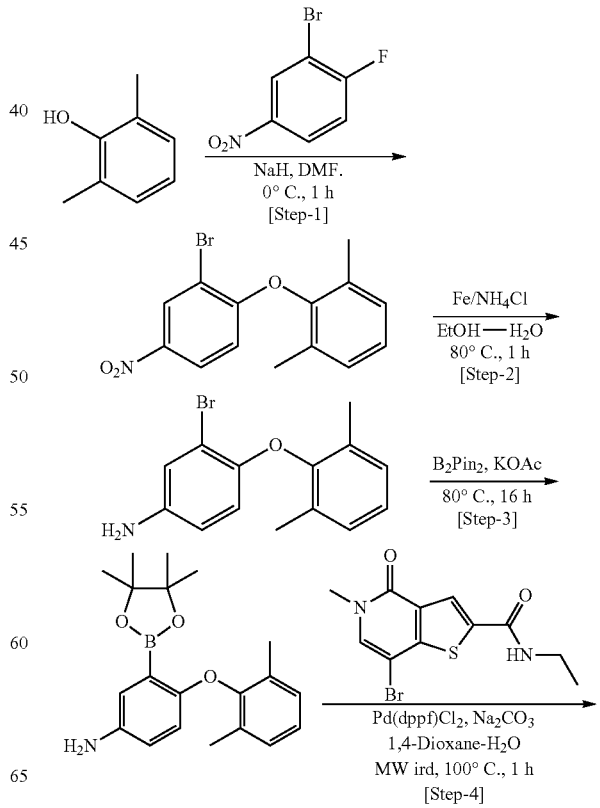

-continued

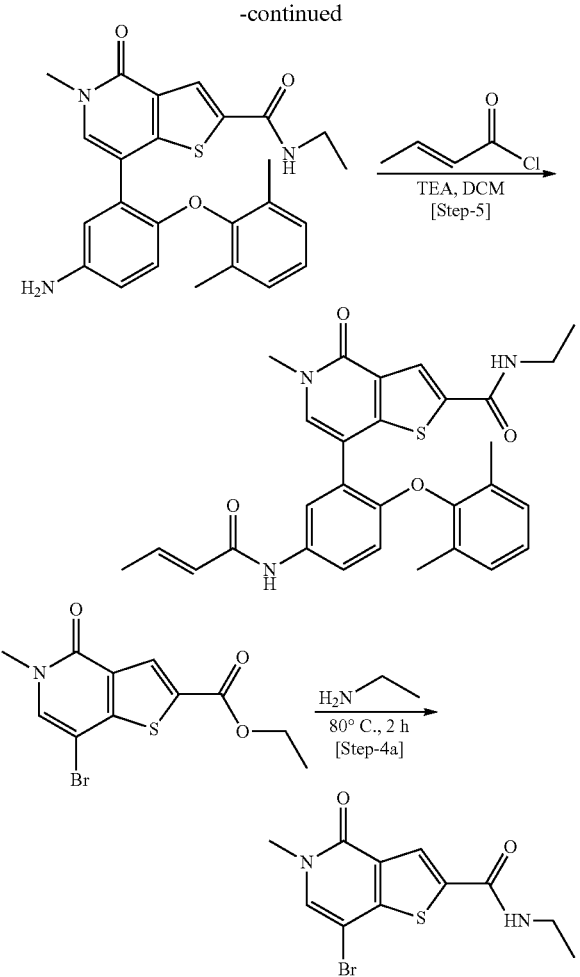

Step 1: Synthesis of 2-(2-bromo-4-nitrophenoxy)-1,3-dimethylbenzene 2-(2-bromo-4-nitrophenoxy)-1,3-dimethylbenzene (4.5 g, 68%, yellow solid) was prepared following General Procedure 18, Step 1 using 2,6-dimethylphenol (2.0 g, 16.03 mmol, 1.0 eq).
LCMS: 322 [M+H]$^+$, 324 [M+2]$^+$

Step 2: Synthesis of 3-bromo-4-(2,6-dimethylphenoxy)aniline 3-bromo-4-(2,6-dimethylphenoxy)aniline (3.5 g, 97%, black viscous liquid) was prepared following General Procedure 1, Step 2 using 2-(2-bromo-4-nitrophenoxy)-1,3-dimethylbenzene (4.0 g, 12.46 mmol, 1.0 eq).
LCMS: 292 [M+1]$^+$, 294 [M+2]$^+$

Step 3: Synthesis of 4-(2,6-dimethylphenoxy)-3-(4,4,5,5-tetramethyl-1,3,2-dioxaborolan-2-yl)aniline 4-(2,6-dimethylphenoxy)-3-(4,4,5,5-tetramethyl-1,3,2-dioxaborolan-2-yl)aniline (0.700 g, 66%, black viscous liquid) was prepared following General Procedure 1, Step 3 using 3-bromo-4-(2,6-dimethylphenoxy)aniline (1.0 g, 45.6 mmol, 1.0 eq).

$^1$H NMR: (400 MHz, CDCl$_3$) δ 6.97-7.11 (m, 3H), 6.58 (m, 2H), 6.14 (d, J=8.77 Hz, 1H), 2.05-2.18 (m, 6H), 1.23-1.28 (m, 12H).

Step 4a: Synthesis of 7-bromo-N-ethyl-5-methyl-4-oxo-4,5-dihydrothieno[3,2-c]pyridine-2-carboxamide 7-bromo-N-ethyl-5-methyl-4-oxo-4,5-dihydrothieno[3,2-c]pyridine-2-carboxamide (100 mg, 67%, brown solid)) was prepared following General Procedure 18, Step 4a using ethyl 7-bromo-5-methyl-4-oxo-4,5-dihydrothieno[3,2-c]pyridine-2-carboxylate (1.0 g, 45.6 mmol, 1.0 eq).
LCMS: 315 [M+1]$^+$, 317 [M+2]$^+$

Step 4: Synthesis of 7-(5-amino-2-(2,6-dimethylphenoxy)phenyl)-N-ethyl-5-methyl-4-oxo-4,5-dihydrothieno[3,2-c]pyridine-2-carboxamide 7-(5-amino-2-(2,6-dimethylphenoxy) phenyl)-N-ethyl-5-methyl-4-oxo-4,5-dihydrothieno[3,2-c]pyridine-2-carboxamide (0.23 g, 30%, brown viscous liquid) was prepared following General Procedure 1, Step 3 using 4-(2,6-dimethylphenoxy)-3-(4,4,5,5-tetramethyl-1,3,2-dioxaborolan-2-yl)aniline (0.807 g, 2.37 mmol, 1.5 eq) and 7-bromo-N-ethyl-5-methyl-4-oxo-4,5-dihydrothieno[3,2-c]pyridine-2-carboxamide (0.50 g, 1.58 mmol, 1 eq).
LCMS: 448 [M+1]$^+$

Step 5: Synthesis of 7-(5-acrylamido-2-(2,6-dimethylphenoxy)phenyl)-N-ethyl-5-methyl-4-oxo-4,5-dihydrothieno[3,2-c]pyridine-2-carboxamide 7-(5-acrylamido-2-(2,6-dimethyl phenoxy)phenyl)-N-ethyl-5-methyl-4-oxo-4,5-dihydrothieno[3,2-c]pyridine-2-carboxamide (12 mg, 10%) was prepared following General Procedure 3 using 7-(5-amino-2-(2,6-dimethylphenoxy) phenyl)-N-ethyl-5-methyl-4-oxo-4,5-dihydrothieno [3,2-c] pyridine-2-carboxamide (0.110 g, 0.246 mmol, 1 eq) and (E)-but-2-enoyl chloride (0.028 g, 0.27 mmol, 1.2 eq).
LCMS: 516 [M+1]$^+$
$^1$H NMR: (400 MHz, Methanol-d$_4$) δ 8.15 (s, 1H), 7.83 (d, J=2.6 Hz, 1H), 7.73 (s, 1H), 7.47 (dd, J=8.9, 2.7 Hz, 1H), 7.12-7.01 (m, 3H), 6.92 (dq, J=13.9, 6.9 Hz, 1H), 6.41 (d, J=9.0 Hz, 1H), 6.10 (dd, J=15.2, 2.0 Hz, 1H), 3.73 (s, 3H), 3.40 (q, J=7.3 Hz, 2H), 2.08 (s, 6H), 1.91 (dd, J=6.9, 1.8 Hz, 3H), 1.29 (t, J=7.3 Hz, 3H).

Example S-68: 4-(5-acrylamido-2-((2,4-difluorophenyl)(methyl)amino)phenyl)-N-ethyl-6-methyl-7-oxo-6,7-dihydrothieno[2,3-c]pyridine-2-carboxamide, Compound 612

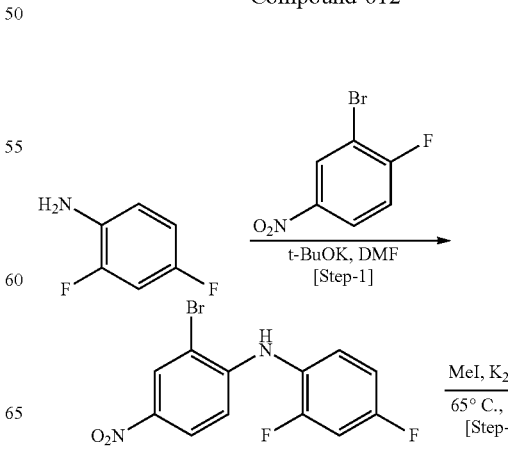

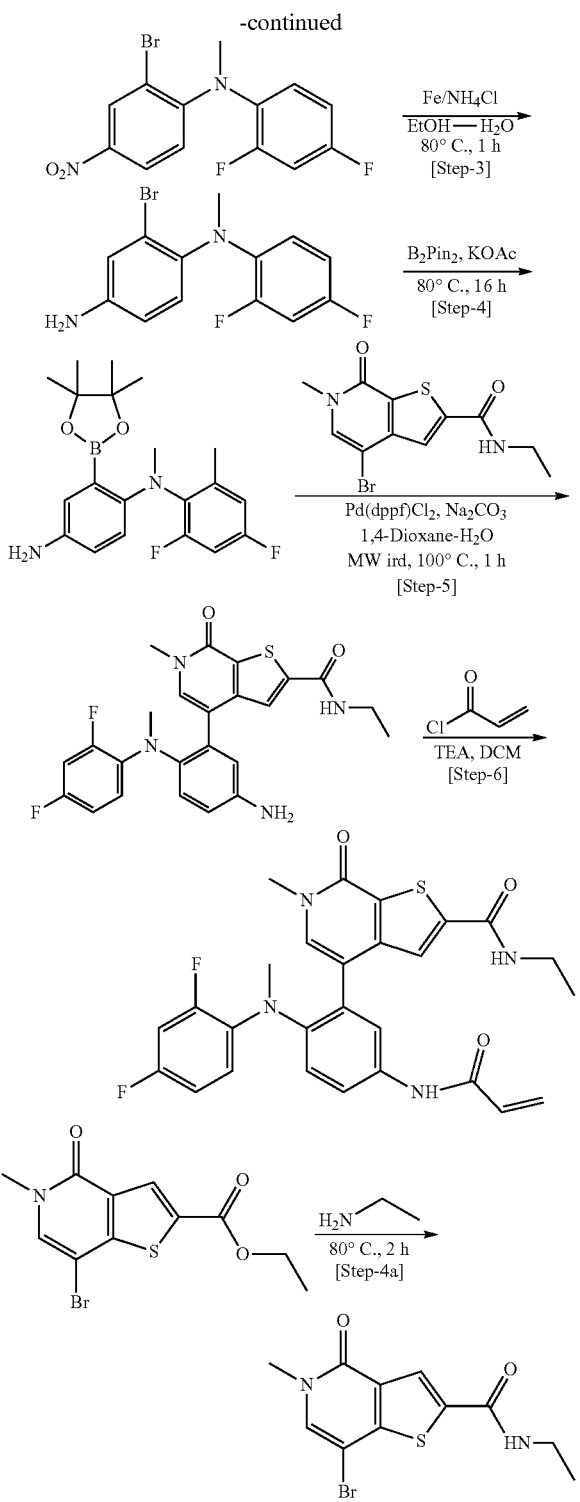

Synthesis of
2-bromo-N-(2,4-difluorophenyl)-4-nitroaniline

To a solution of 2,4-difluoroaniline (5.0 g, 41.3 mmol, 1.0 eq) in DMF (30 mL) was added t-BuONa (20 g, 206 mmol, 5 eq) at −60° C. followed by an addition of 2-bromo-1-fluoro-4-nitrobenzene (10.9 g, 49.5 mmol, 1.2 eq). The temperature of the mixture was gradually increased to RT over a period of 30 min and monitored by TLC and LC-MS. The reaction was complete after 1 h and to the mixture was added ice-cold water (50 mL) to obtain a precipitate which was filtered over Büchner funnel; dried under vacuum to obtain a crude which was purified by CombiFlash chromatography to afford 2-bromo-N-(2,4-difluorophenyl)-4-nitroaniline (1.2 g, 9.5%) as a yellow solid.

LCMS: 329 [M+1]$^+$, 331 [M+2]$^+$

Step 2: Synthesis of 2-bromo-N-(2,4-difluorophenyl)-N-methyl-4-nitroaniline

To 2-bromo-N-(2,4-difluorophenyl)-4-nitroaniline (0.9 g, 2.73 mmol) and K$_2$CO$_3$ (1.1 g, 8.2 mmol, 3 eq) was added MeI (1.5 g, 10.94 mmol, 4 eq) at RT and the mixture was heated at 65° C. for 16 h. The reaction was complete after 16 h and to the mixture was added water (200 mL). The aqueous layer was then extracted with EtOAc (100 mL×2). The combined organic layers were washed with water (50 mL), brine (50 mL), dried over anhydrous Na$_2$SO$_4$, filtered and concentrated under reduced pressure to obtain a crude which was triturated with n-pentane/diethyl ether (10 mL/2 mL) to afford 2-bromo-N-(2,4-difluorophenyl)-N-methyl-4-nitroaniline (0.80 g, 86%) as a yellow solid.

$^1$H NMR: (400 MHz, CDCl$_3$) δ 8.40 (d, J=2.6 Hz, 1H), 8.18 (dd, J=9.2, 2.6 Hz, 1H), 7.21 (d, J=9.2 Hz, 1H), 6.77-6.93 (m, 3H), 3.34 (s, 3H)

Step 3: Synthesis of 2-bromo-N1-(2,4-difluorophenyl)-N$_1$-methylbenzene-1,4-diamine 2-bromo-N1-(2,4-difluorophenyl)-N$_1$-methylbenzene-1,4-diamine (0.70 g, 96%, black viscous liquid) was prepared following General Procedure 1, Step 2 using 2-bromo-N-(2,4-difluorophenyl)-N-methyl-4-nitroaniline (0.8 g, 2.33 mmol, 1.0 eq).

LCMS: 313 [M+1]$^+$, 315 [M+2]$^+$

Step 4: Synthesis of N1-(2,4-difluorophenyl)-N$_1$-methyl-2-(4,4,5,5-tetramethyl-1,3,2-dioxaborolan-2-yl)benzene-1,4-diamine N1-(2,4-difluorophenyl)-N$_1$-methyl-2-(4,4,5,5-tetramethyl-1,3,2-dioxaborolan-2-yl)benzene-1,4-diamine (0.045 mg, 67%, brown solid)) was prepared following General Procedure 1, Step 3 using ethyl 7-bromo-5-methyl-4-oxo-4,5-dihydrothieno[3,2-c]pyridine-2-carboxylate (1.0 g, 45.6 mmol, 1.0 eq).

LCMS: 361 [M+1]$^+$

Step 4a. Synthesis of 4-bromo-N-ethyl-6-methyl-7-oxo-6,7-dihydrothieno[2,3-c]pyridine-2-carboxamide 4-bromo-N-ethyl-6-methyl-7-oxo-6,7-dihydrothieno[2,3-c]pyridine-2-carboxamide (1.23 g, 95%, white solid) was prepared following General Procedure 18, Step 4a using ethyl 4-bromo-6-methyl-7-oxo-6,7-dihydrothieno[2,3-c]pyridine-2-carboxylate (1.5 g, 4.3 mmol, 1 eq).

LCMS: 315 [M+1]$^+$, 317 [M+2]$^+$

Step 5: Synthesis of 4-(5-amino-2-((2,4-difluorophenyl)(methyl)amino)phenyl)-N-ethyl-6-methyl-7-oxo-6,7-dihydrothieno[2,3-c]pyridine-2-carboxamide 4-(5-amino-2-((2,4-difluoro phenyl)(methyl)amino)phenyl)-N-ethyl-6-methyl-7-oxo-6,7-dihydrothieno[2,3-c]pyridine-2-carboxamide (0.04 g, 30%, yellow sticky solid) was prepared following General Procedure 1, Step 3 using using N1-(2,4-difluorophenyl)-N1-methyl-2-(4,4,5,5-tetramethyl-1,3,2-dioxaborolan-2-yl)benzene-1,4-diamine (0.15 g, 0.43 mmol, 1.5 eq) and 4-bromo-N-ethyl-6-methyl-7-oxo-6,7-dihydrothieno[2,3-c]pyridine-2-carboxamide (0.09 g, 0.28 mmol, 1 eq).

LCMS: 469 [M+1]$^+$

Step 6. Synthesis of 4-(5-acrylamido-2-((2,4-difluorophenyl)(methyl)amino)phenyl)-N-ethyl-6-methyl-7-oxo-6,7-dihydrothieno[2,3-c]pyridine-2-carboxamide 4-(5-acrylamido-2-((2,4-difluorophenyl)(methyl)amino) phenyl)-N-ethyl-6-methyl-7-oxo-6,7-dihydrothieno[2,3-c] pyridine-2-carboxamide (0.005 g, 11%, off-white solid) was prepared following General Procedure 3 using 4-(5-amino-2-((2,4-difluorophenyl)(methyl)amino)phenyl)-N-ethyl-6-methyl-7-oxo-6,7-dihydrothieno[2,3-c]pyridine-2-carboxamide (0.04 g, 0.085 mmol, 1 eq).

LCMS: 523 [M+1]$^+$ $^1$H NMR (400 MHz, Methanol-$d_4$): δ 7.72 (dd, J=8.7, 2.6 Hz, 1H), 7.55 (d, J=2.6 Hz, 1H), 7.50 (s, 1H), 7.39 (d, J=8.8 Hz, 1H), 7.17 (s, 1H), 6.65-6.52 (m, 2H), 6.52-6.30 (m, 3H), 5.77 (dd, J=9.6, 2.3 Hz, 1H), 3.53 (s, 3H), 3.42-3.32 (m, 2H), 3.18 (s, 3H), 1.19 (t, J=7.2 Hz, 3H).

Example S-69: N-(4-(2,4-difluorophenoxy)-3-(3-methyl-4-oxoquinolin-(4H)-yl)phenyl) acrylamide, Compound 613

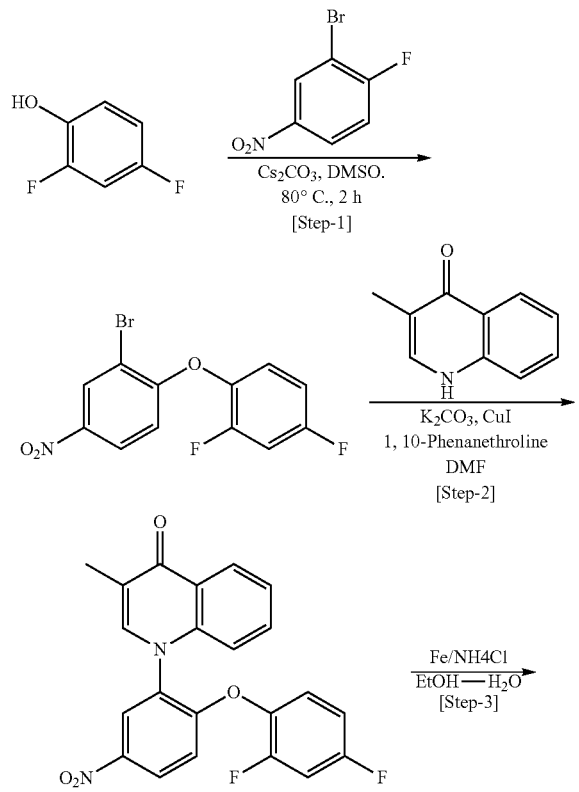

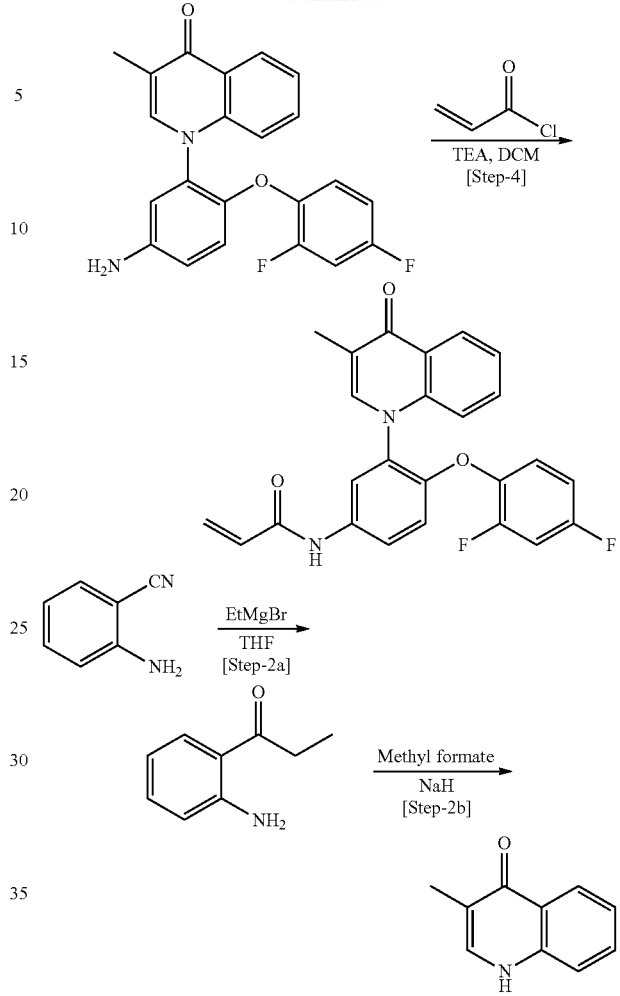

Step 1. Synthesis of 2-bromo-1-(2,4-difluorophenoxy)-4-nitrobenzene 2-bromo-1-(2,4-difluorophenoxy)-4-nitrobenzene (1.2 g, 71%, white solid) was prepared following General Procedure 1, Step 1 using 2,4-difluorophenol (1 g, 7.6 mmol, 1 eq).

LCMS: 330 [M+1]$^+$, 332 [M+2]$^+$

Step 2a: Synthesis of 1-(2-aminophenyl)propan-1-one

To a stirred solution of 2-aminobenzonitrile (3 g, 25.4 mmol, 1 eq) in THF was added ethyl magnesium bromide (1M in THF; 50.8 mL) at 0° C. slowly and the mixture was stirred at RT for 3 h. The reaction was complete after 3 h and the mixture was quenched with saturated NH$_4$Cl solution (100 mL) slowly and extracted with EtOAc (300 mL×2). The combined organic layers were washed with water (200 mL), brine (100 mL), dried over anhydrous Na$_2$SO$_4$, filtered and concentrated under reduced pressure to obtain a crude which was purified by CombiFlash Chromatography to afford 1-(2-aminophenyl)propan-1-one (3.2 g, 85%) as a yellow liquid.

LCMS: 150 [M+1]$^+$

Step 2b. Synthesis of 3-methylquinolin-4(1H)-one

To 1-(2-aminophenyl)propan-1-one (3 g, 20.1 mmol, 1 eq) in methyl formate (60 mL) was added NaH (60% suspension in mineral oil; 2.4 g, 60.4 mmol, 3 eq) at RT and the mixture was heated at 60° C. for 16 h. After 16 h and the mixture was cooled to RT and diluted with water (100 mL). The aqueous layer was then extracted with EtOAc (300 mL×2). The combined organic layers were washed with water (100 mL), brine (50 mL), dried over anhydrous $Na_2SO_4$, filtered and concentrated under reduced pressure to obtain a crude which was purified by CombiFlash Chromatography to afford 3-methylquinolin-4(1H)-one (0.85 g, 26%) as an off-white solid.

LCMS: 160 [M+1]$^+$

Step 2: Synthesis of 1-(2-(2,4-difluorophenoxy)-5-nitrophenyl)-3-methylquinolin-4(1H)-one To 2-bromo-1-(2,4-difluorophenoxy)-4-nitrobenzene (0.5 g, 3.14 mmol, 1 eq) and 3-methylquinolin-4(1H)-one (1.2 g, 3.77 mmol, 1.2 eq) in DMF (10 mL) was added $K_2CO_3$ (0.85 g, 6.28 mmol, 2 eq) at RT and the mixture and degassed under nitrogen for 20 min. 1,10-Phenanthroline (0.11 g, 0.62 mmol, 0.2 eq) and CuI (0.06 g, 0.31 mmol, 0.1 eq) were then added to the mixture and the resultant mixture was heated at 100° C. for 16 h. The reaction was complete after 16 h and to the mixture was added water (100 mL) and extracted with EtOAc (200 mL×2). The combined organic layers were washed with water (100 mL), brine (50 mL), dried over anhydrous $Na_2SO_4$, filtered and concentrated under reduced pressure to obtain a crude which was purified by CombiFlash Chromatography to afford 1-(2-(2,4-difluorophenoxy)-5-nitrophenyl)-3-methylquinolin-4(1H)-one (0.08 g, 13%) as a yellow solid.

LCMS: 409 [M+1]$^+$

Step 3: Synthesis of 1-(5-amino-2-(2,4-difluorophenoxy)phenyl)-3-methylquinolin-4(1H)-one 1-(5-amino-2-(2,4-difluorophenoxy)phenyl)-3-methylquinolin-4(1H)-one (0.055 mg, 71%, light brown solid) was prepared following General Procedure 1, Step 2 using 1-(2-(2,4-difluorophenoxy)-5-nitrophenyl)-3-methylquinolin-4(1H)-one (0.08 g, 0.20 mmol, 1.0 eq).

LCMS: 379[M+1]$^+$

Step 4: Synthesis of N-(4-(2,4-difluorophenoxy)-3-(3-methyl-4-oxoquinolin-1(4H)-yl)phenyl)acrylamide N-(4-(2,4-difluorophenoxy)-3-(3-methyl-4-oxoquinolin-1(4H)-yl) phenyl)acrylamide (0.0055 g, 9.5%, off-white solid)) was prepared following General Procedure 3 using 1-(5-amino-2-(2,4-difluorophenoxy)phenyl)-3-methylquinolin-4(1H)-one (0.05 g, 0.13 mmol, 1.0 eq).

LCMS: 433 [M+1]$^+$ $^1$H NMR (400 MHz, Methanol-d$_4$): δ 8.39-8.32 (m, 1H), 7.95 (s, 1H), 7.68-7.53 (m, 3H), 7.50 (d, J=8.3 Hz, 1H), 7.42 (t, J=7.6 Hz, 1H), 7.19-7.00 (m, 3H), 6.96-6.86 (m, 1H), 6.47-6.31 (m, 2H), 5.80 (dd, J=8.6, 3.3 Hz, 1H), 2.15 (s, 3H).

Example S-70: N-(4-(2,4-difluorophenoxy)-3-(4-methoxy-1-methyl-6-oxo-1,6-dihydropyridin-3-yl)phenyl)ethenesulfonamide, Compound 406

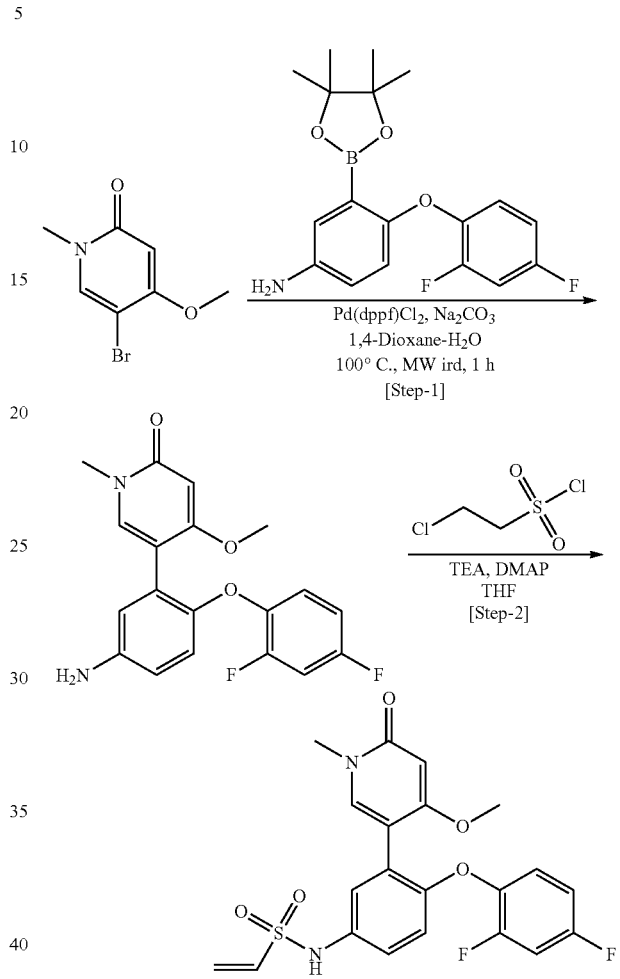

Step 1: Synthesis of 5-(5-amino-2-(2,4-difluorophenoxy)phenyl)-4-methoxy-1-methylpyridin-2(1H)-one 5-(5-amino-2-(2,4-difluorophenoxy)phenyl)-4-methoxy-1-methyl pyridin-2(1H)-one (0.13 g, 66%, off-white solid) was prepared following General Procedure 1, Step 3 using 5-bromo-4-methoxy-1-methylpyridin-2(1H)-one (0.12 g, 0.55 mmol, 1 eq)

LCMS: 359 [M+1]$^+$

Step 2: Synthesis of N-(4-(2,4-difluorophenoxy)-3-(4-methoxy-1-methyl-6-oxo-1,6-dihydropyridin-3-yl)phenyl)ethenesulfonamide N-(4-(2,4-difluorophenoxy)-3-(4-methoxy-1-methyl-6-oxo-1,6-dihydropyridin-3-yl)phenyl)ethenesulfonamide (26 mg, 16%, off-white solid) was prepared following General Procedure 5 using 5-(5-amino-2-(2,4-difluorophenoxy)phenyl)-4-methoxy-1-methylpyridin-2(1H)-one (130 mg, 0.36 mmol, 1 eq).

LCMS: 449 [M+1]$^+$ $^1$H NMR (400 MHz, Methanol-d$_4$): δ 7.52 (s, 1H), 7.19 (dd, J=8.7, 2.8 Hz, 1H), 7.14 (d, J=2.7 Hz, 1H), 7.03 (ddd, J=11.2, 8.5, 2.9 Hz, 1H), 6.98-6.82 (m, 3H), 6.69 (dd, J=16.5, 10.0 Hz, 1H), 6.15 (d, J=16.5 Hz, 1H), 5.99 (d, J=9.9 Hz, 1H), 5.94 (s, 1H), 3.71 (s, 3H), 3.50 (s, 3H).

Example S-71: N-(3-(3-chloro-4-oxoquinolin-1 (4H)-yl)-4-(2,4-difluorophenoxy)phenyl) ethanesulfonamide: (General Procedure 22) Compound 661

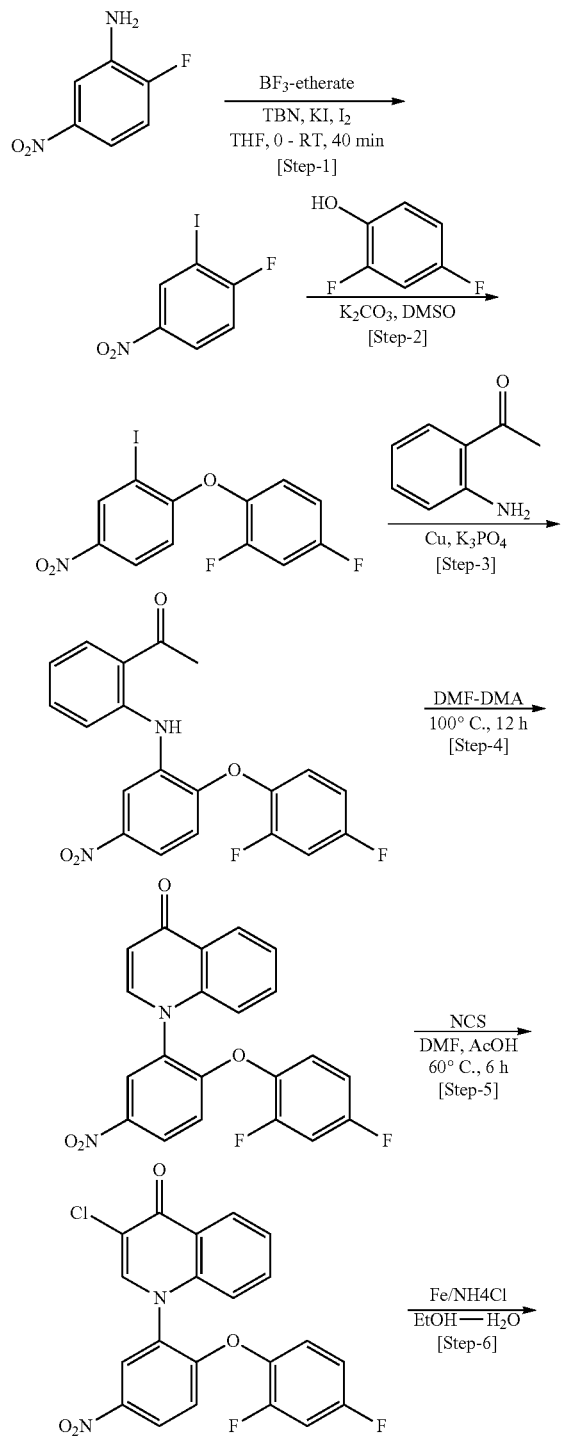

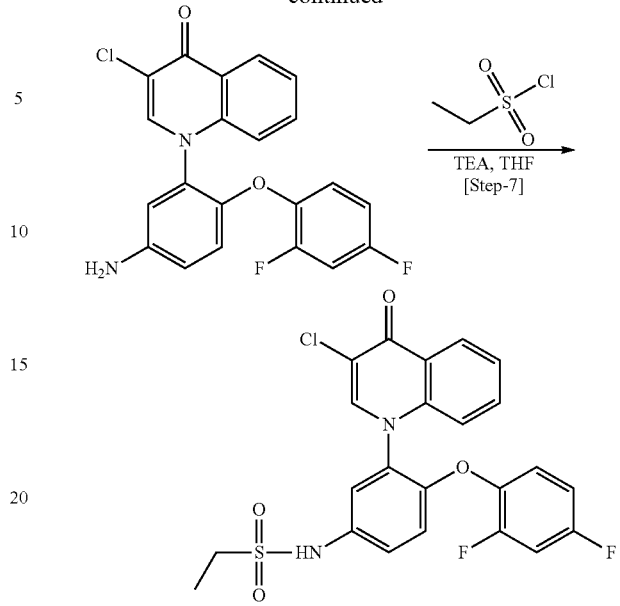

Step 1: Synthesis of 1-fluoro-2-iodo-4-nitrobenzene

To BF$_3$.OEt$_2$ (33.1 mL, 269 mmol, 4.2 eq) was added 2-fluoro-5-nitroaniline (10 g, 64.6 mmol, 1.00 eq) in dry THF (140 mL) at −20° C. followed by the addition of tert-butyl nitrite (25.3 mL, 211 mmol, 3.3 eq) dissolved in THF (60 mL) slowly. The mixture was gradually warmed to 0° C. and then cold diethyl ether (250 mL) was added to the mixture and the resultant mixture was stirred at 0° C. for 10 min to obtain a white precipitate which was filtered off. The solid white precipitate obtained was added in portions to a cooled solution of iodine (5.7 g, 45.4 mmol, 0.71 eq) and potassium iodide (10.5 g, 91 mmol, and 1.42 eq) in MeCN (200 mL). The mixture was warmed to room temperature and stirred for 1 h and monitored by TLC. The reaction was complete after 1 h and to the mixture was added saturated Na$_2$S$_2$O$_3$ (150 mL) solution. The aqueous layer was then extracted with DCM (50 mL×4). The combined organic layers were washed with water (50 mL), brine (50 mL) dried over anhydrous Na$_2$SO$_4$, filtered and concentrated under reduced pressure to afford 1-fluoro-2-iodo-4-nitrobenzene (16 g, 93%) a yellow solid.

$^1$H NMR (400 MHz, CDCl$_3$): δ 8.67 (dd, J=5.3, 2.6 Hz, 1H), 8.25 (s, 1H), 7.21 (dd, J=9.0, 6.8 Hz, 1H).

Step 2: Synthesis of 1-(2,4-difluorophenoxy)-2-iodo-4-nitrobenzene

To a solution of 2,4-difluorophenol (16.0 g, 60 mmol, 1.0 eq) in DMSO (50 mL) was added K$_2$CO$_3$ (16.5 g, 120.00 mmol, 2.0 eq) followed by an addition of 1-fluoro-2-iodo-4-nitrobenzene (6.9 mL g, 72 mmol, 1.2 eq). The mixture was heated at 100° C. for 2 h and monitored by TLC and LC-MS. The reaction was complete after 2 h and to the mixture was added ice-cold water (100 mL) to obtain a precipitate which was filtered over Büchner funnel; dried under vacuum to afford 1-(2,4-difluorophenoxy)-2-iodo-4-nitrobenzene (20 g, 43%) as a yellow solid.

$^1$H NMR (400 MHz, CDCl$_3$): δ 8.75 (d, J=2.6 Hz, 1H), 8.13 (dd, J=2.9, 9.0 Hz, 1H), 7.20 (d, J=5.3 Hz, 1H), 7.07-6.92 (m, 2H), 6.64 (dd, J=0.9, 9.2 Hz, 1H)

Step 3: Synthesis of 1-(2-(2-(2,4-difluorophenoxy)-5-nitrophenylamino)phenyl)ethanone To 1-(2-aminophenyl)ethanone (0.50 g, 3.7 mmol, 1.0 eq) and 1-(2,4-difluorophenoxy)-2-iodo-4-nitrobenzene (2.0 g, 5.5 mmol, 1.5 eq) in 1,4-Dioxane (20 mL) was added $K_3PO_4$ (1.5 g, 7.4 mmol, 2.0 eq) and the mixture was degassed under nitrogen for 20 min. Cu-metal (0.046 g, 0.74 mmol, 0.2 eq) was then added to the mixture and the resultant mixture was heated at 120° C. for 16 h and monitored by TLC and LC-MS. After 16 h, the mixture was diluted with water (100 mL) extracted with EtOAc (100 mL×2). The combined organic layers were washed with water (50 mL), brine (50 mL) dried over anhydrous $Na_2SO_4$, filtered and concentrated under reduced pressure to obtain a crude which was purified by CombiFlash Chromatograph to afford 1-(2-(2-(2,4-difluorophenoxy)-5-nitrophenylamino)phenyl)ethanone (0.40 g, 28%).

LCMS: 385 $[M+1]^+$

Step 4: Synthesis of 1-(2-(2,4-difluorophenoxy)-5-nitrophenyl)quinolin-4(1H)-one To a stirred solution of 1-(2-(2-(2,4-difluorophenoxy)-5-nitrophenylamino)phenyl)ethanone (0.35 g, 0.9 mmol, 1.0 eq) was added N,N-Dimethylformamide dimethyl acetal (8 mL) and the mixture was heated at 100° C. for 16 h and monitored by TLC and LC-MS. The reaction was complete after 16 h and to the mixture was added water (100 mL) and extracted with EtOAc (100 mL×2). The combined organic layers were washed with water (50 mL), brine (50 mL) dried over anhydrous $Na_2SO_4$, filtered and concentrated under reduced pressure to obtain a crude which was purified by CombiFlash Chromatograph to afford 1-(2-(2,4-difluorophenoxy)-5-nitrophenyl)quinolin-4(1H)-one (0.27 g, 75%).

LCMS: 395 $[M+1]^+$

Step 5: Synthesis of 3-chloro-1-(2-(2,4-difluorophenoxy)-5-nitrophenyl)quinolin-4(1H)-one To a stirred solution of 1-(2-(2,4-difluorophenoxy)-5-nitrophenyl)quinolin-4(1H)-one (0.12 g, 0.3 mmol, 1.0 eq) in DMF were added N-chlorosuccinimide (0.06 g, 0.47 mmol, 1.5 eq) and catalytic AcOH (0.5 mL) at RT and the mixture was heated at 60° C. for 5 h and monitored by TLC N,N-Dimethylformamide dimethyl acetal (8 mL) and the mixture was heated at 100° C. for 16 h and monitored by TLC and LC-MS. The reaction was complete after 5 h and to the mixture was added ice-cold water (10 mL) to obtain to obtain precipitate which was filtered over Büchner funnel; dried under vacuum afford 3-chloro-1-(2-(2,4-difluorophenoxy)-5-nitrophenyl)quinolin-4(1H)-one (0.13 g, 95%).

LCMS: 429 $[M+1]^+$

Step 6: Synthesis of 1-(5-amino-2-(2,4-difluorophenoxy)phenyl)-3-chloroquinolin-4(1H)-one 1-(5-amino-2-(2,4-difluorophenoxy)phenyl)-3-chloroquinolin-4(1H)-one (0.12 mg, 96%, dark brown solid) was prepared following General Procedure 1, Step 2 using 3-chloro-1-(2-(2,4-difluorophenoxy)-5-nitrophenyl)quinolin-4(1H)-one (0.135 g, 0.3 mmol, 1.0 eq).

LCMS: 399 $[M+1]^+$

Step 7: Synthesis of N-(3-(3-chloro-4-oxoquinolin-1(4H)-yl)-4-(2,4-difluorophenoxy) phenyl)ethanesulfonamide N-(3-(3-chloro-4-oxoquinolin-1(4H)-yl)-4-(2,4-difluorophenoxy) phenyl)ethanesulfonamide (0.01 mg, 6.8%, off-white solid) was prepared following General Procedure 21, Step 5 using 1-(5-amino-2-(2,4-difluorophenoxy)phenyl)-3-chloroquinolin-4(1H)-one (0.12 g, 0.3 mmol, 1.0 eq).

LCMS: 491 $[M+1]^+$ $^1H$ NMR (400 MHz, Methanol-$d_4$): δ 10.07 (s, 1H), 8.58 (s, 1H), 8.28-8.20 (m, 1H), 7.68 (t, J=7.6 Hz, 1H), 7.51-7.38 (m, 3H), 7.34 (ddd, J=11.2, 8.8, 3.0 Hz, 1H), 7.21 (td, J=9.3, 5.6 Hz, 1H), 7.14 (d, J=8.9 Hz, 1H), 7.09 (d, J=8.6 Hz, 1H), 7.02 (t, J=8.5 Hz, 1H), 3.29-3.14 (m, 2H), 1.24 (t, J=7.3 Hz, 3H)

Example S-72: N-(4-(2,4-difluorophenoxy)-3-(3-methyl-4-oxoquinolin-1(4H)-yl)phenyl) ethanesulfonamide, Compound 616

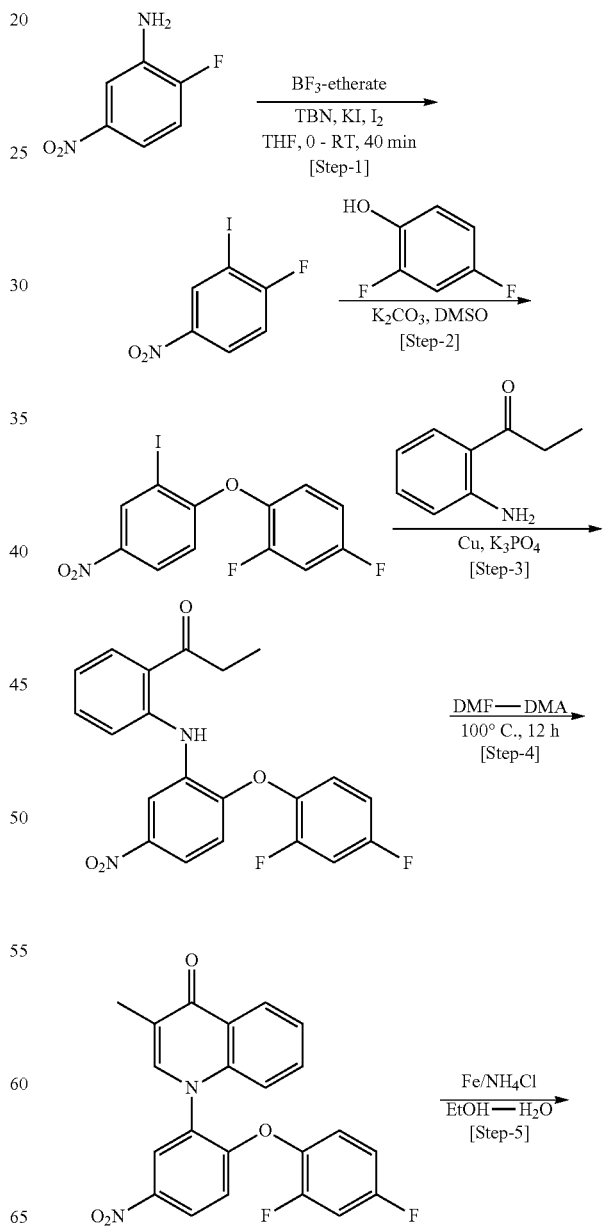

459

-continued

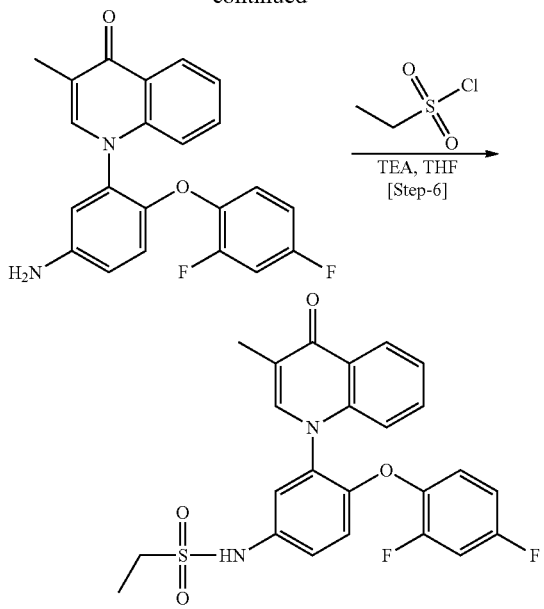

Step 1: Synthesis of 1-fluoro-2-iodo-4-nitrobenzene 1-fluoro-2-iodo-4-nitrobenzene (16 g, 93%, yellow solid) was prepared following General Procedure 22, Step 1 using 2-fluoro-5-nitroaniline (10 g, 64.6 mmol, 1.00 eq).

$^1$H NMR (400 MHz, CDCl$_3$): δ 8.67 (dd, J=5.3, 2.6 Hz, 1H), 8.25 (s, 1H), 7.21 (dd, J=9.0, 6.8 Hz, 1H).

Step 2: Synthesis of 1-(2,4-difluorophenoxy)-2-iodo-4-nitrobenzene 1-(2,4-difluorophenoxy)-2-iodo-4-nitrobenzene (20 g, 43%, yellow solid) was prepared following General Procedure 22, Step 2 using 2,4-difluorophenol (16.0 g, 60 mmol, 1.0 eq) and 1-fluoro-2-iodo-4-nitrobenzene (6.9 mL g, 72 mmol, 1.2 eq).

$^1$H NMR (400 MHz, CDCl$_3$): δ 8.75 (d, J=2.6 Hz, 1H), 8.13 (dd, J=2.9, 9.0 Hz, 1H), 7.20 (d, J=5.3 Hz, 1H), 7.07-6.92 (m, 2H), 6.64 (dd, J=0.9, 9.2 Hz, 1H)

Step 3: Synthesis of 1-(2-(2-(2,4-difluorophenoxy)-5-nitrophenylamino)phenyl)propan-1-one To 1-(2-aminophenyl)propan-1-one (0.58 g, 3.9 mmol, 1.0 eq) and 1-(2,4-difluorophenoxy)-2-iodo-4-nitrobenzene (2.2 g, 5.83 mmol, 1.5 eq) in 1,4-Dioxane (20 mL) was added K$_3$PO$_4$ (1.6 g, 7.7 mmol, 2.0 eq) and the mixture was degassed under nitrogen for 20 min. Cu-metal (0.12 g, 1.94 mmol, 0.5 eq) was then added to the mixture and the resultant mixture was heated at 120° C. for 24 h and monitored by TLC and LC-MS. After 24 h, the mixture was diluted with water (100 mL) extracted with EtOAc (100 mL×2). The combined organic layers were washed with water (50 mL), brine (50 mL) dried over anhydrous Na$_2$SO$_4$, filtered and concentrated under reduced pressure to obtain a crude which was purified by CombiFlash Chromatograph to afford 1-(2-(2-(2,4-difluorophenoxy)-5-nitrophenylamino) phenyl)propan-1-one (0.19 g, 12%).

LCMS: 399 [M+1]$^+$

Step 4: Synthesis of 1-(2-(2,4-difluorophenoxy)-5-nitrophenyl)-3-methylquinolin-4(1H)-one 1-(2-(2-(2,4-difluorophenoxy)-5-nitrophenyl)-3-methylquinolin-4(1H)-one (0.1 g, 65%). was prepared following General Procedure 22, Step 4 using 1-(2-(2-(2,4-difluorophenoxy)-5-nitrophenylamino)phenyl)propan-1-one (0.15 g, 0.37 mmol, 1.0 eq).

LCMS: 409 [M+1]$^+$

Step 5: Synthesis of 1-(5-amino-2-(2,4-difluorophenoxy)phenyl)-3-methylquinolin-4(1H)-one 1-(5-amino-2-(2,4-difluorophenoxy)phenyl)-3-methylquinolin-4(1H)-one (0.09 mg, 98%, dark brown solid) was prepared following General Procedure 1, Step 2 using 1-(2-(2,4-difluorophenoxy)-5-nitrophenyl)-3-methylquinolin-4(1H)-one (0.10 g, 0.24 mmol, 1.0 eq).

LCMS: 379 [M+1]$^+$

Step 6: Synthesis of N-(4-(2,4-difluorophenoxy)-3-(3-methyl-4-oxoquinolin-1(4H)-yl)phenyl) ethanesulfonamide N-(4-(2,4-difluorophenoxy)-3-(3-methyl-4-oxoquinolin-1(4H)-yl)phenyl) ethanesulfonamide (0.002 mg, 2%, off-white solid) was prepared following General Procedure 21, Step 5 using 1-(5-amino-2-(2,4-difluorophenoxy)phenyl)-3-methylquinolin-4(1H)-one (0.9 g, 0.23 mmol, 1.0 eq).

LCMS: 471 [M+1]$^+$ $^1$H NMR (400 MHz, Methanol-d$_4$): δ 8.34 (dd, J=8.4, 1.5 Hz, 1H), 7.94 (s, 1H), 7.62 (td, J=6.8, 3.3 Hz, 1H), 7.51-7.38 (m, 3H), 7.11 (t, J=9.6 Hz, 2H), 7.07-6.93 (m, 2H), 6.89-6.78 (m, 1H), 3.19 (q, J=7.4 Hz, 2H), 2.12 (s, 3H), 1.35 (t, J=7.4 Hz, 3H)

Example S-73: N-(3-(2-acryloyl-1-oxo-1,2-dihydroisoquinolin-4-yl)-4-(2,4-difluorophenoxy) phenyl)ethanesulfonamide, Compound 662

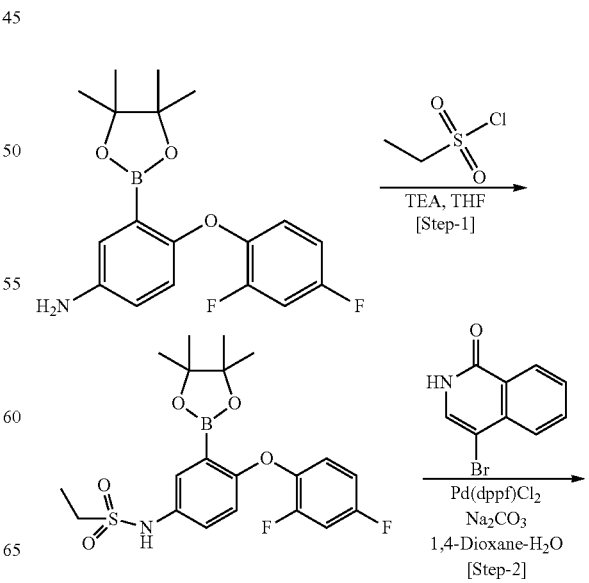

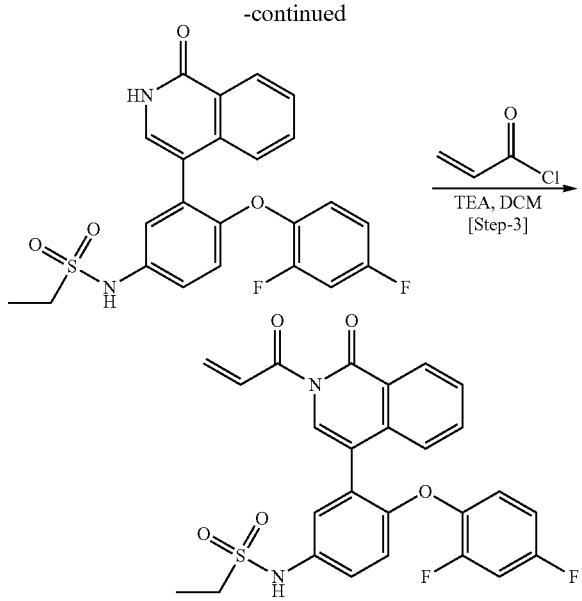

Step 1: Synthesis of 4-(2,4-difluorophenoxy)-3-(4,4,5,5-tetramethyl-1,3,2-dioxaborolan-2-yl)aniline To a stirred solution of 4-(2,4-difluorophenoxy)-3-(4,4,5,5-tetramethyl-1,3,2-dioxaborolan-2-yl)aniline (0.75 g, 2.16 mmol, 1 eq) in THF (10 mL) was added triethylamine (0.65 g, 6.48 mmol, 3 eq) followed by the addition of ethanesulfonyl chloride (0.36 g, 2.8 mmol, 1.3 eq) at 0° C. and the resultant mixture was stirred at RT for 16 h. The reaction was complete after 16 h and to the mixture was added water (30 mL) and extracted with EtOAc (30 mL×2). The combined organic layers was washed with saturated NaHCO$_3$ solution (30 mL), brine (30 mL), dried over anhydrous Na$_2$SO$_4$, filtered and concentrated under reduced pressure to afford 4-(2,4-difluorophenoxy)-3-(4,4,5,5-tetramethyl-1,3,2-dioxaborolan-2-yl)aniline (0.90 g, 95%, crude) which was taken to next step without further purification.
LCMS: 440 [M+1]$^+$

Step 2: Synthesis N-(4-(2,4-difluorophenoxy)-3-(1-oxo-1,2-dihydroisoquinolin-4-yl)phenyl) ethanesulfonamide N-(4-(2,4-difluorophenoxy)-3-(1-oxo-1,2-dihydroisoquinolin-4-yl)phenyl) ethanesulfonamide (0.087 g, 44%, brown solid) was prepared following General Procedure 2, Step 1 using 4-bromoisoquinolin-1(2H)-one (0.25 g, 1.11 mmol, 1 eq) and 4-(2,4-difluorophenoxy)-3-(4,4,5,5-tetramethyl-1,3,2-dioxaborolan-2-yl)aniline (0.95 g, 2.78 mmol, 2.5 eq).
LCMS: 457 [M+1]$^+$

Step 3: Synthesis N-(3-(2-acryloyl-1-oxo-1,2-dihydroisoquinolin-4-yl)-4-(2,4-difluorophenoxy)phenyl)ethanesulfonamide To a stirred solution of N-(4-(2,4-difluorophenoxy)-3-(1-oxo-1,2-dihydroisoquinolin-4-yl)phenyl) ethanesulfonamide (0.07 g, 0.15 mmol, 1 eq) in MeCN (5 mL) was added Cs$_2$CO$_3$ (0.073 g, 0.23 mmol, 1.5 eq) at 0° C. followed by dropwise addition of acryloyl chloride (0.013 mg, 0.15 mmol, 1.0 eq) at 0° C. The reaction mixture was stirred at the same temperature and monitored by TLC. The reaction was complete after 10 min and the mixture was diluted with water (100 mL) and extracted with EtOAc (150 mL). The organic layer was washed with water (75 mL), brine (75 mL), dried over anhydrous Na$_2$SO$_4$, filtered and concentrated under reduced pressure to obtain a crude material which was purified by reversed-phase chromatography to afford N-(3-(2-acryloyl-1-oxo-1,2-dihydroisoquinolin-4-yl)-4-(2,4-difluorophenoxy)phenyl)ethanesulfonamide (0.003 g, 3.7%) as an off-white solid.
LCMS: 511 [M+1]$^+$
$^1$H NMR (400 MHz, Methanol-d$_4$): δ 8.37 (d, J=8.1 Hz, 1H), 7.71 (t, J=7.7 Hz, 1H), 7.56 (t, J=7.7 Hz, 1H), 7.47 (d, J=8.1 Hz, 1H), 7.44-7.37 (m, 2H), 7.35-7.30 (m, 2H) 7.22 (s, 1H), 7.00 (d, J=9.6 Hz, 1H), 6.89 (t, J=9.1 Hz, 1H), 6.47 (d, J=16.6 Hz, 1H), 6.17 (dd, J=16.8, 10.4 Hz, 1H), 5.83 (d, J=10.6 Hz, 1H), 3.79(q, J=7.7 Hz, 2H), 1.43 (t, J=7.5 Hz, 3H).

Example S-74: N-(4-(2,4-difluorophenoxy)-3-(4-oxoquinolin-(4H)-yl)phenyl)ethane sulfonamide, Compound 709

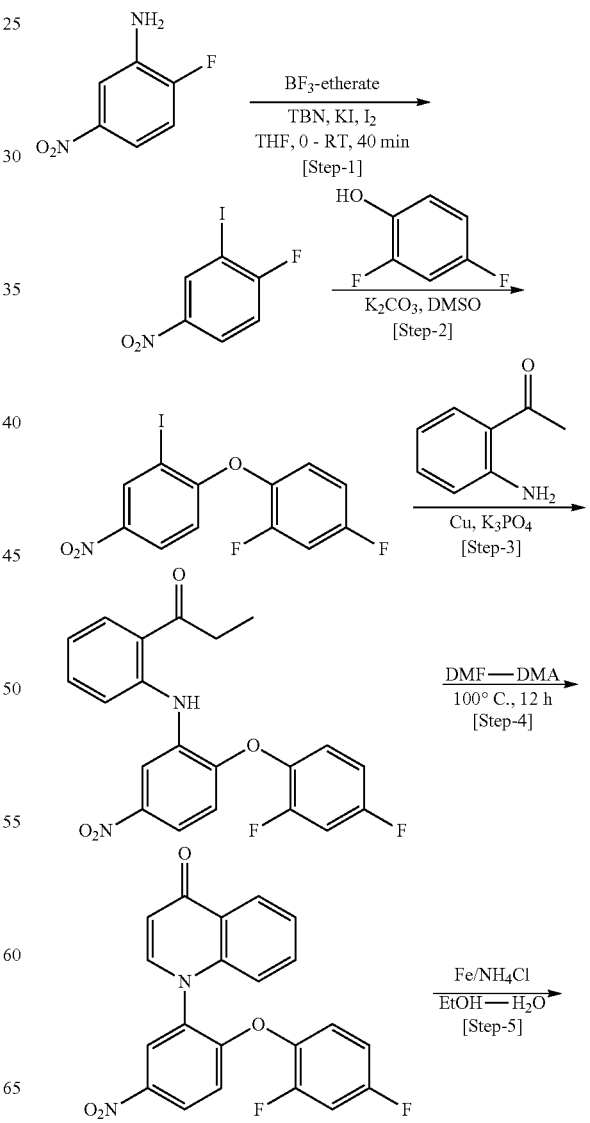

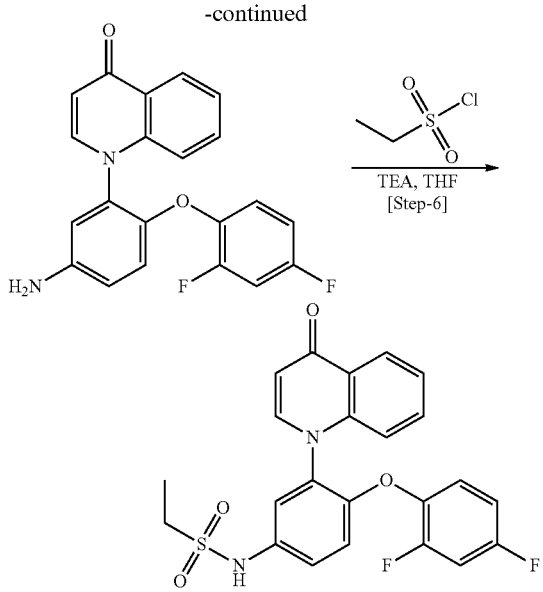

Step 1: Synthesis of 1-fluoro-2-iodo-4-nitrobenzene 1-fluoro-2-iodo-4-nitrobenzene (16 g, 93%, yellow solid) was prepared following General Procedure 22, Step 1 using 2-fluoro-5-nitroaniline (10 g, 64.6 mmol, 1.00 eq).

$^1$H NMR (400 MHz, CDCl$_3$): δ 8.67 (dd, J=5.3, 2.6 Hz, 1H), 8.25 (s, 1H), 7.21 (dd, J=9.0, 6.8 Hz, 1H).

Step 2: Synthesis of 1-(2,4-difluorophenoxy)-2-iodo-4-nitrobenzene 1-(2,4-difluoro phenoxy)-2-iodo-4-nitrobenzene (20 g, 43%, yellow solid) was prepared following General Procedure 22, Step 2 using 2,4-difluorophenol (16.0 g, 60 mmol, 1.0 eq) and 1-fluoro-2-iodo-4-nitrobenzene (6.9 mL g, 72 mmol, 1.2 eq).

$^1$H NMR (400 MHz, CDCl$_3$): δ 8.75 (d, J=2.6 Hz, 1H), 8.13 (dd, J=2.9, 9.0 Hz, 1H), 7.20 (d, J=5.3 Hz, 1H), 7.07-6.92 (m, 2H), 6.64 (dd, J=0.9, 9.2 Hz, 1H)

Step 3: Synthesis of 1-(2-(2-(2,4-difluorophenoxy)-5-nitrophenylamino)phenyl)ethanone 1-(2-(2-(2,4-difluorophenoxy)-5-nitrophenylamino)phenyl)ethanone (0.40 g, 28%, yellow solid) was prepared following General Procedure 22, Step 3 using 1-(2-aminophenyl)ethanone (0.50 g, 3.7 mmol, 1.0 eq) and 1-(2,4-difluorophenoxy)-2-iodo-4-nitrobenzene (2.0 g, 5.5 mmol, 1.5 eq).

LCMS: 385 [M+1]$^+$

Step 4: Synthesis of 1-(2-(2,4-difluorophenoxy)-5-nitrophenyl)-3-methylquinolin-4(1H)-one 1-(2-(2,4-difluorophenoxy)-5-nitrophenyl)-3-methylquinolin-4(1H)-one (0.8 g, 65%). was prepared following General Procedure 22, Step 4 using 1-(2-(2-(2,4-difluorophenoxy)-5-nitrophenylamino)phenyl)ethanone (1.2 g, 3.15 mmol, 1.0 eq).

LCMS: 395 [M+1]$^+$

Step 5: Synthesis of 1-(5-amino-2-(2,4-difluorophenoxy)phenyl)quinolin-4(1H)-one 1-(5-amino-2-(2,4-difluorophenoxy)phenyl)quinolin-4(1H)-one (0.1 mg, 90%, dark brown solid) was prepared following General Procedure 1, Step 2 using 1-(2-(2,4-difluorophenoxy)-5-nitrophenyl)-3-methylquinolin-4(1H)-one (0.12 g, 0.30 mmol, 1.0 eq).

LCMS: 365 [M+H]$^+$

Step 6: Synthesis of N-(4-(2,4-difluorophenoxy)-3-(4-oxoquinolin-1(4H)-yl)phenyl)ethanesulfonamide N-(4-(2,4-difluorophenoxy)-3-(4-oxoquinolin-1(4H)-yl)phenyl)ethanesulfonamide (24 mg, 19%, dark brown solid) was prepared following General Procedure 21, Step 5 using 1-(5-amino-2-(2,4-difluorophenoxy)phenyl)quinolin-4(1H)-one (0.1 g, 0.277 mmol, 1.0 eq).

LCMS: 457 [M+H]$^+$,
$^1$H NMR (400 MHz, DMSO-d$_6$): δ 10.05 (s, 1H), 8.16 (d, J=8.0 Hz, 1H), 7.97 (d, J=7.8 Hz, 1H), 7.63 (t, J=7.8 Hz, 1H), 7.38 (qd, J=8.0, 2.6 Hz, 4H), 7.19 (td, J=9.3, 5.5 Hz, 1H), 7.12 (d, J=8.7 Hz, 1H), 7.08-6.96 (m, 2H), 6.14 (d, J=7.8 Hz, 1H), 3.19 (q, J=7.6 Hz, 2H), 1.23 (t, J=7.2 Hz, 3H).

Example S-75: N-(4-(4-fluoro-2, 6-dimethylphenoxy)-3-(3-methyl-4-oxoquinolin-1(4H)-yl)phenyl)ethanesulfonamide, Compound 570

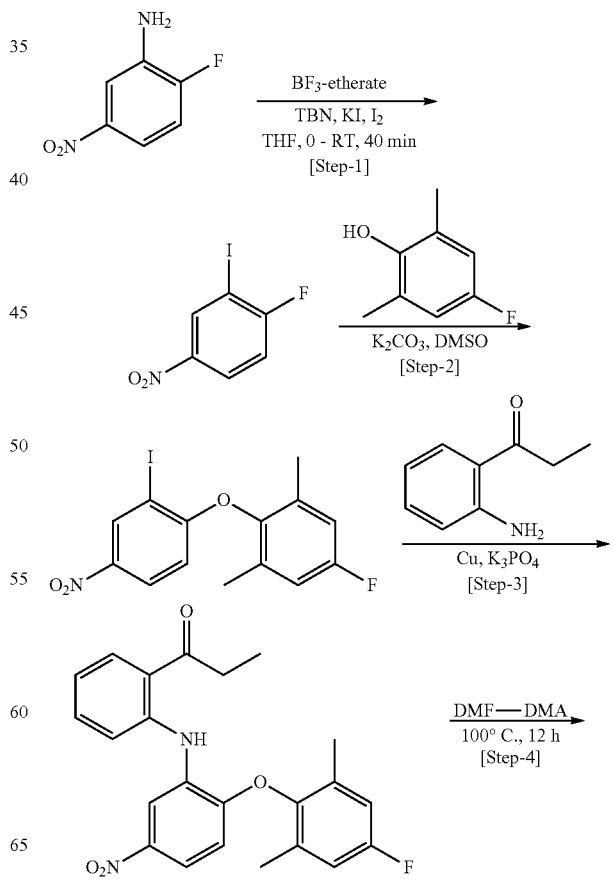

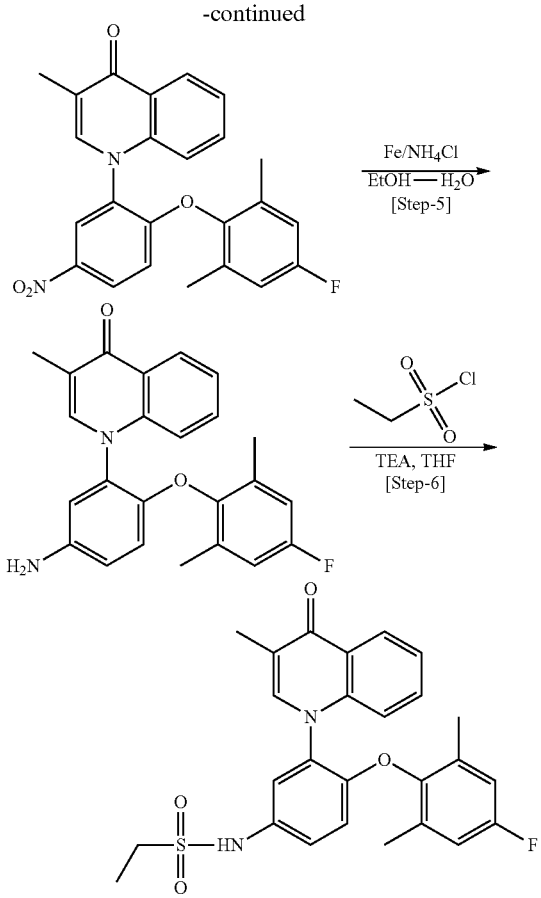

Step 1: Synthesis of 1-fluoro-2-iodo-4-nitrobenzene 1-fluoro-2-iodo-4-nitrobenzene (16 g, 93%, yellow solid) was prepared following General Procedure 22, Step 1 using 2-fluoro-5-nitroaniline (2 g, 64.6 mmol, 1.00 eq).

$^1$H NMR (400 MHz, CDCl$_3$): δ 8.67 (dd, J=5.3, 2.6 Hz, 1H), 8.25 (s, 1H), 7.21 (dd, J=9.0, 6.8 Hz, 1H).

Step 2: Synthesis of 15-fluoro-2-(2-iodo-4-nitrophenoxy)-1,3-dimethylbenzene 5-fluoro-2-(2-iodo-4-nitrophenoxy)-1,3-dimethylbenzene (20 g, 43%, yellow solid) was prepared following General Procedure 22, Step 2 using 4-fluoro-2,6-dimethylphenol (2.0 g, 7.5 mmol, 1.0 eq) and 1-fluoro-2-iodo-4-nitrobenzene (1 g, 9.02 mmol, 1.2 eq).

LCMS: 388 [M+1]$^+$

Step 3: Synthesis of 1-(2-(2-(4-fluoro-2,6-dimethylphenoxy)-5-nitrophenylamino) phenyl)propan-1-one To 1-(2-aminophenyl)propan-1-one (0.55 g, 3.7 mmol, 1.0 eq) and 5-fluoro-2-(2-iodo-4-nitrophenoxy)-1,3-dimethylbenzene (2.1 g, 5.53 mmol, 1.5 eq) in 1,4-Dioxane (20 mL) was added K$_3$PO$_4$ (1.7 g, 8.1 mmol, 2.2 eq) and the mixture was degassed under nitrogen for 20 min. Cu-metal (0.069 g, 1.1 mmol, 0.3 eq) was then added to the mixture and the resultant mixture was heated at 120° C. for 24 h and monitored by TLC and LC-MS. After 24 h, the mixture was diluted with water (100 mL) extracted with EtOAc (100 mL×2). The combined organic layers were washed with water (50 mL), brine (50 mL) dried over anhydrous Na$_2$SO$_4$, filtered and concentrated under reduced pressure to obtain a crude which was purified by CombiFlash Chromatograph to afford 11-(2-(2-(4-fluoro-2,6-dimethylphenoxy)-5-nitrophenylamino)phenyl)propan-1-one (0.5 g, 86%).

LCMS: 409 [M+1]$^+$

Step 4: Synthesis of 1-(2-(4-fluoro-2,6-dimethylphenoxy)-5-nitrophenyl)-3-methylquinolin-4(1H)-one 1-(2-(4-fluoro-2,6-dimethylphenoxy)-5-nitrophenyl)-3-methylquinolin-4(1H)-one (0.5 g, 97%). was prepared following General Procedure 22, Step 4 using 1-(2-(2-(4-fluoro-2,6-dimethylphenoxy)-5-nitrophenylamino) phenyl)propan-1-one (0.15 g, 0.37 mmol, 1.0 eq).

LCMS: 419 [M+H]$^+$

Step 5: Synthesis of 1-(5-amino-2-(4-fluoro-2,6-dimethylphenoxy)phenyl)-3-methylquinolin-4(1H)-one 1-(5-amino-2-(4-fluoro-2,6-dimethylphenoxy)phenyl)-3-methylquinolin-4(1H)-one (0.45 mg, 96%, dark brown solid) was prepared following General Procedure 1, Step 2 using 1-(2-(2,4-difluorophenoxy)-5-nitrophenyl)-3-methylquinolin-4(1H)-one (0.5 g, 1.2 mmol, 1.0 eq).

LCMS: 389 [M+H]$^+$

Step 6: Synthesis of N-(4-(4-fluoro-2,6-dimethylphenoxy)-3-(3-methyl-4-oxoquinolin-1(4H)-yl) phenyl)ethanesulfonamide N-(4-(4-fluoro-2,6-dimethylphenoxy)-3-(3-methyl-4-oxoquinolin-1(4H)-yl)phenyl)ethanesulfonamide (0.0075 mg, 5%, off-white solid) was prepared following General Procedure 21, Step 5 using 1-(5-amino-2-(4-fluoro-2,6-dimethylphenoxy)phenyl)-3-methylquinolin-4(1H)-one (0.12 g, 0.31 mmol, 1.0 eq).

LCMS: 481 [M+H]$^+$, $^1$H NMR (400 MHz, Methanol-d$_4$): δ 8.24 (dd, J=8.2, 1.6 Hz, 1H), 8.06 (s, 1H), 7.63 (ddd, J=8.7, 7.0, 1.8 Hz, 1H), 7.42-7.33 (m, 2H), 7.29 (dd, J=9.1, 2.7 Hz, 1H), 7.04 (d, J=8.5 Hz, 1H), 6.99 (d, J=9.1 Hz, 2H), 6.52 (d, J=9.0 Hz, 1H), 3.14 (q, J=7.6 Hz, 2H), 2.04 (s, 3H), 1.93 (s, 6H), 1.28-1.18 (m, 3H).

Example S-76: N-(4-(4-fluoro-2, 6-dimethylphenoxy)-3-(3-methyl-4-oxoquinolin-1(4H)-yl)phenyl) acetamide, Compound 710

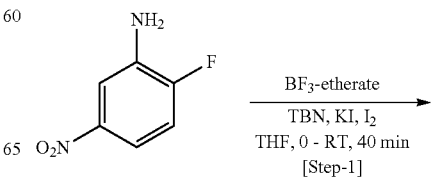

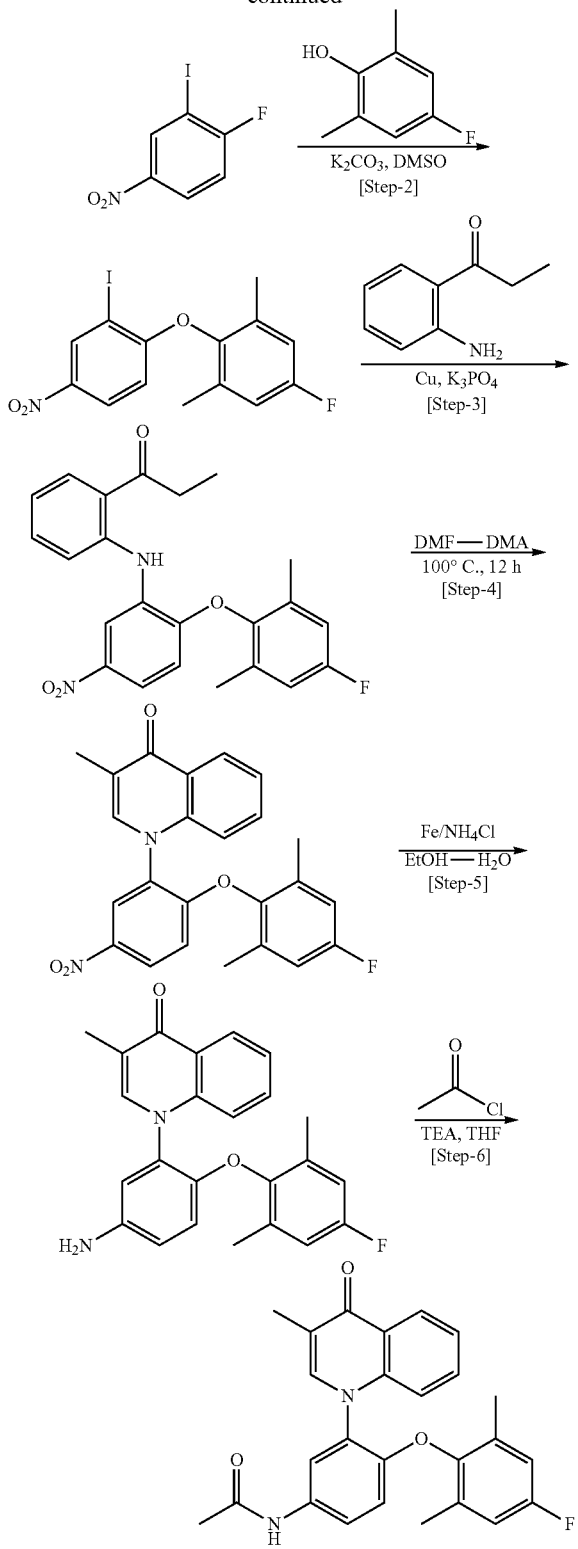

Step 1: Synthesis of 1-fluoro-2-iodo-4-nitrobenzene 1-fluoro-2-iodo-4-nitrobenzene (16 g, 93%, yellow solid) was prepared following General Procedure 22, Step 1 using 2-fluoro-5-nitroaniline (2 g, 64.6 mmol, 1.00 eq).

$^1$H NMR (400 MHz, CDCl3): δ 8.67 (dd, J=5.3, 2.6 Hz, 1H), 8.25 (s, 1H), 7.21 (dd, J=9.0, 6.8 Hz, 1H).

Step 2: Synthesis of 15-fluoro-2-(2-iodo-4-nitrophenoxy)-1,3-dimethylbenzene 5-fluoro-2-(2-iodo-4-nitrophenoxy)-1,3-dimethylbenzene (20 g, 43%, yellow solid) was prepared following General Procedure 22, Step 2 using 4-fluoro-2,6-dimethylphenol (2.0 g, 7.5 mmol, 1.0 eq) and 1-fluoro-2-iodo-4-nitrobenzene (1 g, 9.02 mmol, 1.2 eq).

LCMS: 388 [M+1]$^+$

Step 3: Synthesis of 1-(2-(2-(4-fluoro-2,6-dimethylphenoxy)-5-nitrophenylamino) phenyl)propan-1-one To 1-(2-aminophenyl)propan-1-one (0.55 g, 3.7 mmol, 1.0 eq) and 5-fluoro-2-(2-iodo-4-nitrophenoxy)-1,3-dimethylbenzene (2.1 g, 5.53 mmol, 1.5 eq) in 1,4-Dioxane (20 mL) was added K$_3$PO$_4$ (1.7 g, 8.1 mmol, 2.2 eq) and the mixture was degassed under nitrogen for 20 min. Cu-metal (0.069 g, 1.1 mmol, 0.3 eq) was then added to the mixture and the resultant mixture was heated at 120° C. for 24 h and monitored by TLC and LC-MS. After 24 h, the mixture was diluted with water (100 mL) extracted with EtOAc (100 mL×2). The combined organic layers were washed with water (50 mL), brine (50 mL) dried over anhydrous Na$_2$SO$_4$, filtered and concentrated under reduced pressure to obtain a crude which was purified by CombiFlash Chromatograph to afford 11-(2-(2-(4-fluoro-2,6-dimethylphenoxy)-5-nitrophenylamino)phenyl)propan-1-one (0.5 g, 86%).

LCMS: 409 [M+1]$^+$

Step 4: Synthesis of 1-(2-(4-fluoro-2,6-dimethylphenoxy)-5-nitrophenyl)-3-methylquinolin-4(1H)-one 1-(2-(4-fluoro-2,6-dimethylphenoxy)-5-nitrophenyl)-3-methylquinolin-4(1H)-one (0.5 g, 97%). was prepared following General Procedure 22, Step 4 using 1-(2-(2-(4-fluoro-2,6-dimethylphenoxy)-5-nitrophenylamino) phenyl) propan-1-one (0.15 g, 0.37 mmol, 1.0 eq).

LCMS: 419 [M+H]$^+$

Step 5: Synthesis of 1-(5-amino-2-(4-fluoro-2,6-dimethylphenoxy)phenyl)-3-methylquinolin-4(1H)-one 1-(5-amino-2-(4-fluoro-2,6-dimethylphenoxy)phenyl)-3-methylquinolin-4(1H)-one (0.45 mg, 96%, dark brown solid) was prepared following General Procedure 1, Step 2 using 1-(2-(2,4-difluorophenoxy)-5-nitrophenyl)-3-methylquinolin-4(1H)-one (0.5 g, 1.2 mmol, 1.0 eq).

LCMS: 389 [M+H]$^+$

Step 6: Synthesis of N-(4-(4-fluoro-2,6-dimethylphenoxy)-3-(3-methyl-4-oxoquinolin-1(4H)-yl)phenyl)acetamide To a stirred solution of 1-(5-amino-2-(4-fluoro-2,6-dimethyl phenoxy)phenyl)-3-methylquinolin-4(1H)-one (0.13 g, 0.334 mmol, 1 eq) in DCM was added triethylamine (0.1 g, 1.0 mmol, 3 eq) at 0° C. followed by the addition of acetyl chloride (0.031 g, 0.40 mmol, 1.2 eq) slowly and the mixture was stirred at 0° C. for 15 min and monitored by TLC. The reaction was complete after 15 min, the mixture was diluted with water (50 mL) extracted with DCM (50 mL×2). The combined organic layers were washed with water (50 mL), brine (50 mL) dried over anhydrous $Na_2SO_4$, filtered and concentrated under reduced pressure to obtain a crude which was purified by Reversed Phase HPLC to afford N-(4-(4-fluoro-2,6-dimethylphenoxy)-3-(3-methyl-4-oxoquinolin-1(4H)-yl)phenyl)acetamide (0.004 mg, 2.7%, off-white solid).

LCMS: 431 $[M+H]^+$, $^1H$ NMR (400 MHz, Methanol-$d_4$): δ 8.44-8.36 (m, 1H), 8.07 (s, 1H), 7.86 (d, J=2.6 Hz, 1H), 7.65 (ddd, J=8.7, 7.0, 1.6 Hz, 1H), 7.55 (dd, J=9.1, 2.6 Hz, 1H), 7.44 (t, J=7.6 Hz, 1H), 7.19 (d, J=8.6 Hz, 1H), 6.83 (d, J=8.9 Hz, 2H), 6.54 (d, J=9.0 Hz, 1H), 2.20 (s, 3H), 2.12 (s, 3H), 1.98 (s, 6H).

It is understood that compounds from the Table-1 (33-73, 75-85, 87-166, 168-287, 289-304, 306-308, 310-312, 314-318, 320-380, 382-392, 395, 398-402, 405, 413-582, 586, 590-610, 614-615, 617-660, 663-708, 711-758) are synthesized using the General Synthetic Schemes 1 to 6 or using the experimental procedures as described above and the steps involved in the synthetic routes are clearly familiar to those skilled in the art, wherein the substituents described in compounds of Formula (I), (Ia), (Ia-1 to Ia-12), (Ib), (Ib-1 to Ib-4), (Ic), (Ic-1 to Ic-19), (II), (III), (IV), (IVa to IVk), (IVg-1 to IVg-9), (IV-i-1 to IV-i-11), (IVk-1 to IVk-12), (V), (Va to Ve), (Va-1 to Va-12), (Vb-1 to Vb-12), (Vc-1 to Vc-8), (Vc-1' to Vc-12'), (Vd-1 to Vd-6), (Vd-1' to Vd-12') and (Ve-1 to Ve-5) herein can be varied with a choice of appropriate starting materials and reagents utilized in the steps presented.

Biological Examples

Example B-1

Bromodomain and Extraterminal Domain (BET) Binding Assay

The bromodomain binding assays were performed by Reaction Biology Corp., Malvern, Pa., USA (www.reactionbiology.com). The BET binding assays were conducted in 384 well microplates in assay buffer (50 mM HEPES-HCl, pH 7.5, 100 mM NaCl, 1 mg/ml BSA, 0.05% CHAPS, and 0.5% DMSO) with compounds added as DMSO stocks at a single concentration or with 10-point dose response titrations. BET protein or assay buffer were delivered to the appropriate wells of the microplate. Test compound was then delivered by acoustic technology via a Labcyte Echo550 liquid handler. The microplate was centrifuged for 5 min and pre-incubated for 30 min at RT with gentle shaking. The ligand (histone H4 peptide (1-21) K5/8/12/16Ac-biotin) was delivered and the microplate was again centrifuged for 5 min and allowed to incubate for 30 min at RT with gentle shaking. Donor beads were then added in the absence of light and the microplate was centrifuged and gently shaken. After 5 min, acceptor beads were added in the absence of light and the microplate was centrifuged and gently shaken in the dark for 60 min. The microplate was read using a Perkin Elmer EnSpire Alpha plate reader (λEx/λEm=680/520-620 nm). Percent inhibition was calculated relative to positive and negative controls on a per plate basis. For titration experiments, $IC_{50}$ values were determined by fitting the percent inhibition versus compound concentration.

| Final Protein and Ligand Concentrations | | |
|---|---|---|
| Target | Protein Conc. (nM) | Ligand Conc. (nM) |
| BRD2-1 | 40 | 40 |
| BRD2-2 | 120 | 60 |
| BRD3-1 | 30 | 40 |
| BRD3-2 | 75 | 75 |
| BRD4-1 | 20 | 20 |
| BRD4-2 | 130 | 70 |
| BRDT-1 | 60 | 40 |

Compounds described herein were assayed and found to bind to bromodomain and extraterminal domain proteins. BET profiling for compound 3 is shown in Table 2.

TABLE 2

| | | BET $IC_{50}$ (μM) | | | | | | |
|---|---|---|---|---|---|---|---|---|
| Synthesis Example No. | Compound No. | BRD2-1 | BRD2-2 | BRD3-1 | BRD3-2 | BRD4-1 | BRD4-2 | BRDT-1 |
| S-10 | 3 | 0.016 | 0.012 | 0.035 | 0.029 | 0.024 | 0.021 | 0.031 |

BRD4-1 and BRD4-2 $IC_{50}$ for additional compounds of invention are shown in Table 3. ND means "not determined."

TABLE 3

| | BRD4-1 and BRD4-2 $IC_{50}$ (μM) | | |
|---|---|---|---|
| Synthesis Example No. | Compound No. | BRD4-1 $IC_{50}$ (μM) | BRD4-2 $IC_{50}$ (μM) |
| S-8 | 1 | 0.188 | 0.064 |
| S-9 | 2 | 0.052 | 0.117 |
| S-10 | 3 | 0.024 | 0.021 |
| S-11 | 4 | ND | 0.022 |
| S-12 | 5 | ND | 0.142 |
| S-13 | 6 | ND | 0.120 |
| S-14 | 7 | ND | 0.024 |
| S-15 | 8 | ND | 0.017 |
| S-16 | 9 | ND | 0.319 |
| S-17 | 10 | ND | 0.056 |
| S-18 | 11 | ND | 0.014 |
| S-19 | 12 | ND | 0.037 |
| S-20 | 13 | ND | 0.024 |
| S-21 | 14 | ND | >10 |
| S-22 | 15 | ND | 0.034 |
| S-23 | 16 | 0.006 | 0.026 |
| S-24 | 17 | ND | 0.119 |
| S-25 | 18 | ND | >10 |
| S-26 | 19 | ND | 1.453 |
| S-27 | 20 | ND | 3.856 |
| S-28 | 21 | ND | 0.011 |
| S-29 | 22 | ND | 3.848 |
| S-30 | 23 | ND | >10 |
| S-31 | 24 | ND | 0.779 |
| S-32 | 25 | ND | 0.264 |
| S-33 | 26 | ND | 0.281 |
| S-34 | 27 | ND | 3.25 |

TABLE 3-continued

BRD4-1 and BRD4-2 IC$_{50}$ (µM)

| Synthesis Example No. | Compound No. | BRD4-1 IC$_{50}$ (µM) | BRD4-2 IC$_{50}$ (µM) |
|---|---|---|---|
| S-35 | 28 | ND | 17.9 |
| S-36 | 29 | 0.030 | 0.015 |
| S-37 | 30 | 0.104 | 0.057 |
| S-38 | 31 | ND | 0.413 |
| S-39 | 32 | ND | 0.717 |
| S-40 | 74 | ND | 0.239 |
| S-41 | 409 | 0.479 | 0.075 |
| S-42 | 393 | ND | 0.261 |
| S-43 | 288 | ND | 0.889 |
| S-44 | 305 | 1.71 | 2.170 |
| S-45 | 309 | ND | 2.120 |
| S-46 | 313 | >10 | 0.885 |
| S-47 | 394 | ND | 0.134 |
| S-48 | 407 | 0.183 | 0.011 |
| S-49 | 403 | ND | 0.206 |
| S-50 | 396 | ND | 0.298 |
| S-51 | 412 | 1.740 | 0.004 |
| S-52 | 397 | 9.710 | 0.549 |
| S-53 | 411 | 0.347 | 0.010 |
| S-54 | 404 | ND | 1.827 |
| S-55 | 86 | ND | 0.080 |
| S-56 | 381 | 12.520 | 0.013 |
| S-57 | 410 | ND | 0.758 |
| S-58 | 319 | ND | 1.800 |
| S-59 | 408 | 15.930 | 0.434 |
| S-60 | 167 | 0.424 | 0.017 |
| S-61 | 583 | ND | 0.078 |
| S-62 | 584 | 0.226 | 0.001 |
| S-63 | 585 | 5.068 | 0.043 |
| S-64 | 587 | ND | 0.011 |
| S-65 | 588 | 2.846 | 0.006 |
| S-66 | 589 | 7.193 | 0.012 |
| S-67 | 611 | 7.370 | 0.002 |
| S-68 | 612 | ND | >10 |
| S-69 | 613 | ND | 0.027 |
| S-70 | 406 | 0.022 | 0.003 |
| S-71 | 661 | 0.020 | 0.005 |
| S-72 | 616 | 0.011 | 0.004 |
| S-73 | 662 | ND | >10 |
| S-74 | 709 | 1.208 | 0.093 |
| S-75 | 570 | 1.370 | 0.011 |
| S-76 | 710 | 8.150 | 0.292 |

Example B-2

Cell Viability Assays

A panel of BET-sensitive and insensitive cell lines were profiled for effect on cell viability using compound 3. Cells were cultured in the presence of inhibitors at various concentrations for up to 72 hr. For cell viability assays as previously described (Guo Y, et al. 2012. J Hematol Oncol 5:72; Chen Y, et al. 2016. Oncogene 35:2971-8), 0.08 mg/ml XTT (2,3-bis-(2-methoxy-4-nitro-5-sulfophenyl)-2H-tetrazolium-5-carboxanilide) and 8 µM phenazine methyl sulfate (PMS) were added to the cells at the end of the test compound or vehicle treatment duration, and absorbance at 450 nm was measured after 3 hr incubation at 37° C. Assays were performed in triplicates. IC50 values were estimated using a non-linear mixed effect model fitting a sigmoid curve to the experimental dose response data (Vis D J, et al. 2016. Pharmacogenomics 17(7):691-700). IC$_{50}$ values obtained for the panel of cell lines are shown in Table 4.

TABLE 4

Cell Viability IC$_{50}$ for Compound 3

| Cell Line | IC$_{50}$ (µM) | Cell Line | IC$_{50}$ (µM) |
|---|---|---|---|
| MV-4-11 | 0.1 | OCI-LY18 | 0.42 |
| Molt-4 | 0.3 | U2973 | 0.24 |
| MEG-01 | 0.31 | THP-1 | 0.25 |
| HEL | 0.4 | K562 | 5 |
| SET-2 | 0.09 | Jurkat | 6 |

A panel of AML and DLBCL cell lines was profiled for effects of compound 3 on cell viability. Cells were seeded at a count of 3000-8000 cells per well/40 µl in a 384-well plate and incubated at 37° C., 5% CO$_2$ overnight. Cells were treated with test compounds at 10 concentrations within a desired concentration range (e.g. 0.5 nM-10 µM) for generation of dose response curves by preparing serial dilutions of the test compound in DMSO which were further diluted with culture medium and then added in a volume of 2 µM to each well. Cells were cultured in the presence of inhibitors at various concentrations for 72 hr. The assay was terminated by addition of 25 µM Cell Titer-Glo reagent (Promega, Madison, Wis.) to each well. Contents were mixed, the plate was incubated for 10 min at room temperature and luminescence was measured. The IC$_{50}$ value of each test compound was calculated with XLFit curve fitting software. Seeding densities and IC$_{50}$ values obtained for the panel of cell lines are shown in Table 5.

TABLE 5

Cell Viability IC$_{50}$s for Compound 3 in AML and DLBCL cell lines

| Cell Line | IC$_{50}$ (µM) | Cell Line | IC$_{50}$ (µM) |
|---|---|---|---|
| NOMO-1 | 0.205 | OCI-AML3 | 0.050 |
| RS4; 11 | 0.128 | SU-DHL4 | 0.022 |
| KOPN-8 | 0.009 | SU-DHL6 | 0.047 |
| KG-1a | 0.285 | WSU-DLCL2 | 0.084 |

The effects of test compounds were studied in a second cell viability assay in the MV-4-11 human acute myeloid leukemia cell line. The cells were harvested during the logarithmic growth period and counted. Cells were seeded at a count of 15000 cells per well/100 µl. After seeding, cells were incubated at 37° C., 5% CO$_2$ for 1 hr. Cells were treated with test compounds at 8 concentrations within a desired concentration range (e.g. 5 nM-10 PM) for generation of dose response curves by preparing serial dilutions of the test compound in DMSO which were further diluted with culture medium and then added to each well. The plate was further incubated for another 72 hrs in a humidified incubator at 37° C. and 5% CO$_2$. The assay was terminated by addition of Cell Titer-Glo reagent (Promega, Madison, Wis.) at ¼ the volume of total medium per well. Contents were mixed, the plate was incubated for 10 min at room temperature and luminescence was measured. Cell viability data were plotted using GraphPad Prism (GraphPad Software, Inc., San Diego, Calif.). In addition, a nonlinear regression model with a sigmoidal dose response and variable slope within GraphPad Prism was used to calculate the IC$_{50}$ value of individual test compounds. IC$_{50}$ values are given in Table 6.

TABLE 6

Cell Viability IC$_{50}$s for compounds in MV4-11 cells

| Synthesis No. | Compound No. | IC$_{50}$ (μM) |
|---|---|---|
| S-10 | 3 | 0.028 |
| S-24 | 17 | 0.084 |
| S-41 | 409 | 0.253 |
| S-48 | 407 | 0.051 |
| S-51 | 412 | 0.025 |
| S-53 | 411 | 0.074 |
| S-55 | 86 | 0.273 |
| S-56 | 381 | 0.172 |
| S-60 | 167 | 0.097 |
| S-61 | 583 | 0.254 |
| S-62 | 584 | 0.033 |
| S-63 | 585 | 0.221 |
| S-64 | 587 | 0.045 |
| S-65 | 588 | 0.082 |
| S-66 | 589 | 0.181 |
| S-69 | 613 | 6.019 |
| S-70 | 406 | 0.114 |
| S-71 | 661 | 0.071 |
| S-72 | 616 | 0.038 |
| S-74 | 709 | 0.979 |
| S-75 | 570 | 0.526 |
| S-76 | 710 | 2.458 |

The effects of test compounds were also studied in the 22Rv1 human prostate carcinoma and MDA-MB-231 human breast adenocarcinoma cell lines. The cells were harvested during the logarithmic growth period and counted. Cells were seeded at a count of 3000 cells (22Rv1) or 5000 cells (MDA-MB-231) per well/100 μl in a 96-well plate. After seeding, cells were incubated at 37° C., 5% CO$_2$ for 24 hr. Cells were treated with test compounds at 8 concentrations within a desired concentration range (e.g. 5 nM-10 μM) for generation of dose response curves by preparing serial dilutions of the test compound in DMSO which were further diluted with culture medium and then added to each well. The plate was further incubated for another 72 hrs (22Rv1) or 96 hrs (MDA-MB-231) in humidified incubator at 37° C. and 5% CO$_2$. The assay was terminated by addition of resazurin (# R7017, Sigma). The plate was incubated for 4 hr at 37° C., 5% CO$_2$ and fluorescence was measured using excitation and emission wavelengths of 535 and 590 nm, respectively. Cell viability data were plotted using GraphPad Prism (GraphPad Software, Inc., San Diego, Calif.). In addition, a nonlinear regression model with a sigmoidal dose response and variable slope within GraphPad Prism was used to calculate the IC$_{50}$ value of individual test compounds. IC$_{50}$ values are given in Table 7.

TABLE 7

Cell Viability IC$_{50}$s for compounds in 22Rv1 and MDA-MB-231 cells

| Synthesis No. | Compound No. | 22Rv1 IC$_{50}$ (μM) | MDA-MB-231 IC$_{50}$ (μM) |
|---|---|---|---|
| S-10 | 3 | 0.058 | 0.082 |
| S-75 | 570 | 1.270 | ND |
| S-76 | 710 | 6.658 | ND |

ND: not determined

The effects of test compounds were also studied in the IEC-6 rat intestinal epithelial cell line to assess potential toxicity to non-cancerous cells. The cells were harvested during the logarithmic growth period and counted. In Protocol A, cells were seeded at a count of 3000 cells per well/100 μl in a 96-well plate. After seeding, cells were incubated at 37° C., 5% CO$_2$ for 24 hr. Cells were treated with test compounds at 8 concentrations within a desired concentration range (e.g. 5 nM-10 μM) for generation of dose response curves by preparing serial dilutions of the test compound in DMSO which were further diluted with culture medium and then added to each well. The plate was further incubated for another 96 hrs in humidified incubator at 37° C. and 5% CO$_2$. The assay was terminated by addition of resazurin (# R7017, Sigma). The plate was incubated for 4 hr at 37° C., 5% CO$_2$ and fluorescence was measured using excitation and emission wavelengths of 535 and 590 nm, respectively. Cell viability data were plotted using GraphPad Prism (GraphPad Software, Inc., San Diego, Calif.). In addition, a nonlinear regression model with a sigmoidal dose response and variable slope within GraphPad Prism was used to calculate the IC$_{50}$ value of individual test compounds. Protocol B was the same as Protocol A except that cells were seeded at a count of 4000 cells per well/100 μl in a 96-well plate, and the incubation with test compound was for 48 hrs instead of 96 hrs. IC$_{50}$ values are given in Table 8.

TABLE 8

Cell Viability IC$_{50}$s for compounds in IEC-6 cells

| Synthesis No. | Compound No. | Protocol A IC$_{50}$ (μM) | Protocol B IC$_{50}$ (μM) |
|---|---|---|---|
| S-10 | 3 | 0.339 | 0.173 |
| S-48 | 407 | ND | 0.693 |
| S-71 | 661 | ND | 0.273 |
| S-74 | 709 | ND | 2.9 |
| S-75 | 570 | ND | 2.86 |
| S-76 | 710 | ND | 7.55 |

ND: not determined

Example B-3

Cell Viability Assays after Wash-Off

MV4-11 cells were incubated with compound (at a concentration of 0.5 or 2 μM) or mivebresib (at a concentration of 0.5 or 2 μM) for 2 or 4 hr before wash-off with culture medium and re-plated in fresh culture medium for a total of 48 hr. Cells were stained with FITC-annexin V and 7-AAD before flow cytometric analysis using a Stratedigm flow cytometer. Viable cells are negative for FITC-annexin V and 7-AAD. Results of assay are shown in FIG. 1. Compound 3 displays sustained cell inhibition activity after transient exposure to cells.

A 22Rv1 cell proliferation assay was used to assess durability of test compound effects after transient exposure of test compound to cells. 22Rv1 cells were seeded at 3000 cells per well/100 μl in a 96-well plate and incubated with test compounds at specified dilutions for 2 hr at 37° C. and 5% CO$_2$. Following the incubation, test compound was washed off and replacement culture medium without test compound was added. Wash-off was performed by three PBS washes. The cells were incubated for an additional 96 hr at 37° C. and 5% CO$_2$. In parallel, a mock wash-off was performed with cells that were treated identically except that the replacement culture medium contained test compound. The plate was incubated for 4 hr at 37° C., 5% CO$_2$ and fluorescence was measured using excitation and emission wavelengths of 535 and 590 nm, respectively. Cell viability data were plotted using GraphPad Prism (GraphPad Software, Inc., San Diego, Calif.). In addition, a nonlinear regression model with a sigmoidal dose response and variable slope within GraphPad Prism was used to calculate the $IC_{50}$ value of individual test compounds. $IC_{50}$ values given in Table 9 show durability of effect of test compounds 3 and 406 on cell proliferation. By comparison, the tool compound JQ1 had an $IC_{50}$ of 0.071 µM with mock wash-off and an $IC_{50}$ of >10 µM with wash-off.

TABLE 9

Cell Viability $IC_{50}$ for test compounds in 22Rv1 cells with or without wash-off.

| Synthesis No. | Compound No. | Mock wash-off $IC_{50}$ (µM) | Wash-off $IC_{50}$ (µM) |
|---|---|---|---|
| S-10 | 3 | 0.342 | 0.096 |
| S-70 | 406 | 0.255 | 0.415 |

Example B-4

Histologic Analysis

The inhibitory effects of test compounds on the growth of cells are demonstrated by Wright-Giemsa staining of cells fixed to glass slides after incubation of the test compound or vehicle with the cells for a certain duration (e.g., 48 h). Morphologic changes of treated cells associated with cell cycle arrest, such as condensed nuclei and shrinking or swollen cell membranes are noted.

Example B-5

Measurement of c-Myc Suppression

Figure 2A:
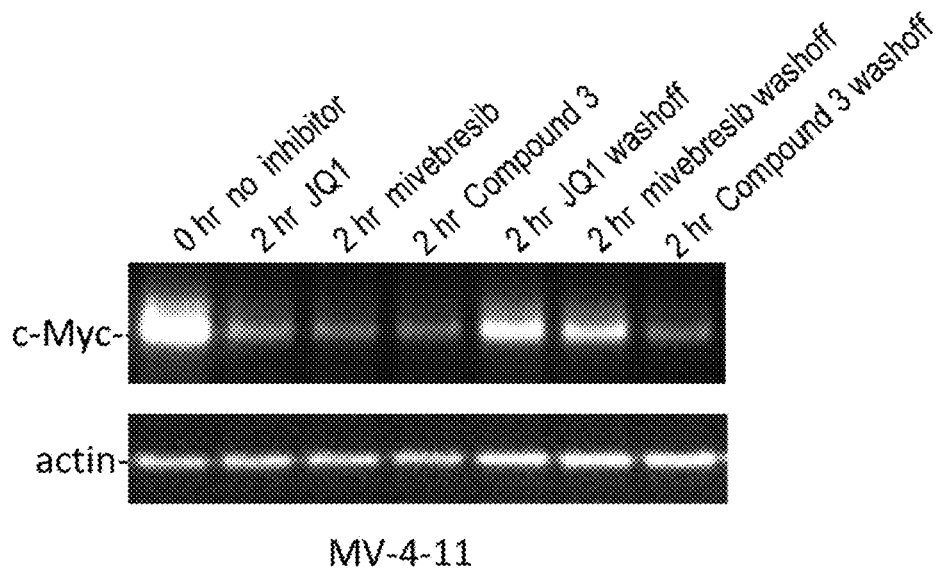
FIG. 2A, FIG. 2B, FIG. 2C, and FIG. 2D illustrate the results of western blot analysis to measure c-Myc suppression in MV4-11 cells incubated with compound for 2 hr then cultured for a further 6 hr after wash-off of compound.
Figure 2B:
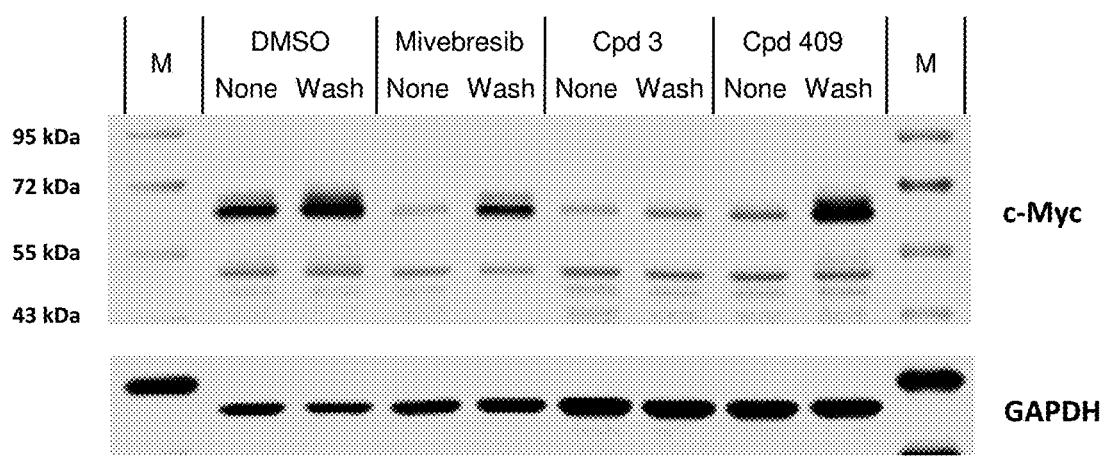
Figure 2C:
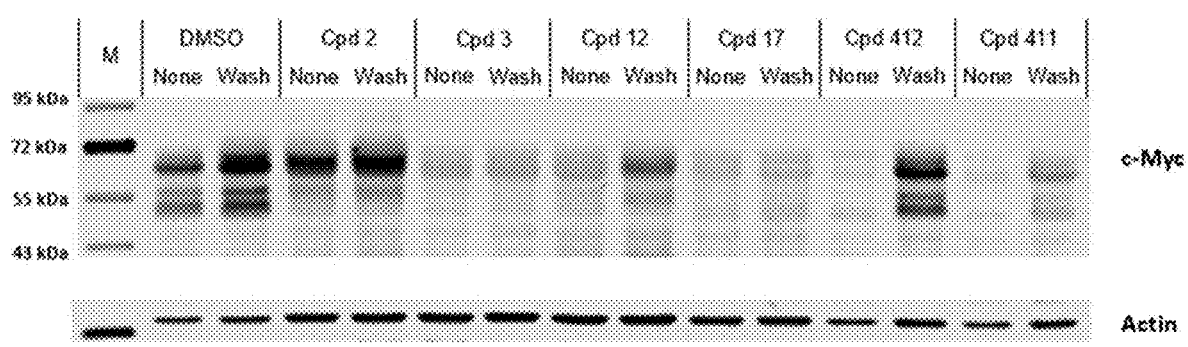
Figure 2D:
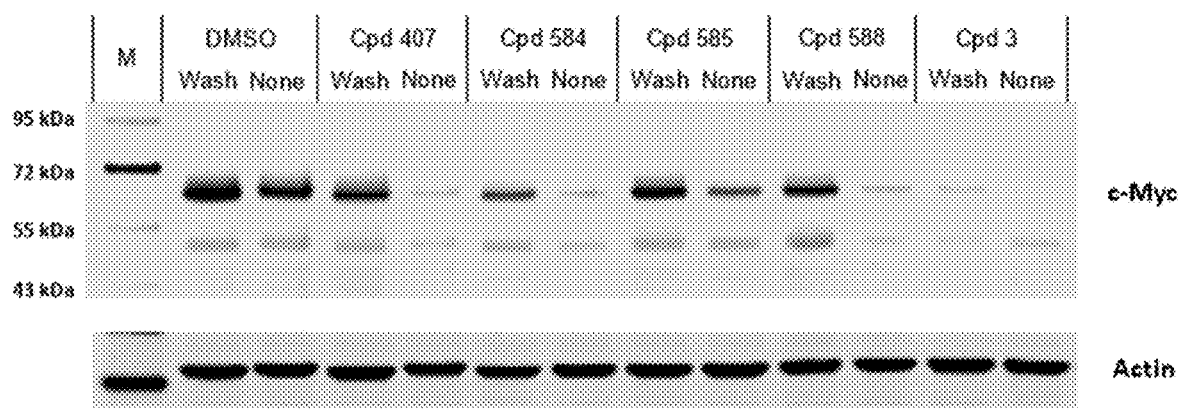

MV4-11 cells were incubated with 2 µM of JQ1, mivebresib or a test compound for 2 hr. The cells were then washed twice with fresh culture medium and further cultured for another 6 hr. Cells were extracted with SDS sample buffers and then subjected to Western blot analysis to measure c-Myc. Compounds 2, 3, 12, 17, 409, 411 and 412 were tested in these assays. Compounds 3 and 17 had sustained c-Myc suppression activity while the remaining compounds had less durable or no suppression activity. As illustrated in FIG. 2A, compound 3 has sustained c-Myc suppression activity after washoff. As illustrated in FIG. 2B, cells treated with either mivebresib or compound 409 showed a rebound in c-Myc expression following washoff. As illustrated in FIG. 2C, compounds 3 and 17 had sustained c-Myc suppression activity while compounds 2, 12, 411 and 412 had less durable or no suppression activity. As illustrated in FIG. 2D, compound 3 had sustained c-Myc suppression activity while compounds 407, 584, 585 and 588 had less durable activity.

Example B-6

In Vivo Efficacy Study

A study to evaluate test compound pharmacodynamics in MV-4-11 systemic leukemia model in NOD SCID mice is conducted. Female NOD SCID mice are inoculated with MV-4-11 cells systemically. Four weeks after cell inoculation, each animal is administered a single IV dose of test compound or vehicle. The dosing volume is 10 mL/kg (0.200 mL/20 g mouse), with volume adjusted according to body weight. Four hours after dosing, animals are sacrificed. Bone marrow and spleen (weight and size are recorded) are dissected, crushed in PBS and made into single cell suspensions for analysis by flow cytometry for the assessment of leukemic engraftment. Western blot analyses of bone marrow and spleen cell extracts with antibody against the housekeeping protein c-Myc are carried out for animals with successful leukemic engraftment.

Example B-7

Mouse Xenograft Model

To examine the in vivo antitumor activity of test compound (as a single agent and in combination with other agents such as enzalutamide) in a castration resistant prostate cancer mouse model, tumor growth experiments are performed in a VCaP cell line mouse xenograft model. Cells are implanted subcutaneously into the flanks of 4-week old male immunodeficient mice (such as nude or SCID mice) and allowed to grow. Tumors are measured using a caliper and tumor volumes calculated using the formula: Tumor volume=$(a \times b^2/2)$ where 'b' is the smallest diameter and 'a' is the largest diameter. Once the established tumors reach approximately 200 $mm^3$, the tumor-bearing mice are surgically castrated. The mice are stratified into treatment groups once the tumors grow back to the pre-castration size. The treatment groups are, for example: vehicle control, enzalutamide alone, test compound alone, and enzalutamide+test compound at 10 mice per group. The exact treatment groups, drug dose, and dosing schedule are determined according to the specific needs of the study. Tumor growth is monitored, and volume recorded at regular intervals. When the individual tumor of each mouse reaches an approximate endpoint (tumor volume>1,500 $mm^3$), the mouse is sacrificed. The tumor growth inhibition (TGI) is calculated by comparing the control group's tumor measurements with the other study groups once the predetermined endpoint is reached in the control group.

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention.

The invention claimed is:
1. A compound of Formula (I):

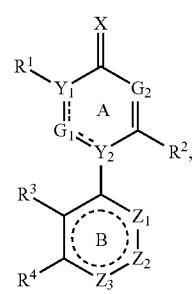

or a stereoisomer or tautomer thereof, or a pharmaceutically acceptable salt of any of the foregoing, wherein:

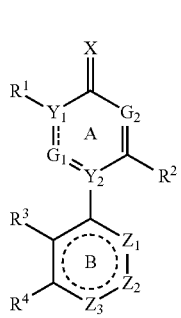 is 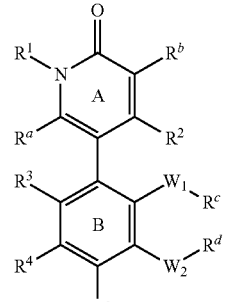 or

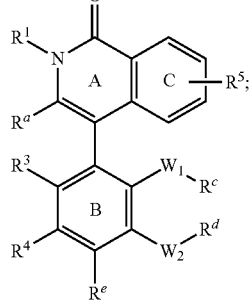

$R^a$ is hydrogen, halogen, or $C_1$-$C_4$ alkyl;

$R^b$ is hydrogen, halogen, cyano, $C_1$-$C_4$ alkyl, $C_1$-$C_4$ haloalkyl, C(O)NR$^{10}$R$^{11}$, NR$^{10}$R$^{11}$, NR$^{10}$C(O)R$^{11}$, NR$^{10}$S(O)$_2$R$^{11}$, OR$^{10}$, S(O)$_2$R$^{10}$, S(O)$_2$NR$^{10}$R$^{11}$, $C_3$-$C_6$ cycloalkyl, or 3- to 6-membered heterocyclyl;

$R^e$ is hydrogen, halogen, cyano, $C_1$-$C_4$ alkyl, or 3- to 6-membered heterocyclyl;

$R^1$ is hydrogen or $C_1$-$C_4$ alkyl, wherein the $C_1$-$C_4$ alkyl is optionally substituted by 1 or more OH substituents;

$R^2$ is hydrogen, halogen, cyano, $C_1$-$C_4$ alkyl, $C_1$-$C_4$ haloalkyl, C(O)NR$^{10}$R$^{11}$, NR$^{10}$R$^{11}$, NR$^{10}$C(O)R$^{11}$, NR$^{10}$S(O)$_2$R$^{11}$, OC$_1$-$C_4$ alkyl, OC$_1$-$C_4$ haloalkyl, S(O)$_2$R$^{10}$, S(O)$_2$NR$^{10}$R$^{11}$, $C_3$-$C_6$ cycloalkyl, or 3- to 6-membered heterocyclyl;

$R^3$ is hydrogen, halogen, cyano, $C_1$-$C_4$ alkyl, (CH$_2$)$_m$W$_3$R$^g$, (CH$_2$)$_m$N(R$^f$)C(O)OR$^h$, (CH$_2$)$_m$N(R$^f$)W$_3$R$^g$, C(O)NR$^{13}$R$^{14}$, NR$^{13}$R$^{14}$, NR$^{13}$C(O)R$^{14}$, NR$^{13}$C(O)NR$^{13}$R$^{14}$, NR$^{13}$S(O)$_2$R$^{14}$, NR$^{13}$S(O)$_2$NR$^{13}$R$^{14}$, OR$^{13}$, S(O)$_2$R$^1$, or S(O)$_2$NR$^{13}$R$^{14}$, wherein the $C_1$-$C_4$ alkyl is optionally substituted by 1 or more substituents independently selected from the group consisting of oxo, halogen, cyano, and OH;

$R^4$ is hydrogen, (CH$_2$)$_m$W$_3$R$^g$, or (CH$_2$)$_m$N(R$^f$)W$_3$R$^g$;

each W$_3$ is independently —C(O)— or —S(O)$_2$—;

each R$^f$ is independently hydrogen, $C_1$-$C_4$ alkyl, or $C_3$-$C_6$ cycloalkyl;

each R$^g$ is independently CR$^{g1}$=CHR$^{g2}$ or C≡CR$^{g2}$;

each R$^{g1}$ is independently hydrogen, cyano, or $C_1$-$C_4$ alkyl, wherein each $C_1$-$C_4$ alkyl is optionally and independently substituted by 1 or more substituents independently selected from the group consisting of NH$_2$, NHCH$_3$, N(CH$_3$)$_2$, OH, and OCH$_3$;

each R$^{g2}$ is independently hydrogen, cyano, or $C_1$-$C_4$ alkyl, wherein each $C_1$-$C_4$ alkyl is optionally and independently substituted by 1 or more substituents independently selected from the group consisting of NH$_2$, NHCH$_3$, N(CH$_3$)$_2$, OH, and OCH$_3$;

each R$^h$ is independently $C_1$-$C_6$ alkyl or $C_3$-$C_6$ cycloalkyl;

each R$^5$ is independently hydrogen, halogen, cyano, $C_1$-$C_4$ alkyl, C(O)NR$^{10}$R$^{11}$, C(O)OR$^{10}$, NR$^{10}$R$^{11}$, NR$^{10}$C(O)R$^{11}$, NR$^{10}$S(O)$_2$R$^{11}$, OR$^{10}$, S(O)$_2$R$^{10}$, S(O)$_2$NR$^{10}$R$^{11}$, $C_3$-$C_6$ cycloalkyl, 3- to 6-membered heterocyclyl, $C_6$-$C_{14}$ aryl, or 5- to 10-membered heteroaryl, wherein each $C_1$-$C_4$ alkyl, $C_1$-$C_4$ haloalkyl, C(O)NR$^{10}$R$^{11}$, C(O)OR$^{10}$, NR$^{10}$R$^{11}$, NR$^{10}$C(O)R$^{11}$, NR$^{10}$S(O)$_2$R$^{11}$, OR$^{10}$, S(O)$_2$R$^{10}$, S(O)$_2$NR$^{10}$R$^{11}$, $C_3$-$C_6$ cycloalkyl, 3- to 6-membered heterocyclyl, $C_6$-$C_{14}$ aryl, and 5- to 10-membered heteroaryl is optionally and independently substituted by 1 or more independently selected R$^{12}$ substituents;

W$_1$ is a bond, —NR$^{w1}$—, or —O—;

R$^{w1}$ is hydrogen, $C_1$-$C_4$ alkyl, or $C_3$-$C_6$ cycloalkyl, wherein the $C_1$-$C_4$ alkyl is optionally substituted by 1 or more substituents independently selected from the group consisting of halogen, oxo, and OH;

R$^c$ is hydrogen, halogen, cyano, $C_1$-$C_4$ alkyl, $C_1$-$C_4$ haloalkyl, $C_3$-$C_6$ cycloalkyl, 3- to 6-membered heterocyclyl, $C_6$-$C_{14}$ aryl, or 5- or 6-membered heteroaryl, wherein the $C_3$-$C_6$ cycloalkyl, 3- to 6-membered heterocyclyl, $C_6$-$C_{14}$ aryl, or 5- or 6-membered heteroaryl is optionally substituted by 1 or more independently selected R$^{c1}$ substituents;

each R$^{c1}$ is independently oxo, halogen, cyano, $C_1$-$C_4$ alkyl, $C_1$-$C_4$ haloalkyl, C(O)NR$^{10}$R$^{11}$, NR$^{10}$R$^{11}$, NR$^{10}$C(O)R$^{11}$, NR$^{10}$S(O)$_2$R$^{11}$, OR$^{10}$, S(O)$_2$R$^{10}$, S(O)$_2$NR$^{10}$R$^{11}$, $C_3$-$C_6$ cycloalkyl, or 3- to 6-membered heterocyclyl;

W$_2$ is a bond;

R$^d$ is hydrogen, $C_1$-$C_4$ alkyl, or 3- to 6-membered heterocyclyl;

each R$^{10}$ is independently hydrogen, $C_1$-$C_4$ alkyl, $C_1$-$C_3$ alkylene-$C_3$-$C_6$ cycloalkyl, $C_1$-$C_3$ alkylene-3- to 6-membered heterocyclyl, $C_2$-$C_4$ alkenyl, C(O)R$^{12}$, $C_3$-$C_6$ cycloalkyl, or 3- to 6-membered heterocyclyl, wherein each $C_1$-$C_4$ alkyl is optionally and independently substituted by 1 or more substituents independently selected from the group consisting of oxo, halogen, cyano, C(O)NR$^{13}$R$^{14}$, NR$^{13}$R$^{14}$, and OH;

each R$^{11}$ is independently hydrogen, $C_1$-$C_4$ alkyl, $C_1$-$C_3$ alkylene-$C_3$-$C_6$ cycloalkyl, $C_1$-$C_3$ alkylene-3- to 6-membered heterocyclyl, $C_2$-$C_4$ alkenyl, C(O)R$^{12}$, $C_3$-$C_6$ cycloalkyl, or 3- to 6-membered heterocyclyl, wherein each $C_1$-$C_4$ alkyl is optionally and independently substituted by 1 or more substituents independently selected from the group consisting of oxo, halogen, cyano, C(O)NR$^{13}$R$^{14}$, NR$^{13}$R$^{14}$, and OH; or each R$^{10}$ and R$^{11}$, taken together with the atoms to which they are attached, form a 3- to 6-membered heterocyclyl, wherein each 3- to 6-membered heterocyclyl is optionally and independently substituted by 1 or more substituents independently selected from the group consisting of oxo, halogen, cyano, $C_1$-$C_4$ alkyl, and OH, and further wherein each $C_1$-$C_4$ alkyl substituent is optionally and independently substituted by 1 or more substituents independently selected from the group consisting of oxo, halogen, cyano, and OH;

each R$^{12}$ is independently halogen, $C_1$-$C_4$ alkyl, $C_3$-$C_6$ cycloalkyl, or 3- to 6-membered heterocyclyl, wherein each $C_1$-$C_4$ alkyl is optionally and independently substituted by 1 or more substituents independently selected from the group consisting of oxo, halogen, cyano, $NR^{13}R^{14}$, $NR^{13}C(O)R^{14}$, and OH;

each $R^{13}$ is independently hydrogen, $C_1$-$C_4$ alkyl, $C_3$-$C_6$ cycloalkyl, or 3- to 6-membered heterocyclyl, wherein each $C_1$-$C_4$ alkyl is optionally and independently substituted by 1 or more substituents independently selected from the group consisting of oxo, halogen, cyano, and OH;

each $R^{14}$ is independently hydrogen, $C_1$-$C_4$ alkyl, $C_3$-$C_6$ cycloalkyl, or 3- to 6-membered heterocyclyl, wherein each $C_1$-$C_4$ alkyl is optionally and independently substituted by 1 or more substituents independently selected from the group consisting of oxo, halogen, cyano, and OH; or each $R^{13}$ and $R^{14}$, taken together with the atoms to which they are attached, form a 3- to 6-membered heterocyclyl, wherein each 3- to 6-membered heterocyclyl is optionally and independently substituted by 1 or more substituents independently selected from the group consisting of oxo, halogen, cyano, $C_1$-$C_4$ alkyl, and OH, and further wherein each $C_1$-$C_4$ alkyl substituent is optionally and independently substituted by 1 or more substituents independently selected from the group consisting of oxo, halogen, cyano, and OH; and each m is independently 0, 1, 2, 3, or 4;

with the proviso that at least one of $R^3$ and $R^4$ is $(CH_2)_m W_3 R^9$ or $(CH_2)_m N(R^f) W_3 R^g$.

2. The compound of claim 1, wherein the compound is of Formula (II):

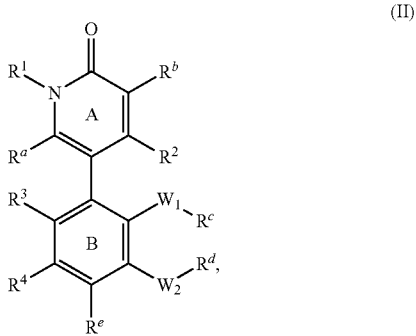

or a stereoisomer or tautomer thereof, or a pharmaceutically acceptable salt of any of the foregoing.

3. The compound of claim 1, wherein the compound is of Formula (V):

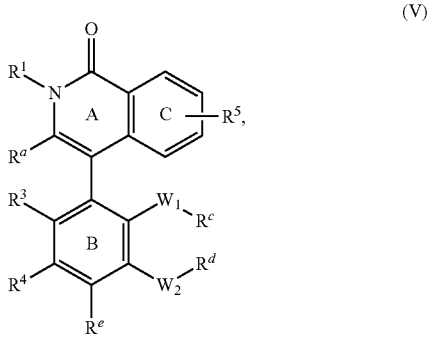

or a stereoisomer or tautomer thereof, or a pharmaceutically acceptable salt of any of the foregoing.

4. The compound of claim 3, or a stereoisomer or tautomer thereof, or a pharmaceutically acceptable salt of any of the foregoing, wherein each $R^5$ is independently hydrogen.

5. The compound of claim 1, or a stereoisomer or tautomer thereof, or a pharmaceutically acceptable salt of any of the foregoing, wherein $R^a$ is hydrogen.

6. The compound of claim 1, or a stereoisomer or tautomer thereof, or a pharmaceutically acceptable salt of any of the foregoing, wherein $R^b$ is hydrogen, $C(O)NR^{10}R^{11}$, $NR^{10}R^{11}$, or $NR^{10}VC(O)R^{11}$.

7. The compound of claim 1, or a stereoisomer or tautomer thereof, or a pharmaceutically acceptable salt of any of the foregoing, wherein $R^b$ is $NR^{10}R^{11}$.

8. The compound of claim 1, or a stereoisomer or tautomer thereof, or a pharmaceutically acceptable salt of any of the foregoing, wherein $R^e$ is hydrogen.

9. The compound of claim 1, or a stereoisomer or tautomer thereof, or a pharmaceutically acceptable salt of any of the foregoing, wherein $R^1$ is hydrogen or $C_1$-$C_4$ alkyl.

10. The compound of claim 1, or a stereoisomer or tautomer thereof, or a pharmaceutically acceptable salt of any of the foregoing, wherein $R^1$ is $C_1$-$C_4$ alkyl.

11. The compound of claim 1, or a stereoisomer or tautomer thereof, or a pharmaceutically acceptable salt of any of the foregoing, wherein $R^2$ is hydrogen, halogen, cyano, $C_1$-$C_4$ alkyl, $C_1$-$C_4$ haloalkyl, $OC_1$-$C_4$ alkyl, or $OC_1$-$C_4$ haloalkyl.

12. The compound of claim 1, or a stereoisomer or tautomer thereof, or a pharmaceutically acceptable salt of any of the foregoing, wherein $R^3$ is hydrogen, $(CH_2)_m W_3 R^9$, or $(CH_2)_m N(R^f) W_3 R^g$.

13. The compound of claim 1, or a stereoisomer or tautomer thereof, or a pharmaceutically acceptable salt of any of the foregoing, wherein $R^3$ is hydrogen.

14. The compound of claim 1, or a stereoisomer or tautomer thereof, or a pharmaceutically acceptable salt of any of the foregoing, wherein $R^4$ is $(CH_2)_m W_3 R^g$ or $(CH_2)_m N(R^f) W_3 R^g$.

15. The compound of claim 1, or a stereoisomer or tautomer thereof, or a pharmaceutically acceptable salt of any of the foregoing, wherein $R^4$ is $(CH_2)_m N(R^f) W_3 R^g$.

16. The compound of claim 1, or a stereoisomer or tautomer thereof, or a pharmaceutically acceptable salt of any of the foregoing, wherein $W_1$ is —O—.

17. The compound of claim 16, or a stereoisomer or tautomer thereof, or a pharmaceutically acceptable salt of any of the foregoing, wherein $R^c$ is phenyl, wherein the phenyl is optionally substituted by 1 or more independently selected $R^{c1}$ substituents.

18. The compound of claim 1, or a stereoisomer or tautomer thereof, or a pharmaceutically acceptable salt of any of the foregoing, wherein $R^d$ is hydrogen.

19. The compound of claim 1, wherein the compound is selected from the group consisting of:

481
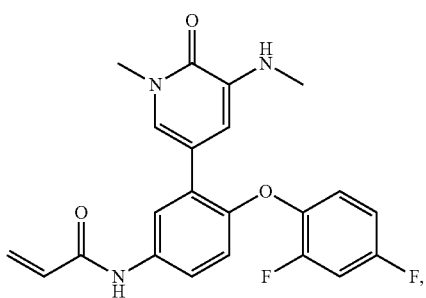
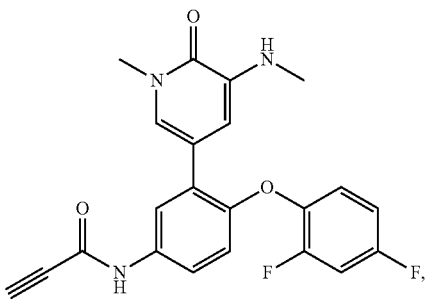
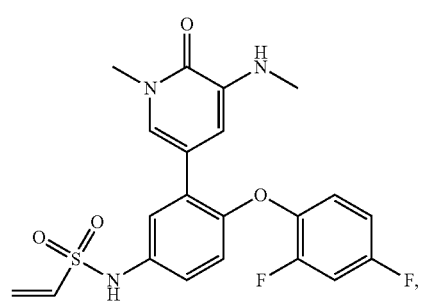
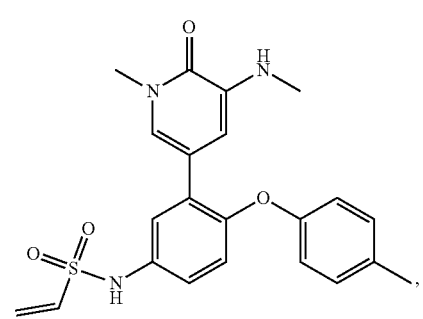
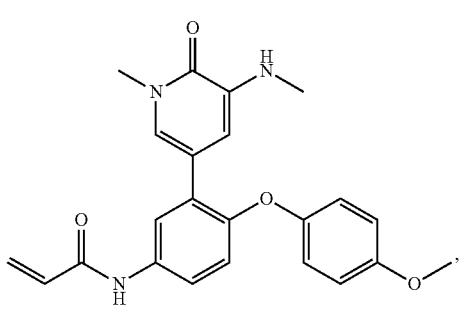
482
-continued
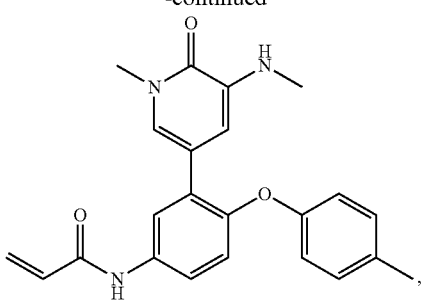
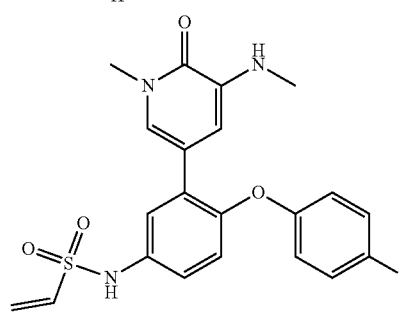
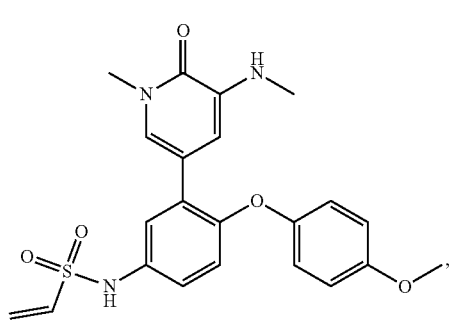
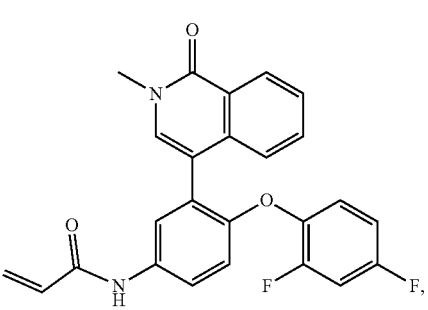
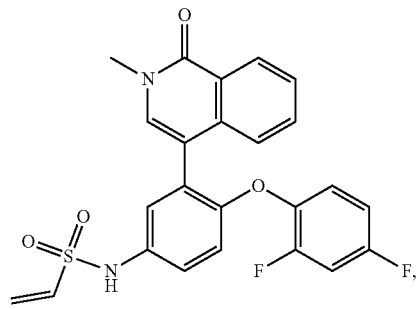

483
-continued
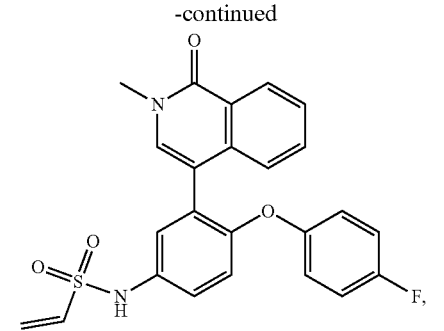
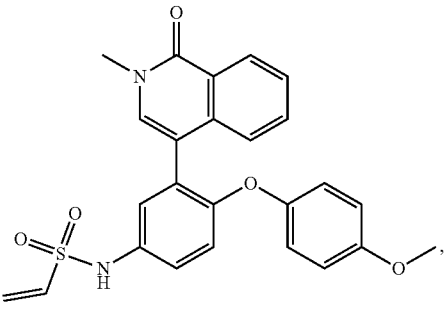
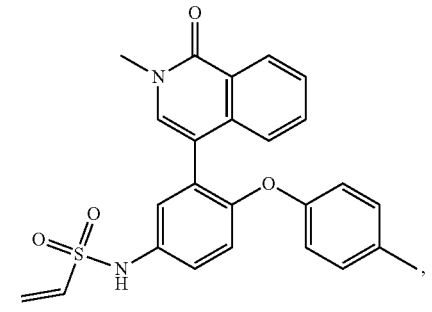
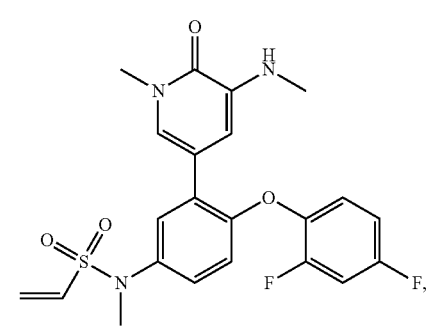
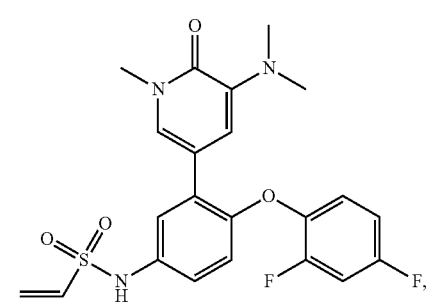
484
-continued
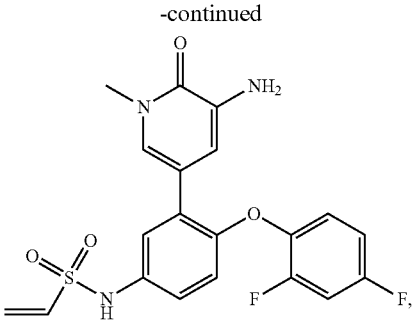
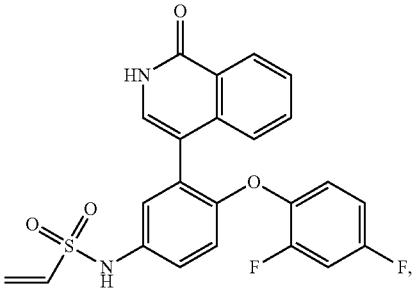
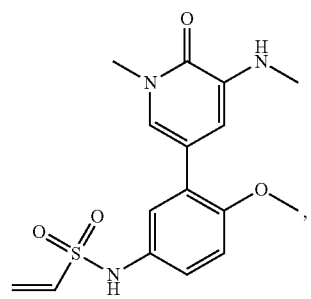
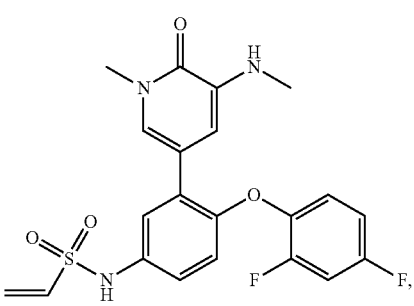
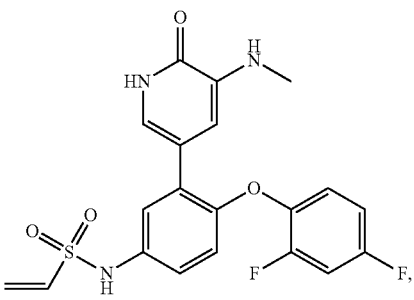

485
-continued

486
-continued

487
-continued
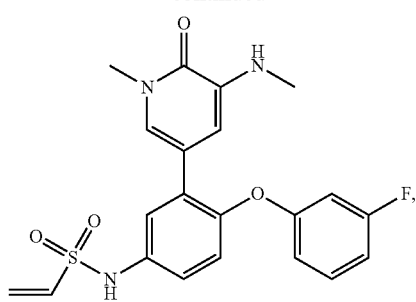
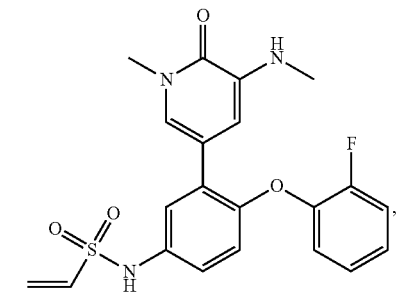
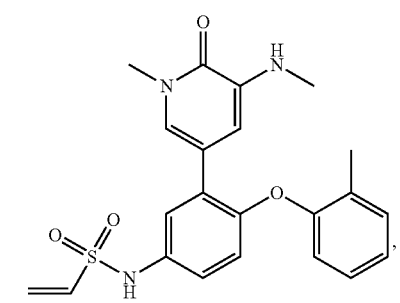
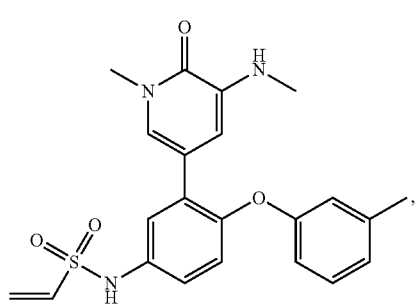
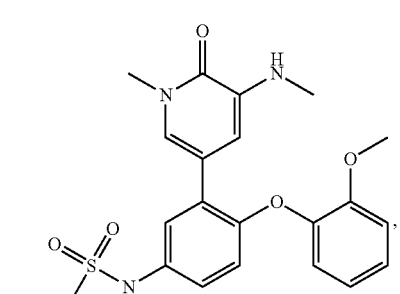
488
-continued
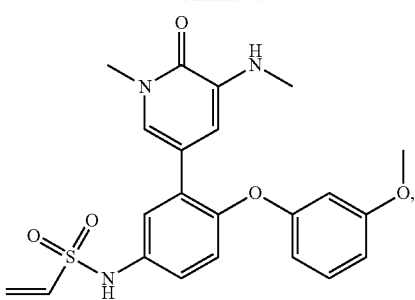
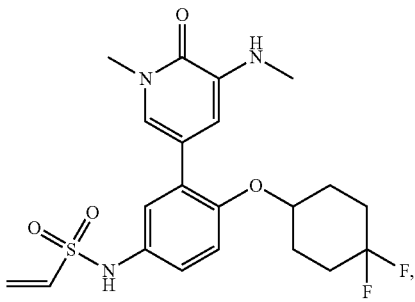
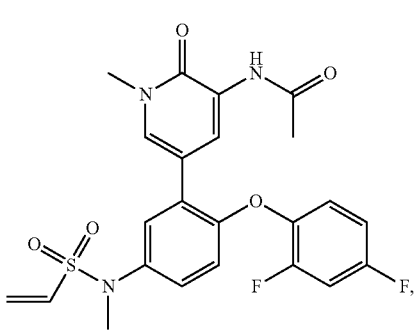
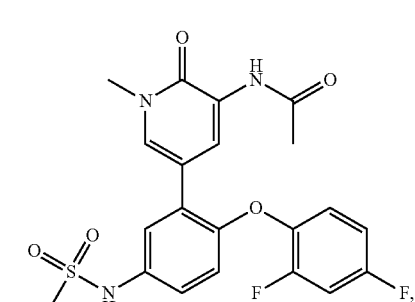
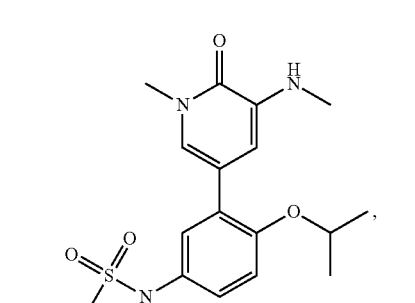

489
-continued
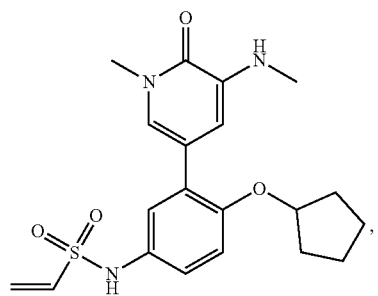
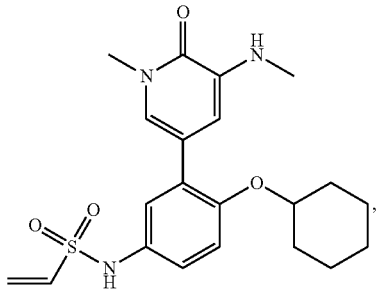
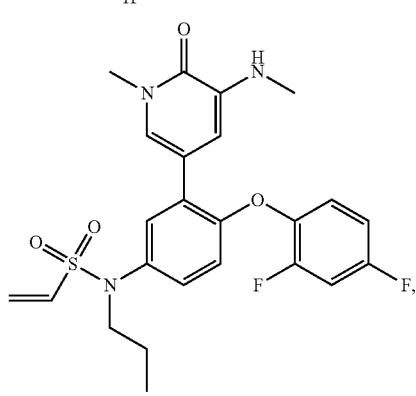
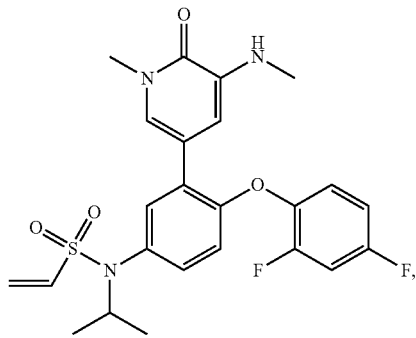
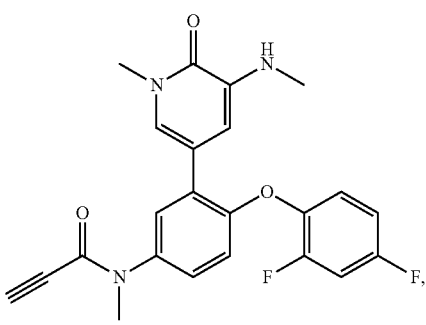
490
-continued
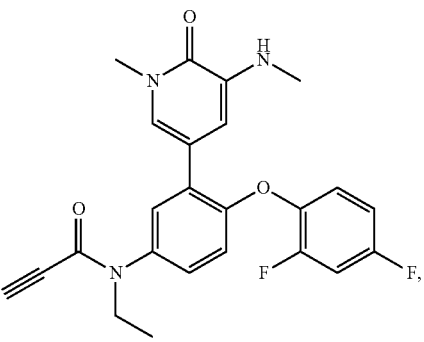
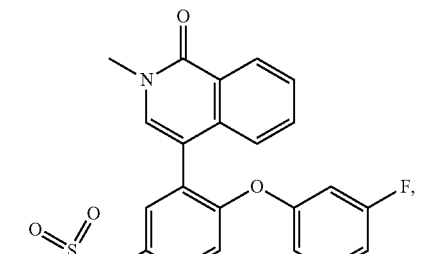
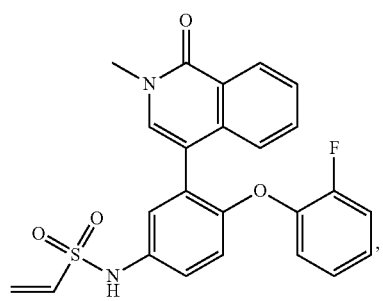
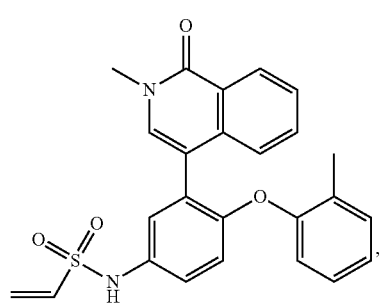
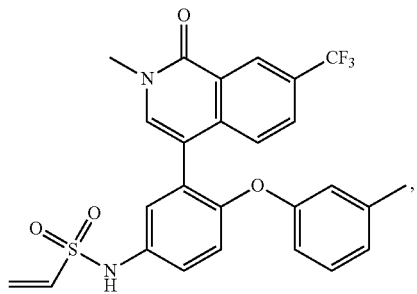

491
-continued
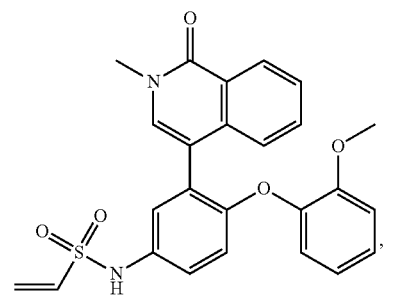
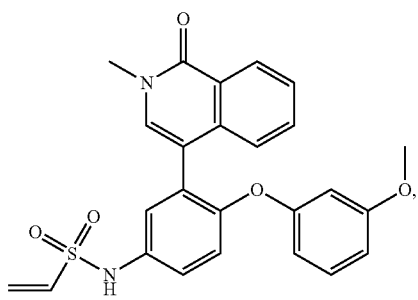
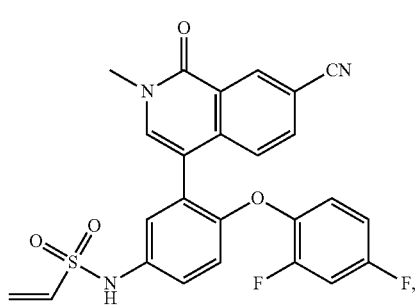
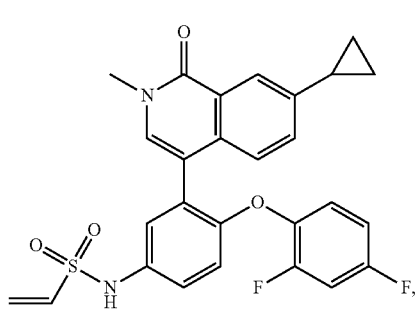
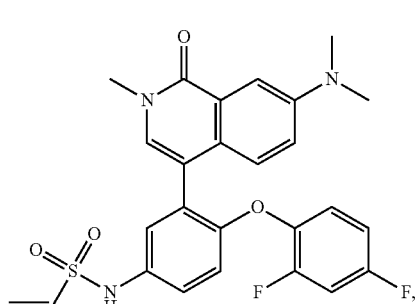
492
-continued
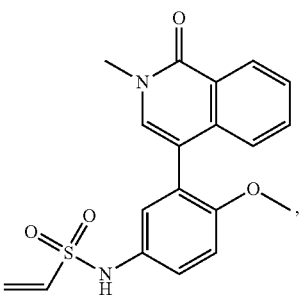
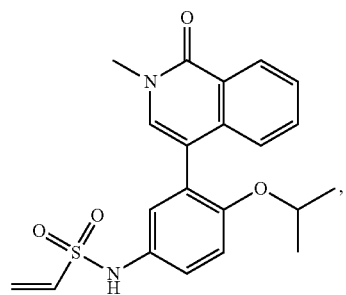
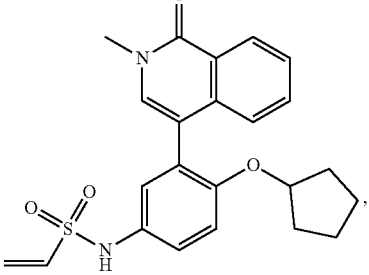
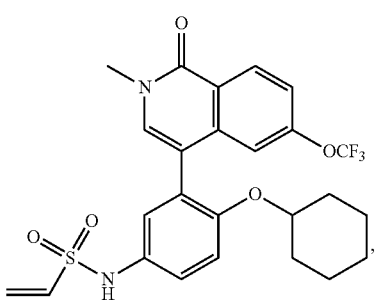
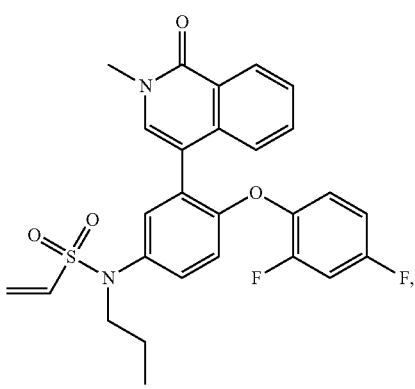

493
-continued
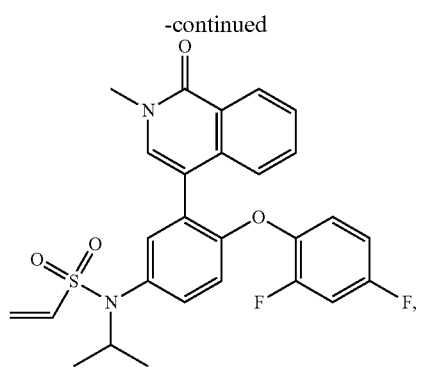
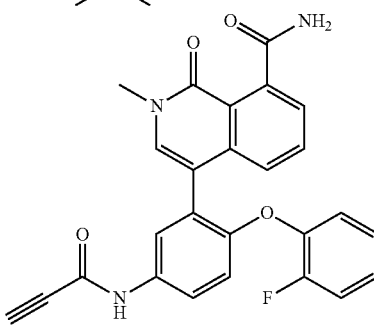
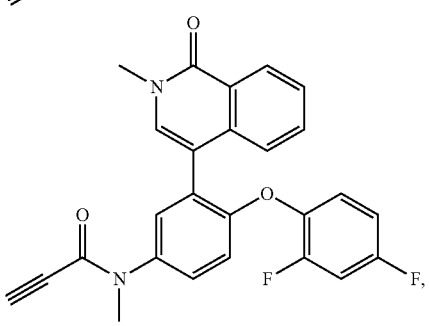
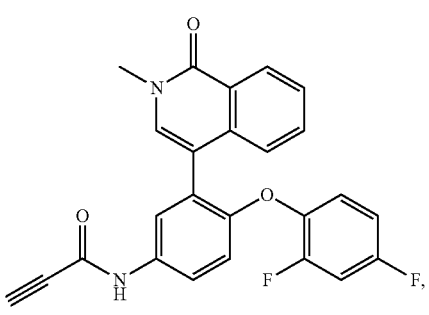
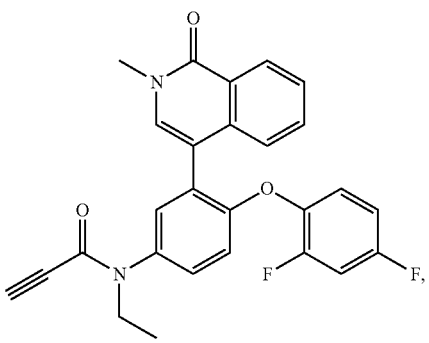
494
-continued
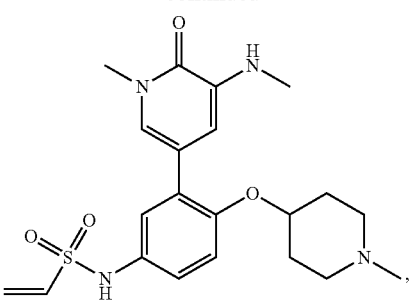
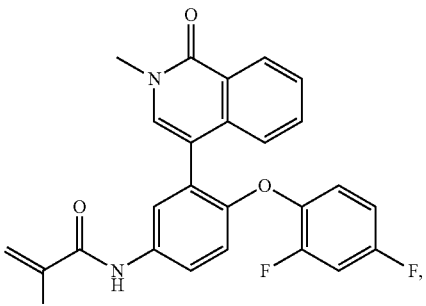
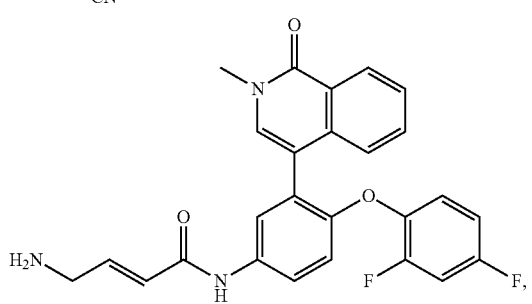
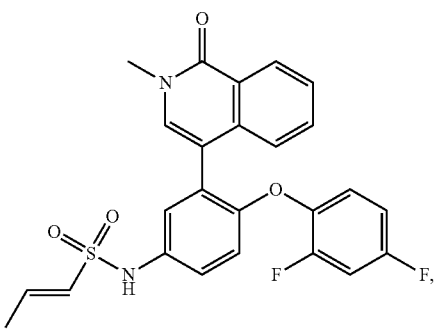
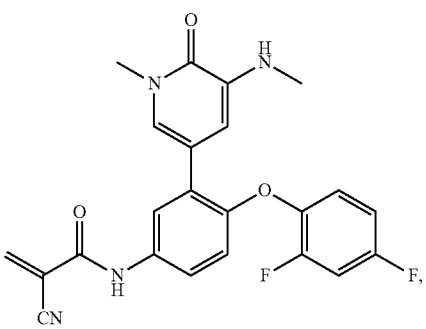

495
-continued
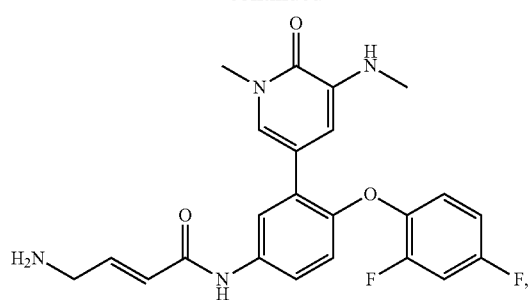
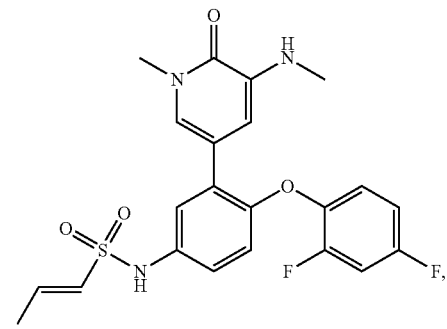
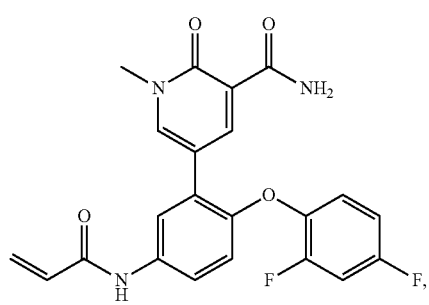
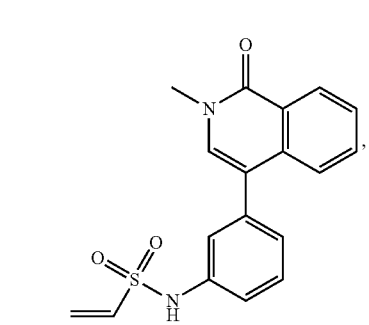
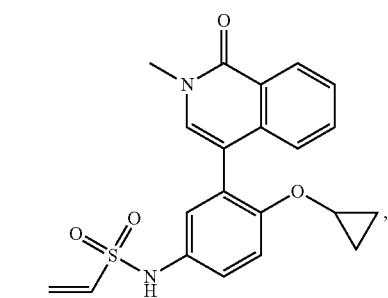
496
-continued
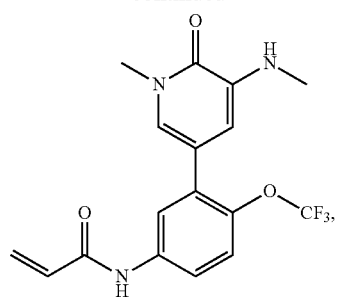
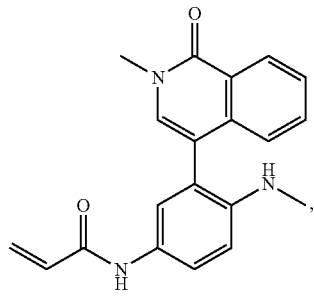
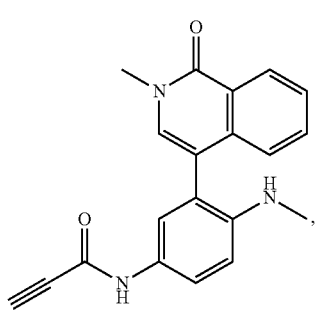
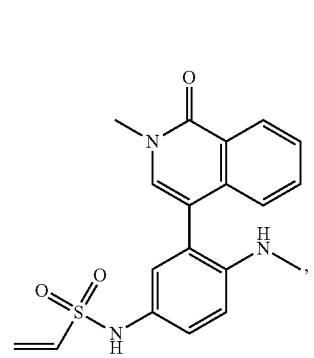
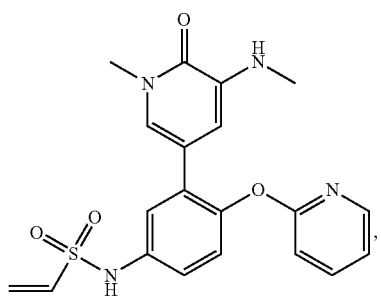

497
-continued
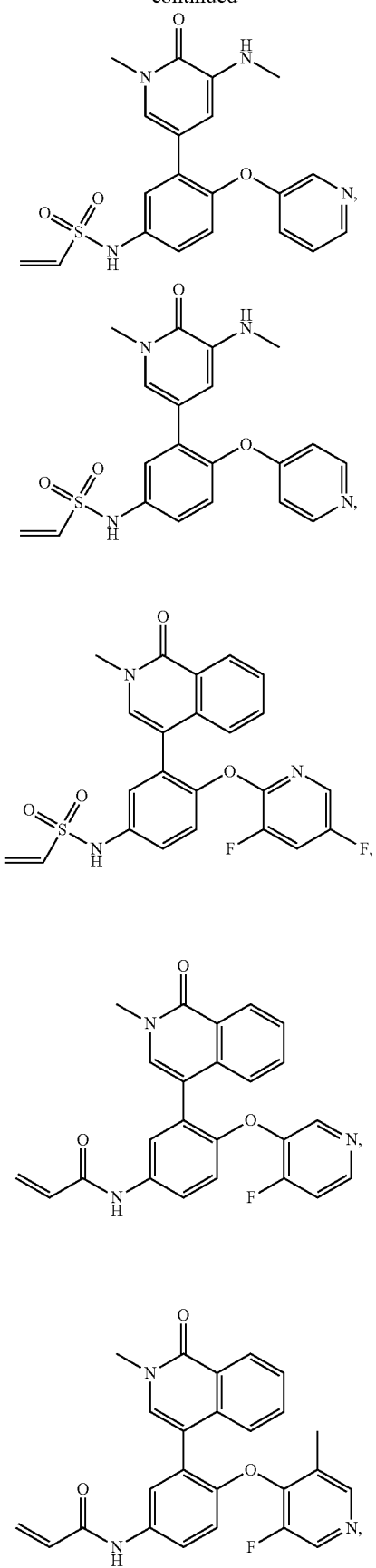
498
-continued
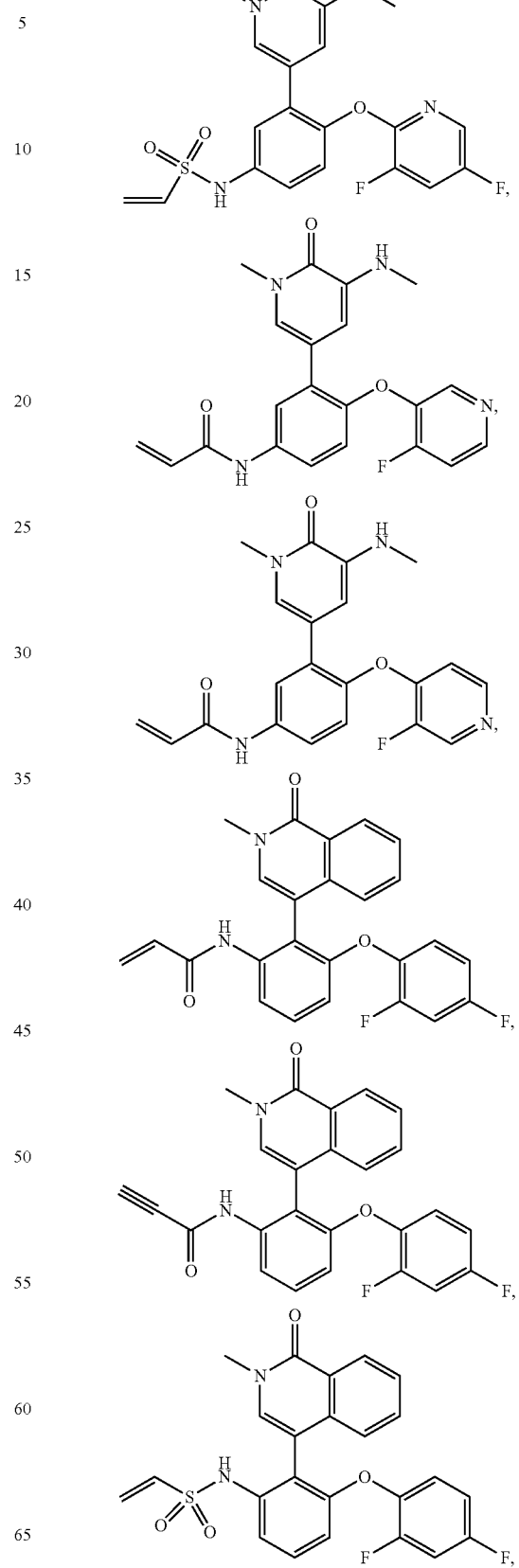

499
-continued
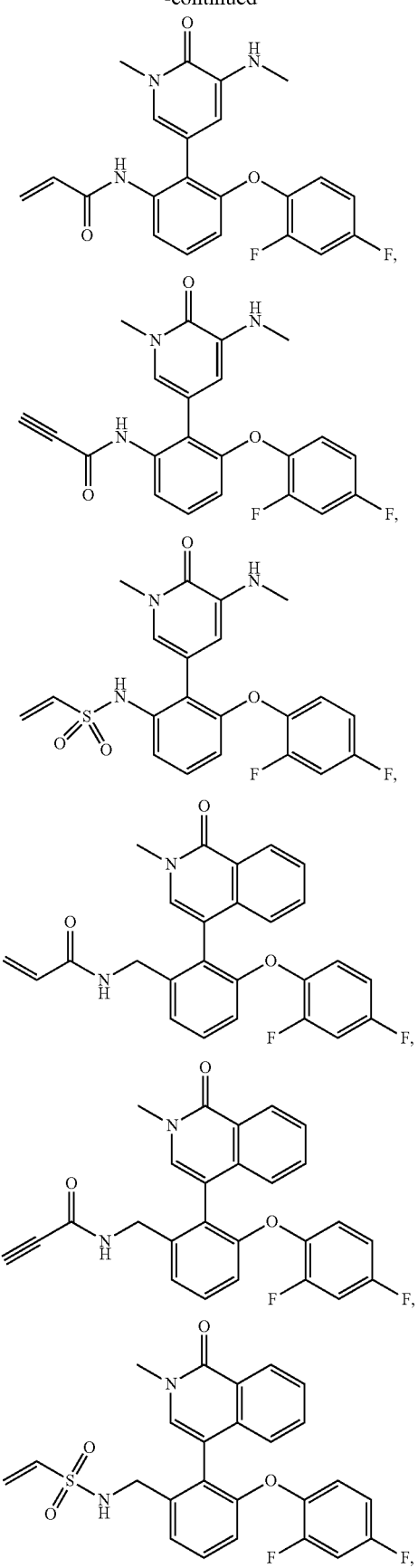
500
-continued
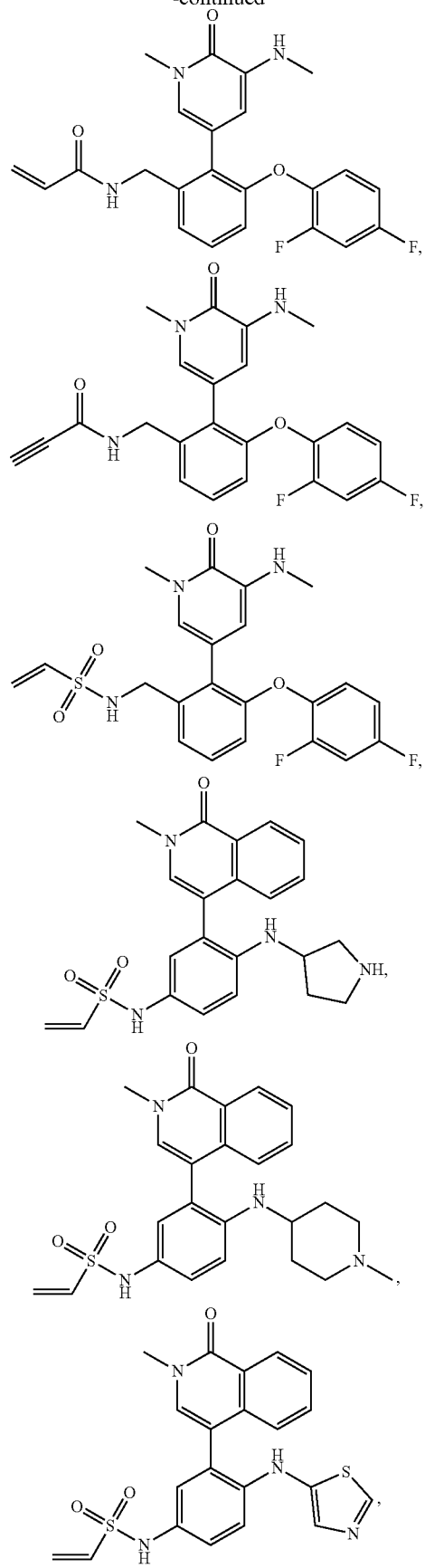

501
-continued
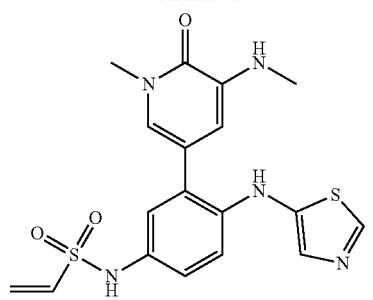
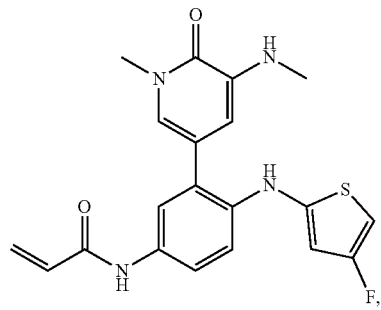
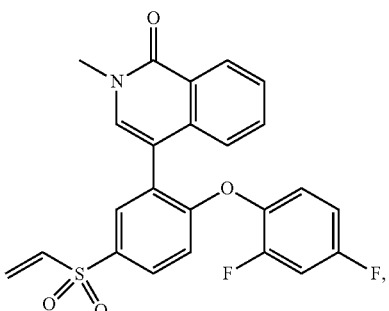
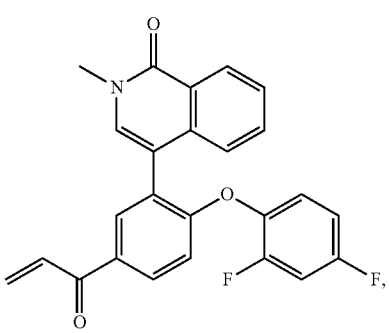
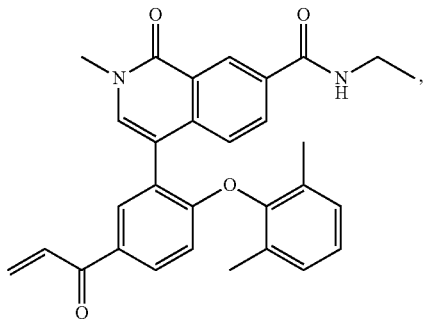
502
-continued
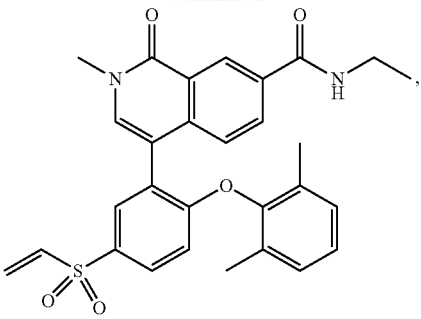
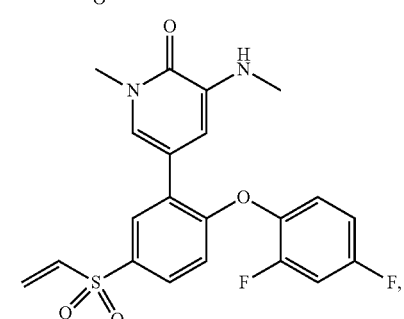
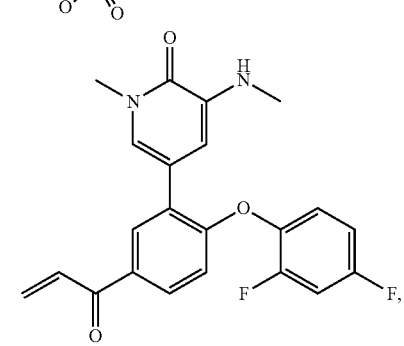
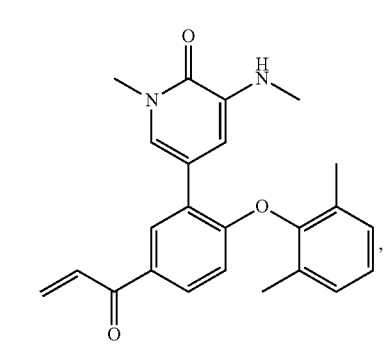
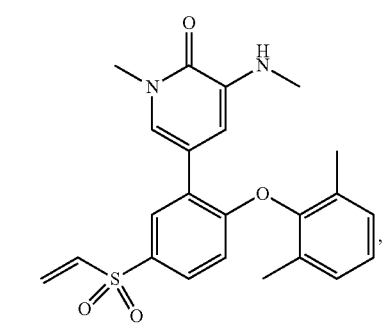

503
-continued
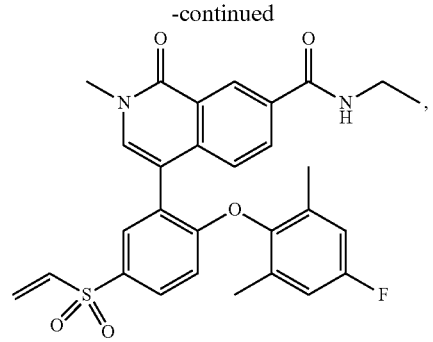
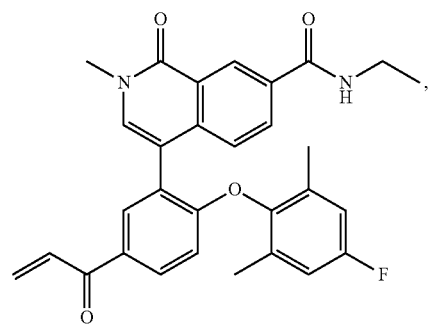
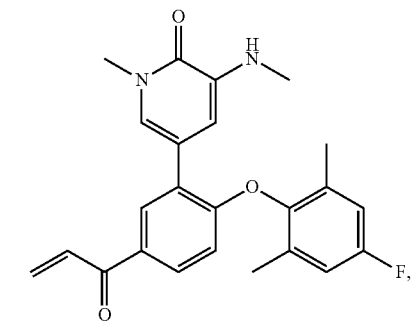
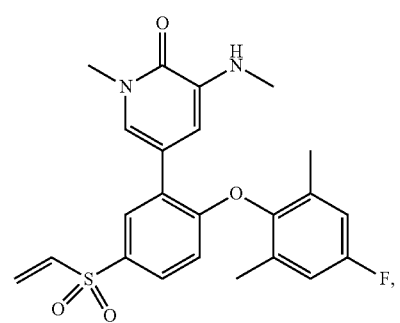
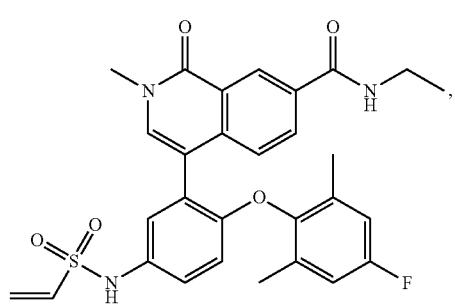
504
-continued
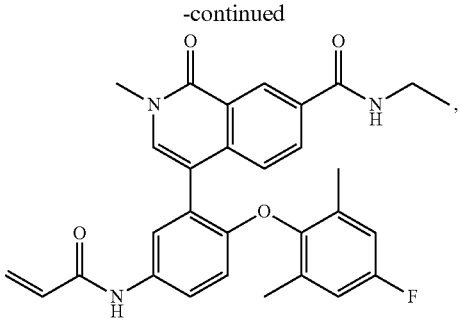
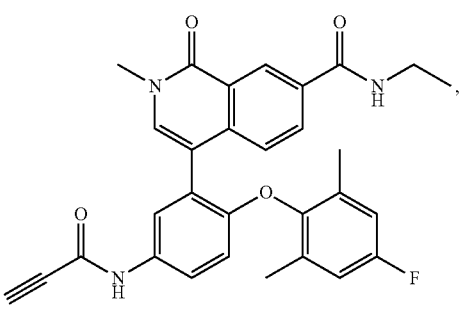
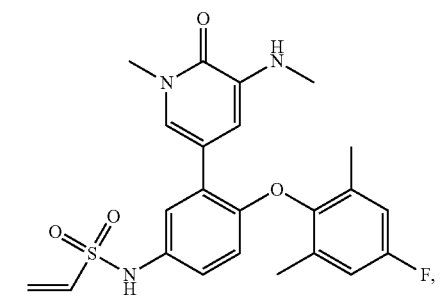
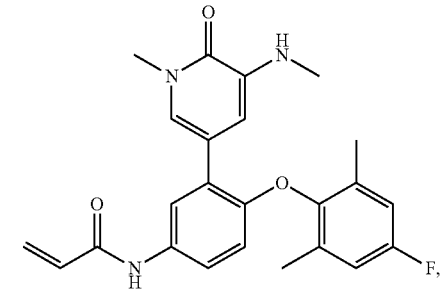
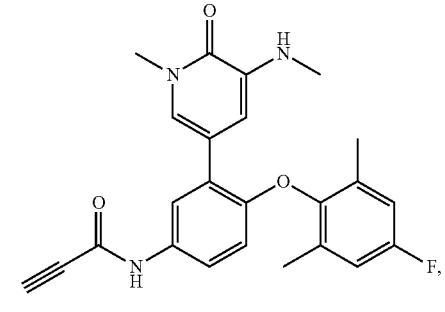

505
-continued
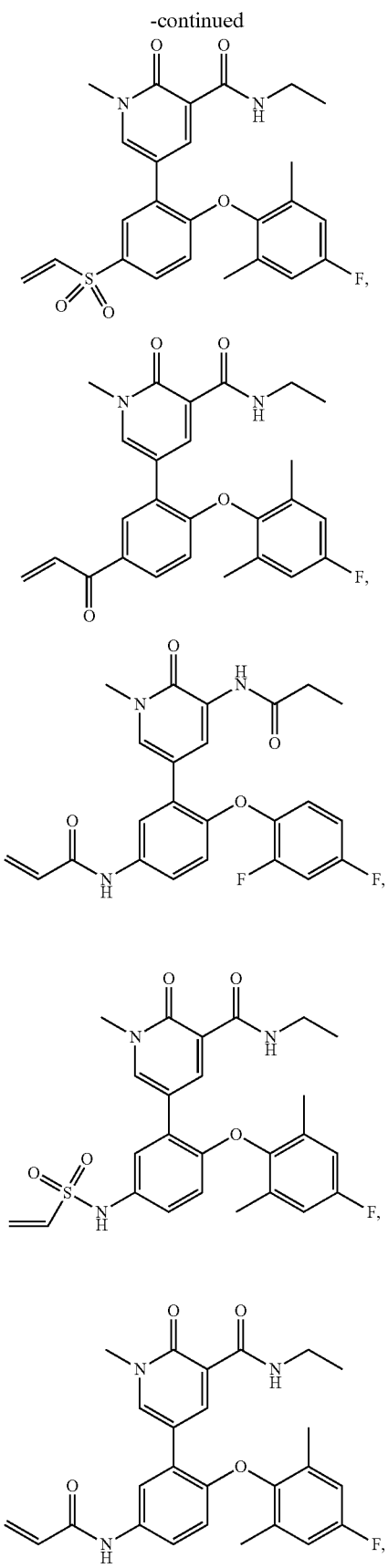
506
-continued
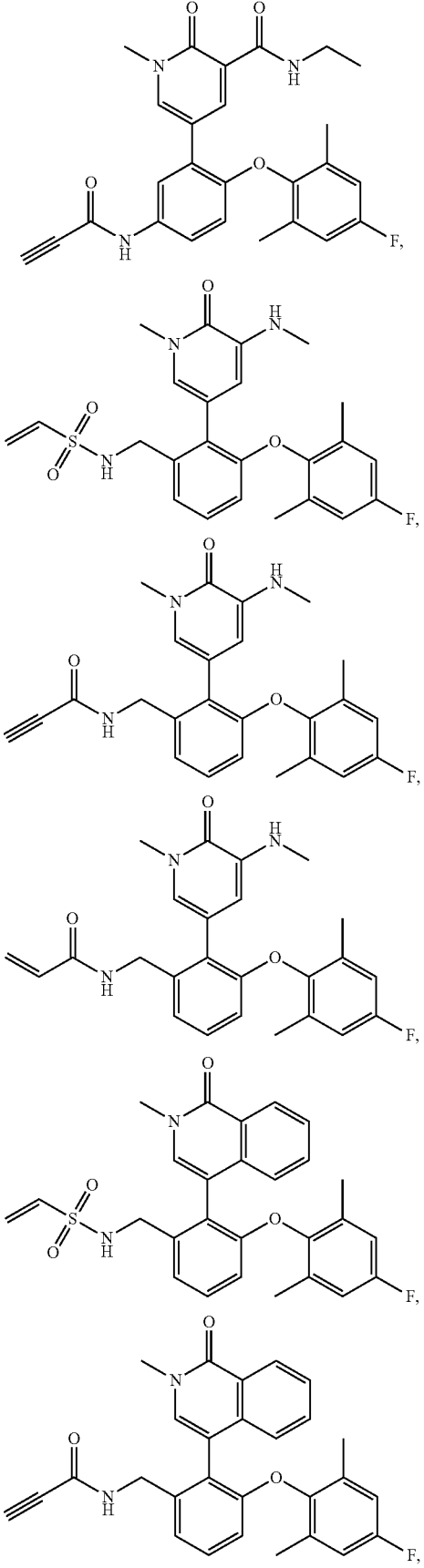

507
-continued
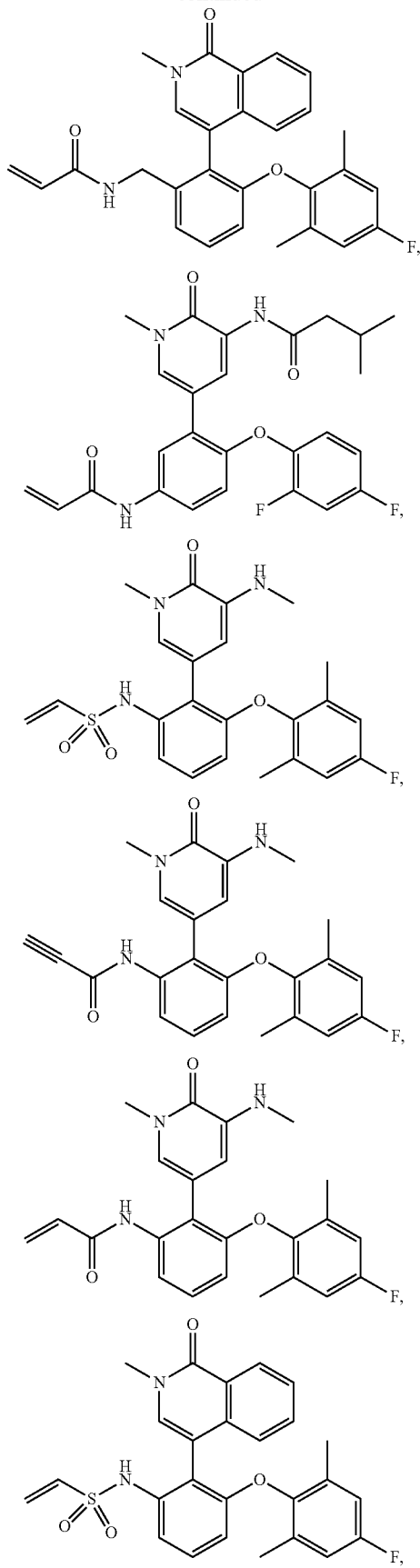
508
-continued
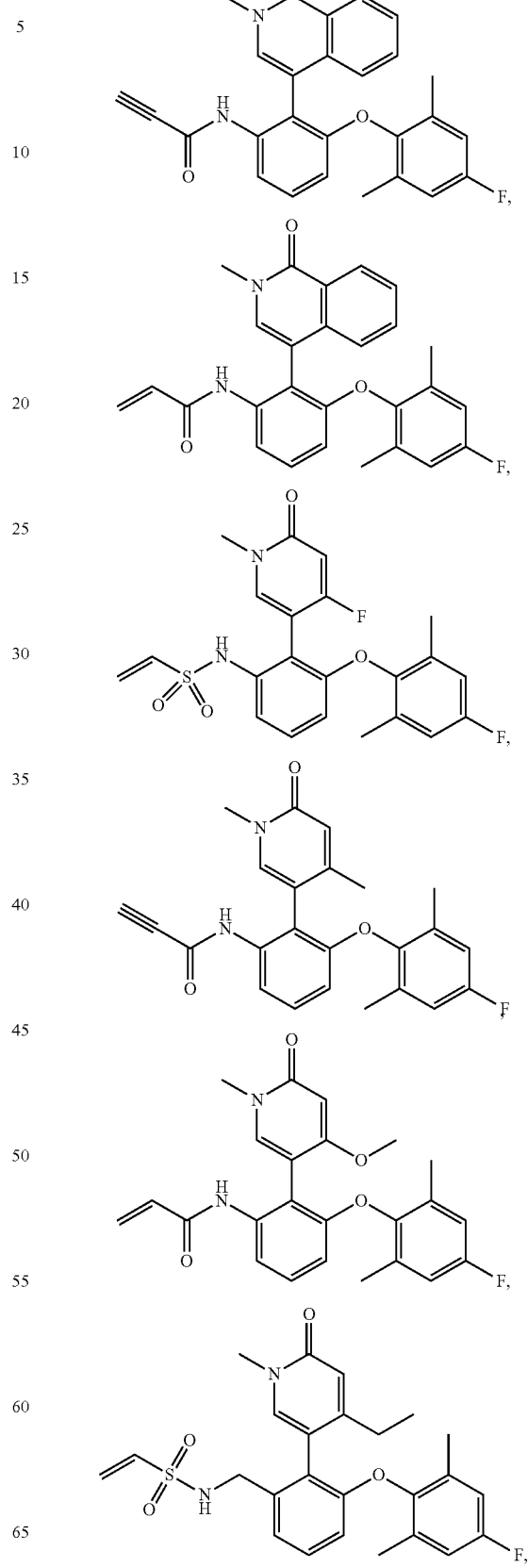

509
-continued
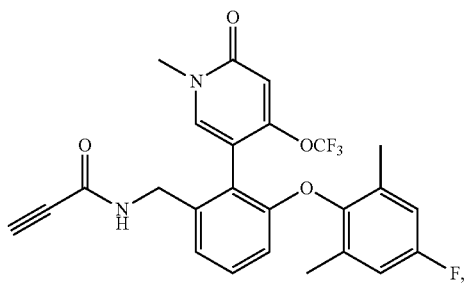
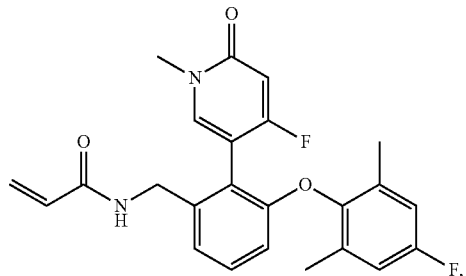
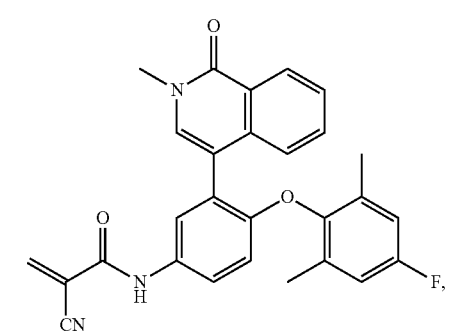
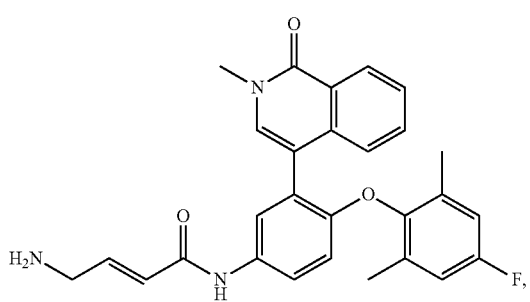
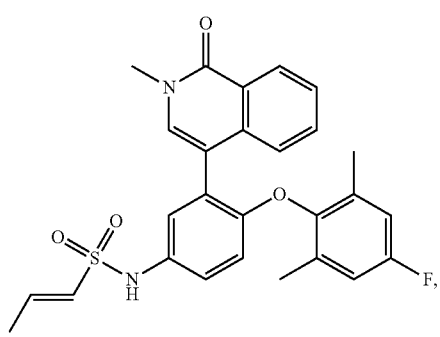
510
-continued
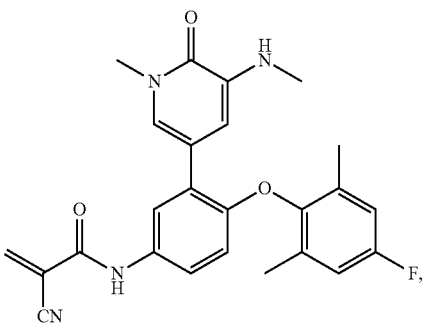
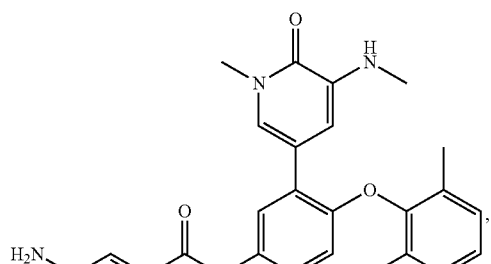
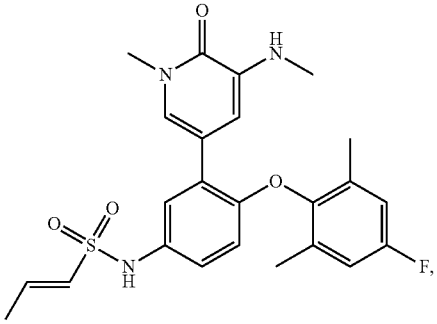
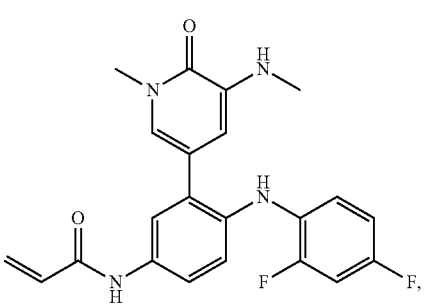
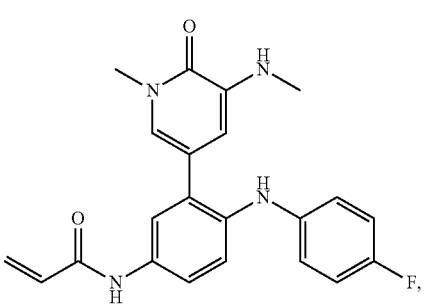

511
-continued
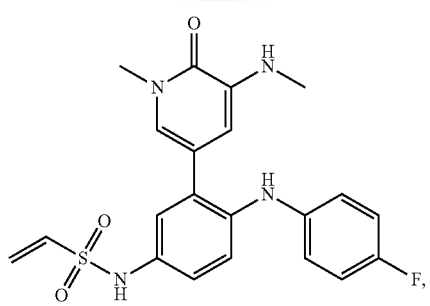
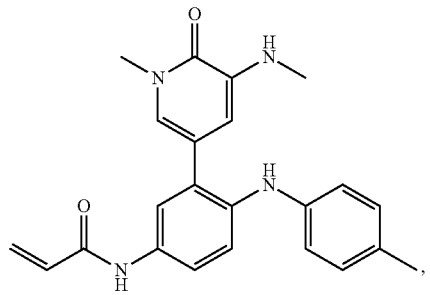
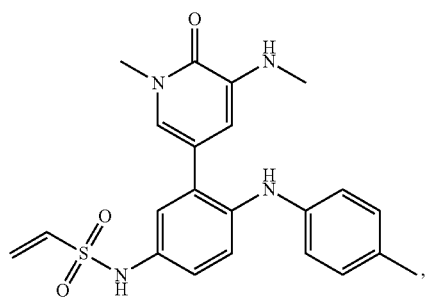
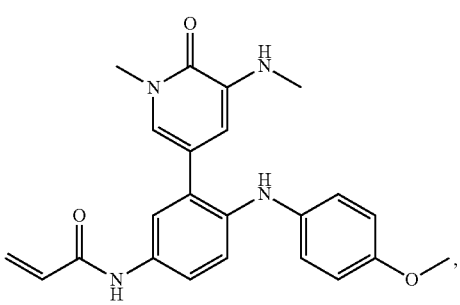
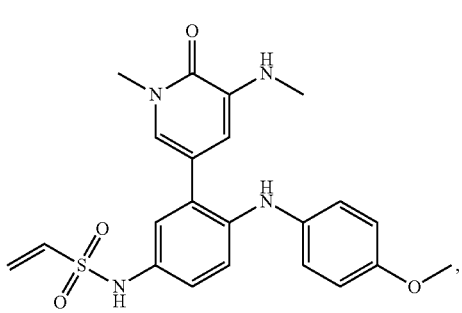
512
-continued
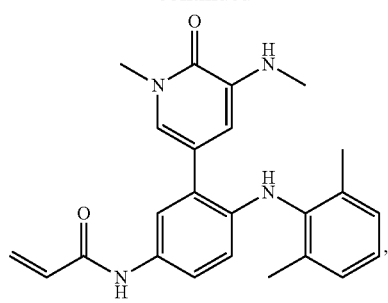
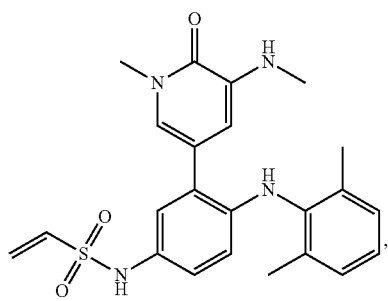
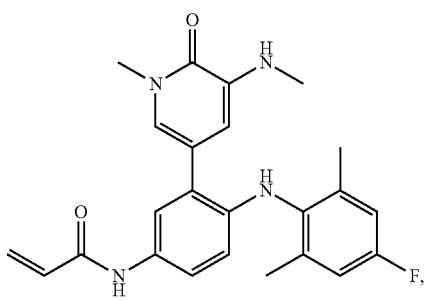
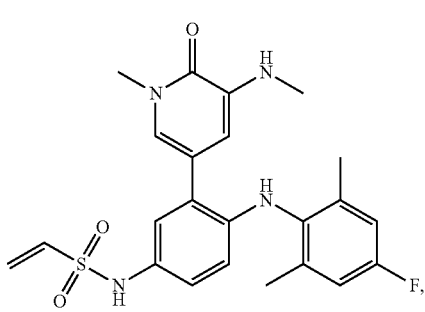
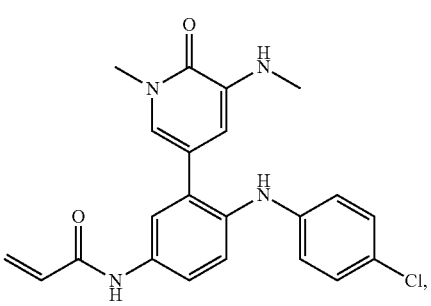

513
-continued
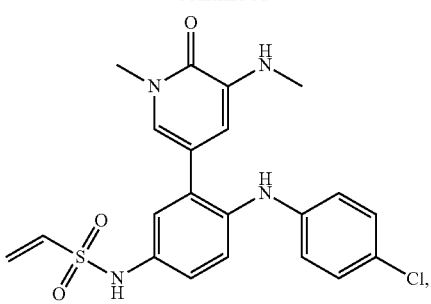
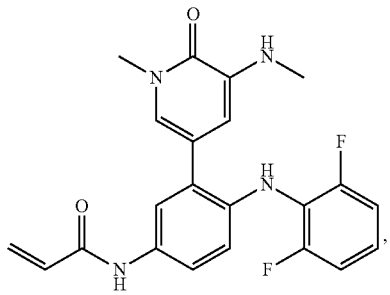
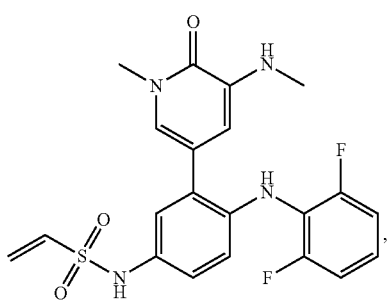
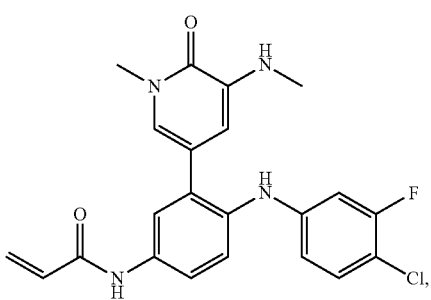
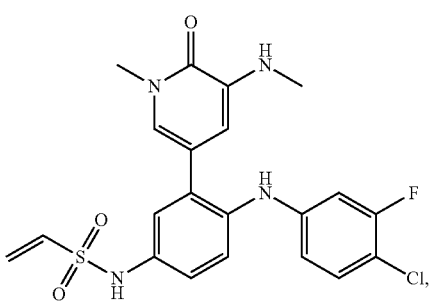
514
-continued
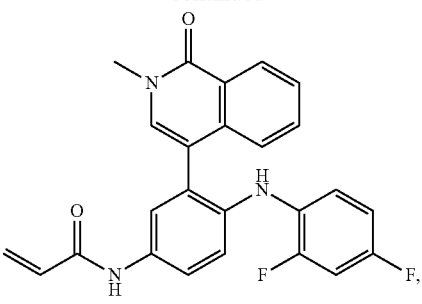
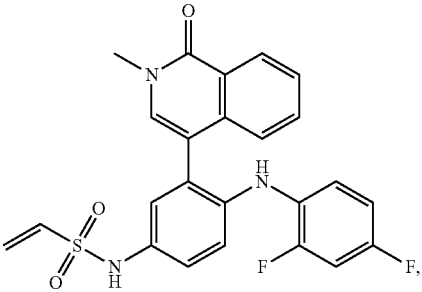
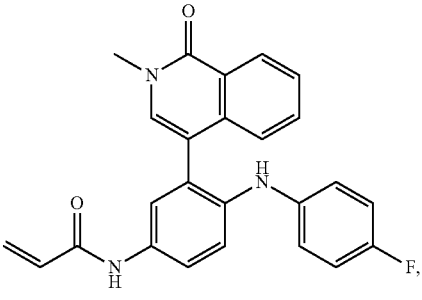
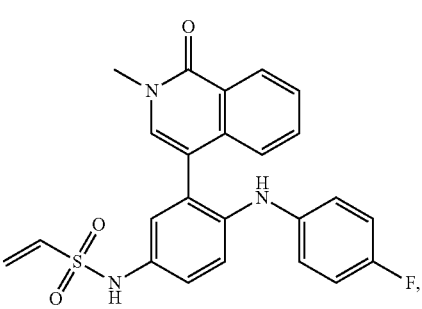
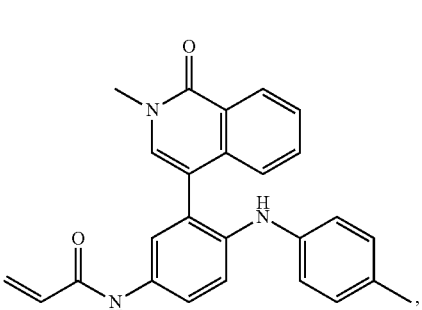

515
-continued
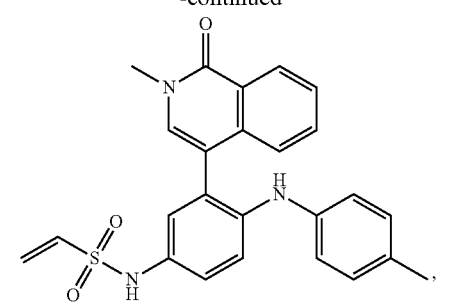
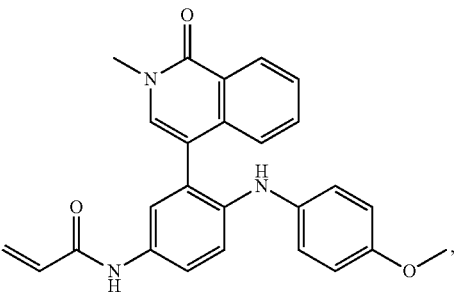
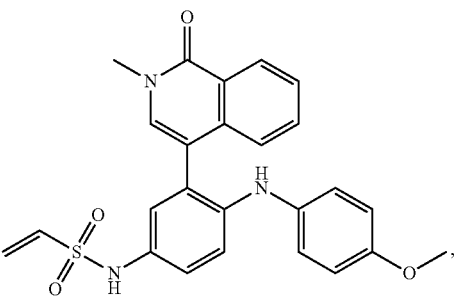
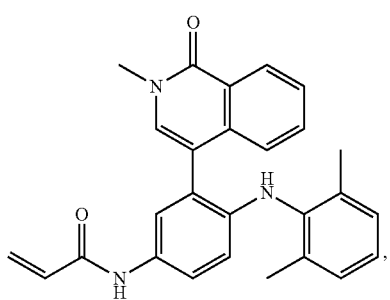
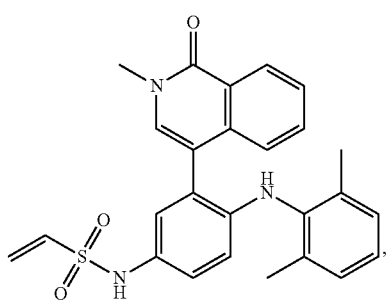
516
-continued
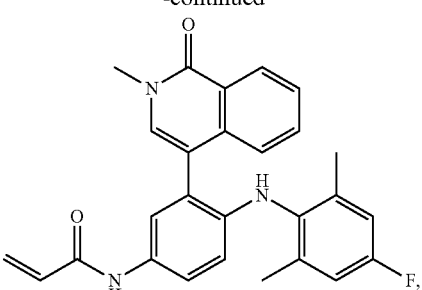
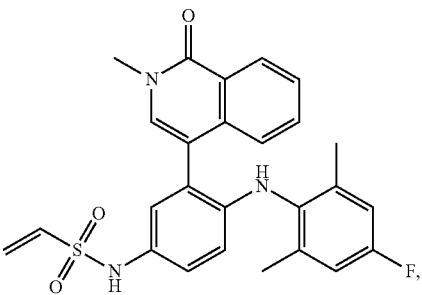
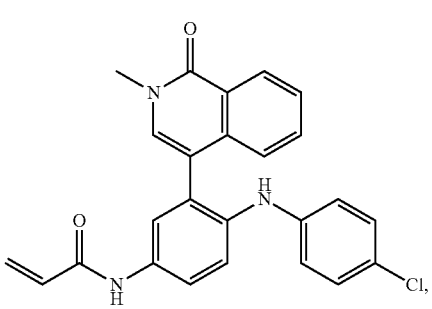
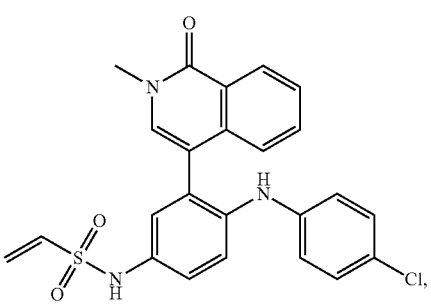
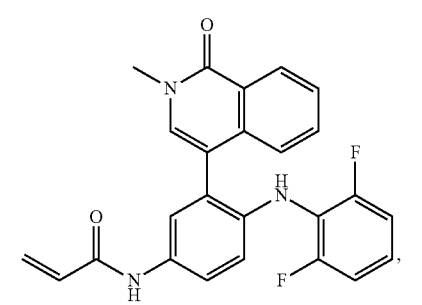

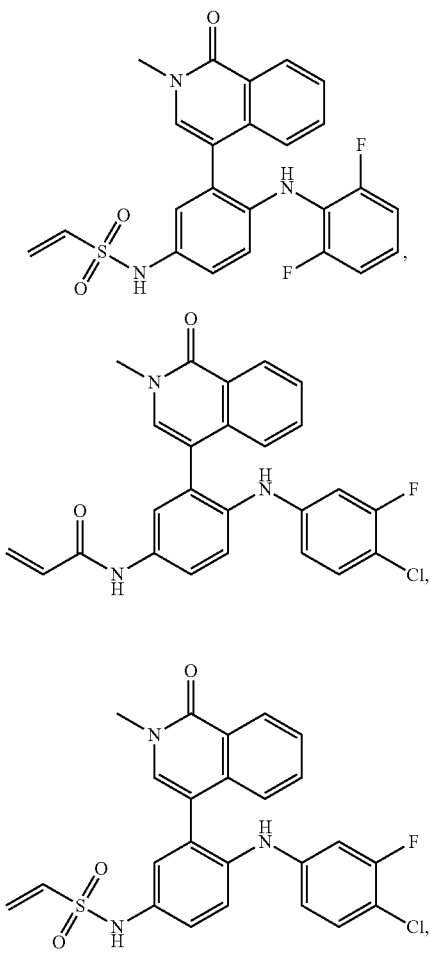
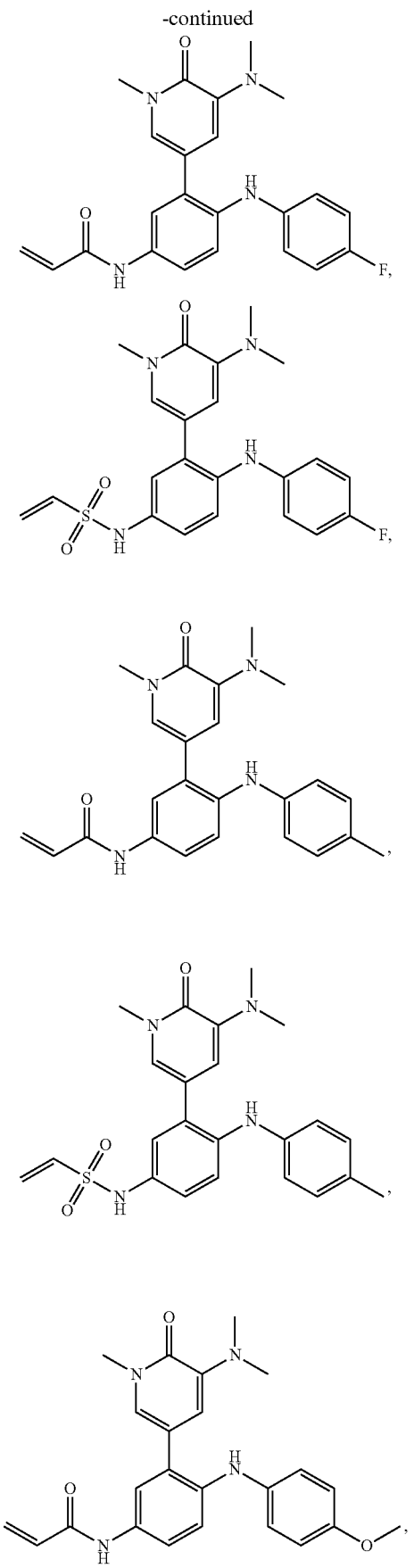

519
-continued
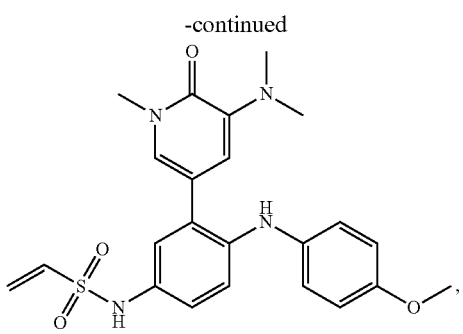
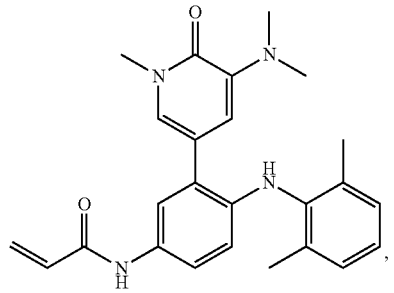
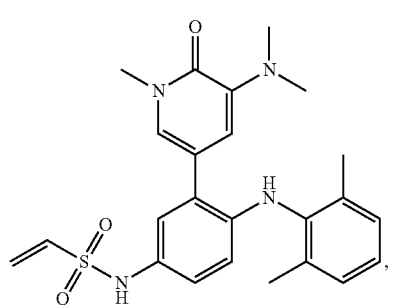
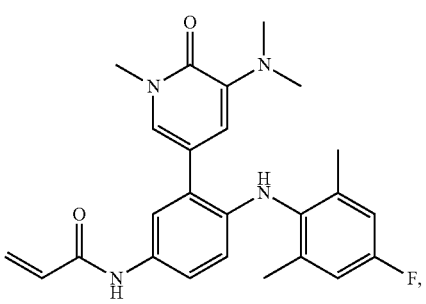
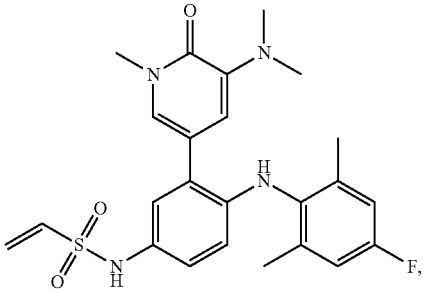
520
-continued
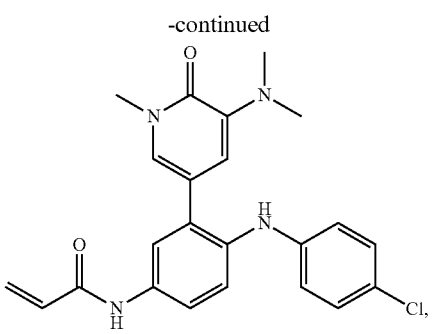
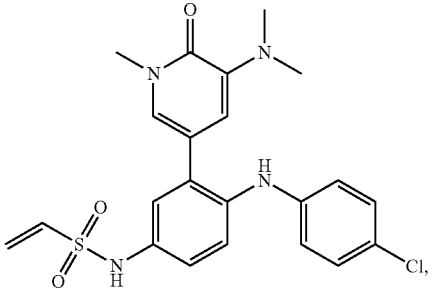
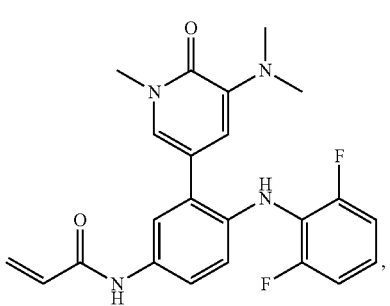
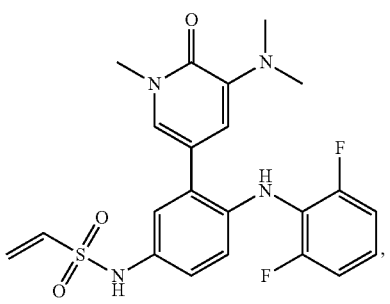
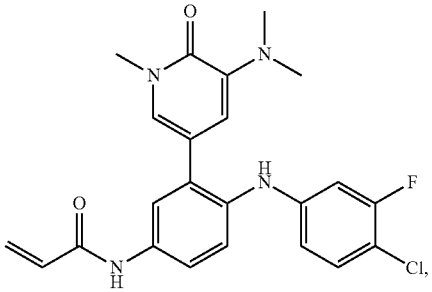

521
-continued
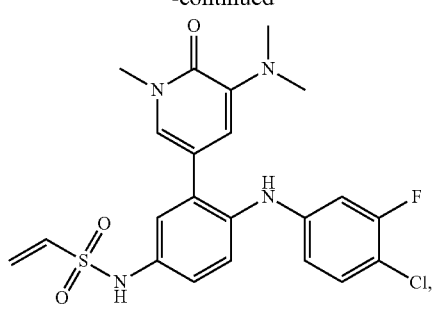
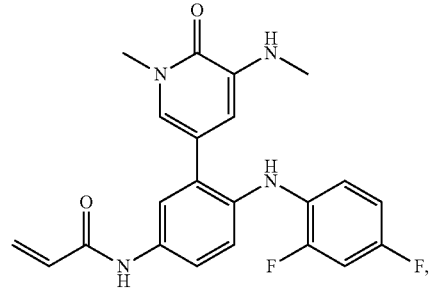
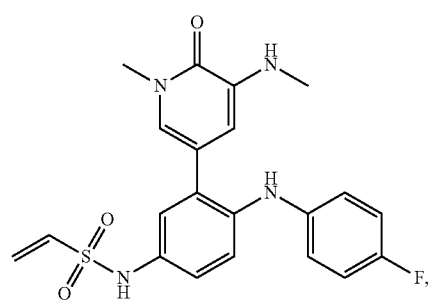
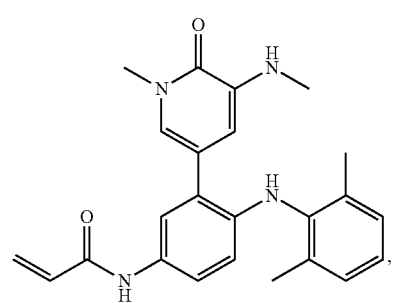
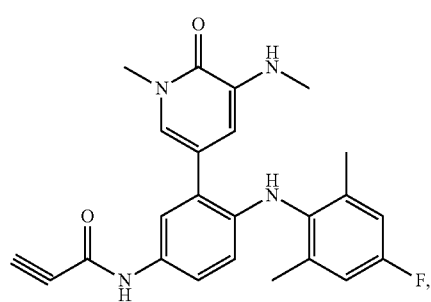
522
-continued
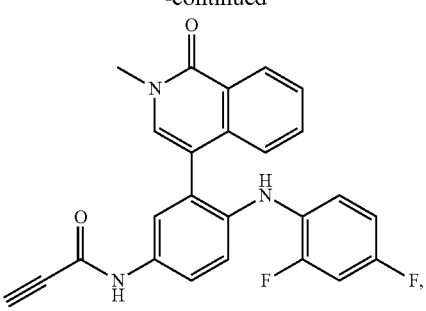
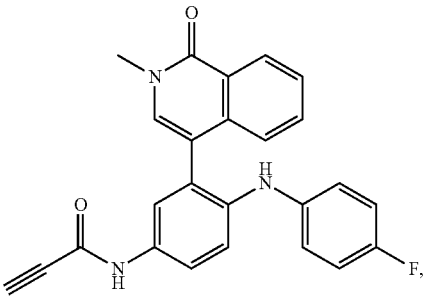
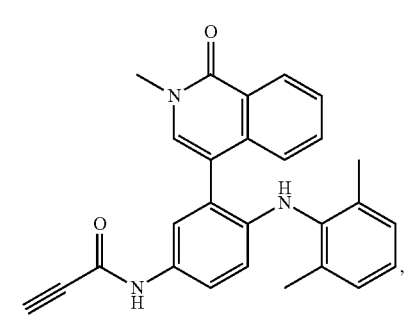
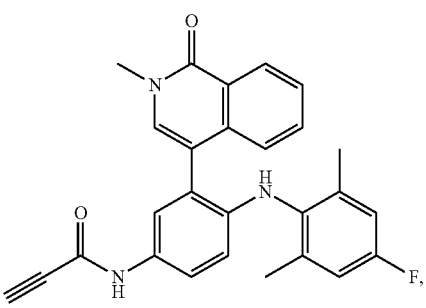
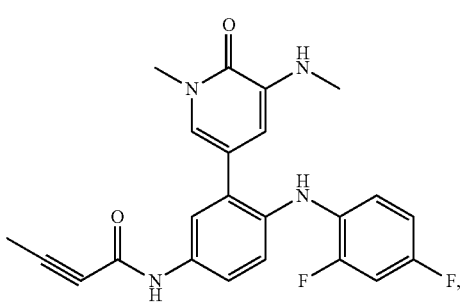

523
-continued
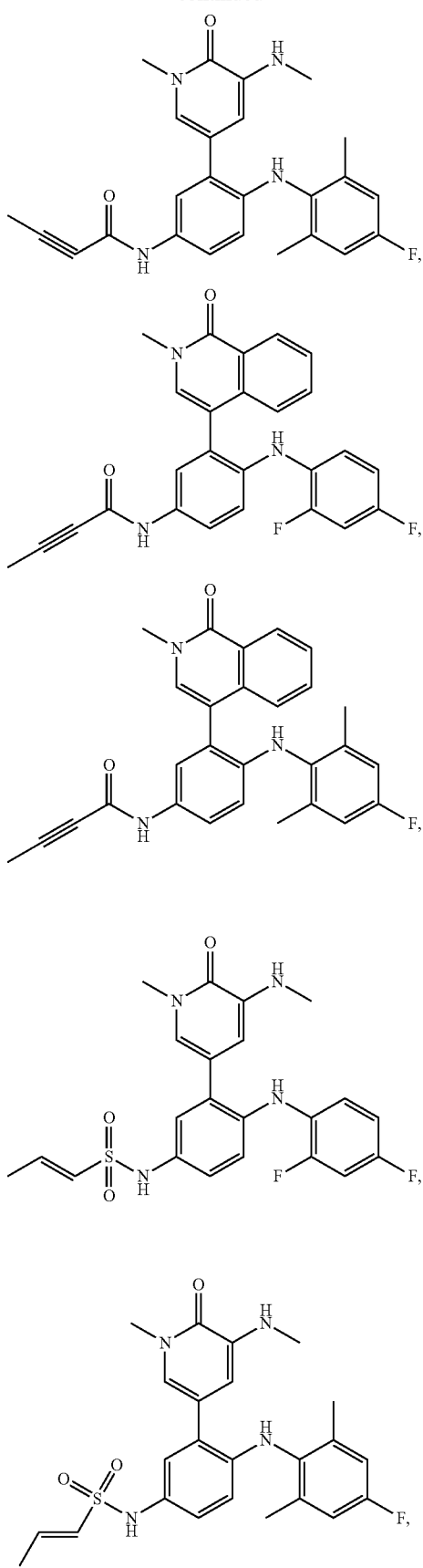
524
-continued
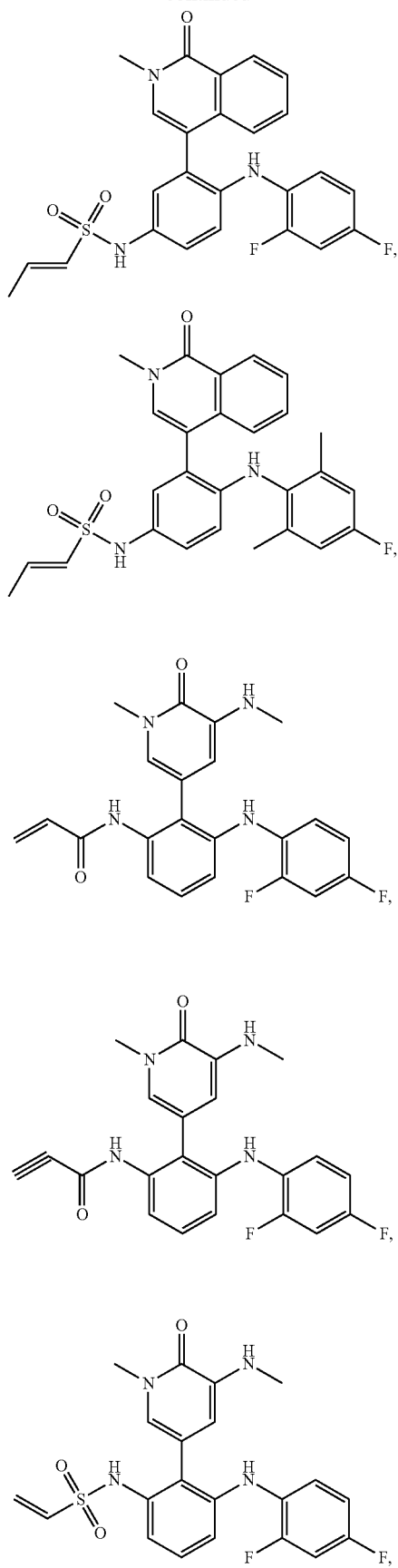

525
-continued
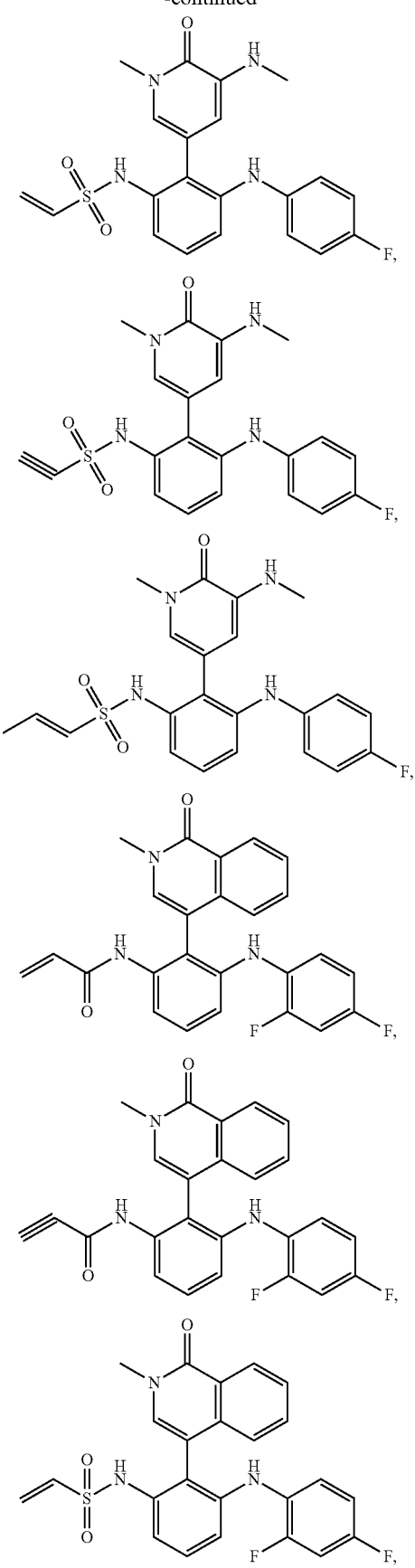
526
-continued
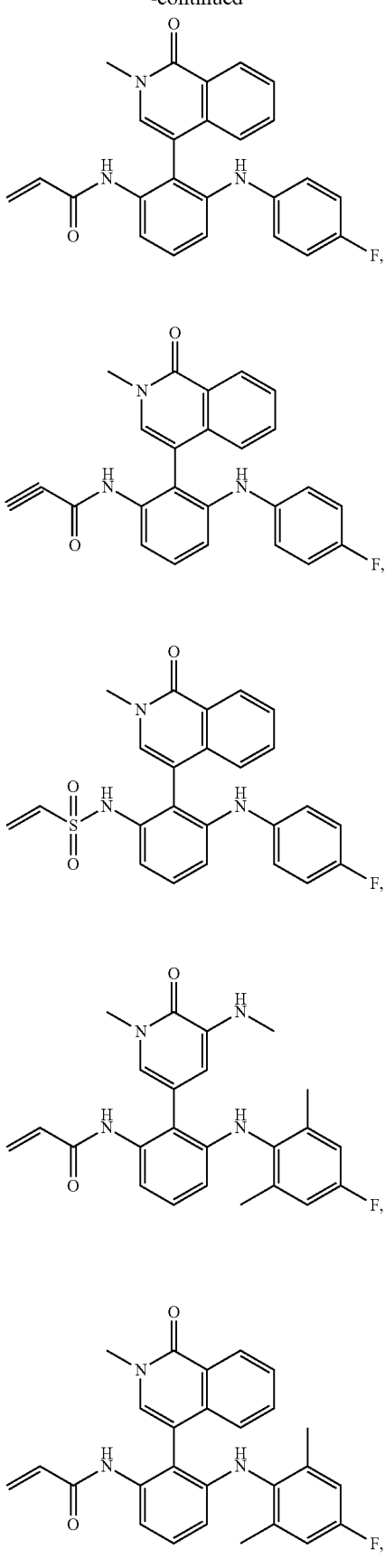

527
-continued
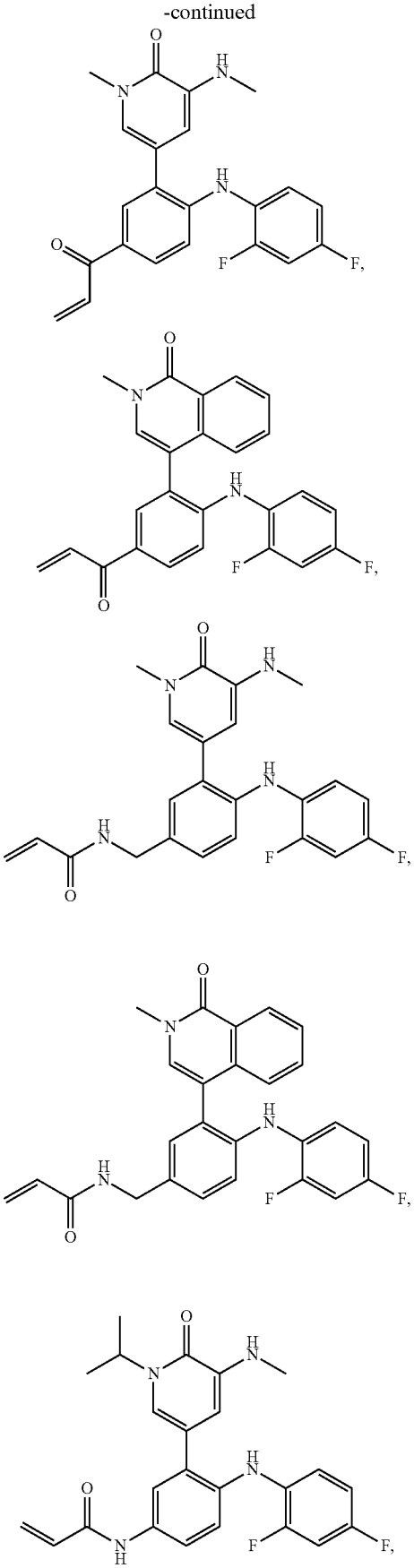
528
-continued
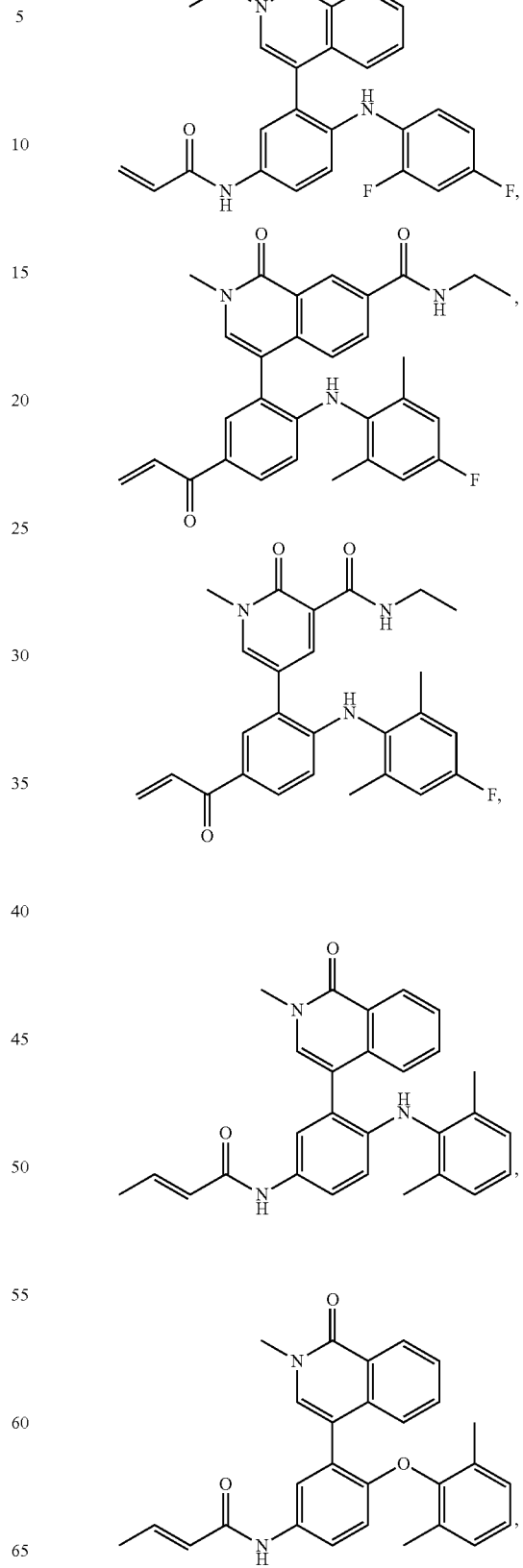

529
-continued
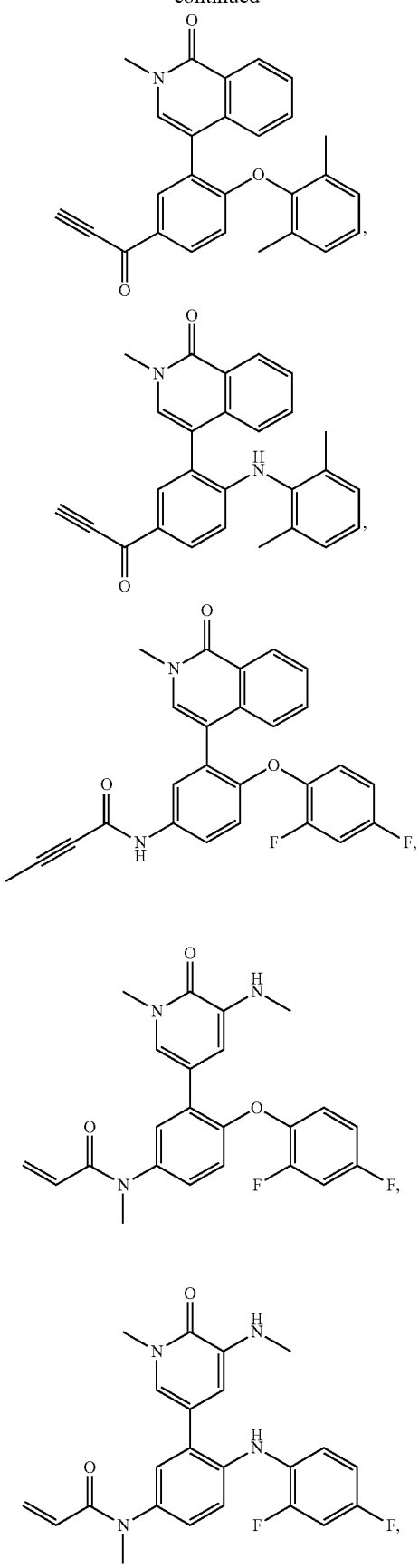
530
-continued
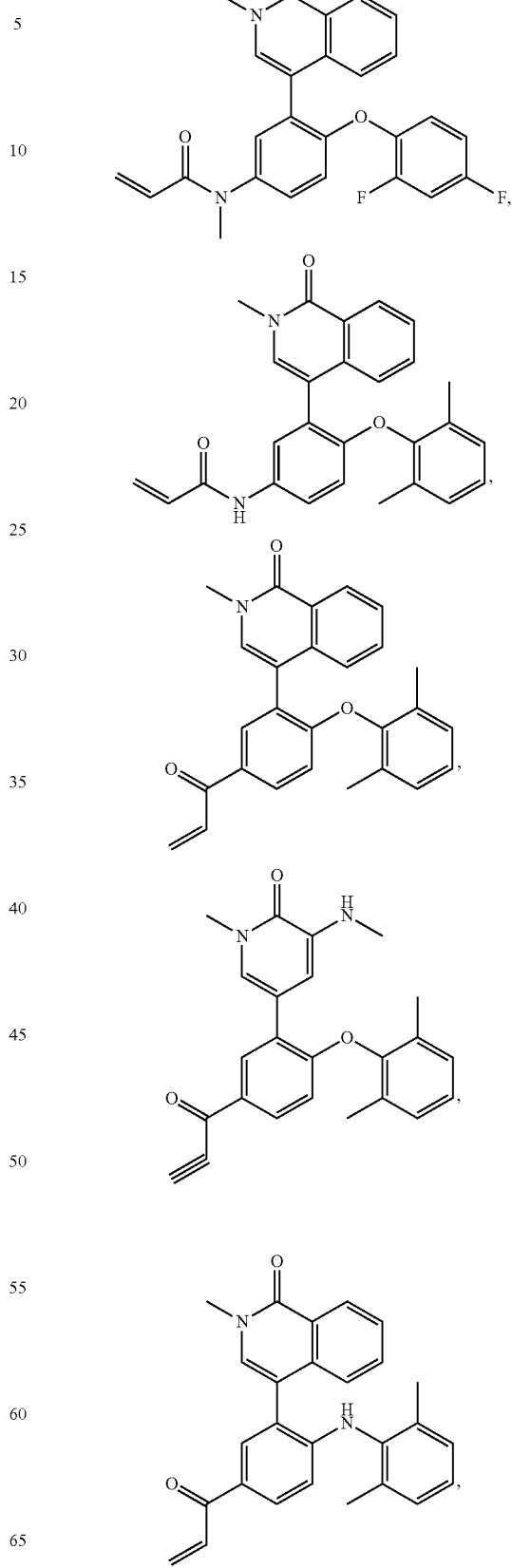

531
-continued
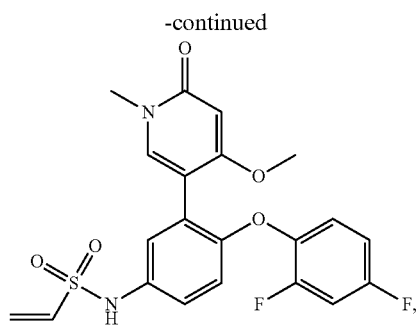
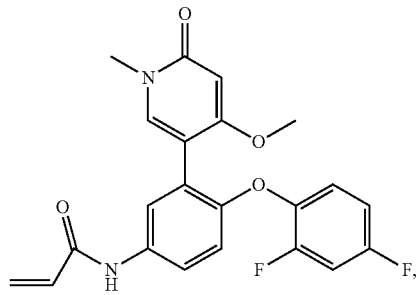
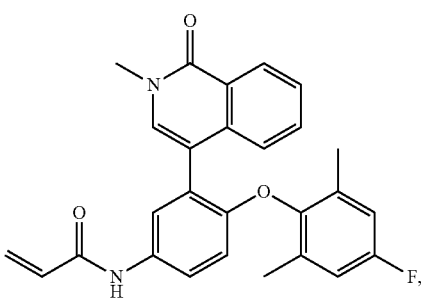
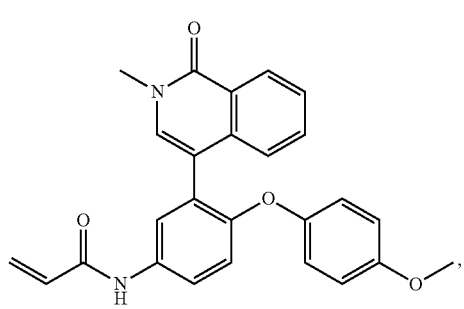
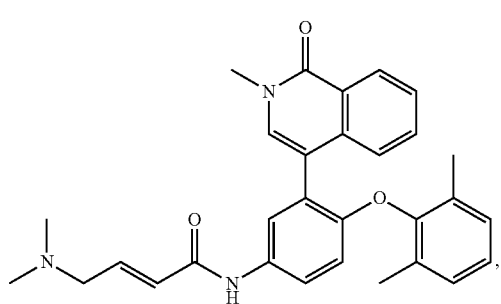
532
-continued
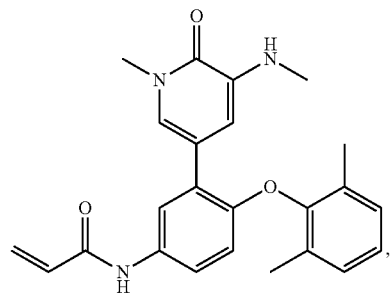
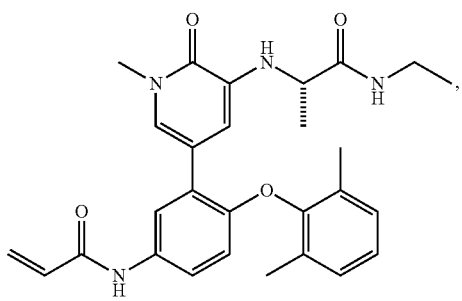
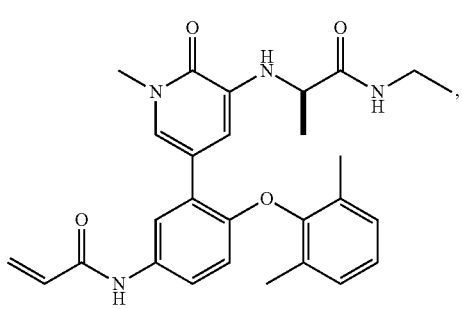
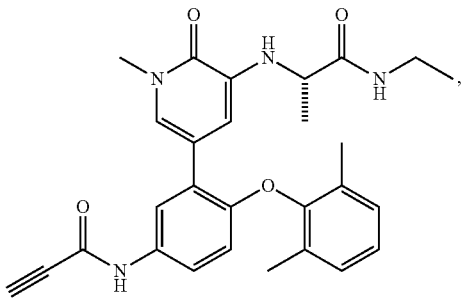
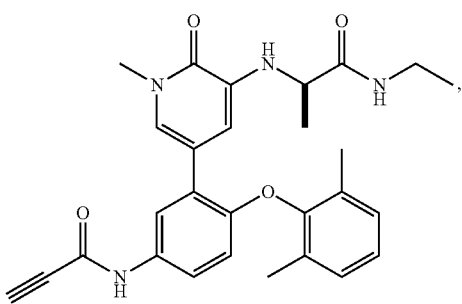

533
-continued
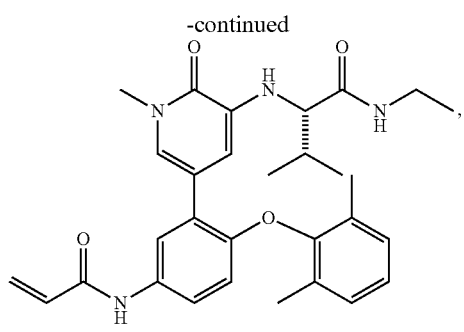
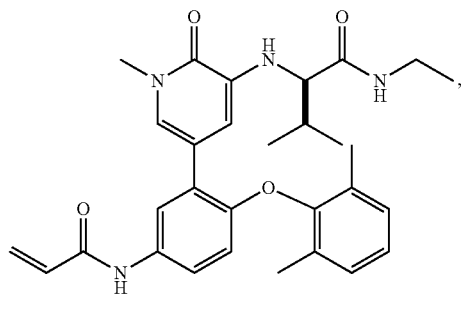
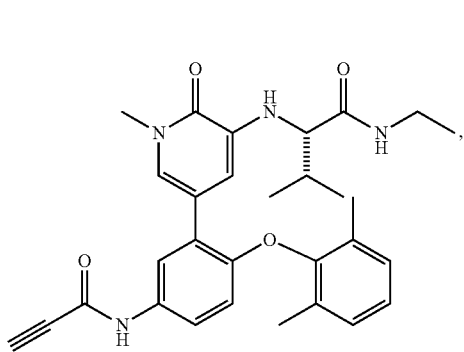
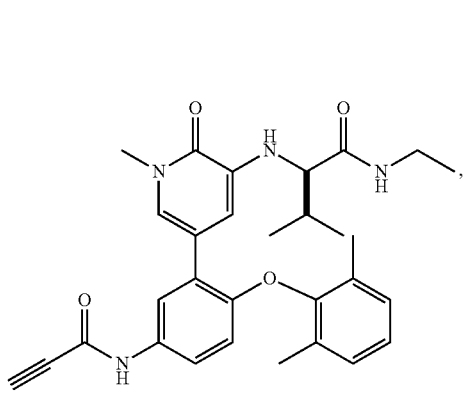
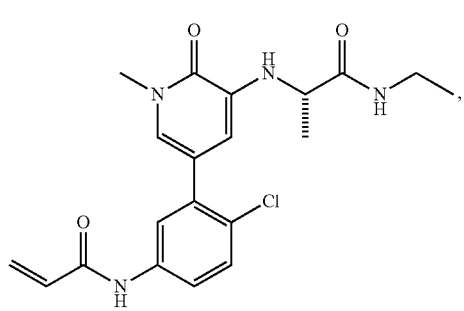
534
-continued
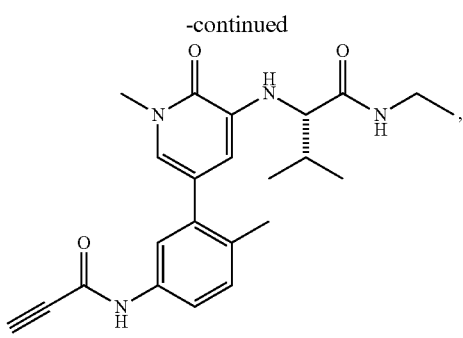
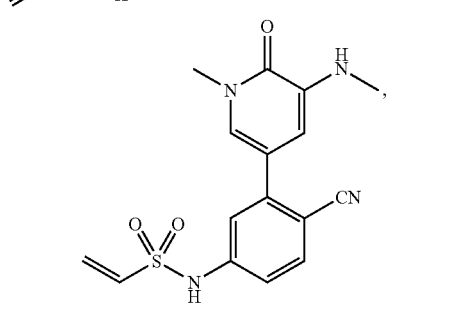
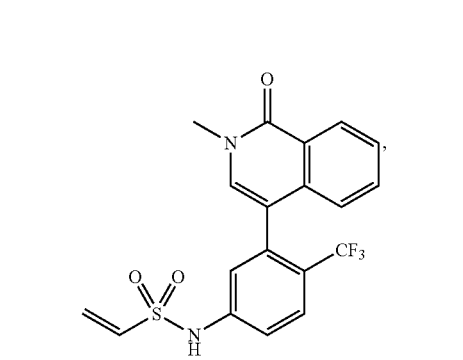
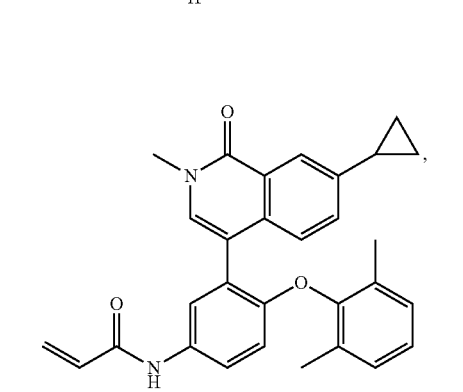
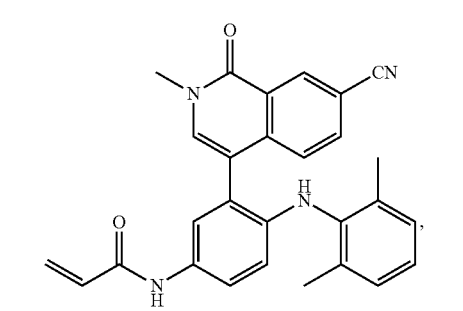

-continued
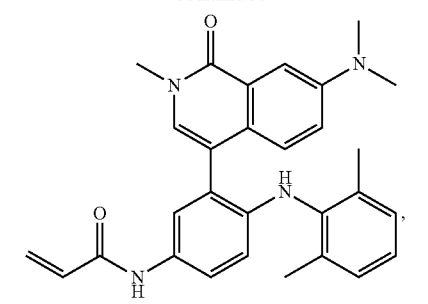
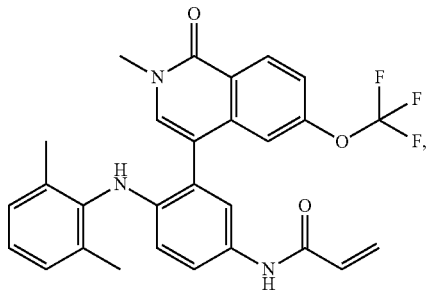
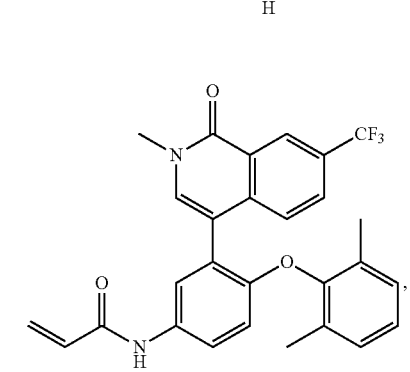
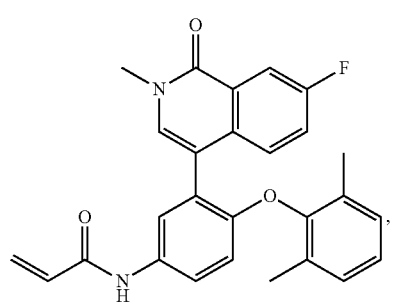
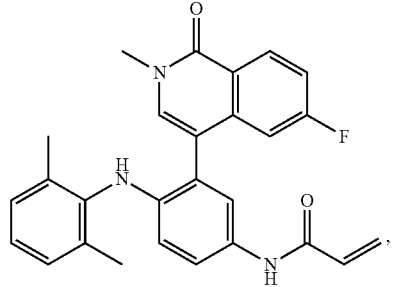
-continued
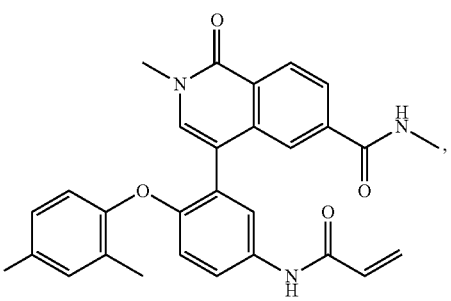
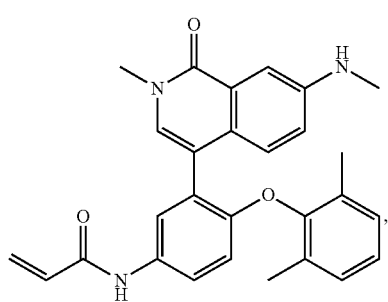
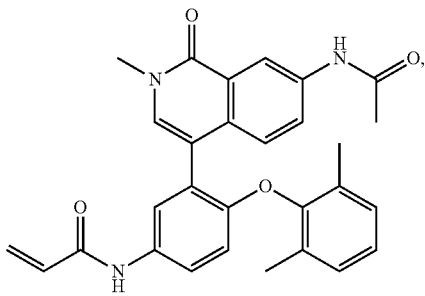

537
-continued
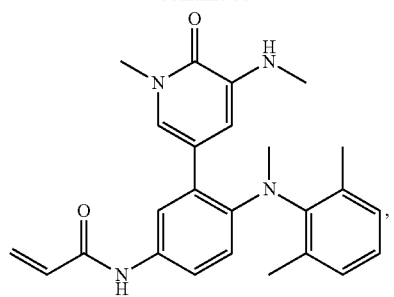
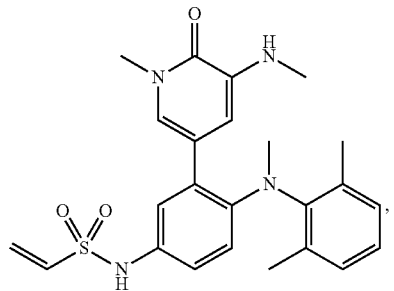
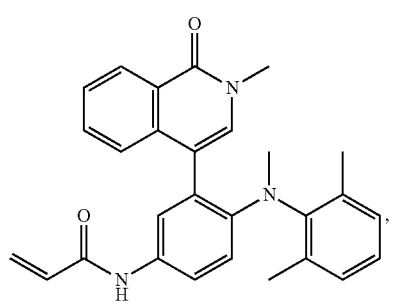
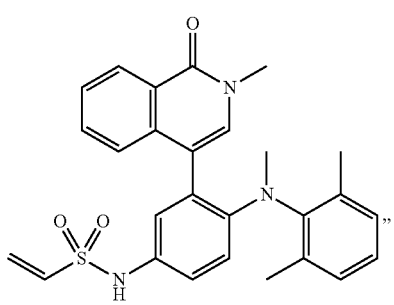
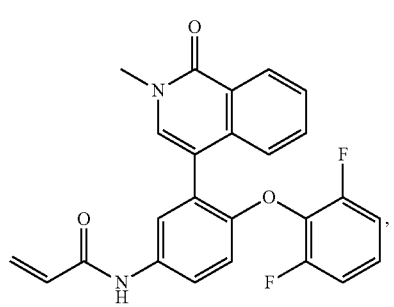
538
-continued
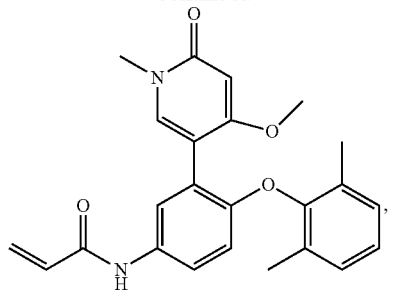
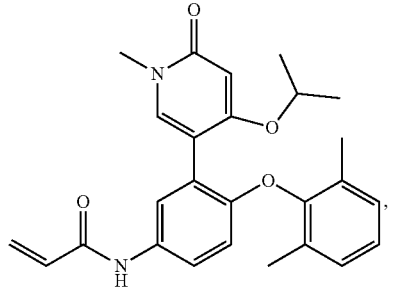
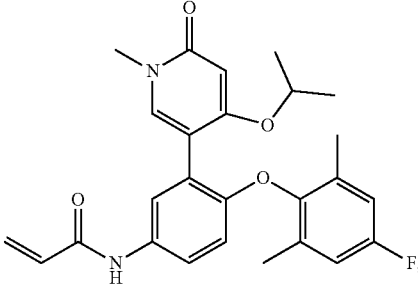
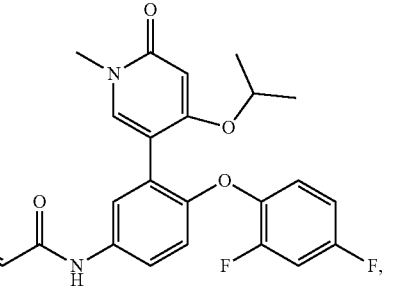
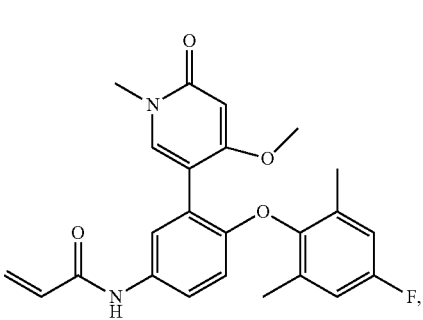
or a pharmaceutically acceptable salt thereof.
20. The compound of claim 1, wherein the compound is selected from the group consisting of:

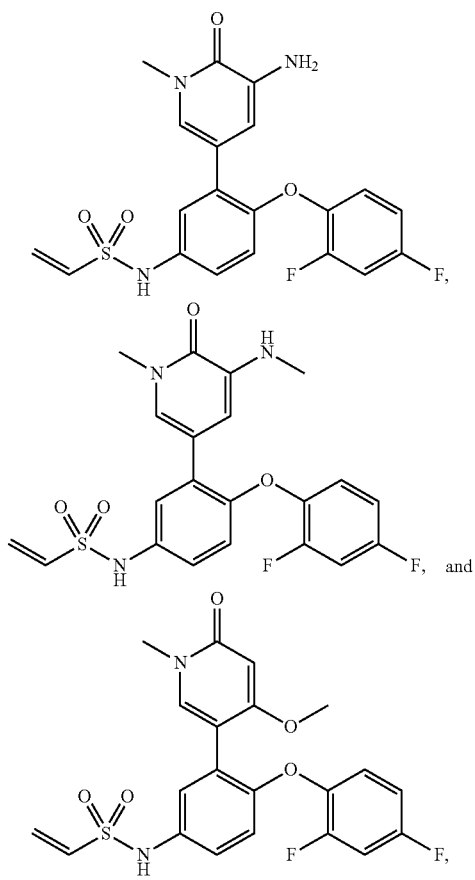

or a pharmaceutically acceptable salt thereof.

21. The compound of claim 1, wherein the compound is:

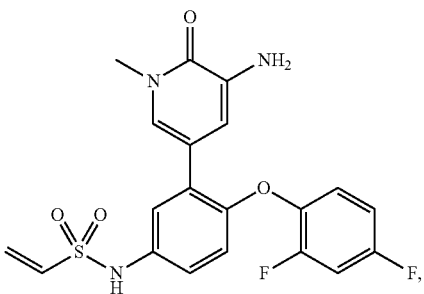 [SMILES: C=CS(=O)(=O)Nc1ccc(Oc2ccc(F)cc2F)c(-c2cc(N)c(=O)n(C)c2)c1]

or a pharmaceutically acceptable salt thereof.

22. The compound of claim 1, wherein the compound is:

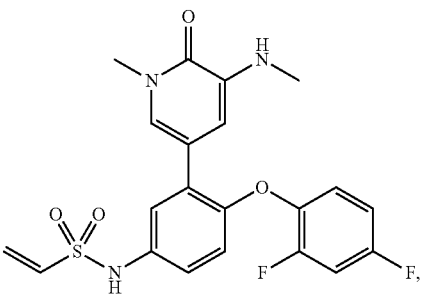

or a pharmaceutically acceptable salt thereof.

23. The compound of claim 1, wherein the compound is:

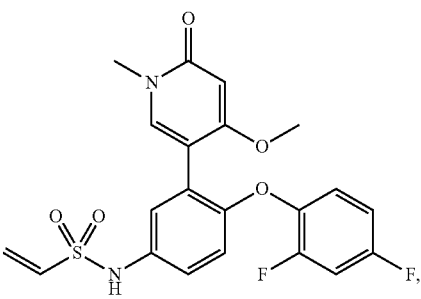 [SMILES: C=CS(=O)(=O)Nc1ccc(Oc2ccc(F)cc2F)c(-c2cn(C)c(=O)cc2OC)c1]

or a pharmaceutically acceptable salt thereof.

24. A pharmaceutical composition comprising a pharmaceutically acceptable carrier and the compound of claim 1, or a stereoisomer or tautomer thereof, or a pharmaceutically acceptable salt of any of the foregoing.

25. A kit comprising the compound of claim 1, or a stereoisomer or tautomer thereof, or a pharmaceutically acceptable salt of any of the foregoing.

* * * * *